US007847154B2

(12) United States Patent
Puthigae et al.

(10) Patent No.: US 7,847,154 B2
(45) Date of Patent: Dec. 7, 2010

(54) COMPOSITIONS AND METHODS FOR THE IMPROVEMENT OF PLANTS

(76) Inventors: Sathish Puthigae, 63 Cranbrook Place, Glendowie Auckland (NZ) 1005; Jonathan Robert Phillips, Rue Konkel 182, B-1200, Brussels (BE); Claudia Jeannette Smith-Espinoza, Rue Konkel 182, B-1200, Brussels (BE); Catherine Jane Bryant, 14 Fairview Road, Papatoetoe, Auckland (NZ); Kieran Michael Elborough, 79 Capehill Road, Pukekohe Franklin (NZ); Colin Robert South, 51 Lowell St., Lexington, MA (US) 02420; Fredy Altpeter, 3415 NW. 60th La., Gainesville, FL (US) 32653

( * ) Notice: Subject to any disclaimer, the term of this patent is extended or adjusted under 35 U.S.C. 154(b) by 0 days.

(21) Appl. No.: 11/875,656

(22) Filed: Oct. 19, 2007

(65) Prior Publication Data

US 2008/0282430 A1 Nov. 13, 2008

Related U.S. Application Data

(60) Provisional application No. 60/853,194, filed on Oct. 20, 2006.

(51) Int. Cl.

| | |
|---|---|
| ***C12N 15/82*** | (2006.01) |
| ***C12N 15/29*** | (2006.01) |
| ***A01H 5/00*** | (2006.01) |
| ***A01H 5/10*** | (2006.01) |

(52) U.S. Cl. .................. 800/289; 536/23.6; 435/320.1; 435/252.3; 435/419; 800/298

(58) Field of Classification Search ...................... None
See application file for complete search history.

(56) References Cited

U.S. PATENT DOCUMENTS 7,291,768 B2 * 11/2007 Yu ............................ 800/298
2006/0150283 A1 * 7/2006 Alexandrov et al. ........ 800/288

OTHER PUBLICATIONS

Whisstock J.C. et al. Prediction of protein function from protein sequence and structure. Q Rev Biophys. Aug. 2003;36(3):307-40. Review.*

Gaxiola et al., Drought- and salt-tolerant plants result from overexpression of the AVP1 H+-pump, Proceedings of the National Academy of Sciences of the USA, Sep. 25, 2001, vol. 98, Issue 20, pp. 11444-11449.

Kasuga et al., Improving plant drought, salt, and freezing tolerance by gene transfer of a single stress-inducible transcription factor, Nature Biotechnology, Mar. 1999, vol. 17, pp. 287-291.

Liu et al., Two Transcription Factors, DREB1 and DREB2, with an EREBP/AP2 DNA Binding Domain Separate Two Cellular Signal Transduction Pathways in Drought- and Low-Temperature-Responsive Gene Expression, Respectively, in *Arabidopsis*, The Plant Cell, Aug. 1998, vol. 10, pp. 1391-1406.

Shinozaki et al., Gene networks involved in drought stress response and tolerance, Journal of Experimental Botany, Oct. 30, 2006, vol. 58, Issue 2, pp. 221-227.

* cited by examiner

*Primary Examiner*—Cynthia Collins
(74) *Attorney, Agent, or Firm*—Knobbe Martens Olson & Bear LLP

(57) ABSTRACT

The invention provides compositions and methods useful for producing plant cells or plants with altered tolerance to at least one environmental stress selected from drought, cold, freezing, heat and salinity.

17 Claims, 71 Drawing Sheets

GGAATTCGATATCAAGCTTGGCACTGGCCGTCGTTTTACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCCTTCCCAACAGTTGCGCAGCCTGAATGGCGAATGCTAG
AGCAGCTTGAGCTTGGATCAGATTGTCGTTTCCCGCCTTCAGTTTAAACTATCAGTGTTTGACAGGATATATTGGCGGGTAAACCTAAGAG
AAAAGAGCGTTTATTAGAATAACGGATATTTAAAAGGGCGTGAAAAGGTTTATCCGTTCGTCCATTTGTATGTGCATGCCAACCACAGGGT
TCCCCTCGGGATCAAAGTACTTTGATCCAACCCCTCCGCTGCTATAGTGCAGTCGGCTTCTGACGTTCAGTGCAGCCGTCTTCTGAAAACG
ACATGTCGCACAAGTCCTAAGTTACGCGACAGGCTGCCGCCCTGCCCTTTTCCTGGCGTTTTCTTGTCGCGTGTTTTAGTCGCATAAAGTA
GAATACTTGCGACTAGAACCGGAGACATTACGCCATGAACAAGAGCGCCGCCGCTGGCCTGCTGGGCTATGCCCGCGTCAGCACCGACGAC
CAGGACTTGACCAACCAACGGGCCGAACTGCACGCGGCCGGCTGCACCAAGCTGTTTTCCGAGAAGATCACCGGCACCAGGCGCGACCGCC
CGGAGCTGGCCAGGATGCTTGACCACCTACGCCCTGGCGACGTTGTGACAGTGACCAGGCTAGACCGCCTGGCCCGCAGCACCCGCGACCT
ACTGGACATTGCCGAGCGCATCCAGGAGGCCGGCGCGGGCCTGCGTAGCCTGGCAGAGCCGTGGGCCGACACCACCACGCCGGCCGGCCGC
ATGGTGTTGACCGTGTTCGCCGGCATTGCCGAGTTCGAGCGTTCCCTAATCATCGACCGCACCCGGAGCGGGCGCGAGGCCGCCAAGGCCC
GAGGCGTGAAGTTTGGCCCCCGCCCTACCCTCACCCCGGCACAGATCGCGCACGCCCGCGAGCTGATCGACCAGGAAGGCCGCACCGTGAA
AGAGGCGGCTGCACTGCTTGGCGTGCATCGCTCGACCCTGTACCGCGCACTTGAGCGCAGCGAGGAAGTGACGCCCACCGAGGCCAGGCGG
CGCGGTGCCTTCCGTGAGGACGCATTGACCGAGGCCGACGCCCTGGCGGCCGCCGAGAATGAACGCCAAGAGGAACAAGCATGAAACCGCA
CCAGGACGGCCAGGACGAACCGTTTTTCATTACCGAAGAGATCGAGGCGGAGATGATCGCGGCCGGGTACGTGTTCGAGCCGCCCGCGCAC
GTCTCAACCGTGCGGCTGCATGAAATCCTGGCCGGTTTGTCTGATGCCAAGCTGGCGGCCTGGCCGGCCAGCTTGGCCGCTGAAGAAACCG
AGCGCCGCCGTCTAAAAAGGTGATGTGTATTTGAGTAAAACAGCTTGCGTCATGCGGTCGCTGCGTATATGATGCGATGAGTAAATAAACA
AATACGCAAGGGGAACGCATGAAGGTTATCGCTGTACTTAACCAGAAAGGCGGGTCAGGCAAGACGACCATCGCAACCCATCTAGCCCGCG
CCCTGCAACTCGCCGGGGCCGATGTTCTGTTAGTCGATTCCGATCCCCAGGGCAGTGCCCGCGATTGGGCGGCCGTGCGGGAAGATCAACC
GCTAACCGTTGTCGGCATCGACCGCCCGACGATTGACCGCGACGTGAAGGCCATCGGCCGGCGCGACTTCGTAGTGATCGACGGAGCGCCC
CAGGCGGCGGACTTGGCTGTGTCCGCGATCAAGGCAGCCGACTTCGTGCTGATTCCGGTGCAGCCAAGCCCTTACGACATATGGGCCACCG
CCGACCTGGTGGAGCTGGTTAAGCAGCGCATTGAGGTCACGGATGGAAGGCTACAAGCGGCCTTTGTCGTGTCGCGGGCGATCAAAGGCAC
GCGCATCGGCGGTGAGGTTGCCGAGGCGCTGGCCGGGTACGAGCTGCCCATTCTTGAGTCCCGTATCACGCAGCGCGTGAGCTACCCAGGC
ACTGCCGCCGCCGGCACAACCGTTCTTGAATCAGAACCCGAGGGCGACGCTGCCCGCGAGGTCCAGGCGCTGGCCGCTGAAATTAAATCAA
AACTCATTTGAGTTAATGAGGTAAAGAGAAAATGAGCAAAAGCACAAACACGCTAAGTGCCGGCCGTCCGAGCGCACGCAGCAGCAAGGCT
GCAACGTTGGCCAGCCTGGCAGACACGCCAGCCATGAAGCGGGTCAACTTTCAGTTGCCGGCGGAGGATCACACCAAGCTGAAGATGTACG
CGGTACGCCAAGGCAAGACCATTACCGAGCTGCTATCTGAATACATCGCGCAGCTACCAGAGTAAATGAGCAAATGAATAAATGAGTAGAT
GAATTTTAGCGGCTAAAGGAGGCGGCATGGAAAATCAAGAACAACCAGGCACCGACGCCGTGGAATGCCCCATGTGTGGAGGAACGGGCGG
TTGGCCAGGCGTAAGCGGCTGGGTTGTCTGCCGGCCCTGCAATGGCACTGGAACCCCCAAGCCCGAGGAATCGGCGTGACGGTCGCAAACC
ATCCGGCCCGGTACAAATCGGCGCGGCGCTGGGTGATGACCTGGTGGAGAAGTTGAAGGCCGCGCAGGCCGCCCAGCGGCAACGCATCGAG
GCAGAAGCACGCCCCGGTGAATCGTGGCAAGCGGCCGCTGATCGAATCCGCAAAGAATCCCGGCAACCGCCGGCAGCCGGTGCGCCGTCGA
TTAGGAAGCCGCCCAAGGGCGACGAGCAACCAGATTTTTTCGTTCCGATGCTCTATGACGTGGGCACCCGCGATAGTCGCAGCATCATGGA
CGTGGCCGTTTTCCGTCTGTCGAAGCGTGACCGACGAGCTGGCGAGGTGATCCGCTACGAGCTTCCAGACGGGCACGTAGAGGTTTCCGCA
GGGCCGGCCGGCATGGCCAGTGTGTGGGATTACGACCTGGTACTGATGGCGGTTTCCCATCTAACCGAATCCATGAACCGATACCGGGAAG
GGAAGGGAGACAAGCCCGGCCGCGTGTTCCGTCCACACGTTGCGGACGTACTCAAGTTCTGCCGGCGAGCCGATGGCGGAAAGCAGAAAGA
CGACCTGGTAGAAACCTGCATTCGGTTAAACACCACGCACGTTGCCATGCAGCGTACGAAGAAGGCCAAGAACGGCCGCCTGGTGACGGTA
TCCGAGGGTGAAGCCTTGATTAGCCGCTACAAGATCGTAAAGAGCGAAACCGGGCGGCCGGAGTACATCGAGATCGAGCTAGCTGATTGGA
TGTACCGCGAGATCACAGAAGGCAAGAACCCGGACGTGCTGACGGTTCACCCCGATTACTTTTTGATCGATCCCGGCATCGGCCGTTTTCT
CTACCGCCTGGCACGCCGCGCCGCAGGCAAGGCAGAAGCCAGATGGTTGTTCAAGACGATCTACGAACGCAGTGGCAGCGCCGGAGAGTTC
AAGAAGTTCTGTTTCACCGTGCGCAAGCTGATCGGGTCAAATGACCTGCCGGAGTACGATTTGAAGGAGGAGGCGGGGCAGGCTGGCCCGA
TCCTAGTCATGCGCTACCGCAACCTGATCGAGGGCGAAGCATCCGCCGGTTCCTAATGTACGGAGCAGATGCTAGGGCAAATTGCCCTAGC
AGGGGAAAAAGGTCGAAAAGGTCTCTTTCCTGTGGATAGCACGTACATTGGGAACCCAAAGCCGTACATTGGGAACCGGAACCCGTACATT
GGGAACCCAAAGCCGTACATTGGGAACCGGTCACACATGTAAGTGACTGATATAAAAGAGAAAAAAGGCGATTTTTCCGCCTAAAACTCTT
TAAAACTTATTAAAACTCTTAAAACCCGCCTGGCCTGTGCATAACTGTCTGGCCAGCGCACAGCCGAAGAGCTGCAAAAAGCGCCTACCCT
TCGGTCGCTGCGCTCCCTACGCCCCGCCGCTTCGCGTCGGCCTATCGCGGCCGCTGGCCGCTCAAAAATGGCTGGCCTACGGCCAGGCAAT
CTACCAGGGCGCGGACAAGCCGCGCCGTCGCCACTCGACCGCCGGCGCCCACATCAAGGCACCCTGCCTCGCGCGTTTCGGTGATGACGGT
GAAAACCTCTGACACATGCAGCTCCCGGAGACGGTCACAGCTTGTCTGTAAGCGGATGCCGGGAGCAGACAAGCCCGTCAGGGCGCGTCAG
CGGGTGTTGGCGGGTGTCGGGGCGCAGCCATGACCCAGTCACGTAGCGATAGCGGAGTGTATACTGGCTTAACTATGCGGCATCAGAGCAG

FIGURE 2-1

ATTGTACTGAGAGTGCACCATATGCGGTGTGAAATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAAAACTCACGTTAAGGGA
TTTTGGTCATGCATTCTAGGTACTAAAACAATTCATCCAGTAAAATATAATATTTTATTTTCTCCCAATCAGGCTTGATCCCCAGTAAGTC
AAAAAATAGCTCGACATACTGTTCTTCCCCGATATCCTCCCTGATCGACCGGACGCAGAAGGCAATGTCATACCACTTGTCCGCCCTGCCG
CTTCTCCCAAGATCAATAAAGCCACTTACTTTGCCATCTTTCACAAAGATGTTGCTGTCTCCCAGGTCGCCGTGGGAAAAGACAAGTTCCT
CTTCGGGCTTTTCCGTCTTTAAAAAATCATACAGCTCGCGCGGATCTTTAAATGGAGTGTCTTCTTCCCAGTTTTCGCAATCCACATCGGC
CAGATCGTTATTCAGTAAGTAATCCAATTCGGCTAAGCGGCTGTCTAAGCTATTCGTATAGGGACAATCCGATATGTCGATGGAGTGAAAG
AGCCTGATGCACTCCGCATACAGCTCGATAATCTTTTCAGGGCTTTGTTCATCTTCATACTCTTCCGAGCAAAGGACGCCATCGGCCTCAC
TCATGAGCAGATTGCTCCAGCCATCATGCCGTTCAAAGTGCAGGACCTTTGGAACAGGCAGCTTTCCTTCCAGCCATAGCATCATGTCCTT
TTCCCGTTCCACATCATAGGTGGTCCCTTTATACCGGCTGTCCGTCATTTTTAAATATAGGTTTTCATTTTCTCCCACCAGCTTATATACC
TTAGCAGGAGACATTCCTTCCGTATCTTTTACGCAGCGGTATTTTTCGATCAGTTTTTTCAATTCCGGTGATATTCTCATTTTAGCCATTT
ATTATTTCCTTCCTCTTTTCTACAGTATTTAAAGATACCCCAAGAAGCTAATTATAACAAGACGAACTCCAATTCACTGTTCCTTGCATTC
TAAAACCTTAAATACCAGAAAACAGCTTTTTCAAAGTTGTTTTCAAAGTTGGCGTATAACATAGTATCGACGGAGCCGATTTTGAAACCGC
GGTGATCACAGGCAGCAACGCTCTGTCATCGTTACAATCAACATGCTACCCTCCGCGAGATCATCCGTGTTTCAAACCCGGCAGCTTAGTT
GCCGTTCTTCCGAATAGCATCGGTAACATGAGCAAAGTCTGCCGCCTTACAACGGCTCTCCCGCTGACGCCGTCCCGGACTGATGGGCTGC
CTGTATCGAGTGGTGATTTTGTGCCGAGCTGCCGGTCGGGGAGCTGTTGGCTGGCTGGTGGCAGGATATATTGTGGTGTAAACAAATTGAC
GCTTAGACAACTTAATAACACATTGCGGACGTTTTTAATGTACTGAATTAACGCCGAATTAATTCGGGGGATCTGGATTTTAGTACTGGAT
TTTGGTTTTAGGAATTAGAAATTTTATTGATAGAAGTATTTTACAAATACAAATACATACTAAGGGTTTCTTATATGCTCAACACATGAGC
GAAACCCTATAGGAACCCTAATTCCCTTATCTGGGAACTACTCACACATTATTATGGAGAAACTCGAGCTTGTCGATCGACAGATCCGGTC
GGCATCTACTCTATTTCTTTGCCCTCGGACGAGTGCTGGGGCGTCGGTTTCCACTATCGGCGAGTACTTCTACACAGCCATCGGTCCAGAC
GGCCGCGCTTCTGCGGGCGATTTGTGTACGCCCGACAGTCCCGGCTCCGGATCGGACGATTGCGTCGCATCGACCCTGCGCCCAAGCTGCA
TCATCGAAATTGCCGTCAACCAAGCTCTGATAGAGTTGGTCAAGACCAATGCGGAGCATATACGCCCGGAGTCGTGGCGATCCTGCAAGCT
CCGGATGCCTCCGCTCGAAGTAGCGCGTCTGCTGCTCCATACAAGCCAACCACGGCCTCCAGAAGAAGATGTTGGCGACCTCGTATTGGGA
ATCCCCGAACATCGCCTCGCTCCAGTCAATGACCGCTGTTATGCGGCCATTGTCCGTCAGGACATTGTTGGAGCCGAAATCCGCGTGCACG
AGGTGCCGGACTTCGGGGCAGTCCTCGGCCCAAAGCATCAGCTCATCGAGAGCCTGCGCGACGGACGCACTGACGGTGTCGTCCATCACAG
TTTGCCAGTGATACACATGGGGATCAGCAATCGCGCATATGAAATCACGCCATGTAGTGTATTGACCGATTCCTTGCGGTCCGAATGGGCC
GAACCCGCTCGTCTGGCTAAGATCGGCCGCAGCGATCGCATCCATAGCCTCCGCGACCGGTTGTAGAACAGCGGGCAGTTCGGTTTCAGGC
AGGTCTTGCAACGTGACACCCTGTGCACGGCGGGAGATGCAATAGGTCAGGCTCTCGCTAAACTCCCCAATGTCAAGCACTTCCGGAATCG
GGAGCGCGGCCGATGCAAAGTGCCGATAAACATAACGATCTTTGTAGAAACCATCGGCGCAGCTATTTACCCGCAGGACATATCCACGCCC
TCCTACATCGAAGCTGAAAGCACGAGATTCTTCGCCCTCCGAGAGCTGCATCAGGTCGGAGACGCTGTCGAACTTTTCGATCAGAAACTTC
TCGACAGACGTCGCGGTGAGTTCAGGCTTTTTCATATCTCATTGCCCCCCGGATCTGCGAAAGCTCGAGAGAGATAGATTTGTAGAGAGA
GACTGGTGATTTCAGCGTGTCCTCTCCAAATGAAATGAACTTCCTTATATAGAGGAAGGTCTTGCGAAGGATAGTGGGATTGTGCGTCATC
CCTTACGTCAGTGGAGATATCACATCAATCCACTTGCTTTGAAGACGTGGTTGGAACGTCTTCTTTTTCCACGATGCTCCTCGTGGGTGGG
GGTCCATCTTTGGGACCACTGTCGGCAGAGGCATCTTGAACGATAGCCTTTCCTTTATCGCAATGATGGCATTTGTAGGTGCCACCTTCCT
TTTCTACTGTCCTTTTGATGAAGTGACAGATAGCTGGGCAATGGAATCCGAGGAGGTTTCCCGATATTACCCTTTGTTGAAAAGTCTCAAT
AGCCCTTTGGTCTTCTGAGACTGTATCTTTGATATTCTTGGAGTAGACGAGAGTGTCGTGCTCCACCATGTTATCACATCAATCCACTTGC
TTTGAAGACGTGGTTGGAACGTCTTCTTTTTCCACGATGCTCCTCGTGGGTGGGGGTCCATCTTTGGGACCACTGTCGGCAGAGGCATCTT
GAACGATAGCCTTTCCTTTATCGCAATGATGGCATTTGTAGGTGCCACCTTCCTTTTCTACTGTCCTTTTGATGAAGTGACAGATAGCTGG
GCAATGGAATCCGAGGAGGTTTCCCGATATTACCCTTTGTTGAAAAGTCTCAATAGCCCTTTGGTCTTCTGAGACTGTATCTTTGATATTC
TTGGAGTAGACGAGAGTGTCGTGCTCCACCATGTTGGCAAGCTGCTCTAGCCAATACGCAAACCGCCTCTCCCCGCGCGTTGGCCGATTCA

FIGURE 2-2

TTAATGCAGCTGGCACGACAGGTTTCCCGACTGGAAAGCGGGCAGTGAGCGCAACGCAATTAATGTGAGTTAGCTCACTCATTAGGCACCC
CAGGCTTTACACTTTATGCTTCCGGCTCGTATGTTGTGTGGAATTGTGAGCGGATAACAATTTCACACAGGAAACAGCTATGACCATGATT
ACGAATTCCCTTAATTAATAAGAGCAGCTTGCCAACATGGTGGAGCACGACACTCTCGTCTACTCCAAGAATATCAAAGATACAGTCTCAG
AAGACCAAAGGGCTATTGAGACTTTTCAACAAAGGGTAATATCGGGAAACCTCCTCGGATTCCATTGCCCAGCTATCTGTCACTTCATCAA
AAGGACAGTAGAAAAGGAAGGTGGCACCTACAAATGCCATCATTGCGATAAAGGAAAGGCTATCGTTCAAGATGCCTCTGCCGACAGTGGT
CCCAAAGATGGACCCCCACCCACGAGGAGCATCGTGGAAAAAGAAGACGTTCCAACCACGTCTTCAAAGCAAGTGGATTGATGTGAACATG
GTGGAGCACGACACTCTCGTCTACTCCAAGAATATCAAAGATACAGTCTCAGAAGGCCAAAGGGCTATTGAGACTTTTCAACAAAGGGTAA
TATCGGGAAACCTCCTCGGATTCCATTGCCCAGCTATCTGTCACTTCATCAAAAGGACAGTAGAAAAGGAAGGTGGCACCTACAAATGCCA
TCATTGCGATAAAGGAAAGGCTATCGTTCAAGATGCTCTGCCGACAGTGGTCCCAAAGATGGACCCCCACCCACGAGGAGCATCGTGGAAA
AAGAAGACGTTCCAACCACGTCTTCAAAGCAAGTGGATTGATGTGATATCTCCACTGACGTAAGGGATGACGCACAATCCCACTATCCTTC
GCAAGACCCTTCCTCTATATAAGGAAGTTCATTTCATTTGGAGAGGACACGCTGAAATCACCAGTCTCTCTCTACAAATCTATCTCTCTCC
ATTAGTCTCTTCACCTTGTCCCACCTGCTCCCCGCCGCATCTCACCAGACACCAGCCATGTGCGGCAGCGCGATCCTCTCCGACATCATCCC
GCCGCCGCGCCGGGTCACGGACGGCCCCCTCTGGCGGAACCAGAAGAAGAAGGGGCCGACGGGAGATGCTCCGGTGGCGAGGCGCCGCCGC
GCGCCCGAGGAGGAGGAGAGCTACGAGGACTTCGAGGCCGACTTCGAGGGCTTCGACGAGGGGCTGGCGAGGCCGAGATCTGGTCCGAGC
ACGAGGCCAAGCCCTTCTCCGCCGCCAGGAAACGCGTCGCCGCAGGTATAGCCGCCCTTTTTGGGTCACCGGCTTTGGATCTGTGGAACCG
CGTGCTAATTCTCTTTACCATTTGGGAGATAGATTTGAGTTTCTCAGCTGATCTGCTGCTCGGATTAGATAGTTGCATCTTCGATTTGTTT
GCTATGAACTTAAATCTGTGCAATTGTTCATCTCAAGTCCGTTAATTCAGCGGCTCCATGTTGTCGATTAGTCTGGTCTCTAGTGCTGTGT
CTTTTTTTTAAAAAAACACAATCTCTGGTGCTGTGTCGATCCTTAGTTTTTAGGATAACTCTCCTAAATCATGAATATGGTATCAACTCTT
ATTGGTGCATACATAGATCGAGCTTCCTCGCAAGCATATGAGTTGGGCTGTTCCTCAGGATTAGACTTTTAATGTCAAGTTTCGACTTAGC
CTGACTTTCTGTATGTAAACTAAAATCTTTATCTCACTGCTTCATCCTGATTGAATAAATGCATGTACAGCTGCTGCTGTTGATGGCTGGG
CATCAGAGTCCGCCAAAAGGAAGAGAAAGACCCAGTTCAGGGGCATCTGCCGCCGCCCTTGGGGTAAATGGGCTGCTGAAATCAGAGACCC
TCGCAAGGGTGTCCGTGTCTGGCTTGGCACTTACAACTCTGCCGAGGAAGCTGCCAGAGCCTATGATGCTGAAGCAAGAAGGATCCGTGGC
AAGAAGGCCAAGGTCAATTTCCCAGATGAGGCTCCTGTGGCTTCTCAAAAGCACTGTGCTAAGCCTACCTTTGTGACGTTGCCTGAGTTCA
ACACCGAAGAGAAGCCGATAGTCAACGCCGTGGCCAACACAAACGCGTATTCCTATCCTCTTGTTGACTACACCGTCTGTGAGCCATTTGT
GCAGCCTCAGAACATGTCATTTGTGCCAGCGGCTAATGCAGTTGAGGTTCCTTTCATGAATCTTTCCTCTGACCAGGGTAGCAACTCCTTT
GGTTGCTCAGACTTTAGCTGGGAGAATGGTACCAAGACTCCTGACATCACATCTGTGCTTGCATCCATTCCCACCTCGACCGAGGTTGATG
AATCTGCATTCCTTCAGAACAATGCCAGTGATGCATCACTACCTCCTGTCATGGATACTGCCAATCTTGATCTCGCCGATTTGGAACCATA
CATGAAGTTCCTCGTGGATGGTGCTTCAGATGAGTCACTTGACAACTTTCTAAGCTGTGACGGGTCTGAGGACATGGTCAGCAACCTGGAC
CTTTGGACTTTCGATGACATGCCCATTTCTGCCGATTTCTACTGAGGCTCTGAGGTCAATTGGTGCCTGTACGTATAGATAATGGGTAAGC
ATCTGCAACTGCGGAAATAACTCACTGTTATACTTCAGTTTCCATTTCCATAACTACCCCACTTCACTTTTCAGGAATAAGTATCTGGAC
ATCAAGAAGTGCTTGTGTCAGGCGCCTCTGTTGAGCAGTAGTTATGTTTGTATACTTTTATATCTAGCTTAAATCTCAGTTTGATCGCAAG
TCTGAAGTGAGGCCTGGTTTCTCCATAATAATGTGTGAGTAGTTCCCAGATAAGGGAATTAGGGTTCCTATAGGGTTTCGCTCATGTGTTG
AGCATATAAGAAACCCTTAGTATGTATTTGTATTTGTAAAATACTTCTATCAATAAAATTTCTAATTCCTAAAACCAAAATCCAGTACTAA
AATCCAGATCCCCCGAATTAATTCGGCGTTAATTCAGTATCGGCGCGCCTTAATTAAGGCGCGCCCTGCA

SEQ ID NO: 244

GCGCACATTTCCCCGAAAAGTGCCACCTGATGCGGTGTGAAATACCGCACAGATGCGTAAGGAGAAAATACCGCATCAGGAAATTGTAAGC
GTTAATATTTTGTTAAAATTCGCGTTAAATTTTTGTTAAATCAGCTCATTTTTTAACCAATAGGCCGAAATCGGCAAAATCCCTTATAAAT
CAAAAGAATAGACCGAGATAGGGTTGAGTGTTGTTCCAGTTTGGAACAAGAGTCCACTATTAAAGAACGTGGACTCCAACGTCAAAGGGCG
AAAAACCGTCTATCAGGGCGATGGCCCACTACGTGAACCATCACCCTAATCAAGTTTTTTGGGGTCGAGGTGCCGTAAAGCACTAAATCGG
AACCCTAAAGGGAGCCCCCGATTTAGAGCTTGACGGGGAAAGCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCCGCCGCGCTTAATGCGCCGCTACAGGGCGCGTCCATTCGCCA
TTCAGGCTGCGCAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAATTGTAATACGACTCACTATAGGGCGAATTGGG
CCCGACGTCGCATGCTCCCGGCCGCCATGGCGGCCGCGGGAATTCGATTGATTGGCGCGCCTTAATTAACGGGCTGGTAAAACAAATATAA
GTATTAATATAAATATAATACAATAGAAGGAAAATAAATAAAATTTCCCTCTGTGCCGTGCAAAAATGCACGGCAATGGGTTGGCCCGCAC
GGCAAAGGCATCGTTGCCGTGTCCACGGCAATGGGTTGGCCCGCACGGCAAAGGCATCGTTGCCGTGTCCACGTCTTTGCCGTGCGCCTTG
GCTCTATCTTTGCCGTGAAGCGTTCTTTGCCGTGTGCCTTTTATTTCTTTGCCGTGGGATGCTGCCTTTGCCGAGCGCTGAGCTGGCGCTT
TGCCGTGCGCGTATTGTTTGCCGTGCTCCCAGAGCTGTACGGCAAAGAATTCATTGCCGTGCACGAGGCACACGGGAAAGAAGTTTC
GCATGGCAAAGGGCGCTGACAGCACACGGCAAAGAGCCCGGCACGGCATTGAGCTTTTTTTCCCGTAATGATAGACGGCATAATATAATGG
ACGCACATGCTGATGTCAGGATGTCACCCACTCATCCTAGTATTTGTGGGACGTGAATTCTTTGTGAGATGGGCAATGGGATGTGAACAAA
ATAAGTTTTGTACTAGTAGATAAACATTTTTACCCATAAACAATTGTTCTGTATTGAATGAAAAATTATTTTGTACTGGATGAAAATCTTC
TGAGTAACTGTGTAAGATTAACATGAATCAAGAGACAAATCCAATGGCTACAAAGTCAACTAATACTTGTTAAAAGTTCCGATACTTAAAA
TTATCAAAACTGATATATAGAATATTGCCCATCTCGCCACCGTGCTAGTTTAACAGACGATGGACGAATATCAGTCTTGTATTGGATAATC
GATGCATGCGAGCTATCGGTCACCTGTCCATGCTTCCAGAAGGAGCCGAGACGTGGCGACTTCGTCCGACGCGCCGACTATCTGCACACGC
CCGGCTTCTCGTCGTGGGCGAGTCAGCAGTCACAGGCTTCCGCCTACCAACTCACACGTAGCGCCCTATCGTGGCGCTTGATCGATGCAA
CAGCGATGCCTATCCCAGCTCCTCAAGCTGCTTATAAGTATGTCCTCGGCCATCACTGCTTACACAACAAACACAGCTACTTATCGCAGTG
TACTAAACAAGACGTACTAGCTAGATTTCGTGAGGTAAAATCAGTGCAATATCACTTGTGCAAGCCATTAGTCTCTTCACCTTGTCCCACC
TGCTCCCGCCCGCATCTCACCAGACACCAGCCATGTGCGGCAGCGCGATCCTCTCCGACATCATCCCGCCGCCGCGCCGGGTCACGGACGGC
CCCCTCTGGCGGAACCAGAAGAAGAAGGGGCCGACGGGAGATGCTCCGGTGGCGAGGCGCCGCCGCGCGCCCGAGGAGGAGGAGAGCTACG
AGGACTTCGAGGCCGACTTCGAGGGCTTCGAGGAGGGGGCTCGGGGAGGCCGAGATCTGGTCCGAGGACGAGGCCAAGCCCTTCTCCGCCGC
CAGGAAACGCGTCGCCGCAGGTATAGCCGCCCTTTTTGGGTCACCGGCTTTGGATCTGTGGAACCGCGTGCTAATTCTGTTTACGATTTGG
GAGATAGATTTGAGTTTCTCAGGTGATCTGCTGCTCGGATTAGATAGTTGCATCTTCGATTTGTTTGCTATGAAGTTAAATCTGTGCAATT
GTTCATCTCAAGTCCGTTAATTCAGCGGGTCCATGTTGTCGATTAGTCTGGTCTCTAGTGCTGTGTCTTTTTTTTAAAAAAACACAATCTC
TGGTGCTGTGTCGATCCTTAGTTTTTAGGATAACTCTCCTAAATCATGAATATGGTATCAACTCTTATTGGTGCATACATAGATCGAGCTT
CCTCGCAAGCATATGAGTTGGGCTGTTCCTCAGGATTAGACTTTTAATGTCAAGTTCGACTTACCCTGACTTTCTGTATGTAAACTAAAA
TCTTTATCTCACTGCTTCATCCTGATTGAATAAATGCATGTACAGCTGCTGCTGTTGATGGCTGGGCATCAGAGTCCGCCAAAAGGAAGAG
AAAGACCCAGTTCAGGGGCATCCGCCGCCGCCCTTGGGGTAAATGGGCTGCTGAAATCAGAGACCCTCGCAAGGGTGTCCGTGTCTGGCTT
GGCACTTACAACTCTGCCGAGGAAGCTGCCAGAGCCTATGATGCTGAAGCAAGAAGGATCCGTGGCAAGAAGGCAAAGGTCAATTTCCCAG
ATGAGGCTCCTGTGGCTTCTCAAAAGCACTGTGCTAAGCCTACCTTTGTGACGTTGCCTGAGTTCAACACCGAAGAGAAGCCGATAGTCAA
CGCCGTGGCCAACACAAACGCGTATTCCTATCCTCTTGTTGACTACACCGTCTGTGAGCCATTTGTGCACCCTCAGAACATGTCATTTGTG
CCAGCGGTTAATGCAGTTGAGGTTCCTTTCATGAATCTTTCCTCTGACCAGGGTAGCAACTCCTTTGGTTGCTCAGACTTTAGCTGGGAGA
ATGGTACCAAGACTCCTGACATCACATCTGTGCTTGCATCCATTCCCACCTCGACCGAGGTTGATGAATCTGCATTCCTTCAGAACAATGC
CAGTGATGCATCACTACCTCCTGTGATGGATACTGCCAATGTTGATCTCGCCGATTTGGAACCATACATGAAGTTCCTCGTGGATGGTGCT
TCAGATGAGTCACTTGACAACTTTCTAAGCTGTGACGGGTCTGAGGACATGGTCAGCAACCTGGACCTTTGGACTTTCGATGACATGCCCA
TTTCTGCCGATTTCTACTGAGGCTCTGAGGTCAATTGGTGCCTGTACGTATAGATAATGGGTAAGCATCTGCAACTGCGGAAATAACTCAC
TGTTATACTTCAGTTTCCATTTCCATAACTACCCCACTTCACTTTTCAGGAATAAGTATTCTGGACATCAAGAAGTGCTTGTGTCAGGCGC
CTCTGTTGAGCAGTAGTTATGTTTGTATACTTTTATATCTAGCTTAAATCTCAGTTTGATCGCAAGTCTGAAGTGAAGGCCTGGTTTCTCC
ATAATAATGTGTGAGTAGTTCCCAGATAAGGGAATTAGGGTTCCTATAGGGTTTCGCTCATGTGTTGAGCATATAAGAAACCCTTAGTATG
TATTTGTATTTGTAAAATACTTCTATCAATAAAATTTCTAATTCCTAAAACCAAAATCCAGTACTAAAATCCAGATCCCCCGAATTAATTC
GGCGTTAATTCAGTATCGGCGCGCCTTAATTAAAATCGAATTTCGACCATATGGGAGAGCTCCCAACGCGTTGGATGCATAGCTTGAGTAT
TCTATAGTGTCACCTAAATAGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTCTATTTCGTTCATCCATAGTTGCCTGACTCCCCG
TCGTGTAGATAACTACGATACGGGAGGGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGCAAAAAAGCGGTTAGCTCCTTCGGTCCTCC
GATCGTTGTCAGAAGTAAGTTGGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCTCTTGCCCGGCGTCAATACGGG
ATAATACCGCGCCACATAGCAGAACTTTAAAAGTGCTCATCATTGGAAAACGTTCTTCGGGGCGAAAACTCTCAAGGATCTTACCGCTGTT
GAGATCCAGTTCGATGTAACCCACTCGTGCACCCAACTGATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCC

SEQ ID NO: 252

GGAATTCGATATCAAGCTTGGCACTGGCCGTCGTTTTACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCCTTCCCAACAGTTGCGCAGCCTGAATGGCGAATGCTAG
AGCAGCTTGAGCTTGGATCAGATTGTCGTTTCCCGCCTTCAGTTTAAACTATCAGTGTTTGACAGGATATATTGGCGGGTAAACCTAAGAG
AAAAGAGCGTTTATTAGAATAACGGATATTTAAAAGGGCGTGAAAAGGTTTATCCGTTCGTCCATTTGTATGTGCATGCCAACCACAGGGT
TCCCCTCGGGATCAAAGTACTTTGATCCAACCCCTCCGCTGCTATAGTGCAGTCGGCTTCTGACGTTCAGTGCAGCCGTCTTCTGAAAACG
ACATGTCGCACAAGTCCTAAGTTACGCGACAGGCTGCCGCCCTGCCCTTTTCCTGGCGTTTTCTTGTCGCGTGTTTTAGTCGCATAAAGTA
GAATACTTGCGACTAGAACCGGAGACATTACGCCATGAACAAGAGCGCCGCCGCTGGCCTGCTGGGCTATGCCCGCGTCAGCACCGACGAC
CAGGACTTGACCAACCAACGGGCCGAACTGCACGCGGCCGGCTGCACCAAGCTGTTTTCCGAGAAGATCACCGGCACCAGGCGCGACCGCC
CGGAGCTGGCCAGGATGCTTGACCACCTACGCCCTGGCGACGTTGTGACAGTGACCAGGCTAGACCGCCTGGCCCGCAGCACCCGCGACCT
ACTGGACATTGCCGAGCGCATCCAGGAGGCCGGCGCGGGCCTGCGTAGCCTGGCAGAGCCGTGGGCCGACACCACCACGCCGGCCGGCCGC
ATGGTGTTGACCGTGTTCGCCGGCATTGCCGAGTTCGAGCGTTCCCTAATCATCGACCGCACCCGGAGCGGGCGCGAGGCCGCCAAGGCCC
GAGGCGTGAAGTTTGGCCCCCGCCCTACCCTCACCCCGGCACAGATCGCGCACGCCCGCGAGCTGATCGACCAGGAAGGCCGCACCGTGAA
AGAGGCGGCTGCACTGCTTGGCGTGCATCGCTCGACCCTGTACCGCGCACTTGAGCGCAGCGAGGAAGTGACGCCCACCGAGGCCAGGCGG
CGCGGTGCCTTCCGTGAGGACGCATTGACCGAGGCCGACGCCCTGGCGGCCGCCGAGAATGAACGCCAAGAGGAACAAGCATGAAACCGCA
CCAGGACGGCCAGGACGAACCGTTTTTCATTACCGAAGAGATCGAGGCGGAGATGATCGCGGCCGGGTACGTGTTCGAGCCGCCCGCGCAC
GTCTCAACCGTGCGGCTGCATGAAATCCTGGCCGGTTTGTCTGATGCCAAGCTGGCGGCCTGGCCGGCCAGCTTGGCCGCTGAAGAAACCG
AGCGCCGCCGTCTAAAAAGGTGATGTGTATTTGAGTAAAACAGCTTGCGTCATGCGGTCGCTGCGTATATGATGCGATGAGTAAATAAACA
AATACGCAAGGGGAACGCATGAAGGTTATCGCTGTACTTAACCAGAAAGGCGGGTCAGGCAAGACGACCATCGCAACCCATCTAGCCCGCG
CCCTGCAACTCGCCGGGGCCGATGTTCTGTTAGTCGATTCCGATCCCCAGGGCAGTGCCCGCGATTGGGCGGCCGTGCGGGAAGATCAACC
GCTAACCGTTGTCGGCATCGACCGCCCGACGATTGACCGCGACGTGAAGGCCATCGGCCGGCGCGACTTCGTAGTGATCGACGGAGCGCCC
CAGGCGGCGGACTTGGCTGTGTCCGCGATCAAGGCAGCCGACTTCGTGCTGATTCCGGTGCAGCCAAGCCCTTACGACATATGGGCCACCG
CCGACCTGGTGGAGCTGGTTAAGCAGCGCATTGAGGTCACGGATGGAAGGCTACAAGCGGCCTTTGTCGTGTCGCGGGCGATCAAAGGCAC
GCGCATCGGCGGTGAGGTTGCCGAGGCGCTGGCCGGGTACGAGCTGCCCATTCTTGAGTCCCGTATCACGCAGCGCGTGAGCTACCCAGGC
ACTGCCGCCGCCGGCACAACCGTTCTTGAATCAGAACCCGAGGGCGACGCTGCCCGCGAGGTCCAGGCGCTGGCCGCTGAAATTAAATCAA
AACTCATTTGAGTTAATGAGGTAAAGAGAAAATGAGCAAAAGCACAAACACGCTAAGTGCCGGCCGTCCGAGCGCACGCAGCAGCAAGGCT
GCAACGTTGGCCAGCCTGGCAGACACGCCAGCCATGAAGCGGGTCAACTTTCAGTTGCCGGCGGAGGATCACACCAAGCTGAAGATGTACG
CGGTACGCCAAGGCAAGACCATTACCGAGCTGCTATCTGAATACATCGCGCAGCTACCAGAGTAAATGAGCAAATGAATAAATGAGTAGAT
GAATTTTAGCGGCTAAAGGAGGCGGCATGGAAAATCAAGAACAACCAGGCACCGACGCCGTGGAATGCCCCATGTGTGGAGGAACGGGCGG
TTGGCCAGGCGTAAGCGGCTGGGTTGTCTGCCGGCCCTGCAATGGCACTGGAACCCCCAAGCCCGAGGAATCGGCGTGACGGTCGCAAACC
ATCCGGCCCGGTACAAATCGGCGCGGCGCTGGGTGATGACCTGGTGGAGAAGTTGAAGGCCGCGCAGGCCGCCCAGCGGCAACGCATCGAG
GCAGAAGCACGCCCCGGTGAATCGTGGCAAGCGGCCGCTGATCGAATCCGCAAAGAATCCCGGCAACCGCCGGCAGCCGGTGCGCCGTCGA
TTAGGAAGCCGCCCAAGGGCGACGAGCAACCAGATTTTTTCGTTCCGATGCTCTATGACGTGGGCACCCGCGATAGTCGCAGCATCATGGA
CGTGGCCGTTTTCCGTCTGTCGAAGCGTGACCGACGAGCTGGCGAGGTGATCCGCTACGAGCTTCCAGACGGGCACGTAGAGGTTTCCGCA
GGGCCGGCCGGCATGGCCAGTGTGTGGGATTACGACCTGGTACTGATGGCGGTTTCCCATCTAACCGAATCCATGAACCGATACCGGGAAG
GGAAGGGAGACAAGCCCGGCCGCGTGTTCCGTCCACACGTTGCGGACGTACTCAAGTTCTGCCGGCGAGCCGATGGCGGAAAGCAGAAAGA
CGACCTGGTAGAAACCTGCATTCGGTTAAACACCACGCACGTTGCCATGCAGCGTACGAAGAAGGCCAAGAACGGCCGCCTGGTGACGGTA
TCCGAGGGTGAAGCCTTGATTAGCCGCTACAAGATCGTAAAGAGCGAAACCGGGCGGCCGGAGTACATCGAGATCGAGCTAGCTGATTGGA
TGTACCGCGAGATCACAGAAGGCAAGAACCCGGACGTGCTGACGGTTCACCCCGATTACTTTTTGATCGATCCCGGCATCGGCCGTTTTCT
CTACCGCCTGGCACGCCGCGCCGCAGGCAAGGCAGAAGCCAGATGGTTGTTCAAGACGATCTACGAACGCAGTGGCAGCGCCGGAGAGTTC
AAGAAGTTCTGTTTCACCGTGCGCAAGCTGATCGGGTCAAATGACCTGCCGGAGTACGATTTGAAGGAGGAGGCGGGGCAGGCTGGCCCGA
TCCTAGTCATGCGCTACCGCAACCTGATCGAGGGCGAAGCATCCGCCGGTTCCTAATGTACGGAGCAGATGCTAGGGCAAATTGCCCTAGC
AGGGGAAAAAAGGTCGAAAAGGTCTCTTTCCTGTGGATAGCACGTACATTGGGAACCCAAAGCCGTACATTGGGAACCGGAACCCGTACATT
GGGAACCCAAAGCCGTACATTGGGAACCGGTCACACATGTAAGTGACTGATATAAAAGAGAAAAAAGGCGATTTTTCCGCCTAAAACTCTT
TAAAACTTATTAAAACTCTTAAAACCCGCCTGGCCTGTGCATAACTGTCTGGCCAGCGCACAGCCGAAGAGCTGCAAAAAGCGCCTACCCT
TCGGTCGCTGCGCTCCCTACGCCCCGCCGCTTCGCGTCGGCCTATCGCGGCCGCTGGCCGCTCAAAAATGGCTGGCCTACGGCCAGGCAAT
CTACCAGGGCGCGGACAAGCCGCGCCGTCGCCACTCGACCGCCGGCGCCCACATCAAGGCACCCTGCCTCGCGCGTTTCGGTGATGACGGT
GAAAACCTCTGACACATGCAGCTCCCGGAGACGGTCACAGCTTGTCTGTAAGCGGATGCCGGGAGCAGACAAGCCCGTCAGGGCGCGTCAG
CGGGTGTTGGCGGGTGTCGGGGCGCAGCCATGACCCAGTCACGTAGCGATAGCGGAGTGTATACTGGCTTAACTATGCGGCATCAGAGCAG
ATTGTACTGAGAGTGCACCATATGCGGTGTGAAATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAAAACTCACGTTAAGGGA
TTTTGGTCATGCATTCTAGGTACTAAAACAATTCATCCAGTAAAATATAATATTTTATTTTCTCCCAATCAGGCTTGATCCCCAGTAAGTC
AAAAAATAGCTCGACATACTGTTCTTCCCCGATATCCTCCCTGATCGACCGGACGCAGAAGGCAATGTCATACCACTTGTCCGCCCTGCCG
CTTCTCCCAAGATCAATAAAGCCACTTACTTTGCCATCTTTCACAAAGATGTTGCTGTCTCCCAGGTCGCCGTGGGAAAAGACAAGTTCCT
CTTCGGGCTTTTCCGTCTTTAAAAAATCATACAGCTCGCGCGGATCTTTAAATGGAGTGTCTTCTTCCCAGTTTTCGCAATCCACATCGGC
CAGATCGTTATTCAGTAAGTAATCCAATTCGGCTAAGCGGCTGTCTAAGCTATTCGTATAGGGACAATCCGATATGTCGATGGAGTGAAAG
AGCCTGATGCACTCCGCATACAGCTCGATAATCTTTTCAGGGCTTTGTTCATCTTCATACTCTTCCGAGCAAAGGACGCCATCGGCCTCAC
TCATGAGCAGATTGCTCCAGCCATCATGCCGTTCAAAGTGCAGGACCTTTGGAACAGGCAGCTTTCCTTCCAGCCATAGCATCATGTCCTT
TTCCCGTTCCACATCATAGGTGGTCCCTTTATACCGGCTGTCCGTCATTTTTAAATATAGGTTTTCATTTTCTCCCACCAGCTTATATACC
TTAGCAGGAGACATTCCTTCCGTATCTTTTACGCAGCGGTATTTTTCGATCAGTTTTTTCAATTCCGGTGATATTCTCATTTTAGCCATTT
ATTATTTCCTTCCTCTTTTCTACAGTATTTAAAGATACCCCAAGAAGCTAATTATAACAAGACGAACTCCAATTCACTGTTCCTTGCATTC
TAAAACCTTAAATACCAGAAAACAGCTTTTTCAAAGTTGTTTTCAAAGTTGGCGTATAACATAGTATCGACGGAGCCGATTTTGAAACCGC
GGTGATCACAGGCAGCAACGCTCTGTCATCGTTACAATCAACATGCTACCCTCCGCGAGATCATCCGTGTTTCAAACCCGGCAGCTTAGTT
GCCGTTCTTCCGAATAGCATCGGTAACATGAGCAAAGTCTGCCGCCTTACAACGGCTCTCCCGCTGACGCCGTCCCGGACTGATGGGCTGC

FIGURE 7-1

CTGTATCGAGTGGTGATTTTGTGCCGAGCTGCCGGTCGGGGAGCTGTTGGCTGGCTGGTGGCAGGATATATTGTGGTGTAAACAAATTGAC
GCTTAGACAACTTAATAACACATTGCGGACGTTTTTAATGTACTGAATTAACGCCGAATTAATTCGGGGGATCTGGATTTTAGTACTGGAT
TTTGGTTTTAGGAATTAGAAATTTTATTGATAGAAGTATTTTACAAATACAAATACATACTAAGGGTTTCTTATATGCTCAACACATGAGC
GAAACCCTATAGGAACCCTAATTCCCTTATCTGGGAACTACTCACACATTATTATGGAGAAACTCGAGCTTGTCGATCGACAGATCCGGTC
GGCATCTACTCTATTTCTTTGCCCTCGGACGAGTGCTGGGGCGTCGGTTTCCACTATCGGCGAGTACTTCTACACAGCCATCGGTCCAGAC
GGCCGCGCTTCTGCGGGCGATTTGTGTACGCCCGACAGTCCCGGCTCCGGATCGGACGATTGCGTCGCATCGACCCTGCGCCCAAGCTGCA
TCATCGAAATTGCCGTCAACCAAGCTCTGATAGAGTTGGTCAAGACCAATGCGGAGCATATACGCCCGGAGTCGTGGCGATCCTGCAAGCT
CCGGATGCCTCCGCTCGAAGTAGCGCGTCTGCTGCTCCATACAAGCCAACCACGGCCTCCAGAAGAAGATGTTGGCGACCTCGTATTGGGA
ATCCCCGAACATCGCCTCGCTCCAGTCAATGACCGCTGTTATGCGGCCATTGTCCGTCAGGACATTGTTGGAGCCGAAATCCGCGTGCACG
AGGTGCCGGACTTCGGGGCAGTCCTCGGCCCAAAGCATCAGCTCATCGAGAGCCTGCGCGACGGACGCACTGACGGTGTCGTCCATCACAG
TTTGCCAGTGATACACATGGGGATCAGCAATCGCGCATATGAAATCACGCCATGTAGTGTATTGACCGATTCCTTGCGGTCCGAATGGGCC
GAACCCGCTCGTCTGGCTAAGATCGGCCGCAGCGATCGCATCCATAGCCTCCGCGACCGGTTGTAGAACAGCGGGCAGTTCGGTTTCAGGC
AGGTCTTGCAACGTGACACCCTGTGCACGGCGGGAGATGCAATAGGTCAGGCTCTCGCTAAACTCCCCAATGTCAAGCACTTCCGGAATCG
GGAGCGCGGCCGATGCAAAGTGCCGATAAACATAACGATCTTTGTAGAAACCATCGGCGCAGCTATTTACCCGCAGGACATATCCACGCCC
TCCTACATCGAAGCTGAAAGCACGAGATTCTTCGCCCTCCGAGAGCTGCATCAGGTCGGAGACGCTGTCGAACTTTTCGATCAGAAACTTC
TCGACAGACGTCGCGGTGAGTTCAGGCTTTTTCATATCTCATTGCCCCCCGGATCTGCGAAAGCTCGAGAGAGATAGATTTGTAGAGAGA
GACTGGTGATTTCAGCGTGTCCTCTCCAAATGAAATGAACTTCCTTATATAGAGGAAGGTCTTGCGAAGGATAGTGGGATTGTGCGTCATC
CCTTACGTCAGTGGAGATATCACATCAATCCACTTGCTTTGAAGACGTGGTTGGAACGTCTTCTTTTTCCACGATGCTCCTCGTGGGTGGG
GGTCCATCTTTGGGACCACTGTCGGCAGAGGCATCTTGAACGATAGCCTTTCCTTTATCGCAATGATGGCATTTGTAGGTGCCACCTTCCT
TTTCTACTGTCCTTTTGATGAAGTGACAGATAGCTGGGCAATGGAATCCGAGGAGGTTTCCCGATATTACCCTTTGTTGAAAAGTCTCAAT
AGCCCTTTGGTCTTCTGAGACTGTATCTTTGATATTCTTGGAGTAGACGAGAGTGTCGTGCTCCACCATGTTATCACATCAATCCACTTGC
TTTGAAGACGTGGTTGGAACGTCTTCTTTTTCCACGATGCTCCTCGTGGGTGGGGGTCCATCTTTGGGACCACTGTCGGCAGAGGCATCTT
GAACGATAGCCTTTCCTTTATCGCAATGATGGCATTTGTAGGTGCCACCTTCCTTTTCTACTGTCCTTTTGATGAAGTGACAGATAGCTGG
GCAATGGAATCCGAGGAGGTTTCCCGATATTACCCTTTGTTGAAAAGTCTCAATAGCCCTTTGGTCTTCTGAGACTGTATCTTTGATATTC
TTGGAGTAGACGAGAGTGTCGTGCTCCACCATGTTGGCAAGCTGCTCTAGCCAATACGCAAACCGCCTCTCCCCGCGCGTTGGCCGATTCA
TTAATGCAGCTGGCACGACAGGTTTCCCGACTGGAAAGCGGGCAGTGAGCGCAACGCAATTAATGTGAGTTAGCTCACTCATTAGGCACCC
CAGGCTTTACACTTTATGCTTCCGGCTCGTATGTTGTGTGGAATTGTGAGCGGATAACAATTTCACACAGGAAACAGCTATGACCATGATT
ACGAATTCCCTTAATTAATAAGAGCAGCTTGCCAACATGGTGGAGCACGACACTCTCGTCTACTCCAAGAATATCAAAGATACAGTCTCAG
AAGACCAAAGGCTATTGAGACTTTTCAACAAAGGGTAATATCGGGAAACCTCCTCGGATTCCATTGCCCAGCTATCTGTCACTTCATCAA
AAGGACAGTAGAAAAGGAAGGTGGCACCTACAAATGCCATCATTGCGATAAAGGAAAGGCTATCGTTCAAGATGCCTCTGCCGACAGTGGT
CCCAAAGATGGACCCCCACCCACGAGGAGCATCGTGGAAAAAGAAGACGTTCCAACCACGTCTTCAAAGCAAGTGGATTGATGTGAACATG
GTGGAGCACGACACTCTCGTCTACTCCAAGAATATCAAAGATACAGTCTCAGAAGGCCAAAGGGCTATTGAGACTTTTCAACAAAGGGTAA
TATCGGGAAACCTCCTCGGATTCCATTGCCCAGCTATCTGTCACTTCATCAAAAGGACAGTAGAAAAGGAAGGTGGCACCTACAAATGCCA
TCATTGCGATAAAGGAAAGGCTATCGTTCAAGATGCTCTGCCGACAGTGGTCCCAAAGATGGACCCCCACCCACGAGGAGCATCGTGGAAA
AAGAAGACGTTCCAACCACGTCTTCAAAGCAAGTGGATTGATGTGATATCTCCACTGACGTAAGGGATGACGCACAATCCCACTATCCTTC
GCAAGACCCTTCCTCTATATAAGGAAGTTCATTTCATTTGGAGAGGACACGCTGAAATCACCAGTCTCTCTCTACAAATCTATCTCTCTCC
ATTAGTTGTTGCTTTCCTGTGCCATCGACTGGCATGGCTCGGAAATGCTCCAGCTGCGGGCATAATGGCCATAACTCCAGGACCTGCAGTG
GCAACAACGGCGGCGGTGGTGCCGGTGGTGGGCTGAGGCTGTTCGGTGTGCAGCTGCAAGTTGGTGCTGCACCTCTGAAGAAGAGCTTCAG
CATGGAGTGCCTCTCGTCGTCGGCCTACTACGCGGCCGCAGCGGTGGCCGCGTCCAACTCGTCGTCGTCCGTGTCATCGTCATCGTCGCTG
GTCTCGGTGGAGGAGAACGCCGAGAAGATGGGCCACGGCTACCTCTCCGATGGTCTCATGGGCAGGGCTCAGGAGAGGAAGAAGGGTGAGT
TCGTGTACTGGTTTCTTGAGCAGTTCGTTGCTCCGGTATACCTCGCTGACACGCTTGATTTGCTATGCTATGGATTTTGGATATTAATCAT
ATTATAGTATGTGATAGCGATCTAACCATCATGCATGATGTCTAAGGCCAGATTAAGAAAACTATTCTGAAATTTTTTTTCCCCCTAGCTA
GAGACTAAAGATCTGAAGATTCTTGTTGATGCATGAGTGGTTGTATCACTTGTTTGTATCCAATTGTGCCATCAGTTGCTATCTGCTATGC
CAAACTTGCAACTAGATAACAGGAAATACTTAGTCTTTCAGGTCTTAACTTTCAGTAATCATGTCTAATAGCTTGCACGAATCAGTTTGTT
CTCTCTTCTTCACCTGAAGATGTCCAGTTACGTTGGGTGAACTAATCGTGTGACGCATGGCATCAGGGGTTCCATGGACGGAGGATGAGCA
CCGGAGGTTCCTGGCCGGCTTAGAGAAGCTCGGGAAAGGCGACTGGCGAGGCATCTCCCGGCACTTCGTCGCCACACGCACCCCGACGCAG
CTGGCCAGCCACGCCCAGAAGTACTTCCTCCGGCAGGCCGGCCTCGCGCAGAAGAAGCGGAGGTCCAGCCTCTTCGACGTGGTACGTGCAC
GCCTCAAAACGCAAGCTGGAGTTGTGGACGTAGTAACAAACCAGCTGACATGCACGAACCTTCCTCTCTTTTCTTCAGGCCGAGAAGAATG
GCGACAAGGCGGCGAAGGAGAGTCGTCCGAGACTGAAACACGAGACTAGCAGCTCCGTGGACGGGATGGCAATTCGGTCATTCCCTGCTCT
GTCTCTAGGACCCAGCAGGCCGAGGCCCGACGCCGCCGTGCTTCCACCATGCCTGACCTTGATGCCGAGCTATTCGTCTGGCCTGGTTTCT
CCATAATAATGTGTGAGTAGTTCCCAGATAAGGGAATTAGGGTTCCTATAGGGTTTCGCTCATGTGTTGAGCATATAAGAAACCCTTAGTA
TGTATTTGTATTTGTAAAATACTTCTATCAATAAAATTTCTAATTCCTAAAACCAAAATCCAGTACTAAAATCCAGATCCCCCGAATTAAT
TCGGCGTTAATTCAGTATCGGCGCGCCTTAATTAAGGCGCGCCCTGCA

SEQ ID NO: 245

FIGURE 7-2

GCGCACATTTCCCCGAAAAGTGCCACCTGATGCGGTGTGAAATACCGCACAGATGCGTAAGGAGAAAATACCGCATCAGGAAATTGTAAGC
GTTAATATTTTGTTAAAATTCGCGTTAAATTTTTGTTAAATCAGCTCATTTTTTAACCAATAGGCCGAAATCGGCAAAATCCCTTATAAAT
CAAAAGAATAGACCGAGATAGGGTTGAGTGTTGTTCCAGTTTGGAACAAGAGTCCACTATTAAAGAACGTGGACTCCAACGTCAAAGGGCG
AAAAACCGTCTATCAGGGCGATGGCCCACTACGTGAACCATCACCCTAATCAAGTTTTTTGGGGTCGAGGTGCCGTAAAGCACTAAATCGG
AACCCTAAAGGGAGCCCCCGATTTAGAGCTTGACGGGGAAAGCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCCGCCGCGCTTAATGCGCCGCTACAGGGCGCGTCCATTCGCCA
TTCAGGCTGCGCAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAATTGTAATACGACTCACTATAGGGCGAATTGGG
CCCGACGTCGCATGCTCCCGGCCGCCATGGCGGCCGCGGGAATTCGATTGATTGGCGCGCCTTAATTAACGGCTGGTAAAACAAATATAA
GTATTAATATAAATATAATACAATAGAAGGAAAATAAATAAAATTTCCCTCTGTGCCGTGCAAAAATGCACGGCAATGGGTTGGCCCGCAC
GGCAAAGGCATCGTTGCCGTGTCCACGGCAATGGGTTGGCCCGCACGGCAAAGGCATCGTTGCCGTGTCCACGTCTTTGCCGTGCGCCTTG
GCTCTATCTTTGCCGTGAAGCGTTCTTTGCCGTGTGCCTTTTATTTCTTTGCCGTGGGATGCTGCCTTTGCCGAGCGCTGAGCTGGCGCTT
TGCCGTGCGCGTATTGTTTGCCGTGCGTCCTCCCAGAGCTGTACGGCAAAGAATTCATTGCCGTGCACGAGGCACACGGGAAAGAAGTTTC
GCATGGCAAAGGGCGCTGACAGCACACGGCAAAGAGCCCGGCACGGCATTGAGCTTTTTTTCCCGTAATGATAGACGGCATAATATAATGG
ACGCACATGCTGATGTCAGGATGTCACCCACTCATCCTAGTATTTGTGGGACGTGAATTCTTTGTGAGATGGGCAATGGGATGTGAACAAA
ATAAGTTTTGTACTAGTAGATAAACATTTTTACCCATAAACAATTGTTCTGTATTGAATGAAAAATTATTTTGTACTGGATGAAAATCTTC
TGAGTAACTGTGTAAGATTAACATGAATCAAGAGACAAATCCAATGGCTACAAAGTCAACTAATACTTGTTAAAAGTTCCGATACTTAAAA
TTATCAAAACTGATATATAGAATATTGCCCATCTCGCCACCGTGCTAGTTTAACAGACGATGGACGAATATCAGTCTTGTATTGGATAATC
GATGCATGCGAGCTATCGGTCACCTGTCCATGCTTCCAGAAGGAGCCGAGACGTGGCGACTTCGTCCGACGCGCCGACTATCTGCACACGC
CCGGCTTCTCGTCGTGGGCGAGTCAGCAGTCACAGGCTTTCCGCCTACCAACTCACACGTAGCGCCCTATCGTGGCGCTTGATCGATGCAA
CAGCGATGCCTATCCCAGCTCCTCAAGCTGCTTATAAGTATGTCCTCGGCCATCACTGCTTACACAACAAACACAGCTACTTATCGCAGTG
TACTAAACAAGACGTACTAGCTAGATTTCGTGAGGTAAAATCAGTGCAATATCACTTGTGCAAGCCATTAGT*TTGTTGCTTTCCTGTGCCA*
*TCGACTGGCATGGCTCGGAAATGCTCCAGCTGCGGGCATAATGGCCATAACTCCAGGACCTGCAGTGGCAACAACGGCGGCGGTGGTGCCG*
*GTGGTGGGCTGAGGCTGTTCGGTGTGCAGCTGCAAGTTGGTGCTGCACCTCTGAAGAAGAGCTTCAGCATGGAGTGCCTCTCGTCGTCGGC*
*CTACTACGCGGCCGCAGCGGTGGCCGCGTCCAACTCGTCGTCGTCCGTGTCATCGTCATCGTCGCTGGTCTCGGTGGAGGAGAACGCCGAG*
*AAGATGGGCCACGGCTACCTCTCCGATGGTCTCATGGGCAGGGCTCAGGAGAGGAAGAAGGGTGAGTTCGTGTACTGGTTTCTTGAGCAGT*
*TCGTTGGTCCGGTATACCTCGCTGACACGCTTGATTTGCTATGCTATGGATTTTGGATATTAATCATATTATAGTATGTGATAGCGATCTA*
*ACCATCATGCATGATGTCTAAGGCCAGATTAAGAAAACTATTCTGAAATTTTTTTTCCCCCTAGCTAGAGACTAAAGATCTGAAGATTCTT*
*GTTGATGCATGAGTGGTTGTATGACTTGTTTGTATCCAATTGTGCCATCAGTTGCTATCTGCTATGCCAGACTTGCAACTAGATAACAGGA*
*AATACTTAGTCTTTCAGGTCCTTAACTTTCAGTAATCATGTCTAATAGCTTGCACGAATCAGTTTGTTCTTTTTTTTTTTCACCTGAAGATG*
*TCCAGTTACGTTGGGTGAACTAATTCGTGTGACGCATGGCATCAGGGGTTCCATGGACGGAGGATGAGCACCGGAGGTTCCTGGCCGGCTT*
*AGAGAAGCTCGGGAAAGGCGACTGGCGAGGCATCTCCCGGCACTTCGTCGCGACACGCACCCCGACGCAGGTGGCCAGCCACGCCCAGAAG*
*TACTTCCTCCGGCAGGCCGGCCTCGCGCAGAAGAAGCGGAGGTCCAGCCTCTTCGACGTGGTACGTGCACGCCTCAAAACGCAAGCTGGAG*
*TTGTGGACGTAGTAACAAACCAGCTGACATGCACGAACCTTCCTCTCTTTTCTTCAGGCCGAGAAGAATGGCGACAAGGCGGCGAAGGAGA*
*GTCGTCCGAGACTGAAACACGAGACTAGCAGCTCCGTGGACGGGATGGCAATTCGGTCATTCCCTGCTCTGTCTCTAGGACCCAGCAGGCC*
*GAGGCCCGACGCCGCCGTGCTTCCACCATGCCTGACCTTGATGCCGAGCTATTCGTC*AGGCCTGGTTTCTCCATAATAATGTGTGAGTAGT
TCCCAGATAAGGGAATTAGGGTTCCTATAGGGTTTCGCTCATGTGTTGAGCATATAAGAAACCCTTAGTATGTATTTGTATTTGTAAAATA
CTTCTATCAATAAAATTTCTAATTCCTAAAACCAAAATCCAGTACTAAAATCCAGATCCCCCGAATTAATTCGGCGTTAATTCAGTATCGG
CGCGCCTTAATTAAAATCGAATTTCGACCATATGGAGAGCTCCCAACGCGTTGGATGCATAGCTTGAGTATTCTATAGTGTCACCTAAAT
AGCTTGGCGTAATCATGGTCATAGCTGTTTCCTGTGTGAAATTGTTATCCGCTCACAATTCCACACAACATACGAGCCGGAAGCATAAAGT
GTAAAGCCTGGGGTGCCTAATGAGTGAGCTAACTCACATTAATTGCGTTGCGCTCACTGCCCGCTTTCCAGTCGGGAAACCTGTCGTGCCA
GCTGCATTAATGAATCGGCCAACGCGCGGGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCCTTATCCGGTAACTATCGTCT

FIGURE 9-1

TGAGTCCAACCCGGTAAGACACGACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGAACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTACGCGCAGAAAAAAAGG
ATCTCAAGAAGATCCTTTGATCTTTTCTACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCATGCCATCCGTAAGATGCTTTTCTGTGACTGGTG
AGTACTCAACCAAGTCATTCTGAGAATAGTGTATGCGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGCAAAAACAGGAAGGCAAAATGCCGCAAAAA
AGGGAATAAGGGCGACACGGAAATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCC

SEQ ID NO: 253

FIGURE 9-2

| | | |
|---|---|---|
| AAU06308.1 | QPQQKMVGMAKGLIDWKPQNEGGGAAGVFSQANGNLLMAPLCGISSYGQK | 279 |
| CAJ30880.1 | Q---KSPCYQKLLFDWNRSSNGGLLG--LGSNYGDRLMSFPSGIAANGIK | 201 |
| AAL78742.1 | SAAATSKLHIQWNQTRNETITGFGSGNMFVSDPYNYMNSNEVGLQGRSPF | 273 |
| AAK91884.1 | WP--IADYVTEAFDTGMLSLPGSVTNCTTDAIEGPSAVNPEKFPLVAALG | 237 |
| CB288054.1 | SPKTFSETGSGDGFPVVPAFPMPINPVVVPVPIQNPMENLTLGQND---- | 233 |
| AAO45178.1 | PPPPPSEPRDAGGFSMVPNFARTVGPAVLPVHIENPMENLALRQANPENS | 232 |
| CF207250.1 | -----TSQTGETDNASSVPSLNLSLNMEFEP------------------- | 221 |
| CF838179.1 | -----SPLARESDNTSSQPSLNLSLSTEFEPMEAVCKETEKDSEEPVIDL | 240 |
| CK281819.1 | HLAPSATKAIETDFADSLPSLDLSLKSDFESMETTPSEPVEEAKPNTTTN | 261 |
| AAS00082.1 | KSYLPSLELSLNNTTEAEEVVATAPRQEKSQEAIEPSNGVSPMLVPGGFF | 260 |
| CD822885.1 | -------------------------------------------------- | 184 |
| CF438607.1 | -------------------------------------------------- | 172 |
| BE130418.1 | PLPPAPALDEECESMASSNSNEVGPTLPKPETSQSCYPSDTPQTIIPLIS | 240 |
| AAO47338.1 | LPPAVEEEVESMESDTSAVAESSGASALMPESLQPTYPMIVPAYFSPFLQ | 231 |
| CF687220.1 | -------------------------------------------------- | 151 |
| ORF66 | RSFPALSLGPSRPRPDAAVLPPCLTLMPSYS------------------- | 234 |
| BJ258031.1 | -------------------------------------------------- | 200 |
| BAD72233.1 | PALSLGISSMAQPEAMLLPPPSLTLTPSCSSPAVSSSSSEQPRTIHPSLM | 287 |
| CD225878.1 | -------------------------------------------------- | 205 |
| CA132547.1 | HGA----------------------------------------------- | 208 |
| AJ615010.1 | -------------------------------------------------- | 218 |
| CAC24845.1 | SPNMASIDLNSTQEDNLAGFPLWSASGASPRAPFPAVLMEQPPHGHGHGH | 241 |
| BG127541.1 | KFIWRKV------------------------------------------- | 217 |
| BQ120809.2 | IALTTKDTLIX--------------------------------------- | 218 |
| BM520331.1 | -------------------------------------------------- | 178 |
| AW570097.1 | -------------------------------------------------- | 144 |
| CO077451.1 | CSDSQTNVAPDLELTLAASRPALEENKSSPTTTTLLIRPHYVT------- | 248 |
| AJ502953.1 | -------------------------------------------------- | 180 |
| BP850240.1 | -------------------------------------------------- | 153 |
| CAD12767.2 | PFTQHNQDDVQSFLHMSSTFSNLVVSTLLQNPAAHVAASFAATFWPYANP | 400 |

FIGURE 10-6

| | | |
|---|---|---|
| AAU06308.1 | LQEQNLLRGTLPGYQFAPYNLIFQMQPMQRQ------------------- | 310 |
| CAI30880.1 | NEQDQELNSAYYGTYSKPHKSIFQFEPSRYQIYG---------------- | 295 |
| AAL78742.1 | GSRNMVFRMHPCFSYPSA-------------------------------- | 281 |
| AAK91894.1 | SELNSSFPGVDEFLQSVEDLIIVPAEGTSGVCHGVDTRTSPSLSVQPSVT | 287 |
| CB289054.1 | VNTRLVRPIPVXXXPPESTDLNLNX------------------------- | 256 |
| AAO45178.1 | TSAKLVHPVALHSAPHATAISDLNLNSTTDASTLTLNLSLSMDSREPSSR | 282 |
| CF207250.1 | -------------------------------------------------- | 221 |
| CF838179.1 | NE------------------------------------------------ | 242 |
| CK281819.1 | EIPSVFPAFLPAY------------------------------------- | 274 |
| AAS09882.1 | PPCFPVTYTIWLPASLHGTEHALNAETSSQQHQVLKPKPGFAKERVNMDE | 330 |
| CD822985.1 | -------------------------------------------------- | 194 |
| CF436607.1 | -------------------------------------------------- | 172 |
| BE130416.1 | NYV----------------------------------------------- | 243 |
| AAO47339.1 | FSVPFWPNQEDGGDLPQETHEIVKPVAVHSQNPINVDELVGMSKLSIWEH | 281 |
| CF667220.1 | -------------------------------------------------- | 151 |
| ORF68 | -------------------------------------------------- | 234 |
| BJ259031.1 | -------------------------------------------------- | 200 |
| BAD72233.1 | VAKPQVQLQLQPPDLELKISTVRQNDQPSSSPRTPFLGTIRVT------- | 310 |
| CD225976.1 | -------------------------------------------------- | 205 |
| CA132547.1 | -------------------------------------------------- | 208 |
| AJ815010.1 | -------------------------------------------------- | 218 |
| CAC24845.1 | HCSPLDVELSMSLSPPSIGT------------------------------ | 281 |
| BG127541.1 | -------------------------------------------------- | 217 |
| BQ128809.2 | -------------------------------------------------- | 218 |
| BM520331.1 | -------------------------------------------------- | 178 |
| AW570097.1 | -------------------------------------------------- | 144 |
| CO077451.1 | -------------------------------------------------- | 248 |
| AJ502953.1 | -------------------------------------------------- | 190 |
| BP850240.1 | -------------------------------------------------- | 153 |
| CAD12787.2 | ETSADSPRCSQGGFTSRQIGSPPSVAAIAAATVAAATAWWAAHGLLPLCL | 450 |

FIGURE 10-7

| | | |
|---|---|---|
| AAU06308.1 | -------------------------------------------------- | 310 |
| CAI30880.1 | -------------------------------------------------- | 295 |
| AAL78742.1 | -------------------------------------------------- | 291 |
| AAK91894.1 | GGTGMYTHPVSFPDVHEFLQEVEDLITVPAEGTSGACHGIDTRTSPSLSL | 337 |
| CB289054.1 | -------------------------------------------------- | 258 |
| AAO45178.1 | HSAFETMQGFSNGDSMISVA------------------------------ | 302 |
| CF207250.1 | -------------------------------------------------- | 221 |
| CF638179.1 | -------------------------------------------------- | 242 |
| CK281818.1 | -------------------------------------------------- | 274 |
| AAS09882.1 | LVGMSQLSIGMATRHETETSPSPLSLRLEPSRPSAFHSNGSVNGADLSKG | 380 |
| CD822965.1 | -------------------------------------------------- | 194 |
| CF438807.1 | -------------------------------------------------- | 172 |
| BE130418.1 | -------------------------------------------------- | 243 |
| AAO47338.1 | GQETVVYTSLSLNLLGGQNRQSAFHANPQTRAQA---------------- | 314 |
| CF687220.1 | -------------------------------------------------- | 151 |
| ORF06 | -------------------------------------------------- | 234 |
| BJ259031.1 | -------------------------------------------------- | 200 |
| BAD72233.1 | -------------------------------------------------- | 310 |
| CD225976.1 | -------------------------------------------------- | 205 |
| CA132547.1 | -------------------------------------------------- | 208 |
| AJ815010.1 | -------------------------------------------------- | 216 |
| CAC24846.1 | -------------------------------------------------- | 281 |
| BG127541.1 | -------------------------------------------------- | 217 |
| BQ120809.2 | -------------------------------------------------- | 218 |
| BM520331.1 | -------------------------------------------------- | 178 |
| AW570097.1 | -------------------------------------------------- | 144 |
| CD077451.1 | -------------------------------------------------- | 248 |
| AJ502953.1 | -------------------------------------------------- | 180 |
| BP950240.1 | -------------------------------------------------- | 153 |
| CAD12787.2 | PLHAAFACPPASVTAVPSMNPPVQDQKHPEYSEAPQAQHSDSKSLAVISS | 500 |

FIGURE 10-8

| | | |
|---|---|---|
| AAU08308.1 | -------------------------------------------------- | 310 |
| CAI30890.1 | -------------------------------------------------- | 295 |
| AAL78742.1 | -------------------------------------------------- | 281 |
| AAK91894.1 | QSSVAGGTRMYTHSVTVPAEGTSGVRCGIDTRTSPSLSLQPSVAGGTRMY | 387 |
| CB289054.1 | -------------------------------------------------- | 258 |
| AAO45178.1 | -------------------------------------------------- | 302 |
| CF207250.1 | -------------------------------------------------- | 221 |
| CF838179.1 | -------------------------------------------------- | 242 |
| CK281819.1 | -------------------------------------------------- | 274 |
| AAS08982.1 | NSAIQAI------------------------------------------- | 387 |
| CD822986.1 | -------------------------------------------------- | 184 |
| CF438807.1 | -------------------------------------------------- | 172 |
| BE130418.1 | -------------------------------------------------- | 243 |
| AAO47338.1 | -------------------------------------------------- | 314 |
| CF667220.1 | -------------------------------------------------- | 151 |
| ORF86 | -------------------------------------------------- | 234 |
| BJ258031.1 | -------------------------------------------------- | 200 |
| BAD72233.1 | -------------------------------------------------- | 310 |
| CD225976.1 | -------------------------------------------------- | 205 |
| CA132547.1 | -------------------------------------------------- | 208 |
| AJ615010.1 | -------------------------------------------------- | 218 |
| CAC24845.1 | -------------------------------------------------- | 281 |
| BG127541.1 | -------------------------------------------------- | 217 |
| BQ120809.2 | -------------------------------------------------- | 218 |
| BM520331.1 | -------------------------------------------------- | 178 |
| AW570097.1 | -------------------------------------------------- | 144 |
| CO077451.1 | -------------------------------------------------- | 248 |
| AJ502853.1 | -------------------------------------------------- | 190 |
| BP850240.1 | -------------------------------------------------- | 153 |
| CAD12767.2 | DSETGNAKLNTSPKATDHYTNETISEHLDSDKTKGRKQVDRSSCGSNTAS | 550 |

FIGURE 10-9

```
AAU08309.1    --------------------------------------------------    310
CAI30880.1    --------------------------------------------------    285
AAL78742.1    --------------------------------------------------    281
AAK81884.1    PHPVNVLAEGTSGASHGVDTRTSPSLSLQPSVAGGSRIYPHPVNVPAEGI    437
CB288054.1    --------------------------------------------------    258
AAO45178.1    --------------------------------------------------    302
CF207250.1    --------------------------------------------------    221
CF838179.1    --------------------------------------------------    242
CK281818.1    --------------------------------------------------    274
AAS08882.1    --------------------------------------------------    387
CD822985.1    --------------------------------------------------    184
CF438807.1    --------------------------------------------------    172
BE1304188.1   --------------------------------------------------    243
AAO47339.1    --------------------------------------------------    314
CF087220.1    --------------------------------------------------    151
ORF88         --------------------------------------------------    234
BJ258031.1    --------------------------------------------------    200
BAD72233.1    --------------------------------------------------    310
CD225878.1    --------------------------------------------------    205
CA132547.1    --------------------------------------------------    208
AJ815010.1    --------------------------------------------------    218
CAC24845.1    --------------------------------------------------    261
BG127541.1    --------------------------------------------------    217
BQ120808.2    --------------------------------------------------    218
BM520331.1    --------------------------------------------------    178
AW570097.1    --------------------------------------------------    144
CO077451.1    --------------------------------------------------    248
AJ502853.1    --------------------------------------------------    180
BP950240.1    --------------------------------------------------    153
CAD12787.2    SSDVETDALGKDEKGKEEPETPDANNLAIEFSNRRRSIYNLTDSWKEVSS    800
```

FIGURE 10-10

```
AAU08308.1    --------------------------------------------------   310
CAI30880.1    --------------------------------------------------   285
AAL78742.1    --------------------------------------------------   291
AAK91864.1    SGVSHGVDTRTSPSLSLQPSVGGGTGMYTHPVTVRVEGTSGARRGVDTRT   467
CB280054.1    --------------------------------------------------   258
AAO45178.1    --------------------------------------------------   302
CF207250.1    --------------------------------------------------   221
CF838179.1    --------------------------------------------------   242
CK281819.1    --------------------------------------------------   274
AAS09882.1    --------------------------------------------------   387
CD822985.1    --------------------------------------------------   184
CF436807.1    --------------------------------------------------   172
BE130418.1    --------------------------------------------------   243
AAO47339.1    --------------------------------------------------   314
CF887220.1    --------------------------------------------------   151
ORF88         --------------------------------------------------   234
BJ258031.1    --------------------------------------------------   200
BAD72233.1    --------------------------------------------------   310
CD225876.1    --------------------------------------------------   205
CA132547.1    --------------------------------------------------   208
AJ815010.1    --------------------------------------------------   218
CAC24846.1    --------------------------------------------------   281
BG127541.1    --------------------------------------------------   217
BQ120808.2    --------------------------------------------------   218
BM520331.1    --------------------------------------------------   178
AW570097.1    --------------------------------------------------   144
CO077451.1    --------------------------------------------------   248
AJ502863.1    --------------------------------------------------   180
BP850240.1    --------------------------------------------------   153
CAD12787.2    EGRLAFQALFSREVLPQSFSPPHALKNKDQMDITNDYKQNIADRNEDLDS   850
```

FIGURE 10-11

```
AAU06308.1    --------------------------------------------------    310
CAI30880.1    --------------------------------------------------    285
AAL78742.1    --------------------------------------------------    291
AAK91884.1    SPSLSLQPSVVGGIGMYTHPIIYPAEGTSGTRRGVDTRTSPSLSFQPSVG    537
CB289054.1    --------------------------------------------------    256
AAO45178.1    --------------------------------------------------    302
CF207250.1    --------------------------------------------------    221
CF838179.1    --------------------------------------------------    242
CK281819.1    --------------------------------------------------    274
AAS09882.1    --------------------------------------------------    367
CD822985.1    --------------------------------------------------    184
CF436807.1    --------------------------------------------------    172
BE130418.1    --------------------------------------------------    243
AAO47338.1    --------------------------------------------------    314
CF687220.1    --------------------------------------------------    151
ORF68         --------------------------------------------------    234
BJ258031.1    --------------------------------------------------    200
BAD72233.1    --------------------------------------------------    310
CD225978.1    --------------------------------------------------    205
CA132547.1    --------------------------------------------------    206
AJ815010.1    --------------------------------------------------    218
CAC24845.1    --------------------------------------------------    281
BG127541.1    --------------------------------------------------    217
BQ120809.2    --------------------------------------------------    218
BM520331.1    --------------------------------------------------    178
AW570097.1    --------------------------------------------------    144
CO077451.1    --------------------------------------------------    248
AJ502953.1    --------------------------------------------------    180
BP950240.1    --------------------------------------------------    153
CAD12767.2    KKCSSNALHKIPSFVENNVGLLTIGLGQGKLKTRRTGFKPYKRCSVEARE    700
```

FIGURE 10-12

```
AAU08309.1    --------------------------------------------------    310
CAI30880.1    --------------------------------------------------    285
AAL78742.1    --------------------------------------------------    291
AAK91894.1    GGTGMYTHPVTVLAEGTSGVRCGVGTRTSPSLGLQPSVAGGTRMYTHAVN    587
CB289054.1    --------------------------------------------------    256
AAO45179.1    --------------------------------------------------    302
CF207250.1    --------------------------------------------------    221
CF830179.1    --------------------------------------------------    242
CK281810.1    --------------------------------------------------    274
AAS90082.1    --------------------------------------------------    387
CD822965.1    --------------------------------------------------    184
CF438807.1    --------------------------------------------------    172
BE130418.1    --------------------------------------------------    243
AAO47339.1    --------------------------------------------------    314
CF687220.1    --------------------------------------------------    151
ORF08         --------------------------------------------------    234
BJ259031.1    --------------------------------------------------    200
BAD72233.1    --------------------------------------------------    310
CD225978.1    --------------------------------------------------    205
CA132547.1    --------------------------------------------------    208
AJ815010.1    --------------------------------------------------    218
CAC24846.1    --------------------------------------------------    261
BG127541.1    --------------------------------------------------    217
BQ120809.2    --------------------------------------------------    218
BM520331.1    --------------------------------------------------    178
AW570097.1    --------------------------------------------------    144
CO077451.1    --------------------------------------------------    248
AJ502853.1    --------------------------------------------------    180
BP850240.1    --------------------------------------------------    153
CAD12787.2    NRVGANCEEKGCKRIRLEGDTST---------------------------    723
```

FIGURE 10-13

| | | |
|---|---|---|
| AAU08308.1 | -------------------------------------------------- | 310 |
| CAI30880.1 | -------------------------------------------------- | 295 |
| AAL78742.1 | -------------------------------------------------- | 281 |
| AAK91884.1 | N V G Y D L E E L M T K Q L V G A S Q E G P S I N T A S L P S P I A D H I G L H G C T T S S S V A K | 637 |
| CB289054.1 | -------------------------------------------------- | 258 |
| AAO45178.1 | -------------------------------------------------- | 302 |
| CF207250.1 | -------------------------------------------------- | 221 |
| CF838179.1 | -------------------------------------------------- | 242 |
| CK281819.1 | -------------------------------------------------- | 274 |
| AAS08982.1 | -------------------------------------------------- | 367 |
| CD822985.1 | -------------------------------------------------- | 194 |
| CF438607.1 | -------------------------------------------------- | 172 |
| BE130418.1 | -------------------------------------------------- | 243 |
| AAO47339.1 | -------------------------------------------------- | 314 |
| CF687220.1 | -------------------------------------------------- | 151 |
| ORF66 | -------------------------------------------------- | 234 |
| BJ259031.1 | -------------------------------------------------- | 200 |
| BAD72233.1 | -------------------------------------------------- | 310 |
| CD225976.1 | -------------------------------------------------- | 205 |
| CA132547.1 | -------------------------------------------------- | 208 |
| AJ615010.1 | -------------------------------------------------- | 218 |
| CAC24845.1 | -------------------------------------------------- | 261 |
| BG127541.1 | -------------------------------------------------- | 217 |
| BQ120809.2 | -------------------------------------------------- | 218 |
| BM520331.1 | -------------------------------------------------- | 178 |
| AW570087.1 | -------------------------------------------------- | 144 |
| CO077451.1 | -------------------------------------------------- | 248 |
| AJ502953.1 | -------------------------------------------------- | 190 |
| BP950240.1 | -------------------------------------------------- | 153 |
| CAD12787.2 | -------------------------------------------------- | 723 |

FIGURE 10-14

| | | |
|---|---|---|
| AAU06308.1 | -------------------------------------------------- | 310 |
| CAI30880.1 | -------------------------------------------------- | 295 |
| AAL78742.1 | -------------------------------------------------- | 291 |
| AAK91894.1 | NGFVSTMEAPGGGFSVDSMQTPSIPGHIGGGTYPCWEPSSKDDSIFDLEY | 667 |
| CB289054.1 | -------------------------------------------------- | 256 |
| AAO45178.1 | -------------------------------------------------- | 302 |
| CF207250.1 | -------------------------------------------------- | 221 |
| CF838179.1 | -------------------------------------------------- | 242 |
| CK281819.1 | -------------------------------------------------- | 274 |
| AAS09882.1 | -------------------------------------------------- | 367 |
| CD822986.1 | -------------------------------------------------- | 184 |
| CF436807.1 | -------------------------------------------------- | 172 |
| BE130418.1 | -------------------------------------------------- | 243 |
| AAO47338.1 | -------------------------------------------------- | 314 |
| CF687220.1 | -------------------------------------------------- | 151 |
| ORF08 | -------------------------------------------------- | 234 |
| BJ250031.1 | -------------------------------------------------- | 200 |
| BAD72233.1 | -------------------------------------------------- | 310 |
| CD225976.1 | -------------------------------------------------- | 205 |
| CA132547.1 | -------------------------------------------------- | 206 |
| AJ615010.1 | -------------------------------------------------- | 216 |
| CAC24845.1 | -------------------------------------------------- | 261 |
| BG127541.1 | -------------------------------------------------- | 217 |
| BQ120809.2 | -------------------------------------------------- | 219 |
| BM520331.1 | -------------------------------------------------- | 179 |
| AW570097.1 | -------------------------------------------------- | 144 |
| CO077451.1 | -------------------------------------------------- | 248 |
| AJ502853.1 | -------------------------------------------------- | 190 |
| BP850240.1 | -------------------------------------------------- | 153 |
| CAD12787.2 | -------------------------------------------------- | 723 |

FIGURE 10-15

| | | |
|---|---|---|
| CO082212.1 | T - - - - - - - - - - - - - - - | 225 |
| CO803744.1 | T T - - - - - - - - - - - - - - | 178 |
| BU835048.1 | N T - - - - - - - - - - - - - - | 184 |
| CO878572.1 | N A - - - - - - - - - - - - - - | 207 |
| CA821208.1 | N A - - - - - - - - - - - - - - | 188 |
| BG351755.1 | - - - - - - - - - - - - - - - - | 259 |
| CD484084.1 | Q S - - - - - - - - - - - - - - | 248 |
| BJ578568.1 | N T - - - - - - - - - - - - - - | 148 |
| BX831747.1 | A H T - - - - - - - - - - - - - | 348 |
| AY011121.1 | - - - - - - - - - - - - - - - - | 388 |
| CB878882.1 | A - - - - - - - - - - - - - - - | 183 |
| BE361081.1 | - - - - - - - - - - - - - - - - | 132 |
| AY077758.1 | G L T V Q S Q - - - - - - - - - | 385 |
| CO210220.1 | S L I V H P - - - - - - - - - - | 118 |
| CF205888.1 | G L M F P S T - - - - - - - - - | 188 |
| CV281884.1 | L I L K Q S E - - - - - - - - - | 248 |
| AAD32878.1 | A A L T P L P E L H K L - - - - | 321 |
| DAA05115.1 | H P P A P P P P L A L P L A - - | 330 |
| ABO20023.1 | N T Q M M V F G S T E E R R E - | 328 |
| CK295284.1 | N S Q M M A F - - - - - - - - - | 322 |
| BT014501.1 | N S S Q M V N F G L M E K K - - | 338 |
| CV707438.1 | V V P A G V G L V F E S T - - - | 183 |
| AAS84778.1 | E T I S S S G V N D L V F A S A | 334 |
| U58834.1 | N T S H I L E S D G L K Q S - - | 341 |
| BP083458.1 | N L I L E S S - - - - - - - - - | 131 |
| BM338249.1 | A A A A Q V - - - - - - - - - - | 118 |
| BF281318.1 | - - - - - - - - - - - - - - - - | 214 |
| CA141214.1 | - - - - - - - - - - - - - - - - | 237 |
| ORF59 | Q A - - - - - - - - - - - - - - | 343 |
| CV000889.1 | - - - - - - - - - - - - - - - - | 188 |
| BM958318.1 | - - - - - - - - - - - - - - - - | 159 |
| AK070648.1 | Q T - - - - - - - - - - - - - - | 398 |
| CV782182.1 | Q A - - - - - - - - - - - - - - | 208 |

FIGURE 10-16

GGAATTCGATATCAAGCTTGGCACTGGCCGTCGTTTTACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCCTTCCCAACAGTTGCGCAGCCTGAATGGCGAATGCTAG
AGCAGCTTGAGCTTGGATCAGATTGTCGTTTCCCGCCTTCAGTTTAAACTATCAGTGTTTGACAGGATATATTGGCGGGTAAACCTAAGAG
AAAAGAGCGTTTATTAGAATAACGGATATTTAAAAGGGCGTGAAAAGGTTTATCCGTTCGTCCATTTGTATGTGCATGCCAACCACAGGGT
TCCCCTCGGGATCAAAGTACTTTGATCCAACCCCTCCGCTGCTATAGTGCAGTCGGCTTCTGACGTTCAGTGCAGCCGTCTTCTGAAAACG
ACATGTCGCACAAGTCCTAAGTTACGCGACAGGCTGCCGCCCTGCCCTTTTCCTGGCGTTTTCTTGTCGCGTGTTTTAGTCGCATAAAGTA
GAATACTTGCGACTAGAACCGGAGACATTACGCCATGAACAAGAGCGCCGCCGCTGGCCTGCTGGGCTATGCCCGCGTCAGCACCGACGAC
CAGGACTTGACCAACCAACGGGCCGAACTGCACGCGGCCGGCTGCACCAAGCTGTTTTCCGAGAAGATCACCGGCACCAGGCGCGACCGCC
CGGAGCTGGCCAGGATGCTTGACCACCTACGCCCTGGCGACGTTGTGACAGTGACCAGGCTAGACCGCCTGGCCCGCAGCACCCGCGACCT
ACTGGACATTGCCGAGCGCATCCAGGAGGCCGGCGCGGGCCTGCGTAGCCTGGCAGAGCCGTGGGCCGACACCACCACGCCGGCCGGCCGC
ATGGTGTTGACCGTGTTCGCCGGCATTGCCGAGTTCGAGCGTTCCCTAATCATCGACCGCACCCGGAGCGGGCGCGAGGCCGCCAAGGCCC
GAGGCGTGAAGTTTGGCCCCCGCCCTACCCTCACCCCGGCACAGATCGCGCACGCCCGCGAGCTGATCGACCAGGAAGGCCGCACCGTGAA
AGAGGCGGCTGCACTGCTTGGCGTGCATCGCTCGACCCTGTACCGCGCACTTGAGCGCAGCGAGGAAGTGACGCCCACCGAGGCCAGGCGG
CGCGGTGCCTTCCGTGAGGACGCATTGACCGAGGCCGACGCCCTGGCGGCCGCCGAGAATGAACGCCAAGAGGAACAAGCATGAAACCGCA
CCAGGACGGCCAGGACGAACCGTTTTTCATTACCGAAGAGATCGAGGCGGAGATGATCGCGGCCGGGTACGTGTTCGAGCCGCCCGCGCAC
GTCTCAACCGTGCGGCTGCATGAAATCCTGGCCGGTTTGTCTGATGCCAAGCTGGCGGCCTGGCCGGCCAGCTTGGCCGCTGAAGAAACCG
AGCGCCGCCGTCTAAAAAGGTGATGTGTATTTGAGTAAAACAGCTTGCGTCATGCGGTCGCTGCGTATATGATGCGATGAGTAAATAAACA
AATACGCAAGGGGAACGCATGAAGGTTATCGCTGTACTTAACCAGAAAGGCGGGTCAGGCAAGACGACCATCGCAACCCATCTAGCCCGCG
CCCTGCAACTCGCCGGGGCCGATGTTCTGTTAGTCGATTCCGATCCCCAGGGCAGTGCCCGCGATTGGGCGGCCGTGCGGGAAGATCAACC
GCTAACCGTTGTCGGCATCGACCGCCCGACGATTGACCGCGACGTGAAGGCCATCGGCCGGCGCGACTTCGTAGTGATCGACGGAGCGCCC
CAGGCGGCGGACTTGGCTGTGTCCGCGATCAAGGCAGCCGACTTCGTGCTGATTCCGGTGCAGCCAAGCCCTTACGACATATGGGCCACCG
CCGACCTGGTGGAGCTGGTTAAGCAGCGCATTGAGGTCACGGATGGAAGGCTACAAGCGGCCTTTGTCGTGTCGCGGGCGATCAAAGGCAC
GCGCATCGGCGGTGAGGTTGCCGAGGCGCTGGCCGGGTACGAGCTGCCCATTCTTGAGTCCCGTATCACGCAGCGCGTGAGCTACCCAGGC
ACTGCCGCCGCCGGCACAACCGTTCTTGAATCAGAACCCGAGGGCGACGCTGCCCGCGAGGTCCAGGCGCTGGCCGCTGAAATTAAATCAA
AACTCATTTGAGTTAATGAGGTAAAGAGAAAATGAGCAAAAGCACAAACACGCTAAGTGCCGGCCGTCCGAGCGCACGCAGCAGCAAGGCT
GCAACGTTGGCCAGCCTGGCAGACACGCCAGCCATGAAGCGGGTCAACTTTCAGTTGCCGGCGGAGGATCACACCAAGCTGAAGATGTACG
CGGTACGCCAAGGCAAGACCATTACCGAGCTGCTATCTGAATACATCGCGCAGCTACCAGAGTAAATGAGCAAATGAATAAATGAGTAGAT
GAATTTTAGCGGCTAAAGGAGGCGGCATGGAAAATCAAGAACAACCAGGCACCGACGCCGTGGAATGCCCCATGTGTGGAGGAACGGGCGG
TTGGCCAGGCGTAAGCGGCTGGGTTGTCTGCCGGCCCTGCAATGGCACTGGAACCCCCAAGCCCGAGGAATCGGCGTGACGGTCGCAAACC
ATCCGGCCCGGTACAAATCGGCGCGGCGCTGGGTGATGACCTGGTGGAGAAGTTGAAGGCCGCGCAGGCCGCCCAGCGGCAACGCATCGAG
GCAGAAGCACGCCCCGGTGAATCGTGGCAAGCGGCCGCTGATCGAATCCGCAAAGAATCCCGGCAACCGCCGGCAGCCGGTGCGCCGTCGA
TTAGGAAGCCGCCCAAGGGCGACGAGCAACCAGATTTTTTCGTTCCGATGCTCTATGACGTGGGCACCCGCGATAGTCGCAGCATCATGGA
CGTGGCCGTTTTCCGTCTGTCGAAGCGTGACCGACGAGCTGGCGAGGTGATCCGCTACGAGCTTCCAGACGGGCACGTAGAGGTTTCCGCA
GGGCCGGCCGGCATGGCCAGTGTGTGGGATTACGACCTGGTACTGATGGCGGTTTCCCATCTAACCGAATCCATGAACCGATACCGGGAAG
GGAAGGGAGACAAGCCCGGCCGCGTGTTCCGTCCACACGTTGCGGACGTACTCAAGTTCTGCCGGCGAGCCGATGGCGGAAAGCAGAAAGA
CGACCTGGTAGAAACCTGCATTCGGTTAAACACCACGCACGTTGCCATGCAGCGTACGAAGAAGGCCAAGAACGGCCGCCTGGTGACGGTA
TCCGAGGGTGAAGCCTTGATTAGCCGCTACAAGATCGTAAAGAGCGAAACCGGGCGGCCGGAGTACATCGAGATCGAGCTAGCTGATTGGA
TGTACCGCGAGATCACAGAAGGCAAGAACCCGGACGTGCTGACGGTTCACCCCGATTACTTTTTGATCGATCCCGGCATCGGCCGTTTTCT
CTACCGCCTGGCACGCCGCGCCGCAGGCAAGGCAGAAGCCAGATGGTTGTTCAAGACGATCTACGAACGCAGTGGCAGCGCCGGAGAGTTC
AAGAAGTTCTGTTTCACCGTGCGCAAGCTGATCGGGTCAAATGACCTGCCGGAGTACGATTTGAAGGAGGAGGCGGGGCAGGCTGGCCCGA
TCCTAGTCATGCGCTACCGCAACCTGATCGAGGGCGAAGCATCCGCCGGTTCCTAATGTACGGAGCAGATGCTAGGGCAAATTGCCCTAGC
AGGGGAAAAAGGTCGAAAAGGTCTCTTTCCTGTGGATAGCACGTACATTGGGAACCCAAAGCCGTACATTGGGAACCGGAACCCGTACATT
GGGAACCCAAAGCCGTACATTGGGAACCGGTCACACATGTAAGTGACTGATATAAAAGAGAAAAAAGGCGATTTTTCCGCCTAAAACTCTT
TAAAACTTATTAAAACTCTTAAAACCCGCCTGGCCTGTGCATAACTGTCTGGCCAGCGCACAGCCGAAGAGCTGCAAAAAGCGCCTACCCT
TCGGTCGCTGCGCTCCCTACGCCCCGCCGCTTCGCGTCGGCCTATCGCGGCCGCTGGCCGCTCAAAAATGGCTGGCCTACGGCCAGGCAAT
CTACCAGGGCGCGGACAAGCCGCGCCGTCGCCACTCGACCGCCGGCGCCCACATCAAGGCACCCTGCCTCGCGCGTTTCGGTGATGACGGT
GAAAACCTCTGACACATGCAGCTCCCGGAGACGGTCACAGCTTGTCTGTAAGCGGATGCCGGGAGCAGACAAGCCCGTCAGGGCGCGTCAG
CGGGTGTTGGCGGGTGTCGGGGCGCAGCCATGACCCAGTCACGTAGCGATAGCGGAGTGTATACTGGCTTAACTATGCGGCATCAGAGCAG
ATTGTACTGAGAGTGCACCATATGCGGTGTGAAATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAAAACTCACGTTAAGGGA
TTTTGGTCATGCATTCTAGGTACTAAAACAATTCATCCAGTAAAATATAATATTTTATTTTCTCCCAATCAGGCTTGATCCCCAGTAAGTC
AAAAAATAGCTCGACATACTGTTCTTCCCCGATATCCTCCCTGATCGACCGGACGCAGAAGGCAATGTCATACCACTTGTCCGCCCTGCCG
CTTCTCCCAAGATCAATAAAGCCACTTACTTTGCCATCTTTCACAAAGATGTTGCTGTCTCCCAGGTCGCCGTGGGAAAAGACAAGTTCCT
CTTCGGGCTTTTCCGTCTTTAAAAAATCATACAGCTCGCGCGGATCTTTAAATGGAGTGTCTTCTTCCCAGTTTTCGCAATCCACATCGGC
CAGATCGTTATTCAGTAAGTAATCCAATTCGGCTAAGCGGCTGTCTAAGCTATTCGTATAGGGACAATCCGATATGTCGATGGAGTGAAAG
AGCCTGATGCACTCCGCATACAGCTCGATAATCTTTTCAGGGCTTTGTTCATCTTCATACTCTTCCGAGCAAAGGACGCCATCGGCCTCAC
TCATGAGCAGATTGCTCCAGCCATCATGCCGTTCAAAGTGCAGGACCTTTGGAACAGGCAGCTTTCCTTCCAGCCATAGCATCATGTCCTT
TTCCCGTTCCACATCATAGGTGGTCCCTTTATACCGGCTGTCCGTCATTTTTAAATATAGGTTTTCATTTTCTCCCACCAGCTTATATACC
TTAGCAGGAGACATTCCTTCCGTATCTTTTACGCAGCGGTATTTTTCGATCAGTTTTTTCAATTCCGGTGATATTCTCATTTTAGCCATTT
ATTATTTCCTTCCTCTTTTCTACAGTATTTAAAGATACCCCAAGAAGCTAATTATAACAAGACGAACTCCAATTCACTGTTCCTTGCATTC
TAAAACCTTAAATACCAGAAAACAGCTTTTTCAAAGTTGTTTTCAAAGTTGGCGTATAACATAGTATCGACGGAGCCGATTTTGAAACCGC
GGTGATCACAGGCAGCAACGCTCTGTCATCGTTACAATCAACATGCTACCCTCCGCGAGATCATCCGTGTTTCAAACCCGGCAGCTTAGTT
GCCGTTCTTCCGAATAGCATCGGTAACATGAGCAAAGTCTGCCGCCTTACAACGGCTCTCCCGCTGACGCCGTCCCGGACTGATGGGCTGC

FIGURE 12-1

CTGTATCGAGTGGTGATTTTGTGCCGAGCTGCCGGTCGGGGAGCTGTTGGCTGGCTGGTGGCAGGATATATTGTGGTGTAAACAAATTGAC
GCTTAGACAACTTAATAACACATTGCGGACGTTTTTAATGTACTGAATTAACGCCGAATTAATTCGGGGGATCTGGATTTTAGTACTGGAT
TTTGGTTTTAGGAATTAGAAATTTTATTGATAGAAGTATTTTACAAATACAAATACATACTAAGGGTTTCTTATATGCTCAACACATGAGC
GAAACCCTATAGGAACCCTAATTCCCTTATCTGGGAACTACTCACACATTATTATGGAGAAACTCGAGCTTGTCGATCGACAGATCCGGTC
GGCATCTACTCTATTTCTTTGCCCTCGGACGAGTGCTGGGGCGTCGGTTTCCACTATCGGCGAGTACTTCTACACAGCCATCGGTCCAGAC
GGCCGCGCTTCTGCGGGCGATTTGTGTACGCCCGACAGTCCCGGCTCCGGATCGGACGATTGCGTCGCATCGACCCTGCGCCCAAGCTGCA
TCATCGAAATTGCCGTCAACCAAGCTCTGATAGAGTTGGTCAAGACCAATGCGGAGCATATACGCCCGGAGTCGTGGCGATCCTGCAAGCT
CCGGATGCCTCCGCTCGAAGTAGCGCGTCTGCTGCTCCATACAAGCCAACCACGGCCTCCAGAAGAAGATGTTGGCGACCTCGTATTGGGA
ATCCCCGAACATCGCCTCGCTCCAGTCAATGACCGCTGTTATGCGGCCATTGTCCGTCAGGACATTGTTGGAGCCGAAATCCGCGTGCACG
AGGTGCCGGACTTCGGGGCAGTCCTCGGCCCAAAGCATCAGCTCATCGAGAGCCTGCGCGACGGACGCACTGACGGTGTCGTCCATCACAG
TTTGCCAGTGATACACATGGGGATCAGCAATCGCGCATATGAAATCACGCCATGTAGTGTATTGACCGATTCCTTGCGGTCCGAATGGGCC
GAACCCGCTCGTCTGGCTAAGATCGGCCGCAGCGATCGCATCCATAGCCTCCGCGACCGGTTGTAGAACAGCGGGCAGTTCGGTTTCAGGC
AGGTCTTGCAACGTGACACCCTGTGCACGGCGGGAGATGCAATAGGTCAGGCTCTCGCTAAACTCCCCAATGTCAAGCACTTCCGGAATCG
GGAGCGCGGCCGATGCAAAGTGCCGATAAACATAACGATCTTTGTAGAAACCATCGGCGCAGCTATTTACCCGCAGGACATATCCACGCCC
TCCTACATCGAAGCTGAAAGCACGAGATTCTTCGCCCTCCGAGAGCTGCATCAGGTCGGAGACGCTGTCGAACTTTTCGATCAGAAACTTC
TCGACAGACGTCGCGGTGAGTTCAGGCTTTTTCATATCTCATTGCCCCCCGGATCTGCGAAAGCTCGAGAGAGATAGATTTGTAGAGAGA
GACTGGTGATTTCAGCGTGTCCTCTCCAAATGAAATGAACTTCCTTATATAGAGGAAGGTCTTGCGAAGGATAGTGGGATTGTGCGTCATC
CCTTACGTCAGTGGAGATATCACATCAATCCACTTGCTTTGAAGACGTGGTTGGAACGTCTTCTTTTTCCACGATGCTCCTCGTGGGTGGG
GGTCCATCTTTGGGACCACTGTCGGCAGAGGCATCTTGAACGATAGCCTTTCCTTTATCGCAATGATGGCATTTGTAGGTGCCACCTTCCT
TTTCTACTGTCCTTTTGATGAAGTGACAGATAGCTGGGCAATGGAATCCGAGGAGGTTTCCCGATATTACCCTTTGTTGAAAAGTCTCAAT
AGCCCTTTGGTCTTCTGAGACTGTATCTTTGATATTCTTGGAGTAGACGAGAGTGTCGTGCTCCACCATGTTATCACATCAATCCACTTGC
TTTGAAGACGTGGTTGGAACGTCTTCTTTTTCCACGATGCTCCTCGTGGGTGGGGGTCCATCTTTGGGACCACTGTCGGCAGAGGCATCTT
GAACGATAGCCTTTCCTTTATCGCAATGATGGCATTTGTAGGTGCCACCTTCCTTTTCTACTGTCCTTTTGATGAAGTGACAGATAGCTGG
GCAATGGAATCCGAGGAGGTTTCCCGATATTACCCTTTGTTGAAAAGTCTCAATAGCCCTTTGGTCTTCTGAGACTGTATCTTTGATATTC
TTGGAGTAGACGAGAGTGTCGTGCTCCACCATGTTGGCAAGCTGCTCTAGCCAATACGCAAACCGCCTCTCCCCGCGCGTTGGCCGATTCA
TTAATGCAGCTGGCACGACAGGTTTCCCGACTGGAAAGCGGGCAGTGAGCGCAACGCAATTAATGTGAGTTAGCTCACTCATTAGGCACCC
CAGGCTTTACACTTTATGCTTCCGGCTCGTATGTTGTGTGGAATTGTGAGCGGATAACAATTTCACACAGGAAACAGCTATGACCATGATT
ACGAATTCCCTTAATTAATAAGAGCAGCTTGCCAACATGGTGGAGCACGACACTCTCGTCTACTCCAAGAATATCAAAGATACAGTCTCAG
AAGACCAAAGGGCTATTGAGACTTTTCAACAAAGGGTAATATCGGGAAACCTCCTCGGATTCCATTGCCCAGCTATCTGTCACTTCATCAA
AAGGACAGTAGAAAAGGAAGGTGGCACCTACAAATGCCATCATTGCGATAAAGGAAAGGCTATCGTTCAAGATGCCTCTGCCGACAGTGGT
CCCAAAGATGGACCCCCACCCACGAGGAGCATCGTGGAAAAAGAAGACGTTCCAACCACGTCTTCAAAGCAAGTGGATTGATGTGAACATG
GTGGAGCACGACACTCTCGTCTACTCCAAGAATATCAAAGATACAGTCTCAGAAGGCCAAAGGGCTATTGAGACTTTTCAACAAAGGGTAA
TATCGGGAAACCTCCTCGGATTCCATTGCCCAGCTATCTGTCACTTCATCAAAAGGACAGTAGAAAAGGAAGGTGGCACCTACAAATGCCA
TCATTGCGATAAAGGAAAGGCTATCGTTCAAGATGCTCTGCCGACAGTGGTCCCAAAGATGGACCCCCACCCACGAGGAGCATCGTGGAAA
AAGAAGACGTTCCAACCACGTCTTCAAAGCAAGTGGATTGATGTGATATCTCCACTGACGTAAGGGATGACGCACAATCCCACTATCCTTC
GCAAGACCCTTCCTCTATATAAGGAAGTTCATTTCATTTGGAGAGGACACGCTGAAATCACCAGTCTCTCTCTACAAATCTATCTCTCTCC
ATTAGTGATCTGCTGTGCTGTGGTGAGAGCTGCCAAGAAGCTGAGCAGTGCTACTCTGGAGGAGCTCACCAAAGCATTGTTTCTGTTTCGG
TTTTGGCAATCACTAAATAATGGAGGAAGTGGAGGAGGCCAACAGGATAGCCGTTGAGAGCTGCCACAGAGTGCTGGGCCTGCTTTCCCAG
TCGCAGGACCCGGCGCAGCTCAGGAGCATAGCTCTGGGCACGGACGACGCCTGCGCCAAGTTCCGCAAGGTGGTCTCCCTCCTCGGCAACG
AAGGAGGAGGGGGAGCAGTAAGCCATCCCAGAGCCAAGGTTGCGAGCAGGAAACAGACCCCGGCCTTCTTGAGCCAGAAGGGCTTCCTGGA
CAACAACACCCCGGTGGTGGTGCTGAACAGCAGCGCCCACCCTTCCACTAGCTCCGCGCAGGCGTATCCTAGGAACACCATTCTGGATTCG
CACACCGCGCACCCGATCGGAGGGCCTCCCAAGCTGGTCCAGCCATTGTCCGCGCACTTCCAGTTCGGCAACGTATCGCGGTATCAGTTCC
AGCATCAGCACCAGCAGCAGAAGATGCAGGCTGAGATGTTCAAGAGAAGCAACAGTATCAGTGGGATTAACCTGAAGTTCGACAGCCCCAG
CGCGGCCACGGGGGCGATGTCGTCCGCGAGATCCTTCATGTCATCTTTGAGCATGGATGGTAGCGTGGCTAGCCTGGATGCCAAGTCTTCC
TCGTTCCATTTGATCGGTGGGCCTGCTATGAGTGACCCGGTGAATGCGCAGCAGGCGCCGAGGAGGCGGTGCACGGGGCGTGGGGAGGATG
GGAATGGCAAGTGCGCTGCAAATGGCAGGTGCCATTGCTCAAAGAGGAGGTAAATACTCTTATCTTAGTGTGTATGATTCTTGCTTGCTCT
TCTATTCAAGGTAGAATACCATGAGAATTGTTCTGTTCCCTATTTCAGCAGGAAGTTGCGGGTGAAGAAGACGATTAAAGTTCCTGCCATT
AGTAATAAAATTGCTGATATACCTCCAGATGAATACTCATGGAGGAAGTATGGGCAGAAGCCAATTAAGGGTTCCCCTCATCCCAGGTATG
AACTGAGCACTATCTGTTAGTGTCATTTTCTTGCACACATATTCTTGATTATACGGTGATGGAGTAGTGGCAATGATGCTATAATCACCAT
GACTCATCAATTTTCTAATTATTTATCATATGTATAACTGCACATATCCCCCATGAACTACTCAAGTGCCTCATGATAAATGATGGCTCTG
TGATAATCAGAACACACTTTATCCATGGTTTGCAGGGTGTTTTACATGCTCCTGATAATCAGAACACTCTTTATACAGTATAGTAATCAAA
ACTCTCCTTATGCAGGGTGTTTTGTATGTTCCTGAATAGTTACTTTGTGAATAATGTCTTTCATTCTTCTTGTGCACACTTTCTTAAAATA
GATCAATCCCGAGTCTTAAAGTGGCCAGTGGCCACTTCGTAATTCAGTCTACCATGATTCAGTCTTTAAGTGGACATCTTTAATGCTATCG
TGATTCAGTCTACTACGTACTATACTTTACCTATTCATATCACTTTCCCACCTTGTCTATCTTAAATTTCCTGATGATAAAATACACAAAT
ATAGCTATACGGTAATAGCAAACGCATGGGTATCTTTTCGAGAAAAAAACAAACACATGGGTATGGCTGTCTGAATTGAGAAAAAACTTTT
CCTCTTTCTAGCAAGCACTAGATATAGAAACACGATTCATGGCGCATCTATTTTTATCTCCAATCCACAATGCTAATTCTGATGTGTCTCT
TAAGACCAATCCACTGATTCCTTAAACATAATGCAGGGGGTACTACAAATGTAGCAGTGTCAGGGGCTGCCCAGCCAGGAAGCATGTTGAA
CGTTGTGTGGATGATGCGTCAATGCTCATTGTGACATACGAGGGTGAACACAACCACACGCGAATGCCGGCTCAGTCTGCACAGGCTTAGG
GAATCACTTTGATCATCACACCCTCTCCAGGGAATACTAACTCGCCTGCCCTTGTCGATGGCCGACTGCACTGTTCTTCTAAATTAGAATT
ACAAAGTGACAAAAACTGGGTTCCATTTGAGCAGTTGATGAGGCCTGGTTTCTCCATAATAATGTGTGAGTAGTTCCCAGATAAGGGAATT
AGGGTTCCTATAGGGTTTCGCTCATGTGTTGAGCATATAAGAAACCCTTAGTATGTATTTGTATTTGTAAAATACTTCTATCAATAAAATT
TCTAATTCCTAAAACCAAAATCCAGTACTAAAATCCAGATCCCCCGAATTAATTCGGCGTTAATTCAGTATCGGCGCGCCTTAATTAAGGC
GCGCCCTGCA

SEQ ID NO: 246

FIGURE 12-2

GCGCACATTTCCCCGAAAAGTGCCACCTGATGCGGTGTGAAATACCGCACAGATGCGTAAGGAGAAAATACCGCATCAGGAAATTGTAAGC
GTTAATATTTTGTTAAAATTCGCGTTAAATTTTTGTTAAATCAGCTCATTTTTTAACCAATAGGCCGAAATCGGCAAAATCCCTTATAAAT
CAAAAGAATAGACCGAGATAGGGTTGAGTGTTGTTCCAGTTTGGAACAAGAGTCCACTATTAAAGAACGTGGACTCCAACGTCAAAGGGCG
AAAAACCGTCTATCAGGGCGATGGCCCACTACGTGAACCATCACCCTAATCAAGTTTTTTGGGGTCGAGGTGCCGTAAAGCACTAAATCGG
AACCCTAAAGGGAGCCCCCGATTTAGAGCTTGACGGGGAAAGCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCCGCCGCGCTTAATGCGCCGCTACAGGGCGCGTCCATTCGCCA
TTCAGGCTGCGCAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAATTGTAATACGACTCACTATAGGGCGAATTGGG
CCCGACGTCGCATGCTCCCGGCCGCCATGGCGGCCGCGGGAATTCGATTGATTGGCGCGCCTTAATTAACGGGCTGGTAAAACAAATATAA
GTATTAATATAAATATAATACAATAGAAGGAAAATAAATAAAATTTCCCTCTGTGCCGTGCAAAAATGCACGGCAATGGGTTGGCCCGCAC
GGCAAAGGCATCGTTGCCGTGTCCACGGCAATGGGTTGGCCCGCACGGCAAAGGCATCGTTGCCGTGTCCACGTCTTTGCCGTGCGCCTTG
GCTCTATCTTTGCCGTGAAGCGTTCTTTGCCGTGTGCCTTTTATTTCTTTGCCGTGGGATGCTGCCTTTGCCGAGCGCTGAGCTGGCGCTT
TGCCGTGCGCGTATTGTTTGCCGTGCGTCCTCCCAGAGCTGTACGGCAAAGAATTCATTGCCGTGCACGAGGCACACGGGAAAGAAGTTTC
GCATGGCAAAGGGCGCTGACAGCACACGGCAAAGAGCCCGGCACGGCATTGAGCTTTTTTTCCCGTAATGATAGACGGCATAATATAATGG
ACGCACATGCTGATGTCAGGATGTCACCCACTCATCCTAGTATTTGTGGACGTGAATTCTTTGTGAGATGGGCAATGGGATGTGAACAAA
ATAAGTTTTGTACTAGTAGATAAACATTTTTACCCATAAACAATTGTTCTGTATTGAATGAAAAATTATTTTGTACTGGATGAAAATCTTC
TGAGTAACTGTGTAAGATTAACATGAATCAAGAGACAAATCCAATGGCTACAAAGTCAACTAATACTTGTTAAAAGTTCCGATACTTAAAA
TTATCAAAACTGATATATAGAATATTGCCCATCTCGCCACCGTGCTAGTTTAACAGACGATGGACGAATATCAGTCTTGTATTGGATAATC
GATGCATGCGAGCTATCGGTCACCTGTCCATGCTTCCAGAAGGAGCCGAGACGTGGCGACTTCGTCCGACGCGCCGACTATCTGCACACGC
CCGGCTTCTCGTCGTGGGCGAGTCAGCAGTCACAGGCTTTCCGCCTACCAACTCACACGTAGCGCCCTATCGTGGCGCTTGATCGATGCAA
CAGCGATGCCTATCCCAGCTCCTCAAGCTGCTTATAAGTATGTCCTCGGCCATCACTGCTTACACAACAAACACAGCTACTTATCGCAGTG
TACTAAACAAGACGTACTAGCTAGATTTCGTGAGGTAAAATCAGTGCAATATCACTTGTGCAAGCCATTAGTGATCTGCTGTGCTGTGGTG
AGAGCTGCCAAGAAGCTGAGCAGTGCTACTCTGGAGGAGCTCACCAAAGGATTGTTTCTGTTTCGGTTTTGGCAATCACTAAATAATGGAG
GAAGTGGAGGAGGCCAACAGGATACCCGTTGACACCTCCCACAGAGTGCTGGGCCTGCTTTCCCAGTCGCAGGACCCGGCGCAGCTCAGGA
GCATAGCTCTGGGCACGGACGACGCCTGCGCCAAGTTCCGCAAGGTGGTCTCCCTCCTCGGCAACGAAGGAGGAGGGGGAGCAGTAAGCCA
TCCCAGAGCCAAGGTTGCGAGCAGGAAACAGACCCCGGCCTTCTTGAGCCAGAAGGGCTTCCTGGACAACAACACCCCGGTGGTGGTGCTG
AACAGCAGCGCCCACCCTTCCACTAGCTCCGCGCAGGCGTATCCTAGGAACACCATTCTGGATTCGCACACCGCGCACCCGATCGGAGGGC
CTCCCAAGCTGGTCCAGCCATTGTCCGCGCACTTCCAGTTCGGCAACGTATCGCGGTATCAGTTCCAGCATCAGCACCAGCAGCAGAAGAT
GCAGGCTGAGATGTTCAAGAGAAGCAACAGTATCAGTGGGATTAACCTGAAGTTCGACAGCCCCAGCGCGGCCACGGGGGCGATGTCGTCC
GCGAGATCCTTCATGTCATCTTTGAGCATGGATGGTAGCGTGGCTAGCCTGGATGCCAAGTCTTCCTCGTTCCATTTGATCGGTGGGCCTG
CTATGAGTGACCCGGTGAATGCGCAGCAGGCGCCGAGGAGGCGGTGCACGGGGCGTGGGGAGGATGGGAATGGCAAGTGCGCTGCAAATGG
CAGGTGCCATTGCTCAAAGAGGAGGTAAATACTCTTATCTTAGTGTGTATGATTCTTGCTTGCTCTTCTATTCAAGGTAGAATACCATGAG
AATTGTTCTGTTCCCTATTTCAGCAGGAAGTTGCGGGTGAAGAAGACGATTAAAGTTCCTGCCATTAGTAATAAAATTGCTGATATACCTC
CAGATGAATACTCATGGAGGAACTATGGGCAGAAGCCAATTAAGGGTTCCCCTCATCCCAGGTATGAACTGAGCACTATCTGTTAGTGTCA
TTTTCTTGCACACATATTCTTGATTATACGGTGATGGAGTAGTGGCAATGATGCTATAATCACCATGACTCATCAATTTTCTAATTATTTA
TCATATGTATAACTGCACATATCCCCCATGAACTACTCAAGTGCCTCATGATAAATGATGGCTCTGTGATAATCAGAACACACTTTATCCA
TGGTTTGCAGGGTGTTTACATGCTCCTGATAATCAGAACACTCTTTATACAGTATAGTAATCAAAACTCTCCTTATGCAGGGTGTTTTGT
ATGTTCCTGAATAGTTACTTTGTGAATAATGTCTTTCATTCTTCTTGTGCACACTTCTTAAAATAGATCAATCCCGAGTCTTAAAGTGGC
CAGTGGCCACTTCGTAATTCAGTCTACCATGATTCAGTCTTTAAGTGGACATCTTTAATGCTATCGTGATTCAGTCTACTACGTACTATAC
TTTACCTATTCATATCACTTTCCCACCTTGTCTATCTTAAATTTCCTGATGATAAAATACACAAATATAGCTATACGGTAATAGCAAACGC
ATGGGTATCTTTTCGAGAAAAAAACAAACACATGGGTATGGCTGTCTGAATTGAGAAAAAACTTTTCCTCTTTCTAGCAAGCACTAGATAT
AGAAACACGATTCATGGCGCATCTATTTTTATCTCCAATCCACAATGCTAATTCTGATGTGTCTCTTAAGACCAATCCACTGATTCCTTAA
ACATAATGCAGGGGGTACTACAAATGTAGCAGTGTCAGGGGCTGCCCAGCCAGGAAGCATGTTGAACGTTGTGGATGATGCGTCAATGC
TCATTGTGACATACGAGGGTGAACACAACCACACGCGAATGCCGGCTCAGTCTGCACAGGCTTAGGGAATCACTTTGATCATCACACCCTC
TCCAGGGAATACTAACTCGCCTGCCCTTGTCGATGGCCGACTGCACTGTTCTTCTAAATTAGAATTACAAAGTGACAAAAACTGGGTTCCA
TTTGAGCAGTTGATGAGGCCTGGTTTCTCCATAATAATGTGTGAGTAGTTCCCAGATAAGGGAATTAGGGTTCCTATAGGGTTTCGCTCAT
GTGTTGAGCATATAAGAAACCCTTAGTATGTATTTGTATTTGTAAAATACTTCTATCAATAAAATTTCTAATTCCTAAAACCAAAATCCAG
TACTAAAATCCAGATCCCCCGAATTAATTCGGCGTTAATTCAGTATCGGCGCGCCTTAATTAAAATCGAATTTCGACCATATGGGAGAGCT
CCCAACGCGTTGGATGCATAGCTTGAGTATTCTATAGTGTCACCTAAATAGCTTGGCGTAATCATGGTCATAGCTGTTTCCTGTGTGAAAT
TGTTATCCGCTCACAATTCCACACAACATACGAGCCGGAAGCATAAAGTGTAAAGCCTGGGGTGCCTAATGAGTGAGCTAACTCACATTAA
TTGCGTTGCGCTCACTGCCCGCTTTCCAGTCGGGAAACCTGTCGTGCCAGCTGCATTAATGAATCGGCCAACGCGCGGGGAGAGGCGGTTT
GCGTATTGGGCGCTCTTCCGCTTCCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACTACGGCTACACTAGAAGA
ACAGTATTTGGTATCTGCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTACCATCTGGCCCCAGTGCTGCAATGATACC
GCGAGACCCACGCTCACCGGCTCCAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGCTCATCATTGGAAAACGTTCTTCGGG
GCGAAAACTCTCAAGGATCTTACCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAAATGTTGAATACTCATACTCT

FIGURE 14-1

TCCTTTTTCAATATTATTGAAGCATTTATCAGGGTTATTGTCTCATGAGCGGATACATATTTGAATGTATTTAGAAAAATAAACAAATAGG
GGTTCC

SEQ ID NO: 254

FIGURE 14-2

| | SEQ ID NO: | | |
|---|---|---|---|
| CO092212.1 | 135 | -------------------------------------------------- | D |
| CO903744.1 | 137 | -------------------------------------------------- | D |
| BU835049.1 | 136 | -------------------------------------------------- | D |
| CO878572.1 | 134 | -------------------------------------------------- | D |
| CA821208.1 | 139 | -------------------------------------------------- | D |
| BG351755.1 | 138 | -------------------------------------------------- | D |
| CD484084.1 | 132 | -------------------------------------------------- | D |
| BJ578569.1 | 140 | -------------------------------------------------- | D |
| BX831747.1 | 133 | -------------------------------------------------R | 1 |
| AY011121.1 | 131 | ------------MEGVEESNREAVQSCHRVLSLLSNPHGQLVPHKELVEA | 38 |
| CB878382.1 | 141 | -------------------------------------------------- | D |
| BE381091.1 | 144 | -------------------------------------------------- | D |
| AY077758.1 | 145 | -----------MGALEILDYNNTLGKRDRDYEVKEAACMGIQNARQLLQS | 39 |
| CO210220.1 | 147 | -------------------------------------------------- | D |
| CF205868.1 | 146 | -------------------------------------------------- | D |
| CV281864.1 | 152 | -------------------------------------------------- | D |
| AAD32876.1 | 155 | -------------------------------------------------- | D |
| DAA05115.1 | 167 | -------------------------------------------------- | D |
| AB020023.1 | 148 | -------------------------------------------------- | D |
| CK285284.1 | 150 | -------------------------------------------------- | D |
| BT014501.1 | 158 | -------------------------------------------------- | D |
| CV707438.1 | 153 | -------------------------------------------------- | D |
| AAS84778.1 | 156 | -------------------------------------------------- | D |
| U56834.1 | 151 | -------------------------------------------------- | D |
| BP083458.1 | 154 | -------------------------------------------------- | D |
| BM338249.1 | 143 | -------------------------------------------------- | D |
| BF281318.1 | 128 | -------------------------------------------------- | D |
| CA141214.1 | 130 | -------------------------------------------------- | D |
| ORF89 | 9 | -------------------------------------------------- | D |
| CV000869.1 | 149 | -------------------------------------------------- | D |
| BM858318.1 | 142 | -------------------------------------------------- | D |
| AK070846.1 | 127 | AARRHGALLRSEELRESEASLAGLAPAAAAAAAMEEEVEAANRAAVESCH | 50 |
| CV782162.1 | 129 | -------------------------------------------------- | D |

FIGURE 15-1

| | | |
|---|---|---|
| CO092212.1 | -------------------------------------------------- | 0 |
| CD803744.1 | -------------------------------------------------- | 0 |
| BU835049.1 | -------------------------------------------------- | 0 |
| CO078572.1 | -------------------------------------------------- | 0 |
| CA821208.1 | -------------------------------------------------- | 0 |
| BG351756.1 | -------------------------------------------------- | 0 |
| CD484084.1 | -------------------------------------------------- | 0 |
| BJ578589.1 | -------------------------------------------------- | 0 |
| BX831747.1 | LSFEVFRFLRVSFVKKKMEEVEAANKAAVESCHGVLNLLSQQTNDSKSIM | 51 |
| AY011121.1 | TGEAVSKFGSVATKIATNGNGRQGHARVRKKINQPMPMFDSSLFLETTAS | 86 |
| CB879882.1 | -------------------------------------------------- | 0 |
| BE361091.1 | -------------------------------------------------- | 0 |
| AY077758.1 | LTQVRSPVVDEECDVMAGAAISKFQKVVSLLSRTGHARFRRRTRNAAVAG | 88 |
| CO210220.1 | -------------------------------------------------- | 0 |
| CF205686.1 | -------------------------------------------------- | 0 |
| CV281864.1 | -------------------------------------------------- | 0 |
| AAO32678.1 | ------MMTMDLMGRYGRADEQVAIQEAAAAGLRGMEHLILQLSRTGTGT | 44 |
| DAA05115.1 | ------MITMDLMSGYGRVDEQVAIQEAAAAGLRGMEHLILQLSQTGTSE | 44 |
| ABO20023.1 | --------MAVDFIGFSKMNEQLALQEAASAGLKSMEHLIRLVSHQQQQQ | 42 |
| CK285264.1 | --------WQLNFVGFSKMNEQLALQEAASAGLKSMEHLIRLVSHQQQQQ | 42 |
| BT014501.1 | ------------MAVLSKMNESFAVEEAASAGLKSMENLIRLVSH----E | 34 |
| CV707438.1 | -------------------------------------------------- | 0 |
| AAS66778.1 | --------MAVDLMRFPKIDDQTAIQEAASQGLQSMEHLIRVLSNRPE-Q | 41 |
| U56834.1 | ----------------------MALDLMNNNSYKFRSKMEETAVQEAAAA | 28 |
| BP083456.1 | -------------------------------------------------- | 0 |
| BM338249.1 | -------------------------------------------------- | 0 |
| BF281318.1 | -------------------------------------------------- | 0 |
| CA141214.1 | -----------------------------------------------SLL | 3 |
| ORF69 | --------MEEVEEANRIAVESCHRVLGLLSQSQDPAQLRSIALGTDDAC | 42 |
| CV000869.1 | -------------------------------------------------- | 0 |
| BM958319.1 | -------------------------------------------------- | 0 |
| AK070848.1 | RVLALLSQQQDPALLRSIASETGEACAKFRKVVSLLGNGGGGGGGGGGGG | 100 |
| CV782182.1 | -------------------------------------------------- | 0 |

FIGURE 15-2

```
CO092212.1    --------------------------------------------------    0
CO903744.1    --------------------------------------------------    0
BU835049.1    --------------------------------------------------    0
CO878572.1    --------------------------------------------------    0
CA821208.1    --------------------------------------------------    0
BG351755.1    -------------------VKTECKIDDHAKALRLLPIDSPENRVLEMGA    31
CD484084.1    ------------------------------------------------SA    2
BJ578589.1    --------------------------------------------------    0
BX831747.1    VETREAVCKFKRVSSLLSRGLGQRKIKKLNNNNYKFSSSLLPQHMFLESP    101
AY011121.1    AADAAAAKTSQPGPDTILRLFPRVQQVEGSSSKDPVRIPAQFPRRLLLEN    138
CB878982.1    --------------------------------------------------    0
BE351081.1    --------------------------------------------------    0
AY077758.1    YAGVFLESSNFFRENSQETSRDRIVSSGHASPSQFTPTSSSKPPQSPELQ    139
CO210220.1    --------------------------------------------------    0
CF205668.1    --------------------------------------------------    0
CV281864.1    -----------------------------------GFKKMISILNRT---    12
AA032878.1    GTSESSLAGASEPAADGQQQQQQVDCREITDMTVSKFKKVISILNHR---    81
DAA05115.1    -------RSPAPAPAQEQQQQQQVDCREITDMTVSKFKKVISMLNR----    83
AB020023.1    PVQLDCREITDFTLSKFKKVVSILDRTGHARFRRGPVQVHP---------    83
CK285284.1    PVQLDCREITDFTVSKFRKVISILDRTGHARFRRGQVQVHP---------    83
BT014501.1    PVQADCREMADFTVSKFKKVISILDRTGHARFRRGPVQAQAPAPVQVRAP    84
CV707438.1    --------------------------------------------------    0
AAS86778.1    QHTVDCSEITDFTVSKFKTVISLLNRTGHARFRRGPVRSSPVVSP-----    88
U58834.1      GLQSVENLIKAISQSNHQTAYLSSSSSSETGDTDYRAVTDVAVNKFKKFI    78
BP083458.1    --------------------------------------------------    0
BM338249.1    --------------------------------------------------    0
BF281318.1    -----------------GTHHPRAKLVSRRQTPGFLSQKSFLDSNTPVVV    33
CA141214.1    SNGGVGVGEAGPSDASGSASHPRAKLVSRRQNPGFLTQKGFLDTNTSVVV    53
ORF09         AKFRKVVSLLGNEGGGGAVSHPRAKVASRKQTPAFLSQKGFLDNNTPVVV    82
CV000669.1    -------------------------------------HRNFMENPIQGID    13
BM858319.1    --------------------------------------------------    0
AK070848.1    HARGRMAGRSRPSAVLREKGFLESSSGGGQLGMVMSGAATPSTSSAAHLR    150
CV782182.1    --------------------------------------------------    0
```

FIGURE 15-3

```
CO082212.1   -------------------LSIWEPHVWNCARMVKTSLPLAQQPPPPAHY   31
CO803744.1   --------------------------------------------------   0
BU835049.1   --------------------------------------------------   0
CO878572.1   --------------------------------------QQQQQQQQQRLL   12
CA821208.1   --------------------------------------------------   0
BG351756.1   NVKCNLTLGSPSLELSSNSRNPLNFGQQTPFPSYNYLQQQQQQQQQQQQQ   81
CD484084.1   RGESPFETFHVPAISTGDTQIEQPISDSKTQLQIQGPNTHLQIIQQQQIQ   52
BJ578589.1   --------------------------------------------------   0
BX831747.1   VCSNNAISGCIPILAPKPLQIVPAGPPPLMLFNQNMCLDKSFLELKPPSS   151
AY011121.1   PSVGSNGPARGPPVQLVQPVSVAPPAGTPAPALPAAHLHFIQQQQSYQRF   188
CB878982.1   --------------------------------------------------   0
BE361081.1   --------------------------------------------------   0
AY077758.1   AIKYKVFPQSSRSADATPASSDPASGVHHPKPLQILHSSMMQQSIPEHIL   189
CO210220.1   --------------------------------------------------   0
CF205688.1   --------------------------------------------------   0
CV281864.1   ---------GHARFRRGPTHQPQDPPPAIHSPTPIQAVMPPAPHSLTLDF   53
AA032878.1   ---------TGHARFRRGPVVAQSQGPSVSEPAPVRTAS--SSRPMTLDF   130
DAA05115.1   ---------TGHARFRRGPVVAQSSGPAASEPAPVRSSPSAVSRPMTLDF   124
AB020023.1   -------DNFTSLSLSPSN---QQLLNLAPAKETPPP--PSVSLPLTALT   121
CK285284.1   -------DNFTSLSLSPSN---QQLLNLAPAKETPPPRPPSVSPPLTALT   123
BT014501.1   VRGPVYPDSFTSLSLAPSLSFATAKERLAPSLSFASAKERPVVQVQTALT   134
CV707438.1   --------------------------------------------------   0
AAS86778.1   ------PLPQIVKTAPIVSQPLRTTTNLSQTAPPPSSFVLPRQPRRSHSD   130
U56834.1     SLLDKNRTGHARFRRGPVQEKTGVEMLVNPIQNQIQNHGSDGFQVYRPTA   136
BP083458.1   --------------------------------------------------   0
BM338249.1   --------------------------------------------------   0
BF201318.1   LN-SAHPSTSSAQVYPRNSILESQP-AHPIGGPPKLVQPLSAHFQFGDSS   81
CA141214.1   LN-SAHPSPTSAQVYPRTAVALDAQGVHPLGGPPKLVQPLSAHFQFGNVP   102
ORF59        LNSSAHPSTSSAQAYPRNTILDSHT-AHPIGGPPKLVQPLSAHFQFGNVS   141
CV000669.1   SSGGNTLQLAKNMFLENPTQELDSSAAAAAVAAAAKNHLQSTHLQFLQ--   81
BM858319.1   --------------------------------------------------   0
AK070848.1   NRIGGGSGVPPDSLRGLDLVSSSSKGGAHQFDPPKLVQPLSVQFQFGATA   200
CV782182.1   -------------------------------------------NKFVQKS   7
```

FIGURE 15-4

| | | |
|---|---|---|
| CO082212.1 | T - - - - - - - - - - - - - - - | 225 |
| CO803744.1 | T T - - - - - - - - - - - - - - | 178 |
| BU835049.1 | N T - - - - - - - - - - - - - - | 184 |
| CO879572.1 | N A - - - - - - - - - - - - - - | 207 |
| CA821208.1 | N A - - - - - - - - - - - - - - | 188 |
| BG351755.1 | - - - - - - - - - - - - - - - - | 259 |
| CD484084.1 | Q S - - - - - - - - - - - - - - | 248 |
| BJ578580.1 | N T - - - - - - - - - - - - - - | 148 |
| BX831747.1 | A H T - - - - - - - - - - - - - | 348 |
| AY011121.1 | - - - - - - - - - - - - - - - - | 388 |
| CB879982.1 | A - - - - - - - - - - - - - - - | 183 |
| BE381081.1 | - - - - - - - - - - - - - - - - | 132 |
| AY077758.1 | G L T V Q S Q - - - - - - - - - | 395 |
| CO210220.1 | S L I V H P - - - - - - - - - - | 118 |
| CF205888.1 | G L M F P S T - - - - - - - - - | 188 |
| CV291864.1 | L I L K Q S E - - - - - - - - - | 248 |
| AAD32878.1 | A A L T P L P E L H K L - - - - | 321 |
| DAA05115.1 | H P P A P P P P L A L P L A - - | 330 |
| AB020023.1 | N T Q M M V F G S T E E R R E - | 328 |
| CK285284.1 | N S Q M M A F - - - - - - - - - | 322 |
| BT014501.1 | N S S Q M V N F G L M E K K - - | 338 |
| CV707438.1 | V V P A G V G L V F E S T - - - | 183 |
| AAS84778.1 | E T I S S S G V N D L V F A S A | 334 |
| U58834.1 | N T S H I L E S D G L K Q S - - | 341 |
| BP083458.1 | N L I L E S S - - - - - - - - - | 131 |
| BM338249.1 | A A A A Q V - - - - - - - - - - | 118 |
| BF281318.1 | - - - - - - - - - - - - - - - - | 214 |
| CA141214.1 | - - - - - - - - - - - - - - - - | 237 |
| ORF89 | Q A - - - - - - - - - - - - - - | 343 |
| CV000689.1 | - - - - - - - - - - - - - - - - | 188 |
| BM858318.1 | - - - - - - - - - - - - - - - - | 159 |
| AK070648.1 | Q T - - - - - - - - - - - - - - | 380 |
| CV782182.1 | Q A - - - - - - - - - - - - - - | 208 |

FIGURE 15-9

GAATTTCTAGTTCTAGATGCATGCTCGAAATTCGATTGGCGCGCCTTAATTAATAAGAGCAGCTTGCCAACATGGTGGAGCACGACACTCT
CGTCTACTCCAAGAATATCAAAGATACAGTCTCAGAAGACCAAAGGGCTATTGAGACTTTTCAACAAAGGGTAATATCGGGAAACCTCCTC
GGATTCCATTGCCCAGCTATCTGTCACTTCATCAAAAGGACAGTAGAAAAGGAAGGTGGCACCTACAAATGCCATCATTGCGATAAAGGAA
AGGCTATCGTTCAAGATGCCTCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGAACATGGTGGAGCACGACACTCTCGTCTACTCCAAGAATATCAAAGATACAGTCTCAGAAGG
CCAAAGGGCTATTGAGACTTTTCAACAAAGGGTAATATCGGGAAACCTCCTCGGATTCCATTGCCCAGCTATCTGTCACTTCATCAAAAGG
ACAGTAGAAAAGGAAGGTGGCACCTACAAATGCCATCATTGCGATAAAGGAAAGGCTATCGTTCAAGATGCCTCTGCCGACAGTGGTCCCAA
AGATGGACCCCCACCCACGAGGAGCATCGTGGAAAAAGAAGACGTTCCAACCACGTCTTCAAAGCAAGTGGATTGATGTGATATCTCCACT
GACGTAAGGGATGACGCACAATCCCACTATCCTTCGCAAGACCCTTCCTCTATATAAGGAAGTTCATTTCATTTGGAGAGGACACGCTGAA
ATCACCAGTCTCTCTCTACAAATCTATCTCTCTCCATTAGTA*ATGGGTTCGGAGACCTTTCTGGAGATCCTGCTGGCCATCCTGCTGCCGC*
*CGCTCGGCGTTTTCCTCCGCTTCGGCATCGGCGTAAGCTACCAAACCATTCAGCGATTTCAGGGTGTGTATGTAATGATAGATATATTGAT*
*TTGATGGTCGGTTCATGCATGTCTGCAGGTGGAGTTCTGGATCTGCCTGCTACTCACCCTGCTGGGCTACATCCCCGGCATCATCTACGCC*
*GTCTTCGTCCTTGTTGCATAGA*GGCCTGGTTTCTCCATAATAATGTGTGAGTAGTTCCCAGATAAGGGAATTAGGGTTCCTATAGGGTTTC
GCTCATGTGTTGAGCATATAAGAAACCCTTAGTATGTATTTGTATTTGTAAAATACTTCTATCAATAAAATTTCTAATTCCTAAAACCAAA
ATCCAGTACTAAAATCCAGATCCCCCGAATTAATTCGGCGTTAATTCAGTATCGGCGCGCCTTAATTAAAATCGAATTTCGACCATACTAG
TGGATCCCCCTCGGACTAGAAGCTTGGCACTGGCCGTCGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCGATCGCCCTTCCCAACAGTTGCGCAGCCTGAATGGCGAA
TGCTAGAGCAGCTTGAGCTTGGATCAGATTGTCGTTTCCCGCCTTCAGTTTAAACTATCAGTGTTTGACAGGATATATTGGCGGGTAAACC
TAAGAGAAAAGAGCGTTTATTAGAATAACGGATATTTAAAAGGGCGTGAAAAGGTTTATCCGTTCGTCCATTTGTATGTGCATGCCAACCA
CAGGGTTCCCCTCGGGATCAAAGTACTTTGATCCAACCCCTCCGCTGCTATAGTGCAGTCGGCTTCTGACGTTCAGTGCAGCCGTCTTCTG
AAAACGACATGTCGCACAAGTCCTAAGTTACGCGACAGGCTGCCGCCCTGCCCTTTTCCTGGCGTTTTCTTGTCGCGTGTTTTAGTCGCAT
AAAGTAGAATACTTGCGACTAGAACCGGAGACATTACGCCATGAACAAGAGCGCCGCCGCTGGCCTGCTGGGCTATGCCCGCGTCAGCACC
GACGACCAGGACTTGACCAACCAACGGGCCGAACTGCACGCGGCCGGCTGCACCAAGCTGTTTTCCGAGAAGATCACCGGCACCAGGCGCG
ACCGCCCGGAGCTGGCCAGGATGCTTGACCACCTACGCCCTGGCGACGTTGTGACAGTGACCAGGCTAGACCGCCTGGCCCGCAGCACCCG
CGACCTACTGGACATTGCCGAGCGCATCCAGGAGGCCGGCGCGGGCCTGCGTAGCCTGGCAGAGCCGTGGGCCGACACCACCACGCCGGCC
GGCCGCATGGTGTTGACCGTGTTCGCCGGCATTGCCGAGTTCGAGCGTTCCCTAATCATCGACCGCACCCGGAGCGGGCGCGAGGCCGCCA
AGGCCCGAGGCGTGAAGTTTGGCCCCCGCCCTACCCTCACCCCGGCACAGATCGCGCACGCCCGCGAGCTGATCGACCAGGAAGGCCGCAC
CGTGAAAGAGGCGGCTGCACTGCTTGGCGTGCATCGCTCGACCCTGTACCGCGCACTTGAGCGCAGCGAGGAAGTGACGCCCACCGAGGCC
AGGCGGCGCGGTGCCTTCCGTGAGGACGCATTGACCGAGGCCGACGCCCTGGCGGCCGCCGAGAATGAACGCCAAGAGGAACAAGCATGAA
ACCGCACCAGGACGGCCAGGACGAACCGTTTTTCATTACCGAAGAGATCGAGGCGGAGATGATCGCGGCCGGGTACGTGTTCGAGCCGCCC
GCGCACGTCTCAACCGTGCGGCTGCATGAAATCCTGGCCGGTTTGTCTGATGCCAAGCTGGCGGCCTGGCCGGCCAGCTTGGCCGCTGAAG
AAACCGAGCGCCGCCGTCTAAAAAGGTGATGTGTATTTGAGTAAAACAGCTTGCGTCATGCGGTCGCTGCGTATATGATGCGATGAGTAAA
TAAACAAATACGCAAGGGGAACGCATGAAGGTTATCGCTGTACTTAACCAGAAAGGCGGGTCAGGCAAGACGACCATCGCAACCCATCTAG
CCCGCGCCCTGCAACTCGCCGGGGCCGATGTTCTGTTAGTCGATTCCGATCCCCAGGGCAGTGCCCGCGATTGGGCGGCCGTGCGGGAAGA
TCAACCGCTAACCGTTGTCGGCATCGACCGCCCGACGATTGACCGCGACGTGAAGGCCATCGGCCGGCGCGACTTCGTAGTGATCGACGGA
GCGCCCCAGGCGGCGGACTTGGCTGTGTCCGCGATCAAGGCAGCCGACTTCGTGCTGATTCCGGTGCAGCCAAGCCCTTACGACATATGGG
CCACCGCCGACCTGGTGGAGCTGGTTAAGCAGCGCATTGAGGTCACGGATGGAAGGCTACAAGCGGCCTTTGTCGTGTCGCGGGCGATCAA
AGGCACGCGCATCGGCGGTGAGGTTGCCGAGGCGCTGGCCGGGTACGAGCTGCCCATTCTTGAGTCCCGTATCACGCAGCGCGTGAGCTAC
CCAGGCACTGCCGCCGCCGGCACAACCGTTCTTGAATCAGAACCCGAGGGCGACGCTGCCCGCGAGGTCCAGGCGCTGGCCGCTGAAATTA
AATCAAAACTCATTTGAGTTAATGAGGTAAAGAGAAAATGAGCAAAAGCACAAACACGCTAAGTGCCGGCCGTCCGAGCGCACGCAGCAGC
AAGGCTGCAACGTTGGCCAGCCTGGCAGACACGCCAGCCATGAAGCGGGTCAACTTTCAGTTGCCGGCGGAGGATCACACCAAGCTGAAGA
TGTACGCGGTACGCCAAGGCAAGACCATTACCGAGCTGCTATCTGAATACATCGCGCAGCTACCAGAGTAAATGAGCAAATGAATAAATGA
GTAGATGAATTTTAGCGGCTAAAGGAGGCGGCATGGAAAATCAAGAACAACCAGGCACCGACGCCGTGGAATGCCCCATGTGTGGAGGAAC
GGGCGGTTGGCCAGGCGTAAGCGGCTGGGTTCTCTGCCGGCCCTGCAATGGCACTGGAACCCCCAAGCCCGAGGAATCGGCGTGACGGTCG
CAAACCATCCGGCCCGGTACAAATCGGCGCGGCGCTGGGTGATGACCTGGTGGAGAAGTTGAAGGCCGCGCAGGCCGCCCAGCGGCAACGC
ATCGAGGCAGAAGCACGCCCCGGTGAATCGTGGCAAGCGGCCGCTGATCGAATCCGCAAAGAATCCCGGCAACCGCCGGCAGCCGGTGCGC
CGTCGATTAGGAAGCCGCCCAAGGGCGACGAGCAACCAGATTTTTTCGTTCCGATGCTCTATGACGTGGGCACCCGCGATAGTCGCAGCAT
CATGGACGTGGCCGTTTTCCGTCTGTCGAAGCGTGACCGACGAGCTGGCGAGGTGATCCGCTACGAGCTTCCAGACGGGCACGTAGAGGTT
TCCGCAGGGCCGGCCGGCATGGCCAGTGTGTGGGATTACGACCTGGTACTGATGGCGGTTTCCCATCTAACCGAATCCATGAACCGATACC
GGGAAGGGAAGGGAGACAAGCCCGGCCGCGTGTTCCGTCCACACGTTGCGGACGTACTCAAGTTCTGCCGGCGAGCCGATGGCGGAAAGCA
GAAAGACGACCTGGTAGAAACCTGCATTCGGTTAAACACCACGCACGTTGCCATGCAGCGTACGAAGAAGGCCAAGAACGGCCGCCTGGTG
ACGGTATCCGAGGGTGAAGCCTTGATTAGCCGCTACAAGATCGTAAAGAGCGAAACCGGGCGGCCGGAGTACATCGAGATCGAGCTAGCTG
ATTGGATGTACCGCGAGATCACAGAAGGCAAGAACCCGGACGTGCTGACGGTTCACCCCGATTACTTTTTGATCGATCCCGGCATCGGCCG
TTTTCTCTACCGCCTGGCACGCCGCGCCGCAGGCAAGGCAGAAGCCAGATGGTTGTTCAAGACGATCTACGAACGCAGTGGCAGCGCCGGA
GAGTTCAAGAAGTTCTGTTTCACCGTGCGCAAGCTGATCGGGTCAAATGACCTGCCGGAGTACGATTTGAAGGAGGAGGCGGGGCAGGCTG
GCCCGATCCTAGTCATGCGCTACCGCAACCTGATCGAGGGCGAAGCATCCGCCGGTTCCTAATGTACGGAGCAGATGCTAGGGCAAATTGC
CCTAGCAGGGGAAAAAGGTCGAAAAGGTCTCTTTCCTGTGGATAGCACGTACATTGGGAACCCAAAGCCGTACATTGGGAACCGGAACCCG
TACATTGGGAACCCAAAGCCGTACATTGGGAACCGGTCACACATGTAAGTGACTGATATAAAAGAGAAAAAAGGCGATTTTTCCGCCTAAA
ACTCTTTAAAACTTATTAAAACTCTTAAAACCCGCCTGGCCTGTGCATAACTGTCTGGCCAGCGCACAGCCGAAGAGCTGCAAAAAGCGCC
TACCCTTCGGTCGCTGCGCTCCCTACGCCCCGCCGCTTCGCGTCGGCCTATCGCGGCCGCTGGCCGCTCAAAAATGGCTGGCCTACGGCCA
GGCAATCTACCAGGGCGCGGACAAGCCGCGCCGTCGCCACTCGACCGCCGGCGCCCACATCAAGGCACCCTGCCTCGCGCGTTTCGGTGAT
GACGGTGAAAACCTCTGACACATGCAGCTCCCGGAGACGGTCACAGCTTGTCTGTAAGCGGATGCCGGGAGCAGACAAGCCCGTCAGGGCG
CGTCAGCGGGTGTTGGCGGGTGTCGGGGCGCAGCCATGACCCAGTCACGTAGCGATAGCGGAGTGTATACTGGCTTAACTATGCGGCATCA
GAGCAGATTGTACTGAGAGTGCACCATATGCGGTGTGAAATACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGGACAGTATTTGGTATCTGCGCTCT

FIGURE 17-1

GCTGAAGCCAGTTACCTTCGGAAAAAGAGTTGGTAGCTCTTGATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTTTTCTACGGGGTCTGACGCTCAGTGGAACGAAAACTCACGTT
AAGGGATTTTGGTCATGCATTCTAGGTACTAAAACAATTCATCCAGTAAAATATAATATTTTATTTTCTCCCAATCAGGCTTGATCCCCAG
TAAGTCAAAAAATAGCTCGACATACTGTTCTTCCCCGATATCCTCCCTGATCGACCGGACGCAGAAGGCAATGTCATACCACTTGTCCGCC
CTGCCGCTTCTCCCAAGATCAATAAAGCCACTTACTTTGCCATCTTTCACAAAGATGTTGCTGTCTCCCAGGTCGCCGTGGGAAAAGACAA
GTTCCTCTTCGGGCTTTTCCGTCTTTAAAAAATCATACAGCTCGCGCGCATCTTTAAATGGAGTGTCTTCTTCCCAGTTTTCGCAATCCAC
ATCGGCCAGATCGTTATTCAGTAAGTAATCCAATTCGGCTAAGCGGCTGTCTAAGCTATTCGTATAGGGACAATCCGATATGTCGATGGAG
TGAAAGAGCCTGATGCACTCCGCATACAGCTCGATAATCTTTTCAGGGCTTTGTTCATCTTCATACTCTTCCGAGCAAAGGACGCCATCGG
CCTCACTCATGAGCAGATTGCTCCAGCCATCATGCCGTTCAAAGTGCAGGACCTTTGGAACAGGCAGCTTTCCTTCCAGCCATAGCATCAT
GTCCTTTTCCCGTTCCACATCATAGGTGGTCCCTTTATACCGGCTGTCCGTCATTTTTAAATATAGGTTTTCATTTTCTCCCACCAGCTTA
TATACCTTAGCAGGAGACATTCCTTCCGTATCTTTTACGCAGCGGTATTTTTCGATCAGTTTTTTCAATTCCGGTGATATTCTCATTTTAG
CCATTTATTATTTCCTTCCTCTTTTCTACAGTATTTAAAGATACCCCAAGAAGCTAATTATAACAAGACGAACTCCAATTCACTGTTCCTT
GCATTCTAAAACCTTAAATACCAGAAAACAGCTTTTTCAAAGTTGTTTTCAAAGTTGGCGTATAACATAGTATCGACGGAGCCGATTTTGA
AACCGCGGTGATCACAGGCAGCAACGCTCTGTCATCGTTACAATCAACATGCTACCCTCCGCGAGATCATCCGTGTTTCAAACCCGGCAGC
TTAGTTGCCGTTCTTCCGAATAGCATCGGTAACATGAGCAAAGTCTGCCGCCTTACAACGGCTCTCCCGCTGACGCCGTCCCGGACTGATG
GGCTGCCTGTATCGAGTGGTGATTTTGTGCCGAGCTGCCGGTCGGGGAGCTGTTGGCTGGCTGGTGGCAGGATATATTGTGGTGTAAACAA
ATTGACGCTTAGACAACTTAATAACACATTGCGGACGTTTTTAATGTACTGAATTAACGCCGAATTAATTCGGGGGATCTGGATTTTAGTA
CTGGATTTTGGTTTTAGGAATTAGAAATTTTATTGATAGAAGTATTTTACAAATACAAATACATACTAAGGGTTTCTTATATGCTCAACAC
ATGAGCGAAACCCTATAGGAACCCTAATTCCCTTATCTGGGAACTACTCACACATTATTATGGAGAAACTCGAGCTTGTCGATCGACAGAT
CCGGTCGGCATCTACTCTATTTCTTTGCCCTCGGACGAGTGCTGGGGCGTCGGTTTCCACTATCGGCGAGTACTTCTACACAGCCATCGGT
CCAGACGGCCGCGCTTCTGCGGGCGATTTGTGTACGCCCGACAGTCCCGGCTCCGGATCGGACGATTGCGTCGCATCGACCCTGCGCCCAA
GCTGCATCATCGAAATTGCCGTCAACCAAGCTCTGATAGAGTTGGTCAAGACCAATGCGGAGCATATACGCCCGGAGTCGTGGCGATCCTG
CAAGCTCCGGATGCCTCCGCTCGAAGTAGCGCGTCTGCTGCTCCATACAAGCCAACCACGGCCTCCAGAAGAAGATGTTGGCGACCTCGTA
TTGGGAATCCCCGAACATCGCCTCGCTCCAGTCAATGACCGCTGTTATGCGGCCATTGTCCGTCAGGACATTGTTGGAGCCGAAATCCGCG
TGCACGAGGTGCCGGACTTCGGGGCAGTCCTCGGCCCAAAGCATCAGCTCATCGAGAGCCTGCGCGACGGACGCACTGACGGTGTCGTCCA
TCACAGTTTGCCAGTGATACACATGGGGATCAGCAATCGCGCATATGAAATCACGCCATGTAGTGTATTGACCGATTCCTTGCGGTCCGAA
TGGGCCGAACCCGCTCGTCTGGCTAAGATCGGCCGCAGCGATCGCATCCATAGCCTCCGCGACCGGTTGTAGAACAGCGGGCAGTTCGGTT
TCAGGCAGGTCTTGCAACGTGACACCCTGTGCACGGCGGGAGATGCAATAGGTCAGGCTCTCGCTAAACTCCCCAATGTCAAGCACTTCCG
GAATCGGGAGCGCGGCCGATGCAAAGTGCCGATAAACATAACGATCTTTGTAGAAACCATCGGCGCAGCTATTTACCCGCAGGACATATCC
ACGCCCTCCTACATCGAAGCTGAAAGCACGAGATTCTTCGCCCTCCGAGAGCTGCATCAGGTCGGAGACGCTGTCGAACTTTTCGATCAGA
AACTTCTCGACAGACGTCGCGGTGAGTTCAGGCTTTTTCATATCTCATTGCCCCCCGGATCTGCGAAAGCTCGAGAGAGATAGATTTGTA
GAGAGAGACTGGTGATTTCAGCGTGTCCTCTCCAAATGAAATGAACTTCCTTATATAGAGGAAGGTCTTGCGAAGGATAGTGGGATTGTGC
GTCATCCCTTACGTCAGTGGAGATATCACATCAATCCACTTGCTTTGAAGACGTGGTTGGAACGTCTTCTTTTTCCACGATGCTCCTCGTG
GGTGGGGGTCCATCTTTGGGACCACTGTCGGCAGAGGCATCTTGAACGATAGCCTTTCCTTTATCGCAATGATGGCATTTGTAGGTGCCAC
CTTCCTTTTCTACTGTCCTTTTGATGAAGTGACAGATAGCTGGGCAATGGAATCCGAGGAGGTTTCCCGATATTACCCTTTGTTGAAAAGT
CTCAATAGCCCTTTGGTCTTCTGAGACTGTATCTTTGATATTCTTGGAGTAGACGAGAGTGTCGTGCTCCACCATGTTATCACATCAATCC
ACTTGCTTTGAAGACGTGGTTGGAACGTCTTCTTTTTCCACGATGCTCCTCGTGGGTGGGGGTCCATCTTTGGGACCACTGTCGGCAGAGG
CATCTTGAACGATAGCCTTTCCTTTATCGCAATGATGGCATTTGTAGGTGCCACCTTCCTTTTCTACTGTCCTTTTGATGAAGTGACAGAT
AGCTGGGCAATGGAATCCGAGGAGGTTTCCCGATATTACCCTTTGTTGAAAAGTCTCAATAGCCCTTTGGTCTTCTGAGACTGTATCTTTG
ATATTCTTGGAGTAGACGAGAGTGTCGTGCTCCACCATGTTGGCAAGCTGCTCTAGCCAATACGCAAACCGCCTCTCCCCGCGCGTTGGCC
GATTCATTAATGCAGCTGGCACGACAGGTTTCCCGACTGGAAAGCGGGCAGTGAGCGCAACGCAATTAATGTGAGTTAGCTCACTCATTAG
GCACCCCAGGCTTTACACTTTATGCTTCCGGCTCGTATGTTGTGTGGAATTGTGAGCGGATAACAATTTCACACAGGAAACAGCTATGACC
ATGATTAC

SEQ ID NO: 247

GCGCACATTTCCCCGAAAAGTGCCACCTGATGCGGTGTGAAATACCGCACAGATGCGTAAGGAGAAAATACCGCATCAG
GAAATTGTAAGCGTTAATATTTTGTTAAAATTCGCGTTAAATTTTTGTTAAATCAGCTCATTTTTTAACCAATAGGCCGAA
ATCGGCAAAATCCCTTATAAATCAAAAGAATAGACCGAGATAGGGTTGAGTGTTGTTCCAGTTTGGAACAAGAGTCCACT
ATTAAAGAACGTGGACTCCAACGTCAAAGGGCGAAAAACCGTCTATCAGGGCGATGGCCCACTACGTGAACCATCACCC
TAATCAAGTTTTTTGGGGTCGAGGTGCCGTAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGCGGGCGCTAGGGCGCTGGCAAGTGTAG
CGGTCACGCTGCGCGTAACCACCACACCCGCCGCGCTTAATGCGCCGCTACAGGGCGCGTCCATTCGCCATTCAGGCTGC
GCAACTGTTGGGAAGGGCGATCGGTGCGGGCCTCTTCGCTATTACGCCAGCTGGCGAAAGGGGGATGTGCTGCAAGGCG
ATTAAGTTGGGTAACGCCAGGGTTTTCCCAGTCACGACGTTGTAAAACGACGGCCAGTGAATTGTAATACGACTCACTAT
AGGGCGAATTGGGCCCGACGTCGCATGCTCCCGGCCGCCATGGCGGCCGCGGGAATTCGATTGATTGGCGCGCCTTAATT
AACGGGCTGGTAAAACAAATATAAGTATTAATATAAATATAATACAATAGAAGGAAAATAAATAAAATTTCCCTCT
GTGCCGTGCAAAAATGCACGGCAATGGGTTGGCCCGCACGGCAAAGGCATCGTTGCCGTGTCCACGGCAATGGGT
TGGCCCGCACGGCAAAGGCATCGTTGCCGTGTCCACGTCTTTGCCGTGCGCCTTGGCTCTATCTTTGCCGTGAAG
CGTTCTTTGCCGTGTGCCTTTTATTTCTTTGCCGTGGGATGCTGCCTTTGCCGAGCGCTGAGCTGGCGCTTTGCCG
TGCGCGTATTGTTTGCCGTGCGTCCTCCCAGAGCTGTACGGCAAAGAATTCATTGCCGTGCACGAGGCACACGGG
AAAGAAGTTTCGCATGGCAAAGGGCGCTGACAGCACACGGCAAAGAGCCCGGCACGGCATTGAGCTTTTTTTCCC
GTAATGATAGACGGCATAATATAATGGACGCACATGCTGATGTCAGGATGTCACCCACTCATCCTAGTATTTGTGG
GACGTGAATTCTTTGTGAGATGGGCAATGGGATGTGAACAAAATAAGTTTTGTACTAGTAGATAAACATTTTTACC
CATAAACAATTGTTCTGTATTGAATGAAAAATTATTTTGTACTGGATGAAAATCTTCTGAGTAACTGTGTAAGATTA
ACATGAATCAAGAGACAAATCCAATGGCTACAAAGTCAACTAATACTTGTTAAAAGTTCCGATACTTAAAATTATC
AAAACTGATATATAGAATATTGCCCATCTCGCCACCGTGCTAGTTTAACAGACGATGGACGAATATCAGTCTTGTA
TTGGATAATCGATGCATGCGAGCTATCGGTCACCTGTCCATGCTTCCAGAAGGAGCCGAGACGTGGCGACTTCGT
CCGACGCGCCGACTATCTGCACACGCCCGGCTTCTCGTCGTGGGCGAGTCAGCAGTCACAGGCTTTCCGCCTACC
AACTCACACGTAGCGCCCTATCGTGGCGCTTGATCGATGCAACAGCGATGCCTATCCCAGCTCCTCAAGCTGCTTA
TAAGTATGTCCTCGGCCATCACTGCTTACACAACAAACACAGCTACTTATCGCAGTGTACTAAACAAGACGTACTAGCTAGATTTCGTGAG
GTAAAATCAGTGCAATATCACTTGTGCAAGCCATTAGT*ATGGGTTCGGAGACCTTTCTGGAGATCCTGCTGGCCATCCTGCTGCCGCCGCT*
*CGGCGTTTTCCTCCGCTTCGGCATCGGCGTAAGCTACCAAACCATTCAGCGATTTCAGGGTGTGTATGTAATGATAGATATATTGATTTGA*
*TGGTCGGTTCATGCATGTCTGCAGGTGGAGTTCTGGATCTGCCTGCTACTCACCCTGCTGGGCTACATCCCCGGCATCATCTACGCCGTCT*
*TCGTCCTTGTTGCATAG*AGGCCTGGTTTCTCCATAATAATGTGTGAGTAGTTCCCAGATAAGGGAATTAGGGTTCCTATAGG
GTTTCGCTCATGTGTTGAGCATATAAGAAACCCTTAGTATGTATTTGTATTTGTAAAATACTTCTATCAATAAAATTTCTA
ATTCCTAAAACCAAAATCCAGTACTAAAATCCAGATCCCCCGAATTAATTCGGCGTTAATTCAGTATCGGCGCGCCTTAA
TTAAAATCGAATTTCGACCATATGGGAGAGCTCCCAACGCGTTGGATGCATAGCTTGAGTATTCTATAGTGTCACCTAAA
TAGCTTGGCGTAATCATGGTCATAGCTGTTTCCTGTGTGAAATTGTTATCCGCTCACAATTCCACACAACATACGAGCCGG
AAGCATAAAGTGTAAAGCCTGGGGTGCCTAATGAGTGAGCTAACTCACATTAATTGCGTTGCGCTCACTGCCCGCTTTCC
AGTCGGGAAACCTGTCGTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAAAAGGCCAGGAACCGTAAA
AAGGCCGCGTTGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTTGGTATCTGCG
CTCTGCTGAAGCCAGTTACCTTCGGAAAAAGAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTATTAATTGTTGCCGGGAAGC
TAGAGTAAGTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGGTTATGGCAGCACTGCATAATT
CTCTTACTGTCATGCCATCCGTAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCC

SEQ ID NO: 243

| | | |
|---|---|---|
| CD913648 | -------------------------------------------------- | 54 |
| BI780134 | -------------------------------------------------- | 54 |
| ORF9 | -------------------------------------------------- | 54 |
| AY107179 | -------------------------------------------------- | 54 |
| CF042363 | -------------------------------------------------- | 54 |
| CD229091 | -------------------------------------------------- | 54 |
| AAS72368 | -------------------------------------------------- | 54 |
| AC093089 | -------------------------------------------------- | 77 |
| CF318949 | -------------------------------------------------- | 54 |
| AY080604 | -------------------------------------------------- | 53 |
| AC005770 | -------------------------------------------------- | 78 |
| CN183349 | -------------------------------------------------- | 53 |
| CA838518 | -------------------------------------------------- | 54 |
| BU870656 | -------------------------------------------------- | 53 |
| Q8ARD5 | -------------------------------------------------- | 54 |
| AJ310895 | -------------------------------------------------- | 80 |
| U00968.1 | -------------------------------------------------- | 53 |
| AJ310894 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY807889 | -------------------------------------------------- | 46 |
| AY105302 | -------------------------------------------------- | 57 |
| NM-183567 | NKPWVGNDLPCDDCDKRLFQAATTINYGNGEKINFWHDKWLQNTCPKDIA | 117 |
| AY554051 | -------------------------------------------------- | 51 |
| NM-184595 | -------------------------------------------------- | 64 |
| AY084701 | -------------------------------------------------- | 52 |
| AB081265 | -------------------------------------------------- | 56 |
| AY316308 | -------------------------------------------------- | 52 |
| AAR87855 | -------------------------------------------------- | 59 |
| BXB42170 | -------------------------------------------------- | 52 |
| BXB25889 | -------------------------------------------------- | 52 |
| AY496072 | -------------------------------------------------- | 49 |
| AB030211 | -------------------------------------------------- | 51 |
| AK062410 | -------------------------------------------------- | 51 |
| AY106884 | -------------------------------------------------- | 51 |
| AAN06944 | DYIYVA-------------------------------------------- | 68 |
| NP-194795 | RPIYSA-------------------------------------------- | 74 |
| NP-179882 | RPIYYVA------------------------------------------- | 75 |
| NP-B74820 | RPLFYAQSP----------------------------------------- | 77 |
| NP-194794 | APLNSA-------------------------------------------- | 73 |
| AAT11798 | APLNSA-------------------------------------------- | 74 |

FIGURE 20-3

```
CD913648    --------------------------------------------------  54
BI780134    --------------------------------------------------  54
ORF9        --------------------------------------------------  54
AY107179    --------------------------------------------------  54
CF042363    --------------------------------------------------  54
CD229091    --------------------------------------------------  54
AAS72365    --------------------------------------------------  54
AC093089    --------------------------------------------------  77
CF319949    --------------------------------------------------  54
AY080504    --------------------------------------------------  53
AC005770    --------------------------------------------------  78
CN183348    --------------------------------------------------  53
CA236518    --------------------------------------------------  54
BU870658    --------------------------------------------------  53
Q6ARD5      --------------------------------------------------  54
AJ310895    --------------------------------------------------  80
U00968.1    --------------------------------------------------  53
AJ310894    --------------------------------------------------  54
Z25537      --------------------------------------------------  53
AK070872    --------------------------------------------------  54
NM-104551   --------------------------------------------------  50
AY103848    --------------------------------------------------  51
AY807489    --------------------------------------------------  46
AY105302    --------------------------------------------------  57
NM-183567   PLCFNLAKRKQRSVKTELTNNSWLLSFRQITTIEEISDLVQLGGMLQNVQ  167
AY554051    --------------------------------------------------  51
NM-184595   --------------------------------------------------  64
AY084701    --------------------------------------------------  52
AB081265    --------------------------------------------------  56
AY316308    --------------------------------------------------  52
AAR87855    --------------------------------------------------  59
BX842170    --------------------------------------------------  52
BX825889    --------------------------------------------------  52
AY496072    --------------------------------------------------  49
AB030211    --------------------------------------------------  51
AK082410    --------------------------------------------------  51
AY108884    --------------------------------------------------  51
AAN08944    --------------------------------------------------  69
NP-194795   --------------------------------------------------  74
NP-179982   --------------------------------------------------  75
NP-974629   --------------------------------------------------  77
NP-194794   --------------------------------------------------  73
AAT11789    --------------------------------------------------  74
```

FIGURE 20-4

| | | |
|---|---|---|
| CD913848 | -------------------------------------------------- | 54 |
| BI780134 | -------------------------------------------------- | 54 |
| ORF9 | -------------------------------------------------- | 54 |
| AY107179 | -------------------------------------------------- | 54 |
| CF042363 | -------------------------------------------------- | 54 |
| CD229091 | -------------------------------------------------- | 54 |
| AAS72368 | -------------------------------------------------- | 54 |
| AC093089 | -------------------------------------------------- | 77 |
| CF319849 | -------------------------------------------------- | 54 |
| AY080604 | -------------------------------------------------- | 53 |
| AC005770 | -------------------------------------------------- | 78 |
| CN183349 | -------------------------------------------------- | 53 |
| CA838518 | -------------------------------------------------- | 54 |
| BU870656 | -------------------------------------------------- | 53 |
| Q9ARD5 | -------------------------------------------------- | 54 |
| AJ310885 | -------------------------------------------------- | 80 |
| U00868.1 | -------------------------------------------------- | 53 |
| AJ310884 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY807689 | -------------------------------------------------- | 48 |
| AY106302 | -------------------------------------------------- | 57 |
| NM-183587 | LLPQTNDDITWNLNESGSYSANSAYLFQFQGSFSSIDFHSIWRCPAEPKM | 217 |
| AY554051 | -------------------------------------------------- | 51 |
| NM-184686 | -------------------------------------------------- | 84 |
| AY084701 | -------------------------------------------------- | 52 |
| AB081265 | -------------------------------------------------- | 56 |
| AY318308 | -------------------------------------------------- | 53 |
| AAR87855 | -------------------------------------------------- | 58 |
| BX842170 | -------------------------------------------------- | 52 |
| BX825889 | -------------------------------------------------- | 52 |
| AY496072 | -------------------------------------------------- | 49 |
| AB030211 | -------------------------------------------------- | 51 |
| AK082410 | -------------------------------------------------- | 51 |
| AY106884 | -------------------------------------------------- | 51 |
| AAN06944 | -------------------------------------------------- | 68 |
| NP-194795 | -------------------------------------------------- | 74 |
| NP-179882 | -------------------------------------------------- | 75 |
| NP-974829 | -------------------------------------------------- | 77 |
| NP-194794 | -------------------------------------------------- | 73 |
| AAT11798 | -------------------------------------------------- | 74 |

FIGURE 20-5

```
CD813846     ---------------------------------------------------  54
BI780134     ---------------------------------------------------  54
ORF9         ---------------------------------------------------  54
AY107179     ---------------------------------------------------  54
CF042363     ---------------------------------------------------  51
CD229091     ---------------------------------------------------  54
AAS72308     ---------------------------------------------------  54
AC003D89     ---------------------------------------------------  77
CF319949     ---------------------------------------------------  54
AY080604     ---------------------------------------------------  53
AC005770     ---------------------------------------------------  78
CN183349     ---------------------------------------------------  53
CA836518     ---------------------------------------------------  54
BU870658     ---------------------------------------------------  53
Q8AR05       ---------------------------------------------------  54
AJ310995     ---------------------------------------------------  80
U00968.1     ---------------------------------------------------  53
AJ310994     ---------------------------------------------------  54
Z25537       ---------------------------------------------------  53
AK070872     ---------------------------------------------------  54
NM-104651    ---------------------------------------------------  50
AY103848     ---------------------------------------------------  51
AY507659     ---------------------------------------------------  48
AY105302     ---------------------------------------------------  57
NM-183567    RFFGWLILLHQKTLTAQNLLRRHWPCNWICSLCGEAFEDTNHLFNVCPFFR  267
AY554051     ---------------------------------------------------  51
NM-184595    ---------------------------------------------------  64
AY084701     ---------------------------------------------------  52
AB081265     ---------------------------------------------------  58
AY318308     ---------------------------------------------------  52
AAR87865     ---------------------------------------------------  59
BX842170     ---------------------------------------------------  52
BX825989     ---------------------------------------------------  52
AY488072     ---------------------------------------------------  49
AB030211     ---------------------------------------------------  51
AK062410     ---------------------------------------------------  51
AY108884     ---------------------------------------------------  51
AAN06944     ---------------------------------------------------  69
NP-194795    ---------------------------------------------------  74
NP-179982    ---------------------------------------------------  75
NP-974629    ---------------------------------------------------  77
NP-194794    ---------------------------------------------------  73
AAT11798     ---------------------------------------------------  74
```

FIGURE 20-6

| | | |
|---|---|---|
| CD813848 | -------------------------------------------------- | 54 |
| BI780134 | -------------------------------------------------- | 54 |
| ORF8 | -------------------------------------------------- | 54 |
| AY107179 | -------------------------------------------------- | 54 |
| CF042363 | -------------------------------------------------- | 54 |
| CD228091 | -------------------------------------------------- | 54 |
| AAS72368 | -------------------------------------------------- | 54 |
| AC093089 | -------------------------------------------------- | 77 |
| CF310942 | -------------------------------------------------- | 54 |
| AY080604 | -------------------------------------------------- | 53 |
| AC005770 | -------------------------------------------------- | 78 |
| CN183342 | -------------------------------------------------- | 53 |
| CA836518 | -------------------------------------------------- | 54 |
| BU870658 | -------------------------------------------------- | 53 |
| Q9ARD5 | -------------------------------------------------- | 54 |
| AJ310895 | -------------------------------------------------- | 80 |
| U00968.1 | -------------------------------------------------- | 53 |
| AJ310894 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY607889 | -------------------------------------------------- | 46 |
| AY106302 | -------------------------------------------------- | 57 |
| NM-183567 | K V W L M V S T C L S I L K V E D M T K S P S L S Q L L I R S C I S N G D A G S P R L V E T T Q P S | 317 |
| AY554051 | -------------------------------------------------- | 51 |
| NM-184595 | -------------------------------------------------- | 64 |
| AY084701 | -------------------------------------------------- | 52 |
| AB081265 | -------------------------------------------------- | 56 |
| AY318308 | -------------------------------------------------- | 52 |
| AAR87655 | -------------------------------------------------- | 59 |
| BX842170 | -------------------------------------------------- | 52 |
| BX825869 | -------------------------------------------------- | 52 |
| AY496072 | -------------------------------------------------- | 49 |
| AB030211 | -------------------------------------------------- | 51 |
| AK062410 | -------------------------------------------------- | 51 |
| AY108884 | -------------------------------------------------- | 51 |
| AAN06944 | -------------------------------------------------- | 69 |
| NP-194785 | -------------------------------------------------- | 74 |
| NP-179882 | -------------------------------------------------- | 75 |
| NP-974829 | -------------------------------------------------- | 77 |
| NP-194794 | -------------------------------------------------- | 73 |
| AAT11708 | -------------------------------------------------- | 74 |

FIGURE 20-7

| | | |
|---|---|---|
| CD913648 | -------------------------------------------------- | 54 |
| BI780134 | -------------------------------------------------- | 54 |
| ORF9 | -------------------------------------------------- | 54 |
| AY107179 | -------------------------------------------------- | 54 |
| CF042363 | -------------------------------------------------- | 54 |
| CD229091 | -------------------------------------------------- | 54 |
| AAS72368 | -------------------------------------------------- | 54 |
| AC093089 | -------------------------------------------------- | 77 |
| CF318949 | -------------------------------------------------- | 54 |
| AY080604 | -------------------------------------------------- | 53 |
| AC005770 | -------------------------------------------------- | 76 |
| CN183349 | -------------------------------------------------- | 53 |
| CA836518 | -------------------------------------------------- | 54 |
| BU870658 | -------------------------------------------------- | 53 |
| Q9AR05 | -------------------------------------------------- | 54 |
| AJ310995 | -------------------------------------------------- | 80 |
| U00968.1 | -------------------------------------------------- | 53 |
| AJ310994 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY807889 | -------------------------------------------------- | 46 |
| AY105302 | -------------------------------------------------- | 57 |
| NM-183567 | SQLIAGDQRYDGVIALASPPPISSPPNLFCAATGALSTAQVSFDPSRAAT | 367 |
| AY554051 | -------------------------------------------------- | 51 |
| NM-184595 | -------------------------------------------------- | 64 |
| AY084701 | -------------------------------------------------- | 52 |
| AB081265 | -------------------------------------------------- | 56 |
| AY316308 | -------------------------------------------------- | 52 |
| AAR87866 | -------------------------------------------------- | 58 |
| BX842170 | -------------------------------------------------- | 52 |
| BX825889 | -------------------------------------------------- | 52 |
| AY496072 | -------------------------------------------------- | 48 |
| AB030211 | -------------------------------------------------- | 51 |
| AK082410 | -------------------------------------------------- | 51 |
| AY108884 | -------------------------------------------------- | 51 |
| AAN06944 | -------------------------------------------------- | 69 |
| NP-194795 | -------------------------------------------------- | 74 |
| NP-179882 | -------------------------------------------------- | 75 |
| NP-974629 | -------------------------------------------------- | 77 |
| NP-194794 | -------------------------------------------------- | 73 |
| AAT11798 | -------------------------------------------------- | 74 |

FIGURE 20-8

| | | |
|---|---|---|
| CD913848 | -------------------------------------------------- | 54 |
| BI780134 | -------------------------------------------------- | 54 |
| ORF9 | -------------------------------------------------- | 54 |
| AY107178 | -------------------------------------------------- | 54 |
| CF042363 | -------------------------------------------------- | 54 |
| CD229091 | -------------------------------------------------- | 54 |
| AAS72388 | -------------------------------------------------- | 54 |
| AC093089 | -------------------------------------------------- | 77 |
| CF318849 | -------------------------------------------------- | 54 |
| AY080604 | -------------------------------------------------- | 53 |
| AC005770 | -------------------------------------------------- | 76 |
| CN183349 | -------------------------------------------------- | 53 |
| CA838518 | -------------------------------------------------- | 54 |
| BU870655 | -------------------------------------------------- | 53 |
| Q9ARD5 | -------------------------------------------------- | 54 |
| AJ310895 | -------------------------------------------------- | 80 |
| U00968.1 | -------------------------------------------------- | 53 |
| AJ310994 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY607888 | -------------------------------------------------- | 48 |
| AY105302 | -------------------------------------------------- | 57 |
| NM-183567 | G A L S T V P P S V R R S L A R C H R I P P H R V A S Q K C K I V I S V D V I N N A T F M F L I Q Y | 417 |
| AY554051 | -------------------------------------------------- | 51 |
| NM-184585 | -------------------------------------------------- | 64 |
| AY084701 | -------------------------------------------------- | 52 |
| AB081265 | -------------------------------------------------- | 56 |
| AY316308 | -------------------------------------------------- | 52 |
| AAR87865 | -------------------------------------------------- | 58 |
| BX842170 | -------------------------------------------------- | 52 |
| BX825889 | -------------------------------------------------- | 52 |
| AY498072 | -------------------------------------------------- | 49 |
| AB030211 | -------------------------------------------------- | 51 |
| AK062410 | -------------------------------------------------- | 51 |
| AY106884 | -------------------------------------------------- | 51 |
| AAN06944 | -------------------------------------------------- | 69 |
| NP-194795 | -------------------------------------------------- | 74 |
| NP-178682 | -------------------------------------------------- | 75 |
| NP-974829 | -------------------------------------------------- | 77 |
| NP-194794 | -------------------------------------------------- | 73 |
| AAT11798 | -------------------------------------------------- | 74 |

FIGURE 20-9

| | | |
|---|---|---|
| CD913648 | -------------------------------------------------- | 54 |
| BI7B0134 | -------------------------------------------------- | 54 |
| ORF9 | -------------------------------------------------- | 54 |
| AY107179 | -------------------------------------------------- | 54 |
| CF042363 | -------------------------------------------------- | 54 |
| CD229091 | -------------------------------------------------- | 54 |
| AAS72368 | -------------------------------------------------- | 54 |
| AC093089 | -------------------------------------------------- | 77 |
| CF310049 | -------------------------------------------------- | 54 |
| AY080604 | -------------------------------------------------- | 53 |
| AC005770 | -------------------------------------------------- | 78 |
| CN183349 | -------------------------------------------------- | 53 |
| CA836518 | -------------------------------------------------- | 54 |
| BU870658 | -------------------------------------------------- | 53 |
| Q6AR05 | -------------------------------------------------- | 54 |
| AJ310995 | -------------------------------------------------- | 80 |
| U00968.1 | -------------------------------------------------- | 53 |
| AJ310994 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY807889 | -------------------------------------------------- | 48 |
| AY165302 | -------------------------------------------------- | 57 |
| NM-183567 | PPKYKLKGFPLANSIGGDKVEGGKLMTMGRRSDYLIVLFDLVFSMRLASW | 465 |
| AY554051 | -------------------------------------------------- | 51 |
| NM-184595 | -------------------------------------------------- | 64 |
| AY084701 | -------------------------------------------------- | 52 |
| ABC81265 | -------------------------------------------------- | 58 |
| AY318308 | -------------------------------------------------- | 52 |
| AAR87855 | -------------------------------------------------- | 59 |
| BX842170 | -------------------------------------------------- | 52 |
| BX825899 | -------------------------------------------------- | 52 |
| AY486072 | -------------------------------------------------- | 49 |
| ABC30211 | -------------------------------------------------- | 51 |
| AK062410 | -------------------------------------------------- | 51 |
| AY108884 | -------------------------------------------------- | 51 |
| AAN08944 | -------------------------------------------------- | 69 |
| NP-194795 | -------------------------------------------------- | 74 |
| NP-179882 | -------------------------------------------------- | 75 |
| NP-974629 | -------------------------------------------------- | 77 |
| NP-194794 | -------------------------------------------------- | 73 |
| AAT11798 | -------------------------------------------------- | 74 |

FIGURE 20-10

| | | |
|---|---|---|
| CD913848 | -------------------------------------------------- | 54 |
| EI780134 | -------------------------------------------------- | 54 |
| ORF9 | -------------------------------------------------- | 54 |
| AY107179 | -------------------------------------------------- | 54 |
| CF042363 | -------------------------------------------------- | 54 |
| CD229091 | -------------------------------------------------- | 54 |
| AAS72368 | -------------------------------------------------- | 54 |
| AC093089 | -------------------------------------------------- | 77 |
| CF319949 | -------------------------------------------------- | 54 |
| AY080604 | -------------------------------------------------- | 53 |
| AC005770 | -------------------------------------------------- | 78 |
| CN183349 | -------------------------------------------------- | 53 |
| CA836518 | -------------------------------------------------- | 54 |
| BU870656 | -------------------------------------------------- | 53 |
| Q9ARD5 | -------------------------------------------------- | 54 |
| AJ310085 | -------------------------------------------------- | 80 |
| U00968.1 | -------------------------------------------------- | 53 |
| AJ310084 | -------------------------------------------------- | 54 |
| Z25537 | -------------------------------------------------- | 53 |
| AK070872 | -------------------------------------------------- | 54 |
| NM-104551 | -------------------------------------------------- | 50 |
| AY103848 | -------------------------------------------------- | 51 |
| AY807888 | -------------------------------------------------- | 48 |
| AY105302 | -------------------------------------------------- | 57 |
| NM-183567 | QSIVDAIELFELLARFAFGYPYVLVWVLETEGVAERLMMNVVFFMGDGDL | 517 |
| AY554051 | -------------------------------------------------- | 51 |
| NM-184595 | -------------------------------------------------- | 84 |
| AY084701 | -------------------------------------------------- | 52 |
| AB081265 | -------------------------------------------------- | 56 |
| AY314308 | -------------------------------------------------- | 52 |
| AAR87855 | -------------------------------------------------- | 59 |
| BX842170 | -------------------------------------------------- | 52 |
| BX825889 | -------------------------------------------------- | 52 |
| AY488072 | -------------------------------------------------- | 49 |
| AB030211 | -------------------------------------------------- | 51 |
| AK062410 | -------------------------------------------------- | 51 |
| AY106884 | -------------------------------------------------- | 51 |
| AAN08944 | -------------------------------------------------- | 69 |
| NP-194785 | -------------------------------------------------- | 74 |
| NP-178982 | -------------------------------------------------- | 75 |
| NP-974629 | -------------------------------------------------- | 77 |
| NP-194794 | -------------------------------------------------- | 73 |
| AAT11798 | -------------------------------------------------- | 74 |

FIGURE 20-11

| | | |
|---|---|---|
| CD813848 | - - - - - - - - - - - - - - - - - - - - | 54 |
| BI780134 | - - - - - - - - - - - - - - - - - - - - | 54 |
| ORF8 | - - - - - - - - - - - - - - - - - - - - | 54 |
| AY107178 | - - - - - - - - - - - - - - - - - - - - | 54 |
| CF042363 | - - - - - - - - - - - - - - - - - - - - | 54 |
| CD228081 | - - - - - - - - - - - - - - - - - - - - | 54 |
| AAS72388 | - - - - - - - - - - - - - - - - - - - - | 54 |
| AC093D88 | - - - - - - - - - - - - - - - - - - - - | 77 |
| CF319849 | - - - - - - - - - - - - - - - - - - - - | 54 |
| AY080604 | - - - - - - - - - - - - - - - - - - - - | 53 |
| AC005770 | - - - - - - - - - - - - - - - - - - - - | 78 |
| CN183349 | - - - - - - - - - - - - - - - - - - - - | 53 |
| CA236516 | - - - - - - - - - - - - - - - - - - - - | 54 |
| BU870656 | - - - - - - - - - - - - - - - - - - - - | 53 |
| Q84RD5 | - - - - - - - - - - - - - - - - - - - - | 54 |
| AJ310895 | - - - - - - - - - - - - - - - - - - - - | 80 |
| U00866.1 | - - - - - - - - - - - - - - - - - - - - | 53 |
| AJ310894 | - - - - - - - - - - - - - - - - - - - - | 54 |
| Z25537 | - - - - - - - - - - - - - - - - - - - - | 53 |
| AK070872 | - - - - - - - - - - - - - - - - - - - - | 54 |
| NM-104551 | - - - - - - - - - - - - - - - - - - - - | 50 |
| AY103848 | - - - - - - - - - - - - - - - - - - - - | 51 |
| AY807888 | - - - - - - - - - - - - - - - - - - - - | 48 |
| AY106302 | - - - - - - - - - - - - - - - - - - - - | 57 |
| NM-183567 | V V L V F D T E F L D K Q S S K F L I D | 537 |
| AY554051 | - - - - - - - - - - - - - - - - - - - - | 51 |
| NM-184585 | - - - - - - - - - - - - - - - - - - - - | 64 |
| AY084701 | - - - - - - - - - - - - - - - - - - - - | 52 |
| AB081265 | - - - - - - - - - - - - - - - - - - - - | 56 |
| AY318308 | - - - - - - - - - - - - - - - - - - - - | 52 |
| AAR87856 | - - - - - - - - - - - - - - - - - - - - | 58 |
| BX842170 | - - - - - - - - - - - - - - - - - - - - | 52 |
| BX825889 | - - - - - - - - - - - - - - - - - - - - | 52 |
| AY448072 | - - - - - - - - - - - - - - - - - - - - | 49 |
| AB030211 | - - - - - - - - - - - - - - - - - - - - | 51 |
| AK082410 | - - - - - - - - - - - - - - - - - - - - | 51 |
| AY102884 | - - - - - - - - - - - - - - - - - - - - | 51 |
| AAN06844 | - - - - - - - - - - - - - - - - - - - - | 68 |
| NP-194795 | - - - - - - - - - - - - - - - - - - - - | 74 |
| NP-178882 | - - - - - - - - - - - - - - - - - - - - | 75 |
| NP-974620 | - - - - - - - - - - - - - - - - - - - - | 77 |
| NP-194794 | - - - - - - - - - - - - - - - - - - - - | 73 |
| AAT11798 | - - - - - - - - - - - - - - - - - - - - | 74 |

FIGURE 20-12

SEQUENCE LISTING

```
<160> NUMBER OF SEQ ID NOS: 255

<210> SEQ ID NO 1
<211> LENGTH: 1264
<212> TYPE: DNA
<213> ORGANISM: Lolium perenne

<400> SEQUENCE: 1

ctcttcacct tgtcccacct gctcccgccg catctcacca gacaccagcc atgtgcggcg      60

gcgcgatcct ctccgacatc atcccgccgc cgcgccgggt cacggacggc cccctctggc     120

ggaaccagaa gaagaagggg ccgacgggag atgctccggt ggcgaggcgc cgccgcgcgc     180

ccgaggagga ggagagctac gaggacttcg aggccgactt cgagggcttc gaggaggggc     240

tcggggaggc cgagatttgg tccgaggacg aggccaagcc cttctccgcc gccaggaaac     300

gcgtcgccgc agctgctgct gttgatggct gtgcatcaga gtccgctaaa aggaagagaa     360
```

-continued

```
agacccagtt caggggcatc cgccgccgcc cttggggtaa atgggctgct gaaatcagag    420

accctcgcaa gggtgtccgt gtctggcttg gcacttacaa ctctgccgag gaagctgcca    480

gagcctatga tgctgaagca agaaggatcc gtggcaagaa ggcaaaggtc aatttcccag    540

atgaggctcc tgtggcttct caaaagcact gtgctaagcc tacctttgtg acgttgcctg    600

agttcaacac cgaagagaag ccgatagtca acgccgtggc caacacaaac gcgtattcct    660

atcctcttgt tgactacacc gtctgtgagc catttgtgca gcctcagaac atgtcatttg    720

tgccagcgat taatgcagtt gaggttcctt tcatgaatct ttcctctgac cagggtagca    780

actcctttgg ttgctcagac tttagctggg agaatggtac caagactcct gacatcacat    840

ctgtgcttgc atccattccc acctcgaccg aggttgatga atctgcattc cttcagaaca    900

atgccagtga tgcatcacta cctcctgtga tggatactgc caatgttgat ctcgccgact    960

tggaaccata catgaagttc ctcatggatg gtgcttcaga tgagtcactt gacaacattc   1020

taagctgtga cgggtctgag gacatggtca gcaacctgga cctttggact ttcgatgaca   1080

tgcccatttc tgccgatttc tactgaggct ctgaggtcaa ttggtgcctg tacatataga   1140

caatgggaat aagtattctg gacatcaaga agtgcttgtg tcaggcgcct ctgttgagca   1200

gtagttatgt ttgtatactt ttatatctag cttaaatctc agtttgatcg caagtctgaa   1260

gtga                                                                1264
```

<210> SEQ ID NO 2
<211> LENGTH: 1824
<212> TYPE: DNA
<213> ORGANISM: Lolium perenne

<400> SEQUENCE: 2

```
ctcttcacct tgtcccacct gctcccgccg catctcacca gacaccagcc atgtgcggca     60

gcgcgatcct ctccgacatc atcccgccgc cgcgccgggt cacggacggc cccctctggc    120

ggaaccagaa gaagaagggg ccgacgggag atgctccggt ggcgaggcgc cgccgcgcgc    180

ccgaggagga ggagagctac gaggacttcg aggccgactt cgagggcttc gaggaggggc    240

tcggggaggc cgagatctgg tccgaggacg aggccaagcc cttctccgcc gccaggaaac    300

gcgtcgccgc aggtatagcc gcccttttg ggtcaccggc tttggatctg tggaaccgcg     360

tgctaattct gtttacgatt tgggagatag atttgagttt ctcaggtgat ctgctgctcg    420

gattagatag ttgcatcttc gatttgtttg ctatgaagtt aaatctgtgc aattgttcat    480

ctcaagtccg ttaattcagc gggtccatgt tgtcgattag tctggtctct agtgctgtgt    540

cttttttta aaaaaacaca atctctggtg ctgtgtcgat ccttagtttt taggataact     600

ctcctaaatc atgaatatgg tatcaactct tattggtgca tacatagatc gagcttcctc    660

gcaagcatat gagttgggct gttcctcagg attagacttt taatgtcaag tttcgactta    720

ccctgacttt ctgtatgtaa actaaaatct ttatctcact gcttcatcct gattgaataa    780

atgcatgtac agctgctgct gttgatggct gggcatcaga gtccgccaaa aggaagagaa    840

agacccagtt caggggcatc cgccgccgcc cttggggtaa atgggctgct gaaatcagag    900

accctcgcaa gggtgtccgt gtctggcttg gcacttacaa ctctgccgag gaagctgcca    960

gagcctatga tgctgaagca agaaggatcc gtggcaagaa ggcaaaggtc aatttcccag   1020

atgaggctcc tgtggcttct caaaagcact gtgctaagcc tacctttgtg acgttgcctg   1080

agttcaacac cgaagagaag ccgatagtca acgccgtggc caacacaaac gcgtattcct   1140

atcctcttgt tgactacacc gtctgtgagc catttgtgca gcctcagaac atgtcatttg   1200
```

-continued

```
tgccagcggt taatgcagtt gaggttcctt tcatgaatct ttcctctgac cagggtagca   1260

actcctttgg ttgctcagac tttagctggg agaatggtac caagactcct gacatcacat   1320

ctgtgcttgc atccattccc acctcgaccg aggttgatga atctgcattc cttcagaaca   1380

atgccagtga tgcatcacta cctcctgtga tggatactgc caatgttgat ctcgccgatt   1440

tggaaccata catgaagttc ctcgtggatg gtgcttcaga tgagtcactt gacaactttc   1500

taagctgtga cgggtctgag gacatggtca gcaacctgga cctttggact ttcgatgaca   1560

tgcccatttc tgccgatttc tactgaggct ctgaggtcaa ttggtgcctg tacgtataga   1620

taatgggtaa gcatctgcaa ctgcggaaat aactcactgt tatacttcag tttccatttc   1680

cataactacc ccacttcact tttcaggaat aagtattctg gacatcaaga agtgcttgtg   1740

tcaggcgcct ctgttgagca gtagttatgt ttgtatactt ttatatctag cttaaatctc   1800

agtttgatcg caagtctgaa gtga                                          1824


<210> SEQ ID NO 3
<211> LENGTH: 351
<212> TYPE: PRT
<213> ORGANISM: Lolium perenne

<400> SEQUENCE: 3

Met Cys Gly Gly Ala Ile Leu Ser Asp Ile Ile Pro Pro Pro Arg Arg
1               5                   10                  15

Val Thr Asp Gly Pro Leu Trp Arg Asn Gln Lys Lys Lys Gly Pro Thr
            20                  25                  30

Gly Asp Ala Pro Val Ala Arg Arg Arg Arg Ala Pro Glu Glu Glu Glu
        35                  40                  45

Ser Tyr Glu Asp Phe Glu Ala Asp Phe Glu Gly Phe Glu Glu Gly Leu
    50                  55                  60

Gly Glu Ala Glu Ile Trp Ser Glu Asp Glu Ala Lys Pro Phe Ser Ala
65                  70                  75                  80

Ala Arg Lys Arg Val Ala Ala Ala Ala Ala Val Asp Gly Cys Ala Ser
                85                  90                  95

Glu Ser Ala Lys Arg Lys Arg Lys Thr Gln Phe Arg Gly Ile Arg Arg
            100                 105                 110

Arg Pro Trp Gly Lys Trp Ala Ala Glu Ile Arg Asp Pro Arg Lys Gly
        115                 120                 125

Val Arg Val Trp Leu Gly Thr Tyr Asn Ser Ala Glu Glu Ala Ala Arg
    130                 135                 140

Ala Tyr Asp Ala Glu Ala Arg Arg Ile Arg Gly Lys Lys Ala Lys Val
145                 150                 155                 160

Asn Phe Pro Asp Glu Ala Pro Val Ala Ser Gln Lys His Cys Ala Lys
                165                 170                 175

Pro Thr Phe Val Thr Leu Pro Glu Phe Asn Thr Glu Glu Lys Pro Ile
            180                 185                 190

Val Asn Ala Val Ala Asn Thr Asn Ala Tyr Ser Tyr Pro Leu Val Asp
        195                 200                 205

Tyr Thr Val Cys Glu Pro Phe Val Gln Pro Gln Asn Met Ser Phe Val
    210                 215                 220

Pro Ala Ile Asn Ala Val Glu Val Pro Phe Met Asn Leu Ser Ser Asp
225                 230                 235                 240

Gln Gly Ser Asn Ser Phe Gly Cys Ser Asp Phe Ser Trp Glu Asn Gly
                245                 250                 255
```

-continued

```
Thr Lys Thr Pro Asp Ile Thr Ser Val Leu Ala Ser Ile Pro Thr Ser
            260                 265                 270

Thr Glu Val Asp Glu Ser Ala Phe Leu Gln Asn Asn Ala Ser Asp Ala
        275                 280                 285

Ser Leu Pro Pro Val Met Asp Thr Ala Asn Val Asp Leu Ala Asp Leu
    290                 295                 300

Glu Pro Tyr Met Lys Phe Leu Met Asp Gly Ala Ser Asp Glu Ser Leu
305                 310                 315                 320

Asp Asn Ile Leu Ser Cys Asp Gly Ser Glu Asp Met Val Ser Asn Leu
                325                 330                 335

Asp Leu Trp Thr Phe Asp Asp Met Pro Ile Ser Ala Asp Phe Tyr
            340                 345                 350


<210> SEQ ID NO 4
<211> LENGTH: 673
<212> TYPE: DNA
<213> ORGANISM: Lolium perenne

<400> SEQUENCE: 4

atggccataa ctccaggacc tgcagtggca acaacggcgg cggtggtgcc ggtggtgggc      60

tgaggctgtt cggtgtgcag ctgcaagttg gtgctgcacc tctgaagaag agcttcagca     120

tggagtgcct ctcgtcgtcg gcctactacg cggccgcagc ggtggccgcg tccaactcgt     180

cgtcgtccgt gtcatcgtca tcgtcgctgg tctcggtgga ggagaacgcc gagaagatgg     240

gccacggcta cctctccgat ggtctcatgg gcagggctca ggagaggaag aaggggggttc    300

catggacgga ggatgagcac cggaggttcc tggccggctt agagaagctc gggaaaggcg     360

actggcgagg catctcccgg cacttcgtcg cgacacgcac cccgacgcag gtggccagcc     420

acgcccagaa gtacttcctc cggcaggccg gcctcgcgca gaagaagcgg aggtccagcc     480

tcttcgacgt ggccgagaag aatggcgaca aggcggcgaa ggagagtcgt ccgagactga     540

aacacgagac tagcagctcc gtggacggga tggcaattcg gtcattccct gctctgtctc     600

taggacccag caggccgagg cccgacgccg ccgtgcttcc accatgcctg accttgatgc     660

cgagctattc gtc                                                        673


<210> SEQ ID NO 5
<211> LENGTH: 1256
<212> TYPE: DNA
<213> ORGANISM: Lolium perenne

<400> SEQUENCE: 5

ttgttgcttt cctgtgccat cgactggcat ggctcggaaa tgctccagct gcgggcataa      60

tggccataac tccaggacct gcagtggcaa caacggcggc ggtggtgccg gtggtgggct     120

gaggctgttc ggtgtgcagc tgcaagttgg tgctgcacct ctgaagaaga gcttcagcat     180

ggagtgcctc tcgtcgtcgg cctactacgc ggccgcagcg gtggccgcgt ccaactcgtc     240

gtcgtccgtg tcatcgtcat cgtcgctggt ctcggtggag gagaacgccg agaagatggg     300

ccacggctac ctctccgatg gtctcatggg cagggctcag gagaggaaga agggtgagtt     360

cgtgtactgg tttcttgagc agttcgttgg tccggtatac ctcgctgaca cgcttgattt     420

gctatgctat ggattttgga tattaatcat attatagtat gtgatagcga tctaaccatc     480

atgcatgatg tctaaggcca gattaagaaa actattctga aattttttt cccccctagct     540

agagactaaa gatctgaaga ttcttgttga tgcatgagtg gttgtatgac ttgtttgtat     600

ccaattgtgc catcagttgc tatctgctat gccaaacttg caactagata acaggaaata     660
```

-continued

```
cttagtcttt caggtcttaa ctttcagtaa tcatgtctaa tagcttgcac gaatcagttt    720

gttctctctt cttcacctga agatgtccag ttacgttggg tgaactaatc gtgtgacgca    780

tggcatcagg ggttccatgg acggaggatg agcaccggag gttcctggcc ggcttagaga    840

agctcgggaa aggcgactgg cgaggcatct cccggcactt cgtcgcgaca cgcaccccga    900

cgcaggtggc cagccacgcc cagaagtact tcctccggca ggccggcctc gcgcagaaga    960

agcggaggtc cagcctcttc gacgtggtac gtgcacgcct caaaacgcaa gctggagttg   1020

tggacgtagt aacaaaccag ctgacatgca cgaaccttcc tctcttttct tcaggccgag   1080

aagaatggcg acaaggcggc gaaggagagt cgtccgagac tgaaacacga gactagcagc   1140

tccgtggacg ggatggcaat tcggtcattc cctgctctgt ctctaggacc cagcaggccg   1200

aggcccgacg ccgccgtgct tccaccatgc ctgaccttga tgccgagcta ttcgtc       1256
```

<210> SEQ ID NO 6
<211> LENGTH: 234
<212> TYPE: PRT
<213> ORGANISM: Lolium perenne

<400> SEQUENCE: 6

```
Met Ala Arg Lys Cys Ser Ser Cys Gly His Asn Gly His Asn Ser Arg
1               5                   10                  15

Thr Cys Ser Gly Asn Asn Gly Gly Gly Gly Ala Gly Gly Gly Leu Arg
            20                  25                  30

Leu Phe Gly Val Gln Leu Gln Val Gly Ala Ala Pro Leu Lys Lys Ser
        35                  40                  45

Phe Ser Met Glu Cys Leu Ser Ser Ser Ala Tyr Tyr Ala Ala Ala Ala
    50                  55                  60

Val Ala Ala Ser Asn Ser Ser Ser Ser Val Ser Ser Ser Ser Ser Leu
65                  70                  75                  80

Val Ser Val Glu Glu Asn Ala Glu Lys Met Gly His Gly Tyr Leu Ser
                85                  90                  95

Asp Gly Leu Met Gly Arg Ala Gln Glu Arg Lys Lys Gly Val Pro Trp
            100                 105                 110

Thr Glu Asp Glu His Arg Arg Phe Leu Ala Gly Leu Glu Lys Leu Gly
        115                 120                 125

Lys Gly Asp Trp Arg Gly Ile Ser Arg His Phe Val Ala Thr Arg Thr
    130                 135                 140

Pro Thr Gln Val Ala Ser His Ala Gln Lys Tyr Phe Leu Arg Gln Ala
145                 150                 155                 160

Gly Leu Ala Gln Lys Lys Arg Arg Ser Ser Leu Phe Asp Val Ala Glu
                165                 170                 175

Lys Asn Gly Asp Lys Ala Ala Lys Glu Ser Arg Pro Arg Leu Lys His
            180                 185                 190

Glu Thr Ser Ser Ser Val Asp Gly Met Ala Ile Arg Ser Phe Pro Ala
        195                 200                 205

Leu Ser Leu Gly Pro Ser Arg Pro Arg Pro Asp Ala Ala Val Leu Pro
    210                 215                 220

Pro Cys Leu Thr Leu Met Pro Ser Tyr Ser
225                 230
```

<210> SEQ ID NO 7
<211> LENGTH: 1274
<212> TYPE: DNA
<213> ORGANISM: Lolium perenne -continued

<400> SEQUENCE: 7

```
gatctgctgt gctgtggtga gagctgccaa gaagctgagc agtgctactc tggaggagtt     60
cgccaaagga tttgtttctg tttcggtttt ggtaatcact aaataatgga ggaagtggag    120
gaggcgaaca ggatagccgt tgagagctgc cacagagtgc tgggcctgct ctcccagtcg    180
cagggcccgg cgcagctcag gtgcatagct ctgggcacgg acgacgcctg cgccaagttc    240
cgcaaggtgg tctccctcct cggcaacgaa gcaggaggag ggggagcagt aagccatccc    300
agagccaagg ttgcgagcag gaaacagaca ccggccttct tgagccagaa gggcttcctg    360
gacaacaaca ccccggtggt ggtgctcaac agcagcgccc acccttccac cagctccgcg    420
caggcgtatc ctaggaacag cattctggat tcgcagaacg cgcacccgat cggagggcct    480
cccaagctgg tccagccatt gtctgcccac ttccagttcg gcaacgtatc gcggtatcag    540
ttccagcatc agcaccagca gcagaagatg caggctgaga tgttcaagag aagcaacagt    600
atcagtggga tcaacctgaa gttcgacagc cccagcgcgg ccacggggac gatgtcgtcc    660
gcgagatcct tcatgtcatc tctgagcatg gatggtagtg tggctagcct ggatgccaag    720
tcttcgtcgt tccatttgat cggcgggcct gctatgagtg accccgtgaa tgcgcagcag    780
gcgccgagga ggcggtgcac ggggcgtggg gaggatggga atggcaagtg cgctgtaaat    840
ggcaggtgcc attgctcaaa gaggagcagg aagttgcggg tgaagaggac gataaaagtt    900
cctgccatta gtaataaaat tgcttatata cctccagatg aatactcatg gaggaagtat    960
gggcagaagc ctattaaggg ttcccctcat cccagggggt actacaaatg tagcagtgtc   1020
aggggctgcc cagccaggaa gcatgttgaa cgttgtgtgg atgatgcgtc aatgctcatt   1080
gtgacatacg aaggtgaaca caaccacacg cgaatgccgg ctcagtctgc acaggcttag   1140
gaagtcactt tgatcatcac accctctcca gggaatacca actcgcctgc ccttgtcgat   1200
ggccgactgc actgttcttc taaattagaa ttacaaagtg acaaaaactg ggttccattt   1260
tgagcagttg atga                                                     1274
```

<210> SEQ ID NO 8
<211> LENGTH: 2128
<212> TYPE: DNA
<213> ORGANISM: Lolium perenne

<400> SEQUENCE: 8

```
gatctgctgt gctgtggtga gagctgccaa gaagctgagc agtgctactc tggaggagct     60
caccaaagga ttgtttctgt ttcggttttg gcaatcacta aataatggag gaagtggagg    120
aggccaacag gatagccgtt gagagctgcc acagagtgct gggcctgctt tcccagtcgc    180
aggacccggc gcagctcagg agcatagctc tgggcacgga cgacgcctgc gccaagttcc    240
gcaaggtggt ctccctcctc ggcaacgaag gaggaggggg agcagtaagc catcccagag    300
ccaaggttgc gagcaggaaa cagaccccgg ccttcttgag ccagaagggc ttcctggaca    360
acaacacccc ggtggtggtg ctgaacagca gcgcccaccc ttccactagc tccgcgcagg    420
cgtatcctag gaacaccatt ctggattcgc acaccgcgca cccgatcgga gggcctccca    480
agctggtcca gccattgtcc gcgcacttcc agttcggcaa cgtatcgcgg tatcagttcc    540
agcatcagca ccagcagcag aagatgcagg ctgagatgtt caagagaagc aacagtatca    600
gtgggattaa cctgaagttc gacagcccca gcgcggccac ggggacgatg tcgtccgcga    660
gatccttcat gtcatctttg agcatggatg gtagcgtggc tagcctggat gccaagtctt    720
cctcgttcca tttgatcggt gggcctgcta tgagtgaccc ggtgaatgcg cagcaggcgc    780
```

-continued

```
cgaggaggcg gtgcacgggg cgtggggagg atgggaatgg caagtgcgct gcaaatggca    840

ggtgccattg ctcaaagagg aggtaaatac tcttatctta gtgtgtatga ttcttgcttg    900

ctcttctatt caaggtagaa taccatgaga attgttctgt tccctatttc agcaggaagt    960

tgcgggtgaa gaagacgatt aaagttcctg ccattagtaa taaaattgct gatatacctc   1020

cagatgaata ctcatggagg aagtatgggc agaagccaat taagggttcc cctcatccca   1080

ggtatgaact gagcactatc tgttagtgtc attttcttgc acacatattc ttgattatac   1140

ggtgatggag tagtggcaat gatgctataa tcaccatgac tcatcaattt tctaattatt   1200

tatcatatgt ataactgcac atatccccca tgaactactc aagtgcctca tgataaatga   1260

tggctctgtg ataatcagaa cacactttat ccatggtttg cagggtgttt tacatgctcc   1320

tgataatcag aacactcttt atacagtata gtaatcaaaa ctctccttat gcagggtgtt   1380

ttgtatgttc ctgaatagtt actttgtgaa taatgtcttt cattcttctt gtgcacactt   1440

tcttaaaata gatcaatccc gagtcttaaa gtggccagtg gccacttcgt aattcagtct   1500

accatgattc agtctttaag tggacatctt taatgctatc gtgattcagt ctactacgta   1560

ctatacttta cctattcata tcactttccc accttgtcta tcttaaattt cctgatgata   1620

aaatacacaa atatagctat acggtaatag caaacgcatg ggtatctttt cgagaaaaaa   1680

acaaacacat gggtatggct gtctgaattg agaaaaaact tttcctcttt ctagcaagca   1740

ctagatatag aaacacgatt catggcgcat ctatttttat ctccaatcca caatgctaat   1800

tctgatgtgt ctcttaagac caatccactg attccttaaa cataatgcag ggggtactac   1860

aaatgtagca gtgtcagggg ctgcccagcc aggaagcatg ttgaacgttg tgtggatgat   1920

gcgtcaatgc tcattgtgac atacgagggt gaacacaacc acacgcgaat gccggctcag   1980

tctgcacagg cttagggaat cactttgatc atcacaccct ctccagggaa tactaactcg   2040

cctgcccttg tcgatggccg actgcactgt tcttctaaat tagaattaca aagtgacaaa   2100

aactgggttc catttgagca gttgatga                                      2128


<210> SEQ ID NO 9
<211> LENGTH: 344
<212> TYPE: PRT
<213> ORGANISM: Lolium perenne

<400> SEQUENCE: 9

Met Glu Glu Val Glu Glu Ala Asn Arg Ile Ala Val Glu Ser Cys His
1               5                   10                  15

Arg Val Leu Gly Leu Leu Ser Gln Ser Gln Asp Pro Ala Gln Leu Arg
            20                  25                  30

Cys Ile Ala Leu Gly Thr Asp Asp Ala Cys Ala Lys Phe Arg Lys Val
        35                  40                  45

Val Ser Leu Leu Gly Asn Glu Ala Gly Gly Gly Gly Ala Val Ser His
    50                  55                  60

Pro Arg Ala Lys Val Ala Ser Arg Lys Gln Thr Pro Ala Phe Leu Ser
65                  70                  75                  80

Gln Lys Gly Phe Leu Asp Asn Asn Thr Pro Val Val Val Leu Asn Ser
                85                  90                  95

Ser Ala His Pro Ser Thr Ser Ser Ala Gln Ala Tyr Pro Arg Asn Ser
            100                 105                 110

Ile Leu Asp Ser Gln Asn Ala His Pro Ile Gly Gly Pro Pro Lys Leu
        115                 120                 125
```

-continued

```
Val Gln Pro Leu Ser Ala His Phe Gln Phe Gly Asn Val Ser Arg Tyr
    130                 135                 140

Gln Phe Gln His Gln His Gln Gln Gln Lys Met Gln Ala Glu Met Phe
145                 150                 155                 160

Lys Arg Ser Asn Ser Ile Ser Gly Ile Asn Leu Lys Phe Asp Ser Pro
                165                 170                 175

Ser Ala Ala Thr Gly Thr Met Ser Ser Ala Arg Ser Phe Met Ser Ser
            180                 185                 190

Leu Ser Met Asp Gly Ser Val Ala Ser Leu Asp Ala Lys Ser Ser Ser
        195                 200                 205

Phe His Leu Ile Gly Gly Pro Ala Met Ser Asp Pro Val Asn Ala Gln
    210                 215                 220

Gln Ala Pro Arg Arg Arg Cys Thr Gly Arg Gly Glu Asp Gly Asn Gly
225                 230                 235                 240

Lys Cys Ala Val Asn Gly Arg Cys His Cys Ser Lys Arg Ser Arg Lys
                245                 250                 255

Leu Arg Val Lys Arg Thr Ile Lys Val Pro Ala Ile Ser Asn Lys Ile
            260                 265                 270

Ala Tyr Ile Pro Pro Asp Glu Tyr Ser Trp Arg Lys Tyr Gly Gln Lys
        275                 280                 285

Pro Ile Lys Gly Ser Pro His Pro Arg Gly Tyr Tyr Lys Cys Ser Ser
    290                 295                 300

Val Arg Gly Cys Pro Ala Arg Lys His Val Glu Arg Cys Val Asp Asp
305                 310                 315                 320

Ala Ser Met Leu Ile Val Thr Tyr Glu Gly Glu His Asn His Thr Arg
                325                 330                 335

Met Pro Ala Gln Ser Ala Gln Ala
            340
```

<210> SEQ ID NO 10
<211> LENGTH: 165
<212> TYPE: DNA
<213> ORGANISM: Lolium perenne

<400> SEQUENCE: 10

```
atgggttcgg agacctttct ggagatcctg ctggccatcc tgctgccgcc gctcggcgtt      60

ttcctccgct tcggcatcgg cgtggagttc tggatctgcc tgctactcac cctgctgggc     120

tacatccccg gcatcatcta cgccgtcttc gtccttgttg catag                     165
```

<210> SEQ ID NO 11
<211> LENGTH: 253
<212> TYPE: DNA
<213> ORGANISM: Lolium perenne

<400> SEQUENCE: 11

```
aatgggttcg gagacctttc tggagatcct gctggccatc ctgctgccgc cgctcggcgt      60

tttcctccgc ttcggcatcg gcgtaagcta ccaaaccatt cagcgatttc agggtgtgta     120

tgtaatgata gatatattga tttgatggtc ggttcatgca tgtctgcagg tggagttctg     180

gatctgcctg ctactcaccc tgctgggcta catccccggc atcatctacg ccgtcttcgt     240

ccttgttgca tag                                                        253
```

<210> SEQ ID NO 12
<211> LENGTH: 54
<212> TYPE: PRT
<213> ORGANISM: Lolium perenne

<400> SEQUENCE: 12

```
Met Gly Ser Glu Thr Phe Leu Glu Ile Leu Leu Ala Ile Leu Leu Pro
1               5                   10                  15

Pro Leu Gly Val Phe Leu Arg Phe Gly Ile Gly Val Glu Phe Trp Ile
            20                  25                  30

Cys Leu Leu Leu Thr Leu Leu Gly Tyr Ile Pro Gly Ile Ile Tyr Ala
        35                  40                  45

Val Phe Val Leu Val Ala
    50
```

<210> SEQ ID NO 13
<211> LENGTH: 1475
<212> TYPE: DNA
<213> ORGANISM: Triticum aestivum
<220> FEATURE:
<221> NAME/KEY: misc_feature
<222> LOCATION: (437)..(437)
<223> OTHER INFORMATION: n is a, c, g, or t

<400> SEQUENCE: 13

```
atcatcacac acacacacac accaacacca caccaaccga cccgtctcgt ctcgcaagcg      60

tttcactctt tccctttcct ttcgcctcgc tctacccgcg gtcccacgtg ctccagcagc     120

catgtgcggc ggcgccatcc tctccgacat catcccgccg ccgcgccggg ccaccggcgg     180

caacgtctgg cgggcggaca agaagaggcg ggccaggccc gacgccgccg cggggaggcc     240

ccgccgtgcg cccgaggagg agttccagga ggaggagggc gacgcggagt tcgaggccga     300

cttcgagggg ttcgtggagg cggaggagga gtccgacggc gaggccaagc ccttccccgt     360

ccgcaggagc ggcttctccg gagatggatt gaaggcaact gctgctggtg atgatgactg     420

tgcctcaggg tctgctnaaa ggaagagaaa gaaccagttc aggggcatcc gccgccgccc     480

ttggggtaaa tgggctgctg aaataagaga tcctcgcaag ggtgtccgtg tctggcttgg     540

tacttacaac tccgctgagg aagctgccag agcctatgat gttgaagccc gcagaattcg     600

tggcaagaag gcagaggtca atttcccaga agaagctcct atggctcctc agcaacgctg     660

cgctactgct gtgaaggtgc ccgagttcaa caccgaacag aagccggtac tcaacaccat     720

gggcaacgca gatgtgtatt cctgctctgc tgttgactac accttaaatc agcaatttgt     780

gcagcctcag aacatgtcgt ttgtgcctac agtgaatgca gttgaggccc ctttcatgaa     840

tttttcctct gaccagggta gcaactcctt tagttgctca gacttcagct gggagaatga     900

tatcaagacc cctgacataa cttctgtgct tgcatccatt cccacctcaa cagaggtcaa     960

tgaatctgca tttctccaga acaatggcat caattcaacg gtacctcctg tgatgggtga    1020

tgctaatgtt gatcttgccg acttggagcc atacatgaag ttcctgatgg acgatggttc    1080

agatgagtca attgacagca ttctaagctg tgatgtaccc caggatgtgg tcggcaacat    1140

gggcctttgg acctttgatg acatgccctt gtctgctggt ttctactgag ggaatcgagg    1200

tcgctgggtg cctgtatata tagacaaagg aataagtatt caggacatca acaagtgctt    1260

gtgtctggtg cctctagaat tgagcagtag cgatgtcagt ctatggttat gtctagctta    1320

aatggtcagg tgactggggt cttttgcaat agacctctgt cttgtgcccc cagactatat    1380

tatatctata tatgagacca gtatgtgatg gggaactgct tattttgtat tcatgtttct    1440

accttattgt aattgctaaa aaaaaaaaaa aaaaa                               1475
```

-continued

<210> SEQ ID NO 14
<211> LENGTH: 1597
<212> TYPE: DNA
<213> ORGANISM: Oryza sativa

<400> SEQUENCE: 14
gaaagaaaag catcacaaat ctcacgcact gtctctcgtt cgcgcaaagc acgctgcttt 60
tctccgcttt gcgagcacca tagcctagcc caccatgtgc ggcggcgcca tcctctccga 120
cctcatcccg ccgccgcggc gggtcaccgc cggcgacctc tggctggaga agaccaagaa 180
gcagcagcag cagaagaaga agaacaaggg cgcgaggagg ctgccactgc gccaagagga 240
ggaggatgat ttcgaggccg acttcgagga gttcgaggtg gattccggcg agtgggaggt 300
ggagtccgac gccgacgagg ccaagccgct cgccgcgccc cggagcggct tcgctaaagg 360
tggattgaaa aacactactg ttgctggtgc tgatgggcct gcagcaaggt ctgctaaaag 420
gaagagaaag aaccaattca ggggtatccg ccagcggcca tggggcaaat gggctgcgga 480
aatcagagat cctcgcaaag gtgtccgcgt ctggcttggc accttcaact ctcctgagga 540
agctgccaga gcttatgatg ctgaagcacg aaggattcga ggcaagaagg ccaaggtcaa 600
tttcccagat ggggctccag tggcttctca gaggagtcat gctgagccct cctccatgaa 660
catgcctgct ttcagcatcg aagagaagcc ggccgtcatg tcagcaggca acaaaaccat 720
gtacaacaca aatgcttatg cctaccctgc tgttgagtac accttacagg agccatttgt 780
gcagattcag aatgtctcat ttgttcctgc aatgaacgcg attgaggata ctttcgtgaa 840
cctgtcctct gatcaaggga gcaactcctt tggttgctcg gactttagcc aggagaatga 900
tatcaagacc cctgacataa cttccatgct tgcaccgacc atgacaggtg ttgatgactc 960
cgcattcctc cagaacaatg ccagtgatgc aatggtacct cctgtgatgg ggaatgctag 1020
cattgatctt gctgacctgg agccgtacat gaaatttctg atcgatggtg gttcggatga 1080
gtcgattgac acccttctga gctctgatgg atctcaggat gtggccagta gcatggacct 1140
ttggagcttc gatgacatgc ccgtgtcggc cgagttctac tgaggggttt ggggtgtagc 1200
aactggtgcc tgtatatata aggacaaatg gaataaacat tctggacatc caagaagcgg 1260
catgtgtctg tcgggcgctt ctagttgcgc tatatagcta tgttagtatg ttagtatgtg 1320
ctgtgtctag cttagatgct gaagtctcaa gtactatttg gcagtgaaac tatctatctg 1380
taactgctat atgaggctgg aacaagttac ttagcttcta ccttatctgt acttgctata 1440
gtggctgtga accttgtgga tctgaactct gaagccaatg tttactatat aatgtggttg 1500
gttttataaa ctctagttga tttggacccc tgtcaatggt catgctatgg ctggggatta 1560
aaaaaaaaaa aaaaaaaaaa aaaaaaaaaa aaaaaaa 1597

<210> SEQ ID NO 15
<211> LENGTH: 1005
<212> TYPE: DNA
<213> ORGANISM: Prunus armeniaca

<400> SEQUENCE: 15
gagaaatctg caaagagaaa gaggaagaac cagtacaggg gaattcgcca gcgcccatgg 60
ggtaagtggg ctgcagagat ccgagatcca aggaaagggg tccgggtttg gcttggaact 120
ttcaacactg cagaagaagc tgcaagggct tatgattccg aggcacgtag aattcgtggc 180
aagaaagcca aggttaattt ccctgatgaa accccacgat cttctgcaaa gcgttctgtc 240
aaggcaaatc ctcagaaaat gcaacccaag acaaacatga atgccattca gcctaatctg 300

-continued

```
aaccagaata tcaattttgt gaatgaccca aatcaggact actacaatgc tatgggtttt    360

ctggatgaaa agccaccgac taataacttt gggtttatgt ccaccttccc tgccaatgat    420

gttgcgctga aatcctctac tccatccgat gctgtccccc tgtatttcgg ctctgatcag    480

ggaagcaatt cttttgattg ttctgacttt ggctggggag aacaaggttc aaagactcca    540

gaaatatcat ctgttctttc atctgttatg gaagaaagtg atgactcact gtttctggag    600

gatgctagcc caacgaagaa actgaggtct aacccagagg atctggtgcc tgttcaagat    660

aatgcaggaa agacactgac tgatgagctc tcagcttttg agatgaagta ctttcagacg    720

ccatatcttg atgggagctg ggatgcttca gtggatgcct tcctcagcgg agatgcaact    780

caggatggtg gcaactcagt ggacctttgg tgcttcgatg acctggttgg gggaggtttc    840

tgagcgaact tttccccatc cattctattt tatgtaaata aagctacatg ttagtgagtt    900

tgattctgca tcagcttcta cattgtttaa ttttatgttt catgttcact ctcattttat    960

tcagaaagag atcctggttg ctttttttaaa aaaaaaaaaa aaaaa                 1005
```

<210> SEQ ID NO 16
<211> LENGTH: 1605
<212> TYPE: DNA
<213> ORGANISM: Fagus sylvatica

<400> SEQUENCE: 16

```
caaacacact gaagaattaa gtcatttggg aatcaggttt cttggaaaaa cccctgccaa     60

agccccttca aggctctcag ctttgagtcc ccagatgtgt ggaggagcta taatctccga    120

ctttatagcg ccaaccgggt cgcggcggtt gacggcggat tatctctggg gcgatcggaa    180

aaaacccatt tcaggaaagc gattctcgaa gcctgtagtc gatttggacg acgaattcga    240

gctcgatttt cagggcttta aggacgagga ggagtctgat atcgacgagg aagaggtcct    300

tgtgcaagat gtcaagccct tcactttttc tgctcctcct agctctggat ctaagcctgt    360

aaaatccgtg gaattcaatg ggcaagctga gaaatctgca aagagaaaga ggaagaatca    420

gtatcggggg atccggcagc gcccatgggg taagtgggct gctgagattc gagacccaag    480

gaaaggggtc cgtgtctggc ttggaacttt taacactgca gaaaaagctg caagagctta    540

tgatgcagag gcacggagaa ttcgtggcaa gaaggctaag gtgaattttc ccgatgagac    600

tccccgtgct tctccaaagc gttcagttaa ggcaaatctg cagaagccac ttgccaaggc    660

aaacctgaac tctgtccagc ccaacctgaa ccaaaatttc aattttatga acaactctga    720

tcaggactat accatgggtt tgatggaaga gaaacctttc acaaaccagt atgggtatat    780

ggattccatc cctgccaatg cagatgttgg actaaaaccc tttgcttcca ataatactac    840

cccgtacttt aactcagatc aggggagtaa ctcgtttgat tgttctgact atggatgggg    900

agaacagggc tctaagactc cagaaatctc atctgttctt tcagctactt tagaagggga    960

tgaatctcag tttgtggagg atgctatgcc cacgaagaaa ttgaagtcag actctgggaa   1020

tgcagtgttc attgaaaata acactgcaaa gacactgtca gaggagctct cagcttttga   1080

gtcccagatg aactttcaga tgccatttct tgagggaagc tgggaatcca acatggaggc   1140

actgttcagt ggggacacaa ctcaggatgg taactcgatg gatctttgga gcttcgatga   1200

cctccccgtt atggctgggg gagttctgtg accgcaaaac tattttccgc atgcttgctg   1260

ttctagttta tgtataaata aggctaaata catgttagaa tggtttgtca ttctgtggag   1320

atggacatgc ctgtggtttc aaacaagctg aacactgaat gcttaagact ctatgaaggg   1380

atgtactgaa gtagtgttgt tctactgttg tatgagggag tacataggtc cctatttagg   1440
```

-continued atccctttga gagactacct tgaagacatt gaattttggg attttgaatt tgatgttttt 1500
gtattgatga ttatgtgtga tgaaacctct gtcataaaaa tactaaacta aaaacctgat 1560
gtatgtcaac tgtgtttagt gtttgtttca aaaaaaaaaa aaaaa 1605

<210> SEQ ID NO 17
<211> LENGTH: 1391
<212> TYPE: DNA
<213> ORGANISM: Lycopersicon esculentum

<400> SEQUENCE: 17
ttcaaattga gctttttctc cattaaaatt ctctctgcaa atttatagtt tttctttttt 60
cactttttga gaagaaatca aaagctatgt gtggtggtgc aattatctcc gatttggtac 120
ctcctagccg gatttctcgc cggttaaccg ctgatttttct atggggtaca tccgatctga 180
acaagaagaa gaagaaccct agtaattacc actcaaagcc cttgaggtct aagtttattg 240
accttgaaga tgaatttgaa gctgactttc agcacttcaa ggataattct gatgatgatg 300
atgatgtgaa ggcatttggc cccaaatccg tgagatctgg tgattcaaac tgcgaagctg 360
acagatcctc caagagaaag aggaagaatc agtaccgggg gatcagacag cgtccttggg 420
gtaagtgggc agctgaaata cgtgatccaa ggaaaggtat tcgagtctgg cttggtactt 480
tcaattcagc cgaagaggca gccagagctt atgatgctga ggcgcgaagg atcagaggca 540
agaaagctaa ggtgaacttt cctgatgaag ctccagtgtc tgtttcaaga cgtgctatta 600
agcaaaatcc ccaaaaggca cttcgtgagg aaaccctgaa cacagttcag cccaacatga 660
cttatattag taacttggat ggtggatctg atgattcgtt cagttttttc gaagagaaac 720
cagcaaccaa gcagtacggc ttcgagaatg tgtcttttac tgctgtagat atgggactgg 780
gctcagtttc cccttcagct ggtacaaatg tttacttcag ctctgatgaa gcaagtaaca 840
cttttgactg ctctgatttc ggttgggctg aaccgtgtgc aaggactcca gagatctcat 900
ctgttctgtc ggaagttctg gaaaccaatg agactcattt tgatgatgat tccagaccag 960
agaaaaaact gaagtcctgt tccagcactt cattgacagt tgacggtaac actgtgaaca 1020
cgctatctga agagctatcg gcttttgaat cccagatgaa gttcttgcag atcccatatc 1080
tcgagggaaa ttgggatgca tcggttgatg ccttcctcaa tacaagtgca attcaggatg 1140
gtggaaacgc catggacctt tggtccttcg atgatgtacc ttctttaatg ggaggtgcct 1200
actaagctgc atacacatct tcccctgcta agttttgtaa ataacgcttc atttgagtga 1260
agtttgcgcc tgcgtttacg tttatcacca aactaaaaga ctatatatgt gttgtattaa 1320
tttattcaaa atttactcgt ttgatatatg taagtatgta tccttgtttt cataaaaaaa 1380
aaaaaaaaaa a 1391

<210> SEQ ID NO 18
<211> LENGTH: 1403
<212> TYPE: DNA
<213> ORGANISM: Gossypium barbade

<400> SEQUENCE: 18
ttgagaatcg atgcccggat taataatttc tgggatgtag tcactaaaaa ggcctttctc 60
atgattttct tgcagttaaa ggtcttaaat tatatttcct tgtgacagtt atgttgtgat 120
ttgtagtttt tcatggatga gtaatgttta tttatggttc atgtatccgt acgatattaa 180
atttttcttt ttgtgctcta tcattgaagg ttcgaactct gaaaagtcca tgcagttcga 240
tggtcaagct gagaaatgtg cgaaaagaaa gaggaagaac cagtatcgtg gaatccggca 300

-continued

```
gcgcccatgg ggtaaatggg ctgctgagat ccgtgaccca aggaaagggg ttagggtctg    360

gttaggaact ttcaatactg ctgaagaagc tgcgagagct tatgatgctg aggcacggag    420

aattcgtggt aagaaagcta aggtgaactt ccctaacgag actccgcgta cctctccaaa    480

gcatgcagtc aagacaaatt ctcagaaacc actttccaag tcgaatttga gccctgttca    540

gctaaatctc gaccagaatt acaattactt gagccagcct gagcaggaat acttcgatac    600

catgggtttc gtagaagaga agccactggt caatcagttt gcatatgtgg accctgttcc    660

tacgtctata gatgctggat ctaatcaatc agataatgcc cccttgtact tcaattcgga    720

ccagggaagt aactccatca attgttccga ctatggctgg ggagaacagg gtgccagaac    780

tcctgaaata tcatccattc ttgaagcttc tgtagtgggt gaagagtttc ttgaggatgc    840

taaccctagc aagaagctga aaccaagttc tgacaatgtt atgcctgccg aagacaactc    900

cgcgaagacc ttgtcggacg agctgttggc tttggacaac cagatgaaat acttccaaat    960

gccgccattt attgaaggaa actgggacgc cactattgat gctttcctca atggagatgc   1020

aacacaggat ggtggaaacc cgatggatct ttggaacttt gatgatttcc ctaccatggc   1080

ggagggtgtt ttctgagcga actttccata ataactagtg tttgtaaata aagcaacatg   1140

aatttggtca aaatctgttg tgaagttgaa gtaaaaacca agctatatgc atgcttaagc   1200

cttgcctgca ctgctttcag aggtttttag tatgtacccc tttttatgt gtttttttgt   1260

agactttgga ctaaatttta aatttgagtg actgtataag taattgtgtc tgaatttgtt   1320

tatgtttgaa tactgaaaaa catatgaatg ttttaaactc tgctatttgt ttctcccaaa   1380

aaaaaaaaaa aaaaaaaaaa aaa                                           1403
```

<210> SEQ ID NO 19
<211> LENGTH: 1413
<212> TYPE: DNA
<213> ORGANISM: Nicotiana tabacum

<400> SEQUENCE: 19

```
gaattcggca cgagaaaaaa gaaagaagtt tactccgtca aaaacgaaac tgatttctgc     60

ataaaacttt tctgctgaga gaaaacaaaa agcatgtgtg gtggtgctat aatctccgat    120

tacattgccc cgagccgaac ttctcgccgg ctcaccgccg agttgctatg ggccggtcc    180

gatctgagta ataagcaaaa aaatcctaac aattatcact ccaagccgtt gagatcccaa    240

gtagttgacc tagacgatga cttcgaggct gattttcagg actttaaaga tttctccgat    300

gacgaggatg ttcaagtcga tgtcaagcca tttgccttct ctgcttcgaa aaactctaat    360

gttgaaggct ccaaatctgt gaaaactgat gattcagaca aggatgctga tagatcctct    420

aagagaaaga ggaagaatca gtatagggg atcagacagc gaccttgggg taagtgggca    480

gctgaaatac gtgacccaag aaaaggggtt cgggtgtggc tgggaacttt caatactgca    540

gaagaagctg ccagagctta tgatgttgag gctaggagga tcagaggcaa taaagctaag    600

gtaaactttc ccgatgaagc tccagtgcct gcctcgagac gtactgttaa ggtgaatcct    660

caaaaggtcc ttcctaagga gatcctggac tcggttcagc ccgactcgac tatcataaac    720

aacatggagg attgctgtta tgattctttg ggatttcttg aagagaaacc catgacgaag    780

cagtttggat gtgaggatgg gagcagtgct tctggagata cgggatttgg ctcatttgcc    840

ccttcagctg gtaccgatat ctacttcaac tctgatgttg gaagtaactc ttttgactgc    900

tctgattttg gttggggaga gccatgtgcc aggactccag agatatcatc cgttctgtca    960

gctgttattg aaagcaatga atctcaactt gttgaagatg ataccagtcc aatgaaaaaa   1020
```

-continued

```
ctgaaatcaa gccccattaa tccagtagct gatgatggaa ataccgcaaa caagctatct   1080

gaagagcttt cagcttttga aacccagatg aagttccttc agatccccta tctggaggga   1140

aattgggatg catcagttga tactttcctc aactcaagtg caactcagga tggtgataat   1200

gctatggact tatggtcctt tgatgatgtt ccttctttat tgggaggtgt cttttaagtc   1260

agcatgcctt gtctagtttt tgtaaataag gcttcatgtg agtgaacttt gctattgttt   1320

tgcctcaaag aaaggctctt tattatgtac agaagctttt tgaaatggta aatagtttaa   1380

tctctgttta aaaaaaaaaa aaaaaaaaaa aaa                                 1413
```

```
<210> SEQ ID NO 20
<211> LENGTH: 1329
<212> TYPE: DNA
<213> ORGANISM: Capsicum annuum

<400> SEQUENCE: 20

agttataata cactacttaa attattagag aaaagaaaaa gctatgtgtg gtggtgcaat     60

tatctccgat ttggtacctc ctagccggat ttcccgccgg ctaaccgccg agttgctatg    120

gggtaactct gatctgagca aaaagaagaa aaatccaggg aattattact caaagccttt    180

gaacaggtct aagtttattg accttgatga ggaatttgaa gctgactttc aggacttcaa    240

ggactatgcc gatgacgatg ttgatgatgt taagcccttc ggttccaaat ctgtgaaatc    300

tggcgattca agctgcgata ctgaaaaatc ttccaagaga aagaggaaga atcagtaccg    360

gggg atcaga cagcgtcctt ggggtaagtg ggcagctgaa attcgtgatc cgaggaaagg    420

gattcgagtt tggcttggaa ctttcaattc tgcggaagaa gcagctagag cttatgatgt    480

tgaggcacga aggatcagag gcaagaaggc taaggtgaac tttcctgatg gatctccagc    540

ttctgcttca agacgtgctg ttaagccaaa tcctcaggag gcacttcgcg aggaaatctt    600

gaacacagtt cagccgaaca caacttatat caacaacttg gacggcggat ctgatgattc    660

gtttggcttt ttcgaagaga aaccagcagc aaagcagtat ggctatgaga atgtttcttt    720

tactgctgga gatatgggac tgggttcaat ttccccttca actggtacaa caaatgttta    780

cttcagttct gatgaaggaa gcaacacctt tgactgctct gatttcggtt ggggtgaacc    840

atgtccgagg actccagaga tctcatctgt tctgtcagaa gttctagaat gtaatggtac    900

tcaatctgat gaagatgcta gaccagagaa aaaactgaag tcgtgttcca acgcttcctt    960

gccagatgag gataacactg tgcacacgct atctgaagag ctatcggctt ttgaatccca   1020

gatgaagttc ttgcagatcc catatcttga gggaaattgg gatgcatcag ttgatgcctt   1080

tgtcaacaca ggcgcaattc aggatggcgg aaatgcgatg gatctctggc cttcgatgat   1140

gttccttctt taatgggagg tgtctataag ccaacacgca ccttccctta ttaagttttg   1200

taaataaagc ttcatttgag tgaagtttgc agttatgttg tctccaaaca aaaaagacta   1260

tatatgtgtt gtattaaatt tatttcataa atttacttgt ttgatgtaaa aaaaaaaaaa   1320

aaaaaaaaa                                                           1329
```

```
<210> SEQ ID NO 21
<211> LENGTH: 1405
<212> TYPE: DNA
<213> ORGANISM: Cicer arietinum

<400> SEQUENCE: 21

ctggttttag agagtttaag gatgattctg atttcgatga agacgaggaa gatgatgatg     60

atgatgaagg cttgttggtc ggtggtaaag gatttacctt ttcttcaaac aacaccaagt    120
```

-continued

```
ctttcaaaac tttctctcgt ggatcaactg ctgcaaaatc cgtgtcaccg aaatcaaatg    180

agcaagctga aaaggcatgt aagagaaaga ggaagaatca atataggggt atccgccaac    240

gtccatgggg aaaatgggca gctgagatcc gcgacccaag gaagggagtt cgtgtctggc    300

ttggaacttt caacactgct gaagaagctg caagagctta cgatgctgaa gctagaagga    360

tccgcggcaa gaaagccaag gtgaattttc ccgaggaagc tccagttact tcctcaaaac    420

gattcaagcc aaatctcgag aataagctgg tgaataaaaa tctgaactct ttcaatccta    480

acgggaacaa aatgttcaac tttggcgaaa atgtggagaa ctactattct cctatggatc    540

aggtggaaca gaaaccactg gtgaacaata acaaccagta tgccaacatg ggaccgttct    600

cgggaaacgg tgttcagcac tcacagattt ctccatctgc tgatgttacc gcttacttca    660

gttcagaaca ttcgagcaat tcgtttgatt attctgatct tggttggggc gaacaaggcc    720

cgaaaactcc cgagatttca tccatgcttt ctgctgctgc tcctctcgaa agcgaatctc    780

agtatgtgca gaacaatatg cagtctaaca acaatcagaa tatgctacct gtggaagata    840

attctgcaaa gacactctct gaggagcttg cagatatcga atcccagctg aagttcttcg    900

aaaccccctta tgatgacaac tggggtgacg catcattggc atctttcctc ggtggagatg    960

caactcaaga cggtggaaac ccgatgaacc tttggagttt tgatgacttg ccttccattt   1020

ccggcggtgt tttctgaaca gccttcgcgt caccgattat gtaaataaag ctacaagatt   1080

gttggttttt tttttattat tgttgatgga atgaggacag gaacaagtta ccagctttaa   1140

gtaaagcatg gagtttattc tcttgtggca aaataaatta tataggtttt ttttaggtat   1200

cctttgtctt atcaaaaacc cttttgagga ttttaagttt gatgttcata aggattatgt   1260

tatggatgat ttaattgtaa actttcttgg ttttctttgt ggcaatttta tcatgactca   1320

taattttttt ctccctttgt ttggtgggat cattttatat gtaacatgaa tgattttgct   1380

ttaaaaaaaa aaaaaaaaaa aaaaa                                         1405
```

<210> SEQ ID NO 22
<211> LENGTH: 1539
<212> TYPE: DNA
<213> ORGANISM: Glycine max

<400> SEQUENCE: 22

```
attgagccaa agctttgtat tttctgcgat aattttccat tgggtggaag aaagtctcaa     60

cctttattcg aaagagcaag gatctgagtt gagttgagtg atcatgtgtg gtggtgcgat    120

tatctccgac ttcataccgg caggtcccgc cagcggggcg cggcgcgtga ccgccgacat    180

cctgtggccg agtttgagga agcgcttctc gaagccgctg ctggacgatg atttcgaggc    240

tgggttcaga gaattcaagg atgattcgga aatcgaggat gttgatgacg aggacgatga    300

agacgaggag gagttgaaga agaagccctt tgggttctct cgctccagca acaaggctgc    360

ttctaagcct ctctctcgtg gagcaacaac tgtgaaatct gtggaatcaa aggggcaagc    420

tgagaagtgt gccaagagaa agaggaagaa ccagtatcgc ggaatccgcc agcgtccatg    480

gggaaagtgg gctgctgaga ttcgcgaccc aagaaagggg gttcgtgttt ggcttggaac    540

tttcagcact gctgaagaag ctgcaagagc ttacgatgct gaagcaagga ggatccgtgg    600

caagaaagcc aaggtgaatt tccctgatga gccttcaggc gctgcttcct caaaacgtct    660

caaggcgaat ccagaggctc agccaatgaa gaaaaatctg aactctgtga agccgaaaat    720

aaaccagatg ttcaattttg gtgacaatct tgagggctac tacagcccta tagatcaggt    780

ggaacagaaa ccactggtta accagtatgt taaccgtgcc ccgtttgctg gaaatggagt    840
```

-continued

```
tcaagtctca cctgttactc catctgctga tgttactgct tacttcagct ctgagcattc    900

gagcaactcg tttgattatt ctgaccttgg atggggtgaa caagtcccca agaccccga     960

gatctcatcc ttgctttctg ctgctccttt ggagggtgct gctgatcagg ttcagaagac   1020

caacaactcg caggatgtgg tggctgcaca agatgattct gcaaaaaccc tttccgaaga   1080

gcttgcagac attgaatccc agctcaagtt ctttgagacc ccttcttttc ttgatgaagc   1140

ctgggctgat gctacattgg cgtctttgct cggcggagac gcaactcatg acgccgccgg   1200

aaaccctatg aacctttgga gcttcgacga cctgccttcc atggcaggag tcttctgaac   1260

accctttatc tccccttta tgtaaataaa gctacaagaa ttgtgatcgt gatgttggtg    1320

atggagtcca cagccaagaa acctgcttaa agcttatgtg gagtttattt tatcttgtag   1380

ctaatgcagt agtataggac tatatatagg tttttattat agggtatcct tttgtgaact   1440

caaagacctc gttttcaggg gattttctgt ttgatgtcct taaggattat caattatgtt   1500

atatatggtc ttggataaaa ataaaaaaaa aaaaaaaaa                          1539


<210> SEQ ID NO 23
<211> LENGTH: 1595
<212> TYPE: DNA
<213> ORGANISM: Arabidopsis thaliana

<400> SEQUENCE: 23

aaaacaacaa agcaaagcgt tgaagagaga agaagaagca aagatataac ccccaaaagt     60

atcaattagt ttccattttc gccgctaaga ttctgttttc gaacatttac accctcaaga    120

atcgccgcca tgtgtggagg agctataata tccgatttca ttccaccgcc gaggtctcgc    180

cgtgttacta gcgagtttat ttggccggat ctgaagaaga atttgaaagg atcgaagaaa    240

agctcgaaga atcgttcgaa tttcttcgat tttgacgctg agttcgaagc tgatttccaa    300

ggtttcaaag atgattcgtc tatcgattgc gatgatgatt tcgacgtcgg tgatgttttc    360

gccgatgtga aaccattcgt tttcacttcg actccaaaac ccgccgtctc cgccgctgcg    420

gaaggttcag tttttggtaa gaaagttact ggcttggatg gggacgctga gaaatctgca    480

aataggaaga ggaagaatca gtaccgaggg attaggcaac gtccttgggg aaaatgggct    540

gctgagatac gtgatccaag ggaaggtgct agaatctggc ttggaacgtt caagacagct    600

gaggaagctg ctagagctta cgatgctgca gcgcggagaa tccgtggatc taaagctaag    660

gtgaatttcc ctgaagaaaa catgaaggct aattctcaga aacgctctgt gaaggctaat    720

cttcagaaac cagtggctaa acctaaccct aacccaagtc cagctttggt tcagaactcg    780

aacatctcct ttgaaaatat gtgtttcatg gaggagaaac accaagtgag caacaacaac    840

aacaaccagt ttgggatgac aaactccgtt gatgctggat gtaatgggta tcagtatttc    900

agctctgacc agggtagtaa ttctttcgat tgttcggagt ttggttggag cgatcaagct    960

ccgataactc ccgacatctc ttctgcggtt atcaacaaca acaactcagc tctgttcttt   1020

gaggaagcca atccagctaa gaagctcaag tctatggatt tcgagacacc ttacaacaac   1080

actgaatggg acgcttcact ggatttcctc aacgaagatg ctgtaacgac tcaggacaat   1140

ggtgcaaacc ctatggacct atggagtatt gatgaaattc attccatgat tggaggagtc   1200

ttctgaagag atccagtttc atgtaaataa ggctgcatgt ttgtgagttt cccgcatcgt   1260

tcgtttatca acctccaaaa ctttctaatg tctgttactt gcatcttctt ctgctgtctc   1320

tgtctgtctc tctcaggagt tcctgtttgc attgcgagaa gccatgagcc tctatcttga   1380

gggtagttgt gatgaagtta agtagaggct tatttttagg ggttgtggta gtttttgttt   1440
```

-continued

```
tagtgaatct tttgaattcg tttgtgtttt gtttttgtta ctttatgccc caaaactcct   1500

ttaacatttg tcataatgtg tttgaacctc tcatctgttt aatcaaataa atcttctttg   1560

tatgctacta agagtatgtg agaactgttg aacat                              1595


<210> SEQ ID NO 24
<211> LENGTH: 2052
<212> TYPE: DNA
<213> ORGANISM: Zea mays

<400> SEQUENCE: 24

gcacgaggcc gcaattccgc atcacgcaga ggcagagcga ccaacccaga accccacccc     60

accgcccgca accgcaagct cagattccct ccccacccca ccccacccca ccgtcccgct    120

cactccagcc cagcccgcgt ccccacagcc cagcgacagc gggcaccggc ggcatccagc    180

catgtgcggc ggcgccatcc tgtcggacat catcccgccg ccgccaccgc ggcgggtcac    240

ggctggccac ctctggcccg agagcaagaa gccgaggagg gctgcatccg gcaggagggg    300

agcccccgtg gagcagcatg agcaggagga ggatttcgag gccgacttcg aggagttcga    360

ggtggagtcc ggcgagtcgg agctcgagtc cgaggacgag cccaagccct tcgccgcccc    420

caggagcgcg ctcgccagag gtggactaaa cactggtgca gctggtgtcg atggccctgc    480

tgcaaattca gttaaaagga agaggaagaa ccagttcagg ggtatccgcc ggcgcccgtg    540

gggcaaatgg gctgctgaga tcagagatcc tcgcaagggc gtgcgcgtct ggctcggtac    600

tttcaactcc cccgaagaag ctgccagagc ttacgacgcc gaggcacgca ggatccgcgg    660

caagaaggct aaagtcaact tcccggatga ggttcctacg gcggtttctc agaagcgccg    720

tgctgctggg cctgcctctc tgaaagcgcc taagatggac gttgaggagg agaagccgat    780

catcaagctc gcagtgaaca atatgaccaa ctcaaacgca tatcactacc ctgccgtcgt    840

cggccacaac atcatacccg agccattcat gcagactcag aacatgccat tcgctcctct    900

ggtgaattat gctgccctag tgaacctgtc ttcagaccaa ggcagcaact cgttcggttg    960

ctcggacttc agcctcgaga acgactccag gacccctgac ataacttcgg tgcctgcgcc   1020

cgttgccacc ttggccgccg ttggcgagtc tgtgttcgtc cagaacaccg ccggccatgc   1080

tgtggcgtct cctgcgacgg ggaacactgg tgttgatctc gccgagttgg agccgtatat   1140

gaatttcctg atggacggtg gttcagacga ctcgatcagc actctcttga gctgtgatgg   1200

atcccaggac gtggtcagca acatggacct ttggagcttc gaggacatgc ccatgtctgc   1260

tggtttctac tgaggctgag gcccagcgac tggtgcttgt gtacataggg ggggacaaag   1320

ggtaagagcc tgcagtaaca gagattggct ctttctggta cttgcaattt ctatcccttc   1380

aactctttct tccgcccccg tgtttcagga ataatgttct ggagatgaag aaacgcttgc   1440

gtgggcgtgc ctgcaggcac gcgtgtagta gctgcggtat tagtatatat gcttagatgt   1500

tcagtcactt cctttaagta caatttggcg ctggacatgt accttatttt actatgtatc   1560

cgtgacaaca gctatgtgtc tgcgtccgcg gggtctgggt actacgacca cacggcactt   1620

atgtatcacg cgatcccgct gtcccagcag ctggagtact tcagggagta ccagacgaag   1680

ctggcggcgg tggccggcgc cgggcaggcg cgctccatcc tcagcggcgc gctgtacatc   1740

gtcagtgccg gcgccagcga cttcgtgcag aactactaca taaacccgct gctgttcaag   1800

acgcagacgg ccgaccagtt ctccgaccgc ctcgtggcca tcttcggccg caccgtgcag   1860

gagctctacg gcatgggggc gcgccgcgtc ggcgtcacgt cgctgccgcc gctgggctgc   1920

ctgccggcgt ccatcacgct gttcgggcac ggcgccgccg ggtgcgtgtc caggctcaac   1980
```

-continued

```
agcgacgcgc agagcttcaa ccggaagatg aacggcaccg tggacgcgct ggcgcggcgg   2040

tacccggacc tc                                                       2052


<210> SEQ ID NO 25
<211> LENGTH: 746
<212> TYPE: DNA
<213> ORGANISM: Triticum monococcum

<400> SEQUENCE: 25

tgaagctcgc agaattcgtg gcaagaaggc aaaggtcaat ttcccagaag aagctcctat     60

ggctcctcag caacgctgcg ctacctctgt gaaggtgcct gagttcaaca ccgaacagaa    120

gccagtactc aacaccatgg gcaacgcaga tgtgtattcc tgccctgctg ttgactacac    180

cataaatcag caatttgtgc agcctcagaa catgtcgttt gtgcctacag tgaatgcagt    240

tgaggcccct ttcatgaatt tttcttctga ccaggggagc aactccttta gttgctcaga    300

cttcagctgg gagaatgata tcaagacccc tgacataaca tctgtgcttg catccattcc    360

cacctcaaca gaggtcaatg aatctgcatt tctccagaac aacggcatta attcaacggt    420

acctcctgtg atgggtgatg ctaatgttga tcttgccgac ttggagccat acatgaagtt    480

cctgatggac gatggttcag atgagtcaat tgacagcatt ctaagctgtg atgtacccca    540

ggacgtggtc agcaacatgg gcctttggac cttcgatgac atgcccttgt ctgctggttt    600

ctactgaggg aatggaggtc gctgggtgcc tgtatatata gacaaaggaa taagtattct    660

ggacatcaac aagtgcttgt gtctggtgcc tctagaatcg agcagtagcg atgtcagtct    720

atggttatgt ctagcttaaa tggtca                                         746


<210> SEQ ID NO 26
<211> LENGTH: 355
<212> TYPE: PRT
<213> ORGANISM: Triticum aestivum
<220> FEATURE:
<221> NAME/KEY: misc_feature
<222> LOCATION: (106)..(106)
<223> OTHER INFORMATION: Xaa can be any naturally occurring amino acid

<400> SEQUENCE: 26

Met Cys Gly Gly Ala Ile Leu Ser Asp Ile Ile Pro Pro Pro Arg Arg
1               5                   10                  15

Ala Thr Gly Gly Asn Val Trp Arg Ala Asp Lys Lys Arg Arg Ala Arg
            20                  25                  30

Pro Asp Ala Ala Ala Gly Arg Pro Arg Arg Ala Pro Glu Glu Glu Phe
        35                  40                  45

Gln Glu Glu Glu Gly Asp Ala Glu Phe Glu Ala Asp Phe Glu Gly Phe
    50                  55                  60

Val Glu Ala Glu Glu Glu Ser Asp Gly Glu Ala Lys Pro Phe Pro Val
65                  70                  75                  80

Arg Arg Ser Gly Phe Ser Gly Asp Gly Leu Lys Ala Thr Ala Ala Gly
                85                  90                  95

Asp Asp Asp Cys Ala Ser Gly Ser Ala Xaa Arg Lys Arg Lys Asn Gln
            100                 105                 110

Phe Arg Gly Ile Arg Arg Arg Pro Trp Gly Lys Trp Ala Ala Glu Ile
        115                 120                 125

Arg Asp Pro Arg Lys Gly Val Arg Val Trp Leu Gly Thr Tyr Asn Ser
    130                 135                 140

Ala Glu Glu Ala Ala Arg Ala Tyr Asp Val Glu Ala Arg Arg Ile Arg
145                 150                 155                 160
```

-continued

```
Gly Lys Lys Ala Glu Val Asn Phe Pro Glu Glu Ala Pro Met Ala Pro
                165                 170                 175

Gln Gln Arg Cys Ala Thr Ala Val Lys Val Pro Glu Phe Asn Thr Glu
            180                 185                 190

Gln Lys Pro Val Leu Asn Thr Met Gly Asn Ala Asp Val Tyr Ser Cys
        195                 200                 205

Ser Ala Val Asp Tyr Thr Leu Asn Gln Gln Phe Val Gln Pro Gln Asn
    210                 215                 220

Met Ser Phe Val Pro Thr Val Asn Ala Val Glu Ala Pro Phe Met Asn
225                 230                 235                 240

Phe Ser Ser Asp Gln Gly Ser Asn Ser Phe Ser Cys Ser Asp Phe Ser
                245                 250                 255

Trp Glu Asn Asp Ile Lys Thr Pro Asp Ile Thr Ser Val Leu Ala Ser
            260                 265                 270

Ile Pro Thr Ser Thr Glu Val Asn Glu Ser Ala Phe Leu Gln Asn Asn
        275                 280                 285

Gly Ile Asn Ser Thr Val Pro Pro Val Met Gly Asp Ala Asn Val Asp
    290                 295                 300

Leu Ala Asp Leu Glu Pro Tyr Met Lys Phe Leu Met Asp Asp Gly Ser
305                 310                 315                 320

Asp Glu Ser Ile Asp Ser Ile Leu Ser Cys Asp Val Pro Gln Asp Val
                325                 330                 335

Val Gly Asn Met Gly Leu Trp Thr Phe Asp Asp Met Pro Leu Ser Ala
            340                 345                 350

Gly Phe Tyr
        355


<210> SEQ ID NO 27
<211> LENGTH: 362
<212> TYPE: PRT
<213> ORGANISM: Oryza sativa

<400> SEQUENCE: 27

Met Cys Gly Gly Ala Ile Leu Ser Asp Leu Ile Pro Pro Pro Arg Arg
1               5                   10                  15

Val Thr Ala Gly Asp Leu Trp Leu Glu Lys Thr Lys Lys Gln Gln Gln
            20                  25                  30

Gln Lys Lys Lys Asn Lys Gly Ala Arg Arg Leu Pro Leu Arg Gln Glu
        35                  40                  45

Glu Glu Asp Asp Phe Glu Ala Asp Phe Glu Glu Phe Glu Val Asp Ser
    50                  55                  60

Gly Glu Trp Glu Val Glu Ser Asp Ala Asp Glu Ala Lys Pro Leu Ala
65                  70                  75                  80

Ala Pro Arg Ser Gly Phe Ala Lys Gly Gly Leu Lys Asn Thr Thr Val
                85                  90                  95

Ala Gly Ala Asp Gly Pro Ala Ala Arg Ser Ala Lys Arg Lys Arg Lys
            100                 105                 110

Asn Gln Phe Arg Gly Ile Arg Gln Arg Pro Trp Gly Lys Trp Ala Ala
        115                 120                 125

Glu Ile Arg Asp Pro Arg Lys Gly Val Arg Val Trp Leu Gly Thr Phe
    130                 135                 140

Asn Ser Pro Glu Glu Ala Ala Arg Ala Tyr Asp Ala Glu Ala Arg Arg
145                 150                 155                 160

Ile Arg Gly Lys Lys Ala Lys Val Asn Phe Pro Asp Gly Ala Pro Val
                165                 170                 175
```

-continued

Ala Ser Gln Arg Ser His Ala Glu Pro Ser Ser Met Asn Met Pro Ala
180 185 190

Phe Ser Ile Glu Glu Lys Pro Ala Val Met Ser Ala Gly Asn Lys Thr
195 200 205

Met Tyr Asn Thr Asn Ala Tyr Ala Tyr Pro Ala Val Glu Tyr Thr Leu
210 215 220

Gln Glu Pro Phe Val Gln Ile Gln Asn Val Ser Phe Val Pro Ala Met
225 230 235 240

Asn Ala Ile Glu Asp Thr Phe Val Asn Leu Ser Ser Asp Gln Gly Ser
245 250 255

Asn Ser Phe Gly Cys Ser Asp Phe Ser Gln Glu Asn Asp Ile Lys Thr
260 265 270

Pro Asp Ile Thr Ser Met Leu Ala Pro Thr Met Thr Gly Val Asp Asp
275 280 285

Ser Ala Phe Leu Gln Asn Asn Ala Ser Asp Ala Met Val Pro Pro Val
290 295 300

Met Gly Asn Ala Ser Ile Asp Leu Ala Asp Leu Glu Pro Tyr Met Lys
305 310 315 320

Phe Leu Ile Asp Gly Gly Ser Asp Glu Ser Ile Asp Thr Leu Leu Ser
325 330 335

Ser Asp Gly Ser Gln Asp Val Ala Ser Ser Met Asp Leu Trp Ser Phe
340 345 350

Asp Asp Met Pro Val Ser Ala Glu Phe Tyr
355 360

<210> SEQ ID NO 28
<211> LENGTH: 280
<212> TYPE: PRT
<213> ORGANISM: Prunus armeniaca

<400> SEQUENCE: 28

Glu Lys Ser Ala Lys Arg Lys Arg Lys Asn Gln Tyr Arg Gly Ile Arg
1 5 10 15

Gln Arg Pro Trp Gly Lys Trp Ala Ala Glu Ile Arg Asp Pro Arg Lys
20 25 30

Gly Val Arg Val Trp Leu Gly Thr Phe Asn Thr Ala Glu Glu Ala Ala
35 40 45

Arg Ala Tyr Asp Ser Glu Ala Arg Arg Ile Arg Gly Lys Lys Ala Lys
50 55 60

Val Asn Phe Pro Asp Glu Thr Pro Arg Ser Ser Ala Lys Arg Ser Val
65 70 75 80

Lys Ala Asn Pro Gln Lys Met Gln Pro Lys Thr Asn Met Asn Ala Ile
85 90 95

Gln Pro Asn Leu Asn Gln Asn Ile Asn Phe Val Asn Asp Pro Asn Gln
100 105 110

Asp Tyr Tyr Asn Ala Met Gly Phe Leu Asp Glu Lys Pro Pro Thr Asn
115 120 125

Asn Phe Gly Phe Met Ser Thr Phe Pro Ala Asn Asp Val Ala Leu Lys
130 135 140

Ser Ser Thr Pro Ser Asp Ala Val Pro Leu Tyr Phe Gly Ser Asp Gln
145 150 155 160

Gly Ser Asn Ser Phe Asp Cys Ser Asp Phe Gly Trp Gly Glu Gln Gly
165 170 175

Ser Lys Thr Pro Glu Ile Ser Ser Val Leu Ser Ser Val Met Glu Glu
180 185 190

-continued

```
Ser Asp Asp Ser Leu Phe Leu Glu Asp Ala Ser Pro Thr Lys Lys Leu
        195                 200                 205

Arg Ser Asn Pro Glu Asp Leu Val Pro Val Gln Asp Asn Ala Gly Lys
    210                 215                 220

Thr Leu Thr Asp Glu Leu Ser Ala Phe Glu Met Lys Tyr Phe Gln Thr
225                 230                 235                 240

Pro Tyr Leu Asp Gly Ser Trp Asp Ala Ser Val Asp Ala Phe Leu Ser
                245                 250                 255

Gly Asp Ala Thr Gln Asp Gly Gly Asn Ser Val Asp Leu Trp Cys Phe
            260                 265                 270

Asp Asp Leu Val Gly Gly Gly Phe
        275                 280


<210> SEQ ID NO 29
<211> LENGTH: 378
<212> TYPE: PRT
<213> ORGANISM: Fagus sylvatica

<400> SEQUENCE: 29

Met Cys Gly Gly Ala Ile Ile Ser Asp Phe Ile Ala Pro Thr Gly Ser
1               5                   10                  15

Arg Arg Leu Thr Ala Asp Tyr Leu Trp Gly Asp Arg Lys Lys Pro Ile
            20                  25                  30

Ser Gly Lys Arg Phe Ser Lys Pro Val Val Asp Leu Asp Asp Glu Phe
        35                  40                  45

Glu Leu Asp Phe Gln Gly Phe Lys Asp Glu Glu Glu Ser Asp Ile Asp
    50                  55                  60

Glu Glu Glu Val Leu Val Gln Asp Val Lys Pro Phe Thr Phe Ser Ala
65                  70                  75                  80

Pro Pro Ser Ser Gly Ser Lys Pro Val Lys Ser Val Glu Phe Asn Gly
                85                  90                  95

Gln Ala Glu Lys Ser Ala Lys Arg Lys Arg Lys Asn Gln Tyr Arg Gly
            100                 105                 110

Ile Arg Gln Arg Pro Trp Gly Lys Trp Ala Ala Glu Ile Arg Asp Pro
        115                 120                 125

Arg Lys Gly Val Arg Val Trp Leu Gly Thr Phe Asn Thr Ala Glu Lys
    130                 135                 140

Ala Ala Arg Ala Tyr Asp Ala Glu Ala Arg Arg Ile Arg Gly Lys Lys
145                 150                 155                 160

Ala Lys Val Asn Phe Pro Asp Glu Thr Pro Arg Ala Ser Pro Lys Arg
                165                 170                 175

Ser Val Lys Ala Asn Leu Gln Lys Pro Leu Ala Lys Ala Asn Leu Asn
            180                 185                 190

Ser Val Gln Pro Asn Leu Asn Gln Asn Phe Asn Phe Met Asn Asn Ser
        195                 200                 205

Asp Gln Asp Tyr Thr Met Gly Leu Met Glu Glu Lys Pro Phe Thr Asn
    210                 215                 220

Gln Tyr Gly Tyr Met Asp Ser Ile Pro Ala Asn Ala Asp Val Gly Leu
225                 230                 235                 240

Lys Pro Phe Ala Ser Asn Asn Thr Thr Pro Tyr Phe Asn Ser Asp Gln
                245                 250                 255

Gly Ser Asn Ser Phe Asp Cys Ser Asp Tyr Gly Trp Gly Glu Gln Gly
            260                 265                 270

Ser Lys Thr Pro Glu Ile Ser Ser Val Leu Ser Ala Thr Leu Glu Gly
        275                 280                 285
```

-continued

```
Asp Glu Ser Gln Phe Val Glu Asp Ala Met Pro Thr Lys Lys Leu Lys
    290                 295                 300

Ser Asp Ser Gly Asn Ala Val Phe Ile Glu Asn Asn Thr Ala Lys Thr
305                 310                 315                 320

Leu Ser Glu Glu Leu Ser Ala Phe Glu Ser Gln Met Asn Phe Gln Met
                325                 330                 335

Pro Phe Leu Glu Gly Ser Trp Glu Ser Asn Met Glu Ala Leu Phe Ser
            340                 345                 350

Gly Asp Thr Thr Gln Asp Gly Asn Ser Met Asp Leu Trp Ser Phe Asp
        355                 360                 365

Asp Leu Pro Val Met Ala Gly Gly Val Leu
    370                 375


<210> SEQ ID NO 30
<211> LENGTH: 372
<212> TYPE: PRT
<213> ORGANISM: Lycopersicon esculentum

<400> SEQUENCE: 30

Met Cys Gly Gly Ala Ile Ile Ser Asp Leu Val Pro Pro Ser Arg Ile
1               5                   10                  15

Ser Arg Arg Leu Thr Ala Asp Phe Leu Trp Gly Thr Ser Asp Leu Asn
            20                  25                  30

Lys Lys Lys Lys Asn Pro Ser Asn Tyr His Ser Lys Pro Leu Arg Ser
        35                  40                  45

Lys Phe Ile Asp Leu Glu Asp Glu Phe Glu Ala Asp Phe Gln His Phe
    50                  55                  60

Lys Asp Asn Ser Asp Asp Asp Asp Asp Val Lys Ala Phe Gly Pro Lys
65                  70                  75                  80

Ser Val Arg Ser Gly Asp Ser Asn Cys Glu Ala Asp Arg Ser Ser Lys
                85                  90                  95

Arg Lys Arg Lys Asn Gln Tyr Arg Gly Ile Arg Gln Arg Pro Trp Gly
            100                 105                 110

Lys Trp Ala Ala Glu Ile Arg Asp Pro Arg Lys Gly Ile Arg Val Trp
        115                 120                 125

Leu Gly Thr Phe Asn Ser Ala Glu Glu Ala Ala Arg Ala Tyr Asp Ala
    130                 135                 140

Glu Ala Arg Arg Ile Arg Gly Lys Lys Ala Lys Val Asn Phe Pro Asp
145                 150                 155                 160

Glu Ala Pro Val Ser Val Ser Arg Arg Ala Ile Lys Gln Asn Pro Gln
                165                 170                 175

Lys Ala Leu Arg Glu Glu Thr Leu Asn Thr Val Gln Pro Asn Met Thr
            180                 185                 190

Tyr Ile Ser Asn Leu Asp Gly Gly Ser Asp Asp Ser Phe Ser Phe Phe
        195                 200                 205

Glu Glu Lys Pro Ala Thr Lys Gln Tyr Gly Phe Glu Asn Val Ser Phe
    210                 215                 220

Thr Ala Val Asp Met Gly Leu Gly Ser Val Ser Pro Ser Ala Gly Thr
225                 230                 235                 240

Asn Val Tyr Phe Ser Ser Asp Glu Ala Ser Asn Thr Phe Asp Cys Ser
                245                 250                 255

Asp Phe Gly Trp Ala Glu Pro Cys Ala Arg Thr Pro Glu Ile Ser Ser
            260                 265                 270

Val Leu Ser Glu Val Leu Glu Thr Asn Glu Thr His Phe Asp Asp Asp
        275                 280                 285
```

-continued

Ser Arg Pro Glu Lys Lys Leu Lys Ser Cys Ser Ser Thr Ser Leu Thr
    290                 295                 300

Val Asp Gly Asn Thr Val Asn Thr Leu Ser Glu Glu Leu Ser Ala Phe
305                 310                 315                 320

Glu Ser Gln Met Lys Phe Leu Gln Ile Pro Tyr Leu Glu Gly Asn Trp
                325                 330                 335

Asp Ala Ser Val Asp Ala Phe Leu Asn Thr Ser Ala Ile Gln Asp Gly
            340                 345                 350

Gly Asn Ala Met Asp Leu Trp Ser Phe Asp Asp Val Pro Ser Leu Met
        355                 360                 365

Gly Gly Ala Tyr
    370

<210> SEQ ID NO 31
<211> LENGTH: 319
<212> TYPE: PRT
<213> ORGANISM: Gossypium barbade

<400> SEQUENCE: 31

Met Ser Asn Val Tyr Leu Trp Phe Met Tyr Pro Tyr Asp Ile Lys Phe
1               5                   10                  15

Phe Phe Leu Cys Ser Ile Ile Glu Gly Ser Asn Ser Glu Lys Ser Met
            20                  25                  30

Gln Phe Asp Gly Gln Ala Glu Lys Cys Ala Lys Arg Lys Arg Lys Asn
        35                  40                  45

Gln Tyr Arg Gly Ile Arg Gln Arg Pro Trp Gly Lys Trp Ala Ala Glu
    50                  55                  60

Ile Arg Asp Pro Arg Lys Gly Val Arg Val Trp Leu Gly Thr Phe Asn
65                  70                  75                  80

Thr Ala Glu Glu Ala Ala Arg Ala Tyr Asp Ala Glu Ala Arg Arg Ile
                85                  90                  95

Arg Gly Lys Lys Ala Lys Val Asn Phe Pro Asn Glu Thr Pro Arg Thr
            100                 105                 110

Ser Pro Lys His Ala Val Lys Thr Asn Ser Gln Lys Pro Leu Ser Lys
        115                 120                 125

Ser Asn Leu Ser Pro Val Gln Leu Asn Leu Asp Gln Asn Tyr Asn Tyr
    130                 135                 140

Leu Ser Gln Pro Glu Gln Glu Tyr Phe Asp Thr Met Gly Phe Val Glu
145                 150                 155                 160

Glu Lys Pro Leu Val Asn Gln Phe Ala Tyr Val Asp Pro Val Pro Thr
                165                 170                 175

Ser Ile Asp Ala Gly Ser Asn Gln Ser Asp Asn Ala Pro Leu Tyr Phe
            180                 185                 190

Asn Ser Asp Gln Gly Ser Asn Ser Ile Asn Cys Ser Asp Tyr Gly Trp
        195                 200                 205

Gly Glu Gln Gly Ala Arg Thr Pro Glu Ile Ser Ser Ile Leu Glu Ala
    210                 215                 220

Ser Val Val Gly Glu Glu Phe Leu Glu Asp Ala Asn Pro Ser Lys Lys
225                 230                 235                 240

Leu Lys Pro Ser Ser Asp Asn Val Met Pro Ala Glu Asp Asn Ser Ala
                245                 250                 255

Lys Thr Leu Ser Asp Glu Leu Leu Ala Leu Asp Asn Gln Met Lys Tyr
            260                 265                 270

Phe Gln Met Pro Pro Phe Ile Glu Gly Asn Trp Asp Ala Thr Ile Asp
        275                 280                 285

-continued

```
Ala Phe Leu Asn Gly Asp Ala Thr Gln Asp Gly Gly Asn Pro Met Asp
    290                 295                 300

Leu Trp Asn Phe Asp Asp Phe Pro Thr Met Ala Glu Gly Val Phe
305                 310                 315


<210> SEQ ID NO 32
<211> LENGTH: 387
<212> TYPE: PRT
<213> ORGANISM: Nicotiana tabacum

<400> SEQUENCE: 32

Met Cys Gly Gly Ala Ile Ile Ser Asp Tyr Ile Ala Pro Ser Arg Thr
1               5                   10                  15

Ser Arg Arg Leu Thr Ala Glu Leu Leu Trp Gly Arg Ser Asp Leu Ser
            20                  25                  30

Asn Lys Gln Lys Asn Pro Asn Asn Tyr His Ser Lys Pro Leu Arg Ser
        35                  40                  45

Gln Val Val Asp Leu Asp Asp Asp Phe Glu Ala Asp Phe Gln Asp Phe
    50                  55                  60

Lys Asp Phe Ser Asp Asp Glu Asp Val Gln Val Asp Val Lys Pro Phe
65                  70                  75                  80

Ala Phe Ser Ala Ser Lys Asn Ser Asn Val Glu Gly Ser Lys Ser Val
                85                  90                  95

Lys Thr Asp Asp Ser Asp Lys Asp Ala Asp Arg Ser Ser Lys Arg Lys
            100                 105                 110

Arg Lys Asn Gln Tyr Arg Gly Ile Arg Gln Arg Pro Trp Gly Lys Trp
        115                 120                 125

Ala Ala Glu Ile Arg Asp Pro Arg Lys Gly Val Arg Val Trp Leu Gly
    130                 135                 140

Thr Phe Asn Thr Ala Glu Glu Ala Ala Arg Ala Tyr Asp Val Glu Ala
145                 150                 155                 160

Arg Arg Ile Arg Gly Asn Lys Ala Lys Val Asn Phe Pro Asp Glu Ala
                165                 170                 175

Pro Val Pro Ala Ser Arg Arg Thr Val Lys Val Asn Pro Gln Lys Val
            180                 185                 190

Leu Pro Lys Glu Ile Leu Asp Ser Val Gln Pro Asp Ser Thr Ile Ile
        195                 200                 205

Asn Asn Met Glu Asp Cys Cys Tyr Asp Ser Leu Gly Phe Leu Glu Glu
    210                 215                 220

Lys Pro Met Thr Lys Gln Phe Gly Cys Glu Asp Gly Ser Ser Ala Ser
225                 230                 235                 240

Gly Asp Thr Gly Phe Gly Ser Phe Ala Pro Ser Ala Gly Thr Asp Ile
                245                 250                 255

Tyr Phe Asn Ser Asp Val Gly Ser Asn Ser Phe Asp Cys Ser Asp Phe
            260                 265                 270

Gly Trp Gly Glu Pro Cys Ala Arg Thr Pro Glu Ile Ser Ser Val Leu
        275                 280                 285

Ser Ala Val Ile Glu Ser Asn Glu Ser Gln Leu Val Glu Asp Asp Thr
    290                 295                 300

Ser Pro Met Lys Lys Leu Lys Ser Ser Pro Ile Asn Pro Val Ala Asp
305                 310                 315                 320

Asp Gly Asn Thr Ala Asn Lys Leu Ser Glu Glu Leu Ser Ala Phe Glu
                325                 330                 335

Thr Gln Met Lys Phe Leu Gln Ile Pro Tyr Leu Glu Gly Asn Trp Asp
            340                 345                 350
```

-continued

Ala Ser Val Asp Thr Phe Leu Asn Ser Ser Ala Thr Gln Asp Gly Asp
355 360 365

Asn Ala Met Asp Leu Trp Ser Phe Asp Asp Val Pro Ser Leu Leu Gly
370 375 380

Gly Val Phe
385

<210> SEQ ID NO 33
<211> LENGTH: 369
<212> TYPE: PRT
<213> ORGANISM: Capsicum annuum

<400> SEQUENCE: 33

Met Cys Gly Gly Ala Ile Ile Ser Asp Leu Val Pro Pro Ser Arg Ile
1 5 10 15

Ser Arg Arg Leu Thr Ala Glu Leu Leu Trp Gly Asn Ser Asp Leu Ser
20 25 30

Lys Lys Lys Lys Asn Pro Gly Asn Tyr Tyr Ser Lys Pro Leu Asn Arg
35 40 45

Ser Lys Phe Ile Asp Leu Asp Glu Glu Phe Glu Ala Asp Phe Gln Asp
50 55 60

Phe Lys Asp Tyr Ala Asp Asp Asp Val Asp Asp Val Lys Pro Phe Gly
65 70 75 80

Ser Lys Ser Val Lys Ser Gly Asp Ser Ser Cys Asp Thr Glu Lys Ser
85 90 95

Ser Lys Arg Lys Arg Lys Asn Gln Tyr Arg Gly Ile Arg Gln Arg Pro
100 105 110

Trp Gly Lys Trp Ala Ala Glu Ile Arg Asp Pro Arg Lys Gly Ile Arg
115 120 125

Val Trp Leu Gly Thr Phe Asn Ser Ala Glu Glu Ala Ala Arg Ala Tyr
130 135 140

Asp Val Glu Ala Arg Arg Ile Arg Gly Lys Lys Ala Lys Val Asn Phe
145 150 155 160

Pro Asp Gly Ser Pro Ala Ser Ala Ser Arg Arg Ala Val Lys Pro Asn
165 170 175

Pro Gln Glu Ala Leu Arg Glu Glu Ile Leu Asn Thr Val Gln Pro Asn
180 185 190

Thr Thr Tyr Ile Asn Asn Leu Asp Gly Gly Ser Asp Asp Ser Phe Gly
195 200 205

Phe Phe Glu Glu Lys Pro Ala Ala Lys Gln Tyr Gly Tyr Glu Asn Val
210 215 220

Ser Phe Thr Ala Gly Asp Met Gly Leu Gly Ser Ile Ser Pro Ser Thr
225 230 235 240

Gly Thr Thr Asn Val Tyr Phe Ser Ser Asp Glu Gly Ser Asn Thr Phe
245 250 255

Asp Cys Ser Asp Phe Gly Trp Gly Glu Pro Cys Pro Arg Thr Pro Glu
260 265 270

Ile Ser Ser Val Leu Ser Glu Val Leu Glu Cys Asn Gly Thr Gln Ser
275 280 285

Asp Glu Asp Ala Arg Pro Glu Lys Lys Leu Lys Ser Cys Ser Asn Ala
290 295 300

Ser Leu Pro Asp Glu Asp Asn Thr Val His Thr Leu Ser Glu Glu Leu
305 310 315 320

Ser Ala Phe Glu Ser Gln Met Lys Phe Leu Gln Ile Pro Tyr Leu Glu
325 330 335

-continued

```
Gly Asn Trp Asp Ala Ser Val Asp Ala Phe Val Asn Thr Gly Ala Ile
            340                 345                 350

Gln Asp Gly Gly Asn Ala Met Asp Leu Trp Pro Ser Met Met Phe Leu
        355                 360                 365

Leu


<210> SEQ ID NO 34
<211> LENGTH: 344
<212> TYPE: PRT
<213> ORGANISM: Cicer arietinum

<400> SEQUENCE: 34

Gly Phe Arg Glu Phe Lys Asp Asp Ser Asp Phe Asp Glu Asp Glu Glu
1               5                   10                  15

Asp Asp Asp Asp Asp Glu Gly Leu Leu Val Gly Gly Lys Gly Phe Thr
            20                  25                  30

Phe Ser Ser Asn Asn Thr Lys Ser Phe Lys Thr Phe Ser Arg Gly Ser
        35                  40                  45

Thr Ala Ala Lys Ser Val Ser Pro Lys Ser Asn Glu Gln Ala Glu Lys
    50                  55                  60

Ala Cys Lys Arg Lys Arg Lys Asn Gln Tyr Arg Gly Ile Arg Gln Arg
65                  70                  75                  80

Pro Trp Gly Lys Trp Ala Ala Glu Ile Arg Asp Pro Arg Lys Gly Val
                85                  90                  95

Arg Val Trp Leu Gly Thr Phe Asn Thr Ala Glu Glu Ala Ala Arg Ala
            100                 105                 110

Tyr Asp Ala Glu Ala Arg Arg Ile Arg Gly Lys Lys Ala Lys Val Asn
        115                 120                 125

Phe Pro Glu Glu Ala Pro Val Thr Ser Ser Lys Arg Phe Lys Pro Asn
    130                 135                 140

Leu Glu Asn Lys Leu Val Asn Lys Asn Leu Asn Ser Phe Asn Pro Asn
145                 150                 155                 160

Gly Asn Lys Met Phe Asn Phe Gly Glu Asn Val Glu Asn Tyr Tyr Ser
                165                 170                 175

Pro Met Asp Gln Val Glu Gln Lys Pro Leu Val Asn Asn Asn Asn Gln
            180                 185                 190

Tyr Ala Asn Met Gly Pro Phe Ser Gly Asn Gly Val Gln His Ser Gln
        195                 200                 205

Ile Ser Pro Ser Ala Asp Val Thr Ala Tyr Phe Ser Ser Glu His Ser
    210                 215                 220

Ser Asn Ser Phe Asp Tyr Ser Asp Leu Gly Trp Gly Glu Gln Gly Pro
225                 230                 235                 240

Lys Thr Pro Glu Ile Ser Ser Met Leu Ser Ala Ala Ala Pro Leu Glu
                245                 250                 255

Ser Glu Ser Gln Tyr Val Gln Asn Asn Met Gln Ser Asn Asn Asn Gln
            260                 265                 270

Asn Met Leu Pro Val Glu Asp Asn Ser Ala Lys Thr Leu Ser Glu Glu
        275                 280                 285

Leu Ala Asp Ile Glu Ser Gln Leu Lys Phe Phe Glu Thr Pro Tyr Asp
    290                 295                 300

Asp Asn Trp Gly Asp Ala Ser Leu Ala Ser Phe Leu Gly Gly Asp Ala
305                 310                 315                 320
```

-continued

```
Thr Gln Asp Gly Gly Asn Pro Met Asn Leu Trp Ser Phe Asp Asp Leu
                325                 330                 335

Pro Ser Ile Ser Gly Gly Val Phe
            340


<210> SEQ ID NO 35
<211> LENGTH: 384
<212> TYPE: PRT
<213> ORGANISM: Glycine max

<400> SEQUENCE: 35

Met Cys Gly Gly Ala Ile Ile Ser Asp Phe Ile Pro Ala Gly Pro Ala
1               5                   10                  15

Ser Gly Ala Arg Arg Val Thr Ala Asp Ile Leu Trp Pro Ser Leu Arg
            20                  25                  30

Lys Arg Phe Ser Lys Pro Leu Leu Asp Asp Asp Phe Glu Ala Gly Phe
        35                  40                  45

Arg Glu Phe Lys Asp Asp Ser Glu Ile Glu Asp Val Asp Asp Glu Asp
    50                  55                  60

Asp Glu Asp Glu Glu Glu Leu Lys Lys Lys Pro Phe Gly Phe Ser Arg
65                  70                  75                  80

Ser Ser Asn Lys Ala Ala Ser Lys Pro Leu Ser Arg Gly Ala Thr Thr
                85                  90                  95

Val Lys Ser Val Glu Ser Lys Gly Gln Ala Glu Lys Cys Ala Lys Arg
            100                 105                 110

Lys Arg Lys Asn Gln Tyr Arg Gly Ile Arg Gln Arg Pro Trp Gly Lys
        115                 120                 125

Trp Ala Ala Glu Ile Arg Asp Pro Arg Lys Gly Val Arg Val Trp Leu
    130                 135                 140

Gly Thr Phe Ser Thr Ala Glu Glu Ala Ala Arg Ala Tyr Asp Ala Glu
145                 150                 155                 160

Ala Arg Arg Ile Arg Gly Lys Lys Ala Lys Val Asn Phe Pro Asp Glu
                165                 170                 175

Pro Ser Gly Ala Ala Ser Ser Lys Arg Leu Lys Ala Asn Pro Glu Ala
            180                 185                 190

Gln Pro Met Lys Lys Asn Leu Asn Ser Val Lys Pro Lys Ile Asn Gln
        195                 200                 205

Met Phe Asn Phe Gly Asp Asn Leu Glu Gly Tyr Tyr Ser Pro Ile Asp
    210                 215                 220

Gln Val Glu Gln Lys Pro Leu Val Asn Gln Tyr Val Asn Arg Ala Pro
225                 230                 235                 240

Phe Ala Gly Asn Gly Val Gln Val Ser Pro Val Thr Pro Ser Ala Asp
                245                 250                 255

Val Thr Ala Tyr Phe Ser Ser Glu His Ser Ser Asn Ser Phe Asp Tyr
            260                 265                 270

Ser Asp Leu Gly Trp Gly Glu Gln Val Pro Lys Thr Pro Glu Ile Ser
        275                 280                 285

Ser Leu Leu Ser Ala Ala Pro Leu Glu Gly Ala Ala Asp Gln Val Gln
    290                 295                 300

Lys Thr Asn Asn Ser Gln Asp Val Val Ala Ala Gln Asp Asp Ser Ala
305                 310                 315                 320

Lys Thr Leu Ser Glu Glu Leu Ala Asp Ile Glu Ser Gln Leu Lys Phe
                325                 330                 335

Phe Glu Thr Pro Ser Phe Leu Asp Glu Ala Trp Ala Asp Ala Thr Leu
            340                 345                 350
```

-continued

```
Ala Ser Leu Leu Gly Gly Asp Ala Thr His Asp Ala Ala Gly Asn Pro
        355                 360                 365

Met Asn Leu Trp Ser Phe Asp Asp Leu Pro Ser Met Ala Gly Val Phe
    370                 375                 380


<210> SEQ ID NO 36
<211> LENGTH: 358
<212> TYPE: PRT
<213> ORGANISM: Arabidopsis thaliana

<400> SEQUENCE: 36

Met Cys Gly Gly Ala Ile Ile Ser Asp Phe Ile Pro Pro Pro Arg Ser
1               5                   10                  15

Arg Arg Val Thr Ser Glu Phe Ile Trp Pro Asp Leu Lys Lys Asn Leu
            20                  25                  30

Lys Gly Ser Lys Lys Ser Ser Lys Asn Arg Ser Asn Phe Phe Asp Phe
        35                  40                  45

Asp Ala Glu Phe Glu Ala Asp Phe Gln Gly Phe Lys Asp Asp Ser Ser
    50                  55                  60

Ile Asp Cys Asp Asp Asp Phe Asp Val Gly Asp Val Phe Ala Asp Val
65                  70                  75                  80

Lys Pro Phe Val Phe Thr Ser Thr Pro Lys Pro Ala Val Ser Ala Ala
                85                  90                  95

Ala Glu Gly Ser Val Phe Gly Lys Lys Val Thr Gly Leu Asp Gly Asp
            100                 105                 110

Ala Glu Lys Ser Ala Asn Arg Lys Arg Lys Asn Gln Tyr Arg Gly Ile
        115                 120                 125

Arg Gln Arg Pro Trp Gly Lys Trp Ala Ala Glu Ile Arg Asp Pro Arg
    130                 135                 140

Glu Gly Ala Arg Ile Trp Leu Gly Thr Phe Lys Thr Ala Glu Glu Ala
145                 150                 155                 160

Ala Arg Ala Tyr Asp Ala Ala Ala Arg Arg Ile Arg Gly Ser Lys Ala
                165                 170                 175

Lys Val Asn Phe Pro Glu Glu Asn Met Lys Ala Asn Ser Gln Lys Arg
            180                 185                 190

Ser Val Lys Ala Asn Leu Gln Lys Pro Val Ala Lys Pro Asn Pro Asn
        195                 200                 205

Pro Ser Pro Ala Leu Val Gln Asn Ser Asn Ile Ser Phe Glu Asn Met
    210                 215                 220

Cys Phe Met Glu Glu Lys His Gln Val Ser Asn Asn Asn Asn Asn Gln
225                 230                 235                 240

Phe Gly Met Thr Asn Ser Val Asp Ala Gly Cys Asn Gly Tyr Gln Tyr
                245                 250                 255

Phe Ser Ser Asp Gln Gly Ser Asn Ser Phe Asp Cys Ser Glu Phe Gly
            260                 265                 270

Trp Ser Asp Gln Ala Pro Ile Thr Pro Asp Ile Ser Ser Ala Val Ile
        275                 280                 285

Asn Asn Asn Asn Ser Ala Leu Phe Phe Glu Glu Ala Asn Pro Ala Lys
    290                 295                 300

Lys Leu Lys Ser Met Asp Phe Glu Thr Pro Tyr Asn Asn Thr Glu Trp
305                 310                 315                 320

Asp Ala Ser Leu Asp Phe Leu Asn Glu Asp Ala Val Thr Thr Gln Asp
                325                 330                 335
```

-continued

Asn Gly Ala Asn Pro Met Asp Leu Trp Ser Ile Asp Glu Ile His Ser
340 345 350

Met Ile Gly Gly Val Phe
355

<210> SEQ ID NO 37
<211> LENGTH: 363
<212> TYPE: PRT
<213> ORGANISM: Zea mays

<400> SEQUENCE: 37

Met Cys Gly Gly Ala Ile Leu Ser Asp Ile Ile Pro Pro Pro Pro Pro
1 5 10 15

Arg Arg Val Thr Ala Gly His Leu Trp Pro Glu Ser Lys Lys Pro Arg
20 25 30

Arg Ala Ala Ser Gly Arg Arg Gly Ala Pro Val Glu Gln His Glu Gln
35 40 45

Glu Glu Asp Phe Glu Ala Asp Phe Glu Glu Phe Glu Val Glu Ser Gly
50 55 60

Glu Ser Glu Leu Glu Ser Glu Asp Glu Pro Lys Pro Phe Ala Ala Pro
65 70 75 80

Arg Ser Ala Leu Ala Arg Gly Gly Leu Asn Thr Gly Ala Ala Gly Val
85 90 95

Asp Gly Pro Ala Ala Asn Ser Val Lys Arg Lys Arg Lys Asn Gln Phe
100 105 110

Arg Gly Ile Arg Arg Arg Pro Trp Gly Lys Trp Ala Ala Glu Ile Arg
115 120 125

Asp Pro Arg Lys Gly Val Arg Val Trp Leu Gly Thr Phe Asn Ser Pro
130 135 140

Glu Glu Ala Ala Arg Ala Tyr Asp Ala Glu Ala Arg Arg Ile Arg Gly
145 150 155 160

Lys Lys Ala Lys Val Asn Phe Pro Asp Glu Val Pro Thr Ala Val Ser
165 170 175

Gln Lys Arg Arg Ala Ala Gly Pro Ala Ser Leu Lys Ala Pro Lys Met
180 185 190

Asp Val Glu Glu Glu Lys Pro Ile Ile Lys Leu Ala Val Asn Asn Met
195 200 205

Thr Asn Ser Asn Ala Tyr His Tyr Pro Ala Val Val Gly His Asn Ile
210 215 220

Ile Pro Glu Pro Phe Met Gln Thr Gln Asn Met Pro Phe Ala Pro Leu
225 230 235 240

Val Asn Tyr Ala Ala Leu Val Asn Leu Ser Ser Asp Gln Gly Ser Asn
245 250 255

Ser Phe Gly Cys Ser Asp Phe Ser Leu Glu Asn Asp Ser Arg Thr Pro
260 265 270

Asp Ile Thr Ser Val Pro Ala Pro Val Ala Thr Leu Ala Ala Val Gly
275 280 285

Glu Ser Val Phe Val Gln Asn Thr Ala Gly His Ala Val Ala Ser Pro
290 295 300

Ala Thr Gly Asn Thr Gly Val Asp Leu Ala Glu Leu Glu Pro Tyr Met
305 310 315 320

Asn Phe Leu Met Asp Gly Gly Ser Asp Asp Ser Ile Ser Thr Leu Leu
325 330 335

-continued

```
Ser Cys Asp Gly Ser Gln Asp Val Val Ser Asn Met Asp Leu Trp Ser
            340                 345                 350

Phe Glu Asp Met Pro Met Ser Ala Gly Phe Tyr
        355                 360


<210> SEQ ID NO 38
<211> LENGTH: 201
<212> TYPE: PRT
<213> ORGANISM: Triticum monococcum

<400> SEQUENCE: 38

Glu Ala Arg Arg Ile Arg Gly Lys Lys Ala Lys Val Asn Phe Pro Glu
1               5                   10                  15

Glu Ala Pro Met Ala Pro Gln Gln Arg Cys Ala Thr Ser Val Lys Val
            20                  25                  30

Pro Glu Phe Asn Thr Glu Gln Lys Pro Val Leu Asn Thr Met Gly Asn
        35                  40                  45

Ala Asp Val Tyr Ser Cys Pro Ala Val Asp Tyr Thr Ile Asn Gln Gln
    50                  55                  60

Phe Val Gln Pro Gln Asn Met Ser Phe Val Pro Thr Val Asn Ala Val
65                  70                  75                  80

Glu Ala Pro Phe Met Asn Phe Ser Ser Asp Gln Gly Ser Asn Ser Phe
                85                  90                  95

Ser Cys Ser Asp Phe Ser Trp Glu Asn Asp Ile Lys Thr Pro Asp Ile
            100                 105                 110

Thr Ser Val Leu Ala Ser Ile Pro Thr Ser Thr Glu Val Asn Glu Ser
        115                 120                 125

Ala Phe Leu Gln Asn Asn Gly Ile Asn Ser Thr Val Pro Pro Val Met
    130                 135                 140

Gly Asp Ala Asn Val Asp Leu Ala Asp Leu Glu Pro Tyr Met Lys Phe
145                 150                 155                 160

Leu Met Asp Asp Gly Ser Asp Glu Ser Ile Asp Ser Ile Leu Ser Cys
                165                 170                 175

Asp Val Pro Gln Asp Val Val Ser Asn Met Gly Leu Trp Thr Phe Asp
            180                 185                 190

Asp Met Pro Leu Ser Ala Gly Phe Tyr
        195                 200


<210> SEQ ID NO 39
<211> LENGTH: 643
<212> TYPE: DNA
<213> ORGANISM: Triticum aestivum

<400> SEQUENCE: 39

ccttccgtcc gccttgttgg tttactgtgc cgtcgatcgg catggcgagg aaatgctcga      60

gctgcggcca caatggccac aactcgagga cctgcggcgg gcaccgaggc gttgagagcg     120

gcggcggcgg tgggctgagg ctgtttgggg tgcagctgca ggtgggcgcc gcgcctctca     180

agaagagctt cagcatggag tgcctgtcgt cgaccgcgtc ggcctactac gcggcggccg     240

cggccgtggg tgtcgccgcg tccaactcgt cgtcgtccgt gtcgtcgtcg tcgtcgctcg     300

tctcggtgga ggagagcccg gagaagatgg gccacgggta cctctccgac gggctcatgg     360

gcagggctca agagaggaag aaaggggttc catggaccga ggacgagcac cggaggttcc     420

tggccggcct ggagaagctc gggaaaggcg actggcgagg catctcccgg cacttcgtca     480

ccacacgcac gccgacgcag gtcgccagcc acgcccagaa gtacttcctc cggcaggccg     540
```

-continued

```
gcctcgcgca gaagaagcgg cggtccagcc tcttcgacgt cgtggagaaa aatggcgaca    600

ggggagccac cgagcgtcgt cacaggctga aacccgatgc cac                      643


<210> SEQ ID NO 40
<211> LENGTH: 933
<212> TYPE: DNA
<213> ORGANISM: Oryza sativa

<400> SEQUENCE: 40

atggccagga aatgctccag ctgcgggaac aatggccaca actccaggac ttgcaccggc     60

caaaggagcc tgcaggagag tggcggcggt tatggcggcg gtggcgccgg tggcgtgagg    120

ttgttcgggg tgcagttgca cgtcggcggt gcgcctctga agaagtgctt cagcatggag    180

tgcctatcgt cgccgtcgcc gtcgccgtcg ccggcgtact acgccgcggt cgccgccgcc    240

gcctccaact cgtcgccgac cgtgtcgtcg tcgtcgtcgc tggtgtcggt ggaggaggcc    300

ggcgagaaga tggccaacgg gtacctctcc gatggcctca tggcgagagc tcaggagagg    360

aagaagggtg ttccatggac tgaagaggag cacaggaaat tcctggtagg gctcgagaag    420

ctcgggaaag gcgactggcg cggcatttcc cggcacttcg tcacgacaag aacaccgacg    480

caggtggcca gccatgccca gaagtatttc ctcaggcaga gcagcctcac gcagaagaag    540

agaagatcca gcctctttga cgtgattgag gatgcagaaa aggctccgag tgtgaatgaa    600

cgtctgaaac tgagacacga gacagcctct gtgcctgctg aaatgggatt ccctgcactg    660

tcactgggta tcagcagcat ggcacagcca gaagccatgc tgctgcctcc tccatcctta    720

accctgacgc caagctgttc atcaccagca gtgagcagca gcagcagcga acaaccaaga    780

acaatccatc cttctctgat ggtggcaaag cctcaggtgc aactgcaact ccagccacct    840

gatctggagc tcaagatctc gactgtccgt cagaacgatc agcccagttc gtcgccgagg    900

acgccttttt tggggacaat cagggtcact tga                                 933


<210> SEQ ID NO 41
<211> LENGTH: 836
<212> TYPE: DNA
<213> ORGANISM: Gossypium raimondii

<400> SEQUENCE: 41

cgctcattga gtttgttatc agagggttgt tggtctgagg attgggtgaa agctttgtca     60

ggaaggaaat gggcaggaag tgctcacatt gtggaaacat aggtcataat tcaaggacct    120

gcaccacttt cagatcttct gctgcaggaa tgggatcagg tcttaggctt ttcggttttc    180

aactacaact ggatgtatct tcaccttctg tagtttccaa tcttatgatg aagaagagtt    240

tcagcatgga ttgcttgtct tcctctccct ctccctctcc ctctccctct ccctcttctt    300

tgtcatcttc tagagtttcc atcgatgaaa attctgataa aacttccatg ggttatctat    360

ctgatggtct catgggccga tctcctgaca gaaaaaaagg agttccatgg acagaagagg    420

aacacagaat ctttctaata gggctggaga agctagggaa aggagactgg agaggcatct    480

ctagaaactt tgtgacaaca aggactccaa cccaagttgc aagccatgct caaaagtatt    540

ttcttcgaca ggcaactctc aacaagaaga accgacgttc cagcctgttt gacatggtta    600

gaagcaatag catgggtgga ccacctagtc ttactaaaat ccctcaactc gatttgcatc    660

atcgtcatcc catgcctgtt gattgcagtg attcgcagac aaatgtggcg cctgatttgg    720

agcttacact tgccgcctca aggccggctt tagaagaaaa caagtcatcc ccaacaacaa    780

caactctcct tattagaccc cattatgtta cttgaccact tttcagttca tgctga        836
```

-continued

<210> SEQ ID NO 42
<211> LENGTH: 616
<212> TYPE: DNA
<213> ORGANISM: Sorghum bicolor

<400> SEQUENCE: 42
catggccagg aagtgctccc actgtggcaa ctacggccac aactccagga cctgcggctt 60
aggacacagc agagaagtca tgctctgcga agccggcgac aatggcggcg gccacggcgg 120
cagcggccta aggctcttcg gagtgcaggt ccgtataggt ggcggtggtg caggctcgtc 180
ggcgtccatg aagaagagct acagcatgga ctgcctgcag ctcgcggcgg ctcaagctgg 240
ctgctccctc gtctcgccgt cgtcgtcgtc ctcgtcgtcg ctgctgctgt cgattgaaga 300
gggcctggag aggggggcgg ccgccaatgg gtacctgtct gatggacctc atggcagagt 360
tgtgcaggag aggaagaaag gagttccatg gagcgaggag gagcacaggc agttccttgc 420
cggcctggag aagctgggca agggcgactg gcgaggcatc tcgaggaact acgtgacgac 480
gaggacgccc acgcaggtcg ccagccatgc gcagaaattc ttcctcaggc agagcagcat 540
ggggaagaag aagcgccgct ccagcctctt tgacatggtg ccgatttgcg agaacagcgc 600
gagcatttcc gatccg 616

<210> SEQ ID NO 43
<211> LENGTH: 748
<212> TYPE: DNA
<213> ORGANISM: Triticum turgidum
<220> FEATURE:
<221> NAME/KEY: misc_feature
<222> LOCATION: (713)..(713)
<223> OTHER INFORMATION: n is a, c, g, or t

<400> SEQUENCE: 43
gaattcggca cgaggctggt ctccacccat ctctcccacc acccgcacca aaagacaacg 60
cagtgcggat cgatttagtc gatttatagc cacaccatgg cgaggaagtg ctcccactgt 120
ggcaactacg gccacaactc aagaacttgc agcagcgcag ctggaaacca gggagaagtt 180
atgctctgcg aaggaggcgg cgggagcagc ggcggcagtg ggctgaggct cttcggggtg 240
caggtccatg tcgctgcggg ccgcagcacc ggcgccggcg cctccatgag gaagagctac 300
agcatggact gcctgcagct cgcggtggcc cctagctcca tcgtctcgcc ttcgtcgtcg 360
tcttcctcgt cggtgcttct gtccatcgat gagggcttgg agagggcttc caatgggtac 420
ctatctgacg gtcctcatgg cagattagtc caggagagga agaaaggagt tccatggagc 480
gaggaggagc accggctatt cctcgtgggc ctcgagaagc tcggaaaggg cgactggcga 540
ggcatctccc ggagctacgt cacgactcga accccgacgc aggttgccag ccacgcgcag 600
aagttcttcc tgaggcagag cagcatgggg aagaagaagc gccgctccag cctctttgac 660
atggtaccga tctgcgagaa cggcattcgc gtttctgagc cgctgaccaa cancagcgga 720
gatgcctcca cctctctgcc gcggtata 748

<210> SEQ ID NO 44
<211> LENGTH: 574
<212> TYPE: DNA
<213> ORGANISM: Glycine soja

<400> SEQUENCE: 44
ggctgagaaa agaatctttg ttgttgaagt aagaataatt aataatgggg aggaagtgct 60
cacattgtgg aaccataggc cataactcaa ggacctgcac atctttgaga ggggctacta 120

-continued

```
ctagtttcgt tggacttcgc ctcttcggcg tgcaattaga cagtactaat tgtgttagca    180

tcaagaaaag ctttagcatg gactccttac cctcatcatc atcttcctca ttctcttcat    240

caagactaac cattgatgaa aattctgacc gaacctcttt tgggtatctc tcagatggtc    300

tcttagctcg agcccaagag aggaagaaag gagtgccatg gacagaagag gaacacagaa    360

tattccttgt tggacttgag aagctgggaa agggtgactg gaggggaatc tctagaaact    420

ttgtgactac aagaacccca acacaagtgg caagccatgc tcaaaagtac tttcttcgat    480

tggcaactat agataagaaa aagcgacgtt caagtctctt tgacttggtt ggtagcaaca    540

aagcaggttc taattcagtt tcggctcatc aaaa                                574
```

<210> SEQ ID NO 45
<211> LENGTH: 786
<212> TYPE: DNA
<213> ORGANISM: Hordeum vulgare

<400> SEQUENCE: 45

```
atgctctgcg aaggaggcgg cggcggcagc accagcggca gtgggctgag gctcttcggg     60

gtgcaggtcc atgtagctgc gggtcgcagc gcccgcgccg gcgcctccat gaggaagagc    120

tacagcatgg actgcctgca gctcgcggca gcccctagct ccatcgtctc gccttcgtcg    180

tcgtcttcgt cgtcggtgct tctgtccatt gatgagggct tggagagggc ttccaatgga    240

tacctgtctg acggtcctca tggcagatta gtccaggaga ggaagaaagg agttccatgg    300

agcgaggagg agcaccggct attccttgtg ggcctcgaga agctcggcaa gggcgactgg    360

cgaggtatct cccggagcta cgtcacgact cgaaccccga cacaggttgc cagccacgcg    420

cagaagttct tcctcaggca gagcagcatg gggaagaaga agcgccgatc cagcctcttt    480

gacatggtgc cgatttgcga gaacggcatt cgcgtttctg agccgctgac caacaacagc    540

gagaatgcct ccacctctct gccgcggtat aattccccca acatggcttc cattgatctc    600

aactccaccc aggaggataa cttggcgggc ttcccacttt ggtcggcgtc gggtgcatca    660

ccgagagcgc catttccggc tgttctgatg gagcagcctc cacatggcca cggacacggt    720

caccactgct ccccgctgga cgtggagctc agcatgtctc tctcgccgcc gtccatcgga    780

acatga                                                               786
```

<210> SEQ ID NO 46
<211> LENGTH: 653
<212> TYPE: DNA
<213> ORGANISM: Medicago truncatula

<400> SEQUENCE: 46

```
gggttggatc tctaatttca atttctccct ctaagagaca ataaacacaa gttttaaggt     60

taaggtttgt gtcggttcaa aaaatgggca gaaagtgctc acattgtgga aacataggtc    120

ataattcaag gacttgtaat tcattaagag gaagtggtag ttttgttgga gttagacttt    180

ttggtgttca acttgattta tcttcttctt gtgtttccat gaaaaagagt tttagcatgg    240

attcttttcc tacttcatct tcttctccta cttcttcctt ttcttcttca agattaacca    300

ttgatgatag agcctctatt ggttatcttt cagatggtct catagttcgt acacaagaaa    360

ggaaaaaagg agttccatgg acagaagaag agcatagaaa attccttgtt ggacttgaga    420

agcttggaaa aggagattgg aggggtatct ctagaaacta tgtgactaca agaacaccaa    480

cacaagttgc aagccatgct caaaagtatt ttattcgact tgcaaccttg aataagaaga    540
```

-continued agagacgttc aagtctcttt gacatggttg gtagtggcaa gacaaacaaa acagttgatc 600
caaataacag ttctaaaagc aagtcaggag attcagtttg tagacatgat cat 653

<210> SEQ ID NO 47
<211> LENGTH: 628
<212> TYPE: DNA
<213> ORGANISM: Saccharum officinarum

<400> SEQUENCE: 47
acggccacaa ctccaggacc tgcggctttg gacacagaga aatcatgctc tgcgaagccg 60
gcgacaatgg cggcggcagc ggcctaaggc tcttcggagt gcaggtccgt atcggcggcg 120
gtggtggtgc aggctcatcg gcgtccatga agaagagcta cagcatggac tgcctgcagc 180
tcgcggctcc agctggctgt tccctcgtct cgccgtcgtc gtcgtcctcg tcgtcgctgc 240
tgctgtcgat tgaagagggc ctggagaggg ggacggccaa tgggtacctg tctgacggac 300
ctcatgggag agttgtgcag gagaggaaga aaggagttcc atggagtgag gaggagcaca 360
ggcagttcct cgccggcctg gagaagctgg gcaagggcga ctggcgaggc atctccagga 420
actatgtgac gacgaggacc ccgacgcagg tcgccagcca tgcgcagaaa ttcttcctca 480
ggcagagcag catggggaag aagaagcgcc ggtccagcct ctttgacatg gtgccgattt 540
gcgagaacag tgcgagcatt tccgatccgt tgaacagtga aggggcctcg acctttttgt 600
cgctggacgt ggcacgccat ggcgcccg 628

<210> SEQ ID NO 48
<211> LENGTH: 750
<212> TYPE: DNA
<213> ORGANISM: Lycopersicon esculentum

<400> SEQUENCE: 48
ttgtgaaact aattcttttt tgtgtatgtg aaaatgggga ggaagtgttc acattgtggc 60
tatattggtc ataattcaag aacttgtagc actttgaaaa gtgctattag tggtagtaat 120
tttaatggtg gattaaggct ttttggagtg caacttgata tttctaattc ttgtttttct 180
agtcataata ataataataa taataatttg aagaaaagtt ttagtttgga ttgtttgtct 240
ttaacaaata gccacttatt attattatca tcttcttctt ctccatctct taatgaaaat 300
agtagtacta attctattga taataatggt tatctctctg atggtactct tgtaggttgt 360
gttggtgaaa ggaaaaaagg agttccatgg acagaagagg aacatagaag attcttaaat 420
ggacttgaaa agttaggtaa aggagattgg agaggaattt caagaaattt tgtgacaaca 480
aggactccaa cacaagttgc aagtcatgca caaaaatatt ttctaagaca atcaagtctc 540
aacaaaaaaa aaaagacgtt caagtctctt cgatatggca aggagcaaca acaaatatgt 600
agatttttgt caaaattacc aagaagattg tcaagaaatt acaagatcat ctccattaga 660
cctaaattca tttggagaaa agtgtgaaga ttctatttgg agttatggat cacaaaattc 720
tcatcaaaat aaattccaaa taatccattt 750

<210> SEQ ID NO 49
<211> LENGTH: 667
<212> TYPE: DNA
<213> ORGANISM: Solanum tuberosum

<400> SEQUENCE: 49
gctaaccaag gtcttgtgga tatgggaagg aagtgttcac attgtggtaa tataggtcac 60
aattcaagaa cttgtagcac tttcaagtta ggtgctagtg ctagctttgt tggtggatta 120

-continued

```
aggctctttg gagtccaact aattgacatc tcttcttcat cttctgcatc atcttcttct    180

tcttcttctt atgatatcca cttgaagaaa agtttaagct tagattgcat gtcttcacct    240

caagtatcat catcatcatc acttgttact cttaatgaaa agagtactac ttgcacaaat    300

ggagattatc tatctgattg tctcttaggt caacctcaag agagaaggaa aggagttgga    360

tggacagagg aggaacatag gagattcttg atgggactag aaaagctagg gaaaggagat    420

tggagaggaa tttcgaggaa gttcgtcaca acaagaactc caacacaagt agctagtcat    480

gctcaaaaat atttcctcag acagtactca actcatctca ataaaaagaa gcgccgttct    540

agactctttg acatggaaag gaggaagaac aaaatggaag aaagcaagga agagtatgga    600

aattcaacaa gtccaattag tatgatggat gaagagatag cattaacaac caaagatact    660

ctaattt                                                              667
```

<210> SEQ ID NO 50
<211> LENGTH: 474
<212> TYPE: DNA
<213> ORGANISM: Bruguiera gymnorrhiza

<400> SEQUENCE: 50

```
ggtttgggga gaaaatgggc aggaggtgct cgcattgtgg gaacataggc cacaattcaa     60

gaacttgcac ctctacctct ttcagaggcg tagtggttgc tggtgggcta aggctttttg    120

gagtgcgact tgacattcct tcttcacctt gtgtccccat tcaaaagagc attagcatgg    180

actctttgtc cttgtcttcc tccacatccc catctttctc ttctttgcgt tcatctcgaa    240

tttccattga cgacaattcc gataaattgt ccattgggta tctttctgat agtctcttcg    300

gacctgtcca ggagagaaag aagggagtcc cctggacaga agaggagcac cgaacgttct    360

taattgggct tgaaaagcta ggaaagggag actggagagg catctccaga aactttgtga    420

ctacaagaac tcccactcaa gttgctagtc atgctcagaa atatttcctt cgcc          474
```

<210> SEQ ID NO 51
<211> LENGTH: 757
<212> TYPE: DNA
<213> ORGANISM: Vitis vinifera

<400> SEQUENCE: 51

```
catttttag atttacatgt gatcgtcttc actcgttttc ccttcacacc gagtaagctt      60

attcttctct cgagtcacgc ggcggcgact cgatatgact cgtcgctgct cacactgtag    120

caccaacgga cacaactccc gcacctgccc ctcccgcggt ggaggcgcag tcgccggcgg    180

tatcggcgga gtgaagttgt tcggagttcg gctcacagat ggctccatca tcaagaagag    240

cgcaagtatg ggtagcctct cctccgctca ctaccactcc tcctcctccg ccgcggcttc    300

gccgaaccct agctcgccgt cctccgaccc cctccgcgac gcgattcacg agcccgacgg    360

ctacttatcg gacgatcctg gccaggccac ttgctcctcc aatcgccgtg gtgaacggaa    420

gaaaggtgta ccttggacag aagaggagca ccggctattc ttatttggtc tccagaggtt    480

gggtaaagga gactggcgtg ggatatcacg taactatgtc atttcaagaa ctcctaccca    540

ggtagcaagt catgcccaga agtatttcat tcggcagagt aatgctaccc gaagaaagag    600

gcgttccagc ctttttgata tggttccaga catggtcaca gatacacctc ctgtgccaga    660

agaacagttc ttggtcccga cttctcagac tggagaaact gacaatgcaa gctcagtacc    720

ctctctaaat ctctcactta acatggaatt cgaaccc                             757
```

-continued

<210> SEQ ID NO 52
<211> LENGTH: 1164
<212> TYPE: DNA
<213> ORGANISM: Arabidopsis thaliana

<400> SEQUENCE: 52
atgactcgtc ggtgttcgca ttgtagcaac aatgggcaca attcacgcac gtgtccaacg 60
cgtggtggtg gcacgtgcgg tggaagtggc ggaggaggag gaggtggtgg tggaggaggg 120
tctggttcct cctccgccat gaagttattt ggtgtgaggt taacggatgg ctcgattatt 180
aaaaagagtg cgagtatggg taatctctcg gcattggctg ttgcggcggc ggcggcaacg 240
caccaccgtt tatctccgtc gtctcctctg gcgacgtcaa atcttaatga ttcgccgtta 300
tcggatcatg cccgatactc taatttgcat cataatgaag ggtatttatc tgatgatcct 360
gctcatggtt ctgggtctag tcaccgtcgt ggtgagagga agagaggtgt tccttggact 420
gaagaggaac atagactatt cttagtcggt cttcagaaac tcgggaaagg agattggcgc 480
ggtatttcga gaaactatgt aacgtcaaga actcctacac aagtggctag tcatgctcaa 540
aagtatttta ttcgacatac tagttcaagc cgcaggaaaa gacggtctag cctcttcgac 600
atggttacag atgagatggt aaccgattca tcgccaacac aggaagagca gaccttaaac 660
ggttcctctc caagcaagga acctgaaaag aaaagctacc ttccttcact tgagctctca 720
ctcaataata ccacagaagc tgaagaggtc gtagccacgg cgccacgaca ggaaaaatct 780
caagaagcta tagaaccatc aaatggtgtt tcaccaatgc tagtcccggg tggcttcttt 840
cctccttgtt ttccagtgac ttacacgatt tggctccctg cgtcacttca cggaacagaa 900
catgccttaa acgctgagac ttcttctcag cagcatcagg tcctaaaacc aaaacctgga 960
tttgctaaag aacgtgtgaa catggacgag ttggtcggta tgtctcagct tagcatagga 1020
atggcgacaa gacacgaaac cgaaacttcc ccttccccgc tatctttgag actagagccc 1080
tcaaggccat cagcgtttca ctcgaatggc tcggttaatg gtgcagattt gagtaaaggc 1140
aacagcgcga ttcaggctat ctaa 1164

<210> SEQ ID NO 53
<211> LENGTH: 846
<212> TYPE: DNA
<213> ORGANISM: Citrus sinensis

<400> SEQUENCE: 53
cacacgcaca ccctctctcc cccctcaaaa tttccaagat aattataatt taaatagtca 60
atttaattaa tttattagag atatccgaat tttatcgagt cgcggcagcg gtaaccggcg 120
atgacgcggc gctgctcgca ttgcagcaac aacgggcaca actcgcgaac gtgtcccgcg 180
cggggcggcg gctcgtcgcc gggcgtgggc ggcctgaagt tgtttggcgt ccggcttacg 240
gatggctcga taatcaagaa gagcgcgagc atggggaact tatcggcgct gcactaccat 300
agctcctcgt cggcagccgc ttcgccgaat cctgactccc cgttatcgga tcacgtgcgt 360
gacccgaatc acttgaccga cggttacttg tcggatgacc cggcgcacgg gtctggttca 420
tcgaatcggc gttgcgagag aaagaaaggt gtcccatgga cagaagagga gcatcgcctg 480
tttctaattg gccttcagaa attagggaag ggagactggc gtggtatagc acgaaattat 540
gtcatgtcca ggactccaac ccaggtggca agtcatgcac agaagtattt tatccggcag 600
agtaatgcta ctcgaagaaa gaggcgctcc agtctttttg acatggttgc ggatgatatg 660
gccacagata ccccaccggt gccagaagag caagtaatgc ttccatctcc tcttgccaga 720

-continued

```
gaatctgaca atacaagctc acaaccttct ctaaatcttt ctctgagtac cgaatttgaa    780

cccatggaag ccgtatgtaa agaaacagag aaggattctg aagaacctgt gattgatttg    840

aatgag                                                                846


<210> SEQ ID NO 54
<211> LENGTH: 880
<212> TYPE: DNA
<213> ORGANISM: Nicotiana benthamiana

<400> SEQUENCE: 54

caaaaaaaga aaaaaaaaag aatcttatcc aaaactccaa tcgccgagtc aatttaccat     60

gactcggcgg tgttcccatt gcaacaacaa tggccacaat tcccggactt gtcccaccac    120

caggggtggc acccccaccg gcggtgtagg tagttcctcc ggcggcggcg gcggagcaag    180

tggaggtgta cggctatttg gtgtacggct tacagatggg tcgatcatga agaaaagtgc    240

aagcatggga aatttatctt ctctccactc ttatcattct tcttcttcgc ctaatccgcc    300

aggttcccct tcttctgatg gtcctcattt gcctgatggt tacctctctg atgatcccaa    360

tacgcatgcc tctatttctg ctaatcgccg acttgaaagg aaaaaaggtg ttccatggac    420

agaggaagag caccggcttt tcctgcttgg tttacagaaa ttaggcaaag gagattggcg    480

gggtatatct cgaaacttcg tgacatcaag gactcccacc caggtagcta gccatgctca    540

gaagtatttt attcggcaga gtaatgctac tcggagaaag agaagatcca gtctttttga    600

cattgttgca gattcgggga ctgatgcttc ccatccacta ccagaagaac aatttatgct    660

cccacctaga gcaatagaaa gtgataagga acacttagcg ccttctgcaa caaaagcaat    720

agaaactgat tttgcagatt cactcccttc cttagatctt tctctcaagt cagattttga    780

atccatggaa acaactccaa gtgaacctgt tgaagaagcg aaaccaaata ccacaaccaa    840

cgagatccct tcagtatttc cagcattcct cccagcttac                          880


<210> SEQ ID NO 55
<211> LENGTH: 435
<212> TYPE: DNA
<213> ORGANISM: Glycine max

<400> SEQUENCE: 55

gcacgaggag gctactacta gtttcgttgg acttcgcctc ttcggcgtgc aattagacag     60

tactaattgt gttagcatca agaaaagctt tagcatggac tccttaccct catcatcatc    120

ttcctcattc tcttcatcaa gactaaccat tgatgaaaat tctgaccgaa cctcttttgg    180

gtatctctca gatggtctct tagctcgagc ccaagagagg aagaaaggag tgccatggac    240

agaagaggaa cacagaatat tccttgttgg acttgagaag ctgggaaagg gtgactggag    300

gggaatctct agaaactttg tgactacaag aaccccaaca caagtggcaa gccatgctca    360

aaagtacttt cttcgattgg caactataga taagaaaaag cgacgttcaa gtctctttga    420

cttggttggt agcaa                                                      435


<210> SEQ ID NO 56
<211> LENGTH: 800
<212> TYPE: DNA
<213> ORGANISM: Vitis aestivalis
<220> FEATURE:
<221> NAME/KEY: misc_feature
<222> LOCATION: (14)..(15)
<223> OTHER INFORMATION: n is a, c, g, or t
```

-continued

<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (765)..(767)
<223> OTHER INFORMATION: n is a, c, g, or t

<400> SEQUENCE: 56

```
tcggagtctc cgannttgct ccggcgacat gtctcgctgc tgttctcagt gtggtcataa     60

tggtcataat tctcgcacgt gtgcggagtc cggtggcggt ggcggtggtg gtgatggtgg    120

ttccgaaggg atcatgctgt ttggagtgag agtcactgtg gattcgatgc gtaagagcgt    180

cagtttgaac aatctgtcgc agtatgagca gcctcacgag tcttccaacg ccgatgccac    240

ccccgccgct ggatacgttt ccgccgacga tgtggctcac cactcctcag ggaatcgtga    300

gcgcaagcga ggtgtcccat ggaccgaaga agaacacaag cttttcctgg ttggattgca    360

gaaagttgga aaaggagact ggcgaggaat ctccaggaat ttcgtgaaaa ctcgaactcc    420

aacacaggtc gcaagtcatg ctcagaagta ctttctccgc agaaacaatc tcaatcgacg    480

acgccgcaga tctagcctct tcgacatcac caccgaatcg gtcacggcag ttccaatgga    540

agaagagcaa gtacttcatc atcaagagaa cacatctcaa tcccagcagt ctcctaagac    600

tttttccgag accggcagtg gcgatggatt tccggttgtg ccagcttttc caatgccgat    660

aaatccggtg gttgtaccag ttccgattca gaatccaatg gaaaacctaa ctctaggaca    720

aaatgatgtt aatacaaggc tggtccgtcc gattcccgtt nntcnnnttc ctcccgagtc    780

aacggatctc aacttgaatc                                                800
```

<210> SEQ ID NO 57
<211> LENGTH: 708
<212> TYPE: DNA
<213> ORGANISM: Brassica napus

<400> SEQUENCE: 57

```
gataataaaa atcaaaaaca aaattacaca tctctctcta tcgaacttgt tgtatatacg     60

caaaaaacta tatacggagg agcttttatt acagattaaa gtgttttggc tttttgtgtt    120

gtgtggatga ctcgtcggtg ttcgcattgt agctacaatg ggcataactc ccgcacgtgc    180

ccgactcgtg gggtggtgg tggcggcacg tgcggtggaa acggaggaga atctgcttct     240

tcctcctcct ctgctgccgt gaagctgttc ggcgtgaggt taacggatgg gtcgattatc    300

aagaagagtg cgagtatggg taacctctct gcattggccg tgcaccaccg tttgtctcct    360

ttggcgacgg gtaatcataa cgactcgccg ttgtcggatc atgggaggta ctctagtcaa    420

gagaacggag ggtatttgtc ggatgatcca ggtcatggtt ctgggtctat ccaccaccgt    480

cgtgtggaga ggaagagagg cgttccttgg acggaggagg agcacaggct attcttagtg    540

ggtcttcaga agctaggaaa aggagattgg cgtggtattt caagaaatta tgtaacttca    600

agaactccaa cacaagtggc tagtcatgct caaaagtatt tcatccgcca tacttgttcc    660

acccggagga aaagacgttc tagcctcttc gacatggtta ccgatgaa                 708
```

<210> SEQ ID NO 58
<211> LENGTH: 703
<212> TYPE: DNA
<213> ORGANISM: Pinus taeda -continued

<400> SEQUENCE: 58
cggttcgatc gattgattga atgaaagaac tacactcctc ctccccccttt tattgacttt 60 tatatagcgt ctgtatctgg ataattagat taggtatcga tctctgattt ggatctgcct 120
tcggttttgg attttggatt ctctggttcc tggcatctct gtaatttggt acgaattggg 180
ctctgtctgg tttttttttt tttttgtctg tctcttggct ttcgattaat tatatccaaa 240
gccggtaaac atgacaagga agtgttcgca ctgtgggcac aatggccata attccagaac 300
atgccccaac cgtggtgtga aattgtttgg agttcggcta actgatgggc cgatacgcaa 360
gagtgtgagt atgggaaatt tgttgcatta ttccaacaac gcctcttcct ctaataacag 420
cccggcctca gcttcagcta tggagccttg cgaatcagtt gctaatgctg ctgcttctgc 480
agatggttat gtatccgatg gtctcgttca taacaattct cgaggagaga ggaagaaagg 540
ggttccatgg actgaagagg aacaccgcat gtttcttatt ggccttcaaa agcttggaaa 600
gggtgattgg agaggtatat caagaaactt tgtgccgaca agaactccta ctcaggttgc 660
tagtcatgca caaaagtatt ttattaggca gagtaatcta acc 703

<210> SEQ ID NO 59
<211> LENGTH: 711
<212> TYPE: DNA
<213> ORGANISM: Allium cepa

<400> SEQUENCE: 59
catatccatc tcgaatctcc gccacgtgta cggcccgatt cataccttct tcctcctcaa 60
atctcaaaac cctaacatct taatactact ttcatgtact ccaataattg aaatctggtg 120
agttatgacg agaaaatgtt cccattgcag ccacaacggg cacaactcgc gcacatgccc 180
caataaaggt gtgaagctgt tcggtgtgag attgacggat ggatcttctt caatcaggaa 240
gagcgttagc atgggtaatc tctcacacta cgcggcagca gctggcggtg gagcgtctcc 300
ggctgacgga ggagatcatg gtactgacgt ggcggatggg tatgcgtctg aggatttcgt 360
tgcaggttct agttctggat cgagggaacg aaagagaggt gtgccatgga ctgaagaaga 420
acacagaatg ttcttacttg gcttgcaaaa acttggaaaa ggtgattggc gaggaatagc 480
ccgcaccttt gtaaaaacaa gaacacctac tcaagttgct agccatgcac aaaagttttt 540
cattcgacaa actaatatgg gtagaagaaa gagaagatct agcctcttcg atattgtacc 600
tgatgaagct gccgattcac agttcttacc tatgaacgat caagaccccg aactgattgg 660
aaacggttca gtgccagtac ctcaaactgt cgatgaagaa tgcgaaatca t 711

<210> SEQ ID NO 60
<211> LENGTH: 810
<212> TYPE: DNA
<213> ORGANISM: Mesembryanthemum crystallinum

<400> SEQUENCE: 60
accccattct ctttctctct ctagcacccc cattttctct ctcttcccaa cccgatcacc 60
gaacccgggt cgacccgcca tgactcggcg gtgctcccat tgcagccaca atgggcacaa 120
ctctcggacc tgcccgaacc ggggggtcaa gctctttggg gtccgattaa ccgacggatc 180
aatccgaaag agtgctagta tgggcaatct cagtcactat caccaaaacg gcgccgttgg 240
gagcaccaca cctgggtctc ccgccggcga tcataccccc gaccatggtg gctccgccgc 300
tggcgatggc tacggctctg aggatttcgt acctgggtcc tcttctagcc gtgagcgtaa 360
aaaaggtgtt ccatggactg aggaggaaca ccgaatgttt ctgcttggac tgcaaaagct 420

-continued

```
tgggaaaggc gattggcggg gaatatctcg taattatgta atatcgagga cacccactca    480

agtggccagc catgctcaaa aatattttat caggcaaagc aacgtgtcca gaaggaaaag    540

gcggtccagc ttgtttgata ttatagctga tgagtcgggc gatacaccaa tggtgtcaca    600

tgatttcctt tctgcgcact cagcagagaa tgatacagag aatagcaatc cattgccccc    660

tgctccagcg ctcgatgaag aatgcgaatc tatggcatct agcaactcca atgaggtggg    720

acctactcta cctaaaccgg aaacctcaca aagctgctat ccaagtgata ctccccagac    780

tattattccg ttgatatcca actatgttct                                     810
```

<210> SEQ ID NO 61
<211> LENGTH: 909
<212> TYPE: DNA
<213> ORGANISM: Malus xiaojinensis

<400> SEQUENCE: 61

```
atgtcgtccg gcacgtgctc caccgtcgag cccgcgggcg cgggagagat catgctgttc     60

ggcgtgcgct tggtggtcga ttccatgagg aagagcgtca gtttgaacaa tctctcgcag    120

tacgagcacc ctcaggaggc cgcctccaac aacggcaata acggcaccgc cgccggaaag    180

gatgacgcgg cacccggtta cgcctccgag aacgacgtcg ttcacaattc tggcgggaat    240

cgcgagcgcg aacgcaagcg aggggttcca tggacggagg aagagcacaa gcttttcttg    300

cttggattgc agaaagcagg gaaaggagat tggagaggga tctcaagaaa cttcgtgaag    360

actcgcaccc cgactcaggt tgccagccat gcacagaaat actatctgcg ccggagcaac    420

ctcaatcgcc ggcgccgcag gtctagcctc ttcgacatca ccactgatac ggtcgctcca    480

actccaatgg atgaagagca agtacagcat caagataaca tatctcagtc ccagttgcat    540

ccgttgccac ccccgccacc atccgagcct cgcgatgctg gtggattttc gatggtgcca    600

aattttgcaa ggactgtagg tccagctgtc ttgccagttc acattgagaa cccaatggaa    660

aatctagctc ttcgacaagc aaatcccgag aatagtactt cggccaagct cgtccatcca    720

gttgcccttc attcggcccc tcatgcgacc gcaatatctg acctaaactt gaactcaaca    780

acggacgcat cgaccctaac tctcaacctc tccttgtcaa tggactcgag ggaaccgtcg    840

tcaaggcatt cggctttcga gacaatgcaa ggattcagca acggggatag catgatcagt    900

gtcgcttga                                                            909
```

<210> SEQ ID NO 62
<211> LENGTH: 945
<212> TYPE: DNA
<213> ORGANISM: Zea mays

<400> SEQUENCE: 62

```
atgacgcggc ggtgctcgca ctgcagccac aacgggcaca actcgcggac gtgccccaac     60

cgcggggtca agatcttcgg ggtgcacctc accgatggct cggccatccg caagagcgcg    120

agcatgggga acctctccct cctctccgcg ggatccacca gcggcggcgc gtcccccgcc    180

gacgggcccg acctcgccga cggcggcggg ggctacgcct ccgacgactt cgtccagggg    240

tcgtcctccg ccagccgcga tcgaaagaag gtgttccttg gactggagaa gaacaccgga    300

gtttttgctg ggattacaaa agctcgggaa aggggatggc gaggaatttc tcgtaatttt    360

gtggtctcaa gaacacctac tcaagtagca agtcatgctc aaaagtattt tatacgccaa    420

tcaaatatga gcagaaggaa gagaaggtct agccttttcg acatggttcc tgatgagtcc    480

atggaccttc cgccccttcc tggaagtcaa gaaccagaga cctcaatgtt aaatcaaccg    540
```

-continued

```
ccactgcctc ctgctgtgga ggaggaggtg gaatcgatgg agtcagatac ttctgctgtc    600

gcagagagtt ctggagcttc tgctctcatg cccgagagtt tacagcctac ctatccgatg    660

attgttccag cttatttctc gccgttcttg caattctcag ttcctttctg gccaaatcag    720

gaagatggag gcgatcttcc ccaagaaaca cacgagattg tcaagcctgt tgcagttcat    780

tcccagaatc caattaatgt tgatgaactc gtgggcatgt caaagctaag catatgggag    840

catggtcagg agacagtgta tacttctctg tcgctaaatc tgctaggggg tcaaaatagg    900

cagtcggctt tccatgcaaa ccctcaaaca agagctcaag cctga                    945
```

<210> SEQ ID NO 63
<211> LENGTH: 933
<212> TYPE: DNA
<213> ORGANISM: Hevea brasiliensis

<400> SEQUENCE: 63

```
atggatcggg gaattgaaat cctctctcca gcctcttatc ttcagaattc caattggttg     60

tttccagaaa ccagggctac caaatggacc cctgaagaaa acaagcagtt tgagaatgcg    120

ctggccttat atgataagga tgaacctgat cgatggcaga gagttgcagc cgtgatccca    180

ggcaagactg ttggtgatgt aatcaaacag tatagggaat tggaggaaga tgtcagtgat    240

atagaggcag ggctgatccc aattcctgga tacagcagca gtgatgcttt tactttggag    300

tggttcaata ataatcaagg ttacgatggc ttcagacact attatactcc tggaggcaag    360

agaaccaccg ctgccaggtc ttctgagcag gaaaggaaga aaggtgtgcc gtggactgag    420

gaggagcata ggcagttcct catgggtctg caaaagtatg gtaaagggga ctggagaaat    480

atttctcgca actttgtgac cactagaaca ccaactcagg tggctagcca tgctcagaag    540

tattttatca ggcagagcac aggagggaag gataagagaa ggtccagcat ccatgatatc    600

actaccgtca atcttccaga caccaagtct ccttcacctg atgagaagaa atcatcccca    660

gatcattcta ccacaagtct acaatcacag ccacaacaaa aaatggttgg catggccaaa    720

ggattaatag actggaaacc acaaaatgaa ggcggaggag cagctggtgt tttcagccaa    780

gcaaatggca atttgttgat ggcccccttta tgtggaatat catcatatgg acaaaaaacta    840

caggagcaaa atctgcttag aggaactctt ccagggtatc aatttgcacc ttacaatttg    900

atttttcaga tgcaaccgat gcaacgccag taa                                933
```

<210> SEQ ID NO 64
<211> LENGTH: 876
<212> TYPE: DNA
<213> ORGANISM: Antirrhinum majus

<400> SEQUENCE: 64

```
atggagattt taaccccaag ttcatatttt tccaattcaa atttgtttgt ggaggagagc     60

tggagcccaa aatggactgc tgcagataac aaagcctttg agaatgctct tgccgtgttc    120

gatgaatata ctcctcatcg atgggaaagg gtggctgaaa tagtccctgg aaagacagtg    180

tgggatgtaa ttaggcatta caaggaactg gaagatgatg tgactagtat agaagcaggg    240

cttgtcccag ttcctggtta caacacgtct ttgccattta cactagagtg gggcagtggc    300

catggctttg atggatttat gcaatcttat gtagtcggag ggaggaaatc ctcgtgctct    360

aggccgtctg atcaagaacg gaagaagggt gttccttgga cagaagaaga acacaagttg    420

tttctgatgg ggcttaaaaa gtatggaaaa ggagactgga gaaatatatc gcgcaatttt    480

gtgattacta gaacaccgac tcaagttgct agccatgctc agaagtactt catcaggcaa    540
```

-continued ctttctgggg gaaaagataa gaggagggca agtattcatg acataacaac agtgaacctt 600
aacgacggcc aaacctttcc acgagagaac aaaattaaac aatcttcgcc tttggcacat 660
caatcgaatt ctgctgctgc cacttccaaa cttcatattc aatggaatca gacaagaaat 720
gagacgatca cgggttttgg cagtgggaat atgtttgtgt ctgatcctta caattacatg 780
aatagtaatg aagttggact gcagggtcga tcgccgttcg gatctcgaaa tatggtgttt 840
cggatgcatc catgttttag ctatcctagt gcatga 876

<210> SEQ ID NO 65
<211> LENGTH: 888
<212> TYPE: DNA
<213> ORGANISM: Cucumis sativus

<400> SEQUENCE: 65
atggaaactc tgtatccatc ttcacatctc tcgagctctg cttggtttgt gcttgataat 60
ccaagcacaa agtggactaa agaagagaac aagatgtttg agagtgctct tgctatatat 120
gataaagaaa cacctgatag atggttcaaa gtagctgctt tgatccctgg aaaaactgtg 180
agtgatgtga ttaagcaata taaggagctt gaagaagatg tttgtgaaat agaagccggg 240
agattccctg tcccaggtta tgatcttgcc tcttcttttt catttgagtt cgttgatgat 300
cgaaatttcg atgtgtatag aaggaaatct tctgttggta ggggctctga gcatgaaagg 360
aagaaagggg tcccatggac agaggaagaa cacaagcaat ttctaagggg actttttgaag 420 tatggaaaag ggattggag aaatatctca agaaactttg tgaactccaa aactcctaca 480
caagtggcaa gccatgctca aaagtacttc atgaggcagc tttcaggagg gaaagacaag 540
agaaggccaa gcatccatga tatcacgact gttaatctta cagagcccac agcatcagag 600
aatgagaagt tgtcttcaat ggatcaattt tccaagcttc cttcactgca gaagtcaccc 660
tgctatcaaa agcttttgtt tgattggaac cgatccagta acggggggtt gcttggttta 720
ggatctaact atggcgatcg tctcatgtcg tttccatctg ggattgctgc aaatggaata 780
aagaatgagc aagatcaaga actgaacagt gcatattatg gaacttattc caaacctcac 840
aaatccatat tccaatttga accctcaaga tatcaaattt acggatga 888

<210> SEQ ID NO 66
<211> LENGTH: 2097
<212> TYPE: DNA
<213> ORGANISM: Solanum demissum

<400> SEQUENCE: 66
atgagcctca accgaacatg caatagctcc ttctggacca aggaggaaga caaagcattt 60
gagaatgctt tggctgtatt ttctggagat aatgataaat ttctgaagat cgctgctgct 120
gttcctggga aatctcttca agaaattata gatcattata atgtattagt tgaagatatt 180
aatgacatag agtctggcaa agttccgcta cctaaatatg agagaatgca aagttcttct 240
agctgcagac gtagatcatt gggagcaggg gtagaacgac gaaaagggct tccttggact 300
gcagaggaac acaggtcatt tctccaggga ttggcaaaac acggaaaggg tgattggcgg 360
ggtatatcaa ggaactttgt gttttctaga acaccaacac aggtggcaag ccatgcccag 420
aagtactaca gtcgattaaa tgacaataac gcaaagagga gaaaaagcat tcatgatgtc 480
actagtgtgg gtgctgctaa tattactgaa ccttcacaag gacaaaaatc tgacgagttg 540
acaggacctt gtggaggaca atctcagtgg ccaattgccg actatgtgac tgaagctttc 600
gacacaggga tgctatcttt accagggtca gttacaaact gcacgactga tgctattgaa 660

-continued

```
ggaccatcag ctgttaaccc cgagaaattc ccacttgttg ctgctcttgg tagtgagttg    720

aatagttcat ttcccggtgt ggatgagttc ctgcaaagtg tagaagacct aatcattgta    780

ccggcagaag gcacctctgg agtatgccat ggggttgaca ctaggacatc tccatcactt    840

agcgtgcaac catcagttac tggtggcacc ggaatgtaca ctcatccagt ttcatttcct    900

gacgtgcatg agttcctgca agaggtagaa gacctaatca ctgtaccggc agagggcacc    960

tctggagcat gccatgggat tgacactagg acatctccat cacttagctt gcaatcatca   1020

gttgctggtg gcaccagaat gtacactcat tcggtcactg taccggcaga gggcacctct   1080

ggagtgaggt gtggaattga cactagaaca tctccatcac ttagcttgca accatcagtt   1140

gctggtggca ccagaatgta ccctcatcca gtcaatgtac tggcagaggg cacctctgga   1200

gcgagccatg ggttgacac taggacatct ccttcactta gcttgcaacc atcagttgct   1260

ggtggctcta gaatataccc tcatccagtc aatgtaccgg cagagggcat ctctggagtg   1320

agccatgggg ttgacactag gacatctcca tcacttagct tgcaaccatc agttggtggt   1380

ggcacgggaa tgtacacaca tccagtcact gtacgggtag agggcacctc tggagcgagg   1440

cgtggggttg acactaggac atctccatca cttagcttgc aaccatcagt tgttggtggc   1500

atcggaatgt acactcatcc aatcattgta ccggcagagg gcacctctgg aacgaggcgt   1560

ggggttgaca ctaggacatc tccatcacta agctttcaac catcagttgg tggtggcacc   1620

ggaatgtaca ctcatccagt cactgtactg gcagagggca cctctggagt aaggtgtggg   1680

gttggcacta ggacatctcc atcacttggc ttgcaaccat cagttgctgg tggtaccaga   1740

atgtacactc atgcagtcaa taatgttggg tatgatctgg aagagctaat gactaagcag   1800

ttggttggag ctagtcaaga aggtcctagc attaacactg caagtttgcc atcaccaatt   1860

gctgatcata ttggactcca tggttgtaca acttctagca gtgtcgctaa gaatggtttt   1920

gtgagtacca tggaagctcc tgggggaggt ttttctgttg attccatgca gacaccatca   1980

attcctggcc atattggagg tggaacttat ccctgttggg aacctagcag caaggacgac   2040

agtatctttg atctggaata cctatacaca gatcacatgt ttggttttcg caaataa      2097
```

<210> SEQ ID NO 67
<211> LENGTH: 200
<212> TYPE: PRT
<213> ORGANISM: Triticum aestivum

<400> SEQUENCE: 67

```
Met Ala Arg Lys Cys Ser Ser Cys Gly His Asn Gly His Asn Ser Arg
1               5                   10                  15

Thr Cys Gly Gly His Arg Gly Val Glu Ser Gly Gly Gly Gly Gly Leu
            20                  25                  30

Arg Leu Phe Gly Val Gln Leu Gln Val Gly Ala Ala Pro Leu Lys Lys
        35                  40                  45

Ser Phe Ser Met Glu Cys Leu Ser Ser Thr Ala Ser Ala Tyr Tyr Ala
    50                  55                  60

Ala Ala Ala Ala Val Gly Val Ala Ala Ser Asn Ser Ser Ser Ser Val
65                  70                  75                  80

Ser Ser Ser Ser Ser Leu Val Ser Val Glu Glu Ser Pro Glu Lys Met
                85                  90                  95

Gly His Gly Tyr Leu Ser Asp Gly Leu Met Gly Arg Ala Gln Glu Arg
            100                 105                 110

Lys Lys Gly Val Pro Trp Thr Glu Asp Glu His Arg Arg Phe Leu Ala
        115                 120                 125
```

-continued

```
Gly Leu Glu Lys Leu Gly Lys Gly Asp Trp Arg Gly Ile Ser Arg His
    130                 135                 140

Phe Val Thr Thr Arg Thr Pro Thr Gln Val Ala Ser His Ala Gln Lys
145                 150                 155                 160

Tyr Phe Leu Arg Gln Ala Gly Leu Ala Gln Lys Lys Arg Arg Ser Ser
                165                 170                 175

Leu Phe Asp Val Val Glu Lys Asn Gly Asp Arg Gly Ala Thr Glu Arg
            180                 185                 190

Arg His Arg Leu Lys Pro Asp Ala
        195                 200


<210> SEQ ID NO 68
<211> LENGTH: 310
<212> TYPE: PRT
<213> ORGANISM: Oryza sativa

<400> SEQUENCE: 68

Met Ala Arg Lys Cys Ser Ser Cys Gly Asn Asn Gly His Asn Ser Arg
1               5                   10                  15

Thr Cys Thr Gly Gln Arg Ser Leu Gln Glu Ser Gly Gly Gly Tyr Gly
            20                  25                  30

Gly Gly Gly Ala Gly Gly Val Arg Leu Phe Gly Val Gln Leu His Val
        35                  40                  45

Gly Gly Ala Pro Leu Lys Lys Cys Phe Ser Met Glu Cys Leu Ser Ser
    50                  55                  60

Pro Ser Pro Ser Pro Ser Pro Ala Tyr Tyr Ala Ala Val Ala Ala Ala
65                  70                  75                  80

Ala Ser Asn Ser Ser Pro Thr Val Ser Ser Ser Ser Ser Leu Val Ser
                85                  90                  95

Val Glu Glu Ala Gly Glu Lys Met Ala Asn Gly Tyr Leu Ser Asp Gly
            100                 105                 110

Leu Met Ala Arg Ala Gln Glu Arg Lys Lys Gly Val Pro Trp Thr Glu
        115                 120                 125

Glu Glu His Arg Lys Phe Leu Val Gly Leu Glu Lys Leu Gly Lys Gly
    130                 135                 140

Asp Trp Arg Gly Ile Ser Arg His Phe Val Thr Thr Arg Thr Pro Thr
145                 150                 155                 160

Gln Val Ala Ser His Ala Gln Lys Tyr Phe Leu Arg Gln Ser Ser Leu
                165                 170                 175

Thr Gln Lys Lys Arg Arg Ser Ser Leu Phe Asp Val Ile Glu Asp Ala
            180                 185                 190

Glu Lys Ala Pro Ser Val Asn Glu Arg Leu Lys Leu Arg His Glu Thr
        195                 200                 205

Ala Ser Val Pro Ala Glu Met Gly Phe Pro Ala Leu Ser Leu Gly Ile
    210                 215                 220

Ser Ser Met Ala Gln Pro Glu Ala Met Leu Leu Pro Pro Pro Ser Leu
225                 230                 235                 240

Thr Leu Thr Pro Ser Cys Ser Ser Pro Ala Val Ser Ser Ser Ser Ser
                245                 250                 255

Glu Gln Pro Arg Thr Ile His Pro Ser Leu Met Val Ala Lys Pro Gln
            260                 265                 270

Val Gln Leu Gln Leu Gln Pro Pro Asp Leu Glu Leu Lys Ile Ser Thr
        275                 280                 285
```

-continued

```
Val Arg Gln Asn Asp Gln Pro Ser Ser Ser Pro Arg Thr Pro Phe Leu
    290                 295                 300

Gly Thr Ile Arg Val Thr
305                 310


<210> SEQ ID NO 69
<211> LENGTH: 248
<212> TYPE: PRT
<213> ORGANISM: Gossypium raimondii

<400> SEQUENCE: 69

Met Gly Arg Lys Cys Ser His Cys Gly Asn Ile Gly His Asn Ser Arg
1               5                   10                  15

Thr Cys Thr Thr Phe Arg Ser Ser Ala Ala Gly Met Gly Ser Gly Leu
            20                  25                  30

Arg Leu Phe Gly Phe Gln Leu Gln Leu Asp Val Ser Ser Pro Ser Val
        35                  40                  45

Val Ser Asn Leu Met Met Lys Lys Ser Phe Ser Met Asp Cys Leu Ser
    50                  55                  60

Ser Ser Pro Ser Pro Ser Pro Ser Pro Ser Pro Ser Ser Leu Ser Ser
65                  70                  75                  80

Ser Arg Val Ser Ile Asp Glu Asn Ser Asp Lys Thr Ser Met Gly Tyr
                85                  90                  95

Leu Ser Asp Gly Leu Met Gly Arg Ser Pro Asp Arg Lys Lys Gly Val
            100                 105                 110

Pro Trp Thr Glu Glu Glu His Arg Ile Phe Leu Ile Gly Leu Glu Lys
        115                 120                 125

Leu Gly Lys Gly Asp Trp Arg Gly Ile Ser Arg Asn Phe Val Thr Thr
    130                 135                 140

Arg Thr Pro Thr Gln Val Ala Ser His Ala Gln Lys Tyr Phe Leu Arg
145                 150                 155                 160

Gln Ala Thr Leu Asn Lys Lys Asn Arg Arg Ser Ser Leu Phe Asp Met
                165                 170                 175

Val Arg Ser Asn Ser Met Gly Gly Pro Pro Ser Leu Thr Lys Ile Pro
            180                 185                 190

Gln Leu Asp Leu His His Arg His Pro Met Pro Val Asp Cys Ser Asp
        195                 200                 205

Ser Gln Thr Asn Val Ala Pro Asp Leu Glu Leu Thr Leu Ala Ala Ser
    210                 215                 220

Arg Pro Ala Leu Glu Glu Asn Lys Ser Ser Pro Thr Thr Thr Thr Leu
225                 230                 235                 240

Leu Ile Arg Pro His Tyr Val Thr
                245


<210> SEQ ID NO 70
<211> LENGTH: 205
<212> TYPE: PRT
<213> ORGANISM: Sorghum bicolor

<400> SEQUENCE: 70

Met Ala Arg Lys Cys Ser His Cys Gly Asn Tyr Gly His Asn Ser Arg
1               5                   10                  15

Thr Cys Gly Leu Gly His Ser Arg Glu Val Met Leu Cys Glu Ala Gly
            20                  25                  30

Asp Asn Gly Gly Gly His Gly Gly Ser Gly Leu Arg Leu Phe Gly Val
        35                  40                  45
```

-continued

```
Gln Val Arg Ile Gly Gly Gly Gly Ala Gly Ser Ser Ala Ser Met Lys
    50                  55                  60

Lys Ser Tyr Ser Met Asp Cys Leu Gln Leu Ala Ala Ala Gln Ala Gly
65                  70                  75                  80

Cys Ser Leu Val Ser Pro Ser Ser Ser Ser Ser Ser Ser Leu Leu Leu
                85                  90                  95

Ser Ile Glu Glu Gly Leu Glu Arg Gly Ala Ala Ala Asn Gly Tyr Leu
            100                 105                 110

Ser Asp Gly Pro His Gly Arg Val Val Gln Glu Arg Lys Lys Gly Val
        115                 120                 125

Pro Trp Ser Glu Glu Glu His Arg Gln Phe Leu Ala Gly Leu Glu Lys
    130                 135                 140

Leu Gly Lys Gly Asp Trp Arg Gly Ile Ser Arg Asn Tyr Val Thr Thr
145                 150                 155                 160

Arg Thr Pro Thr Gln Val Ala Ser His Ala Gln Lys Phe Phe Leu Arg
                165                 170                 175

Gln Ser Ser Met Gly Lys Lys Lys Arg Arg Ser Ser Leu Phe Asp Met
            180                 185                 190

Val Pro Ile Cys Glu Asn Ser Ala Ser Ile Ser Asp Pro
        195                 200                 205


<210> SEQ ID NO 71
<211> LENGTH: 218
<212> TYPE: PRT
<213> ORGANISM: Triticum turgidum
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid

<400> SEQUENCE: 71

Met Ala Arg Lys Cys Ser His Cys Gly Asn Tyr Gly His Asn Ser Arg
1               5                   10                  15

Thr Cys Ser Ser Ala Ala Gly Asn Gln Gly Glu Val Met Leu Cys Glu
            20                  25                  30

Gly Gly Gly Gly Ser Ser Gly Gly Ser Gly Leu Arg Leu Phe Gly Val
        35                  40                  45

Gln Val His Val Ala Ala Gly Arg Ser Thr Gly Ala Gly Ala Ser Met
    50                  55                  60

Arg Lys Ser Tyr Ser Met Asp Cys Leu Gln Leu Ala Val Ala Pro Ser
65                  70                  75                  80

Ser Ile Val Ser Pro Ser Ser Ser Ser Ser Ser Ser Val Leu Leu Ser
                85                  90                  95

Ile Asp Glu Gly Leu Glu Arg Ala Ser Asn Gly Tyr Leu Ser Asp Gly
            100                 105                 110

Pro His Gly Arg Leu Val Gln Glu Arg Lys Lys Gly Val Pro Trp Ser
        115                 120                 125

Glu Glu Glu His Arg Leu Phe Leu Val Gly Leu Glu Lys Leu Gly Lys
    130                 135                 140

Gly Asp Trp Arg Gly Ile Ser Arg Ser Tyr Val Thr Thr Arg Thr Pro
145                 150                 155                 160

Thr Gln Val Ala Ser His Ala Gln Lys Phe Phe Leu Arg Gln Ser Ser
                165                 170                 175
```

-continued

```
Met Gly Lys Lys Lys Arg Arg Ser Ser Leu Phe Asp Met Val Pro Ile
            180                 185                 190

Cys Glu Asn Gly Ile Arg Val Ser Glu Pro Leu Thr Asn Xaa Ser Gly
        195                 200                 205

Asp Ala Ser Thr Ser Leu Pro Arg Tyr Xaa
    210                 215


<210> SEQ ID NO 72
<211> LENGTH: 176
<212> TYPE: PRT
<213> ORGANISM: Glycine soja

<400> SEQUENCE: 72

Met Gly Arg Lys Cys Ser His Cys Gly Thr Ile Gly His Asn Ser Arg
1               5                   10                  15

Thr Cys Thr Ser Leu Arg Gly Ala Thr Thr Ser Phe Val Gly Leu Arg
            20                  25                  30

Leu Phe Gly Val Gln Leu Asp Ser Thr Asn Cys Val Ser Ile Lys Lys
        35                  40                  45

Ser Phe Ser Met Asp Ser Leu Pro Ser Ser Ser Ser Ser Ser Phe Ser
    50                  55                  60

Ser Ser Arg Leu Thr Ile Asp Glu Asn Ser Asp Arg Thr Ser Phe Gly
65                  70                  75                  80

Tyr Leu Ser Asp Gly Leu Leu Ala Arg Ala Gln Glu Arg Lys Lys Gly
                85                  90                  95

Val Pro Trp Thr Glu Glu Glu His Arg Ile Phe Leu Val Gly Leu Glu
            100                 105                 110

Lys Leu Gly Lys Gly Asp Trp Arg Gly Ile Ser Arg Asn Phe Val Thr
        115                 120                 125

Thr Arg Thr Pro Thr Gln Val Ala Ser His Ala Gln Lys Tyr Phe Leu
    130                 135                 140

Arg Leu Ala Thr Ile Asp Lys Lys Lys Arg Arg Ser Ser Leu Phe Asp
145                 150                 155                 160

Leu Val Gly Ser Asn Lys Ala Gly Ser Asn Ser Val Ser Ala His Gln
                165                 170                 175


<210> SEQ ID NO 73
<211> LENGTH: 261
<212> TYPE: PRT
<213> ORGANISM: Hordeum vulgare

<400> SEQUENCE: 73

Met Leu Cys Glu Gly Gly Gly Gly Gly Ser Thr Ser Gly Ser Gly Leu
1               5                   10                  15

Arg Leu Phe Gly Val Gln Val His Val Ala Ala Gly Arg Ser Ala Arg
            20                  25                  30

Ala Gly Ala Ser Met Arg Lys Ser Tyr Ser Met Asp Cys Leu Gln Leu
        35                  40                  45

Ala Ala Ala Pro Ser Ser Ile Val Ser Pro Ser Ser Ser Ser Ser Ser
    50                  55                  60

Ser Val Leu Leu Ser Ile Asp Glu Gly Leu Glu Arg Ala Ser Asn Gly
65                  70                  75                  80

Tyr Leu Ser Asp Gly Pro His Gly Arg Leu Val Gln Glu Arg Lys Lys
                85                  90                  95

Gly Val Pro Trp Ser Glu Glu Glu His Arg Leu Phe Leu Val Gly Leu
            100                 105                 110
```

-continued

```
Glu Lys Leu Gly Lys Gly Asp Trp Arg Gly Ile Ser Arg Ser Tyr Val
        115                 120                 125

Thr Thr Arg Thr Pro Thr Gln Val Ala Ser His Ala Gln Lys Phe Phe
    130                 135                 140

Leu Arg Gln Ser Ser Met Gly Lys Lys Lys Arg Arg Ser Ser Leu Phe
145                 150                 155                 160

Asp Met Val Pro Ile Cys Glu Asn Gly Ile Arg Val Ser Glu Pro Leu
                165                 170                 175

Thr Asn Asn Ser Glu Asn Ala Ser Thr Ser Leu Pro Arg Tyr Asn Ser
            180                 185                 190

Pro Asn Met Ala Ser Ile Asp Leu Asn Ser Thr Gln Glu Asp Asn Leu
        195                 200                 205

Ala Gly Phe Pro Leu Trp Ser Ala Ser Gly Ala Ser Pro Arg Ala Pro
    210                 215                 220

Phe Pro Ala Val Leu Met Glu Gln Pro Pro His Gly His Gly His Gly
225                 230                 235                 240

His His Cys Ser Pro Leu Asp Val Glu Leu Ser Met Ser Leu Ser Pro
                245                 250                 255

Pro Ser Ile Gly Thr
            260


<210> SEQ ID NO 74
<211> LENGTH: 190
<212> TYPE: PRT
<213> ORGANISM: Medicago truncatula

<400> SEQUENCE: 74

Met Gly Arg Lys Cys Ser His Cys Gly Asn Ile Gly His Asn Ser Arg
1               5                   10                  15

Thr Cys Asn Ser Leu Arg Gly Ser Gly Ser Phe Val Gly Val Arg Leu
            20                  25                  30

Phe Gly Val Gln Leu Asp Leu Ser Ser Ser Cys Val Ser Met Lys Lys
        35                  40                  45

Ser Phe Ser Met Asp Ser Phe Pro Thr Ser Ser Ser Ser Pro Thr Ser
    50                  55                  60

Ser Phe Ser Ser Ser Arg Leu Thr Ile Asp Asp Arg Ala Ser Ile Gly
65                  70                  75                  80

Tyr Leu Ser Asp Gly Leu Ile Val Arg Thr Gln Glu Arg Lys Lys Gly
                85                  90                  95

Val Pro Trp Thr Glu Glu Glu His Arg Lys Phe Leu Val Gly Leu Glu
            100                 105                 110

Lys Leu Gly Lys Gly Asp Trp Arg Gly Ile Ser Arg Asn Tyr Val Thr
        115                 120                 125

Thr Arg Thr Pro Thr Gln Val Ala Ser His Ala Gln Lys Tyr Phe Ile
    130                 135                 140

Arg Leu Ala Thr Leu Asn Lys Lys Lys Arg Arg Ser Ser Leu Phe Asp
145                 150                 155                 160

Met Val Gly Ser Gly Lys Thr Asn Lys Thr Val Asp Pro Asn Asn Ser
                165                 170                 175

Ser Lys Ser Lys Ser Gly Asp Ser Val Cys Arg His Asp His
            180                 185                 190


<210> SEQ ID NO 75
<211> LENGTH: 208
<212> TYPE: PRT
<213> ORGANISM: Saccharum officinarum
```

-continued

<400> SEQUENCE: 75

Gly His Asn Ser Arg Thr Cys Gly Phe Gly His Arg Glu Ile Met Leu
1 5 10 15

Cys Glu Ala Gly Asp Asn Gly Gly Gly Ser Gly Leu Arg Leu Phe Gly
20 25 30

Val Gln Val Arg Ile Gly Gly Gly Gly Gly Ala Gly Ser Ser Ala Ser
35 40 45

Met Lys Lys Ser Tyr Ser Met Asp Cys Leu Gln Leu Ala Ala Pro Ala
50 55 60

Gly Cys Ser Leu Val Ser Pro Ser Ser Ser Ser Ser Ser Ser Leu Leu
65 70 75 80

Leu Ser Ile Glu Glu Gly Leu Glu Arg Gly Thr Ala Asn Gly Tyr Leu
85 90 95

Ser Asp Gly Pro His Gly Arg Val Val Gln Glu Arg Lys Lys Gly Val
100 105 110

Pro Trp Ser Glu Glu Glu His Arg Gln Phe Leu Ala Gly Leu Glu Lys
115 120 125

Leu Gly Lys Gly Asp Trp Arg Gly Ile Ser Arg Asn Tyr Val Thr Thr
130 135 140

Arg Thr Pro Thr Gln Val Ala Ser His Ala Gln Lys Phe Phe Leu Arg
145 150 155 160

Gln Ser Ser Met Gly Lys Lys Lys Arg Arg Ser Ser Leu Phe Asp Met
165 170 175

Val Pro Ile Cys Glu Asn Ser Ala Ser Ile Ser Asp Pro Leu Asn Ser
180 185 190

Glu Gly Ala Ser Thr Phe Leu Ser Leu Asp Val Ala Arg His Gly Ala
195 200 205

<210> SEQ ID NO 76
<211> LENGTH: 217
<212> TYPE: PRT
<213> ORGANISM: Lycopersicon esculentum

<400> SEQUENCE: 76

Met Gly Arg Lys Cys Ser His Cys Gly Tyr Ile Gly His Asn Ser Arg
1 5 10 15

Thr Cys Ser Thr Leu Lys Ser Ala Ile Ser Gly Ser Asn Phe Asn Gly
20 25 30

Gly Leu Arg Leu Phe Gly Val Gln Leu Asp Ile Ser Asn Ser Cys Phe
35 40 45

Ser Ser His Asn Asn Asn Asn Asn Asn Asn Leu Lys Lys Ser Phe Ser
50 55 60

Leu Asp Cys Leu Ser Leu Thr Asn Ser His Leu Leu Leu Leu Ser Ser
65 70 75 80

Ser Ser Ser Pro Ser Leu Asn Glu Asn Ser Ser Thr Asn Ser Ile Asp
85 90 95

Asn Asn Gly Tyr Leu Ser Asp Gly Thr Leu Val Gly Cys Val Gly Glu
100 105 110

Arg Lys Lys Gly Val Pro Trp Thr Glu Glu Glu His Arg Arg Phe Leu
115 120 125

Asn Gly Leu Glu Lys Leu Gly Lys Gly Asp Trp Arg Gly Ile Ser Arg
130 135 140

Asn Phe Val Thr Thr Arg Thr Pro Thr Gln Val Ala Ser His Ala Gln
145 150 155 160

-continued

```
Lys Tyr Phe Leu Arg Gln Ser Ser Leu Asn Lys Lys Lys Lys Thr Phe
                165                 170                 175

Lys Ser Leu Arg Tyr Gly Lys Glu Gln Gln Gln Ile Cys Arg Phe Leu
            180                 185                 190

Ser Lys Leu Pro Arg Arg Leu Ser Arg Asn Tyr Lys Ile Ile Ser Ile
        195                 200                 205

Arg Pro Lys Phe Ile Trp Arg Lys Val
    210                 215


<210> SEQ ID NO 77
<211> LENGTH: 216
<212> TYPE: PRT
<213> ORGANISM: Solanum tuberosum
<220> FEATURE:
<221> NAME/KEY: misc_feature
<222> LOCATION: (216)..(216)
<223> OTHER INFORMATION: Xaa can be any naturally occurring amino acid

<400> SEQUENCE: 77

Met Gly Arg Lys Cys Ser His Cys Gly Asn Ile Gly His Asn Ser Arg
1               5                   10                  15

Thr Cys Ser Thr Phe Lys Leu Gly Ala Ser Ala Ser Phe Val Gly Gly
            20                  25                  30

Leu Arg Leu Phe Gly Val Gln Leu Ile Asp Ile Ser Ser Ser Ser Ser
        35                  40                  45

Ala Ser Ser Ser Ser Ser Ser Ser Tyr Asp Ile His Leu Lys Lys Ser
    50                  55                  60

Leu Ser Leu Asp Cys Met Ser Ser Pro Gln Val Ser Ser Ser Ser Ser
65                  70                  75                  80

Leu Val Thr Leu Asn Glu Lys Ser Thr Thr Cys Thr Asn Gly Asp Tyr
                85                  90                  95

Leu Ser Asp Cys Leu Leu Gly Gln Pro Gln Glu Arg Arg Lys Gly Val
            100                 105                 110

Gly Trp Thr Glu Glu Glu His Arg Arg Phe Leu Met Gly Leu Glu Lys
        115                 120                 125

Leu Gly Lys Gly Asp Trp Arg Gly Ile Ser Arg Lys Phe Val Thr Thr
    130                 135                 140

Arg Thr Pro Thr Gln Val Ala Ser His Ala Gln Lys Tyr Phe Leu Arg
145                 150                 155                 160

Gln Tyr Ser Thr His Leu Asn Lys Lys Lys Arg Arg Ser Arg Leu Phe
                165                 170                 175

Asp Met Glu Arg Arg Lys Asn Lys Met Glu Glu Ser Lys Glu Glu Tyr
            180                 185                 190

Gly Asn Ser Thr Ser Pro Ile Ser Met Met Asp Glu Glu Ile Ala Leu
        195                 200                 205

Thr Thr Lys Asp Thr Leu Ile Xaa
    210                 215


<210> SEQ ID NO 78
<211> LENGTH: 153
<212> TYPE: PRT
<213> ORGANISM: Bruguiera gymnorrhiza

<400> SEQUENCE: 78

Met Gly Arg Arg Cys Ser His Cys Gly Asn Ile Gly His Asn Ser Arg
1               5                   10                  15

Thr Cys Thr Ser Thr Ser Phe Arg Gly Val Val Val Ala Gly Gly Leu
            20                  25                  30
```

-continued

Arg Leu Phe Gly Val Arg Leu Asp Ile Pro Ser Ser Pro Cys Val Pro
35 40 45

Ile Gln Lys Ser Ile Ser Met Asp Ser Leu Ser Leu Ser Ser Ser Thr
50 55 60

Ser Pro Ser Phe Ser Ser Leu Arg Ser Ser Arg Ile Ser Ile Asp Asp
65 70 75 80

Asn Ser Asp Lys Leu Ser Ile Gly Tyr Leu Ser Asp Ser Leu Phe Gly
85 90 95

Pro Val Gln Glu Arg Lys Lys Gly Val Pro Trp Thr Glu Glu Glu His
100 105 110

Arg Thr Phe Leu Ile Gly Leu Glu Lys Leu Gly Lys Gly Asp Trp Arg
115 120 125

Gly Ile Ser Arg Asn Phe Val Thr Thr Arg Thr Pro Thr Gln Val Ala
130 135 140

Ser His Ala Gln Lys Tyr Phe Leu Arg
145 150

<210> SEQ ID NO 79
<211> LENGTH: 221
<212> TYPE: PRT
<213> ORGANISM: Vitis vinifera

<400> SEQUENCE: 79

Met Thr Arg Arg Cys Ser His Cys Ser Thr Asn Gly His Asn Ser Arg
1 5 10 15

Thr Cys Pro Ser Arg Gly Gly Gly Ala Val Ala Gly Gly Ile Gly Gly
20 25 30

Val Lys Leu Phe Gly Val Arg Leu Thr Asp Gly Ser Ile Ile Lys Lys
35 40 45

Ser Ala Ser Met Gly Ser Leu Ser Ser Ala His Tyr His Ser Ser Ser
50 55 60

Ser Ala Ala Ala Ser Pro Asn Pro Ser Ser Pro Ser Ser Asp Pro Leu
65 70 75 80

Arg Asp Ala Ile His Glu Pro Asp Gly Tyr Leu Ser Asp Asp Pro Gly
85 90 95

Gln Ala Thr Cys Ser Ser Asn Arg Arg Gly Glu Arg Lys Lys Gly Val
100 105 110

Pro Trp Thr Glu Glu Glu His Arg Leu Phe Leu Phe Gly Leu Gln Arg
115 120 125

Leu Gly Lys Gly Asp Trp Arg Gly Ile Ser Arg Asn Tyr Val Ile Ser
130 135 140

Arg Thr Pro Thr Gln Val Ala Ser His Ala Gln Lys Tyr Phe Ile Arg
145 150 155 160

Gln Ser Asn Ala Thr Arg Arg Lys Arg Arg Ser Ser Leu Phe Asp Met
165 170 175

Val Pro Asp Met Val Thr Asp Thr Pro Pro Val Pro Glu Glu Gln Phe
180 185 190

Leu Val Pro Thr Ser Gln Thr Gly Glu Thr Asp Asn Ala Ser Ser Val
195 200 205

Pro Ser Leu Asn Leu Ser Leu Asn Met Glu Phe Glu Pro
210 215 220

<210> SEQ ID NO 80
<211> LENGTH: 387
<212> TYPE: PRT
<213> ORGANISM: Arabidopsis thaliana -continued

<400> SEQUENCE: 80

Met Thr Arg Arg Cys Ser His Cys Ser Asn Asn Gly His Asn Ser Arg
1               5                   10                  15

Thr Cys Pro Thr Arg Gly Gly Gly Thr Cys Gly Gly Ser Gly Gly Gly
            20                  25                  30

Gly Gly Gly Gly Gly Gly Gly Gly Ser Gly Ser Ser Ser Ala Met Lys
        35                  40                  45

Leu Phe Gly Val Arg Leu Thr Asp Gly Ser Ile Ile Lys Lys Ser Ala
    50                  55                  60

Ser Met Gly Asn Leu Ser Ala Leu Ala Val Ala Ala Ala Ala Ala Thr
65                  70                  75                  80

His His Arg Leu Ser Pro Ser Ser Pro Leu Ala Thr Ser Asn Leu Asn
                85                  90                  95

Asp Ser Pro Leu Ser Asp His Ala Arg Tyr Ser Asn Leu His His Asn
            100                 105                 110

Glu Gly Tyr Leu Ser Asp Asp Pro Ala His Gly Ser Gly Ser Ser His
        115                 120                 125

Arg Arg Gly Glu Arg Lys Arg Gly Val Pro Trp Thr Glu Glu Glu His
    130                 135                 140

Arg Leu Phe Leu Val Gly Leu Gln Lys Leu Gly Lys Gly Asp Trp Arg
145                 150                 155                 160

Gly Ile Ser Arg Asn Tyr Val Thr Ser Arg Thr Pro Thr Gln Val Ala
                165                 170                 175

Ser His Ala Gln Lys Tyr Phe Ile Arg His Thr Ser Ser Ser Arg Arg
            180                 185                 190

Lys Arg Arg Ser Ser Leu Phe Asp Met Val Thr Asp Glu Met Val Thr
        195                 200                 205

Asp Ser Ser Pro Thr Gln Glu Glu Gln Thr Leu Asn Gly Ser Ser Pro
    210                 215                 220

Ser Lys Glu Pro Glu Lys Lys Ser Tyr Leu Pro Ser Leu Glu Leu Ser
225                 230                 235                 240

Leu Asn Asn Thr Thr Glu Ala Glu Glu Val Val Ala Thr Ala Pro Arg
                245                 250                 255

Gln Glu Lys Ser Gln Glu Ala Ile Glu Pro Ser Asn Gly Val Ser Pro
            260                 265                 270

Met Leu Val Pro Gly Gly Phe Phe Pro Pro Cys Phe Pro Val Thr Tyr
        275                 280                 285

Thr Ile Trp Leu Pro Ala Ser Leu His Gly Thr Glu His Ala Leu Asn
    290                 295                 300

Ala Glu Thr Ser Ser Gln Gln His Gln Val Leu Lys Pro Lys Pro Gly
305                 310                 315                 320

Phe Ala Lys Glu Arg Val Asn Met Asp Glu Leu Val Gly Met Ser Gln
                325                 330                 335

Leu Ser Ile Gly Met Ala Thr Arg His Glu Thr Glu Thr Ser Pro Ser
            340                 345                 350

Pro Leu Ser Leu Arg Leu Glu Pro Ser Arg Pro Ser Ala Phe His Ser
        355                 360                 365

Asn Gly Ser Val Asn Gly Ala Asp Leu Ser Lys Gly Asn Ser Ala Ile
    370                 375                 380

Gln Ala Ile
385

-continued

<210> SEQ ID NO 81
<211> LENGTH: 242
<212> TYPE: PRT
<213> ORGANISM: Citrus sinensis

<400> SEQUENCE: 81

```
Met Thr Arg Arg Cys Ser His Cys Ser Asn Asn Gly His Asn Ser Arg
1               5                   10                  15

Thr Cys Pro Ala Arg Gly Gly Gly Ser Ser Pro Gly Val Gly Gly Leu
            20                  25                  30

Lys Leu Phe Gly Val Arg Leu Thr Asp Gly Ser Ile Ile Lys Lys Ser
        35                  40                  45

Ala Ser Met Gly Asn Leu Ser Ala Leu His Tyr His Ser Ser Ser Ser
    50                  55                  60

Ala Ala Ala Ser Pro Asn Pro Asp Ser Pro Leu Ser Asp His Val Arg
65                  70                  75                  80

Asp Pro Asn His Leu Thr Asp Gly Tyr Leu Ser Asp Asp Pro Ala His
                85                  90                  95

Gly Ser Gly Ser Ser Asn Arg Arg Cys Glu Arg Lys Lys Gly Val Pro
            100                 105                 110

Trp Thr Glu Glu Glu His Arg Leu Phe Leu Ile Gly Leu Gln Lys Leu
        115                 120                 125

Gly Lys Gly Asp Trp Arg Gly Ile Ala Arg Asn Tyr Val Met Ser Arg
    130                 135                 140

Thr Pro Thr Gln Val Ala Ser His Ala Gln Lys Tyr Phe Ile Arg Gln
145                 150                 155                 160

Ser Asn Ala Thr Arg Arg Lys Arg Arg Ser Ser Leu Phe Asp Met Val
                165                 170                 175

Ala Asp Asp Met Ala Thr Asp Thr Pro Pro Val Pro Glu Glu Gln Val
            180                 185                 190

Met Leu Pro Ser Pro Leu Ala Arg Glu Ser Asp Asn Thr Ser Ser Gln
        195                 200                 205

Pro Ser Leu Asn Leu Ser Leu Ser Thr Glu Phe Glu Pro Met Glu Ala
    210                 215                 220

Val Cys Lys Glu Thr Glu Lys Asp Ser Glu Glu Pro Val Ile Asp Leu
225                 230                 235                 240

Asn Glu
```

<210> SEQ ID NO 82
<211> LENGTH: 274
<212> TYPE: PRT
<213> ORGANISM: Nicotiana benthamiana

<400> SEQUENCE: 82

```
Met Thr Arg Arg Cys Ser His Cys Asn Asn Asn Gly His Asn Ser Arg
1               5                   10                  15

Thr Cys Pro Thr Thr Arg Gly Gly Thr Pro Thr Gly Gly Val Gly Ser
            20                  25                  30

Ser Ser Gly Gly Gly Gly Gly Ala Ser Gly Gly Val Arg Leu Phe Gly
        35                  40                  45

Val Arg Leu Thr Asp Gly Ser Ile Met Lys Lys Ser Ala Ser Met Gly
    50                  55                  60

Asn Leu Ser Ser Leu His Ser Tyr His Ser Ser Ser Ser Pro Asn Pro
65                  70                  75                  80

Pro Gly Ser Pro Ser Ser Asp Gly Pro His Leu Pro Asp Gly Tyr Leu
                85                  90                  95
```

-continued

```
Ser Asp Asp Pro Asn Thr His Ala Ser Ile Ser Ala Asn Arg Arg Leu
            100                 105                 110

Glu Arg Lys Lys Gly Val Pro Trp Thr Glu Glu Glu His Arg Leu Phe
        115                 120                 125

Leu Leu Gly Leu Gln Lys Leu Gly Lys Gly Asp Trp Arg Gly Ile Ser
    130                 135                 140

Arg Asn Phe Val Thr Ser Arg Thr Pro Thr Gln Val Ala Ser His Ala
145                 150                 155                 160

Gln Lys Tyr Phe Ile Arg Gln Ser Asn Ala Thr Arg Arg Lys Arg Arg
                165                 170                 175

Ser Ser Leu Phe Asp Ile Val Ala Asp Ser Gly Thr Asp Ala Ser His
            180                 185                 190

Pro Leu Pro Glu Glu Gln Phe Met Leu Pro Pro Arg Ala Ile Glu Ser
        195                 200                 205

Asp Lys Glu His Leu Ala Pro Ser Ala Thr Lys Ala Ile Glu Thr Asp
    210                 215                 220

Phe Ala Asp Ser Leu Pro Ser Leu Asp Leu Ser Leu Lys Ser Asp Phe
225                 230                 235                 240

Glu Ser Met Glu Thr Thr Pro Ser Glu Pro Val Glu Glu Ala Lys Pro
                245                 250                 255

Asn Thr Thr Thr Asn Glu Ile Pro Ser Val Phe Pro Ala Phe Leu Pro
            260                 265                 270

Ala Tyr


<210> SEQ ID NO 83
<211> LENGTH: 144
<212> TYPE: PRT
<213> ORGANISM: Glycine max

<400> SEQUENCE: 83

His Glu Glu Ala Thr Thr Ser Phe Val Gly Leu Arg Leu Phe Gly Val
1               5                   10                  15

Gln Leu Asp Ser Thr Asn Cys Val Ser Ile Lys Lys Ser Phe Ser Met
            20                  25                  30

Asp Ser Leu Pro Ser Ser Ser Ser Ser Ser Phe Ser Ser Ser Arg Leu
        35                  40                  45

Thr Ile Asp Glu Asn Ser Asp Arg Thr Ser Phe Gly Tyr Leu Ser Asp
    50                  55                  60

Gly Leu Leu Ala Arg Ala Gln Glu Arg Lys Lys Gly Val Pro Trp Thr
65                  70                  75                  80

Glu Glu Glu His Arg Ile Phe Leu Val Gly Leu Glu Lys Leu Gly Lys
                85                  90                  95

Gly Asp Trp Arg Gly Ile Ser Arg Asn Phe Val Thr Thr Arg Thr Pro
            100                 105                 110

Thr Gln Val Ala Ser His Ala Gln Lys Tyr Phe Leu Arg Leu Ala Thr
        115                 120                 125

Ile Asp Lys Lys Lys Arg Arg Ser Ser Leu Phe Asp Leu Val Gly Ser
    130                 135                 140


<210> SEQ ID NO 84
<211> LENGTH: 258
<212> TYPE: PRT
<213> ORGANISM: Vitis aestivalis
<220> FEATURE:
<221> NAME/KEY: misc_feature
<222> LOCATION: (245)..(247)
<223> OTHER INFORMATION: Xaa can be any naturally occurring amino acid
```

-continued

<220> FEATURE:
<221> NAME/KEY: misc_feature
<222> LOCATION: (258)..(258)
<223> OTHER INFORMATION: Xaa can be any naturally occurring amino acid

<400> SEQUENCE: 84

Met Ser Arg Cys Cys Ser Gln Cys Gly His Asn Gly His Asn Ser Arg
1 5 10 15

Thr Cys Ala Glu Ser Gly Gly Gly Gly Gly Gly Gly Asp Gly Gly Ser
20 25 30

Glu Gly Ile Met Leu Phe Gly Val Arg Val Thr Val Asp Ser Met Arg
35 40 45

Lys Ser Val Ser Leu Asn Asn Leu Ser Gln Tyr Glu Gln Pro His Glu
50 55 60

Ser Ser Asn Ala Asp Ala Thr Pro Ala Ala Gly Tyr Val Ser Ala Asp
65 70 75 80

Asp Val Ala His His Ser Ser Gly Asn Arg Glu Arg Lys Arg Gly Val
85 90 95

Pro Trp Thr Glu Glu Glu His Lys Leu Phe Leu Val Gly Leu Gln Lys
100 105 110

Val Gly Lys Gly Asp Trp Arg Gly Ile Ser Arg Asn Phe Val Lys Thr
115 120 125

Arg Thr Pro Thr Gln Val Ala Ser His Ala Gln Lys Tyr Phe Leu Arg
130 135 140

Arg Asn Asn Leu Asn Arg Arg Arg Arg Arg Ser Ser Leu Phe Asp Ile
145 150 155 160

Thr Thr Glu Ser Val Thr Ala Val Pro Met Glu Glu Glu Gln Val Leu
165 170 175

His His Gln Glu Asn Thr Ser Gln Ser Gln Gln Ser Pro Lys Thr Phe
180 185 190

Ser Glu Thr Gly Ser Gly Asp Gly Phe Pro Val Val Pro Ala Phe Pro
195 200 205

Met Pro Ile Asn Pro Val Val Val Pro Val Pro Ile Gln Asn Pro Met
210 215 220

Glu Asn Leu Thr Leu Gly Gln Asn Asp Val Asn Thr Arg Leu Val Arg
225 230 235 240

Pro Ile Pro Val Xaa Xaa Xaa Pro Pro Glu Ser Thr Asp Leu Asn Leu
245 250 255

Asn Xaa

<210> SEQ ID NO 85
<211> LENGTH: 194
<212> TYPE: PRT
<213> ORGANISM: Brassica napus

<400> SEQUENCE: 85

Met Thr Arg Arg Cys Ser His Cys Ser Tyr Asn Gly His Asn Ser Arg
1 5 10 15

Thr Cys Pro Thr Arg Gly Gly Gly Gly Gly Gly Thr Cys Gly Gly Asn
20 25 30

Gly Gly Glu Ser Ala Ser Ser Ser Ser Ser Ala Ala Val Lys Leu Phe
35 40 45

Gly Val Arg Leu Thr Asp Gly Ser Ile Ile Lys Lys Ser Ala Ser Met
50 55 60

Gly Asn Leu Ser Ala Leu Ala Val His His Arg Leu Ser Pro Leu Ala
65 70 75 80

-continued

```
Thr Gly Asn His Asn Asp Ser Pro Leu Ser Asp His Gly Arg Tyr Ser
                85                  90                  95

Ser Gln Glu Asn Gly Gly Tyr Leu Ser Asp Asp Pro Gly His Gly Ser
            100                 105                 110

Gly Ser Ile His His Arg Arg Val Glu Arg Lys Arg Gly Val Pro Trp
        115                 120                 125

Thr Glu Glu Glu His Arg Leu Phe Leu Val Gly Leu Gln Lys Leu Gly
    130                 135                 140

Lys Gly Asp Trp Arg Gly Ile Ser Arg Asn Tyr Val Thr Ser Arg Thr
145                 150                 155                 160

Pro Thr Gln Val Ala Ser His Ala Gln Lys Tyr Phe Ile Arg His Thr
                165                 170                 175

Cys Ser Thr Arg Arg Lys Arg Arg Ser Ser Leu Phe Asp Met Val Thr
            180                 185                 190

Asp Glu


<210> SEQ ID NO 86
<211> LENGTH: 151
<212> TYPE: PRT
<213> ORGANISM: Pinus taeda

<400> SEQUENCE: 86

Met Thr Arg Lys Cys Ser His Cys Gly His Asn Gly His Asn Ser Arg
1               5                   10                  15

Thr Cys Pro Asn Arg Gly Val Lys Leu Phe Gly Val Arg Leu Thr Asp
            20                  25                  30

Gly Pro Ile Arg Lys Ser Val Ser Met Gly Asn Leu Leu His Tyr Ser
        35                  40                  45

Asn Asn Ala Ser Ser Ser Asn Asn Ser Pro Ala Ser Ala Ser Ala Met
    50                  55                  60

Glu Pro Cys Glu Ser Val Ala Asn Ala Ala Ala Ser Ala Asp Gly Tyr
65                  70                  75                  80

Val Ser Asp Gly Leu Val His Asn Asn Ser Arg Gly Glu Arg Lys Lys
                85                  90                  95

Gly Val Pro Trp Thr Glu Glu Glu His Arg Met Phe Leu Ile Gly Leu
            100                 105                 110

Gln Lys Leu Gly Lys Gly Asp Trp Arg Gly Ile Ser Arg Asn Phe Val
        115                 120                 125

Pro Thr Arg Thr Pro Thr Gln Val Ala Ser His Ala Gln Lys Tyr Phe
    130                 135                 140

Ile Arg Gln Ser Asn Leu Thr
145                 150


<210> SEQ ID NO 87
<211> LENGTH: 172
<212> TYPE: PRT
<213> ORGANISM: Allium cepa

<400> SEQUENCE: 87

Met Thr Arg Lys Cys Ser His Cys Ser His Asn Gly His Asn Ser Arg
1               5                   10                  15

Thr Cys Pro Asn Lys Gly Val Lys Leu Phe Gly Val Arg Leu Thr Asp
            20                  25                  30

Gly Ser Ser Ser Ile Arg Lys Ser Val Ser Met Gly Asn Leu Ser His
        35                  40                  45
```

-continued

```
Tyr Ala Ala Ala Ala Gly Gly Gly Ala Ser Pro Ala Asp Gly Gly Asp
    50                  55                  60

His Gly Thr Asp Val Ala Asp Gly Tyr Ala Ser Glu Asp Phe Val Ala
65                  70                  75                  80

Gly Ser Ser Ser Gly Ser Arg Glu Arg Lys Arg Gly Val Pro Trp Thr
                85                  90                  95

Glu Glu Glu His Arg Met Phe Leu Leu Gly Leu Gln Lys Leu Gly Lys
            100                 105                 110

Gly Asp Trp Arg Gly Ile Ala Arg Thr Phe Val Lys Thr Arg Thr Pro
        115                 120                 125

Thr Gln Val Ala Ser His Ala Gln Lys Phe Phe Ile Arg Gln Thr Asn
    130                 135                 140

Met Gly Arg Arg Lys Arg Arg Ser Ser Leu Phe Asp Ile Val Pro Asp
145                 150                 155                 160

Glu Ala Ala Asp Ser Gln Phe Leu Pro Met Asn Asp
                165                 170


<210> SEQ ID NO 88
<211> LENGTH: 243
<212> TYPE: PRT
<213> ORGANISM: Mesembryanthemum crystallinum

<400> SEQUENCE: 88

Met Thr Arg Arg Cys Ser His Cys Ser His Asn Gly His Asn Ser Arg
1               5                   10                  15

Thr Cys Pro Asn Arg Gly Val Lys Leu Phe Gly Val Arg Leu Thr Asp
            20                  25                  30

Gly Ser Ile Arg Lys Ser Ala Ser Met Gly Asn Leu Ser His Tyr His
        35                  40                  45

Gln Asn Gly Ala Val Gly Ser Thr Thr Pro Gly Ser Pro Ala Gly Asp
    50                  55                  60

His Thr Pro Asp His Gly Gly Ser Ala Ala Gly Asp Gly Tyr Gly Ser
65                  70                  75                  80

Glu Asp Phe Val Pro Gly Ser Ser Ser Ser Arg Glu Arg Lys Lys Gly
                85                  90                  95

Val Pro Trp Thr Glu Glu Glu His Arg Met Phe Leu Leu Gly Leu Gln
            100                 105                 110

Lys Leu Gly Lys Gly Asp Trp Arg Gly Ile Ser Arg Asn Tyr Val Ile
        115                 120                 125

Ser Arg Thr Pro Thr Gln Val Ala Ser His Ala Gln Lys Tyr Phe Ile
    130                 135                 140

Arg Gln Ser Asn Val Ser Arg Arg Lys Arg Arg Ser Ser Leu Phe Asp
145                 150                 155                 160

Ile Ile Ala Asp Glu Ser Gly Asp Thr Pro Met Val Ser His Asp Phe
                165                 170                 175

Leu Ser Ala His Ser Ala Glu Asn Asp Thr Glu Asn Ser Asn Pro Leu
            180                 185                 190

Pro Pro Ala Pro Ala Leu Asp Glu Glu Cys Glu Ser Met Ala Ser Ser
        195                 200                 205

Asn Ser Asn Glu Val Gly Pro Thr Leu Pro Lys Pro Glu Thr Ser Gln
    210                 215                 220

Ser Cys Tyr Pro Ser Asp Thr Pro Gln Thr Ile Ile Pro Leu Ile Ser
225                 230                 235                 240

Asn Tyr Val
```

-continued

<210> SEQ ID NO 89
<211> LENGTH: 302
<212> TYPE: PRT
<213> ORGANISM: Malus xiaojinensis

<400> SEQUENCE: 89

```
Met Ser Ser Gly Thr Cys Ser Thr Val Glu Pro Ala Gly Ala Gly Glu
1               5                   10                  15

Ile Met Leu Phe Gly Val Arg Leu Val Val Asp Ser Met Arg Lys Ser
            20                  25                  30

Val Ser Leu Asn Asn Leu Ser Gln Tyr Glu His Pro Gln Glu Ala Ala
        35                  40                  45

Ser Asn Asn Gly Asn Asn Gly Thr Ala Ala Gly Lys Asp Asp Ala Ala
    50                  55                  60

Pro Gly Tyr Ala Ser Glu Asn Asp Val Val His Asn Ser Gly Gly Asn
65                  70                  75                  80

Arg Glu Arg Glu Arg Lys Arg Gly Val Pro Trp Thr Glu Glu Glu His
                85                  90                  95

Lys Leu Phe Leu Leu Gly Leu Gln Lys Ala Gly Lys Gly Asp Trp Arg
            100                 105                 110

Gly Ile Ser Arg Asn Phe Val Lys Thr Arg Thr Pro Thr Gln Val Ala
        115                 120                 125

Ser His Ala Gln Lys Tyr Tyr Leu Arg Arg Ser Asn Leu Asn Arg Arg
    130                 135                 140

Arg Arg Arg Ser Ser Leu Phe Asp Ile Thr Thr Asp Thr Val Ala Pro
145                 150                 155                 160

Thr Pro Met Asp Glu Glu Gln Val Gln His Gln Asp Asn Ile Ser Gln
                165                 170                 175

Ser Gln Leu His Pro Leu Pro Pro Pro Pro Pro Ser Glu Pro Arg Asp
            180                 185                 190

Ala Gly Gly Phe Ser Met Val Pro Asn Phe Ala Arg Thr Val Gly Pro
        195                 200                 205

Ala Val Leu Pro Val His Ile Glu Asn Pro Met Glu Asn Leu Ala Leu
    210                 215                 220

Arg Gln Ala Asn Pro Glu Asn Ser Thr Ser Ala Lys Leu Val His Pro
225                 230                 235                 240

Val Ala Leu His Ser Ala Pro His Ala Thr Ala Ile Ser Asp Leu Asn
                245                 250                 255

Leu Asn Ser Thr Thr Asp Ala Ser Thr Leu Thr Leu Asn Leu Ser Leu
            260                 265                 270

Ser Met Asp Ser Arg Glu Pro Ser Ser Arg His Ser Ala Phe Glu Thr
        275                 280                 285

Met Gln Gly Phe Ser Asn Gly Asp Ser Met Ile Ser Val Ala
    290                 295                 300
```

<210> SEQ ID NO 90
<211> LENGTH: 314
<212> TYPE: PRT
<213> ORGANISM: Zea mays

<400> SEQUENCE: 90

```
Met Thr Arg Arg Cys Ser His Cys Ser His Asn Gly His Asn Ser Arg
1               5                   10                  15

Thr Cys Pro Asn Arg Gly Val Lys Ile Phe Gly Val His Leu Thr Asp
            20                  25                  30
```

-continued

Gly Ser Ala Ile Arg Lys Ser Ala Ser Met Gly Asn Leu Ser Leu Leu
35 40 45

Ser Ala Gly Ser Thr Ser Gly Gly Ala Ser Pro Ala Asp Gly Pro Asp
50 55 60

Leu Ala Asp Gly Gly Gly Gly Tyr Ala Ser Asp Asp Phe Val Gln Gly
65 70 75 80

Ser Ser Ser Ala Ser Arg Asp Arg Lys Lys Val Phe Leu Gly Leu Glu
85 90 95

Lys Asn Thr Gly Val Phe Ala Gly Ile Thr Lys Ala Arg Glu Arg Gly
100 105 110

Trp Arg Gly Ile Ser Arg Asn Phe Val Val Ser Arg Thr Pro Thr Gln
115 120 125

Val Ala Ser His Ala Gln Lys Tyr Phe Ile Arg Gln Ser Asn Met Ser
130 135 140

Arg Arg Lys Arg Arg Ser Ser Leu Phe Asp Met Val Pro Asp Glu Ser
145 150 155 160

Met Asp Leu Pro Pro Leu Pro Gly Ser Gln Glu Pro Glu Thr Ser Met
165 170 175

Leu Asn Gln Pro Pro Leu Pro Pro Ala Val Glu Glu Glu Val Glu Ser
180 185 190

Met Glu Ser Asp Thr Ser Ala Val Ala Glu Ser Ser Gly Ala Ser Ala
195 200 205

Leu Met Pro Glu Ser Leu Gln Pro Thr Tyr Pro Met Ile Val Pro Ala
210 215 220

Tyr Phe Ser Pro Phe Leu Gln Phe Ser Val Pro Phe Trp Pro Asn Gln
225 230 235 240

Glu Asp Gly Gly Asp Leu Pro Gln Glu Thr His Glu Ile Val Lys Pro
245 250 255

Val Ala Val His Ser Gln Asn Pro Ile Asn Val Asp Glu Leu Val Gly
260 265 270

Met Ser Lys Leu Ser Ile Trp Glu His Gly Gln Glu Thr Val Tyr Thr
275 280 285

Ser Leu Ser Leu Asn Leu Leu Gly Gly Gln Asn Arg Gln Ser Ala Phe
290 295 300

His Ala Asn Pro Gln Thr Arg Ala Gln Ala
305 310

<210> SEQ ID NO 91
<211> LENGTH: 310
<212> TYPE: PRT
<213> ORGANISM: Hevea brasiliensis

<400> SEQUENCE: 91

Met Asp Arg Gly Ile Glu Ile Leu Ser Pro Ala Ser Tyr Leu Gln Asn
1 5 10 15

Ser Asn Trp Leu Phe Pro Glu Thr Arg Ala Thr Lys Trp Thr Pro Glu
20 25 30

Glu Asn Lys Gln Phe Glu Asn Ala Leu Ala Leu Tyr Asp Lys Asp Glu
35 40 45

Pro Asp Arg Trp Gln Arg Val Ala Ala Val Ile Pro Gly Lys Thr Val
50 55 60

Gly Asp Val Ile Lys Gln Tyr Arg Glu Leu Glu Glu Asp Val Ser Asp
65 70 75 80

Ile Glu Ala Gly Leu Ile Pro Ile Pro Gly Tyr Ser Ser Ser Asp Ala
85 90 95

-continued

```
Phe Thr Leu Glu Trp Phe Asn Asn Asn Gln Gly Tyr Asp Gly Phe Arg
            100                 105                 110

His Tyr Tyr Thr Pro Gly Gly Lys Arg Thr Thr Ala Ala Arg Ser Ser
        115                 120                 125

Glu Gln Glu Arg Lys Lys Gly Val Pro Trp Thr Glu Glu Glu His Arg
    130                 135                 140

Gln Phe Leu Met Gly Leu Gln Lys Tyr Gly Lys Gly Asp Trp Arg Asn
145                 150                 155                 160

Ile Ser Arg Asn Phe Val Thr Thr Arg Thr Pro Thr Gln Val Ala Ser
                165                 170                 175

His Ala Gln Lys Tyr Phe Ile Arg Gln Ser Thr Gly Gly Lys Asp Lys
            180                 185                 190

Arg Arg Ser Ser Ile His Asp Ile Thr Thr Val Asn Leu Pro Asp Thr
        195                 200                 205

Lys Ser Pro Ser Pro Asp Glu Lys Lys Ser Ser Pro Asp His Ser Thr
    210                 215                 220

Thr Ser Leu Gln Ser Gln Pro Gln Gln Lys Met Val Gly Met Ala Lys
225                 230                 235                 240

Gly Leu Ile Asp Trp Lys Pro Gln Asn Glu Gly Gly Gly Ala Ala Gly
                245                 250                 255

Val Phe Ser Gln Ala Asn Gly Asn Leu Leu Met Ala Pro Leu Cys Gly
            260                 265                 270

Ile Ser Ser Tyr Gly Gln Lys Leu Gln Glu Gln Asn Leu Leu Arg Gly
        275                 280                 285

Thr Leu Pro Gly Tyr Gln Phe Ala Pro Tyr Asn Leu Ile Phe Gln Met
    290                 295                 300

Gln Pro Met Gln Arg Gln
305                 310


<210> SEQ ID NO 92
<211> LENGTH: 291
<212> TYPE: PRT
<213> ORGANISM: Antirrhinum majus

<400> SEQUENCE: 92

Met Glu Ile Leu Thr Pro Ser Ser Tyr Phe Ser Asn Ser Asn Leu Phe
1               5                   10                  15

Val Glu Glu Ser Trp Ser Pro Lys Trp Thr Ala Ala Asp Asn Lys Ala
            20                  25                  30

Phe Glu Asn Ala Leu Ala Val Phe Asp Glu Tyr Thr Pro His Arg Trp
        35                  40                  45

Glu Arg Val Ala Glu Ile Val Pro Gly Lys Thr Val Trp Asp Val Ile
    50                  55                  60

Arg His Tyr Lys Glu Leu Glu Asp Asp Val Thr Ser Ile Glu Ala Gly
65                  70                  75                  80

Leu Val Pro Val Pro Gly Tyr Asn Thr Ser Leu Pro Phe Thr Leu Glu
                85                  90                  95

Trp Gly Ser Gly His Gly Phe Asp Gly Phe Met Gln Ser Tyr Val Val
            100                 105                 110

Gly Gly Arg Lys Ser Ser Cys Ser Arg Pro Ser Asp Gln Glu Arg Lys
        115                 120                 125

Lys Gly Val Pro Trp Thr Glu Glu Glu His Lys Leu Phe Leu Met Gly
    130                 135                 140

Leu Lys Lys Tyr Gly Lys Gly Asp Trp Arg Asn Ile Ser Arg Asn Phe
145                 150                 155                 160
```

-continued

```
Val Ile Thr Arg Thr Pro Thr Gln Val Ala Ser His Ala Gln Lys Tyr
                165                 170                 175

Phe Ile Arg Gln Leu Ser Gly Gly Lys Asp Lys Arg Arg Ala Ser Ile
            180                 185                 190

His Asp Ile Thr Thr Val Asn Leu Asn Asp Gly Gln Thr Phe Pro Arg
        195                 200                 205

Glu Asn Lys Ile Lys Gln Ser Ser Pro Leu Ala His Gln Ser Asn Ser
    210                 215                 220

Ala Ala Ala Thr Ser Lys Leu His Ile Gln Trp Asn Gln Thr Arg Asn
225                 230                 235                 240

Glu Thr Ile Thr Gly Phe Gly Ser Gly Asn Met Phe Val Ser Asp Pro
                245                 250                 255

Tyr Asn Tyr Met Asn Ser Asn Glu Val Gly Leu Gln Gly Arg Ser Pro
            260                 265                 270

Phe Gly Ser Arg Asn Met Val Phe Arg Met His Pro Cys Phe Ser Tyr
        275                 280                 285

Pro Ser Ala
    290


<210> SEQ ID NO 93
<211> LENGTH: 295
<212> TYPE: PRT
<213> ORGANISM: Cucumis sativus

<400> SEQUENCE: 93

Met Glu Thr Leu Tyr Pro Ser Ser His Leu Ser Ser Ser Ala Trp Phe
1               5                   10                  15

Val Leu Asp Asn Pro Ser Thr Lys Trp Thr Lys Glu Glu Asn Lys Met
            20                  25                  30

Phe Glu Ser Ala Leu Ala Ile Tyr Asp Lys Glu Thr Pro Asp Arg Trp
        35                  40                  45

Phe Lys Val Ala Ala Leu Ile Pro Gly Lys Thr Val Ser Asp Val Ile
    50                  55                  60

Lys Gln Tyr Lys Glu Leu Glu Glu Asp Val Cys Glu Ile Glu Ala Gly
65                  70                  75                  80

Arg Phe Pro Val Pro Gly Tyr Asp Leu Ala Ser Ser Phe Ser Phe Glu
                85                  90                  95

Phe Val Asp Asp Arg Asn Phe Asp Val Tyr Arg Arg Lys Ser Ser Val
            100                 105                 110

Gly Arg Gly Ser Glu His Glu Arg Lys Lys Gly Val Pro Trp Thr Glu
        115                 120                 125

Glu Glu His Lys Gln Phe Leu Arg Gly Leu Leu Lys Tyr Gly Lys Gly
    130                 135                 140

Asp Trp Arg Asn Ile Ser Arg Asn Phe Val Asn Ser Lys Thr Pro Thr
145                 150                 155                 160

Gln Val Ala Ser His Ala Gln Lys Tyr Phe Met Arg Gln Leu Ser Gly
                165                 170                 175

Gly Lys Asp Lys Arg Arg Pro Ser Ile His Asp Ile Thr Thr Val Asn
            180                 185                 190

Leu Thr Glu Pro Thr Ala Ser Glu Asn Glu Lys Leu Ser Ser Met Asp
        195                 200                 205

Gln Phe Ser Lys Leu Pro Ser Leu Gln Lys Ser Pro Cys Tyr Gln Lys
    210                 215                 220

Leu Leu Phe Asp Trp Asn Arg Ser Ser Asn Gly Gly Leu Leu Gly Leu
225                 230                 235                 240
```

-continued

```
Gly Ser Asn Tyr Gly Asp Arg Leu Met Ser Phe Pro Ser Gly Ile Ala
                245                 250                 255

Ala Asn Gly Ile Lys Asn Glu Gln Asp Gln Glu Leu Asn Ser Ala Tyr
            260                 265                 270

Tyr Gly Thr Tyr Ser Lys Pro His Lys Ser Ile Phe Gln Phe Glu Pro
        275                 280                 285

Ser Arg Tyr Gln Ile Tyr Gly
    290                 295


<210> SEQ ID NO 94
<211> LENGTH: 698
<212> TYPE: PRT
<213> ORGANISM: Solanum demissum

<400> SEQUENCE: 94

Met Ser Leu Asn Arg Thr Cys Asn Ser Ser Phe Trp Thr Lys Glu Glu
1               5                   10                  15

Asp Lys Ala Phe Glu Asn Ala Leu Ala Val Phe Ser Gly Asp Asn Asp
            20                  25                  30

Lys Phe Leu Lys Ile Ala Ala Ala Val Pro Gly Lys Ser Leu Gln Glu
        35                  40                  45

Ile Ile Asp His Tyr Asn Val Leu Val Glu Asp Ile Asn Asp Ile Glu
    50                  55                  60

Ser Gly Lys Val Pro Leu Pro Lys Tyr Glu Arg Met Gln Ser Ser Ser
65                  70                  75                  80

Ser Cys Arg Arg Arg Ser Leu Gly Ala Gly Val Glu Arg Arg Lys Gly
                85                  90                  95

Leu Pro Trp Thr Ala Glu Glu His Arg Ser Phe Leu Gln Gly Leu Ala
            100                 105                 110

Lys His Gly Lys Gly Asp Trp Arg Gly Ile Ser Arg Asn Phe Val Phe
        115                 120                 125

Ser Arg Thr Pro Thr Gln Val Ala Ser His Ala Gln Lys Tyr Tyr Ser
    130                 135                 140

Arg Leu Asn Asp Asn Asn Ala Lys Arg Arg Lys Ser Ile His Asp Val
145                 150                 155                 160

Thr Ser Val Gly Ala Ala Asn Ile Thr Glu Pro Ser Gln Gly Gln Lys
                165                 170                 175

Ser Asp Glu Leu Thr Gly Pro Cys Gly Gly Gln Ser Gln Trp Pro Ile
            180                 185                 190

Ala Asp Tyr Val Thr Glu Ala Phe Asp Thr Gly Met Leu Ser Leu Pro
        195                 200                 205

Gly Ser Val Thr Asn Cys Thr Thr Asp Ala Ile Glu Gly Pro Ser Ala
    210                 215                 220

Val Asn Pro Glu Lys Phe Pro Leu Val Ala Ala Leu Gly Ser Glu Leu
225                 230                 235                 240

Asn Ser Ser Phe Pro Gly Val Asp Glu Phe Leu Gln Ser Val Glu Asp
                245                 250                 255

Leu Ile Ile Val Pro Ala Glu Gly Thr Ser Gly Val Cys His Gly Val
            260                 265                 270

Asp Thr Arg Thr Ser Pro Ser Leu Ser Val Gln Pro Ser Val Thr Gly
        275                 280                 285

Gly Thr Gly Met Tyr Thr His Pro Val Ser Phe Pro Asp Val His Glu
    290                 295                 300

Phe Leu Gln Glu Val Glu Asp Leu Ile Thr Val Pro Ala Glu Gly Thr
305                 310                 315                 320
```

-continued

```
Ser Gly Ala Cys His Gly Ile Asp Thr Arg Thr Ser Pro Ser Leu Ser
                325                 330                 335

Leu Gln Ser Ser Val Ala Gly Gly Thr Arg Met Tyr Thr His Ser Val
            340                 345                 350

Thr Val Pro Ala Glu Gly Thr Ser Gly Val Arg Cys Gly Ile Asp Thr
        355                 360                 365

Arg Thr Ser Pro Ser Leu Ser Leu Gln Pro Ser Val Ala Gly Gly Thr
    370                 375                 380

Arg Met Tyr Pro His Pro Val Asn Val Leu Ala Glu Gly Thr Ser Gly
385                 390                 395                 400

Ala Ser His Gly Val Asp Thr Arg Thr Ser Pro Ser Leu Ser Leu Gln
                405                 410                 415

Pro Ser Val Ala Gly Gly Ser Arg Ile Tyr Pro His Pro Val Asn Val
            420                 425                 430

Pro Ala Glu Gly Ile Ser Gly Val Ser His Gly Val Asp Thr Arg Thr
        435                 440                 445

Ser Pro Ser Leu Ser Leu Gln Pro Ser Val Gly Gly Gly Thr Gly Met
    450                 455                 460

Tyr Thr His Pro Val Thr Val Arg Val Glu Gly Thr Ser Gly Ala Arg
465                 470                 475                 480

Arg Gly Val Asp Thr Arg Thr Ser Pro Ser Leu Ser Leu Gln Pro Ser
                485                 490                 495

Val Val Gly Gly Ile Gly Met Tyr Thr His Pro Ile Ile Val Pro Ala
            500                 505                 510

Glu Gly Thr Ser Gly Thr Arg Arg Gly Val Asp Thr Arg Thr Ser Pro
        515                 520                 525

Ser Leu Ser Phe Gln Pro Ser Val Gly Gly Gly Thr Gly Met Tyr Thr
    530                 535                 540

His Pro Val Thr Val Leu Ala Glu Gly Thr Ser Gly Val Arg Cys Gly
545                 550                 555                 560

Val Gly Thr Arg Thr Ser Pro Ser Leu Gly Leu Gln Pro Ser Val Ala
                565                 570                 575

Gly Gly Thr Arg Met Tyr Thr His Ala Val Asn Asn Val Gly Tyr Asp
            580                 585                 590

Leu Glu Glu Leu Met Thr Lys Gln Leu Val Gly Ala Ser Gln Glu Gly
        595                 600                 605

Pro Ser Ile Asn Thr Ala Ser Leu Pro Ser Pro Ile Ala Asp His Ile
    610                 615                 620

Gly Leu His Gly Cys Thr Thr Ser Ser Ser Val Ala Lys Asn Gly Phe
625                 630                 635                 640

Val Ser Thr Met Glu Ala Pro Gly Gly Gly Phe Ser Val Asp Ser Met
                645                 650                 655

Gln Thr Pro Ser Ile Pro Gly His Ile Gly Gly Gly Thr Tyr Pro Cys
            660                 665                 670

Trp Glu Pro Ser Ser Lys Asp Asp Ser Ile Phe Asp Leu Glu Tyr Leu
        675                 680                 685

Tyr Thr Asp His Met Phe Gly Phe Arg Lys
    690                 695
```

<210> SEQ ID NO 95
<211> LENGTH: 2047
<212> TYPE: DNA
<213> ORGANISM: Oryza sativa -continued

<400> SEQUENCE: 95

```
gagctacggt tttttttct ctttctttct cagcttcttc tccaactcct ctctcttctt     60
cttcctctag tcctctcctg cctgcttcgt ctactcctct cccaactccg atcccctcct    120
ctccgcgctc ccggtggccg gacccgtccg gcgacgacga tgagccgctc gccggcacgg    180
cgccctgctc agatctgaag agctgcgaga atccgaggct tctcttgctg gtttagctcc    240
ggcggcggcg gcggcggcgg cgatggagga ggaggtggag gcggcgaaca gggcggcggt    300
ggagagttgc cacagggtgc tggccttgct gtcgcagcag caggaccctg cgttgctcag    360
gagcatagct tcagagacag gagaggcctg tgccaagttc aggaaggtgg tctccctcct    420
cggcaatggc ggcggcggcg gcggcggcgg cggcggtggt ggacatgcta gaggcaggat    480
ggccgggaga agcaggcctt cggcggtgct gagagagaag ggattcttgg agagcagcag    540
cggcggcggc cagctgggga tggtgatgtc cggtgctgcc actccgtcta ctagctccgc    600
cgcgcatttg cgcaaccgga ttggcggagg cagcggcgtg ccaccggatt cgttgcgggg    660
gctcgatttg gtcagctcga gcagcaaggg tggtgctcat cagttcgatc ctccgaagct    720
ggtgcagccg ttgtcggttc agttccagtt cggcgctacc gcgcataggt acccgttcca    780
gcagcatcag catcagcaga agttgcaggc tgagatgttc aagaggagca acagcgggat    840
cagccttaag tttgatagcc ctagtgccac cgggacgatg tcgtcggcgt tcatgtcgtc    900
gcttagcatg gacggcagcg tggctagctt ggaagggaag ccgccgttcc atttgatcag    960
cggcccggtc gcgagcgacc cggtgaacgc tcaccatgtg cccaaacggc ggtgcacggg   1020
gagaggggag gatggaagtg gcaagtgtgc cacaaccgga aggtgccatt gctcaaagag   1080
gaggaagttg cgaattaaga ggtcaattaa agtgcccgcc attagcaaca aaatagcaga   1140
catacctcca gatgaatact catggcgaaa gtatggtcag aagccgatta agggttcgcc   1200
tcatccaagg ggttactaca aatgtagcag cgtccggggc tgcccagcga ggaagcacgt   1260
cgagcggtgc gtagacgacc cggcgatgct catcgtgacg tatgaaggtg agcataacca   1320
tactcggctg ccaacacagt cagcccagac ctaggaaacc tgtagtattt cacgcgagcc   1380
attcagaaaa tgcagaggct ccaagctttt gctcggggac ggtcggaccg gtcatgtgaa   1440
agtaggtcag caaactgtga aagtaggagt aacaaacagg gaagccatct gatgagagct   1500
atagtgattc gcttgggtcc ttaactgagc tacaagccat gtcgcatttc tgctatggtc   1560
tcaatgttct actgtccaaa gtggggacat acacaacttg ttctctcttt tatgagctat   1620
ggcactatca gattaagaga gaatggagga agaacatgtg attggatagt gaccggcaag   1680
atttgctcaa agaagggagg gattaggttt gaagatttca aaggaagatt gacaaaagga   1740
agtgaacaac tgaaacatcg tgtaagcctg gaaaaggata agcaggattt ggcttttagc   1800
gtgcacaagt ttacttgcaa tgacttgcct ctgtatgttg cttttgcttt attgaaagat   1860
caaaatttc ttttggcaga agaatcattc agcattaaag ctgtttctac ttgctaacat    1920
actgacacac ttggaccatc agggtttttt tttccaggtg ttagctgttg ggtatgattt   1980
ctcagtcgta cttctgcttt tgtgtaaagc attccatgtt atgttaatga ctttgacatc   2040
aactgcc                                                             2047
```

<210> SEQ ID NO 96
<211> LENGTH: 643
<212> TYPE: DNA
<213> ORGANISM: Aegilops speltoides -continued

<400> SEQUENCE: 96
gggaacccac catcccagag ccaagctcgt gagcagaagg cagacccccg ggttcttgag 60
ccagaagagc ttcctggaca gcaacacccc ggtggtggtg ctgaacagcg cgcacccttc 120
gaccagctcc gcgcaggtgt atcccagaaa cagcattctg gagtcacagc ccgcgcaccc 180
aatcggaggg ccgcccaagc tggtgcagcc gttgtccgcg catttccagt tcggcgattc 240
gtcgcggtac aatcagttcc agcagcatca gcaccagcag cagaagatgc gggccgagat 300
gttcaagaga agcaacagcg ggatcaacct gaagtttgac agccccagtg gcaccgggac 360
gatgtcgtcg gcgaggtcct tcatgtcgtc tctgagcatg gatggcagcg tggccagcct 420
cgatgccaag tcttcctcgt tccatttgat cggcgggcct gccatgagcg acccggtgaa 480
tgcgcagcag gctccaagga ggcgatgctc agggcgtggg gaggatggaa atggcaagtg 540
tgctgcaact ggcaggtgcc attgctcaaa gagaagcagg aagttgcggg tgaagaggac 600
gattaaagtt cccgcaatta gtaataaaat tgctgatata cct 643

<210> SEQ ID NO 97
<211> LENGTH: 869
<212> TYPE: DNA
<213> ORGANISM: Triticum aestivum

<400> SEQUENCE: 97
gaccttaggc ctatttaggt gacactatag aacaagtttg tacaaaaaag caggctggta 60
ccggtccgga attcccggga tatcgtcgac ccacgcgtcc gcgagatgtt caagagaagc 120
aacagtggga tcaacttgaa gtttgacagc cccagtggca cggggacgat gtcgtccgcg 180
aggtccttca tgtcgtcttt gagcatggat ggcagcgtgg ccagcctgga tgccaagtct 240
tcctccttcc atttgatcgg tgggcctgcc atgagcgacc cggtgaatgc gcagcaggcg 300
ccaaggaggc gatgctcagg gcgtggggag gatggaaatg gcaagtgtgc tgcaactggc 360
aggtgccatt gttctaagag aagcaggaag ttgcggttga agaggacgat taaagttccc 420
gcaattagta ataaaattgc tgatatacct ccagatgaat actcctggag gaagtatggg 480
cagaagccaa ttaagggctc ccctcatccc agggggtact acaaatgcag cagtgtgagg 540
ggctgccctg cgcggaagca tgttgaacgt tgcgtggatg atccgtcgat gctcattgtg 600
acatacgagg gcgaacataa ccatacgcga atgccaactc agtctgcgca agcttaggga 660 atccccccaat tatcactctt ttcaggaaag gcaactcgcc ggcacttgtt ggacagactg 720
cgttgttctc ctaaatagga ttgcgaaggg acaattatgg aattcatttg agcacatgaa 780
tggtcgattg gcccccctga cctacatgtt ttgtgaacga ggggccaagg gggaaggatt 840
gcaaaaatgg tgtttctccc ccttaaggg 869

<210> SEQ ID NO 98
<211> LENGTH: 947
<212> TYPE: DNA
<213> ORGANISM: Saccharum officinarum
<220> FEATURE:
<221> NAME/KEY: misc_feature
<222> LOCATION: (759)..(760)
<223> OTHER INFORMATION: n is a, c, g, or t

<400> SEQUENCE: 98
ctccctactc agcaatggag gagtgggggt aggagaagcc ggaccatcag acgcaagcgg 60
aagcgcaagc catccgagag ctaagcttgt tagcagaaga cagaatccag ggttcttaac 120
tcagaaaggc ttcctggata ctaacacctc ggtcgtggtg ttgaacagcg cccatccttc 180

-continued

```
tcctacctcc gcgcaggtgt atcctagaac tgctgtagct ctggatgcgc agggcgtgca    240

tcccctcgga ggacctccta agctggtcca gccgttgtct gcacatttcc agtttggcaa    300

tgtgccgtca ccgtatcagt tcccaaatca gcagcagcag cagcagaagt tgcaggctga    360

gatgttcaag agaagcaaca gcgggattaa cttgaagttt gagagcacca gtggcactgg    420

gacaatgtca tcggcgaggt ccttcttgtc gtctctgagc atggatggta gcgtggctag    480

cctggatggc aagtcatcgt cgttccactt gatcggtggg cctgcaatga gcaaatccgt    540

gaacgctcaa gcaggcccca agaggcgatg cacgggtcgt ggggaggatg ggactggcaa    600

gtgcactgtg acagggggt gccattgttc aaagagaagt aggaaagttc gggtgaagag    660

gtcgaataag gttcctgcca ttagtaataa gattgctgat ataccttccg gatgaaaact    720

tctggaggaa gtatgggcag aaacccaatt aagggtttnn gtaaggcgag ggggaacccc    780

cccccgccat attttggggg ggttgcccac cttggaaagc ttgtctaaac ggggggtgga    840

ttgaataatt gatgcttatt tggggccatt gaggggggagg gcaaacccca cccaaaatgc   900

caaagtgagt ttgcccccag ttttaaaaaa acccaccctc tttttag                 947
```

<210> SEQ ID NO 99
<211> LENGTH: 1753
<212> TYPE: DNA
<213> ORGANISM: Dactylis glomerata

<400> SEQUENCE: 99

```
ctgctcctcc tgctcgtcgc tccttctctt cctctgtacc agccgagagt gcctctcgtc     60

ctctccccctg cccgaggagc agaggtggcg acgccggcaa cggccgcgag atagggggga   120

gggagtcggc gatggagggc gtggaggagt ccaacaggga ggcggtgcag agctgccaca    180

gggtgctcag cctgctctcc aacccgcacg gccagctcgt cccccacaag gagctcgtgg    240

aggccaccgg agaggccgtc tccaagttcg gctccgtggc caccaagatc gccaccaatg    300

gcaatggccg acagggccat gccagggtta ggaagaagat caatcaaccc atgcctatgt    360

tcgacagcag cctcttcttg gagaccactg cgtcggctgc tgatgctgcg gcagctaaaa    420

catcccagcc ggggccggac actattctcc ggctgtttcc gaggtaccag caggtggagg    480

gctcctcttc aaaggatccc gtcaggatcc ctgcccagtt cccccgaagg ctgcttctag    540

agaacccttc ggtcggttcg aacgggccgg ctcgcggacc tccggtccag ctcgtccagc    600

cggtgtctgt ggcgcccccg gcggggacgc cagcgccggc attgccagcg gcacatcttc    660

atttcatcca gcagcagcag agctaccaga ggttccagct catgcaccag atgaagctgc    720

agagtgagat gatgaagagg ggtggccttg gtgagcaggg tggcagcaat ggtggtgtca    780

atctcaagtt tgctagctct aactgtacgg gatcatcctc ccgttcattc ctgtcatctc    840

tgagcatgga agggagcatg gcgagtttgg atgtcagtcg ctctagccgg cccttccagc    900

tcgttagtgg ttcgcagacg tcaagcactc cagagttagg ccttatgcag aggaagaggt    960

gcgctggtaa ggaggatggg agtggacgat gtgccaccgg gggcaggtgt cactgtgcca   1020

agaaaagaaa gctaaggata aggaggtcta ttaaagtccc tgcaatcagt aataaggtcg   1080

ccgacatccc tgctgatgaa ttctcctggc gcaagtatgg gcagaagcca ataaagggat   1140

cccctcatcc gaggggttac tacaagtgta gcagcgtgag ggctgccca gcgaggaagc   1200

atgtcgagag gtgcgtcgac gaccccgcga tgttgatcgt tacctacgag ggcgatcaca   1260

accacaaccg agctgcagcc cagccagcct gacctttcag gcttccagtc ccagaatgct   1320

ttcaataacc tctgtttcta gaaaaaagaa gagatgaaaa aaagaagaag agcctagttt   1380
```

-continued

```
gtacatattc ttctgaccct aactgctggg gggaggaggg agaatcagct ctttcaggag   1440

aatccatggc gaaagagttt tatcgcgtag atcggtcgat gtagtgtttc tctcatcaaa   1500

ctaataattt tgtagctttg ttttgtaccc tttctttctg tttatgtcgg tccttaggac   1560

tgtcctgtgt cgtgcagtgt aacattgagc tgcagttata tgtcgggggt tggtgttact   1620

gtaactctgg aagtggggat agggagctgg tagcaggcag tgcttgttgc aacacctagg   1680

aacaaaatgt accctcatct tcggtcaatt ggattggtgc aatcttgtcg atggtaaaaa   1740

aaaaaaaaaa aaa                                                      1753
```

<210> SEQ ID NO 100
<211> LENGTH: 780
<212> TYPE: DNA
<213> ORGANISM: Amborella trichopoda
<220> FEATURE:
<221> NAME/KEY: misc_feature
<222> LOCATION: (749)..(749)
<223> OTHER INFORMATION: n is a, c, g, or t

<400> SEQUENCE: 100

```
agtggatccc cgcggctgat aatcggcacg aggggaaagc cccttcgaaa ccttccacgt     60

gccagcaatc tctactggag acacccaaat cgaacaaccc atctctgatt ccaaaaccca    120

acttcaaatt cagggaccga acacccattt acagattatt cagcaacagc agattcagca    180

catgatgcag tttcagcaac aaatgaagtt gcaggcccaa gctgatctca tgtacaggag    240

aagcaacagt gggagcatga atttgaagtt tgataattcg agctgtacgc cgacgatttc    300

atcgaggtca ttcatttcat cactgagcat ggatggaagt gtagctagta tggatgggaa    360

gccgttccat ttgattcctg cttcttccca ggatagaagt ggtcatagcc agaagaggag    420

gtgctctggt aaaggtgaag atgggagtgg gaaatgtggc accagtggga gatgtcattg    480

ttcaaagaga aggaaaatta gggtgaagag atccattaag gttcctgcaa ttagtaacaa    540

gcttgctgat atccctcctg atgagtattc atggaggaag tatggacaaa aaccaattaa    600

aggttctcct catccaaggg gatattacaa atgtagcagc atgaggggtt gccctgctag    660

gaaacatgtc gagaggtgct tagaagaccc ttcaatgcta atagtcactt atgaagggga    720

gcacaaccat tcgcgtatat tatcccaanc caatcaatct tagtgtatca acttggctag    780
```

<210> SEQ ID NO 101
<211> LENGTH: 1319
<212> TYPE: DNA
<213> ORGANISM: Arabidopsis thaliana

<400> SEQUENCE: 101

```
ctccactctc ccttctctca ccaatctcga agctttgctt tatactgaga gaagaatatt     60

tgtttcttct tcttacagtg agagaacaat tttctgcttt taacccttgt tcttgagcta    120

ttattttgat ttttatggtt tccatgtttg agctagctca tgatgattat tcttttcttt    180

tgaaatagtt ttttttagcg tttgagtttt gaggtttttc gttttttaag agtatccttt    240

gtgaagaaga aaatggaaga agttgaagct gcaaacaaag cagcagtaga aagttgtcat    300

ggagtattga atctcttatc acaacaaacc aatgattcca aatcaataat ggttgaaaca    360

agagaagctg tttgcaagtt caagagagtc tcctctcttt tgtctagagg gttaggtcaa    420

aggaagataa agaaactcaa caacaacaac tacaagttta gctcttcttt gttgccacaa    480

cacatgtttt tggagagtcc tgtttgcagt aataatgcta taagtggttg tattccaatt    540

ctagcaccaa agcctcttca gattgtacca gctggtcctc ctccattgat gttgtttaac    600
```

-continued

```
cagaatatgt gtcttgataa gtcgtttctc gagctgaagc caccctcttc acgagctgtt    660

gatccaaaac cttatcagtt tattcatacc catcagcaag gagtgtactc aaggagcaaa    720

agtggtttga atctaaagtt tgatgggtct attggtgcta gttgttattc accaagtata    780

tcaaatgggt caagatcgtt tgtttcatct cttagtatgg atggtagtgt gacggattac    840

gatagaaact cttttcattt gattggatta cctcaaggtt ccgatcatat atcgcaacat    900

tctaggagga ctagttgctc tggtagttta aaatgtggaa gtaaaagcaa atgccattgt    960

tccaagaaaa ggaaattaag ggtgaaacga tcgattaaag taccggcaat cagtaacaag   1020

attgcggaca tacctcccga tgaatattca tggaggaaat acggacaaaa gccgattaag   1080

ggttctcctc atcctagggg atactataaa tgtagcagtg tgcgcggttg tccagcgagg   1140

aagcatgttg agcgatgtgt agaagaaact tcgatgctta ttgtgactta tgaaggcgag   1200

cataaccatt caagaatact ctcttctcaa tcagctcata cttgattgat tgtagtaacg   1260

gtcttcaatt gtatattcta ctttgcaaac tcgaattttt gtgcataaca atttggctt    1319
```

```
<210> SEQ ID NO 102
<211> LENGTH: 793
<212> TYPE: DNA
<213> ORGANISM: Glycine max

<400> SEQUENCE: 102

aacggctggt tagccaaact atccaaaaga caaaatctgc gccaacaata tccatcatcc     60

ctgcttgttt gcatcactta aaatatgtac agcagcatct caagccaatc acagagaggt    120

tttgacaaat tgaatgatgg gcttgatctg gttaagctct ccacatagtt catgcatttg    180

cagattgtgt tggtaacttg gggtggttat gttcgccttc ataggtaaca attagcatgg    240

taggctcttc caagcacctc tcaacatgct tccttgcagg acaccctctc atgctgctgc    300

acttataata tcccctaggg tgaggagagc ccttgattgg cttctgccca tacttcctcc    360

acgaataatc atcaggaggg atatctgcaa gtttgttgct gatagcgggc accttaattg    420

ccctcttcac tctatgtttc ctcttcttag agcaatggca tctagcactg ctcccacatt    480

tcaagcttcc ctcatcacct ctggcagaac actttctctt gtgctgctgg gaattctgat    540

cagaagagtg tggagctccg attaaatgga aggcacttcc atccaagtta gccacacttc    600

catctatgct caaggaagag ataaaagacc tagtggatga cattgttggt gtgcagctag    660

tactgtcaaa attcaggttt atgccactgt tgttccttcg gaacatcatt tctgcttgat    720

gcttcatttg ttgttgttgt tgttgctgct gctgcagcaa cagcctttgc tgttgctgtt    780

gttgctgctg ctg                                                       793
```

```
<210> SEQ ID NO 103
<211> LENGTH: 794
<212> TYPE: DNA
<213> ORGANISM: Gossypium raimondii

<400> SEQUENCE: 103

ctctctctat ttgggaaccc catgtttgga actgcgctcg aatggtaaaa acctctcttc     60

cactcgccca acagccacct cctcctgccc actatcattt cctccaccaa cgagggctac    120

agctccaaca gcatcaagct gaaatgttgt ctaggaagag taattgtggg attaacttca    180

actttgatag ctctagctgc acacctacca tgtcatcaac taggtctttc atttcttctc    240

tgagtataga tggtagtgta gctaacatgg atagtgggaa tgccttccat ttaatcggcg    300

cacctcgatc ctcggatcag ggttcccaac acaaaaagaa gtgttctggt aagggagaag    360
```

-continued

```
atgggagtgt caaatgtgga agtagtggga aatgccactg ctcaaaaaag aggaaacaga    420

gagtaaagag atcaatcaag gttcctgcta tcagtaccaa gcttgctgat attcctcctg    480

atgattattc atggaggaaa tatgggcaga agccaatcaa gggttctcct caccccaggg    540

gatattataa atgtagcagt atgagaggtt gccctgcgag gaaacatgtg gagaggtgct    600

tggaagagcc gtcgatgctt attgttacgt atgaaggtga gcacaaccac ccaaagttac    660

cgtcacaagc aacgacataa tctcagtgga aacattgcta aagaattctt caagtctttc    720

aatgttcaat ctggtcatgt acatattttg catggttcaa gcatgggata aataggagca    780

gtttctttct tctt                                                      794
```

<210> SEQ ID NO 104
<211> LENGTH: 602
<212> TYPE: DNA
<213> ORGANISM: Populus tremula x Populus tremuloides

<400> SEQUENCE: 104

```
gagttctagc tgcacaccta caatgtcatc caccagatct tttatatctt ccttgagtat     60

agatggtagt gtggctaatt tggaaggaag tgcattccat ttaatggggc cggctcgctc    120

ctcggatcag agctcacagc aacacaagag gaaatgttcc gggagaggag aagatggaag    180

tgtgaaatgt ggaagcagtg gtagatgtca ttgctcaaag aagaggaaac atagggtgaa    240

gaggtcgatc aaggtacctg ctattagcaa caagcttgct gatatccccc ctgatgatta    300

ttcctggaga aagtatggac agaagcccat caagggctct cctcatccca ggggatatta    360

caagtgtagc agtatgagag gttgtcctgc aaggaagcat gtggagaggt gcttggaaga    420

tccgtccatg cttattgtta cctatgaagg tgaacataac cacccgagga ttccagcaca    480

atctgcaaac acataaaagc ctcatgcaat actttcaagg ttctcactgt ttaatgaaaa    540

cttgtcgtga ttggctcctg tacatactta gcatggttca atcctgggat atagtcggag    600

ca                                                                   602
```

<210> SEQ ID NO 105
<211> LENGTH: 568
<212> TYPE: DNA
<213> ORGANISM: Malus x domestica
<220> FEATURE:
<221> NAME/KEY: misc_feature
<222> LOCATION: (440)..(440)
<223> OTHER INFORMATION: n is a, c, g, or t

<400> SEQUENCE: 105

```
tcgtaggagc aatagtggca taaatctgaa ttttgatagc tctagctgca cacctacaat     60

gtcatctaca agatccttca tttcttcctt gagcatagat ggaagtgtgg ctaacttcga    120

tggtaattcc tttcatttga tcggggctcc tctctcttcg gatcagaatt cacaacataa    180

gaggaagtgt tctgctaggg gagacgatgg gagtgtaaaa tgcggtggta gcagtggtag    240

atgtcactgc tcaaagaaga ggaagcatag ggttaaaagg tcaattaagg tgcctgctat    300

cagtaacaag cttgcagata tccctcctga tgattattca tggcggaaat atggccagaa    360

gccaatcaag ggttcccctc accctagggg atactataaa tgcagtagca tgagaggttg    420

tccagcaagg aagcatgtcn agaggtgctt ggaagaacca tccatgctta tggttaccta    480

cgaaggtgag cataaccacc caaggatacc atcgcaatcc acaacaacat gaaattcatg    540

gagagcctcg gtgagctcaa gcccaaca                                       568
```

-continued

<210> SEQ ID NO 106
<211> LENGTH: 780
<212> TYPE: DNA
<213> ORGANISM: Solanum tuberosum

<400> SEQUENCE: 106
ctgtgaaaac cgaatgcaaa atcgatgatc atgcgaaagc tcttaggtta cttcctatcg 60
actctcctga aaaccgagtc ctagagatgg gtgctaatgt gaaatgtaat ctaactttag 120
gaagcccttc tctggaatta agttcaaata gtagaaatcc ccttaatttt ggccaacaaa 180
cgcctttccc gagctataac tatcttcaac agcaacaaca gcaacaacag cagcagcaac 240
aacaacggcg gtttctactt cagcagcagc agcaattgaa acacccccgcg gagatgatgt 300 acaggcggag caatagtggt gttagtctta attttgatag ctcgacatgt actccgacca 360
tgtcttcgac taggtcattt atatcctcat tgagtgtgga cggtagtgtt gctaatggta 420
atagctttca tttaattggg gcttcacact ctgcggatca gagctcgttc caacacaaga 480
gaaaatgctc cggaagggga gacgagggaa gcgggaaatg tggaagcagt ggaagatgtc 540
actgttcaaa gaagaggaaa cacagagtaa agagatcaat caaaatacct gcggtaagta 600
acaagctagc tgatattcct tccgatgagt attcttggag aaagtatgga caaaagccga 660
tcaaaggttc tccacatcct aggggatact ataaatgtag cagcatgaga ggttgccctg 720
cccggaaaca tgtcgagaga tgcttggaag atgcttcaat gcttatcgtg acatacgaag 780

<210> SEQ ID NO 107
<211> LENGTH: 782
<212> TYPE: DNA
<213> ORGANISM: Medicago truncatula

<400> SEQUENCE: 107
tttccaagac aatttccatt aatttagaga accctgaaat gtttaatgac atacttaaga 60
aaaataaaat tgttcttacg aattgaaact atccaatttt acatactcct gcacttaacc 120
agtgatcttc atcactccct ctaaataaac gactccccaa ccaagctacc caaaaggcaa 180
aatctgcagt cctgctcgca tcacttgaaa tatgtacaga aacatctcaa gccaatcaca 240
tagaggtctt cacaaattga atgtgactct ccatgtagtt catgcatttg caggttgtgt 300
tggtaccttg gcgtgattat gctcgccttc ataggtaacc attagcatag taggctcatc 360
caagcacctc tcaacatgct tcctagcagg gcagcctctc atgctgctgc atttataata 420
gcccctaggg tgaggagagc ccttgatagg cttctgcccg tacttcctcc acgagtaatc 480
atcaggaggg atatccgcaa gcttgttgct gatagcaggc accttaattg atctcttcac 540
tctatgcttc cttttctttg agcaatgaca tttagaactg ctactacatt tcaagcttcc 600
ctcatcacct ctagcagaac atttcctctt gtgctgtgaa ttctgatctg aagagatcgg 660
agctcctatc aaatggaagg gacttccatc cacgtttgct acgcttccgt ctatgctcaa 720
ggaggaaaat gaagacctag tagacgacat ttgtggtgtg ctgctagtag ccttgtcaaa 780
tt 782

<210> SEQ ID NO 108
<211> LENGTH: 747
<212> TYPE: DNA
<213> ORGANISM: Ipomoea nil
<220> FEATURE:
<221> NAME/KEY: misc_feature
<222> LOCATION: (744)..(744)
<223> OTHER INFORMATION: n is a, c, g, or t -continued

<400> SEQUENCE: 108

```
agttctataa aaccaaagtc atattttcat catcatgaga acaaacattc ttacaaccaa     60

aaacccaaat ttttaacact gagctctcta accctaaacc atagaattca cattttacct    120

ttcaaacatc tcgaagaaag gcgtaggcct atccctttga accatatatc ttcggctccc    180

tccctcccta cctcaaagcc taaactagca aaatatgtac aagacaattg aagccgttaa    240

gaaacaaaga ccataaacct cttgtcatat cttgcccgag actccccccc actagcgcat    300

ttatgtgttt gccgactgcg atggcaccct aggatggtta tggtctccct cataagtgac    360

aattaacatt gacgggtctt ccaagcatct ctccacgtgc ttcctcgcag ggcagcctct    420

catgctacta catttatagt atccccttgg gtgaggagaa cccttgattg gcttctgccc    480

gtactttctc caagaatatt cgtcttgagg gatatcagct agcttgttac tgatagcggg    540

aactttaatt gaccttttca cccgatgttt cctcttcttg gagcagtggc atctactgct    600

gcttccacat ttcgtgcttc catcctctcc ccgtccagaa caccttttct tgtgctgata    660

cgagctcaga tcagcggaac gagaggcacc gattaaatgg aaggcattcc cgtccatatt    720

tgcaacgctc ccatcaatac tcanaga                                        747
```

<210> SEQ ID NO 109
<211> LENGTH: 546
<212> TYPE: DNA
<213> ORGANISM: Hordeum vulgare

<400> SEQUENCE: 109

```
ccagaaacgg aggctatcga aagcggtctg cgacgacgat gaaagccgaa aggtcaggct     60

ggttgggctg ctgcagctcg gttgtggttg tgatcgcctt cataggtaac gatcaacatc    120

gcggggtcgt cgacgcacct ctcgacatgc ttcctcgctg ggcagcccct cacgctgcta    180

cacttgtagt aacccctagg atgaggggat ccctttattg gcttctggcc atacttccgc    240

cacgagaatt catcagccgg gatgtcggcc accttattgc tgattgcagg gactttgata    300

gacctcctta tccttagctt ccttttcttt gcacagtgac acctgctccc agttgcacag    360

cgtccactcc catcctcctt gccggcacac ctcctcctct gctgcatgag gcccaattcc    420

ggggtgctcg acgtctgcga gccactaact agttggaagg gacggctgga gcggctgcca    480

tccatgctcg ccatgctccc ctccaagctc agagatgtca ggaatgaacg ggaggatgcc    540

tcgtgc                                                               546
```

<210> SEQ ID NO 110
<211> LENGTH: 482
<212> TYPE: DNA
<213> ORGANISM: Crocus sativus

<400> SEQUENCE: 110

```
gatcggtcga ctgcagaagc ttcaggccga gatgttcaag aggagcaaca gcggcataaa     60

tctcaagttt gacaactcca gctgtactcc cgccatgtca tcgaccaggt ccttcttgtc    120

ttcccttagc acggaaggga gtgtggccag tctgcagggg aagccgttcc agctcattgg    180

gggctcgctg tcgtcagaac cggtgaatct ccacccccacg ccgaagcgta gatgcctttg    240

caccgggagg ggagaggatg ggaaatgtgc ggctagtgga agatgccatt gctccaagag    300

gaggaagctt cgggttaaga ggtccattaa ggtgcctgct atcagtaaca agcttgctga    360

tatccctccg gatgagttct cgtggaggaa gtacggtcag aaaccgatca agggttcgcc    420
```

-continued acatccaagg ggatactaca aatgcagcag tatcacgtca tacctgcttt tcaatcacta 480
gt 482

<210> SEQ ID NO 111
<211> LENGTH: 563
<212> TYPE: DNA
<213> ORGANISM: Zea mays

<400> SEQUENCE: 111
gcgacagcca gctgccccca caaatggatt agaaagtctt gtgtacaccc acactccatt 60
ctcgctacag atcttgtggg cgcaagcagg accagacatc tcgacgacct ggtgaccaac 120
agaggccatg ttggtggtgc cacttcgtcc tcaaggaggg ggaggcgggg gtgcagtgat 180
gaactgatga tgagttctct acgactacac ggctacacct gtgctgctgc tgctgctgac 240
tgagctggca ttccggtgtg gttgtgctcg ccctcgtatg tcacgatgag catcgccgaa 300
tcatccacac accgttccac gtgcttccta gctggacagc cctcacact gctgcatttg 360 tagtagcccc taggatgagg ggaacccttg atcggcttct gcccatactt cctccacgag 420
tactcatccg gaggtatatc agcgatcttg ttactaacgg caggaacctt aatcgacctc 480
ttcacccgca acttcttact tctctttgaa caatggcacc tgcccgccaa agcgcacttg 540
ccattgttta aaaaaaaaaa aaa 563

<210> SEQ ID NO 112
<211> LENGTH: 636
<212> TYPE: DNA
<213> ORGANISM: Sorghum bicolor

<400> SEQUENCE: 112
gcacgaggct agttagtggc tctcagacat ctagcacacc ggagatgggc ctggtgcata 60
ggaaaaggtg cgctggtagg gaggatgggg gtggtcggtg cactaccggg agccggtgcc 120
attgttcaaa gaaaaggaag cttaggataa ggaggtccat caaggtccct gcaataagca 180
acaaggttgc agacatccca gctgatgagt tctcgtggag gaagtatggg cagaagccaa 240
ttaagggatc cccacatcct aggggttatt acaagtgtag cagcgtgaga gggtgccccg 300
cgaggaagca tgtcgagagg tgcgtggacg acccctcgat gctgattgtt acctatgaag 360
gtgaccacaa ccacaaccga gttctagccc aaccagcctg atctttcagg ctatcaattc 420
aagatcgctt ctatagtcac cctccttccc ctagaggaag ggaggacaac aacaacaaga 480
agaagagcct agtgtctgta catattttct gcttctaaca gttgggggga gagagagtca 540
gttagctagc tctttcagaa gaatcaaatc aatggtgaca gaaggaaact tatcgcgtcg 600
atggagaaag ggagagtgcc tcatcaaatc aaatac 636

<210> SEQ ID NO 113
<211> LENGTH: 1929
<212> TYPE: DNA
<213> ORGANISM: Physcomitrella patens

<400> SEQUENCE: 113
caggatcgtt tccaaggctg agacacagct tgaggtttta taagcggcat atcttcatga 60
gcggcgcagc agcaacagcg gaagcacatg aaatgagatc tctgggataa ccatgcggcc 120
gcaactagag taacgacgcg gcgcggtgag cagatgtgcc tcttacgaac tgctacagaa 180
gcttcatgaa tcacacagca attggccttt aaatcgtatg gcttaacttt tgatagcaac 240
ccttctacaa gagtggagtg cttaatgaaa gtacgccaat aaacgtagtt cctgcgacgt 300

-continued

```
cttcccagcg aacatggggg cgttggagat attagattac aacaacactt taggaaagag    360

agacagggac tatgaagtga aggaagcggc atgcatggga atacaaaacg ctaggcagct    420

gctccagtcc ctgacgcagg tgcgatctcc agtggtggac gaagaatgcg atgtcatggc    480

tggcgctgcc atatccaagt ttcagaaggt ggtgtcacta ctgagtcgca ctggtcatgc    540

acggtttcgt aggagaacgc gcaacgctgc tgttgccggt tacgcaggcg tcttcttaga    600

gagctccaac ttcttcagag aaaattccca ggagacgtcg agggacagaa tcgtctcgtc    660

gggccatgct agcccatctc agttcacgcc gacgtcctcg tccaagcctc ctcagtcacc    720

tgaattgcag gcgatcaaat ataaggtgtt tcctcaaagc tctcgttccg ctgatgcgac    780

gcctgcctcc agtgaccctg cttcaggagt ccatcatcca aagccacttc agatccttca    840

cagctccatg atgcagcaaa gcattccaga acatatactg cgtccagtgg ctagtgctgc    900

gtatcggcca actgcccttc ccccgaatcc gttcaacaaa caggaggtgg gcagcaagga    960

gggggtgagc ggccacagtc cggacagttc gttgagctca ggacctccgc aatcaactac   1020

aacggcgtcg ttcccaacca tgagtgtgca ggatgcgagg ataacgagcc tgcagaatat   1080

gaaaacagcc gagcaacctt cggcgttgcc ccctcgcccg cagccaccaa ctcccaagaa   1140

aaagtgctcc gggcaatccg atgagaacgg tgcaacttgc gcaatccttg gccgctgcca   1200

ttgttcaaaa cgcaggaaat tgcggttgaa gaggacaatc acggttcgag caatcagcag   1260

caagttggct gatatacctt cggatgagta ttcatggcgt aagtatggcc agaagcctat   1320

caaaggatca ccacatccga gaggatacta caagtgcagc agcatacgag gctgtccagc   1380

gagaaaacac gtagagcggt caatggaaga ctcatctatg ttgattgtga catacgaagg   1440

cgatcataac catccgcaat cgtcatctgc taatggcgga ttaacagtgc agtcgcaata   1500

gacaacacgc acgtacattg ccttcgcatt atcgcctagt aatgaggaaa gcacaaactc   1560

ctctcaatgg cttacgcgtg aggatgtctg caagcatttc aagtttttgc ccagtttgtg   1620

ctccatgttt ttttgttagg acattaccta tggcacaatg cccccgtccg acgaagcccg   1680

tgacttatgt tctgtagcaa tgttctcatg cgtgattggc tagagaagtg tgctcgacga   1740

gtcaggaaca ttaacctcct aggtgtgccc ccaaagttgg aagcgttctg cttatcaggg   1800

atcaagaggt acgcacagac gaagatatct acaggtgatg ccttttaatt cttcggtgct   1860

caatggctcc acctctggag cggagagaga gaagaatgaa tatgaatgca agtatccttc   1920

gcgatgcgc                                                           1929
```

```
<210> SEQ ID NO 114
<211> LENGTH: 656
<212> TYPE: DNA
<213> ORGANISM: Vitis sp

<400> SEQUENCE: 114

gacttcgtct ttcttgtcgt cgattaccgg agacggcagc gtgtcgaacg gaaaattagg     60

gacttctctg tttgcacctc ctccggctcc ggcggtttcc gccggtaaac cgccactttc    120

gtcgtctcaa cggaggaaat gtcatgagca tggatcctcc gacaacatct ccggaaaact    180

ctctgtttcc ggccgctgcc attgctcgaa aagaaggaaa aatcgtgtga agaggacgat    240

cagagttcct gcgataagct cgaagatcgc cgatattccc gccgacgagt actcttggag    300

aaagtacggt cagaagccga tcaagggctc accataccca cgaggctact acaaatgtag    360

cagcgtgaga ggctgcccag cgagaaaaca cgtggagcgc gcaccagacg atccggcgat    420

gctcatcgtc acgtacgagg gagagcaccg ccactctcaa actccggcac cggccggtgg    480
```

-continued

```
cctcatgttc ccatcaacct gacgctcctc ccctgccccc aatcaggatc ggctgtcagg    540

gagcaagttg tcacagccag gtggccatag attccccggg gcacaaaagt caaagaagcg    600

tcaaacttac tgttccggag aatagggaaa aaaaaaaaaa aaaaaaaaaa aaaaaa        656


<210> SEQ ID NO 115
<211> LENGTH: 720
<212> TYPE: DNA
<213> ORGANISM: Picea engelmannii x Picea sitchensis

<400> SEQUENCE: 115

gagaaaatgt tccggtaaag gtgatgacag cagtaaatgt ggaagtactg gaaggtgcca     60

ctgctcaaaa cggaggaagc taagagtcaa gcgtactatt agagtgcctg ctattagtag    120

caaattagca gacattccac cagatgaatt ttcctggagg aaatatggtc aaaaaccaat    180

caagggctct ccacatccca ggggttatta caagtgcagc agtatgagag gctgccctgc    240

caggaaacac gtggagcgct ccttggaaga tgcttccatg ttgattgtga catatgaagg    300

cgaacataac cattcacgtt tgctatcatc aaattcaagt ctgatagttc acccatagat    360

tcccatgcag tattttgcta ttttggctgc ataggttact cctgcaacaa taacgtgaag    420

gtgacaaatc tctaatgtgg attttaaacc cattgtgggc agtataaagc gccatccttg    480

aggaaaaatt aacactgcaa tccttcgaag gaacttgtcc atgggttacg aagtgatttt    540

cacaattttg atccacacat ttagtgttca tatttgattt attaggacaa aggtgtagtc    600

aaggcgtaca ggatagcaaa tgatttgtca gatacagtat aatgtatgga tgagctctgt    660

accttaaatg caaggccttc gctgccacaa gactttctgt ccaaaaaaaa aaaaaaaaaa    720


<210> SEQ ID NO 116
<211> LENGTH: 1038
<212> TYPE: DNA
<213> ORGANISM: Nicotiana tabacum

<400> SEQUENCE: 116

atctccaaaa aatggcagtt gattttattg ggttttcgaa aatgaatgag caattagctc     60

ttcaagaagc tgcttcagcc ggtttaaaat ctatggaaca tttgatccgg ttggtttctc    120

atcaacaaca gcagcagccg gttcagctcg attgccgtga gataactgac ttcactcttt    180

cgaaatttaa gaaggttgtt tctattttgg accggaccgg tcatgctcgg ttccgccgtg    240

gtccggttca ggttcatcct gataatttta cttctctgtc tctttctccg tcaaatcagc    300

agctgttaaa cttagctccg gcgaaagaga cacctccacc accgtcagtg tcgctgccgt    360

taacggcgtt gacgcttgac tttacgaagc caaacgttga ccgtccgacg ggaaattcta    420

atgctattgt tgctgtgaag tcaaaggaga ctttctgtat atctacgccg atggcgactt    480

cggcgaactc gtcatcgttc atgtcgtcga ttaccggcga aggaagtgta tcaaacggaa    540

aacaaggttc gtcagtattt ttgcctccgg caccgtctgt ttccgctggt aaacctccaa    600

tctctggtaa aagatgccgc gagcacgagc cctccgaaga tatctccggc aaatccaacg    660

gctccggcaa gtgtcactgc aaaaagagga aatctcgtgt aaagaaagtt gtaagaatcc    720

cagcgataag ttcgagaatc gccgatatac caggagacga gtattcgtgg agaaagtacg    780

ggcagaagcc gatcaagggt tcaccatacc cacggggata ttataagtgt agcagcgtaa    840

gaggatgtcc agcgaggaaa cacgtggaaa gggcaatgga tgatcctgct atgctgattg    900

tgacttatga aggggaacat cgacatacga taggcgcaat gcaggagaac aatactcaaa    960
```

-continued

```
tgatggtgtt tgggtcaacg gaagagagga gggagtgaaa tgaaagctag atttagagtt   1020

ttaggggtat ttttgtag                                                 1038
```

<210> SEQ ID NO 117
<211> LENGTH: 588
<212> TYPE: DNA
<213> ORGANISM: Liriodendron tulipifera

<400> SEQUENCE: 117

```
cataggaatt tcatggaaaa cccaattcaa ggaattgatt ctagtggtgg caatactctc     60

cagcttgcga aaaatatgtt tttagaaaac ccaactcagg aattggattc ttctgctgct    120

gccgccgctg tggctgctgc tgctaaaaat cacctccaat ccacccactt gcaattcctc    180

caacagcagc agcagcggtt tcagtttcag cagcagcaga tgaaattcca agctgatatg    240

ttcaggagga gcaacaatgg gataaacctc aagtatgata attctagctg cacgccgacc    300

atgtcatcca cgagatcttt tgtgtcttcg ctgagcatgg atggtagtgt ggctagcttg    360

gacggtaagg cctttcattt gattggcggg ccacagacgt cgtccgatcg gaacccaaat    420

cagcctccga agaggaggtg ctctggtaga ggggaagatg ggagtgggaa atgtgggacc    480

agtgggagat gccactgttc aaagaggagg aaattgcgga tgaaacgatc gatcaaggtg    540

cctgccatta gtaacaagct tgcagatatt cctcctgatg agtattca                588
```

<210> SEQ ID NO 118
<211> LENGTH: 969
<212> TYPE: DNA
<213> ORGANISM: Nicotiana benthamiana

<400> SEQUENCE: 118

```
aatggcagtt gaattttgtt gggttttcaa aaatgaatga gcaattagct cttcaagaag     60

ctgcttcagc cggtttaaaa tctatggaac atttaatccg gttggtttct caccaacaac    120

agcagcagcc ggttcagctc gattgccgcg agataactga ctttaccgtc tcgaaattta    180

ggaaggttat ttctattctg gaccggaccg gtcatgctcg gttccgccgt ggtcaggttc    240

aggttcatcc tgataatttt acttctctgt ccctttctcc gtcaaatcag cagctgttaa    300

acttagctcc ggcgaaagag acaccgccgc ctcggccacc atcagtgtcg ccgccattaa    360

cggcgttgac gcttgacttt acgaagccaa acgttgaccg tccggcggga aattctaatg    420

ctattgttgc tgtgaagtca aaggagactt tctgtatatc tacgccgatg gcgacttcga    480

cgaactcgtc gtcgttcatt tcgtcgatta ccggcgaagg aagtgtatca aacggaaaac    540

aaggttcgtc aatgttttg cctccggcac aagctgtttc cgccgggaaa ccaccagtag    600

ccggtaaaag atgccgcgag cacgaatact ctgaagatat ctctggcaaa tccaccggct    660

ccggcagatg tcactgcaaa aagaggaaat ctcgtgtaaa gaaagttgta agaatcccag    720

cgataagttc gagaattgcc gatataccgg gagatgagtt ctcgtggaga aaatacgggc    780

agaagccgat caagggttca ccatacccac ggggatatta taagtgtagc agcgtaagag    840

gatgtccagc gaagaaacac gtggaaaggg caattgatga tcctgctatg ctgattgtga    900

cttatgaagg ggaacatcgt catacgatag gcgcaataca ggagaacaat tctcaaatga    960

tggcgtttg                                                            969
```

<210> SEQ ID NO 119
<211> LENGTH: 1291
<212> TYPE: DNA
<213> ORGANISM: Petroselinum crispum -continued

<400> SEQUENCE: 119
aatcccccca ctttctctcc ctcccccaac ctatacttac aatttcttgt aagcatttct 60
gggtctatct ccaatggccc ttgatttgat gaacaacaat agttacaaat tccggtccaa 120
aatggaagaa accgcggttc aagaagcggc cgccgccggt ttacaaagcg tggagaattt 180
gatcaaagct atatcccagt ctaatcatca aactgcatat ttatcttctt catcttcatc 240
tgaaaccggt gatacagatt atagagctgt tacagatgtg gctgtcaaca agttcaagaa 300
gttcatttct ttgttggata agaaccgaac cggacatgcc cggttcagaa gaggaccggt 360
tcaggaaaaa accggagttg aaatgttggt taatccgatt cagaatcaga ttcagaatca 420
tgggtctgat gggtttcaag tttataggcc tactgccgtt catccagttc agccggttca 480
accggttcag attcaaccgg ttcagttggt tcagccggtt caacgtttac caccggttcc 540
caaaaaggaa aatattagta ctacaataaa ttttgctgct ccagctgtag ctgttgctgc 600
accagcgacg tcgtttatgt cgtcgttgac cggagataca gatgggtcgg gttttcagat 660
tacgaatatg tccggttttt cgtcgggtag ccgaccggtt tcgtcgttga agaggaagtg 720
tagctcgatg aatgatgttt cagccaagtg ttctggctct tctagtggtc gatgccattg 780
tcctaagaaa aagaagttga gagtgaagaa agtggtgaga atgccagcta taagtatgaa 840
gacatctgat ataccaccag atgatttttc ttggagaaaa tatggtcaaa agcctatcaa 900
aggctctcca caccccagag ggtattacaa gtgcagtagt gtaagagggt gtccggcaag 960
aaagcatgta gagagggcag tggatgatcc gacaatgctg atagtaactt acgaagggga 1020
gcataaccat tcccagtctt cgaatgaaaa cacaaacact tctcatatcc ttgaatctga 1080
tggcctcaaa caatcataac aagagactat atagactgat catgtttcag aatgttggat 1140
gcttgggttt cagttgtgtg ttgattgaat gattatgcaa ctgctttatt tggtgttgta 1200
gttcaaaact tggagaatgc catttaattt aagccctgag ttgttccttt ggtttacttc 1260
attttggtaa ttataagatt ccatttcttg c 1291

<210> SEQ ID NO 120
<211> LENGTH: 842
<212> TYPE: DNA
<213> ORGANISM: Asparagus officinalis

<400> SEQUENCE: 120
gggttcaaga agatgatctc gatcttgaac cgaaccggcc acgcccggtt caggcggggg 60
ccaactcatc agcctcagga cccgccgccg gcgattcatt cgccgactcc gatccaggct 120
gtaatgccac cggcacctca tagcttgact cttgacttca cgaagccgaa gacagcgggc 180
gagatcgcga cgatgaacag ccaatactcg aaggatacga gcaatttcag catctcgtcc 240
gcgaactcct cgtttttgtc gtcgatcacc ggagatggta gcgtttcgaa tggaaagaac 300
gggtcgtcga tgctactccc tcctctgcct cctgccgccg ccgtctccgc cgggaaaccg 360
ccgctgtcga cctcattcaa gaagaggtgt cacagccacg gcactgagat ggccgggagc 420
ttctcggcct ctggtggtcg ctgccactgc tcgaagaaaa gaaaatctcg tgtgaagaga 480
actatacgag taccggcgaa aagttctaag gtggctgata ttccctccga cgagttctcg 540
tggaggaagt acggtcagaa gccgatcaaa ggatcccctt atcctcgggg ttattacaag 600
tgcagcagta tgaggggatg cccggctcga aagcacgtgg agagagctcc cgatgatccc 660
tcaatgctca tcgtcaccta cgaaggcgag caccgccaca ctcacagtcc gatccccgat 720
gcactaatct taaagcaatc agagtgatct aggccgtcga tctttgttct ctttctctct 780

-continued

```
ctctctcccc ttttttttt ggctttcccc cctctgttcg gactgcagag gtttagactt    840

tg                                                                  842


<210> SEQ ID NO 121
<211> LENGTH: 796
<212> TYPE: DNA
<213> ORGANISM: Poncirus trifoliata

<400> SEQUENCE: 121

gtgtgtcgtc gaactcgtcc ttcatgtcct ctgctatcac cggagacggc agcgtttcga     60

acgggaagca aggaggatct tcgatcttct tggcgccaca agctcctgct gtttccgccg    120

gaaagccgcc gctcgcggct cagccttaca agaagaggtg tcaagatcag cacgatcatt    180

ccgatggtct ttccggcaag ttctccggct ccacctctgg cagcaacaag tgtcactgct    240

ctaagagaag gaaaaaccga gtaaagaaaa ctataagggt gccggcgatt agttcaaaaa    300

tagccgatat tccaccggac gagtattctt ggaggaagta tggtcaaaag ccgatcaagg    360

gctcaccata cccacgcggc tattacaagt gcagtacaat gcgagggtgc ccagccagga    420

aacacgtgga gagggcacca gacgatccaa cgatgctgat tgtgacgtac gaaggagagc    480

accgtcattc gcaggccgcg atgcaggaga acgtggtccc tgctggagtg ggtttggttt    540

tcgagtcaac gtgagaaaat gaacaaaaaa gaaaaagtag agagagagag agagagaatt    600

gataaaggaa agtgggtggg aactgggaag ataatgacaa gacgcggtag catttttctaa    660

atatcgatgt tgttgcgggc gccgatggat ggtctgatgg agggttttaa tgtaaatttt    720

gttggagtaa aattaaaaaa aaaattaatt aattaaattg tcattcggta gttatatgat    780

aaaaaaaaaa aaaaaa                                                    796


<210> SEQ ID NO 122
<211> LENGTH: 468
<212> TYPE: DNA
<213> ORGANISM: Lotus corniculatus var. japonicus

<400> SEQUENCE: 122

aaaatctaat gatcatcatt catcaacatc aattaccttt gaaattgctt gtcacattga     60

ttaacatgaa cttaagatga ttctaaaatg agattagtag catctgctgc agagagagcg    120

tgattgtgct ctccttcata ggtcactacc agcatagcag catcatccag ggctcgttct    180

acatgttttc ttgctgggca acctctcaca ctactgcact tgtaatatcc ccttggatga    240

ggggatcctt taataggttt ctgaccatat tttctccagg aataatcatc tggtggaata    300

tcagccatct tcaagcttat tgctggtacc ctcacaaccc ttttcaacct cattttcctg    360

ctttttgggg aacaatgaca gcgtccagat gaactgccac actttccaga acccaaggtt    420

tcagagctgc acttcctctt taaggaggat gatgacagag gaggcttc                 468


<210> SEQ ID NO 123
<211> LENGTH: 1206
<212> TYPE: DNA
<213> ORGANISM: Avena sativa

<400> SEQUENCE: 123

agcagagcac cggtacttgg gacgcagagg cggtcgcgat gatgaccatg gatctgatgg     60

gaaggtacgg gagggcggac gagcaggtgg ccatccagga ggcggccgcg gcggggctgc    120

gcggcatgga gcacctcatc ctgcagctct cccggacagg cacaggcaca ggcacgagcg    180

agagctcgct ggctggggcc tcggagccgg ccgcgcaggg acagcagcag cagcagcagg    240
```

-continued

```
tggactgccg ggagatcacc gatatgaccg tgtccaagtt caagaaggtg atttctatcc    300

tcaaccaccg caccggccac gccaggttca ggcgcggacc tgtggtggcg cagtctcagg    360

ggccctccgt gtccgagccg gcgccggtga ggacggcgtc ttcgtcgagg cccatgacgc    420

tggacttctc caagtccgca tccgtgttcg ggaataagga cgccgcgtac agcgtgtcag    480

ccgcgagctc gtcgttcctg tcgtcggtga caggcgacgg gagcgtgtcg aacggacgcg    540

gtggcgggtc ctcgctgatg ctcccgccgc caccttcggc cagctgcggg aagccaccgc    600

tggcggccgc cgccgccggc ccgaagcgga agtgccacga gcacgcgcac tccgagaacg    660

tcgccggcgc ctccggtggc cgctgccact gctccaagcg caggaagtcc cgggtgaagc    720

ggatgacccg cgtgccggcg atcagctcga aggcggcgga gatccccgcg gacgacttct    780

cgtggcgcaa gtacgggcag aagcccatca agggctcccc atacccacga ggctactaca    840

aatgcagcac ggtgcgcggg tgcccagcgc ggaagcacgt ggagcgcgac cccagcgacc    900

cctcgatgct catcgtgacc tacgagggcg accaccgcca cacccccggc gaccaggaag    960

cagcagcagc gctcaccccg ctcccggagc tgcacaagct ctgaagtttc tacccactgc   1020

tactacaccg acctgttaat taattaaact tagcctgtca tggtgttccc tttgtcgccg   1080

tatagtagta gctagtagag tttcttcttt tttgtttggt cgcaccagtg tattagcagc   1140

atgtaaaaga atcaacttag ggaagctttg agcagctttg gttggagaaa aaaaaaaaaa   1200

aaaaaa                                                              1206
```

<210> SEQ ID NO 124
<211> LENGTH: 1411
<212> TYPE: DNA
<213> ORGANISM: Capsella rubella

<400> SEQUENCE: 124

```
atggccgtcg atctaatgcg tttccccaag atagatgatc aaacggctat tcaagaagct     60

gcatcgcaag gtttacagag tatggagcat ctgatccgcg tcctctctaa ccgtcccgaa    120

caacaacaca ccgttgactg ctccgagatc actgatttca ccgtttccaa attcaaaacc    180

gtcatttctc ttcttaaccg taccggtcac gcccggttta gacgcggacc tgttcgctca    240

tcccccgtcg tatctcctcc actcccacag atcgttaaaa ctgctccgat tgtttcgcag    300

ccgttaagaa caacgactaa tctttctcaa accgctcctc ctccgtcgag cttcgtcctt    360

ccgaggcagc ccaggcggtc acactcggat ttctctaaac cgaccatctt cggttccaaa    420

tccaaaagct ccgacctaga gttctcgaag gagaacttca gcgtctcttt aaactcttcc    480

tacatgtcgt cggcgattac cggagacggc agcgtctcaa acgggaaaat cttcctcgcc    540

tctgctccgt cgcagccagt tacctcctca ggaaagccac cgttggccgg tcatccttac    600

agaaagagat gcctcgagca cgagcactcc gagagtttct ccggcagagt ctccggctca    660

ggtcacggga aatgccattg caaaaaaagg tattgttacg ttacgttacg tcgcccgcct    720

gtcgctttta acaaacttac tcaagtgact tccgttattt ttaatttcga tatattccaa    780

ccccttggtt ggctattatt accctcctcg atacatcatt gattaaatta ctacttaatt    840

attcaattag gtaaaccgtt aacattattc ccggtttagt caatagttat ataggtttag    900

ctcgccgaca actactttta aaaacctggg ttttgaccat tgacttttta aatccgaacc    960

agctcattaa ttgattgtta atttttatat gaatgaagca ggaaaaacaa gatgaagaga   1020

acagtgaggg taccggcgat aagtgcaaag atcgccgata ttccaccgga cgagtactcg   1080

tggaggaagt acggacaaaa gccgatcaaa ggctcaccac acccacggta actatcgtct   1140
```

-continued

```
atttatccac cgttgataaa taaattaatt cccattgcaa tctataaaga tctaacggtg   1200

gttatttgtt tatgatcgat gcagtggtta ctacaagtgc agtacgtata gaggatgtcc   1260

agcaaggaaa cacgtggaac gagcgttaga tgatccaacg atgcttatcg ttacgtacga   1320

aggagagcac cgtcacaacc aatccgcggg gggaatgcac gagactattt cttcttcagg   1380

cgttaatgat ttagtgtttg cctcggcttg a                                  1411
```

<210> SEQ ID NO 125
<211> LENGTH: 1141
<212> TYPE: DNA
<213> ORGANISM: Oryza sativa subsp.indica

<400> SEQUENCE: 125

```
atgattacca tggatctgat gagtgggtac gggcgggtgg acgagcaggt ggccatccag     60

gaggcggcgg cggcggggct gagggggatg gagcatctta ttctgcagct gtcccagact    120

gggacgagcg agaggtcgcc ggcgccggcg ccggcgcagg agcagcagca gcagcagcag    180

gtggactgca gggagatcac ggacatgacg gtgtccaagt tcaagaaggt gatctccatg    240

ctgaaccgca ccggccacgc gcggttccgg cggggcccgg tggtggcgca gtcgtctggc    300

ccggcggcgt ccgagccggc gccggtgagg tcgtccccgt cggcggtgtc gaggcccatg    360

acgctcgact tcaccaaggc ggcgtccgga tacggcaagg acgccgggtt cagcgtctcc    420

ggcatctccg ccgcgagctc gtccttcctc tcgtcggtca ccggcgacgg cagcgtgtcc    480

aacgggcgcg gcggcgggtc atcctccctg atgcttcccc caccgccggc gaccagctgc    540

ggcaagccac cgctgtcctc cgccgccgcc gccatgtcag ccggcgtcgg ccacaagcgc    600

aagtgccacg accacgcgca ctccgagaac atcgccggcg gcaagtacgg ctccaccggc    660

ggccgctgcc actgctccaa gcgccggtaa aaatcttcac gactccctcc atttccccca    720

cctcgaattg aactcatcgg aattaatttt ccaggaagca tcgggtgaag aggacgatcc    780

gcgtgccggc gataagctcg aaggtggcgg acatccccgc cgacgacttc tcgtggcgga    840

agtacgggca gaagcccatc aagggctccc ccttcccacg gtgagcaccg cactgccccg    900

ccgtctctcc tcactccgtc gacattaaca cttaaaacta atagtcgcct catttttttag    960

aggatactac aagtgcagca cgctgcgcgg gtgcccggcg aggaagcacg tggagcgcga   1020

ccccgccgac ccgtccatgc tcatcgtcac ctacgagggc gagcaccgcc acacccccctc   1080

cgccgccggc caggaccacc cgccggcgcc gcctccgccg ctggcgctgc cgctcgcctg   1140

a                                                                   1141
```

<210> SEQ ID NO 126
<211> LENGTH: 1245
<212> TYPE: DNA
<213> ORGANISM: Lycopersicon esculentum

<400> SEQUENCE: 126

```
atcatgagta gaaccaaatg gctgttttat caaaaatgaa tgaaagtttt gctgttgaag     60

aagcagcttc cgccggtttg aaatcaatgg agaatttaat ccgattggtt tctcatgaac    120

cggttcaggc tgattgccgt gaaatggctg attttacggt ttcgaagttc aaaaaggtga    180

tttcaatttt ggaccggacc ggtcatgctc ggttccggcg aggaccggtt caggctcagg    240

ctccggctcc ggttcaggtt agagctccgg ttcgtggtcc ggtttatcct gattcgttta    300

cttcgttgtc tcttgctccg tcgttaagct ttgctacggc gaaggagaga cttgctccgt    360

cgttaagctt tgcttcggcg aaggagagac cggtggtgca ggtgcagacg gcgttgacgc    420
```

-continued

```
ttgacttttc gaagctgaat gttaaccgtc cgatcgggaa ttcaagtgct tttactgctt    480

ttactgtgaa atctaaggag gttttaatgg cggatccgac gccgacgaac tcgtcgtcgt    540

ttatgtcgac gattaccggc gaagcaactg tatctaatgg taagcaagtt tcttcttcta    600

tgttgttgct tccgccacag gctgtgaatt ttccgaccac cggaaaacgt tgccgcgagc    660

atgaacaatc tgatgctatc tccggcagca aatccaccgg ctccggcaag tgtcactgca    720

aaaagaggaa agctaaggat cggaaagtga ttaggattcc ggcgataagt acgagggtgg    780

ctgatatacc gggagacgag ttttcatgga ggaaatacgg gcaaaagccg atcaagggtt    840

caaaataccc aaggggttat tacaagtgta gcagcttacg tggatgtcca gcaaggaaac    900

acgtggagcg cgcgatggac gatccaacga tgctgattgt gacttatgaa gatgaacatt    960

gtcataatcc agttgctgcg atgcatggga acagttctca aatggtgaat tttgggttaa   1020

tggaaaagaa gtagggggtg aaatgaagat agaggagagt tgtagggtga ttttgtagtt   1080

tggaatagtt ggggggttga agttatattt gggaaaagtt ataagggtta aaagagtaga   1140

gagtaggaag ttgtgggaat tggtttgtta tgtaaatttg gaaagatttt aggggttgaa   1200

agagaaaaaa aaagaaaagt ttcgcaaaaa aaaaaaaaaa aaaaa                   1245
```

<210> SEQ ID NO 127
<211> LENGTH: 396
<212> TYPE: PRT
<213> ORGANISM: Genus species

<400> SEQUENCE: 127

```
Ala Ala Arg Arg His Gly Ala Leu Leu Arg Ser Glu Glu Leu Arg Glu
1               5                   10                  15

Ser Glu Ala Ser Leu Ala Gly Leu Ala Pro Ala Ala Ala Ala Ala Ala
            20                  25                  30

Ala Met Glu Glu Glu Val Glu Ala Ala Asn Arg Ala Ala Val Glu Ser
        35                  40                  45

Cys His Arg Val Leu Ala Leu Leu Ser Gln Gln Gln Asp Pro Ala Leu
    50                  55                  60

Leu Arg Ser Ile Ala Ser Glu Thr Gly Glu Ala Cys Ala Lys Phe Arg
65                  70                  75                  80

Lys Val Val Ser Leu Leu Gly Asn Gly Gly Gly Gly Gly Gly Gly Gly
                85                  90                  95

Gly Gly Gly Gly His Ala Arg Gly Arg Met Ala Gly Arg Ser Arg Pro
            100                 105                 110

Ser Ala Val Leu Arg Glu Lys Gly Phe Leu Glu Ser Ser Ser Gly Gly
        115                 120                 125

Gly Gln Leu Gly Met Val Met Ser Gly Ala Ala Thr Pro Ser Thr Ser
    130                 135                 140

Ser Ala Ala His Leu Arg Asn Arg Ile Gly Gly Gly Ser Gly Val Pro
145                 150                 155                 160

Pro Asp Ser Leu Arg Gly Leu Asp Leu Val Ser Ser Ser Ser Lys Gly
                165                 170                 175

Gly Ala His Gln Phe Asp Pro Pro Lys Leu Val Gln Pro Leu Ser Val
            180                 185                 190

Gln Phe Gln Phe Gly Ala Thr Ala His Arg Tyr Pro Phe Gln Gln His
        195                 200                 205

Gln His Gln Gln Lys Leu Gln Ala Glu Met Phe Lys Arg Ser Asn Ser
    210                 215                 220
```

-continued

```
Gly Ile Ser Leu Lys Phe Asp Ser Pro Ser Ala Thr Gly Thr Met Ser
225                 230                 235                 240

Ser Ala Phe Met Ser Ser Leu Ser Met Asp Gly Ser Val Ala Ser Leu
                245                 250                 255

Glu Gly Lys Pro Pro Phe His Leu Ile Ser Gly Pro Val Ala Ser Asp
            260                 265                 270

Pro Val Asn Ala His His Val Pro Lys Arg Arg Cys Thr Gly Arg Gly
        275                 280                 285

Glu Asp Gly Ser Gly Lys Cys Ala Thr Thr Gly Arg Cys His Cys Ser
    290                 295                 300

Lys Arg Arg Lys Leu Arg Ile Lys Arg Ser Ile Lys Val Pro Ala Ile
305                 310                 315                 320

Ser Asn Lys Ile Ala Asp Ile Pro Pro Asp Glu Tyr Ser Trp Arg Lys
                325                 330                 335

Tyr Gly Gln Lys Pro Ile Lys Gly Ser Pro His Pro Arg Gly Tyr Tyr
            340                 345                 350

Lys Cys Ser Ser Val Arg Gly Cys Pro Ala Arg Lys His Val Glu Arg
        355                 360                 365

Cys Val Asp Asp Pro Ala Met Leu Ile Val Thr Tyr Glu Gly Glu His
    370                 375                 380

Asn His Thr Arg Leu Pro Thr Gln Ser Ala Gln Thr
385                 390                 395
```

<210> SEQ ID NO 128
<211> LENGTH: 214
<212> TYPE: PRT
<213> ORGANISM: Aegilops speltoides

<400> SEQUENCE: 128

```
Gly Thr His His Pro Arg Ala Lys Leu Val Ser Arg Arg Gln Thr Pro
1               5                   10                  15

Gly Phe Leu Ser Gln Lys Ser Phe Leu Asp Ser Asn Thr Pro Val Val
            20                  25                  30

Val Leu Asn Ser Ala His Pro Ser Thr Ser Ser Ala Gln Val Tyr Pro
        35                  40                  45

Arg Asn Ser Ile Leu Glu Ser Gln Pro Ala His Pro Ile Gly Gly Pro
    50                  55                  60

Pro Lys Leu Val Gln Pro Leu Ser Ala His Phe Gln Phe Gly Asp Ser
65                  70                  75                  80

Ser Arg Tyr Asn Gln Phe Gln Gln His Gln His Gln Gln Gln Lys Met
                85                  90                  95

Arg Ala Glu Met Phe Lys Arg Ser Asn Ser Gly Ile Asn Leu Lys Phe
            100                 105                 110

Asp Ser Pro Ser Gly Thr Gly Thr Met Ser Ser Ala Arg Ser Phe Met
        115                 120                 125

Ser Ser Leu Ser Met Asp Gly Ser Val Ala Ser Leu Asp Ala Lys Ser
    130                 135                 140

Ser Ser Phe His Leu Ile Gly Gly Pro Ala Met Ser Asp Pro Val Asn
145                 150                 155                 160

Ala Gln Gln Ala Pro Arg Arg Arg Cys Ser Gly Arg Gly Glu Asp Gly
                165                 170                 175

Asn Gly Lys Cys Ala Ala Thr Gly Arg Cys His Cys Ser Lys Arg Ser
            180                 185                 190
```

-continued

```
Arg Lys Leu Arg Val Lys Arg Thr Ile Lys Val Pro Ala Ile Ser Asn
        195                 200                 205

Lys Ile Ala Asp Ile Pro
    210


<210> SEQ ID NO 129
<211> LENGTH: 208
<212> TYPE: PRT
<213> ORGANISM: Triticum aestivum

<400> SEQUENCE: 129

Asn Lys Phe Val Gln Lys Ser Arg Leu Val Pro Val Arg Asn Ser Arg
1               5                   10                  15

Asp Ile Val Asp Pro Arg Val Arg Glu Met Phe Lys Arg Ser Asn Ser
            20                  25                  30

Gly Ile Asn Leu Lys Phe Asp Ser Pro Ser Gly Thr Gly Thr Met Ser
        35                  40                  45

Ser Ala Arg Ser Phe Met Ser Ser Leu Ser Met Asp Gly Ser Val Ala
    50                  55                  60

Ser Leu Asp Ala Lys Ser Ser Ser Phe His Leu Ile Gly Gly Pro Ala
65                  70                  75                  80

Met Ser Asp Pro Val Asn Ala Gln Gln Ala Pro Arg Arg Arg Cys Ser
                85                  90                  95

Gly Arg Gly Glu Asp Gly Asn Gly Lys Cys Ala Ala Thr Gly Arg Cys
            100                 105                 110

His Cys Ser Lys Arg Ser Arg Lys Leu Arg Leu Lys Arg Thr Ile Lys
        115                 120                 125

Val Pro Ala Ile Ser Asn Lys Ile Ala Asp Ile Pro Pro Asp Glu Tyr
    130                 135                 140

Ser Trp Arg Lys Tyr Gly Gln Lys Pro Ile Lys Gly Ser Pro His Pro
145                 150                 155                 160

Arg Gly Tyr Tyr Lys Cys Ser Ser Val Arg Gly Cys Pro Ala Arg Lys
                165                 170                 175

His Val Glu Arg Cys Val Asp Asp Pro Ser Met Leu Ile Val Thr Tyr
            180                 185                 190

Glu Gly Glu His Asn His Thr Arg Met Pro Thr Gln Ser Ala Gln Ala
        195                 200                 205


<210> SEQ ID NO 130
<211> LENGTH: 237
<212> TYPE: PRT
<213> ORGANISM: Saccharum officinarum

<400> SEQUENCE: 130

Ser Leu Leu Ser Asn Gly Gly Val Gly Val Gly Glu Ala Gly Pro Ser
1               5                   10                  15

Asp Ala Ser Gly Ser Ala Ser His Pro Arg Ala Lys Leu Val Ser Arg
            20                  25                  30

Arg Gln Asn Pro Gly Phe Leu Thr Gln Lys Gly Phe Leu Asp Thr Asn
        35                  40                  45

Thr Ser Val Val Val Leu Asn Ser Ala His Pro Ser Pro Thr Ser Ala
    50                  55                  60

Gln Val Tyr Pro Arg Thr Ala Val Ala Leu Asp Ala Gln Gly Val His
65                  70                  75                  80

Pro Leu Gly Gly Pro Pro Lys Leu Val Gln Pro Leu Ser Ala His Phe
                85                  90                  95
```

-continued

```
Gln Phe Gly Asn Val Pro Ser Pro Tyr Gln Phe Pro Asn Gln Gln Gln
            100                 105                 110

Gln Gln Gln Lys Leu Gln Ala Glu Met Phe Lys Arg Ser Asn Ser Gly
        115                 120                 125

Ile Asn Leu Lys Phe Glu Ser Thr Ser Gly Thr Gly Thr Met Ser Ser
    130                 135                 140

Ala Arg Ser Phe Leu Ser Ser Leu Ser Met Asp Gly Ser Val Ala Ser
145                 150                 155                 160

Leu Asp Gly Lys Ser Ser Ser Phe His Leu Ile Gly Gly Pro Ala Met
                165                 170                 175

Ser Lys Ser Val Asn Ala Gln Ala Gly Pro Lys Arg Arg Cys Thr Gly
            180                 185                 190

Arg Gly Glu Asp Gly Thr Gly Lys Cys Thr Val Thr Gly Gly Cys His
        195                 200                 205

Cys Ser Lys Arg Ser Arg Lys Val Arg Val Lys Arg Ser Asn Lys Val
    210                 215                 220

Pro Ala Ile Ser Asn Lys Ile Ala Asp Ile Pro Ser Gly
225                 230                 235


<210> SEQ ID NO 131
<211> LENGTH: 386
<212> TYPE: PRT
<213> ORGANISM: Dactylis glomerata

<400> SEQUENCE: 131

Met Glu Gly Val Glu Glu Ser Asn Arg Glu Ala Val Gln Ser Cys His
1               5                   10                  15

Arg Val Leu Ser Leu Leu Ser Asn Pro His Gly Gln Leu Val Pro His
            20                  25                  30

Lys Glu Leu Val Glu Ala Thr Gly Glu Ala Val Ser Lys Phe Gly Ser
        35                  40                  45

Val Ala Thr Lys Ile Ala Thr Asn Gly Asn Gly Arg Gln Gly His Ala
    50                  55                  60

Arg Val Arg Lys Lys Ile Asn Gln Pro Met Pro Met Phe Asp Ser Ser
65                  70                  75                  80

Leu Phe Leu Glu Thr Thr Ala Ser Ala Ala Asp Ala Ala Ala Ala Lys
                85                  90                  95

Thr Ser Gln Pro Gly Pro Asp Thr Ile Leu Arg Leu Phe Pro Arg Tyr
            100                 105                 110

Gln Gln Val Glu Gly Ser Ser Ser Lys Asp Pro Val Arg Ile Pro Ala
        115                 120                 125

Gln Phe Pro Arg Arg Leu Leu Leu Glu Asn Pro Ser Val Gly Ser Asn
    130                 135                 140

Gly Pro Ala Arg Gly Pro Pro Val Gln Leu Val Gln Pro Val Ser Val
145                 150                 155                 160

Ala Pro Pro Ala Gly Thr Pro Ala Pro Ala Leu Pro Ala Ala His Leu
                165                 170                 175

His Phe Ile Gln Gln Gln Gln Ser Tyr Gln Arg Phe Gln Leu Met His
            180                 185                 190

Gln Met Lys Leu Gln Ser Glu Met Met Lys Arg Gly Gly Leu Gly Glu
        195                 200                 205

Gln Gly Gly Ser Asn Gly Gly Val Asn Leu Lys Phe Ala Ser Ser Asn
    210                 215                 220

Cys Thr Gly Ser Ser Ser Arg Ser Phe Leu Ser Ser Leu Ser Met Glu
225                 230                 235                 240
```

-continued

```
Gly Ser Met Ala Ser Leu Asp Val Ser Arg Ser Ser Arg Pro Phe Gln
                245                 250                 255

Leu Val Ser Gly Ser Gln Thr Ser Ser Thr Pro Glu Leu Gly Leu Met
            260                 265                 270

Gln Arg Lys Arg Cys Ala Gly Lys Glu Asp Gly Ser Gly Arg Cys Ala
        275                 280                 285

Thr Gly Gly Arg Cys His Cys Ala Lys Lys Arg Lys Leu Arg Ile Arg
    290                 295                 300

Arg Ser Ile Lys Val Pro Ala Ile Ser Asn Lys Val Ala Asp Ile Pro
305                 310                 315                 320

Ala Asp Glu Phe Ser Trp Arg Lys Tyr Gly Gln Lys Pro Ile Lys Gly
                325                 330                 335

Ser Pro His Pro Arg Gly Tyr Tyr Lys Cys Ser Ser Val Arg Gly Cys
            340                 345                 350

Pro Ala Arg Lys His Val Glu Arg Cys Val Asp Asp Pro Ala Met Leu
        355                 360                 365

Ile Val Thr Tyr Glu Gly Asp His Asn His Asn Arg Ala Ala Ala Gln
    370                 375                 380

Pro Ala
385


<210> SEQ ID NO 132
<211> LENGTH: 246
<212> TYPE: PRT
<213> ORGANISM: Amborella trichopoda
<220> FEATURE:
<221> NAME/KEY: misc_feature
<222> LOCATION: (243)..(243)
<223> OTHER INFORMATION: Xaa can be any naturally occurring amino acid

<400> SEQUENCE: 132

Ser Ala Arg Gly Glu Ser Pro Phe Glu Thr Phe His Val Pro Ala Ile
1               5                   10                  15

Ser Thr Gly Asp Thr Gln Ile Glu Gln Pro Ile Ser Asp Ser Lys Thr
            20                  25                  30

Gln Leu Gln Ile Gln Gly Pro Asn Thr His Leu Gln Ile Ile Gln Gln
        35                  40                  45

Gln Gln Ile Gln His Met Met Gln Phe Gln Gln Gln Met Lys Leu Gln
    50                  55                  60

Ala Gln Ala Asp Leu Met Tyr Arg Arg Ser Asn Ser Gly Ser Met Asn
65                  70                  75                  80

Leu Lys Phe Asp Asn Ser Ser Cys Thr Pro Thr Ile Ser Ser Arg Ser
                85                  90                  95

Phe Ile Ser Ser Leu Ser Met Asp Gly Ser Val Ala Ser Met Asp Gly
            100                 105                 110

Lys Pro Phe His Leu Ile Pro Ala Ser Ser Gln Asp Arg Ser Gly His
        115                 120                 125

Ser Gln Lys Arg Arg Cys Ser Gly Lys Gly Glu Asp Gly Ser Gly Lys
    130                 135                 140

Cys Gly Thr Ser Gly Arg Cys His Cys Ser Lys Arg Arg Lys Ile Arg
145                 150                 155                 160

Val Lys Arg Ser Ile Lys Val Pro Ala Ile Ser Asn Lys Leu Ala Asp
                165                 170                 175

Ile Pro Pro Asp Glu Tyr Ser Trp Arg Lys Tyr Gly Gln Lys Pro Ile
            180                 185                 190
```

-continued

```
Lys Gly Ser Pro His Pro Arg Gly Tyr Tyr Lys Cys Ser Ser Met Arg
        195                 200                 205

Gly Cys Pro Ala Arg Lys His Val Glu Arg Cys Leu Glu Asp Pro Ser
    210                 215                 220

Met Leu Ile Val Thr Tyr Glu Gly Glu His Asn His Ser Arg Ile Leu
225                 230                 235                 240

Ser Gln Xaa Asn Gln Ser
                245


<210> SEQ ID NO 133
<211> LENGTH: 348
<212> TYPE: PRT
<213> ORGANISM: Arabidopsis thaliana

<400> SEQUENCE: 133

Arg Leu Ser Phe Glu Val Phe Arg Phe Leu Arg Val Ser Phe Val Lys
1               5                   10                  15

Lys Lys Met Glu Glu Val Glu Ala Ala Asn Lys Ala Ala Val Glu Ser
            20                  25                  30

Cys His Gly Val Leu Asn Leu Leu Ser Gln Gln Thr Asn Asp Ser Lys
        35                  40                  45

Ser Ile Met Val Glu Thr Arg Glu Ala Val Cys Lys Phe Lys Arg Val
    50                  55                  60

Ser Ser Leu Leu Ser Arg Gly Leu Gly Gln Arg Lys Ile Lys Lys Leu
65                  70                  75                  80

Asn Asn Asn Asn Tyr Lys Phe Ser Ser Ser Leu Leu Pro Gln His Met
                85                  90                  95

Phe Leu Glu Ser Pro Val Cys Ser Asn Asn Ala Ile Ser Gly Cys Ile
            100                 105                 110

Pro Ile Leu Ala Pro Lys Pro Leu Gln Ile Val Pro Ala Gly Pro Pro
        115                 120                 125

Pro Leu Met Leu Phe Asn Gln Asn Met Cys Leu Asp Lys Ser Phe Leu
    130                 135                 140

Glu Leu Lys Pro Pro Ser Ser Arg Ala Val Asp Pro Lys Pro Tyr Gln
145                 150                 155                 160

Phe Ile His Thr His Gln Gln Gly Val Tyr Ser Arg Ser Lys Ser Gly
                165                 170                 175

Leu Asn Leu Lys Phe Asp Gly Ser Ile Gly Ala Ser Cys Tyr Ser Pro
            180                 185                 190

Ser Ile Ser Asn Gly Ser Arg Ser Phe Val Ser Ser Leu Ser Met Asp
        195                 200                 205

Gly Ser Val Thr Asp Tyr Asp Arg Asn Ser Phe His Leu Ile Gly Leu
    210                 215                 220

Pro Gln Gly Ser Asp His Ile Ser Gln His Ser Arg Arg Thr Ser Cys
225                 230                 235                 240

Ser Gly Ser Leu Lys Cys Gly Ser Lys Ser Lys Cys His Cys Ser Lys
                245                 250                 255

Lys Arg Lys Leu Arg Val Lys Arg Ser Ile Lys Val Pro Ala Ile Ser
            260                 265                 270

Asn Lys Ile Ala Asp Ile Pro Pro Asp Glu Tyr Ser Trp Arg Lys Tyr
        275                 280                 285

Gly Gln Lys Pro Ile Lys Gly Ser Pro His Pro Arg Gly Tyr Tyr Lys
    290                 295                 300

Cys Ser Ser Val Arg Gly Cys Pro Ala Arg Lys His Val Glu Arg Cys
305                 310                 315                 320
```

-continued

```
Val Glu Glu Thr Ser Met Leu Ile Val Thr Tyr Glu Gly Glu His Asn
                325                 330                 335

His Ser Arg Ile Leu Ser Ser Gln Ser Ala His Thr
            340                 345


<210> SEQ ID NO 134
<211> LENGTH: 207
<212> TYPE: PRT
<213> ORGANISM: Glycine max

<400> SEQUENCE: 134

Gln Gln Gln Gln Gln Gln Gln Gln Gln Arg Leu Leu Leu Gln Gln Gln
1               5                   10                  15

Gln Gln Gln Gln Gln Gln Met Lys His Gln Ala Glu Met Met Phe Arg
            20                  25                  30

Arg Asn Asn Ser Gly Ile Asn Leu Asn Phe Asp Ser Thr Ser Cys Thr
        35                  40                  45

Pro Thr Met Ser Ser Thr Arg Ser Phe Ile Ser Ser Leu Ser Ile Asp
    50                  55                  60

Gly Ser Val Ala Asn Leu Asp Gly Ser Ala Phe His Leu Ile Gly Ala
65                  70                  75                  80

Pro His Ser Ser Asp Gln Asn Ser Gln Gln His Lys Arg Lys Cys Ser
                85                  90                  95

Ala Arg Gly Asp Glu Gly Ser Leu Lys Cys Gly Ser Ser Ala Arg Cys
            100                 105                 110

His Cys Ser Lys Lys Arg Lys His Arg Val Lys Arg Ala Ile Lys Val
        115                 120                 125

Pro Ala Ile Ser Asn Lys Leu Ala Asp Ile Pro Pro Asp Asp Tyr Ser
    130                 135                 140

Trp Arg Lys Tyr Gly Gln Lys Pro Ile Lys Gly Ser Pro His Pro Arg
145                 150                 155                 160

Gly Tyr Tyr Lys Cys Ser Ser Met Arg Gly Cys Pro Ala Arg Lys His
                165                 170                 175

Val Glu Arg Cys Leu Glu Glu Pro Thr Met Leu Ile Val Thr Tyr Glu
            180                 185                 190

Gly Glu His Asn His Pro Lys Leu Pro Thr Gln Ser Ala Asn Ala
        195                 200                 205


<210> SEQ ID NO 135
<211> LENGTH: 225
<212> TYPE: PRT
<213> ORGANISM: Gossypium raimondii

<400> SEQUENCE: 135

Leu Ser Ile Trp Glu Pro His Val Trp Asn Cys Ala Arg Met Val Lys
1               5                   10                  15

Thr Ser Leu Pro Leu Ala Gln Gln Pro Pro Pro Pro Ala His Tyr His
            20                  25                  30

Phe Leu His Gln Arg Gly Leu Gln Leu Gln Gln His Gln Ala Glu Met
        35                  40                  45

Leu Ser Arg Lys Ser Asn Cys Gly Ile Asn Phe Asn Phe Asp Ser Ser
    50                  55                  60

Ser Cys Thr Pro Thr Met Ser Ser Thr Arg Ser Phe Ile Ser Ser Leu
65                  70                  75                  80

Ser Ile Asp Gly Ser Val Ala Asn Met Asp Ser Gly Asn Ala Phe His
                85                  90                  95
```

-continued

```
Leu Ile Gly Ala Pro Arg Ser Ser Asp Gln Gly Ser Gln His Lys Lys
            100                 105                 110

Lys Cys Ser Gly Lys Gly Glu Asp Gly Ser Val Lys Cys Gly Ser Ser
        115                 120                 125

Gly Lys Cys His Cys Ser Lys Lys Arg Lys Gln Arg Val Lys Arg Ser
    130                 135                 140

Ile Lys Val Pro Ala Ile Ser Thr Lys Leu Ala Asp Ile Pro Pro Asp
145                 150                 155                 160

Asp Tyr Ser Trp Arg Lys Tyr Gly Gln Lys Pro Ile Lys Gly Ser Pro
                165                 170                 175

His Pro Arg Gly Tyr Tyr Lys Cys Ser Ser Met Arg Gly Cys Pro Ala
            180                 185                 190

Arg Lys His Val Glu Arg Cys Leu Glu Glu Pro Ser Met Leu Ile Val
        195                 200                 205

Thr Tyr Glu Gly Glu His Asn His Pro Lys Leu Pro Ser Gln Ala Thr
    210                 215                 220

Thr
225


<210> SEQ ID NO 136
<211> LENGTH: 164
<212> TYPE: PRT
<213> ORGANISM: Populus tremula x Populus tremuloides

<400> SEQUENCE: 136

Ser Ser Ser Cys Thr Pro Thr Met Ser Ser Thr Arg Ser Phe Ile Ser
1               5                   10                  15

Ser Leu Ser Ile Asp Gly Ser Val Ala Asn Leu Glu Gly Ser Ala Phe
            20                  25                  30

His Leu Met Gly Pro Ala Arg Ser Ser Asp Gln Ser Ser Gln Gln His
        35                  40                  45

Lys Arg Lys Cys Ser Gly Arg Gly Glu Asp Gly Ser Val Lys Cys Gly
    50                  55                  60

Ser Ser Gly Arg Cys His Cys Ser Lys Lys Arg Lys His Arg Val Lys
65                  70                  75                  80

Arg Ser Ile Lys Val Pro Ala Ile Ser Asn Lys Leu Ala Asp Ile Pro
                85                  90                  95

Pro Asp Asp Tyr Ser Trp Arg Lys Tyr Gly Gln Lys Pro Ile Lys Gly
            100                 105                 110

Ser Pro His Pro Arg Gly Tyr Tyr Lys Cys Ser Ser Met Arg Gly Cys
        115                 120                 125

Pro Ala Arg Lys His Val Glu Arg Cys Leu Glu Asp Pro Ser Met Leu
    130                 135                 140

Ile Val Thr Tyr Glu Gly Glu His Asn His Pro Arg Ile Pro Ala Gln
145                 150                 155                 160

Ser Ala Asn Thr


<210> SEQ ID NO 137
<211> LENGTH: 176
<212> TYPE: PRT
<213> ORGANISM: Malus x domestica
<220> FEATURE:
<221> NAME/KEY: misc_feature
<222> LOCATION: (147)..(147)
<223> OTHER INFORMATION: Xaa can be any naturally occurring amino acid
```

-continued

<400> SEQUENCE: 137

Arg Arg Ser Asn Ser Gly Ile Asn Leu Asn Phe Asp Ser Ser Ser Cys
1               5                   10                  15

Thr Pro Thr Met Ser Ser Thr Arg Ser Phe Ile Ser Ser Leu Ser Ile
            20                  25                  30

Asp Gly Ser Val Ala Asn Phe Asp Gly Asn Ser Phe His Leu Ile Gly
        35                  40                  45

Ala Pro Leu Ser Ser Asp Gln Asn Ser Gln His Lys Arg Lys Cys Ser
    50                  55                  60

Ala Arg Gly Asp Asp Gly Ser Val Lys Cys Gly Gly Ser Ser Gly Arg
65                  70                  75                  80

Cys His Cys Ser Lys Lys Arg Lys His Arg Val Lys Arg Ser Ile Lys
                85                  90                  95

Val Pro Ala Ile Ser Asn Lys Leu Ala Asp Ile Pro Pro Asp Asp Tyr
            100                 105                 110

Ser Trp Arg Lys Tyr Gly Gln Lys Pro Ile Lys Gly Ser Pro His Pro
        115                 120                 125

Arg Gly Tyr Tyr Lys Cys Ser Ser Met Arg Gly Cys Pro Ala Arg Lys
    130                 135                 140

His Val Xaa Arg Cys Leu Glu Glu Pro Ser Met Leu Met Val Thr Tyr
145                 150                 155                 160

Glu Gly Glu His Asn His Pro Arg Ile Pro Ser Gln Ser Thr Thr Thr
                165                 170                 175

<210> SEQ ID NO 138
<211> LENGTH: 259
<212> TYPE: PRT
<213> ORGANISM: Solanum tuberosum

<400> SEQUENCE: 138

Val Lys Thr Glu Cys Lys Ile Asp Asp His Ala Lys Ala Leu Arg Leu
1               5                   10                  15

Leu Pro Ile Asp Ser Pro Glu Asn Arg Val Leu Glu Met Gly Ala Asn
            20                  25                  30

Val Lys Cys Asn Leu Thr Leu Gly Ser Pro Ser Leu Glu Leu Ser Ser
        35                  40                  45

Asn Ser Arg Asn Pro Leu Asn Phe Gly Gln Gln Thr Pro Phe Pro Ser
    50                  55                  60

Tyr Asn Tyr Leu Gln Gln Gln Gln Gln Gln Gln Gln Gln Gln Gln Gln
65                  70                  75                  80

Gln Arg Arg Phe Leu Leu Gln Gln Gln Gln Gln Leu Lys His Pro Ala
                85                  90                  95

Glu Met Met Tyr Arg Arg Ser Asn Ser Gly Val Ser Leu Asn Phe Asp
            100                 105                 110

Ser Ser Thr Cys Thr Pro Thr Met Ser Ser Thr Arg Ser Phe Ile Ser
        115                 120                 125

Ser Leu Ser Val Asp Gly Ser Val Ala Asn Gly Asn Ser Phe His Leu
    130                 135                 140

Ile Gly Ala Ser His Ser Ala Asp Gln Ser Ser Phe Gln His Lys Arg
145                 150                 155                 160

Lys Cys Ser Gly Arg Gly Asp Glu Gly Ser Gly Lys Cys Gly Ser Ser
                165                 170                 175

Gly Arg Cys His Cys Ser Lys Lys Arg Lys His Arg Val Lys Arg Ser
            180                 185                 190

-continued

```
Ile Lys Ile Pro Ala Val Ser Asn Lys Leu Ala Asp Ile Pro Ser Asp
        195                 200                 205

Glu Tyr Ser Trp Arg Lys Tyr Gly Gln Lys Pro Ile Lys Gly Ser Pro
    210                 215                 220

His Pro Arg Gly Tyr Tyr Lys Cys Ser Ser Met Arg Gly Cys Pro Ala
225                 230                 235                 240

Arg Lys His Val Glu Arg Cys Leu Glu Asp Ala Ser Met Leu Ile Val
                245                 250                 255

Thr Tyr Glu


<210> SEQ ID NO 139
<211> LENGTH: 166
<212> TYPE: PRT
<213> ORGANISM: Medicago truncatula

<400> SEQUENCE: 139

Phe Asp Lys Ala Thr Ser Ser Thr Pro Gln Met Ser Ser Thr Arg Ser
1               5                   10                  15

Ser Phe Ser Ser Leu Ser Ile Asp Gly Ser Val Ala Asn Val Asp Gly
            20                  25                  30

Ser Pro Phe His Leu Ile Gly Ala Pro Ile Ser Ser Asp Gln Asn Ser
        35                  40                  45

Gln His Lys Arg Lys Cys Ser Ala Arg Gly Asp Glu Gly Ser Leu Lys
    50                  55                  60

Cys Ser Ser Ser Ser Lys Cys His Cys Ser Lys Lys Arg Lys His Arg
65                  70                  75                  80

Val Lys Arg Ser Ile Lys Val Pro Ala Ile Ser Asn Lys Leu Ala Asp
                85                  90                  95

Ile Pro Pro Asp Asp Tyr Ser Trp Arg Lys Tyr Gly Gln Lys Pro Ile
            100                 105                 110

Lys Gly Ser Pro His Pro Arg Gly Tyr Tyr Lys Cys Ser Ser Met Arg
        115                 120                 125

Gly Cys Pro Ala Arg Lys His Val Glu Arg Cys Leu Asp Glu Pro Thr
    130                 135                 140

Met Leu Met Val Thr Tyr Glu Gly Glu His Asn His Ala Lys Val Pro
145                 150                 155                 160

Thr Gln Pro Ala Asn Ala
                165


<210> SEQ ID NO 140
<211> LENGTH: 148
<212> TYPE: PRT
<213> ORGANISM: Ipomoea nil
<220> FEATURE:
<221> NAME/KEY: misc_feature
<222> LOCATION: (2)..(2)
<223> OTHER INFORMATION: Xaa can be any naturally occurring amino acid

<400> SEQUENCE: 140

Ser Xaa Ser Ile Asp Gly Ser Val Ala Asn Met Asp Gly Asn Ala Phe
1               5                   10                  15

His Leu Ile Gly Ala Ser Arg Ser Ala Asp Leu Ser Ser Tyr Gln His
            20                  25                  30

Lys Lys Arg Cys Ser Gly Arg Gly Glu Asp Gly Ser Thr Lys Cys Gly
        35                  40                  45

Ser Ser Ser Arg Cys His Cys Ser Lys Lys Arg Lys His Arg Val Lys
    50                  55                  60
```

-continued

Arg Ser Ile Lys Val Pro Ala Ile Ser Asn Lys Leu Ala Asp Ile Pro
65 70 75 80

Gln Asp Glu Tyr Ser Trp Arg Lys Tyr Gly Gln Lys Pro Ile Lys Gly
85 90 95

Ser Pro His Pro Arg Gly Tyr Tyr Lys Cys Ser Ser Met Arg Gly Cys
100 105 110

Pro Ala Arg Lys His Val Glu Arg Cys Leu Glu Asp Pro Ser Met Leu
115 120 125

Ile Val Thr Tyr Glu Gly Asp His Asn His Pro Arg Val Pro Ser Gln
130 135 140

Ser Ala Asn Thr
145

<210> SEQ ID NO 141
<211> LENGTH: 163
<212> TYPE: PRT
<213> ORGANISM: Hordeum vulgare

<400> SEQUENCE: 141

His Glu Ala Ser Ser Arg Ser Phe Leu Thr Ser Leu Ser Leu Glu Gly
1 5 10 15

Ser Met Ala Ser Met Asp Gly Ser Arg Ser Ser Arg Pro Phe Gln Leu
20 25 30

Val Ser Gly Ser Gln Thr Ser Ser Thr Pro Glu Leu Gly Leu Met Gln
35 40 45

Gln Arg Arg Arg Cys Ala Gly Lys Glu Asp Gly Ser Gly Arg Cys Ala
50 55 60

Thr Gly Ser Arg Cys His Cys Ala Lys Lys Arg Lys Leu Arg Ile Arg
65 70 75 80

Arg Ser Ile Lys Val Pro Ala Ile Ser Asn Lys Val Ala Asp Ile Pro
85 90 95

Ala Asp Glu Phe Ser Trp Arg Lys Tyr Gly Gln Lys Pro Ile Lys Gly
100 105 110

Ser Pro His Pro Arg Gly Tyr Tyr Lys Cys Ser Ser Val Arg Gly Cys
115 120 125

Pro Ala Arg Lys His Val Glu Arg Cys Val Asp Asp Pro Ala Met Leu
130 135 140

Ile Val Thr Tyr Glu Gly Asp His Asn His Asn Arg Ala Ala Ala Ala
145 150 155 160

Gln Pro Ala

<210> SEQ ID NO 142
<211> LENGTH: 159
<212> TYPE: PRT
<213> ORGANISM: Crocus sativus

<400> SEQUENCE: 142

Ile Gly Arg Leu Gln Lys Leu Gln Ala Glu Met Phe Lys Arg Ser Asn
1 5 10 15

Ser Gly Ile Asn Leu Lys Phe Asp Asn Ser Ser Cys Thr Pro Ala Met
20 25 30

Ser Ser Thr Arg Ser Phe Leu Ser Ser Leu Ser Thr Glu Gly Ser Val
35 40 45

Ala Ser Leu Gln Gly Lys Pro Phe Gln Leu Ile Gly Gly Ser Leu Ser
50 55 60

-continued

```
Ser Glu Pro Val Asn Leu His Pro Thr Pro Lys Arg Arg Cys Leu Cys
65                  70                  75                  80

Thr Gly Arg Gly Glu Asp Gly Lys Cys Ala Ala Ser Gly Arg Cys His
                85                  90                  95

Cys Ser Lys Arg Arg Lys Leu Arg Val Lys Arg Ser Ile Lys Val Pro
            100                 105                 110

Ala Ile Ser Asn Lys Leu Ala Asp Ile Pro Pro Asp Glu Phe Ser Trp
        115                 120                 125

Arg Lys Tyr Gly Gln Lys Pro Ile Lys Gly Ser Pro His Pro Arg Gly
    130                 135                 140

Tyr Tyr Lys Cys Ser Ser Ile Thr Ser Tyr Leu Leu Phe Asn His
145                 150                 155


<210> SEQ ID NO 143
<211> LENGTH: 116
<212> TYPE: PRT
<213> ORGANISM: Zea mays

<400> SEQUENCE: 143

Phe Phe Phe Phe Leu Asn Asn Gly Lys Cys Ala Leu Ala Gly Arg Cys
1               5                   10                  15

His Cys Ser Lys Arg Ser Lys Lys Leu Arg Val Lys Arg Ser Ile Lys
            20                  25                  30

Val Pro Ala Val Ser Asn Lys Ile Ala Asp Ile Pro Pro Asp Glu Tyr
        35                  40                  45

Ser Trp Arg Lys Tyr Gly Gln Lys Pro Ile Lys Gly Ser Pro His Pro
    50                  55                  60

Arg Gly Tyr Tyr Lys Cys Ser Ser Val Arg Gly Cys Pro Ala Arg Lys
65                  70                  75                  80

His Val Glu Arg Cys Val Asp Asp Ser Ala Met Leu Ile Val Thr Tyr
                85                  90                  95

Glu Gly Glu His Asn His Thr Gly Met Pro Ala Gln Ser Ala Ala Ala
            100                 105                 110

Ala Ala Gln Val
        115


<210> SEQ ID NO 144
<211> LENGTH: 132
<212> TYPE: PRT
<213> ORGANISM: Sorghum bicolor

<400> SEQUENCE: 144

Thr Arg Leu Val Ser Gly Ser Gln Thr Ser Ser Thr Pro Glu Met Gly
1               5                   10                  15

Leu Val His Arg Lys Arg Cys Ala Gly Arg Glu Asp Gly Gly Gly Arg
            20                  25                  30

Cys Thr Thr Gly Ser Arg Cys His Cys Ser Lys Lys Arg Lys Leu Arg
        35                  40                  45

Ile Arg Arg Ser Ile Lys Val Pro Ala Ile Ser Asn Lys Val Ala Asp
    50                  55                  60

Ile Pro Ala Asp Glu Phe Ser Trp Arg Lys Tyr Gly Gln Lys Pro Ile
65                  70                  75                  80

Lys Gly Ser Pro His Pro Arg Gly Tyr Tyr Lys Cys Ser Ser Val Arg
                85                  90                  95

Gly Cys Pro Ala Arg Lys His Val Glu Arg Cys Val Asp Asp Pro Ser
            100                 105                 110
```

-continued

```
Met Leu Ile Val Thr Tyr Glu Gly Asp His Asn His Asn Arg Val Leu
        115                 120                 125

Ala Gln Pro Ala
    130


<210> SEQ ID NO 145
<211> LENGTH: 395
<212> TYPE: PRT
<213> ORGANISM: Physcomitrella patens

<400> SEQUENCE: 145

Met Gly Ala Leu Glu Ile Leu Asp Tyr Asn Asn Thr Leu Gly Lys Arg
1               5                   10                  15

Asp Arg Asp Tyr Glu Val Lys Glu Ala Ala Cys Met Gly Ile Gln Asn
            20                  25                  30

Ala Arg Gln Leu Leu Gln Ser Leu Thr Gln Val Arg Ser Pro Val Val
        35                  40                  45

Asp Glu Glu Cys Asp Val Met Ala Gly Ala Ala Ile Ser Lys Phe Gln
    50                  55                  60

Lys Val Val Ser Leu Leu Ser Arg Thr Gly His Ala Arg Phe Arg Arg
65                  70                  75                  80

Arg Thr Arg Asn Ala Ala Val Ala Gly Tyr Ala Gly Val Phe Leu Glu
                85                  90                  95

Ser Ser Asn Phe Phe Arg Glu Asn Ser Gln Glu Thr Ser Arg Asp Arg
            100                 105                 110

Ile Val Ser Ser Gly His Ala Ser Pro Ser Gln Phe Thr Pro Thr Ser
        115                 120                 125

Ser Ser Lys Pro Pro Gln Ser Pro Glu Leu Gln Ala Ile Lys Tyr Lys
    130                 135                 140

Val Phe Pro Gln Ser Ser Arg Ser Ala Asp Ala Thr Pro Ala Ser Ser
145                 150                 155                 160

Asp Pro Ala Ser Gly Val His His Pro Lys Pro Leu Gln Ile Leu His
                165                 170                 175

Ser Ser Met Met Gln Gln Ser Ile Pro Glu His Ile Leu Arg Pro Val
            180                 185                 190

Ala Ser Ala Ala Tyr Arg Pro Thr Ala Leu Pro Pro Asn Pro Phe Asn
        195                 200                 205

Lys Gln Glu Val Gly Ser Lys Glu Gly Val Ser Gly His Ser Pro Asp
    210                 215                 220

Ser Ser Leu Ser Ser Gly Pro Pro Gln Ser Thr Thr Thr Ala Ser Phe
225                 230                 235                 240

Pro Thr Met Ser Val Gln Asp Ala Arg Ile Thr Ser Leu Gln Asn Met
                245                 250                 255

Lys Thr Ala Glu Gln Pro Ser Ala Leu Pro Pro Arg Pro Gln Pro Pro
            260                 265                 270

Thr Pro Lys Lys Lys Cys Ser Gly Gln Ser Asp Glu Asn Gly Ala Thr
        275                 280                 285

Cys Ala Ile Leu Gly Arg Cys His Cys Ser Lys Arg Arg Lys Leu Arg
    290                 295                 300

Leu Lys Arg Thr Ile Thr Val Arg Ala Ile Ser Ser Lys Leu Ala Asp
305                 310                 315                 320

Ile Pro Ser Asp Glu Tyr Ser Trp Arg Lys Tyr Gly Gln Lys Pro Ile
                325                 330                 335

Lys Gly Ser Pro His Pro Arg Gly Tyr Tyr Lys Cys Ser Ser Ile Arg
            340                 345                 350
```

-continued

```
Gly Cys Pro Ala Arg Lys His Val Glu Arg Ser Met Glu Asp Ser Ser
        355                 360                 365

Met Leu Ile Val Thr Tyr Glu Gly Asp His Asn His Pro Gln Ser Ser
    370                 375                 380

Ser Ala Asn Gly Gly Leu Thr Val Gln Ser Gln
385                 390                 395


<210> SEQ ID NO 146
<211> LENGTH: 166
<212> TYPE: PRT
<213> ORGANISM: Vitis sp

<400> SEQUENCE: 146

Thr Ser Ser Phe Leu Ser Ser Ile Thr Gly Asp Gly Ser Val Ser Asn
1               5                   10                  15

Gly Lys Leu Gly Thr Ser Leu Phe Ala Pro Pro Pro Ala Pro Ala Val
            20                  25                  30

Ser Ala Gly Lys Pro Pro Leu Ser Ser Ser Gln Arg Arg Lys Cys His
        35                  40                  45

Glu His Gly Ser Ser Asp Asn Ile Ser Gly Lys Leu Ser Val Ser Gly
    50                  55                  60

Arg Cys His Cys Ser Lys Arg Arg Lys Asn Arg Val Lys Arg Thr Ile
65                  70                  75                  80

Arg Val Pro Ala Ile Ser Ser Lys Ile Ala Asp Ile Pro Ala Asp Glu
                85                  90                  95

Tyr Ser Trp Arg Lys Tyr Gly Gln Lys Pro Ile Lys Gly Ser Pro Tyr
            100                 105                 110

Pro Arg Gly Tyr Tyr Lys Cys Ser Ser Val Arg Gly Cys Pro Ala Arg
        115                 120                 125

Lys His Val Glu Arg Ala Pro Asp Asp Pro Ala Met Leu Ile Val Thr
    130                 135                 140

Tyr Glu Gly Glu His Arg His Ser Gln Thr Pro Ala Pro Ala Gly Gly
145                 150                 155                 160

Leu Met Phe Pro Ser Thr
                165


<210> SEQ ID NO 147
<211> LENGTH: 118
<212> TYPE: PRT
<213> ORGANISM: Picea engelmannii x Picea sitchensis

<400> SEQUENCE: 147

Arg Lys Cys Ser Gly Lys Gly Asp Asp Ser Ser Lys Cys Gly Ser Thr
1               5                   10                  15

Gly Arg Cys His Cys Ser Lys Arg Arg Lys Leu Arg Val Lys Arg Thr
            20                  25                  30

Ile Arg Val Pro Ala Ile Ser Ser Lys Leu Ala Asp Ile Pro Pro Asp
        35                  40                  45

Glu Phe Ser Trp Arg Lys Tyr Gly Gln Lys Pro Ile Lys Gly Ser Pro
    50                  55                  60

His Pro Arg Gly Tyr Tyr Lys Cys Ser Ser Met Arg Gly Cys Pro Ala
65                  70                  75                  80

Arg Lys His Val Glu Arg Ser Leu Glu Asp Ala Ser Met Leu Ile Val
                85                  90                  95
```

-continued

```
Thr Tyr Glu Gly Glu His Asn His Ser Arg Leu Leu Ser Ser Asn Ser
            100                 105                 110

Ser Leu Ile Val His Pro
        115


<210> SEQ ID NO 148
<211> LENGTH: 328
<212> TYPE: PRT
<213> ORGANISM: Nicotiana tabacum

<400> SEQUENCE: 148

Met Ala Val Asp Phe Ile Gly Phe Ser Lys Met Asn Glu Gln Leu Ala
1               5                   10                  15

Leu Gln Glu Ala Ala Ser Ala Gly Leu Lys Ser Met Glu His Leu Ile
            20                  25                  30

Arg Leu Val Ser His Gln Gln Gln Gln Gln Pro Val Gln Leu Asp Cys
        35                  40                  45

Arg Glu Ile Thr Asp Phe Thr Leu Ser Lys Phe Lys Lys Val Val Ser
    50                  55                  60

Ile Leu Asp Arg Thr Gly His Ala Arg Phe Arg Arg Gly Pro Val Gln
65                  70                  75                  80

Val His Pro Asp Asn Phe Thr Ser Leu Ser Leu Ser Pro Ser Asn Gln
                85                  90                  95

Gln Leu Leu Asn Leu Ala Pro Ala Lys Glu Thr Pro Pro Pro Pro Ser
            100                 105                 110

Val Ser Leu Pro Leu Thr Ala Leu Thr Leu Asp Phe Thr Lys Pro Asn
        115                 120                 125

Val Asp Arg Pro Thr Gly Asn Ser Asn Ala Ile Val Ala Val Lys Ser
    130                 135                 140

Lys Glu Thr Phe Cys Ile Ser Thr Pro Met Ala Thr Ser Ala Asn Ser
145                 150                 155                 160

Ser Ser Phe Met Ser Ser Ile Thr Gly Glu Gly Ser Val Ser Asn Gly
                165                 170                 175

Lys Gln Gly Ser Ser Val Phe Leu Pro Pro Ala Pro Ser Val Ser Ala
            180                 185                 190

Gly Lys Pro Pro Ile Ser Gly Lys Arg Cys Arg Glu His Glu Pro Ser
        195                 200                 205

Glu Asp Ile Ser Gly Lys Ser Asn Gly Ser Gly Lys Cys His Cys Lys
    210                 215                 220

Lys Arg Lys Ser Arg Val Lys Lys Val Val Arg Ile Pro Ala Ile Ser
225                 230                 235                 240

Ser Arg Ile Ala Asp Ile Pro Gly Asp Glu Tyr Ser Trp Arg Lys Tyr
                245                 250                 255

Gly Gln Lys Pro Ile Lys Gly Ser Pro Tyr Pro Arg Gly Tyr Tyr Lys
            260                 265                 270

Cys Ser Ser Val Arg Gly Cys Pro Ala Arg Lys His Val Glu Arg Ala
        275                 280                 285

Met Asp Asp Pro Ala Met Leu Ile Val Thr Tyr Glu Gly Glu His Arg
    290                 295                 300

His Thr Ile Gly Ala Met Gln Glu Asn Asn Thr Gln Met Met Val Phe
305                 310                 315                 320

Gly Ser Thr Glu Glu Arg Arg Glu
                325
```

<210> SEQ ID NO 149
<211> LENGTH: 196
<212> TYPE: PRT
<213> ORGANISM: Liriodendron tulipifera

<400> SEQUENCE: 149

```
His Arg Asn Phe Met Glu Asn Pro Ile Gln Gly Ile Asp Ser Ser Gly
1               5                   10                  15

Gly Asn Thr Leu Gln Leu Ala Lys Asn Met Phe Leu Glu Asn Pro Thr
            20                  25                  30

Gln Glu Leu Asp Ser Ser Ala Ala Ala Ala Ala Val Ala Ala Ala Ala
        35                  40                  45

Lys Asn His Leu Gln Ser Thr His Leu Gln Phe Leu Gln Gln Gln Gln
    50                  55                  60

Gln Arg Phe Gln Phe Gln Gln Gln Gln Met Lys Phe Gln Ala Asp Met
65                  70                  75                  80

Phe Arg Arg Ser Asn Asn Gly Ile Asn Leu Lys Tyr Asp Asn Ser Ser
                85                  90                  95

Cys Thr Pro Thr Met Ser Ser Thr Arg Ser Phe Val Ser Ser Leu Ser
            100                 105                 110

Met Asp Gly Ser Val Ala Ser Leu Asp Gly Lys Ala Phe His Leu Ile
        115                 120                 125

Gly Gly Pro Gln Thr Ser Ser Asp Arg Asn Pro Asn Gln Pro Pro Lys
    130                 135                 140

Arg Arg Cys Ser Gly Arg Gly Glu Asp Gly Ser Gly Lys Cys Gly Thr
145                 150                 155                 160

Ser Gly Arg Cys His Cys Ser Lys Arg Arg Lys Leu Arg Met Lys Arg
                165                 170                 175

Ser Ile Lys Val Pro Ala Ile Ser Asn Lys Leu Ala Asp Ile Pro Pro
            180                 185                 190

Asp Glu Tyr Ser
        195
```

<210> SEQ ID NO 150
<211> LENGTH: 322
<212> TYPE: PRT
<213> ORGANISM: Nicotiana benthamiana

<400> SEQUENCE: 150

```
Trp Gln Leu Asn Phe Val Gly Phe Ser Lys Met Asn Glu Gln Leu Ala
1               5                   10                  15

Leu Gln Glu Ala Ala Ser Ala Gly Leu Lys Ser Met Glu His Leu Ile
            20                  25                  30

Arg Leu Val Ser His Gln Gln Gln Gln Gln Pro Val Gln Leu Asp Cys
        35                  40                  45

Arg Glu Ile Thr Asp Phe Thr Val Ser Lys Phe Arg Lys Val Ile Ser
    50                  55                  60

Ile Leu Asp Arg Thr Gly His Ala Arg Phe Arg Arg Gly Gln Val Gln
65                  70                  75                  80

Val His Pro Asp Asn Phe Thr Ser Leu Ser Leu Ser Pro Ser Asn Gln
                85                  90                  95

Gln Leu Leu Asn Leu Ala Pro Ala Lys Glu Thr Pro Pro Pro Arg Pro
            100                 105                 110

Pro Ser Val Ser Pro Pro Leu Thr Ala Leu Thr Leu Asp Phe Thr Lys
        115                 120                 125
```

-continued

Pro Asn Val Asp Arg Pro Ala Gly Asn Ser Asn Ala Ile Val Ala Val
    130                 135                 140

Lys Ser Lys Glu Thr Phe Cys Ile Ser Thr Pro Met Ala Thr Ser Thr
145                 150                 155                 160

Asn Ser Ser Ser Phe Ile Ser Ser Ile Thr Gly Glu Gly Ser Val Ser
                165                 170                 175

Asn Gly Lys Gln Gly Ser Ser Met Phe Leu Pro Pro Ala Gln Ala Val
            180                 185                 190

Ser Ala Gly Lys Pro Pro Val Ala Gly Lys Arg Cys Arg Glu His Glu
        195                 200                 205

Tyr Ser Glu Asp Ile Ser Gly Lys Ser Thr Gly Ser Gly Arg Cys His
    210                 215                 220

Cys Lys Lys Arg Lys Ser Arg Val Lys Lys Val Val Arg Ile Pro Ala
225                 230                 235                 240

Ile Ser Ser Arg Ile Ala Asp Ile Pro Gly Asp Glu Phe Ser Trp Arg
                245                 250                 255

Lys Tyr Gly Gln Lys Pro Ile Lys Gly Ser Pro Tyr Pro Arg Gly Tyr
            260                 265                 270

Tyr Lys Cys Ser Ser Val Arg Gly Cys Pro Ala Lys Lys His Val Glu
        275                 280                 285

Arg Ala Ile Asp Asp Pro Ala Met Leu Ile Val Thr Tyr Glu Gly Glu
    290                 295                 300

His Arg His Thr Ile Gly Ala Ile Gln Glu Asn Asn Ser Gln Met Met
305                 310                 315                 320

Ala Phe

<210> SEQ ID NO 151
<211> LENGTH: 341
<212> TYPE: PRT
<213> ORGANISM: Petroselinum crispum

<400> SEQUENCE: 151

Met Ala Leu Asp Leu Met Asn Asn Asn Ser Tyr Lys Phe Arg Ser Lys
1               5                   10                  15

Met Glu Glu Thr Ala Val Gln Glu Ala Ala Ala Ala Gly Leu Gln Ser
            20                  25                  30

Val Glu Asn Leu Ile Lys Ala Ile Ser Gln Ser Asn His Gln Thr Ala
        35                  40                  45

Tyr Leu Ser Ser Ser Ser Ser Ser Glu Thr Gly Asp Thr Asp Tyr Arg
    50                  55                  60

Ala Val Thr Asp Val Ala Val Asn Lys Phe Lys Lys Phe Ile Ser Leu
65                  70                  75                  80

Leu Asp Lys Asn Arg Thr Gly His Ala Arg Phe Arg Arg Gly Pro Val
                85                  90                  95

Gln Glu Lys Thr Gly Val Glu Met Leu Val Asn Pro Ile Gln Asn Gln
            100                 105                 110

Ile Gln Asn His Gly Ser Asp Gly Phe Gln Val Tyr Arg Pro Thr Ala
        115                 120                 125

Val His Pro Val Gln Pro Val Gln Pro Val Gln Ile Gln Pro Val Gln
    130                 135                 140

Leu Val Gln Pro Val Gln Arg Leu Pro Pro Val Pro Lys Lys Glu Asn
145                 150                 155                 160

Ile Ser Thr Thr Ile Asn Phe Ala Ala Pro Ala Val Ala Val Ala Ala
                165                 170                 175

-continued

```
Pro Ala Thr Ser Phe Met Ser Ser Leu Thr Gly Asp Thr Asp Gly Ser
            180                 185                 190

Gly Phe Gln Ile Thr Asn Met Ser Gly Phe Ser Ser Gly Ser Arg Pro
        195                 200                 205

Val Ser Ser Leu Lys Arg Lys Cys Ser Ser Met Asn Asp Val Ser Ala
    210                 215                 220

Lys Cys Ser Gly Ser Ser Gly Arg Cys His Cys Pro Lys Lys Lys
225                 230                 235                 240

Lys Leu Arg Val Lys Lys Val Val Arg Met Pro Ala Ile Ser Met Lys
                245                 250                 255

Thr Ser Asp Ile Pro Pro Asp Asp Phe Ser Trp Arg Lys Tyr Gly Gln
            260                 265                 270

Lys Pro Ile Lys Gly Ser Pro His Pro Arg Gly Tyr Tyr Lys Cys Ser
        275                 280                 285

Ser Val Arg Gly Cys Pro Ala Arg Lys His Val Glu Arg Ala Val Asp
    290                 295                 300

Asp Pro Thr Met Leu Ile Val Thr Tyr Glu Gly Glu His Asn His Ser
305                 310                 315                 320

Gln Ser Ser Asn Glu Asn Thr Asn Thr Ser His Ile Leu Glu Ser Asp
                325                 330                 335

Gly Leu Lys Gln Ser
            340


<210> SEQ ID NO 152
<211> LENGTH: 248
<212> TYPE: PRT
<213> ORGANISM: Asparagus officinalis

<400> SEQUENCE: 152

Gly Phe Lys Lys Met Ile Ser Ile Leu Asn Arg Thr Gly His Ala Arg
1               5                   10                  15

Phe Arg Arg Gly Pro Thr His Gln Pro Gln Asp Pro Pro Pro Ala Ile
            20                  25                  30

His Ser Pro Thr Pro Ile Gln Ala Val Met Pro Pro Ala Pro His Ser
        35                  40                  45

Leu Thr Leu Asp Phe Thr Lys Pro Lys Thr Ala Gly Glu Ile Ala Thr
    50                  55                  60

Met Asn Ser Gln Tyr Ser Lys Asp Thr Ser Asn Phe Ser Ile Ser Ser
65                  70                  75                  80

Ala Asn Ser Ser Phe Leu Ser Ser Ile Thr Gly Asp Gly Ser Val Ser
                85                  90                  95

Asn Gly Lys Asn Gly Ser Ser Met Leu Leu Pro Pro Leu Pro Pro Ala
            100                 105                 110

Ala Ala Val Ser Ala Gly Lys Pro Pro Leu Ser Thr Ser Phe Lys Lys
        115                 120                 125

Arg Cys His Ser His Gly Thr Glu Met Ala Gly Ser Phe Ser Ala Ser
    130                 135                 140

Gly Gly Arg Cys His Cys Ser Lys Lys Arg Lys Ser Arg Val Lys Arg
145                 150                 155                 160

Thr Ile Arg Val Pro Ala Lys Ser Ser Lys Val Ala Asp Ile Pro Ser
                165                 170                 175

Asp Glu Phe Ser Trp Arg Lys Tyr Gly Gln Lys Pro Ile Lys Gly Ser
            180                 185                 190

Pro Tyr Pro Arg Gly Tyr Tyr Lys Cys Ser Ser Met Arg Gly Cys Pro
        195                 200                 205
```

-continued

```
Ala Arg Lys His Val Glu Arg Ala Pro Asp Asp Pro Ser Met Leu Ile
    210                 215                 220

Val Thr Tyr Glu Gly Glu His Arg His Thr His Ser Pro Ile Pro Asp
225                 230                 235                 240

Ala Leu Ile Leu Lys Gln Ser Glu
                245
```

<210> SEQ ID NO 153
<211> LENGTH: 183
<212> TYPE: PRT
<213> ORGANISM: Poncirus trifoliata

<400> SEQUENCE: 153

```
Val Ser Ser Asn Ser Ser Phe Met Ser Ser Ala Ile Thr Gly Asp Gly
1               5                   10                  15

Ser Val Ser Asn Gly Lys Gln Gly Gly Ser Ser Ile Phe Leu Ala Pro
            20                  25                  30

Gln Ala Pro Ala Val Ser Ala Gly Lys Pro Pro Leu Ala Ala Gln Pro
        35                  40                  45

Tyr Lys Lys Arg Cys Gln Asp Gln His Asp His Ser Asp Gly Leu Ser
    50                  55                  60

Gly Lys Phe Ser Gly Ser Thr Ser Gly Ser Asn Lys Cys His Cys Ser
65                  70                  75                  80

Lys Arg Arg Lys Asn Arg Val Lys Lys Thr Ile Arg Val Pro Ala Ile
                85                  90                  95

Ser Ser Lys Ile Ala Asp Ile Pro Pro Asp Glu Tyr Ser Trp Arg Lys
            100                 105                 110

Tyr Gly Gln Lys Pro Ile Lys Gly Ser Pro Tyr Pro Arg Gly Tyr Tyr
        115                 120                 125

Lys Cys Ser Thr Met Arg Gly Cys Pro Ala Arg Lys His Val Glu Arg
    130                 135                 140

Ala Pro Asp Asp Pro Thr Met Leu Ile Val Thr Tyr Glu Gly Glu His
145                 150                 155                 160

Arg His Ser Gln Ala Ala Met Gln Glu Asn Val Val Pro Ala Gly Val
                165                 170                 175

Gly Leu Val Phe Glu Ser Thr
            180
```

<210> SEQ ID NO 154
<211> LENGTH: 131
<212> TYPE: PRT
<213> ORGANISM: Lotus corniculatus var. japonicus

<400> SEQUENCE: 154

```
Lys Pro Pro Leu Ser Ser Ser Ser Leu Lys Arg Lys Cys Ser Ser Glu
1               5                   10                  15

Thr Leu Gly Ser Gly Lys Cys Gly Ser Ser Ser Gly Arg Cys His Cys
            20                  25                  30

Ser Gln Lys Ser Arg Lys Met Arg Leu Lys Arg Val Val Arg Val Pro
        35                  40                  45

Ala Ile Ser Leu Lys Met Ala Asp Ile Pro Pro Asp Asp Tyr Ser Trp
    50                  55                  60

Arg Lys Tyr Gly Gln Lys Pro Ile Lys Gly Ser Pro His Pro Arg Gly
65                  70                  75                  80

Tyr Tyr Lys Cys Ser Ser Val Arg Gly Cys Pro Ala Arg Lys His Val
                85                  90                  95
```

-continued

```
Glu Arg Ala Leu Asp Asp Ala Ala Met Leu Val Val Thr Tyr Glu Gly
            100                 105                 110

Glu His Asn His Ala Leu Ser Ala Ala Asp Ala Thr Asn Leu Ile Leu
        115                 120                 125

Glu Ser Ser
    130


<210> SEQ ID NO 155
<211> LENGTH: 321
<212> TYPE: PRT
<213> ORGANISM: Avena sativa

<400> SEQUENCE: 155

Met Met Thr Met Asp Leu Met Gly Arg Tyr Gly Arg Ala Asp Glu Gln
1               5                   10                  15

Val Ala Ile Gln Glu Ala Ala Ala Ala Gly Leu Arg Gly Met Glu His
            20                  25                  30

Leu Ile Leu Gln Leu Ser Arg Thr Gly Thr Gly Thr Gly Thr Ser Glu
        35                  40                  45

Ser Ser Leu Ala Gly Ala Ser Glu Pro Ala Ala Gln Gly Gln Gln Gln
    50                  55                  60

Gln Gln Gln Val Asp Cys Arg Glu Ile Thr Asp Met Thr Val Ser Lys
65                  70                  75                  80

Phe Lys Lys Val Ile Ser Ile Leu Asn His Arg Thr Gly His Ala Arg
                85                  90                  95

Phe Arg Arg Gly Pro Val Val Ala Gln Ser Gln Gly Pro Ser Val Ser
            100                 105                 110

Glu Pro Ala Pro Val Arg Thr Ala Ser Ser Ser Arg Pro Met Thr Leu
        115                 120                 125

Asp Phe Ser Lys Ser Ala Ser Val Phe Gly Asn Lys Asp Ala Ala Tyr
    130                 135                 140

Ser Val Ser Ala Ala Ser Ser Ser Phe Leu Ser Ser Val Thr Gly Asp
145                 150                 155                 160

Gly Ser Val Ser Asn Gly Arg Gly Gly Gly Ser Ser Leu Met Leu Pro
                165                 170                 175

Pro Pro Pro Ser Ala Ser Cys Gly Lys Pro Pro Leu Ala Ala Ala Ala
            180                 185                 190

Ala Gly Pro Lys Arg Lys Cys His Glu His Ala His Ser Glu Asn Val
        195                 200                 205

Ala Gly Ala Ser Gly Gly Arg Cys His Cys Ser Lys Arg Arg Lys Ser
    210                 215                 220

Arg Val Lys Arg Met Thr Arg Val Pro Ala Ile Ser Ser Lys Ala Ala
225                 230                 235                 240

Glu Ile Pro Ala Asp Asp Phe Ser Trp Arg Lys Tyr Gly Gln Lys Pro
                245                 250                 255

Ile Lys Gly Ser Pro Tyr Pro Arg Gly Tyr Tyr Lys Cys Ser Thr Val
            260                 265                 270

Arg Gly Cys Pro Ala Arg Lys His Val Glu Arg Asp Pro Ser Asp Pro
        275                 280                 285

Ser Met Leu Ile Val Thr Tyr Glu Gly Asp His Arg His Thr Pro Gly
    290                 295                 300

Asp Gln Glu Ala Ala Ala Ala Leu Thr Pro Leu Pro Glu Leu His Lys
305                 310                 315                 320

Leu
```

-continued

<210> SEQ ID NO 156
<211> LENGTH: 334
<212> TYPE: PRT
<213> ORGANISM: Capsella rubella

<400> SEQUENCE: 156

```
Met Ala Val Asp Leu Met Arg Phe Pro Lys Ile Asp Asp Gln Thr Ala
1               5                   10                  15

Ile Gln Glu Ala Ala Ser Gln Gly Leu Gln Ser Met Glu His Leu Ile
            20                  25                  30

Arg Val Leu Ser Asn Arg Pro Glu Gln Gln His Thr Val Asp Cys Ser
        35                  40                  45

Glu Ile Thr Asp Phe Thr Val Ser Lys Phe Lys Thr Val Ile Ser Leu
    50                  55                  60

Leu Asn Arg Thr Gly His Ala Arg Phe Arg Arg Gly Pro Val Arg Ser
65                  70                  75                  80

Ser Pro Val Val Ser Pro Pro Leu Pro Gln Ile Val Lys Thr Ala Pro
                85                  90                  95

Ile Val Ser Gln Pro Leu Arg Thr Thr Thr Asn Leu Ser Gln Thr Ala
            100                 105                 110

Pro Pro Pro Ser Ser Phe Val Leu Pro Arg Gln Pro Arg Arg Ser His
        115                 120                 125

Ser Asp Phe Ser Lys Pro Thr Ile Phe Gly Ser Lys Ser Lys Ser Ser
    130                 135                 140

Asp Leu Glu Phe Ser Lys Glu Asn Phe Ser Val Ser Leu Asn Ser Ser
145                 150                 155                 160

Tyr Met Ser Ser Ala Ile Thr Gly Asp Gly Ser Val Ser Asn Gly Lys
                165                 170                 175

Ile Phe Leu Ala Ser Ala Pro Ser Gln Pro Val Thr Ser Ser Gly Lys
            180                 185                 190

Pro Pro Leu Ala Gly His Pro Tyr Arg Lys Arg Cys Leu Glu His Glu
        195                 200                 205

His Ser Glu Ser Phe Ser Gly Arg Val Ser Gly Ser Gly His Gly Lys
    210                 215                 220

Cys His Cys Lys Lys Ser Arg Lys Asn Lys Met Lys Arg Thr Val Arg
225                 230                 235                 240

Val Pro Ala Ile Ser Ala Lys Ile Ala Asp Ile Pro Pro Asp Glu Tyr
                245                 250                 255

Ser Trp Arg Lys Tyr Gly Gln Lys Pro Ile Lys Gly Ser Pro His Pro
            260                 265                 270

Arg Gly Tyr Tyr Lys Cys Ser Thr Tyr Arg Gly Cys Pro Ala Arg Lys
        275                 280                 285

His Val Glu Arg Ala Leu Asp Asp Pro Thr Met Leu Ile Val Thr Tyr
    290                 295                 300

Glu Gly Glu His Arg His Asn Gln Ser Ala Gly Gly Met His Glu Thr
305                 310                 315                 320

Ile Ser Ser Ser Gly Val Asn Asp Leu Val Phe Ala Ser Ala
                325                 330
```

<210> SEQ ID NO 157
<211> LENGTH: 330
<212> TYPE: PRT
<213> ORGANISM: Oryza sativa subsp.indica -continued

<400> SEQUENCE: 157

Met Ile Thr Met Asp Leu Met Ser Gly Tyr Gly Arg Val Asp Glu Gln
1               5                   10                  15

Val Ala Ile Gln Glu Ala Ala Ala Ala Gly Leu Arg Gly Met Glu His
            20                  25                  30

Leu Ile Leu Gln Leu Ser Gln Thr Gly Thr Ser Glu Arg Ser Pro Ala
        35                  40                  45

Pro Ala Pro Ala Gln Glu Gln Gln Gln Gln Gln Gln Val Asp Cys Arg
    50                  55                  60

Glu Ile Thr Asp Met Thr Val Ser Lys Phe Lys Lys Val Ile Ser Met
65                  70                  75                  80

Leu Asn Arg Thr Gly His Ala Arg Phe Arg Arg Gly Pro Val Val Ala
                85                  90                  95

Gln Ser Ser Gly Pro Ala Ala Ser Glu Pro Ala Pro Val Arg Ser Ser
            100                 105                 110

Pro Ser Ala Val Ser Arg Pro Met Thr Leu Asp Phe Thr Lys Ala Ala
        115                 120                 125

Ser Gly Tyr Gly Lys Asp Ala Gly Phe Ser Val Ser Gly Ile Ser Ala
    130                 135                 140

Ala Ser Ser Ser Phe Leu Ser Ser Val Thr Gly Asp Gly Ser Val Ser
145                 150                 155                 160

Asn Gly Arg Gly Gly Gly Ser Ser Ser Leu Met Leu Pro Pro Pro Pro
                165                 170                 175

Ala Thr Ser Cys Gly Lys Pro Pro Leu Ser Ser Ala Ala Ala Ala Met
            180                 185                 190

Ser Ala Gly Val Gly His Lys Arg Lys Cys His Asp His Ala His Ser
        195                 200                 205

Glu Asn Ile Ala Gly Gly Lys Tyr Gly Ser Thr Gly Gly Arg Cys His
    210                 215                 220

Cys Ser Lys Arg Arg Lys His Arg Val Lys Arg Thr Ile Arg Val Pro
225                 230                 235                 240

Ala Ile Ser Ser Lys Val Ala Asp Ile Pro Ala Asp Asp Phe Ser Trp
                245                 250                 255

Arg Lys Tyr Gly Gln Lys Pro Ile Lys Gly Ser Pro Phe Pro Arg Gly
            260                 265                 270

Tyr Tyr Lys Cys Ser Thr Leu Arg Gly Cys Pro Ala Arg Lys His Val
        275                 280                 285

Glu Arg Asp Pro Ala Asp Pro Ser Met Leu Ile Val Thr Tyr Glu Gly
    290                 295                 300

Glu His Arg His Thr Pro Ser Ala Ala Gly Gln Asp His Pro Pro Ala
305                 310                 315                 320

Pro Pro Pro Pro Leu Ala Leu Pro Leu Ala
                325                 330

<210> SEQ ID NO 158
<211> LENGTH: 338
<212> TYPE: PRT
<213> ORGANISM: Lycopersicon esculentum

<400> SEQUENCE: 158

Met Ala Val Leu Ser Lys Met Asn Glu Ser Phe Ala Val Glu Glu Ala
1               5                   10                  15

Ala Ser Ala Gly Leu Lys Ser Met Glu Asn Leu Ile Arg Leu Val Ser
            20                  25                  30

-continued

His Glu Pro Val Gln Ala Asp Cys Arg Glu Met Ala Asp Phe Thr Val
35 40 45

Ser Lys Phe Lys Lys Val Ile Ser Ile Leu Asp Arg Thr Gly His Ala
50 55 60

Arg Phe Arg Arg Gly Pro Val Gln Ala Gln Ala Pro Ala Pro Val Gln
65 70 75 80

Val Arg Ala Pro Val Arg Gly Pro Val Tyr Pro Asp Ser Phe Thr Ser
85 90 95

Leu Ser Leu Ala Pro Ser Leu Ser Phe Ala Thr Ala Lys Glu Arg Leu
100 105 110

Ala Pro Ser Leu Ser Phe Ala Ser Ala Lys Glu Arg Pro Val Val Gln
115 120 125

Val Gln Thr Ala Leu Thr Leu Asp Phe Ser Lys Leu Asn Val Asn Arg
130 135 140

Pro Ile Gly Asn Ser Ser Ala Phe Thr Ala Phe Thr Val Lys Ser Lys
145 150 155 160

Glu Val Leu Met Ala Asp Pro Thr Pro Thr Asn Ser Ser Ser Phe Met
165 170 175

Ser Thr Ile Thr Gly Glu Ala Thr Val Ser Asn Gly Lys Gln Val Ser
180 185 190

Ser Ser Met Leu Leu Leu Pro Pro Gln Ala Val Asn Phe Pro Thr Thr
195 200 205

Gly Lys Arg Cys Arg Glu His Glu Gln Ser Asp Ala Ile Ser Gly Ser
210 215 220

Lys Ser Thr Gly Ser Gly Lys Cys His Cys Lys Lys Arg Lys Ala Lys
225 230 235 240

Asp Arg Lys Val Ile Arg Ile Pro Ala Ile Ser Thr Arg Val Ala Asp
245 250 255

Ile Pro Gly Asp Glu Phe Ser Trp Arg Lys Tyr Gly Gln Lys Pro Ile
260 265 270

Lys Gly Ser Lys Tyr Pro Arg Gly Tyr Tyr Lys Cys Ser Ser Leu Arg
275 280 285

Gly Cys Pro Ala Arg Lys His Val Glu Arg Ala Met Asp Asp Pro Thr
290 295 300

Met Leu Ile Val Thr Tyr Glu Asp Glu His Cys His Asn Pro Val Ala
305 310 315 320

Ala Met His Gly Asn Ser Ser Gln Met Val Asn Phe Gly Leu Met Glu
325 330 335

Lys Lys

<210> SEQ ID NO 159
<211> LENGTH: 207
<212> TYPE: DNA
<213> ORGANISM: Triticum aestivum

<400> SEQUENCE: 159
tgccggtgcc tggagatcct gtgcgccatc ctcctcccgc ccctcggcgt ctgcctccgc 60
cacggctgct gctccatgga gttctggatc agcgtgctgc tcaccatcct cggctacctc 120
cccggcgtcc tctacgccgc ctacgtcatc tgctccgtcg accccgaccg cgtccgccgc 180
cgcgacgacg actacatcta cgtcgcc 207

-continued

<210> SEQ ID NO 160
<211> LENGTH: 165
<212> TYPE: DNA
<213> ORGANISM: Oryza sativa

<400> SEQUENCE: 160
atgggttcag agacgttctt ggagatcttg ctggccatcc tgctgccgcc gctcggcgtc 60
ttcctccgct acggcatcgg catggagttc tggatcgccc tgctgctcac catcctggga 120
tacttacccg gcatcatcta cgctgtttat gtgcttgttg cttaa 165

<210> SEQ ID NO 161
<211> LENGTH: 165
<212> TYPE: DNA
<213> ORGANISM: Hordeum vulgare

<400> SEQUENCE: 161
atggcctcag caacgttcat agaggtgatc ctcgccatca tcctgcctcc agtaggcgtc 60
ttcctgcgct acggcctcgc cgtggagttc tggatctgtc tcttgctgac cctactgggg 120
tacataccgg ggatcatcta cgcggtgtac gtgctggtgg cttaa 165

<210> SEQ ID NO 162
<211> LENGTH: 698
<212> TYPE: DNA
<213> ORGANISM: Zea mays

<400> SEQUENCE: 162
gttccagcgt ctgcttgctt gctaccacgc ctcctcatct gctgccaccg gcgtctctcc 60
ttcccagctg ggccctgag ctgagagcag agcagggagc gaaactttgc gctgagattg 120
agctgctcct acttggaagg cggcggcgtc ggcaatgggg tcggagacgt tcgtggagat 180
cctgctggcc atcctgctgc cgccggtcgg cgtcttcctc cgctacggca tcggggttga 240
gttctggatc tgcctgctgc tcaccatcct gggatacatc ccgggcatca tctacgccgt 300
ctacgtcctc gtcgcgtgaa agcacaacat ggtgtggtag gtatgacgac gatggtgacc 360
gtccgcccgc ccgccgggga gctggaatat atgagaccca gacccagtgc ttctgatcca 420
tccattccat gcatgcagtg atgcaggcat acgtacgttt agcccatgct gtatgtttgt 480
gtcttgcttt agttagcttt agctagctgc ttgcagctta gcttctctca gctcgtctac 540
cggtccgttt tgctgtgccc atggacatgg atgggaagaa ggaaccgtag cttgtatgca 600
agtgtgtact agagtccaga gtttctactc tgctactgat tctgaatcca gacatgtttt 660
ctgagatctt ccttcgtgct aaaaaaaaaa aaaaaaaa 698

<210> SEQ ID NO 163
<211> LENGTH: 488
<212> TYPE: DNA
<213> ORGANISM: Oryza sativa

<400> SEQUENCE: 163
tgagttccag ccatttcgtc agtgagggag agagagaggt ctgagaagag gagagagagc 60
cttctgcctg acaagaaatt ctgagaagag ggagaatggc gtcggcgacg ttcctggagg 120
tgctcctagc catcttcctg ccgccggtcg gcgtcttcct gcgctacggc ttgggtattg 180
agttctggat cgatctcttg ctgaccatac tgggatacat cccggggatc atctacgcgg 240
tgtatgtgct ggtggcctga tcgaaagagt tcgagcagag ccagcgtcgg gtgatcgagc 300
gatcgtgcaa cggtgcaata gcaactgatg ctgtgctgtg gtgttaagag tacatttgta 360

-continued

```
tgtgtgaaaa tgtgatttat gcgatgagat tagggtcttg acgtcttgtg atgagagtct    420

ttatgctatt ttagagactg taattgggtg tcatgttgct tgtttctctt atctaagata    480

cttttttg                                                             488
```

<210> SEQ ID NO 164
<211> LENGTH: 165
<212> TYPE: DNA
<213> ORGANISM: Oryza sativa

<400> SEQUENCE: 164

```
atgggttcag agacgttctt ggagatcttg ctggccatcc tgctgccgcc gctcggcgtc     60

ttcctccgct acggcatcgg catggagttc tggatcgccc tgctgctcac catcctggga    120

tacttacccg gcatcatcta cgctgtttat gtgcttgttg cttaa                   165
```

<210> SEQ ID NO 165
<211> LENGTH: 740
<212> TYPE: DNA
<213> ORGANISM: Oryza sativa

<400> SEQUENCE: 165

```
tcctgtaata atctcctcgg cgcgacgcca cgccaccgac caacgcgaca aggcgagacg     60

acgcgcacgc gacacacagc cagcggaagc agcagcagga cgacgaggag gaggaggaga    120

tagcttagat cccgctcgcc tctgatcccc ccggatccga tccgagatcc tccacccatg    180

gcgtccggcc ggtgctgcac gttcctcgag atcctgctcg ccatcatcct cccgcccctc    240

ggcgtcttcc tccgcttcgg atgctgcagc atggagttct gcatctgctt gcttctcacc    300

atccttggct atgtccctgg catcatctac gcagtctatg tgcttgttgc tcttgactca    360

gaccagtacc agagggaata tcataccctt gcttaggcag tccacttcaa ttctgtcgaa    420

acctatgctc tatccagaac agccaagttc tgctgttgaa ttggtatctg gtaacttggt    480

ctgggttttt tgatatggcg ttgtgaatct tgtgattata aagtagaaac agtggttcgt    540

atcaaggagg acgaggaggc acctagtcat ttggtcgtta aatctcccta ttcatctgtt    600

ttgtgctaaa tgtataattt tatctggatc tcttgactcc ttatttcagt ctgttaaatg    660

ctcaaactgt ggtctggtct ccattctgta attttgattc aagaaaataa gttgttgagg    720

gtaaaaaaaa aaaaaaaaaa                                                740
```

<210> SEQ ID NO 166
<211> LENGTH: 620
<212> TYPE: DNA
<213> ORGANISM: Oryza sativa

<400> SEQUENCE: 166

```
agatcccgct cgcctctgat ccccccggat ccgatccgag atcctccacc catggcgtcc     60

ggccggtgct gcacgttcct cgagatcctg ctcgccatca tcctcccgcc cctcggcgtc    120

ttcctccgct tcggatgctg cagcatggag ttctgcatct gcttgcttct caccatcctt    180

ggctatgtcc ctggcatcat ctacgcagtc tatgtgcttg ttgctcttga ctcagaccag    240

taccagaggg aatatcatac ccttgcttag gcagtccact tcaattctgt cgaaacctat    300

gctctatcca gaacagccaa gttctgctgt tgaattggta tctggtaact tcgtctgggt    360

tttttgatat ggcgttgtga atcttgtgat tataaagtag aaacagtggt tcgtatcaag    420

gaggacgagg aggcacctag tcatttggtc gttaaatctc cctattcatc tgttttgtgc    480

taaatgtata attttatctg gatctcttga ctccttattt cagtctgtta aatgctcaaa    540
```

-continued ctgtggtctg gtctccattc tgtaattttg attcaagaaa ataagttgtt gagggtaaat 600
attattggtg tttgtatgtc 620

<210> SEQ ID NO 167
<211> LENGTH: 846
<212> TYPE: DNA
<213> ORGANISM: Zea mays

<400> SEQUENCE: 167
gcacgagcca ccacgcaccc caccaaccca tacccatacc agaggctctc tgattttact 60
tctccgcggt agatcggctg agcgagcgag cgaggcacac ggagctagct aaacagagca 120
cacgggtaga aaagcaagat gtcggacggc acggcgacct gcatcgacat catcctcgcc 180
atcatcctgc cgccgctcgg ggtcttcttc aagttcggct gcggggttga gttctggatc 240
tgccttatcc tcaccttcct cggctacctc cccggcatca tctacgccgt ctgggccatc 300
accaagtagc cggccggagc agatgaacca cggtcccctg ccagtgccag gcagctagct 360
gtgactccgt cgcgtgcgtt agcatgcaat gcaagcgcag ggtggtctcg tggggggacg 420
tggtgtgcgc gtgtcttgag atgtgattcc ttccttcttt gtttagttgc tgctgctcct 480
gctggtgtag tactggtgta tccagtcctt ttaatttctt gattagtttg ctcggctgaa 540
gaaatcagga cgcgtgcctg gtgtcgctcc tcagctccat gtacttgtac aaccgttcct 600
ccctgcagct gctgcccctt ctctcttttt tgtttacctt gggttgatgg gttgttaaat 660
tcgttgtttg tctctttttt aaccttcgcg attgtagtac tgggttggtt gcttgcttgg 720
ttggtttcgg ttgggagatc gatgggaata agtctatgat atatatcagt acaacaaaag 780
agagaaagaa attgccgccg tcaaaaaaaa aaaaaaaaaa aaaaaaaaaa aaaaaaaaaa 840
aaaaaa 846

<210> SEQ ID NO 168
<211> LENGTH: 626
<212> TYPE: DNA
<213> ORGANISM: Zea mays

<400> SEQUENCE: 168
gcacgagctt ctttcagaag acgaaatcca ctcaggagcg aggaaagagg gacagaggag 60
ggatagatcc ccgggctcca cgcctccaca accatccgtc ccgatcccga ccagctttga 120
gatcgcgatg gcggacggcc gctgctgcac cttcctggag atcctcttcg ccatcatcct 180
cccgcccctc ggcgtcttcc tccgattcgg ctgctgcaga atagagttct gcatctgcct 240
gctgctcaca atccttggct acgtccccgg aatcatctac gcgatctatg tccttgttgc 300
tctcgactct gaccagcacg agagggaata ctacaccctt gcttagagca tctggttgtg 360
ccaggcgggc ctgcacagtt gagtcgaaat cagtattttt tttctcatgt ggattgtctg 420
acatggcata agcggcaatg ggtaaccaag tgttgtggtc tatatctctg ttacccaact 480
tgtgagctct ctttattgtg ctccagttat tcaatctgta attgtgatac tacaagagaa 540
taagatgcgc atgtatctct gagagcaact gtgatttatg attggtgcta ccttgggctc 600
aaaaacatgt gaacagtcgc tcgtgc 626

<210> SEQ ID NO 169
<211> LENGTH: 547
<212> TYPE: DNA
<213> ORGANISM: Oryza sativa -continued

<400> SEQUENCE: 169
tactttactt tgcagctatt ttgcttctgc ttcttcttgt tcttgttgct ggttggtaat 60
actgcgagag aaattaatca gtagagtgtt catctactat caatttttga tcgaggagag 120
atggcgggaa cggcgaactg catcgacatc ctcatcgcca tcatcctccc gcccctcggc 180
gtcttcctca agttcggatg cgggcatgag ttctggatct gcctgttgct caccttcctc 240
ggctacatcc ccggcatcat ctacgccatc tacgccatca ccaagtaatt catcattagt 300
tactacatca tcaaccaaat cctcaaggga tgggctccaa accgcttcat ctatcttctc 360
gattgccgtg tgcttgttgg aatttggaaa tgatatatgc atccaaaatt cagtcctgag 420
tgctccaatt cttgtcatct agtcattttc aatgtccccc cagtctcttc ctctaatgtt 480
tgatgatatg tagaatctct tgctgttaat ctgttgcttt cgtgtgaata aaaaaaaaaa 540
aaaaaaa 547

<210> SEQ ID NO 170
<211> LENGTH: 716
<212> TYPE: DNA
<213> ORGANISM: Hordeum vulgare

<400> SEQUENCE: 170
tgggcaatac caaaggacaa attctttgct tggttggcat tgcaaaactc tattttcctc 60
ttatttaata aaaaattatt gctttcacct tacctgctgc aattcgaact tgcatggtta 120
aatacgagta cgagactaat ctgtcgtcat gtttatgatt tacttctgaa ttagattaac 180
ataaaatatt gctgatttac taaccactta ttacttctcc atagaagatg ctacgtggag 240
tcacaggtgg ctaagccgtg tgtttgccaa tgacacgtac accagcacca aataaaacca 300
gagcagttgc tgaaaacacc cgaaatcttg tctatatata cgaacgtgta cacgatcttg 360
caatccaaat caaccacaac cacccaccgt cccaccccat cccaagcgct tctttcaaaa 420
aggaagagca gagaaagaaa caagccagaa agcctcgagt aaggtgagcc atggcctcag 480
caacgttcat agaggtgatc ctcgccatca tcctgcctcc agtaggcgtc ttcctgcgct 540
acggcctcgc cgtaagtggc tactctttct aattttacgg gtttcgccgt tccttgcgta 600
gtcccctatc tgatctggat gtgtcaattc aggtggagtt ctggatctgt ctcttgctga 660
ccctactggg gtacataccg gggatcatct acgcggtgta cgtgctggtg gcttaa 716

<210> SEQ ID NO 171
<211> LENGTH: 652
<212> TYPE: DNA
<213> ORGANISM: Lophopyrum elongatum

<400> SEQUENCE: 171
ccggggacac gtacaccacc tacacatcaa agtatcaaac cacaccagtt actaaaaaca 60
cccgaagtct tgtctatata aatggacgtg tgctacatga tatggcaatc caaatcatcc 120
aatccaggcg cctctttcag aagggaaagc agagagaaag aaagaagcca gaaagcctcg 180
agtgaagttt atagctagcc atgggctcgg caacagtcct ggaggtgatc ctcgccatta 240
tcctgcctcc cgtcggcgtc ttcctacgct acaaactcgg cgtggagttc tggatctgtc 300
tcttgctgac catactcggc tacataccgg ggatcatcta cgcggtgtac gtgctggtag 360
tttaagcaac aacctctgct gcagggtcca ggcttggacg agcgagtcgc tgtgcaagag 420
caactgatgc tgtctgtgtt aagatagcat gtctttgtgt atgcttgtat gtattgaata 480
ttgcggattt tttttttgga actcggtatt gttgattctg tgatgtcacg agtgtacgta 540

-continued

```
gctcgagggc tttagggcat tcgtcggctc cagtgtctgt gatcttaaat ttaaagtctt    600

gatgtccaaa tgatcttcgg aatcaatcga agtgggaggt cagtactatt gc            652


<210> SEQ ID NO 172
<211> LENGTH: 616
<212> TYPE: DNA
<213> ORGANISM: Oryza sativa

<400> SEQUENCE: 172

tcctttcttg actcctctct cttcgtctca gcttggagct ccctctttga tttttcttct     60

tcttcttgtt tgtgcaattg tgcatcgttg ttagctggga acaagcagaa gaatggcgga    120

cagcacggcg acctgcatcg acatcatcct cgccatcatc ctgccgccgc tcggcgtctt    180

cttcaagttc ggctgcggga ttgagttctg gatctgcttg ctgctcacct tcttcggcta    240

cctccccggc atcatctacg ctgtctgggt catcaccaag taggaggaga attactaccc    300

ttccaaggtg atggtgaatt ggtgatccgg agcctgtgat tggttgtgcc tggtgtaagc    360

ggcagttgtc aaagctgtga ttttctggtt ctttggacgg atggtgctcg ctgtggtgtt    420

gtgtatgctg tacatctgtt ttggtgtttg tgcttaggtc cctcttctgt tacaacaatt    480

gttttctccc tgttcttccg gggtaccttc tccagtttat cttctgcacc ttctcgtccc    540

tgtactttga atattaatta attaattaat taattgctcc ttgttaaaaa aaaaaaaaaa    600

aaaaaaaaaa aaaaaa                                                    616


<210> SEQ ID NO 173
<211> LENGTH: 195
<212> TYPE: DNA
<213> ORGANISM: Oryza sativa

<400> SEQUENCE: 173

atggcggaca ggccgccggc gatggccgac aggacggcga cgttcgtgga cctcgtcatc     60

gccatcatcc tgcctcccct cggcgtcttc ctcaaggtcg gctgcgagat cgagttctgg    120

atctgcctct tgctcacatt cttgggctac ttcccgggga tcatctacgc cgtctgggta    180

attgtcaatc actag                                                     195


<210> SEQ ID NO 174
<211> LENGTH: 553
<212> TYPE: DNA
<213> ORGANISM: Zea mays

<400> SEQUENCE: 174

gcacgaggcg tggacgcatc gtcatcattc gagcagaggg gagagagaga gagagagaga     60

gagagatgaa ggagggcacg gcgaactgca tcgacatcct catcgccatc atcctcccgc    120

ctctcggcgt cttcctcaag ttcggctgca aggtcgaatt ctggctctgc ctcctgctca    180

ccttcctcgc ctatctcccc gggatcatct acgcgatata cgttatcacc aaggactagc    240

cagctagcgc cgtaaaccgg gacaaggtga gagagctagc tgatcagcca gcggaggtaa    300

tggagatgaa ctgctgagat cacttgccct gctgctcaat gtttctggat ggagactgaa    360

tctcagctgt gctgtgctgt gctgtgctgt gctgtgatgc tgctatatac taccgattga    420

tcctgaaatt tgtcgctttt cgttcgtgtc tgcatagtat gtgatgcata gtctgtaaaa    480

tttctctcag actcttgtgc tatagtatgt gatgcatgca tgtgtttgct tgatgaaaaa    540

aaaaaaaaaa aaa                                                       553
```

-continued

<210> SEQ ID NO 175
<211> LENGTH: 1693
<212> TYPE: DNA
<213> ORGANISM: Hordeum vulgare

<400> SEQUENCE: 175
agcttatcga tgtaaaagtc agttcctttc ctttcggaaa actcttctct attgcattgt 60
ttgaagagaa tatcatacgg aaaccaacat ttggtggaaa ctggtaaaaa ccacaagaaa 120
actatgtttt gaagtttaga aaaacctgaa acaaatactg gatcgttaag aggatcgatc 180
gttttattgt caccgcaaaa tttcaaatcg taacacatta caaattgtaa gctatggaaa 240
agaaatcacc tttgaataat gccaaatagt aatgtcacta ttcagcgctg aaatttgtca 300
ttttcgtagc tcaaatctcc taatgtgttt caacttgaaa ttttgtgtgg caataaacat 360
cattatctaa acattccatt tttttgaatt ctttgaaact ttaaaatatg atttttacaa 420
agttttcgtt gaatgttggt tttcgtacta tgttctcccc actgtttggg atcagttcgc 480
gcaacaacaa caaaaagcct tccaaagtct gcataggcgt ttcgtggaca accaaaattg 540
ggtctctagt accacgggca gcacacaaga acgaacccat cacagccgtg gatgctgcaa 600
aagcaagggc tccagctatg aatactttgg aaacacccca aagggccgtg cgacatgcat 660
agatttttca cgggaagtgc cacatgcatg gatacaacca ggcagggaca caaaaaggat 720
caggcacagc tcatcggaca agaacacgcc accagcaaac agagattttt aagagcaaag 780
gatttagggg atgtttcttt ctaggtattt tttatgtagg gactaaaaaa agtccctttt 840
agtcccatgt gaaagaaata ggagggactt ttagagatta aaaggggtat ctgagactca 900
aggaagaagt ccctatggga gggacttttt gtgacttttt tggctctttt tcaacaatgc 960
ccctacttta gcatgtcatt taataacttc taatatattt ctaggagtaa catggtcttt 1020
ttgcatgtta tttaatgacc tctagtccat gtttggtttt tgaaaagaaa caggtacgga 1080
ctaaaaactt tttagttggg actaaaaaag ttttcaggat tttttaaaaa acaggacctt 1140
agtctaatct ccagagctcc agtatccaat attcgcacgc ggctccagaa gaagatgcta 1200
cgtggagtgc aggtggccaa gccgcgtgca ggcccgggga cacgtacacc acctccacat 1260
caaaccacac cagttactaa aacaacccgg agtcttgtct atataaatgg acgtgtacat 1320
gatctggcaa tccaaatcaa ccaatccagg cgcctctttc agaagtgaaa gcaaggagaa 1380
agaaagaaac cagactcaag tgaagcaaac catgggctct gcaacagtct tggaggtgat 1440
cctcgccatc attctgccac cggtcggcgt cttcctgcgc tacaaactcg gtgtaagtgc 1500
ctactcgttc tatttgtctt gcctactcgt tctatttgtc tacgggtttc gttgagcctt 1560
attgtagtcc ctatctgatc tggttcctgg cgcggatgtg tcgattcagg tggagttctg 1620
gatctgtctc ttgctgacca ttctggggta cataccgggg atcatctacg cggtgtatgt 1680
gctggtggtt taa 1693

<210> SEQ ID NO 176
<211> LENGTH: 569
<212> TYPE: DNA
<213> ORGANISM: Sorghum bicolor

<400> SEQUENCE: 176
ccggggcaaa attttgcact gagattgagc tactacctcc tccagcgcct cttcttgcgc 60
acctagaata gaaagagaac tactgtagaa atatacagct acgagaacta gaaggcggcg 120
agcacatcgg cggcaatggg gtcggagacg ttcctggaga tcctgctggc catcctgctg 180

-continued

```
ccgccggtcg gcgtcttcct ccgctacggc atcggggttg agttctggat ctgcctgctg    240

ctcaccatcc tgggatacat cccgggcatt atctatgccg tctacgtcct cgtcgcatga    300

ttatgattat tatatataat tatgatgtgt gataatgacc ggccgggagc tagattggtt    360

cgagaccacg ggtttctgaa ttctgatcca tccattccat acatgtagcc catgctgtat    420

gttcttgtat cttctaaatt agcttagcta gcggttgttt ctcttgtgtc ctgatccatt    480

ttgttgtgcc catggacaag gatgggagaa aggaactgta gcttcgatgc ttcgtctatg    540

caagtgtgct agatctagtc tagagtttc                                      569
```

<210> SEQ ID NO 177
<211> LENGTH: 516
<212> TYPE: DNA
<213> ORGANISM: Triticum aestivum

<400> SEQUENCE: 177

```
ccacgcgtcc gctagctctg gcctgcttgc tcactctccc acggcaagct agcaccatcg     60

accacatctg tttctcatcg gaggagagaa gctctgcgag agaggaagtt ggttgcgatg    120

ggttcggaga cgttcgtgga gatcctgctg gccatcttgc tgccgccggt cggcgtcttc    180

ctccgctacg gcatcggcgt ggagttctgg atctgcctgc tgctcacggt gctgggctac    240

atccccggca tcatctacgc catcttcgtc ctcgtcgcat agcttgttca cacaattaat    300

cagatcggac tcttggagat agctagatag atagatccag aggcatcttt gttccagttg    360

ctctatctgt tcatggatga gatggctggc gcatcggtgt aagcaggacc tctgctccat    420

gaataaccac catgcatgcc ggttcagtta ctagaccagc tactactgtt tttgtactct    480

tgtgcttagc gctatgtact gccgttctgt gcgtat                               516
```

<210> SEQ ID NO 178
<211> LENGTH: 468
<212> TYPE: DNA
<213> ORGANISM: Hordeum vulgare

<400> SEQUENCE: 178

```
ctttttcaga gaacatatca ccggagaaga agcaggctct gcgactgcga gccagacagg     60

aatttgactg cgatgggttc ggagactttt gtggagatcc tgctggccat cctgctgccg    120

ccggtcggcg tcttcctccg ctacggcatc ggcatggagt tctggatctg cctgctgctc    180

accttgctgg gctacatccc cggcatcatc tacgccatct tcgtcctcgt cgcttaaata    240

gtttcagttt cagcaattaa gcagtacgga ctagtgtgcg gagatggatc gttaccaggc    300

agcatctctg ttccagttgc tctagcggtt catggacgag ctggctggcg catcagtgca    360

agcaggatct ttgctccatg actgaccacc ctgcatgtcg gtccagttac taggccggct    420

accactgttg tgttgagtgc tatattgccg ttctgtgcgt accacttt                 468
```

<210> SEQ ID NO 179
<211> LENGTH: 562
<212> TYPE: DNA
<213> ORGANISM: Zea mays

<400> SEQUENCE: 179

```
tagcgtggtc gcggccgagg tacgcgggga cgcctcgcct cctcatctgc tgccaccggc     60

gtctctcctt cccagctggg gccctgagct gagagccgag ccgggagcga aactttgcgc    120

tgagattgag ctgctcctct acttactact actagaaggc ggcggcgtcg gcgtcggcgt    180

cggcaatggg gtcggagacg ttcgtggaga tcctgctggc catcctgctg ccgccggtcg    240
```

-continued gcgtcttcct ccgctacggc atcggggttg agttctggat ctgcctgccg ctcaccatcc 300
tgggctacat cccgggcatc atctacgccg tctacgtcct cgtcgcgtga cagcacaaca 360
tggtgtggta ggtatgacga tggtgaccgt ccgcccgccg gccgggagct ggaatatatg 420
agacttgaga cccagtgctt ctgatccatc cattccatgc atgcagtgat gcaggcatac 480
gtacgtttag cccatgctgt atgtttgtgt cttgctttag ttagctttag ctagctgctg 540
cagcttagct tctctcagct cg 562

<210> SEQ ID NO 180
<211> LENGTH: 488
<212> TYPE: DNA
<213> ORGANISM: Oryza sativa

<400> SEQUENCE: 180
actacactga agaagaatcg atcgatatct gaaggaagtg aactaagtga tgggttcaaa 60
gacgttcttg gagatcttgc tggccatcct gctgccgccg ctcggcgtct tcctccgcta 120
cggcatcggc atggagttct ggatcgccct gctgctcacc atcctgggat acttacccgg 180
catcatctac gctgtttatg tgcttgttgc ttaattagtt agttactacc aatgatctgt 240
tctgatcgat cgattatgtt agtatcatgg tttagtttag gtggtttcta ttatgtaagt 300
cgtactagct gctacttacg gcatgttctt cggttcctgc ttgcctggat cagtggagct 360
attcgcctat actagacatc gatctctgta gtttctgtca gcattcataa aagtgtgatc 420
tgaattctga ctttctgatg gatcgatgac tatggatgat tcatgtgtga tctgaatgga 480
tgatgatc 488

<210> SEQ ID NO 181
<211> LENGTH: 1614
<212> TYPE: DNA
<213> ORGANISM: Oryza sativa

<400> SEQUENCE: 181
atgtcggacg gcacggccaa ctgcatcgac atcctcatcg ccatcatcct ccctcctctc 60
ggcgtcttcc tcaagttcgg atgcaaggtg gagttctggc tctgtcttct gctcaccttc 120
ttcggctatc tcccggggat catctacgcg gtctatgcta tcaccaaact acggtggctc 180
tggttcaaat ggaaagagga caacaagcct tgggttggaa tggatttacc ttgcgatgac 240
tgcgacaaaa gactctttca ggctgccact acgataaatg tcggcaatgg agaaaaaata 300
aatttttggc atgataagtg gctgcaaaat acatgtccaa aagacattgc acccttgtgt 360
ttcaacctag ctaagcgcaa acagagatcg gttaaaacgg aattgacaaa caattcttgg 420
cttctttcct ttcggcaaat aactacaatt gaagaaatca gcgatcttgt ccagcttggg 480
ggaatgctgc aaaatgttca gcttctaccg caaaccaatg acgacatcac ttggaacctg 540
aacgaatcgg gatcctactc tgcaaacagt gcttatttat ttcagttcca agggtccttc 600
tcttcgattg actttcattc catttggagg tgcccagctg aaccaaagat gcgcttcttt 660
ggatggctaa tccttcacca aaaaactctc acggcccaaa atcttttgcg ccggcactgg 720
ccttgcaatt ggatttgtag cctgtgtgga gaggcgtttg aagacactaa ccatctcttc 780
aatgtctgcc ccttcttcag aaaagtttgg cttatggttt cgacttgctt gtcaatcttg 840
aaagttgagg acatgacaaa atcaccaagc cttagtcaat tgctgattag atcatgcatc 900
tccaatggag atgcaggttc tccacgatta gttgagacca cgcagccgtc gtctcaactt 960
atcgccggtg accaacgtta cgacggggtc atcgccctcg cctcgcctcc tccgatctcc 1020

-continued

```
tcaccaccga atctcttttg cgccgcaacc ggcgccctct ccacagcgca agtcagcttc   1080

gatccctcgc gcgctgccac cggcgccctc tccaccgtgc cgccatcagt tcgtcgatcc   1140

ctcgcgcgtt gccaccggat tccaccccac cgcgtcgcaa gtcagaaatg caaaatcgtt   1200

atatcagtgg atgtgattaa taatgcaact ttcatgtttc ttatacaata tcccccaaaa   1260

gtcaagctca aaggatttcc ccttgccaat agcattggtg gagataaagt ggaaggtgga   1320

aaactaatga ccatgggaag aaggtctgac tatctcattg tcttatttga cctgtatttc   1380

agtatgcgtt tagcttcttg gcaatcaatt gtggatgcaa tagaactgtt tgagcttctt   1440

gctagattcg catttggata tccgtacgtg ttggtgtggg tcctcgagac cgagggagta   1500

gctgagagac tgatgatgaa cgttgtgttt ttcatgggcg atggtgatct ggtggtgctg   1560

gtgtttgaca cggaattttt agataaacag agtagcaaat ttttgataga ctaa         1614
```

<210> SEQ ID NO 182
<211> LENGTH: 521
<212> TYPE: DNA
<213> ORGANISM: Hordeum vulgare

<400> SEQUENCE: 182

```
tgaaagcaag gagaaagaaa gaaaccagac tcaagtgaag caaaccatgg gctctgcaac     60

agtcttggag gtgatcctcg ccatcattct gccaccggtc ggcgtcttcc tgcgctacaa    120

actcggtgtg gagttctgga tctgtctctt gctgaccatt ctggggtaca taccggggat    180

catctacgcg gtgtatgtgc tggtggttta agcaacagcc tctgctgcag ggtccggcgt    240

ttggacgagc gagtcgctgt gcaagatcaa ctgatgctca tgctctatgg gttaagagag    300

aatgtatgcg tgtatgtatg ggttaagaga gtatgtgtat cgatgtatct attgaatatt    360

gtggatttca tttttttttc tggaactcgg tattgttgat cctgtgatgt cacgagtgta    420

cctagctagc tcgagggcat ttgtagtaga gcattcgtcg gccacattgt ttgtgatctt    480

aaatttaaag tattggacgt cgaaaaaaaa aaaaaaaaaa a                        521
```

<210> SEQ ID NO 183
<211> LENGTH: 234
<212> TYPE: DNA
<213> ORGANISM: Arabidopsis thaliana

<400> SEQUENCE: 183

```
atggcgaatg ggtgcgagat ttgctgtgaa ataatgatcg ccatactcat ccctcctcta     60

ggggtttgtc tgaggcatgg ctgttgcact acggaattca tgatatgtct gatcctaacg    120

ctcttgggat acgtaccggg gatcatctac gcactctatg caatcgtgta cgtggatcgt    180

gatcaatttt tcgatgagta ccgtcgtcca cttttctatg cccagtcacc gtga          234
```

<210> SEQ ID NO 184
<211> LENGTH: 367
<212> TYPE: DNA
<213> ORGANISM: Arabidopsis thaliana

<400> SEQUENCE: 184

```
tctcatctca tctctctgaa aaaatgccga gcaactgtga gattctgtgc gagatcatta     60

tcgcgatcct tcttcctcct ctcggagttt gcttcaggaa aggatgctgc actgtggagt    120

ttttgatatg cctggtgttg acgatcttag gctatgtccc ggggataata tatgcgattt    180

acgtgattgt gtttcagcac cgtgaagagt actttgatga atacagacgc cccatctact    240

ctgcttgatt tctgtttctt tggaactgtg ttgctttgac ttgtaccaat aaagttgctt    300
```

-continued

```
tgcagttgtt ttcagagatt tgaaaacgtt tgtgtgtcat ttatatgcaa tattgaaagt    360

ttcttct                                                              367


<210> SEQ ID NO 185
<211> LENGTH: 575
<212> TYPE: DNA
<213> ORGANISM: Arabidopsis thaliana

<400> SEQUENCE: 185

ctaccgacta ctttcagtgt tctcttcttc tccactaatt cagatcacat tcaagaatct     60

tcttcactca catctctgaa aaaatggcga gcaacatgga agttttctgc gagatcttaa    120

tcgcgatcct tcttccacct cttggagttt gtctcaaacg tggctgttgc actgtagagt    180

tcttgatttg cttggtgctg acaatcttag gatacatccc agggataatt tatgcactat    240

acgtgatcgt gtttcaaaac cgtgaaggct ctaccgaact tggagctcca cttaactcag    300

cttgatctgt tttggtccat tacacggatc aatatgttgt tgaaactgtt ttacttatca    360

tgtaccaaat aataagttgc tttgcaattt ttatgtattg aagatttgag aacattgtcg    420

cgttattgat acattgctta tctttttgat gtataacttg ttggcttttg caaagtcagg    480

ctacggacct tcctaagagt taatgtatca aattctttgc caagattgta tttaccggag    540

tttaaacttc gcaaaatgcg gaagcatttt tgagt                               575


<210> SEQ ID NO 186
<211> LENGTH: 400
<212> TYPE: DNA
<213> ORGANISM: Brassica rapa

<400> SEQUENCE: 186

cgctctagat catctctgag aaaaaatggc tagcaatatg gaagttttct gcgagatctt     60

aatagcgatc cttcttccac ctcttggagt ctgcctcaag cgtggctgtt gcactgtaga    120

gttcttgata tgcttggtgt tgactatctt aggctacatc ccagggataa tctatgcgct    180

ttacgtgatc gtgttccaga accgtgaagg ggaaactcag gattacagtg ctccactcaa    240

ctcagcttga gattatctgt cggtccatac aacatgtctt tcacttgaaa ctgtttactt    300

atggaaccac tcaataaagt tgcaatctat ctgattcctt cttatatgta attcaagtat    360

ggcaatttca tgttaaaaaa aaaaaaaaaa aaaaaaaaaa                          400


<210> SEQ ID NO 187
<211> LENGTH: 354
<212> TYPE: DNA
<213> ORGANISM: Arabidopsis thaliana

<400> SEQUENCE: 187

ctcttcttct ctttttcaag tcatcaaatc tgatctaatc tccgtaaatt aatggcgagt     60

agttgcgagc tttgctgcga gatcttcatc gcaattcttc ttcctcctgt cggagtttgt    120

ctcaggcatg gctgttgcac tgttgagttc ttcatttgtt tgatactgac ttgcttaggc    180

tacttaccag gaataatata cgcaatttac gcaatttgtt tcttgcaccg cgatgagtat    240

tttgatgaat acagacgccc aatctactat gttgcttgac ctcttgattg attcttgctc    300

ttgagcacac atattgtact ttaaagtgta atttacttgt atcctggaga taat          354


<210> SEQ ID NO 188
<211> LENGTH: 165
<212> TYPE: DNA
<213> ORGANISM: Arabidopsis thaliana
```

-continued

<400> SEQUENCE: 188
atgggatcag aaactttctt ggaaattatt ctggcgattc ttctacctcc cgtcggcgtt 60
ttccttcgat atggttgtgg ggtagagttc tggatctgtc tcttgttgac gatactgggt 120
tacatccctg ggatcatcta tgctatctac gttcttgtcg gatga 165

<210> SEQ ID NO 189
<211> LENGTH: 428
<212> TYPE: DNA
<213> ORGANISM: Arabidopsis thaliana

<400> SEQUENCE: 189
tttgaagctt ttataatatt ttctcagaaa ctttcaaaga gcttagaaaa atgagtacag 60
ctactttcgt tgatattatt atcgccatcc tcttgcctcc actcggtgtc tttctcagat 120
ttggttgcgg ggttgagttt tggatatgtt tggttttgac gctacttggg tatattcctg 180
ggatcatata cgccatttat gtcctcacca aatgatttac catctatcat catctccttg 240
aacagctgtt ccgtcgtgtt ctcctatctt tgtgactgat tcagcgtttc tttttctttc 300
atcagagttt ttatgtttca agtaatttaa ttaatcatca ctgttgtgtt tgcattgtta 360
tataaatgtt gtgttgatat aaaagaagag agcgttggtt tgtactttgt gtgaagattt 420
tttaaaaa 428

<210> SEQ ID NO 190
<211> LENGTH: 771
<212> TYPE: DNA
<213> ORGANISM: Arabidopsis thaliana

<400> SEQUENCE: 190
aaaaaacaat ttgaagcttt tttttttttt tctctgtttc tttcttagag cttagaaaaa 60
tgagtacagc tactttcgtt gatattatta tcgccatcct cttgcatcaa ctcggtgtct 120
ttctcagatt tggttgcggg gttgagtttt ggatatgttt ggttttgacg ctacttgggt 180
atattcctgg gatcatatac gccatttatg tcctcaccaa atgatttacc atctatcatc 240
atctccttgt aagctctctc tctctctctc tctctttacc ctttggctca ctctcagagt 300
catttttgat atagttttct tgtatgaagc tttttcattg ggaaagttta agtaaatgtt 360
tggtaaacct acacatttca gaacaagtaa attcggataa tttggtttaa agcaaacgaa 420
aattttgcta tgaaaacatg gtttcatgtt ataaatatta ttatgataat attttaagat 480
attgttcaaa ccacataatt aatgtgtaca gatagagata aatatctact tattaataag 540
ataagattat gagaaatgtc tgacacaaaa gagagtaata agactctaat gtggttttgt 600
gttttttttt ttttttgtgg cctggccttt tgacttgact tacatttgtt gtttattgtg 660
ctggaacagc tgttccgtcg tgttctccta cctttgtgac ttgattcagc gtttcttttt 720
ctctcaacaa aaaatttatg ttcaattatt ttaattaatc ttctctgttg t 771

<210> SEQ ID NO 191
<211> LENGTH: 705
<212> TYPE: DNA
<213> ORGANISM: Poncirus trifoliata

<400> SEQUENCE: 191
tttcataaac aaaaatacga agtacaaata acaaaagcag ttactcaaaa ccctaaacac 60
ttctttaatc aaagttcttg ttctttgact ctaaatttta ttttattcca ttttatactt 120
tttaagaatc aatcaaagat gggcacagca acatgcgtag atattatctt ggctgttatc 180

-continued

```
ttgcctcctc taggtgtctt tctcaaattt ggttgcaagg ctgagttttg gatctgtttg    240

ctcttgacaa ttctggggta tatccctgga attatttatg ctgtttatgt catcaccaag    300

tagtgatctc tcttcttcat ctttgattac aaaagcaatt ggagaatttg ataaagactt    360

acgaatcaat atcatccttc ttacaagctt tgtaattttt cttttgactt gttttgacag    420

atggagagat cccaagggca tcatgtgttt atgagatctt ttatttacaa ccgttagatg    480

gacagctctg atttgatgta gccagatggg ttctgattct taatcaactg gggtgtgcgt    540

gcgtgtggga gagagagcac ttgttccgtt tgttaatctt tatcgttttg ttttctttaa    600

tttgtccttt ttaatgaatt ttaattcaat atgttgatgt aaagtggagt attattgagt    660

gagtaaattg ccttgtgaat cattacaagt cccccacaaa aaaaa                   705
```

<210> SEQ ID NO 192
<211> LENGTH: 386
<212> TYPE: DNA
<213> ORGANISM: Arabidopsis thaliana

<400> SEQUENCE: 192

```
aaaacatcaa aaatgggatc agaaactttc ttggaaatta ttctggcgat tcttctacct     60

cccgtcggcg ttttccttcg atatggttgt ggggtaagca ctaaattaca tctttactta    120

gttttatgat taatgaatga atcgttaatt gattattgat aattaatgtg ttaatgaatg    180

caggtagagt tctggatctg tctcttgttg acgatactgg gttacatccc tgggatcatc    240

tatgctatct acgttcttgt cggatgatga ccaaattctc ttgtaaattt ttcataatct    300

ttatttagcc tttgttgttc ttttcttatc gctctttgta ataaacaact cttgcgtttt    360

cgctaaataa aatactattt ttgctt                                         386
```

<210> SEQ ID NO 193
<211> LENGTH: 484
<212> TYPE: DNA
<213> ORGANISM: Arabidopsis thaliana

<400> SEQUENCE: 193

```
ataatcatca agatttagtg tttaagcata ataaatattt tctttgaaat ttgaagagct     60

tgaaaatgag tacagccact ttcgtagaga ttattcttgc tatcatcttg cctcctctcg    120

gcgtctttct caaatttggt tgcaaggttg agttttggat atgtttgatt ttgacgctgt    180

ttggttatct tcccggaatc ctttacgctc tttatatcat caccaagtga tttttcctat    240

ctcctctgtt ctttcctctt gctcctcgaa gaacagctgt ttcgtcgtgc tcttctccct    300

ttgggactga ttcatcattt attttatgtt atgagcaatt gtattctcat tgttgtattt    360

gcattattgt atactttctg ctgatatcaa gaaaaaatcg ttggtttatg tgaggaattt    420

atttatttcg tttaatttgt acaattggta aaatgttgca atgagcaggt ttggattccg    480

gacc                                                                 484
```

<210> SEQ ID NO 194
<211> LENGTH: 159
<212> TYPE: DNA
<213> ORGANISM: Arabidopsis thaliana

<400> SEQUENCE: 194

```
atgggtagct tccttgaggt tctttgtgca atcttcatac ctcctgttgg tgtgttcctc     60

agatatggcc ttgggttgga gttttgggtc tgtttgcttc taacgttatt cgcttttatc    120

cccggactga tatatgccat ctacgttctc accaagtag                           159
```

-continued

<210> SEQ ID NO 195
<211> LENGTH: 469
<212> TYPE: DNA
<213> ORGANISM: Solanum tuberosum

<400> SEQUENCE: 195
aaatctgtta tttaattagt atttgattat cagaagaaga agagaaaaat gggagacagc 60
acaatgacat gtgtagacat tcttttggca atcatcttgc ctcctcttgg tgttttcctc 120
aagtttggct gcaaggtgga gttctggatc tgtgttttgt tgactctttt tggatggcta 180
cctggtattg tctatgctgt ttgggttctt accaagtgat catctcctct agagaagaga 240
aaaaaggtga atatgtgatg aagcccatta ctttatttcc cctaatggag tacattatct 300
agctgttgtt ttatttattt cttggatgta ttttttcaaa gtttatcccc tcctttttct 360
ttattggcca ctattctctc ttgtcaggag tgttggttgt gtacttccat tctgttattt 420
taattgatga ataaccaata attgttttaa aaaaaaaaaa aaaaaaaaa 469

<210> SEQ ID NO 196
<211> LENGTH: 356
<212> TYPE: DNA
<213> ORGANISM: Mesembryanthemum crystallinum

<400> SEQUENCE: 196
gattggggag cagttttggt tgcaaattat tagatcgatt gatcgatcaa ttgatactac 60
tactatttga tagtcagaat caagaaggaa ggaaggaagg aaggaaataa taataataat 120
aatgggttca gagacattca ttgaagtcat ccttgctatt cttctccctc ctgttggtgt 180
ctttctccgt tatggctgtg ggtcgagtt ttggatctgc ttgttgttga cgatattggg 240
gtacattcca gggataatat acgcactata tgtgctcgtc gcatagaatg aactcgtaat 300
gcaatgttaa ttcttggtcg tcctatattt gtaactgctg tgtgtttgta aagttc 356

<210> SEQ ID NO 197
<211> LENGTH: 333
<212> TYPE: DNA
<213> ORGANISM: Citrus sinensis

<400> SEQUENCE: 197
gaggattaac aaacccaatt gtcaacatta catctattag ttcaccaaca aatttggaca 60
aaaaaaaaaa aaaaagacat caaattaact ccgttacaac atcataattt ttaatttatc 120
atccaactaa cacataaatc gcatatataa tccccggtat gtagcccaat actgtcagca 180
acaaacatat ccagaactcc accccacagc cataacgtag gaagacacca acaggaggaa 240
gcagaatggc cagaatcact tccaggaaag tctcggaacc cattcacaag aagaagaaga 300
agcagcagca gccgatgatg ataactgatg aaa 333

<210> SEQ ID NO 198
<211> LENGTH: 426
<212> TYPE: DNA
<213> ORGANISM: Populus balsamifera

<400> SEQUENCE: 198
ggaagcttag ctgcgattta ggatattaaa acaccacaac caccatcacc aacgatagca 60
acatgggttc agagaccttc ctagaagtga tattggcgat tatccttcca cccgtcgggg 120
tcttcctgcg ttatggctgt ggagtggagt tttggatatg tttgctgttg accatactgg 180
gatatattcc agggattata tatgccctct atgtattagt tggatagtgt ataaaatctc 240

-continued

```
tcttggtgag gtttgctgtt tttacgtttc aaggacaatc ctgtttgctc ctcttgtttt    300

attgccttat cagctgtttt cacttcttgt cagataatca ctctttgttt cagtatggtt    360

tagatcatgg taaacctctt tgttcttaag tttttgacag tttgaacatt aataaatgtc    420

gtgtca                                                                426
```

<210> SEQ ID NO 199
<211> LENGTH: 875
<212> TYPE: DNA
<213> ORGANISM: Physcomitrella patens

<400> SEQUENCE: 199

```
cggcgcgcca gaggacgaga caagggggga tcaggagata aagcttccac tccatcgcag     60

cagaatctct tctctcagac ccacttccct gccttcatat ttgcgccatt ccgggtgtgt    120

cctttgcccc tgctgcattg tccagtgctc tgcttgtttc gccgtcgaca tatccagaga    180

aggaggatca cctttttctc ccttcgcagc cccgagcatt ttgcgaagat gccgatcggt    240

tcacgaggcg cttacacgtt cgttgatgtg ctgttggcca tcatcttgcc gccgttgggg    300

gtcttcctca agtatggcct tcagagtgag ttctggattt gtctcgtgct gacaatcctg    360

ggttacttgc ccgggatcat ctacgccatc tacgtcatcg ttggctaggc aatgagtccc    420

tcttcctcca tgagagtagg tgtggatctt gtgtctccac cgccggcatt ccttagcctc    480

atcggagtga atcacagcac ttagtggtga ggcgtggctc agagccatgc atctttcaca    540

ccatgtacag gtttgagatt gttttctaca cgctgagatt tcatggatta ggtagtttta    600

ctcaaagtcg gccgacgaat tgtgttacct ggagattttg tacagaaatt tgtttagagt    660

tgtatgagtt gcatcggatt tcttcagaag ttttgatggc actcttcatc atgccatatg    720

caatgaattc gactgatggc tcttgtagca tgagcagctt gaagtcaaga taaaactgaa    780

aaccagtaat agcagatccc accttagcat cttccttacc catcatcatg tacagtaaac    840

ttgcactttt aatttcaata cctttcaatg ttaac                               875
```

<210> SEQ ID NO 200
<211> LENGTH: 698
<212> TYPE: DNA
<213> ORGANISM: Physcomitrella patens

<400> SEQUENCE: 200

```
aggacaggca gaggacgaga caagggggt tatcgaatat ttgatcgagg tgtgaggttg     60

ttcactagct attgttcgca taactcgatt tggtgctgca cagaagcgag atttgttttc    120

tggtcttagt cctgcgctcc gtgggccgag agaaacatct tgagaagtta ggcttgtgat    180

ctcatttgca aacatgggca agggaggctc cactgcgacc ttttgcgagg tcttgttagc    240

tattctgttg ccgcctctgg gcgtgtttct aagatatgcc tgcgggctgg agttctggat    300

ttgtctactt ttgaccatcc tgggatatat tcctgggatc ttgtatgcgc tttacgtcat    360

tgtaagataa ttctggaagg tctgctcgag gtcttgtgcg ccagacgggg cgaacacaac    420

agagagacgt ccatggtcgt ggactaggat tttgatacct agcacttcaa tggttcaaag    480

gcgtgttatc tatcggtctg ctgttttctt gtagataaag accatgctat cagctttagg    540

atctcaacag gagtttcacc ttgggaaggc tgcagtgatc atcggaccgt ttgggtgctc    600

gcggtaacca caccagaaat gatcatgttt tgtgaatgtt tgtaagagta gatgaatagt    660

ttatcttttg ttgcaataaa tttcatacgt tgaaactc                            698
```

-continued

<210> SEQ ID NO 201
<211> LENGTH: 69
<212> TYPE: PRT
<213> ORGANISM: Triticum aestivum

<400> SEQUENCE: 201

```
Cys Arg Cys Leu Glu Ile Leu Cys Ala Ile Leu Leu Pro Pro Leu Gly
1               5                   10                  15

Val Cys Leu Arg His Gly Cys Cys Ser Met Glu Phe Trp Ile Ser Val
            20                  25                  30

Leu Leu Thr Ile Leu Gly Tyr Leu Pro Gly Val Leu Tyr Ala Ala Tyr
        35                  40                  45

Val Ile Cys Ser Val Asp Pro Asp Arg Val Arg Arg Arg Asp Asp Asp
    50                  55                  60

Tyr Ile Tyr Val Ala
65
```

<210> SEQ ID NO 202
<211> LENGTH: 54
<212> TYPE: PRT
<213> ORGANISM: Oryza sativa

<400> SEQUENCE: 202

```
Met Gly Ser Glu Thr Phe Leu Glu Ile Leu Leu Ala Ile Leu Leu Pro
1               5                   10                  15

Pro Leu Gly Val Phe Leu Arg Tyr Gly Ile Gly Met Glu Phe Trp Ile
            20                  25                  30

Ala Leu Leu Leu Thr Ile Leu Gly Tyr Leu Pro Gly Ile Ile Tyr Ala
        35                  40                  45

Val Tyr Val Leu Val Ala
    50
```

<210> SEQ ID NO 203
<211> LENGTH: 54
<212> TYPE: PRT
<213> ORGANISM: Hordeum vulgare

<400> SEQUENCE: 203

```
Met Ala Ser Ala Thr Phe Ile Glu Val Ile Leu Ala Ile Ile Leu Pro
1               5                   10                  15

Pro Val Gly Val Phe Leu Arg Tyr Gly Leu Ala Val Glu Phe Trp Ile
            20                  25                  30

Cys Leu Leu Leu Thr Leu Leu Gly Tyr Ile Pro Gly Ile Ile Tyr Ala
        35                  40                  45

Val Tyr Val Leu Val Ala
    50
```

<210> SEQ ID NO 204
<211> LENGTH: 54
<212> TYPE: PRT
<213> ORGANISM: Zea mays

<400> SEQUENCE: 204

```
Met Gly Ser Glu Thr Phe Val Glu Ile Leu Leu Ala Ile Leu Leu Pro
1               5                   10                  15

Pro Val Gly Val Phe Leu Arg Tyr Gly Ile Gly Val Glu Phe Trp Ile
            20                  25                  30
```

-continued

```
Cys Leu Leu Leu Thr Ile Leu Gly Tyr Ile Pro Gly Ile Ile Tyr Ala
        35                  40                  45

Val Tyr Val Leu Val Ala
    50


<210> SEQ ID NO 205
<211> LENGTH: 54
<212> TYPE: PRT
<213> ORGANISM: Oryza sativa

<400> SEQUENCE: 205

Met Ala Ser Ala Thr Phe Leu Glu Val Leu Leu Ala Ile Phe Leu Pro
1               5                   10                  15

Pro Val Gly Val Phe Leu Arg Tyr Gly Leu Gly Ile Glu Phe Trp Ile
            20                  25                  30

Asp Leu Leu Leu Thr Ile Leu Gly Tyr Ile Pro Gly Ile Ile Tyr Ala
        35                  40                  45

Val Tyr Val Leu Val Ala
    50


<210> SEQ ID NO 206
<211> LENGTH: 77
<212> TYPE: PRT
<213> ORGANISM: Oryza sativa

<400> SEQUENCE: 206

Met Gly Ser Glu Thr Phe Leu Glu Ile Leu Leu Ala Ile Leu Leu Pro
1               5                   10                  15

Pro Leu Gly Val Phe Leu Arg Tyr Gly Ile Gly Val Ser Ser Ser Ser
            20                  25                  30

Phe Ile Leu Val Leu Phe Asp Leu Ile Phe Phe Met His Ser Cys Trp
        35                  40                  45

Leu Gln Met Glu Phe Trp Ile Ala Leu Leu Leu Thr Ile Leu Gly Tyr
    50                  55                  60

Leu Pro Gly Ile Ile Tyr Ala Val Tyr Val Leu Val Ala
65                  70                  75


<210> SEQ ID NO 207
<211> LENGTH: 51
<212> TYPE: PRT
<213> ORGANISM: Oryza sativa

<400> SEQUENCE: 207

Thr Phe Leu Glu Ile Leu Leu Ala Ile Ile Leu Pro Pro Leu Gly Val
1               5                   10                  15

Phe Leu Arg Phe Gly Cys Cys Ser Met Glu Phe Cys Ile Cys Leu Leu
            20                  25                  30

Leu Thr Ile Leu Gly Tyr Val Pro Gly Ile Ile Tyr Ala Val Tyr Val
        35                  40                  45

Leu Val Ala
    50


<210> SEQ ID NO 208
<211> LENGTH: 51
<212> TYPE: PRT
<213> ORGANISM: Oryza sativa
```

-continued

<400> SEQUENCE: 208

```
Thr Phe Leu Glu Ile Leu Leu Ala Ile Ile Leu Pro Pro Leu Gly Val
1               5                   10                  15

Phe Leu Arg Phe Gly Cys Cys Ser Met Glu Phe Cys Ile Cys Leu Leu
            20                  25                  30

Leu Thr Ile Leu Gly Tyr Val Pro Gly Ile Ile Tyr Ala Val Tyr Val
        35                  40                  45

Leu Val Ala
    50
```

<210> SEQ ID NO 209
<211> LENGTH: 51
<212> TYPE: PRT
<213> ORGANISM: Zea mays

<400> SEQUENCE: 209

```
Gly Thr Ala Thr Cys Ile Asp Ile Ile Leu Ala Ile Ile Leu Pro Pro
1               5                   10                  15

Leu Gly Val Phe Phe Lys Phe Gly Cys Gly Val Glu Phe Trp Ile Cys
            20                  25                  30

Leu Ile Leu Thr Phe Leu Gly Tyr Leu Pro Gly Ile Ile Tyr Ala Val
        35                  40                  45

Trp Ala Ile
    50
```

<210> SEQ ID NO 210
<211> LENGTH: 51
<212> TYPE: PRT
<213> ORGANISM: Zea mays

<400> SEQUENCE: 210

```
Thr Phe Leu Glu Ile Leu Phe Ala Ile Ile Leu Pro Pro Leu Gly Val
1               5                   10                  15

Phe Leu Arg Phe Gly Cys Cys Arg Ile Glu Phe Cys Ile Cys Leu Leu
            20                  25                  30

Leu Thr Ile Leu Gly Tyr Val Pro Gly Ile Ile Tyr Ala Ile Tyr Val
        35                  40                  45

Leu Val Ala
    50
```

<210> SEQ ID NO 211
<211> LENGTH: 51
<212> TYPE: PRT
<213> ORGANISM: Oryza sativa

<400> SEQUENCE: 211

```
Gly Thr Ala Asn Cys Ile Asp Ile Leu Ile Ala Ile Ile Leu Pro Pro
1               5                   10                  15

Leu Gly Val Phe Leu Lys Phe Gly Cys Gly His Glu Phe Trp Ile Cys
            20                  25                  30

Leu Leu Leu Thr Phe Leu Gly Tyr Ile Pro Gly Ile Ile Tyr Ala Ile
        35                  40                  45

Tyr Ala Ile
    50
```

<210> SEQ ID NO 212
<211> LENGTH: 80
<212> TYPE: PRT
<213> ORGANISM: Hordeum vulgare -continued

<400> SEQUENCE: 212

Met Ala Ser Ala Thr Phe Ile Glu Val Ile Leu Ala Ile Ile Leu Pro
1 5 10 15

Pro Val Gly Val Phe Leu Arg Tyr Gly Leu Ala Val Ser Gly Tyr Ser
20 25 30

Phe Phe Tyr Gly Phe Arg Arg Ser Leu Arg Ser Pro Leu Ser Asp Leu
35 40 45

Asp Val Ser Ile Gln Val Glu Phe Trp Ile Cys Leu Leu Leu Thr Leu
50 55 60

Leu Gly Tyr Ile Pro Gly Ile Ile Tyr Ala Val Tyr Val Leu Val Ala
65 70 75 80

<210> SEQ ID NO 213
<211> LENGTH: 53
<212> TYPE: PRT
<213> ORGANISM: Lophopyrum elongatum

<400> SEQUENCE: 213

Met Gly Ser Ala Thr Val Leu Glu Val Ile Leu Ala Ile Ile Leu Pro
1 5 10 15

Pro Val Gly Val Phe Leu Arg Tyr Lys Leu Gly Val Glu Phe Trp Ile
20 25 30

Cys Leu Leu Leu Thr Ile Leu Gly Tyr Ile Pro Gly Ile Ile Tyr Ala
35 40 45

Val Tyr Val Leu Val
50

<210> SEQ ID NO 214
<211> LENGTH: 48
<212> TYPE: PRT
<213> ORGANISM: Oryza sativa

<400> SEQUENCE: 214

Thr Cys Ile Asp Ile Ile Leu Ala Ile Ile Leu Pro Pro Leu Gly Val
1 5 10 15

Phe Phe Lys Phe Gly Cys Gly Ile Glu Phe Trp Ile Cys Leu Leu Leu
20 25 30

Thr Phe Phe Gly Tyr Leu Pro Gly Ile Ile Tyr Ala Val Trp Val Ile
35 40 45

<210> SEQ ID NO 215
<211> LENGTH: 64
<212> TYPE: PRT
<213> ORGANISM: Oryza sativa

<400> SEQUENCE: 215

Met Ala Asp Arg Pro Pro Ala Met Ala Asp Arg Thr Ala Thr Phe Val
1 5 10 15

Asp Leu Val Ile Ala Ile Ile Leu Pro Pro Leu Gly Val Phe Leu Lys
20 25 30

Val Gly Cys Glu Ile Glu Phe Trp Ile Cys Leu Leu Leu Thr Phe Leu
35 40 45

Gly Tyr Phe Pro Gly Ile Ile Tyr Ala Val Trp Val Ile Val Asn His
50 55 60

<210> SEQ ID NO 216
<211> LENGTH: 57
<212> TYPE: PRT
<213> ORGANISM: Zea mays

-continued

<400> SEQUENCE: 216

Met Lys Glu Gly Thr Ala Asn Cys Ile Asp Ile Leu Ile Ala Ile Ile
1 5 10 15

Leu Pro Pro Leu Gly Val Phe Leu Lys Phe Gly Cys Lys Val Glu Phe
20 25 30

Trp Leu Cys Leu Leu Leu Thr Phe Leu Ala Tyr Leu Pro Gly Ile Ile
35 40 45

Tyr Ala Ile Tyr Val Ile Thr Lys Asp
50 55

<210> SEQ ID NO 217
<211> LENGTH: 54
<212> TYPE: PRT
<213> ORGANISM: Hordeum vulgare

<400> SEQUENCE: 217

Met Gly Ser Ala Thr Val Leu Glu Val Ile Leu Ala Ile Ile Leu Pro
1 5 10 15

Pro Val Gly Val Phe Leu Arg Tyr Lys Leu Gly Val Glu Phe Trp Ile
20 25 30

Cys Leu Leu Leu Thr Ile Leu Gly Tyr Ile Pro Gly Ile Ile Tyr Ala
35 40 45

Val Tyr Val Leu Val Val
50

<210> SEQ ID NO 218
<211> LENGTH: 54
<212> TYPE: PRT
<213> ORGANISM: Sorghum bicolor

<400> SEQUENCE: 218

Met Gly Ser Glu Thr Phe Leu Glu Ile Leu Leu Ala Ile Leu Leu Pro
1 5 10 15

Pro Val Gly Val Phe Leu Arg Tyr Gly Ile Gly Val Glu Phe Trp Ile
20 25 30

Cys Leu Leu Leu Thr Ile Leu Gly Tyr Ile Pro Gly Ile Ile Tyr Ala
35 40 45

Val Tyr Val Leu Val Ala
50

<210> SEQ ID NO 219
<211> LENGTH: 54
<212> TYPE: PRT
<213> ORGANISM: Triticum aestivum

<400> SEQUENCE: 219

Met Gly Ser Glu Thr Phe Val Glu Ile Leu Leu Ala Ile Leu Leu Pro
1 5 10 15

Pro Val Gly Val Phe Leu Arg Tyr Gly Ile Gly Val Glu Phe Trp Ile
20 25 30

Cys Leu Leu Leu Thr Val Leu Gly Tyr Ile Pro Gly Ile Ile Tyr Ala
35 40 45

Ile Phe Val Leu Val Ala
50

<210> SEQ ID NO 220
<211> LENGTH: 54
<212> TYPE: PRT
<213> ORGANISM: Hordeum vulgare

<400> SEQUENCE: 220

Met Gly Ser Glu Thr Phe Val Glu Ile Leu Leu Ala Ile Leu Leu Pro
1 5 10 15

Pro Val Gly Val Phe Leu Arg Tyr Gly Ile Gly Met Glu Phe Trp Ile
20 25 30

Cys Leu Leu Leu Thr Leu Leu Gly Tyr Ile Pro Gly Ile Ile Tyr Ala
35 40 45

Ile Phe Val Leu Val Ala
50

<210> SEQ ID NO 221
<211> LENGTH: 54
<212> TYPE: PRT
<213> ORGANISM: Zea mays

<400> SEQUENCE: 221

Met Gly Ser Glu Thr Phe Val Glu Ile Leu Leu Ala Ile Leu Leu Pro
1 5 10 15

Pro Val Gly Val Phe Leu Arg Tyr Gly Ile Gly Val Glu Phe Trp Ile
20 25 30

Cys Leu Pro Leu Thr Ile Leu Gly Tyr Ile Pro Gly Ile Ile Tyr Ala
35 40 45

Val Tyr Val Leu Val Ala
50

<210> SEQ ID NO 222
<211> LENGTH: 54
<212> TYPE: PRT
<213> ORGANISM: Oryza sativa

<400> SEQUENCE: 222

Met Gly Ser Lys Thr Phe Leu Glu Ile Leu Leu Ala Ile Leu Leu Pro
1 5 10 15

Pro Leu Gly Val Phe Leu Arg Tyr Gly Ile Gly Met Glu Phe Trp Ile
20 25 30

Ala Leu Leu Leu Thr Ile Leu Gly Tyr Leu Pro Gly Ile Ile Tyr Ala
35 40 45

Val Tyr Val Leu Val Ala
50

<210> SEQ ID NO 223
<211> LENGTH: 537
<212> TYPE: PRT
<213> ORGANISM: Oryza sativa

<400> SEQUENCE: 223

Met Ser Asp Gly Thr Ala Asn Cys Ile Asp Ile Leu Ile Ala Ile Ile
1 5 10 15

Leu Pro Pro Leu Gly Val Phe Leu Lys Phe Gly Cys Lys Val Glu Phe
20 25 30

Trp Leu Cys Leu Leu Leu Thr Phe Phe Gly Tyr Leu Pro Gly Ile Ile
35 40 45

Tyr Ala Val Tyr Ala Ile Thr Lys Leu Arg Trp Leu Trp Phe Lys Trp
50 55 60

Lys Glu Asp Asn Lys Pro Trp Val Gly Met Asp Leu Pro Cys Asp Asp
65 70 75 80

Cys Asp Lys Arg Leu Phe Gln Ala Ala Thr Thr Ile Asn Val Gly Asn
85 90 95

-continued

```
Gly Glu Lys Ile Asn Phe Trp His Asp Lys Trp Leu Gln Asn Thr Cys
            100                 105                 110

Pro Lys Asp Ile Ala Pro Leu Cys Phe Asn Leu Ala Lys Arg Lys Gln
        115                 120                 125

Arg Ser Val Lys Thr Glu Leu Thr Asn Asn Ser Trp Leu Leu Ser Phe
    130                 135                 140

Arg Gln Ile Thr Thr Ile Glu Glu Ile Ser Asp Leu Val Gln Leu Gly
145                 150                 155                 160

Gly Met Leu Gln Asn Val Gln Leu Leu Pro Gln Thr Asn Asp Asp Ile
                165                 170                 175

Thr Trp Asn Leu Asn Glu Ser Gly Ser Tyr Ser Ala Asn Ser Ala Tyr
            180                 185                 190

Leu Phe Gln Phe Gln Gly Ser Phe Ser Ser Ile Asp Phe His Ser Ile
        195                 200                 205

Trp Arg Cys Pro Ala Glu Pro Lys Met Arg Phe Phe Gly Trp Leu Ile
    210                 215                 220

Leu His Gln Lys Thr Leu Thr Ala Gln Asn Leu Leu Arg Arg His Trp
225                 230                 235                 240

Pro Cys Asn Trp Ile Cys Ser Leu Cys Gly Glu Ala Phe Glu Asp Thr
                245                 250                 255

Asn His Leu Phe Asn Val Cys Pro Phe Phe Arg Lys Val Trp Leu Met
            260                 265                 270

Val Ser Thr Cys Leu Ser Ile Leu Lys Val Glu Asp Met Thr Lys Ser
        275                 280                 285

Pro Ser Leu Ser Gln Leu Leu Ile Arg Ser Cys Ile Ser Asn Gly Asp
    290                 295                 300

Ala Gly Ser Pro Arg Leu Val Glu Thr Thr Gln Pro Ser Ser Gln Leu
305                 310                 315                 320

Ile Ala Gly Asp Gln Arg Tyr Asp Gly Val Ile Ala Leu Ala Ser Pro
                325                 330                 335

Pro Pro Ile Ser Ser Pro Pro Asn Leu Phe Cys Ala Ala Thr Gly Ala
            340                 345                 350

Leu Ser Thr Ala Gln Val Ser Phe Asp Pro Ser Arg Ala Ala Thr Gly
        355                 360                 365

Ala Leu Ser Thr Val Pro Pro Ser Val Arg Arg Ser Leu Ala Arg Cys
    370                 375                 380

His Arg Ile Pro Pro His Arg Val Ala Ser Gln Lys Cys Lys Ile Val
385                 390                 395                 400

Ile Ser Val Asp Val Ile Asn Asn Ala Thr Phe Met Phe Leu Ile Gln
                405                 410                 415

Tyr Pro Pro Lys Val Lys Leu Lys Gly Phe Pro Leu Ala Asn Ser Ile
            420                 425                 430

Gly Gly Asp Lys Val Glu Gly Gly Lys Leu Met Thr Met Gly Arg Arg
        435                 440                 445

Ser Asp Tyr Leu Ile Val Leu Phe Asp Leu Tyr Phe Ser Met Arg Leu
    450                 455                 460

Ala Ser Trp Gln Ser Ile Val Asp Ala Ile Glu Leu Phe Glu Leu Leu
465                 470                 475                 480

Ala Arg Phe Ala Phe Gly Tyr Pro Tyr Val Leu Val Trp Val Leu Glu
                485                 490                 495

Thr Glu Gly Val Ala Glu Arg Leu Met Met Asn Val Val Phe Phe Met
            500                 505                 510
```

-continued

```
Gly Asp Gly Asp Leu Val Val Leu Val Phe Asp Thr Glu Phe Leu Asp
        515                 520                 525

Lys Gln Ser Ser Lys Phe Leu Ile Asp
    530                 535


<210> SEQ ID NO 224
<211> LENGTH: 53
<212> TYPE: PRT
<213> ORGANISM: Hordeum vulgare

<400> SEQUENCE: 224

Met Gly Ser Ala Thr Val Leu Glu Val Ile Leu Ala Ile Ile Leu Pro
1               5                   10                  15

Pro Val Gly Val Phe Leu Arg Tyr Lys Leu Gly Val Glu Phe Trp Ile
            20                  25                  30

Cys Leu Leu Leu Thr Ile Leu Gly Tyr Ile Pro Gly Ile Ile Tyr Ala
        35                  40                  45

Val Tyr Val Leu Val
    50


<210> SEQ ID NO 225
<211> LENGTH: 77
<212> TYPE: PRT
<213> ORGANISM: Arabidopsis thaliana

<400> SEQUENCE: 225

Met Ala Asn Gly Cys Glu Ile Cys Cys Glu Ile Met Ile Ala Ile Leu
1               5                   10                  15

Ile Pro Pro Leu Gly Val Cys Leu Arg His Gly Cys Cys Thr Thr Glu
            20                  25                  30

Phe Met Ile Cys Leu Ile Leu Thr Leu Leu Gly Tyr Val Pro Gly Ile
        35                  40                  45

Ile Tyr Ala Leu Tyr Ala Ile Val Tyr Val Asp Arg Asp Gln Phe Phe
    50                  55                  60

Asp Glu Tyr Arg Arg Pro Leu Phe Tyr Ala Gln Ser Pro
65                  70                  75


<210> SEQ ID NO 226
<211> LENGTH: 74
<212> TYPE: PRT
<213> ORGANISM: Arabidopsis thaliana

<400> SEQUENCE: 226

Met Pro Ser Asn Cys Glu Ile Leu Cys Glu Ile Ile Ile Ala Ile Leu
1               5                   10                  15

Leu Pro Pro Leu Gly Val Cys Phe Arg Lys Gly Cys Cys Thr Val Glu
            20                  25                  30

Phe Leu Ile Cys Leu Val Leu Thr Ile Leu Gly Tyr Val Pro Gly Ile
        35                  40                  45

Ile Tyr Ala Ile Tyr Val Ile Val Phe Gln His Arg Glu Glu Tyr Phe
    50                  55                  60

Asp Glu Tyr Arg Arg Pro Ile Tyr Ser Ala
65                  70


<210> SEQ ID NO 227
<211> LENGTH: 73
<212> TYPE: PRT
<213> ORGANISM: Arabidopsis thaliana
```

<400> SEQUENCE: 227

Met Ala Ser Asn Met Glu Val Phe Cys Glu Ile Leu Ile Ala Ile Leu
1               5                   10                  15

Leu Pro Pro Leu Gly Val Cys Leu Lys Arg Gly Cys Cys Thr Val Glu
            20                  25                  30

Phe Leu Ile Cys Leu Val Leu Thr Ile Leu Gly Tyr Ile Pro Gly Ile
        35                  40                  45

Ile Tyr Ala Leu Tyr Val Ile Val Phe Gln Asn Arg Glu Gly Ser Thr
    50                  55                  60

Glu Leu Gly Ala Pro Leu Asn Ser Ala
65                  70

<210> SEQ ID NO 228
<211> LENGTH: 74
<212> TYPE: PRT
<213> ORGANISM: Brassica rapa

<400> SEQUENCE: 228

Met Ala Ser Asn Met Glu Val Phe Cys Glu Ile Leu Ile Ala Ile Leu
1               5                   10                  15

Leu Pro Pro Leu Gly Val Cys Leu Lys Arg Gly Cys Cys Thr Val Glu
            20                  25                  30

Phe Leu Ile Cys Leu Val Leu Thr Ile Leu Gly Tyr Ile Pro Gly Ile
        35                  40                  45

Ile Tyr Ala Leu Tyr Val Ile Val Phe Gln Asn Arg Glu Gly Glu Thr
    50                  55                  60

Gln Asp Tyr Ser Ala Pro Leu Asn Ser Ala
65                  70

<210> SEQ ID NO 229
<211> LENGTH: 75
<212> TYPE: PRT
<213> ORGANISM: Arabidopsis thaliana

<400> SEQUENCE: 229

Met Ala Ser Ser Cys Glu Leu Cys Cys Glu Ile Phe Ile Ala Ile Leu
1               5                   10                  15

Leu Pro Pro Val Gly Val Cys Leu Arg His Gly Cys Cys Thr Val Glu
            20                  25                  30

Phe Phe Ile Cys Leu Ile Leu Thr Cys Leu Gly Tyr Leu Pro Gly Ile
        35                  40                  45

Ile Tyr Ala Ile Tyr Ala Ile Cys Phe Leu His Arg Asp Glu Tyr Phe
    50                  55                  60

Asp Glu Tyr Arg Arg Pro Ile Tyr Tyr Val Ala
65                  70                  75

<210> SEQ ID NO 230
<211> LENGTH: 53
<212> TYPE: PRT
<213> ORGANISM: Arabidopsis thaliana

<400> SEQUENCE: 230

Met Gly Ser Glu Thr Phe Leu Glu Ile Ile Leu Ala Ile Leu Leu Pro
1               5                   10                  15

Pro Val Gly Val Phe Leu Arg Tyr Gly Cys Gly Val Glu Phe Trp Ile
            20                  25                  30

-continued

```
Cys Leu Leu Leu Thr Ile Leu Gly Tyr Ile Pro Gly Ile Ile Tyr Ala
        35                  40                  45

Ile Tyr Val Leu Val
    50


<210> SEQ ID NO 231
<211> LENGTH: 52
<212> TYPE: PRT
<213> ORGANISM: Arabidopsis thaliana

<400> SEQUENCE: 231

Met Ser Thr Ala Thr Phe Val Asp Ile Ile Ile Ala Ile Leu Leu Pro
1               5                   10                  15

Pro Leu Gly Val Phe Leu Arg Phe Gly Cys Gly Val Glu Phe Trp Ile
            20                  25                  30

Cys Leu Val Leu Thr Leu Leu Gly Tyr Ile Pro Gly Ile Ile Tyr Ala
        35                  40                  45

Ile Tyr Val Leu
    50


<210> SEQ ID NO 232
<211> LENGTH: 52
<212> TYPE: PRT
<213> ORGANISM: Arabidopsis thaliana

<400> SEQUENCE: 232

Met Ser Thr Ala Thr Phe Val Asp Ile Ile Ile Ala Ile Leu Leu His
1               5                   10                  15

Gln Leu Gly Val Phe Leu Arg Phe Gly Cys Gly Val Glu Phe Trp Ile
            20                  25                  30

Cys Leu Val Leu Thr Leu Leu Gly Tyr Ile Pro Gly Ile Ile Tyr Ala
        35                  40                  45

Ile Tyr Val Leu
    50


<210> SEQ ID NO 233
<211> LENGTH: 52
<212> TYPE: PRT
<213> ORGANISM: Poncirus trifoliata

<400> SEQUENCE: 233

Met Gly Thr Ala Thr Cys Val Asp Ile Ile Leu Ala Val Ile Leu Pro
1               5                   10                  15

Pro Leu Gly Val Phe Leu Lys Phe Gly Cys Lys Ala Glu Phe Trp Ile
            20                  25                  30

Cys Leu Leu Leu Thr Ile Leu Gly Tyr Ile Pro Gly Ile Ile Tyr Ala
        35                  40                  45

Val Tyr Val Ile
    50


<210> SEQ ID NO 234
<211> LENGTH: 78
<212> TYPE: PRT
<213> ORGANISM: Arabidopsis thaliana

<400> SEQUENCE: 234

Met Gly Ser Glu Thr Phe Leu Glu Ile Ile Leu Ala Ile Leu Leu Pro
1               5                   10                  15

Pro Val Gly Val Phe Leu Arg Tyr Gly Cys Gly Val Ser Thr Lys Leu
            20                  25                  30
```

-continued

```
His Leu Tyr Leu Val Leu Leu Met Asn Glu Ser Leu Ile Asp Tyr Leu
        35                  40                  45

Met Cys Met Gln Val Glu Phe Trp Ile Cys Leu Leu Leu Thr Ile Leu
    50                  55                  60

Gly Tyr Ile Pro Gly Ile Ile Tyr Ala Ile Tyr Val Leu Val
65                  70                  75


<210> SEQ ID NO 235
<211> LENGTH: 52
<212> TYPE: PRT
<213> ORGANISM: Arabidopsis thaliana

<400> SEQUENCE: 235

Met Ser Thr Ala Thr Phe Val Glu Ile Ile Leu Ala Ile Ile Leu Pro
1               5                   10                  15

Pro Leu Gly Val Phe Leu Lys Phe Gly Cys Lys Val Glu Phe Trp Ile
            20                  25                  30

Cys Leu Ile Leu Thr Leu Phe Gly Tyr Leu Pro Gly Ile Leu Tyr Ala
        35                  40                  45

Leu Tyr Ile Ile
    50


<210> SEQ ID NO 236
<211> LENGTH: 50
<212> TYPE: PRT
<213> ORGANISM: Arabidopsis thaliana

<400> SEQUENCE: 236

Met Gly Ser Phe Leu Glu Val Leu Cys Ala Ile Phe Ile Pro Pro Val
1               5                   10                  15

Gly Val Phe Leu Arg Tyr Gly Leu Gly Leu Glu Phe Trp Val Cys Leu
            20                  25                  30

Leu Leu Thr Leu Phe Ala Phe Ile Pro Gly Leu Ile Tyr Ala Ile Tyr
        35                  40                  45

Val Leu
    50


<210> SEQ ID NO 237
<211> LENGTH: 56
<212> TYPE: PRT
<213> ORGANISM: Solanum tuberosum

<400> SEQUENCE: 237

Met Gly Asp Ser Thr Met Thr Cys Val Asp Ile Leu Leu Ala Ile Ile
1               5                   10                  15

Leu Pro Pro Leu Gly Val Phe Leu Lys Phe Gly Cys Lys Val Glu Phe
            20                  25                  30

Trp Ile Cys Val Leu Leu Thr Leu Phe Gly Trp Leu Pro Gly Ile Val
        35                  40                  45

Tyr Ala Val Trp Val Leu Thr Lys
    50                  55


<210> SEQ ID NO 238
<211> LENGTH: 54
<212> TYPE: PRT
<213> ORGANISM: Mesembryanthemum crystallinum
```

<400> SEQUENCE: 238

```
Met Gly Ser Glu Thr Phe Ile Glu Val Ile Leu Ala Ile Leu Leu Pro
1               5                   10                  15

Pro Val Gly Val Phe Leu Arg Tyr Gly Cys Gly Val Glu Phe Trp Ile
            20                  25                  30

Cys Leu Leu Leu Thr Ile Leu Gly Tyr Ile Pro Gly Ile Ile Tyr Ala
        35                  40                  45

Leu Tyr Val Leu Val Ala
    50
```

<210> SEQ ID NO 239
<211> LENGTH: 53
<212> TYPE: PRT
<213> ORGANISM: Citrus sinensis

<400> SEQUENCE: 239

```
Met Gly Ser Glu Thr Phe Leu Glu Val Ile Leu Ala Ile Leu Leu Pro
1               5                   10                  15

Pro Val Gly Val Phe Leu Arg Tyr Gly Cys Gly Val Glu Phe Trp Ile
            20                  25                  30

Cys Leu Leu Leu Thr Val Leu Gly Tyr Ile Pro Gly Ile Ile Tyr Ala
        35                  40                  45

Ile Tyr Val Leu Val
    50
```

<210> SEQ ID NO 240
<211> LENGTH: 53
<212> TYPE: PRT
<213> ORGANISM: Populus balsamifera

<400> SEQUENCE: 240

```
Met Gly Ser Glu Thr Phe Leu Glu Val Ile Leu Ala Ile Ile Leu Pro
1               5                   10                  15

Pro Val Gly Val Phe Leu Arg Tyr Gly Cys Gly Val Glu Phe Trp Ile
            20                  25                  30

Cys Leu Leu Leu Thr Ile Leu Gly Tyr Ile Pro Gly Ile Ile Tyr Ala
        35                  40                  45

Leu Tyr Val Leu Val
    50
```

<210> SEQ ID NO 241
<211> LENGTH: 59
<212> TYPE: PRT
<213> ORGANISM: Physcomitrella patens

<400> SEQUENCE: 241

```
Met Pro Ile Gly Ser Arg Gly Ala Tyr Thr Phe Val Asp Val Leu Leu
1               5                   10                  15

Ala Ile Ile Leu Pro Pro Leu Gly Val Phe Leu Lys Tyr Gly Leu Gln
            20                  25                  30

Ser Glu Phe Trp Ile Cys Leu Val Leu Thr Ile Leu Gly Tyr Leu Pro
        35                  40                  45

Gly Ile Ile Tyr Ala Ile Tyr Val Ile Val Gly
    50                  55
```

<210> SEQ ID NO 242
<211> LENGTH: 49
<212> TYPE: PRT
<213> ORGANISM: Physcomitrella patens -continued

<400> SEQUENCE: 242

```
Thr Phe Cys Glu Val Leu Leu Ala Ile Leu Leu Pro Pro Leu Gly Val
1               5                   10                  15

Phe Leu Arg Tyr Ala Cys Gly Leu Glu Phe Trp Ile Cys Leu Leu Leu
            20                  25                  30

Thr Ile Leu Gly Tyr Ile Pro Gly Ile Leu Tyr Ala Leu Tyr Val Ile
        35                  40                  45

Val
```

<210> SEQ ID NO 243
<211> LENGTH: 1178
<212> TYPE: DNA
<213> ORGANISM: Artificial Sequence
<220> FEATURE:
<223> OTHER INFORMATION: Vector
<220> FEATURE:
<221> NAME/KEY: misc_feature
<222> LOCATION: (681)..(681)
<223> OTHER INFORMATION: n is a, c, g, or t

<400> SEQUENCE: 243

```
ggctggtaaa acaaatataa gtattaatat aaatataata caatagaagg aaaataaata     60

aaatttccct ctgtgccgtg caaaaatgca cggcaatggg ctggcccgca cggcaaaggc    120

atcgttgccg tgtccacggc aatgggttgg cccgcacggc aaaggcatcg ttgccgtgtc    180

cacgtcttcg ccgtgcgcct tggctctatc tttgccgtga agcgttcttt gccgtgtgcc    240

ttttatttct ttgccgtggg atgctgcctt tgccgagcgc tgagctggcg ctttgccgtg    300

cgcgtattgt ttgccgtgcg tcgtcccaga gctgtacggc aaagaattca ctgccgtgca    360

cgagacacac gggaaagaag ttttgcatgg caaagggcgc tgacagcaca cggcaaagag    420

cctggcacgg cattgagctt ttttcccgta atgatagacg gcataatata atggacgcac    480

atgctgatgt caggatgtca cccactcatc ctagtatttg tgggacgtga attctttgtg    540

agatgggcaa tggggtgtga acaaaataag ttttgtacta gtagataaac atttttaccc    600

ataaacaatt gttctgtatt gaatgagaaa ttattttgta ctggatgaaa attttctgag    660

taactgtgta agattaacat naatcaagag acaaatccaa tggctacaaa gtcaactaat    720

acttgttaaa agttccgata cttaaaatta tcaaaactga tatatagaat attgcccatc    780

tcgccaccgt gctagtttaa cagacgatgg acgaatatca gtcttgtatt ggataatcga    840

tgcatgcgag ctatcggcca cctgtccatg cttccagaag gagccgagac gtggcgactt    900

cgtccgacgc gccgactatc tgcacacgcc cggcttctcg tcgtgggcga gtcagcagtt    960

acgggctttc cgcctaccaa ctcacacgta gcgccctatc gtggcgcttg atcgatgcaa   1020

cagcgatgcc tatcccagct cctcaagctg cttataagta tgtcctcggc catcactgct   1080

tacacaacaa acacagctac ttatcgcagt gtactaaaca agacgtacta gctagatttc   1140

gtgaggtaaa atcagtgcaa tatcacttgt gcaagatg                           1178
```

<210> SEQ ID NO 244
<211> LENGTH: 11809
<212> TYPE: DNA
<213> ORGANISM: Artificial Sequence
<220> FEATURE:
<223> OTHER INFORMATION: Vector -continued

<400> SEQUENCE: 244
ggaattcgat atcaagcttg gcactggccg tcgttttaca acgtcgtgac tgggaaaacc 60
ctggcgttac ccaacttaat cgccttgcag cacatccccc tttcgccagc tggcgtaata 120
gcgaagaggc ccgcaccgat cgcccttccc aacagttgcg cagcctgaat ggcgaatgct 180
agagcagctt gagcttggat cagattgtcg tttcccgcct tcagtttaaa ctatcagtgt 240
ttgacaggat atattggcgg gtaaacctaa gagaaaagag cgtttattag aataacggat 300
atttaaaagg gcgtgaaaag gtttatccgt tcgtccattt gtatgtgcat gccaaccaca 360
gggttcccct cgggatcaaa gtactttgat ccaacccctc cgctgctata gtgcagtcgg 420
cttctgacgt tcagtgcagc cgtcttctga aaacgacatg tcgcacaagt cctaagttac 480
gcgacaggct gccgccctgc ccttttcctg gcgttttctt gtcgcgtgtt ttagtcgcat 540
aaagtagaat acttgcgact agaaccggag acattacgcc atgaacaaga gcgccgccgc 600
tggcctgctg ggctatgccc gcgtcagcac cgacgaccag gacttgacca accaacgggc 660
cgaactgcac gcggccggct gcaccaagct gttttccgag aagatcaccg gcaccaggcg 720
cgaccgcccg gagctggcca ggatgcttga ccacctacgc cctggcgacg ttgtgacagt 780
gaccaggcta gaccgcctgg cccgcagcac ccgcgaccta ctggacattg ccgagcgcat 840
ccaggaggcc ggcgcgggcc tgcgtagcct ggcagagccg tgggccgaca ccaccacgcc 900
ggccggccgc atggtgttga ccgtgttcgc cggcattgcc gagttcgagc gttccctaat 960
catcgaccgc acccggagcg ggcgcgaggc cgccaaggcc cgaggcgtga agtttggccc 1020
ccgccctacc ctcaccccgg cacagatcgc gcacgcccgc gagctgatcg accaggaagg 1080
ccgcaccgtg aaagaggcgg ctgcactgct tggcgtgcat cgctcgaccc tgtaccgcgc 1140
acttgagcgc agcgaggaag tgacgcccac cgaggccagg cggcgcggtg ccttccgtga 1200
ggacgcattg accgaggccg acgccctggc ggccgccgag aatgaacgcc aagaggaaca 1260
agcatgaaac cgcaccagga cggccaggac gaaccgtttt tcattaccga agagatcgag 1320
gcggagatga tcgcggccgg gtacgtgttc gagccgcccg cgcacgtctc aaccgtgcgg 1380
ctgcatgaaa tcctggccgg tttgtctgat gccaagctgg cggcctggcc ggccagcttg 1440
gccgctgaag aaaccgagcg ccgccgtcta aaaaggtgat gtgtatttga gtaaaacagc 1500
ttgcgtcatg cggtcgctgc gtatatgatg cgatgagtaa ataaacaaat acgcaagggg 1560
aacgcatgaa ggttatcgct gtacttaacc agaaaggcgg gtcaggcaag acgaccatcg 1620
caacccatct agcccgcgcc ctgcaactcg ccggggccga tgttctgtta gtcgattccg 1680
atccccaggg cagtgcccgc gattgggcgg ccgtgcggga agatcaaccg ctaaccgttg 1740
tcggcatcga ccgcccgacg attgaccgcg acgtgaaggc catcggccgg cgcgacttcg 1800
tagtgatcga cggagcgccc caggcggcgg acttggctgt gtccgcgatc aaggcagccg 1860
acttcgtgct gattccggtg cagccaagcc cttacgacat atgggccacc gccgacctgg 1920
tggagctggt taagcagcgc attgaggtca cggatggaag gctacaagcg gcctttgtcg 1980
tgtcgcgggc gatcaaaggc acgcgcatcg gcggtgaggt tgccgaggcg ctggccgggt 2040
acgagctgcc cattcttgag tcccgtatca cgcagcgcgt gagctaccca ggcactgccg 2100
ccgccggcac aaccgttctt gaatcagaac ccgagggcga cgctgcccgc gaggtccagg 2160
cgctggccgc tgaaattaaa tcaaaactca tttgagttaa tgaggtaaag agaaaatgag 2220
caaaagcaca aacacgctaa gtgccggccg tccgagcgca cgcagcagca aggctgcaac 2280
gttggccagc ctggcagaca cgccagccat gaagcgggtc aactttcagt tgccggcgga 2340

-continued

```
ggatcacacc aagctgaaga tgtacgcggt acgccaaggc aagaccatta ccgagctgct   2400

atctgaatac atcgcgcagc taccagagta aatgagcaaa tgaataaatg agtagatgaa   2460

ttttagcggc taaaggaggc ggcatggaaa atcaagaaca accaggcacc gacgccgtgg   2520

aatgccccat gtgtggagga acgggcggtt ggccaggcgt aagcggctgg gttgtctgcc   2580

ggccctgcaa tggcactgga acccccaagc ccgaggaatc ggcgtgacgg tcgcaaacca   2640

tccggcccgg tacaaatcgg cgcggcgctg ggtgatgacc tggtggagaa gttgaaggcc   2700

gcgcaggccg cccagcggca acgcatcgag gcagaagcac gccccggtga atcgtggcaa   2760

gcggccgctg atcgaatccg caaagaatcc cggcaaccgc cggcagccgg tgcgccgtcg   2820

attaggaagc cgcccaaggg cgacgagcaa ccagattttt tcgttccgat gctctatgac   2880

gtgggcaccc gcgatagtcg cagcatcatg gacgtggccg ttttccgtct gtcgaagcgt   2940

gaccgacgag ctggcgaggt gatccgctac gagcttccag acgggcacgt agaggtttcc   3000

gcagggccgg ccggcatggc cagtgtgtgg gattacgacc tggtactgat ggcggtttcc   3060

catctaaccg aatccatgaa ccgataccgg gaagggaagg gagacaagcc cggccgcgtg   3120

ttccgtccac acgttgcgga cgtactcaag ttctgccggc gagccgatgg cggaaagcag   3180

aaagacgacc tggtagaaac ctgcattcgg ttaaacacca cgcacgttgc catgcagcgt   3240

acgaagaagg ccaagaacgg ccgcctggtg acggtatccg agggtgaagc cttgattagc   3300

cgctacaaga tcgtaaagag cgaaaccggg cggccggagt acatcgagat cgagctagct   3360

gattggatgt accgcgagat cacagaaggc aagaacccgg acgtgctgac ggttcacccc   3420

gattactttt tgatcgatcc cggcatcggc cgttttctct accgcctggc acgccgcgcc   3480

gcaggcaagg cagaagccag atggttgttc aagacgatct acgaacgcag tggcagcgcc   3540

ggagagttca agaagttctg tttcaccgtg cgcaagctga tcgggtcaaa tgacctgccg   3600

gagtacgatt tgaaggagga ggcggggcag gctggcccga tcctagtcat gcgctaccgc   3660

aacctgatcg agggcgaagc atccgccggt tcctaatgta cggagcagat gctagggcaa   3720

attgccctag caggggaaaa aggtcgaaaa ggtctctttc ctgtggatag cacgtacatt   3780

gggaacccaa agccgtacat tgggaaccgg aacccgtaca ttgggaaccc aaagccgtac   3840

attgggaacc ggtcacacat gtaagtgact gatataaaag agaaaaaagg cgatttttcc   3900

gcctaaaact ctttaaaact tattaaaact cttaaaaccc gcctggcctg tgcataactg   3960

tctggccagc gcacagccga agagctgcaa aaagcgccta cccttcggtc gctgcgctcc   4020

ctacgccccg ccgcttcgcg tcggcctatc gcggccgctg gccgctcaaa aatggctggc   4080

ctacggccag gcaatctacc agggcgcgga caagccgcgc cgtcgccact cgaccgccgg   4140

cgcccacatc aaggcaccct gcctcgcgcg tttcggtgat gacggtgaaa acctctgaca   4200

catgcagctc ccggagacgg tcacagcttg tctgtaagcg gatgccggga gcagacaagc   4260

ccgtcagggc gcgtcagcgg gtgttggcgg gtgtcggggc gcagccatga cccagtcacg   4320

tagcgatagc ggagtgtata ctggcttaac tatgcggcat cagagcagat tgtactgaga   4380

gtgcaccata tgcggtgtga aataccgcac agatgcgtaa ggagaaaata ccgcatcagg   4440

cgctcttccg cttcctcgct cactgactcg ctgcgctcgg tcgttcggct gcggcgagcg   4500

gtatcagctc actcaaaggc ggtaatacgg ttatccacag aatcagggga taacgcagga   4560

aagaacatgt gagcaaaagg ccagcaaaag gccaggaacc gtaaaaaggc cgcgttgctg   4620

gcgtttttcc ataggctccg cccccctgac gagcatcaca aaaatcgacg ctcaagtcag   4680

aggtggcgaa acccgacagg actataaaga taccaggcgt ttccccctgg aagctccctc   4740
```

-continued

```
gtgcgctctc ctgttccgac cctgccgctt accggatacc tgtccgcctt tctcccttcg   4800

ggaagcgtgg cgctttctca tagctcacgc tgtaggtatc tcagttcggt gtaggtcgtt   4860

cgctccaagc tgggctgtgt gcacgaaccc cccgttcagc ccgaccgctg cgccttatcc   4920

ggtaactatc gtcttgagtc caacccggta agacacgact tatcgccact ggcagcagcc   4980

actggtaaca ggattagcag agcgaggtat gtaggcggtg ctacagagtt cttgaagtgg   5040

tggcctaact acggctacac tagaaggaca gtatttggta tctgcgctct gctgaagcca   5100

gttaccttcg gaaaaagagt tggtagctct tgatccggca aacaaaccac cgctggtagc   5160

ggtggttttt ttgtttgcaa gcagcagatt acgcgcagaa aaaaaggatc tcaagaagat   5220

cctttgatct tttctacggg gtctgacgct cagtggaacg aaaactcacg ttaagggatt   5280

ttggtcatgc attctaggta ctaaaacaat tcatccagta aaatataata ttttattttc   5340

tcccaatcag gcttgatccc cagtaagtca aaaaatagct cgacatactg ttcttccccg   5400

atatcctccc tgatcgaccg gacgcagaag gcaatgtcat accacttgtc cgccctgccg   5460

cttctcccaa gatcaataaa gccacttact ttgccatctt tcacaaagat gttgctgtct   5520

cccaggtcgc cgtgggaaaa gacaagttcc tcttcgggct tttccgtctt taaaaaatca   5580

tacagctcgc gcggatcttt aaatggagtg tcttcttccc agttttcgca atccacatcg   5640

gccagatcgt tattcagtaa gtaatccaat tcggctaagc ggctgtctaa gctattcgta   5700

tagggacaat ccgatatgtc gatggagtga aagagcctga tgcactccgc atacagctcg   5760

ataatctttt cagggctttg ttcatcttca tactcttccg agcaaaggac gccatcggcc   5820

tcactcatga gcagattgct ccagccatca tgccgttcaa agtgcaggac ctttggaaca   5880

ggcagctttc cttccagcca tagcatcatg tccttttccc gttccacatc ataggtggtc   5940

cctttatacc ggctgtccgt catttttaaa tataggtttt cattttctcc caccagctta   6000

tataccttag caggagacat tccttccgta tcttttacgc agcggtattt ttcgatcagt   6060

tttttcaatt ccggtgatat tctcatttta gccatttatt atttccttcc tcttttctac   6120

agtatttaaa gataccccaa gaagctaatt ataacaagac gaactccaat tcactgttcc   6180

ttgcattcta aaaccttaaa taccagaaaa cagctttttc aaagttgttt tcaaagttgg   6240

cgtataacat agtatcgacg gagccgattt tgaaaccgcg gtgatcacag gcagcaacgc   6300

tctgtcatcg ttacaatcaa catgctaccc tccgcgagat catccgtgtt tcaaacccgg   6360

cagcttagtt gccgttcttc cgaatagcat cggtaacatg agcaaagtct gccgccttac   6420

aacggctctc ccgctgacgc cgtcccggac tgatgggctg cctgtatcga gtggtgattt   6480

tgtgccgagc tgccggtcgg ggagctgttg gctggctggt ggcaggatat attgtggtgt   6540

aaacaaattg acgcttagac aacttaataa cacattgcgg acgtttttaa tgtactgaat   6600

taacgccgaa ttaattcggg ggatctggat tttagtactg gattttggtt ttaggaatta   6660

gaaattttat tgatagaagt attttacaaa tacaaataca tactaagggt ttcttatatg   6720

ctcaacacat gagcgaaacc ctataggaac cctaattccc ttatctggga actactcaca   6780

cattattatg gagaaactcg agcttgtcga tcgacagatc cggtcggcat ctactctatt   6840

tctttgccct cggacgagtg ctggggcgtc ggtttccact atcggcgagt acttctacac   6900

agccatcggt ccagacggcc gcgcttctgc gggcgatttg tgtacgcccg acagtcccgg   6960

ctccggatcg gacgattgcg tcgcatcgac cctgcgccca agctgcatca tcgaaattgc   7020

cgtcaaccaa gctctgatag agttggtcaa gaccaatgcg gagcatatac gcccggagtc   7080

gtggcgatcc tgcaagctcc ggatgcctcc gctcgaagta gcgcgtctgc tgctccatac   7140
```

-continued

```
aagccaacca cggcctccag aagaagatgt tggcgacctc gtattgggaa tccccgaaca   7200
tcgcctcgct ccagtcaatg accgctgtta tgcggccatt gtccgtcagg acattgttgg   7260
agccgaaatc cgcgtgcacg aggtgccgga cttcggggca gtcctcggcc caaagcatca   7320
gctcatcgag agcctgcgcg acggacgcac tgacggtgtc gtccatcaca gtttgccagt   7380
gatacacatg gggatcagca atcgcgcata tgaaatcacg ccatgtagtg tattgaccga   7440
ttccttgcgg tccgaatggg ccgaacccgc tcgtctggct aagatcggcc gcagcgatcg   7500
catccatagc ctccgcgacc ggttgtagaa cagcgggcag ttcggtttca ggcaggtctt   7560
gcaacgtgac accctgtgca cggcgggaga tgcaataggt caggctctcg ctaaactccc   7620
caatgtcaag cacttccgga atcgggagcg cggccgatgc aaagtgccga taaacataac   7680
gatctttgta gaaaccatcg gcgcagctat ttacccgcag gacatatcca cgccctccta   7740
catcgaagct gaaagcacga gattcttcgc cctccgagag ctgcatcagg tcggagacgc   7800
tgtcgaactt ttcgatcaga aacttctcga cagacgtcgc ggtgagttca ggcttttca    7860
tatctcattg cccccccgga tctgcgaaag ctcgagagag atagatttgt agagagagac   7920
tggtgatttc agcgtgtcct ctccaaatga aatgaacttc cttatataga ggaaggtctt   7980
gcgaaggata gtgggattgt gcgtcatccc ttacgtcagt ggagatatca catcaatcca   8040
cttgctttga agacgtggtt ggaacgtctt ctttttccac gatgctcctc gtgggtgggg   8100
gtccatcttt gggaccactg tcggcagagg catcttgaac gatagccttt cctttatcgc   8160
aatgatggca tttgtaggtg ccaccttcct tttctactgt ccttttgatg aagtgacaga   8220
tagctgggca atggaatccg aggaggtttc ccgatattac cctttgttga aaagtctcaa   8280
tagccctttg gtcttctgag actgtatctt tgatattctt ggagtagacg agagtgtcgt   8340
gctccaccat gttatcacat caatccactt gctttgaaga cgtggttgga acgtcttctt   8400
tttccacgat gctcctcgtg ggtgggggtc catctttggg accactgtcg gcagaggcat   8460
cttgaacgat agcctttcct ttatcgcaat gatggcattt gtaggtgcca ccttcctttt   8520
ctactgtcct tttgatgaag tgacagatag ctgggcaatg gaatccgagg aggtttcccg   8580
atattaccct ttgttgaaaa gtctcaatag ccctttggtc ttctgagact gtatctttga   8640
tattcttgga gtagacgaga gtgtcgtgct ccaccatgtt ggcaagctgc tctagccaat   8700
acgcaaaccg cctctccccg cgcgttggcc gattcattaa tgcagctggc acgacaggtt   8760
tcccgactgg aaagcgggca gtgagcgcaa cgcaattaat gtgagttagc tcactcatta   8820
ggcaccccag gctttacact ttatgcttcc ggctcgtatg ttgtgtggaa ttgtgagcgg   8880
ataacaattt cacacaggaa acagctatga ccatgattac gaattccctt aattaataag   8940
agcagcttgc caacatggtg gagcacgaca ctctcgtcta ctccaagaat atcaaagata   9000
cagtctcaga agaccaaagg gctattgaga cttttcaaca aagggtaata tcgggaaacc   9060
tcctcggatt ccattgccca gctatctgtc acttcatcaa aaggacagta gaaaaggaag   9120
gtggcaccta caaatgccat cattgcgata aaggaaaggc tatcgttcaa gatgcctctg   9180
ccgacagtgg tcccaaagat ggacccccac ccacgaggag catcgtggaa aaagaagacg   9240
ttccaaccac gtcttcaaag caagtggatt gatgtgaaca tggtggagca cgacactctc   9300
gtctactcca agaatatcaa agatacagtc tcagaaggcc aaagggctat tgagactttt   9360
caacaaaggg taatatcggg aaacctcctc ggattccatt gcccagctat ctgtcacttc   9420
atcaaaagga cagtagaaaa ggaaggtggc acctacaaat gccatcattg cgataaagga   9480
aaggctatcg ttcaagatgc tctgccgaca gtggtcccaa agatggaccc ccacccacga   9540
```

-continued

```
ggagcatcgt ggaaaaagaa gacgttccaa ccacgtcttc aaagcaagtg gattgatgtg    9600
atatctccac tgacgtaagg gatgacgcac aatcccacta tccttcgcaa gacccttcct    9660
ctatataagg aagttcattt catttggaga ggacacgctg aaatcaccag tctctctcta    9720
caaatctatc tctctccatt agtctcttca ccttgtccca cctgctcccg ccgcatctca    9780
ccagacacca gccatgtgcg gcagcgcgat cctctccgac atcatcccgc cgccgcgccg    9840
ggtcacggac ggccccctct ggcggaacca gaagaagaag gggccgacgg gagatgctcc    9900
ggtggcgagg cgccgccgcg cgcccgagga ggaggagagc tacgaggact tcgaggccga    9960
cttcgagggc ttcgaggagg ggctcgggga ggccgagatc tggtccgagg acgaggccaa   10020
gcccttctcc gccgccagga aacgcgtcgc cgcaggtata gccgcccttt ttgggtcacc   10080
ggctttggat ctgtggaacc gcgtgctaat tctgtttacg atttgggaga tagatttgag   10140
tttctcaggt gatctgctgc tcggattaga tagttgcatc ttcgatttgt ttgctatgaa   10200
gttaaatctg tgcaattgtt catctcaagt ccgttaattc agcgggtcca tgttgtcgat   10260
tagtctggtc tctagtgctg tgtctttttt ttaaaaaaac acaatctctg gtgctgtgtc   10320
gatccttagt ttttaggata actctcctaa atcatgaata tggtatcaac tcttattggt   10380
gcatacatag atcgagcttc ctcgcaagca tatgagttgg gctgttcctc aggattagac   10440
ttttaatgtc aagtttcgac ttaccctgac tttctgtatg taaactaaaa tctttatctc   10500
actgcttcat cctgattgaa taaatgcatg tacagctgct gctgttgatg gctgggcatc   10560
agagtccgcc aaaaggaaga gaaagaccca gttcaggggc atccgccgcc gcccttgggg   10620
taaatgggct gctgaaatca gagaccctcg caagggtgtc cgtgtctggc ttggcactta   10680
caactctgcc gaggaagctg ccagagccta tgatgctgaa gcaagaagga tccgtggcaa   10740
gaaggcaaag gtcaatttcc cagatgaggc tcctgtggct tctcaaaagc actgtgctaa   10800
gcctaccttt gtgacgttgc ctgagttcaa caccgaagag aagccgatag tcaacgccgt   10860
ggccaacaca aacgcgtatt cctatcctct tgttgactac accgtctgtg agccatttgt   10920
gcagcctcag aacatgtcat ttgtgccagc ggttaatgca gttgaggttc ctttcatgaa   10980
tctttcctct gaccagggta gcaactcctt tggttgctca gactttagct gggagaatgg   11040
taccaagact cctgacatca catctgtgct tgcatccatt cccacctcga ccgaggttga   11100
tgaatctgca ttccttcaga acaatgccag tgatgcatca ctacctcctg tgatggatac   11160
tgccaatgtt gatctcgccg atttggaacc atacatgaag ttcctcgtgg atggtgcttc   11220
agatgagtca cttgacaact ttctaagctg tgacgggtct gaggacatgg tcagcaacct   11280
ggacctttgg actttcgatg acatgcccat ttctgccgat ttctactgag gctctgaggt   11340
caattggtgc ctgtacgtat agataatggg taagcatctg caactgcgga aataactcac   11400
tgttatactt cagtttccat ttccataact accccacttc acttttcagg aataagtatt   11460
ctggacatca agaagtgctt gtgtcaggcg cctctgttga gcagtagtta tgtttgtata   11520
cttttatatc tagcttaaat ctcagtttga tcgcaagtct gaagtgaggc ctggtttctc   11580
cataataatg tgtgagtagt tcccagataa gggaattagg gttcctatag ggtttcgctc   11640
atgtgttgag catataagaa acccttagta tgtatttgta tttgtaaaat acttctatca   11700
ataaaatttc taattcctaa aaccaaaatc cagtactaaa atccagatcc cccgaattaa   11760
ttcggcgtta attcagtatc ggcgcgcctt aattaaggcg cgccctgca               11809
```

-continued

<210> SEQ ID NO 245
<211> LENGTH: 11241
<212> TYPE: DNA
<213> ORGANISM: Artificial Sequence
<220> FEATURE:
<223> OTHER INFORMATION: Vector

<400> SEQUENCE: 245

```
ggaattcgat atcaagcttg gcactggccg tcgttttaca acgtcgtgac tgggaaaacc     60
ctggcgttac ccaacttaat cgccttgcag cacatccccc tttcgccagc tggcgtaata    120
gcgaagaggc ccgcaccgat cgcccttccc aacagttgcg cagcctgaat ggcgaatgct    180
agagcagctt gagcttggat cagattgtcg tttcccgcct tcagtttaaa ctatcagtgt    240
ttgacaggat atattggcgg gtaaacctaa gagaaaagag cgtttattag aataacggat    300
atttaaaagg gcgtgaaaag gtttatccgt tcgtccattt gtatgtgcat gccaaccaca    360
gggttcccct cgggatcaaa gtactttgat ccaacccctc cgctgctata gtgcagtcgg    420
cttctgacgt tcagtgcagc cgtcttctga aaacgacatg tcgcacaagt cctaagttac    480
gcgacaggct gccgccctgc ccttttcctg gcgttttctt gtcgcgtgtt ttagtcgcat    540
aaagtagaat acttgcgact agaaccggag acattacgcc atgaacaaga gcgccgccgc    600
tggcctgctg ggctatgccc gcgtcagcac cgacgaccag gacttgacca accaacgggc    660
cgaactgcac gcggccggct gcaccaagct gttttccgag aagatcaccg gcaccaggcg    720
cgaccgcccg gagctggcca ggatgcttga ccacctacgc cctggcgacg ttgtgacagt    780
gaccaggcta gaccgcctgg cccgcagcac ccgcgaccta ctggacattg ccgagcgcat    840
ccaggaggcc ggcgcgggcc tgcgtagcct ggcagagccg tgggccgaca ccaccacgcc    900
ggccggccgc atggtgttga ccgtgttcgc cggcattgcc gagttcgagc gttccctaat    960
catcgaccgc acccggagcg ggcgcgaggc cgccaaggcc cgaggcgtga agtttggccc   1020
ccgccctacc ctcaccccgg cacagatcgc gcacgcccgc gagctgatcg accaggaagg   1080
ccgcaccgtg aaagaggcgg ctgcactgct tggcgtgcat cgctcgaccc tgtaccgcgc   1140
acttgagcgc agcgaggaag tgacgcccac cgaggccagg cggcgcggtg ccttccgtga   1200
ggacgcattg accgaggccg acgccctggc ggccgccgag aatgaacgcc aagaggaaca   1260
agcatgaaac cgcaccagga cggccaggac gaaccgtttt tcattaccga agagatcgag   1320
gcggagatga tcgcggccgg gtacgtgttc gagccgcccg cgcacgtctc aaccgtgcgg   1380
ctgcatgaaa tcctggccgg tttgtctgat gccaagctgg cggcctggcc ggccagcttg   1440
gccgctgaag aaaccgagcg ccgccgtcta aaaaggtgat gtgtatttga gtaaaacagc   1500
ttgcgtcatg cggtcgctgc gtatatgatg cgatgagtaa ataaacaaat acgcaagggg   1560
aacgcatgaa ggttatcgct gtacttaacc agaaaggcgg gtcaggcaag acgaccatcg   1620
caacccatct agcccgcgcc ctgcaactcg ccggggccga tgttctgtta gtcgattccg   1680
atccccaggg cagtgcccgc gattgggcgg ccgtgcggga agatcaaccg ctaaccgttg   1740
tcggcatcga ccgcccgacg attgaccgcg acgtgaaggc catcggccgg cgcgacttcg   1800
tagtgatcga cggagcgccc caggcggcgg acttggctgt gtccgcgatc aaggcagccg   1860
acttcgtgct gattccggtg cagccaagcc cttacgacat atgggccacc gccgacctgg   1920
tggagctggt taagcagcgc attgaggtca cggatggaag gctacaagcg gcctttgtcg   1980
tgtcgcgggc gatcaaaggc acgcgcatcg gcggtgaggt tgccgaggcg ctggccgggt   2040
acgagctgcc cattcttgag tcccgtatca cgcagcgcgt gagctaccca ggcactgccg   2100
```

-continued

```
ccgccggcac aaccgttctt gaatcagaac ccgagggcga cgctgcccgc gaggtccagg   2160
cgctggccgc tgaaattaaa tcaaaactca tttgagttaa tgaggtaaag agaaaatgag   2220
caaaagcaca aacacgctaa gtgccggccg tccgagcgca cgcagcagca aggctgcaac   2280
gttggccagc ctggcagaca cgccagccat gaagcgggtc aactttcagt tgccggcgga   2340
ggatcacacc aagctgaaga tgtacgcggt acgccaaggc aagaccatta ccgagctgct   2400
atctgaatac atcgcgcagc taccagagta aatgagcaaa tgaataaatg agtagatgaa   2460
ttttagcggc taaaggaggc ggcatggaaa atcaagaaca accaggcacc gacgccgtgg   2520
aatgccccat gtgtggagga acgggcggtt ggccaggcgt aagcggctgg gttgtctgcc   2580
ggccctgcaa tggcactgga acccccaagc ccgaggaatc ggcgtgacgg tcgcaaacca   2640
tccggcccgg tacaaatcgg cgcggcgctg ggtgatgacc tggtggagaa gttgaaggcc   2700
gcgcaggccg cccagcggca acgcatcgag gcagaagcac gccccggtga atcgtggcaa   2760
gcggccgctg atcgaatccg caaagaatcc cggcaaccgc cggcagccgg tgcgccgtcg   2820
attaggaagc cgcccaaggg cgacgagcaa ccagattttt tcgttccgat gctctatgac   2880
gtgggcaccc gcgatagtcg cagcatcatg gacgtggccg ttttccgtct gtcgaagcgt   2940
gaccgacgag ctggcgaggt gatccgctac gagcttccag acgggcacgt agaggtttcc   3000
gcagggccgg ccggcatggc cagtgtgtgg gattacgacc tggtactgat ggcggtttcc   3060
catctaaccg aatccatgaa ccgataccgg gaagggaagg gagacaagcc cggccgcgtg   3120
ttccgtccac acgttgcgga cgtactcaag ttctgccggc gagccgatgg cggaaagcag   3180
aaagacgacc tggtagaaac ctgcattcgg ttaaacacca cgcacgttgc catgcagcgt   3240
acgaagaagg ccaagaacgg ccgcctggtg acggtatccg agggtgaagc cttgattagc   3300
cgctacaaga tcgtaaagag cgaaaccggg cggccggagt acatcgagat cgagctagct   3360
gattggatgt accgcgagat cacagaaggc aagaacccgg acgtgctgac ggttcacccc   3420
gattactttt tgatcgatcc cggcatcggc cgttttctct accgcctggc acgccgcgcc   3480
gcaggcaagg cagaagccag atggttgttc aagacgatct acgaacgcag tggcagcgcc   3540
ggagagttca agaagttctg tttcaccgtg cgcaagctga tcgggtcaaa tgacctgccg   3600
gagtacgatt tgaaggagga ggcggggcag gctggcccga tcctagtcat gcgctaccgc   3660
aacctgatcg agggcgaagc atccgccggt tcctaatgta cggagcagat gctagggcaa   3720
attgccctag caggggaaaa aggtcgaaaa ggtctctttc ctgtggatag cacgtacatt   3780
gggaacccaa agccgtacat tgggaaccgg aacccgtaca ttgggaaccc aaagccgtac   3840
attgggaacc ggtcacacat gtaagtgact gatataaaag agaaaaaagg cgatttttcc   3900
gcctaaaact ctttaaaact tattaaaact cttaaaaccc gcctggcctg tgcataactg   3960
tctggccagc gcacagccga agagctgcaa aaagcgccta cccttcggtc gctgcgctcc   4020
ctacgccccg ccgcttcgcg tcggcctatc gcggccgctg gccgctcaaa aatggctggc   4080
ctacggccag gcaatctacc agggcgcgga caagccgcgc cgtcgccact cgaccgccgg   4140
cgcccacatc aaggcaccct gcctcgcgcg tttcggtgat gacggtgaaa acctctgaca   4200
catgcagctc ccggagacgg tcacagcttg tctgtaagcg gatgccggga gcagacaagc   4260
ccgtcagggc gcgtcagcgg gtgttggcgg gtgtcggggc gcagccatga cccagtcacg   4320
tagcgatagc ggagtgtata ctggcttaac tatgcggcat cagagcagat tgtactgaga   4380
gtgcaccata tgcggtgtga aataccgcac agatgcgtaa ggagaaaata ccgcatcagg   4440
cgctcttccg cttcctcgct cactgactcg ctgcgctcgg tcgttcggct gcggcgagcg   4500
```

-continued

```
gtatcagctc actcaaaggc ggtaatacgg ttatccacag aatcagggga taacgcagga   4560
aagaacatgt gagcaaaagg ccagcaaaag gccaggaacc gtaaaaaggc cgcgttgctg   4620
gcgtttttcc ataggctccg cccccctgac gagcatcaca aaaatcgacg ctcaagtcag   4680
aggtggcgaa acccgacagg actataaaga taccaggcgt ttccccctgg aagctccctc   4740
gtgcgctctc ctgttccgac cctgccgctt accggatacc tgtccgcctt tctcccttcg   4800
ggaagcgtgg cgctttctca tagctcacgc tgtaggtatc tcagttcggt gtaggtcgtt   4860
cgctccaagc tgggctgtgt gcacgaaccc cccgttcagc ccgaccgctg cgccttatcc   4920
ggtaactatc gtcttgagtc caacccggta agacacgact tatcgccact ggcagcagcc   4980
actggtaaca ggattagcag agcgaggtat gtaggcggtg ctacagagtt cttgaagtgg   5040
tggcctaact acggctacac tagaaggaca gtatttggta tctgcgctct gctgaagcca   5100
gttaccttcg gaaaaagagt tggtagctct tgatccggca aacaaaccac cgctggtagc   5160
ggtggttttt ttgtttgcaa gcagcagatt acgcgcagaa aaaaaggatc tcaagaagat   5220
cctttgatct tttctacggg gtctgacgct cagtggaacg aaaactcacg ttaagggatt   5280
ttggtcatgc attctaggta ctaaaacaat tcatccagta aaatataata ttttattttc   5340
tcccaatcag gcttgatccc cagtaagtca aaaaatagct cgacatactg ttcttccccg   5400
atatcctccc tgatcgaccg gacgcagaag gcaatgtcat accacttgtc cgccctgccg   5460
cttctcccaa gatcaataaa gccacttact ttgccatctt tcacaaagat gttgctgtct   5520
cccaggtcgc cgtgggaaaa gacaagttcc tcttcgggct tttccgtctt taaaaaatca   5580
tacagctcgc gcggatcttt aaatggagtg tcttcttccc agttttcgca atccacatcg   5640
gccagatcgt tattcagtaa gtaatccaat tcggctaagc ggctgtctaa gctattcgta   5700
tagggacaat ccgatatgtc gatggagtga aagagcctga tgcactccgc atacagctcg   5760
ataatctttt cagggctttg ttcatcttca tactcttccg agcaaaggac gccatcggcc   5820
tcactcatga gcagattgct ccagccatca tgccgttcaa agtgcaggac ctttggaaca   5880
ggcagctttc cttccagcca tagcatcatg tccttttccc gttccacatc ataggtggtc   5940
cctttatacc ggctgtccgt catttttaaa tataggtttt cattttctcc caccagctta   6000
tataccttag caggagacat tccttccgta tcttttacgc agcggtattt ttcgatcagt   6060
tttttcaatt ccggtgatat tctcatttta gccatttatt atttccttcc tcttttctac   6120
agtatttaaa gataccccaa gaagctaatt ataacaagac gaactccaat tcactgttcc   6180
ttgcattcta aaaccttaaa taccagaaaa cagctttttc aaagttgttt tcaaagttgg   6240
cgtataacat agtatcgacg gagccgattt tgaaaccgcg gtgatcacag gcagcaacgc   6300
tctgtcatcg ttacaatcaa catgctaccc tccgcgagat catccgtgtt tcaaacccgg   6360
cagcttagtt gccgttcttc cgaatagcat cggtaacatg agcaaagtct gccgccttac   6420
aacggctctc ccgctgacgc cgtcccggac tgatgggctg cctgtatcga gtggtgattt   6480
tgtgccgagc tgccggtcgg ggagctgttg gctggctggt ggcaggatat attgtggtgt   6540
aaacaaattg acgcttagac aacttaataa cacattgcgg acgtttttaa tgtactgaat   6600
taacgccgaa ttaattcggg ggatctggat tttagtactg gattttggtt ttaggaatta   6660
gaaattttat tgatagaagt attttacaaa tacaaataca tactaagggt ttcttatatg   6720
ctcaacacat gagcgaaacc ctataggaac cctaattccc ttatctggga actactcaca   6780
cattattatg gagaaactcg agcttgtcga tcgacagatc cggtcggcat ctactctatt   6840
tctttgccct cggacgagtg ctggggcgtc ggtttccact atcggcgagt acttctacac   6900
```

-continued

```
agccatcggt ccagacggcc gcgcttctgc gggcgatttg tgtacgcccg acagtcccgg   6960
ctccggatcg gacgattgcg tcgcatcgac cctgcgccca agctgcatca tcgaaattgc   7020
cgtcaaccaa gctctgatag agttggtcaa gaccaatgcg gagcatatac gcccggagtc   7080
gtggcgatcc tgcaagctcc ggatgcctcc gctcgaagta gcgcgtctgc tgctccatac   7140
aagccaacca cggcctccag aagaagatgt tggcgacctc gtattgggaa tccccgaaca   7200
tcgcctcgct ccagtcaatg accgctgtta tgcggccatt gtccgtcagg acattgttgg   7260
agccgaaatc cgcgtgcacg aggtgccgga cttcggggca gtcctcggcc caaagcatca   7320
gctcatcgag agcctgcgcg acggacgcac tgacggtgtc gtccatcaca gtttgccagt   7380
gatacacatg gggatcagca atcgcgcata tgaaatcacg ccatgtagtg tattgaccga   7440
ttccttgcgg tccgaatggg ccgaacccgc tcgtctggct aagatcggcc gcagcgatcg   7500
catccatagc ctccgcgacc ggttgtagaa cagcgggcag ttcggtttca ggcaggtctt   7560
gcaacgtgac accctgtgca cggcgggaga tgcaataggt caggctctcg ctaaactccc   7620
caatgtcaag cacttccgga atcgggagcg cggccgatgc aaagtgccga taaacataac   7680
gatctttgta gaaaccatcg gcgcagctat ttacccgcag gacatatcca cgccctccta   7740
catcgaagct gaaagcacga gattcttcgc cctccgagag ctgcatcagg tcggagacgc   7800
tgtcgaactt ttcgatcaga aacttctcga cagacgtcgc ggtgagttca ggctttttca   7860
tatctcattg ccccccgga tctgcgaaag ctcgagagag atagatttgt agagagagac   7920
tggtgatttc agcgtgtcct ctccaaatga aatgaacttc cttatataga ggaaggtctt   7980
gcgaaggata gtgggattgt gcgtcatccc ttacgtcagt ggagatatca catcaatcca   8040
cttgctttga agacgtggtt ggaacgtctt ctttttccac gatgctcctc gtgggtgggg   8100
gtccatcttt gggaccactg tcggcagagg catcttgaac gatagccttt cctttatcgc   8160
aatgatggca tttgtaggtg ccaccttcct tttctactgt ccttttgatg aagtgacaga   8220
tagctgggca atggaatccg aggaggtttc ccgatattac cctttgttga aaagtctcaa   8280
tagccctttg gtcttctgag actgtatctt tgatattctt ggagtagacg agagtgtcgt   8340
gctccaccat gttatcacat caatccactt gctttgaaga cgtggttgga acgtcttctt   8400
tttccacgat gctcctcgtg ggtgggggtc catctttggg accactgtcg gcagaggcat   8460
cttgaacgat agcctttcct ttatcgcaat gatggcattt gtaggtgcca ccttcctttt   8520
ctactgtcct tttgatgaag tgacagatag ctgggcaatg gaatccgagg aggtttcccg   8580
atattaccct ttgttgaaaa gtctcaatag ccctttggtc ttctgagact gtatctttga   8640
tattcttgga gtagacgaga gtgtcgtgct ccaccatgtt ggcaagctgc tctagccaat   8700
acgcaaaccg cctctccccg cgcgttggcc gattcattaa tgcagctggc acgacaggtt   8760
tcccgactgg aaagcgggca gtgagcgcaa cgcaattaat gtgagttagc tcactcatta   8820
ggcaccccag gctttacact ttatgcttcc ggctcgtatg ttgtgtggaa ttgtgagcgg   8880
ataacaattt cacacaggaa acagctatga ccatgattac gaattccctt aattaataag   8940
agcagcttgc caacatggtg gagcacgaca ctctcgtcta ctccaagaat atcaaagata   9000
cagtctcaga agaccaaagg gctattgaga cttttcaaca aagggtaata tcgggaaacc   9060
tcctcggatt ccattgccca gctatctgtc acttcatcaa aaggacagta gaaaaggaag   9120
gtggcaccta caaatgccat cattgcgata aaggaaaggc tatcgttcaa gatgcctctg   9180
ccgacagtgg tcccaaagat ggacccccac ccacgaggag catcgtggaa aaagaagacg   9240
ttccaaccac gtcttcaaag caagtggatt gatgtgaaca tggtggagca cgacactctc   9300
```

-continued gtctactcca agaatatcaa agatacagtc tcagaaggcc aaagggctat tgagactttt 9360
caacaaaggg taatatcggg aaacctcctc ggattccatt gcccagctat ctgtcacttc 9420
atcaaaagga cagtagaaaa ggaaggtggc acctacaaat gccatcattg cgataaagga 9480
aaggctatcg ttcaagatgc tctgccgaca gtggtcccaa agatggaccc ccacccacga 9540
ggagcatcgt ggaaaaagaa gacgttccaa ccacgtcttc aaagcaagtg gattgatgtg 9600
atatctccac tgacgtaagg gatgacgcac aatcccacta tccttcgcaa gacccttcct 9660
ctatataagg aagttcattt catttggaga ggacacgctg aaatcaccag tctctctcta 9720
caaatctatc tctctccatt agttgttgct ttcctgtgcc atcgactggc atggctcgga 9780
aatgctccag ctgcgggcat aatggccata actccaggac ctgcagtggc aacaacggcg 9840
gcggtggtgc cggtggtggg ctgaggctgt tcggtgtgca gctgcaagtt ggtgctgcac 9900
ctctgaagaa gagcttcagc atggagtgcc tctcgtcgtc ggcctactac gcggccgcag 9960
cggtggccgc gtccaactcg tcgtcgtccg tgtcatcgtc atcgtcgctg gtctcggtgg 10020
aggagaacgc cgagaagatg ggccacggct acctctccga tggtctcatg ggcagggctc 10080
aggagaggaa gaagggtgag ttcgtgtact ggtttcttga gcagttcgtt ggtccggtat 10140
acctcgctga cacgcttgat ttgctatgct atggattttg gatattaatc atattatagt 10200
atgtgatagc gatctaacca tcatgcatga tgtctaaggc cagattaaga aaactattct 10260
gaaatttttt ttccccctag ctagagacta aagatctgaa gattcttgtt gatgcatgag 10320
tggttgtatg acttgtttgt atccaattgt gccatcagtt gctatctgct atgccaaact 10380
tgcaactaga taacaggaaa tacttagtct ttcaggtctt aactttcagt aatcatgtct 10440
aatagcttgc acgaatcagt ttgttctctc ttcttcacct gaagatgtcc agttacgttg 10500
ggtgaactaa tcgtgtgacg catggcatca ggggttccat ggacggagga tgagcaccgg 10560
aggttcctgg ccggcttaga gaagctcggg aaaggcgact ggcgaggcat ctcccggcac 10620
ttcgtcgcga cacgcacccc gacgcaggtg gccagccacg cccagaagta cttcctccgg 10680
caggccggcc tcgcgcagaa gaagcggagg tccagcctct tcgacgtggt acgtgcacgc 10740
ctcaaaacgc aagctggagt tgtggacgta gtaacaaacc agctgacatg cacgaacctt 10800
cctctctttt cttcaggccg agaagaatgg cgacaaggcg gcgaaggaga gtcgtccgag 10860
actgaaacac gagactagca gctccgtgga cgggatggca attcggtcat tccctgctct 10920
gtctctagga cccagcaggc cgaggcccga cgccgccgtg cttccaccat gcctgacctt 10980
gatgccgagc tattcgtctg gcctggtttc tccataataa tgtgtgagta gttcccagat 11040
aagggaatta gggttcctat agggtttcgc tcatgtgttg agcatataag aaacccttag 11100
tatgtatttg tatttgtaaa atacttctat caataaaatt tctaattcct aaaaccaaaa 11160
tccagtacta aaatccagat cccccgaatt aattcggcgt taattcagta tcggcgcgcc 11220
ttaattaagg cgcgccctgc a 11241

<210> SEQ ID NO 246
<211> LENGTH: 12113
<212> TYPE: DNA
<213> ORGANISM: Artificial Sequence
<220> FEATURE:
<223> OTHER INFORMATION: Vector

<400> SEQUENCE: 246
ggaattcgat atcaagcttg gcactggccg tcgttttaca acgtcgtgac tgggaaaacc 60
ctggcgttac ccaacttaat cgccttgcag cacatccccc tttcgccagc tggcgtaata 120

-continued

```
gcgaagaggc ccgcaccgat cgcccttccc aacagttgcg cagcctgaat ggcgaatgct    180
agagcagctt gagcttggat cagattgtcg tttcccgcct tcagtttaaa ctatcagtgt    240
ttgacaggat atattggcgg gtaaacctaa gagaaaagag cgtttattag aataacggat    300
atttaaaagg gcgtgaaaag gtttatccgt tcgtccattt gtatgtgcat gccaaccaca    360
gggttcccct cgggatcaaa gtactttgat ccaacccctc cgctgctata gtgcagtcgg    420
cttctgacgt tcagtgcagc cgtcttctga aaacgacatg tcgcacaagt cctaagttac    480
gcgacaggct gccgccctgc ccttttcctg gcgttttctt gtcgcgtgtt ttagtcgcat    540
aaagtagaat acttgcgact agaaccggag acattacgcc atgaacaaga gcgccgccgc    600
tggcctgctg ggctatgccc gcgtcagcac cgacgaccag gacttgacca accaacgggc    660
cgaactgcac gcggccggct gcaccaagct gttttccgag aagatcaccg gcaccaggcg    720
cgaccgcccg gagctggcca ggatgcttga ccacctacgc cctggcgacg ttgtgacagt    780
gaccaggcta gaccgcctgg cccgcagcac ccgcgaccta ctggacattg ccgagcgcat    840
ccaggaggcc ggcgcgggcc tgcgtagcct ggcagagccg tgggccgaca ccaccacgcc    900
ggccggccgc atggtgttga ccgtgttcgc cggcattgcc gagttcgagc gttccctaat    960
catcgaccgc acccggagcg ggcgcgaggc cgccaaggcc cgaggcgtga agtttggccc   1020
ccgccctacc ctcaccccgg cacagatcgc gcacgcccgc gagctgatcg accaggaagg   1080
ccgcaccgtg aaagaggcgg ctgcactgct tggcgtgcat cgctcgaccc tgtaccgcgc   1140
acttgagcgc agcgaggaag tgacgcccac cgaggccagg cggcgcggtg ccttccgtga   1200
ggacgcattg accgaggccg acgccctggc ggccgccgag aatgaacgcc aagaggaaca   1260
agcatgaaac cgcaccagga cggccaggac gaaccgtttt tcattaccga agagatcgag   1320
gcggagatga tcgcggccgg gtacgtgttc gagccgcccg cgcacgtctc aaccgtgcgg   1380
ctgcatgaaa tcctggccgg tttgtctgat gccaagctgg cggcctggcc ggccagcttg   1440
gccgctgaag aaaccgagcg ccgccgtcta aaaaggtgat gtgtatttga gtaaaacagc   1500
ttgcgtcatg cggtcgctgc gtatatgatg cgatgagtaa ataaacaaat acgcaagggg   1560
aacgcatgaa ggttatcgct gtacttaacc agaaaggcgg gtcaggcaag acgaccatcg   1620
caacccatct agcccgcgcc ctgcaactcg ccggggccga tgttctgtta gtcgattccg   1680
atccccaggg cagtgcccgc gattgggcgg ccgtgcggga agatcaaccg ctaaccgttg   1740
tcggcatcga ccgcccgacg attgaccgcg acgtgaaggc catcggccgg cgcgacttcg   1800
tagtgatcga cggagcgccc caggcggcgg acttggctgt gtccgcgatc aaggcagccg   1860
acttcgtgct gattccggtg cagccaagcc cttacgacat atgggccacc gccgacctgg   1920
tggagctggt taagcagcgc attgaggtca cggatggaag gctacaagcg gcctttgtcg   1980
tgtcgcgggc gatcaaaggc acgcgcatcg gcggtgaggt tgccgaggcg ctggccgggt   2040
acgagctgcc cattcttgag tcccgtatca cgcagcgcgt gagctaccca ggcactgccg   2100
ccgccggcac aaccgttctt gaatcagaac ccgagggcga cgctgcccgc gaggtccagg   2160
cgctggccgc tgaaattaaa tcaaaactca tttgagttaa tgaggtaaag agaaaatgag   2220
caaaagcaca aacacgctaa gtgccggccg tccgagcgca cgcagcagca aggctgcaac   2280
gttggccagc ctggcagaca cgccagccat gaagcgggtc aactttcagt tgccggcgga   2340
ggatcacacc aagctgaaga tgtacgcggt acgccaaggc aagaccatta ccgagctgct   2400
atctgaatac atcgcgcagc taccagagta aatgagcaaa tgaataaatg agtagatgaa   2460
ttttagcggc taaaggaggc ggcatggaaa atcaagaaca accaggcacc gacgccgtgg   2520
```

-continued

```
aatgccccat gtgtggagga acgggcggtt ggccaggcgt aagcggctgg gttgtctgcc   2580

ggccctgcaa tggcactgga acccccaagc ccgaggaatc ggcgtgacgg tcgcaaacca   2640

tccggcccgg tacaaatcgg cgcggcgctg ggtgatgacc tggtggagaa gttgaaggcc   2700

gcgcaggccg cccagcggca acgcatcgag gcagaagcac gccccggtga atcgtggcaa   2760

gcggccgctg atcgaatccg caaagaatcc cggcaaccgc cggcagccgg tgcgccgtcg   2820

attaggaagc cgcccaaggg cgacgagcaa ccagattttt tcgttccgat gctctatgac   2880

gtgggcaccc gcgatagtcg cagcatcatg gacgtggccg ttttccgtct gtcgaagcgt   2940

gaccgacgag ctggcgaggt gatccgctac gagcttccag acgggcacgt agaggtttcc   3000

gcagggccgg ccggcatggc cagtgtgtgg gattacgacc tggtactgat ggcggtttcc   3060

catctaaccg aatccatgaa ccgataccgg gaagggaagg gagacaagcc cggccgcgtg   3120

ttccgtccac acgttgcgga cgtactcaag ttctgccggc gagccgatgg cggaaagcag   3180

aaagacgacc tggtagaaac ctgcattcgg ttaaacacca cgcacgttgc catgcagcgt   3240

acgaagaagg ccaagaacgg ccgcctggtg acggtatccg agggtgaagc cttgattagc   3300

cgctacaaga tcgtaaagag cgaaaccggg cggccggagt acatcgagat cgagctagct   3360

gattggatgt accgcgagat cacagaaggc aagaacccgg acgtgctgac ggttcacccc   3420

gattactttt tgatcgatcc cggcatcggc cgttttctct accgcctggc acgccgcgcc   3480

gcaggcaagg cagaagccag atggttgttc aagacgatct acgaacgcag tggcagcgcc   3540

ggagagttca agaagttctg tttcaccgtg cgcaagctga tcgggtcaaa tgacctgccg   3600

gagtacgatt tgaaggagga ggcggggcag gctggcccga tcctagtcat gcgctaccgc   3660

aacctgatcg agggcgaagc atccgccggt tcctaatgta cggagcagat gctagggcaa   3720

attgccctag caggggaaaa aggtcgaaaa ggtctctttc ctgtggatag cacgtacatt   3780

gggaacccaa agccgtacat tgggaaccgg aacccgtaca ttgggaaccc aaagccgtac   3840

attgggaacc ggtcacacat gtaagtgact gatataaaag agaaaaaagg cgatttttcc   3900

gcctaaaact ctttaaaact tattaaaact cttaaaaccc gcctggcctg tgcataactg   3960

tctggccagc gcacagccga agagctgcaa aaagcgccta cccttcggtc gctgcgctcc   4020

ctacgccccg ccgcttcgcg tcggcctatc gcggccgctg gccgctcaaa aatggctggc   4080

ctacggccag gcaatctacc agggcgcgga caagccgcgc cgtcgccact cgaccgccgg   4140

cgcccacatc aaggcaccct gcctcgcgcg tttcggtgat gacggtgaaa acctctgaca   4200

catgcagctc ccggagacgg tcacagcttg tctgtaagcg gatgccggga gcagacaagc   4260

ccgtcagggc gcgtcagcgg gtgttggcgg gtgtcggggc gcagccatga cccagtcacg   4320

tagcgatagc ggagtgtata ctggcttaac tatgcggcat cagagcagat tgtactgaga   4380

gtgcaccata tgcggtgtga aataccgcac agatgcgtaa ggagaaaata ccgcatcagg   4440

cgctcttccg cttcctcgct cactgactcg ctgcgctcgg tcgttcggct gcggcgagcg   4500

gtatcagctc actcaaaggc ggtaatacgg ttatccacag aatcagggga taacgcagga   4560

aagaacatgt gagcaaaagg ccagcaaaag gccaggaacc gtaaaaaggc cgcgttgctg   4620

gcgtttttcc ataggctccg cccccctgac gagcatcaca aaaatcgacg ctcaagtcag   4680

aggtggcgaa acccgacagg actataaaga taccaggcgt ttccccctgg aagctccctc   4740

gtgcgctctc ctgttccgac cctgccgctt accggatacc tgtccgcctt tctcccttcg   4800

ggaagcgtgg cgctttctca tagctcacgc tgtaggtatc tcagttcggt gtaggtcgtt   4860

cgctccaagc tgggctgtgt gcacgaaccc cccgttcagc ccgaccgctg cgccttatcc   4920
```

-continued

```
ggtaactatc gtcttgagtc caacccggta agacacgact tatcgccact ggcagcagcc   4980
actggtaaca ggattagcag agcgaggtat gtaggcggtg ctacagagtt cttgaagtgg   5040
tggcctaact acggctacac tagaaggaca gtatttggta tctgcgctct gctgaagcca   5100
gttaccttcg gaaaaagagt tggtagctct tgatccggca aacaaaccac cgctggtagc   5160
ggtggttttt ttgtttgcaa gcagcagatt acgcgcagaa aaaaaggatc tcaagaagat   5220
cctttgatct tttctacggg gtctgacgct cagtggaacg aaaactcacg ttaagggatt   5280
ttggtcatgc attctaggta ctaaaacaat tcatccagta aaatataata ttttattttc   5340
tcccaatcag gcttgatccc cagtaagtca aaaaatagct cgacatactg ttcttccccg   5400
atatcctccc tgatcgaccg gacgcagaag gcaatgtcat accacttgtc cgccctgccg   5460
cttctcccaa gatcaataaa gccacttact ttgccatctt tcacaaagat gttgctgtct   5520
cccaggtcgc cgtgggaaaa gacaagttcc tcttcgggct tttccgtctt taaaaaatca   5580
tacagctcgc gcggatcttt aaatggagtg tcttcttccc agttttcgca atccacatcg   5640
gccagatcgt tattcagtaa gtaatccaat tcggctaagc ggctgtctaa gctattcgta   5700
tagggacaat ccgatatgtc gatggagtga aagagcctga tgcactccgc atacagctcg   5760
ataatctttt cagggctttg ttcatcttca tactcttccg agcaaaggac gccatcggcc   5820
tcactcatga gcagattgct ccagccatca tgccgttcaa agtgcaggac ctttggaaca   5880
ggcagctttc cttccagcca tagcatcatg tccttttccc gttccacatc ataggtggtc   5940
cctttatacc ggctgtccgt catttttaaa tataggtttt cattttctcc caccagctta   6000
tataccttag caggagacat tccttccgta tcttttacgc agcggtattt ttcgatcagt   6060
tttttcaatt ccggtgatat tctcatttta gccatttatt atttccttcc tcttttctac   6120
agtatttaaa gataccccaa gaagctaatt ataacaagac gaactccaat tcactgttcc   6180
ttgcattcta aaaccttaaa taccagaaaa cagctttttc aaagttgttt tcaaagttgg   6240
cgtataacat agtatcgacg gagccgattt tgaaaccgcg gtgatcacag gcagcaacgc   6300
tctgtcatcg ttacaatcaa catgctaccc tccgcgagat catccgtgtt tcaaacccgg   6360
cagcttagtt gccgttcttc cgaatagcat cggtaacatg agcaaagtct gccgccttac   6420
aacggctctc ccgctgacgc cgtcccggac tgatgggctg cctgtatcga gtggtgattt   6480
tgtgccgagc tgccggtcgg ggagctgttg gctggctggt ggcaggatat attgtggtgt   6540
aaacaaattg acgcttagac aacttaataa cacattgcgg acgtttttaa tgtactgaat   6600
taacgccgaa ttaattcggg ggatctggat tttagtactg gattttggtt ttaggaatta   6660
gaaattttat tgatagaagt attttacaaa tacaaataca tactaagggt ttcttatatg   6720
ctcaacacat gagcgaaacc ctataggaac cctaattccc ttatctggga actactcaca   6780
cattattatg gagaaactcg agcttgtcga tcgacagatc cggtcggcat ctactctatt   6840
tctttgccct cggacgagtg ctggggcgtc ggtttccact atcggcgagt acttctacac   6900
agccatcggt ccagacggcc gcgcttctgc gggcgatttg tgtacgcccg acagtcccgg   6960
ctccggatcg gacgattgcg tcgcatcgac cctgcgccca agctgcatca tcgaaattgc   7020
cgtcaaccaa gctctgatag agttggtcaa gaccaatgcg gagcatatac gcccggagtc   7080
gtggcgatcc tgcaagctcc ggatgcctcc gctcgaagta gcgcgtctgc tgctccatac   7140
aagccaacca cggcctccag aagaagatgt tggcgacctc gtattgggaa tccccgaaca   7200
tcgcctcgct ccagtcaatg accgctgtta tgcggccatt gtccgtcagg acattgttgg   7260
agccgaaatc cgcgtgcacg aggtgccgga cttcggggca gtcctcggcc caaagcatca   7320
```

-continued

```
gctcatcgag agcctgcgcg acggacgcac tgacggtgtc gtccatcaca gtttgccagt   7380
gatacacatg gggatcagca atcgcgcata tgaaatcacg ccatgtagtg tattgaccga   7440
ttccttgcgg tccgaatggg ccgaacccgc tcgtctggct aagatcggcc gcagcgatcg   7500
catccatagc ctccgcgacc ggttgtagaa cagcgggcag ttcggtttca ggcaggtctt   7560
gcaacgtgac accctgtgca cggcgggaga tgcaataggt caggctctcg ctaaactccc   7620
caatgtcaag cacttccgga atcgggagcg cggccgatgc aaagtgccga taaacataac   7680
gatctttgta gaaaccatcg gcgcagctat ttacccgcag gacatatcca cgccctccta   7740
catcgaagct gaaagcacga gattcttcgc cctccgagag ctgcatcagg tcggagacgc   7800
tgtcgaactt ttcgatcaga aacttctcga cagacgtcgc ggtgagttca ggctttttca   7860
tatctcattg ccccccccgga tctgcgaaag ctcgagagag atagatttgt agagagagac   7920
tggtgatttc agcgtgtcct ctccaaatga aatgaacttc cttatataga ggaaggtctt   7980
gcgaaggata gtgggattgt gcgtcatccc ttacgtcagt ggagatatca catcaatcca   8040
cttgctttga agacgtggtt ggaacgtctt ctttttccac gatgctcctc gtgggtgggg   8100
gtccatcttt gggaccactg tcggcagagg catcttgaac gatagccttt cctttatcgc   8160
aatgatggca tttgtaggtg ccaccttcct tttctactgt ccttttgatg aagtgacaga   8220
tagctgggca atggaatccg aggaggtttc ccgatattac cctttgttga aaagtctcaa   8280
tagccctttg gtcttctgag actgtatctt tgatattctt ggagtagacg agagtgtcgt   8340
gctccaccat gttatcacat caatccactt gctttgaaga cgtggttgga acgtcttctt   8400
tttccacgat gctcctcgtg ggtgggggtc catctttggg accactgtcg gcagaggcat   8460
cttgaacgat agcctttcct ttatcgcaat gatggcattt gtaggtgcca ccttcctttt   8520
ctactgtcct tttgatgaag tgacagatag ctgggcaatg gaatccgagg aggtttcccg   8580
atattaccct ttgttgaaaa gtctcaatag ccctttggtc ttctgagact gtatctttga   8640
tattcttgga gtagacgaga gtgtcgtgct ccaccatgtt ggcaagctgc tctagccaat   8700
acgcaaaccg cctctccccg cgcgttggcc gattcattaa tgcagctggc acgacaggtt   8760
tcccgactgg aaagcgggca gtgagcgcaa cgcaattaat gtgagttagc tcactcatta   8820
ggcaccccag gctttacact ttatgcttcc ggctcgtatg ttgtgtggaa ttgtgagcgg   8880
ataacaattt cacacaggaa acagctatga ccatgattac gaattccctt aattaataag   8940
agcagcttgc caacatggtg gagcacgaca ctctcgtcta ctccaagaat atcaaagata   9000
cagtctcaga agaccaaagg gctattgaga cttttcaaca aagggtaata tcgggaaacc   9060
tcctcggatt ccattgccca gctatctgtc acttcatcaa aaggacagta gaaaaggaag   9120
gtggcaccta caaatgccat cattgcgata aaggaaaggc tatcgttcaa gatgcctctg   9180
ccgacagtgg tcccaaagat ggacccccac ccacgaggag catcgtggaa aaagaagacg   9240
ttccaaccac gtcttcaaag caagtggatt gatgtgaaca tggtggagca cgacactctc   9300
gtctactcca agaatatcaa agatacagtc tcagaaggcc aaagggctat tgagactttt   9360
caacaaaggg taatatcggg aaacctcctc ggattccatt gcccagctat ctgtcacttc   9420
atcaaaagga cagtagaaaa ggaaggtggc acctacaaat gccatcattg cgataaagga   9480
aaggctatcg ttcaagatgc tctgccgaca gtggtcccaa agatggaccc ccacccacga   9540
ggagcatcgt ggaaaaagaa gacgttccaa ccacgtcttc aaagcaagtg gattgatgtg   9600
atatctccac tgacgtaagg gatgacgcac aatcccacta tccttcgcaa gacccttcct   9660
ctatataagg aagttcattt catttggaga ggacacgctg aaatcaccag tctctctcta   9720
```

-continued

```
caaatctatc tctctccatt agtgatctgc tgtgctgtgg tgagagctgc caagaagctg   9780
agcagtgcta ctctggagga gctcaccaaa ggattgtttc tgtttcggtt ttggcaatca   9840
ctaaataatg gaggaagtgg aggaggccaa caggatagcc gttgagagct gccacagagt   9900
gctgggcctg ctttcccagt cgcaggaccc ggcgcagctc aggagcatag ctctgggcac   9960
ggacgacgcc tgcgccaagt tccgcaaggt ggtctccctc ctcggcaacg aaggaggagg  10020
gggagcagta agccatccca gagccaaggt tgcgagcagg aaacagaccc cggccttctt  10080
gagccagaag ggcttcctgg acaacaacac cccggtggtg gtgctgaaca gcagcgccca  10140
cccttccact agctccgcgc aggcgtatcc taggaacacc attctggatt cgcacaccgc  10200
gcacccgatc ggagggcctc ccaagctggt ccagccattg tccgcgcact tccagttcgg  10260
caacgtatcg cggtatcagt tccagcatca gcaccagcag cagaagatgc aggctgagat  10320
gttcaagaga agcaacagta tcagtgggat taacctgaag ttcgacagcc ccagcgcggc  10380
cacgggggcg atgtcgtccg cgagatcctt catgtcatct ttgagcatgg atggtagcgt  10440
ggctagcctg gatgccaagt cttcctcgtt ccatttgatc ggtgggcctg ctatgagtga  10500
cccggtgaat gcgcagcagg cgccgaggag gcggtgcacg gggcgtgggg aggatgggaa  10560
tggcaagtgc gctgcaaatg gcaggtgcca ttgctcaaag aggaggtaaa tactcttatc  10620
ttagtgtgta tgattcttgc ttgctcttct attcaaggta gaataccatg agaattgttc  10680
tgttccctat ttcagcagga agttgcgggt gaagaagacg attaaagttc ctgccattag  10740
taataaaatt gctgatatac ctccagatga atactcatgg aggaagtatg ggcagaagcc  10800
aattaagggt tcccctcatc ccaggtatga actgagcact atctgttagt gtcatttttct  10860
tgcacacata ttcttgatta tacggtgatg gagtagtggc aatgatgcta taatcaccat  10920
gactcatcaa ttttctaatt atttatcata tgtataactg cacatatccc ccatgaacta  10980
ctcaagtgcc tcatgataaa tgatggctct gtgataatca gaacacactt tatccatggt  11040
ttgcagggtg ttttacatgc tcctgataat cagaacactc tttatacagt atagtaatca  11100
aaactctcct tatgcagggt gttttgtatg ttcctgaata gttactttgt gaataatgtc  11160
tttcattctt cttgtgcaca ctttcttaaa atagatcaat cccgagtctt aaagtggcca  11220
gtggccactt cgtaattcag tctaccatga ttcagtcttt aagtggacat ctttaatgct  11280
atcgtgattc agtctactac gtactatact ttacctattc atatcacttt cccaccttgt  11340
ctatcttaaa tttcctgatg ataaaataca caaatatagc tatacggtaa tagcaaacgc  11400
atgggtatct tttcgagaaa aaaacaaaca catgggtatg gctgtctgaa ttgagaaaaa  11460
acttttcctc tttctagcaa gcactagata tagaaacacg attcatggcg catctatttt  11520
tatctccaat ccacaatgct aattctgatg tgtctcttaa gaccaatcca ctgattcctt  11580
aaacataatg caggggggtac tacaaatgta gcagtgtcag gggctgccca gccaggaagc  11640
atgttgaacg ttgtgtggat gatgcgtcaa tgctcattgt gacatacgag ggtgaacaca  11700
accacacgcg aatgccggct cagtctgcac aggcttaggg aatcactttg atcatcacac  11760
cctctccagg gaatactaac tcgcctgccc ttgtcgatgg ccgactgcac tgttcttcta  11820
aattagaatt acaaagtgac aaaaactggg ttccatttga gcagttgatg aggcctggtt  11880
tctccataat aatgtgtgag tagttcccag ataagggaat tagggttcct atagggtttc  11940
gctcatgtgt tgagcatata agaaaccctt agtatgtatt tgtatttgta aaatacttct  12000
atcaataaaa tttctaattc ctaaaaccaa aatccagtac taaaatccag atcccccgaa  12060
ttaattcggc gttaattcag tatcggcgcg ccttaattaa ggcgcgccct gca        12113
```

-continued

<210> SEQ ID NO 247
<211> LENGTH: 10291
<212> TYPE: DNA
<213> ORGANISM: Artificial Sequence
<220> FEATURE:
<223> OTHER INFORMATION: Vector

<400> SEQUENCE: 247
gaatttctag ttctagatgc atgctcgaaa ttcgattggc gcgccttaat taataagagc 60
agcttgccaa catggtggag cacgacactc tcgtctactc caagaatatc aaagatacag 120
tctcagaaga ccaaagggct attgagactt ttcaacaaag ggtaatatcg ggaaacctcc 180
tcggattcca ttgcccagct atctgtcact tcatcaaaag gacagtagaa aaggaaggtg 240
gcacctacaa atgccatcat tgcgataaag gaaaggctat cgttcaagat gcctctgccg 300
acagtggtcc caaagatgga cccccaccca cgaggagcat cgtggaaaaa gaagacgttc 360
caaccacgtc ttcaaagcaa gtggattgat gtgaacatgg tggagcacga cactctcgtc 420
tactccaaga atatcaaaga tacagtctca gaaggccaaa gggctattga gacttttcaa 480
caaagggtaa tatcgggaaa cctcctcgga ttccattgcc cagctatctg tcacttcatc 540
aaaaggacag tagaaaagga aggtggcacc tacaaatgcc atcattgcga taaaggaaag 600
gctatcgttc aagatgctct gccgacagtg gtcccaaaga tggaccccca cccacgagga 660
gcatcgtgga aaaagaagac gttccaacca cgtcttcaaa gcaagtggat tgatgtgata 720
tctccactga cgtaagggat gacgcacaat cccactatcc ttcgcaagac ccttcctcta 780
tataaggaag ttcatttcat ttggagagga cacgctgaaa tcaccagtct ctctctacaa 840
atctatctct ctccattagt aatgggttcg gagacctttc tggagatcct gctggccatc 900
ctgctgccgc cgctcggcgt tttcctccgc ttcggcatcg gcgtaagcta ccaaaccatt 960
cagcgatttc agggtgtgta tgtaatgata gatatattga tttgatggtc ggttcatgca 1020
tgtctgcagg tggagttctg gatctgcctg ctactcaccc tgctgggcta catccccggc 1080
atcatctacg ccgtcttcgt ccttgttgca tagaggcctg gtttctccat aataatgtgt 1140
gagtagttcc cagataaggg aattagggtt cctatagggt ttcgctcatg tgttgagcat 1200
ataagaaacc cttagtatgt atttgtattt gtaaaatact tctatcaata aaatttctaa 1260
ttcctaaaac caaaatccag tactaaaatc cagatccccc gaattaattc ggcgttaatt 1320
cagtatcggc gcgccttaat taaaatcgaa tttcgaccat actagtggat ccccctcgga 1380
ctagaagctt ggcactggcc gtcgttttac aacgtcgtga ctgggaaaac cctggcgtta 1440
cccaacttaa tcgccttgca gcacatcccc ctttcgccag ctggcgtaat agcgaagagg 1500
cccgcaccga tcgcccttcc caacagttgc gcagcctgaa tggcgaatgc tagagcagct 1560
tgagcttgga tcagattgtc gtttcccgcc ttcagtttaa actatcagtg tttgacagga 1620
tatattggcg ggtaaaccta agagaaaaga gcgtttatta gaataacgga tatttaaaag 1680
ggcgtgaaaa ggtttatccg ttcgtccatt tgtatgtgca tgccaaccac agggttcccc 1740
tcgggatcaa agtactttga tccaacccct ccgctgctat agtgcagtcg gcttctgacg 1800
ttcagtgcag ccgtcttctg aaaacgacat gtcgcacaag tcctaagtta cgcgacaggc 1860
tgccgccctg cccttttcct ggcgttttct tgtcgcgtgt tttagtcgca taaagtagaa 1920
tacttgcgac tagaaccgga gacattacgc catgaacaag agcgccgccg ctggcctgct 1980
gggctatgcc cgcgtcagca ccgacgacca ggacttgacc aaccaacggg ccgaactgca 2040
cgcggccggc tgcaccaagc tgttttccga gaagatcacc ggcaccaggc gcgaccgccc 2100

-continued

```
ggagctggcc aggatgcttg accacctacg ccctggcgac gttgtgacag tgaccaggct   2160
agaccgcctg gcccgcagca cccgcgacct actggacatt gccgagcgca tccaggaggc   2220
cggcgcgggc ctgcgtagcc tggcagagcc gtgggccgac accaccacgc cggccggccg   2280
catggtgttg accgtgttcg ccggcattgc cgagttcgag cgttccctaa tcatcgaccg   2340
cacccggagc gggcgcgagg ccgccaaggc ccgaggcgtg aagtttggcc cccgccctac   2400
cctcaccccg gcacagatcg cgcacgcccg cgagctgatc gaccaggaag gccgcaccgt   2460
gaaagaggcg gctgcactgc ttggcgtgca tcgctcgacc ctgtaccgcg cacttgagcg   2520
cagcgaggaa gtgacgccca ccgaggccag gcggcgcggt gccttccgtg aggacgcatt   2580
gaccgaggcc gacgccctgg cggccgccga gaatgaacgc caagaggaac aagcatgaaa   2640
ccgcaccagg acggccagga cgaaccgttt ttcattaccg aagagatcga ggcggagatg   2700
atcgcggccg ggtacgtgtt cgagccgccc gcgcacgtct caaccgtgcg gctgcatgaa   2760
atcctggccg gtttgtctga tgccaagctg gcggcctggc cggccagctt ggccgctgaa   2820
gaaaccgagc gccgccgtct aaaaaggtga tgtgtatttg agtaaaacag cttgcgtcat   2880
gcggtcgctg cgtatatgat gcgatgagta aataaacaaa tacgcaaggg gaacgcatga   2940
aggttatcgc tgtacttaac cagaaaggcg ggtcaggcaa gacgaccatc gcaacccatc   3000
tagcccgcgc cctgcaactc gccggggccg atgttctgtt agtcgattcc gatccccagg   3060
gcagtgcccg cgattgggcg gccgtgcggg aagatcaacc gctaaccgtt gtcggcatcg   3120
accgcccgac gattgaccgc gacgtgaagg ccatcggccg gcgcgacttc gtagtgatcg   3180
acggagcgcc ccaggcggcg gacttggctg tgtccgcgat caaggcagcc gacttcgtgc   3240
tgattccggt gcagccaagc ccttacgaca tatgggccac cgccgacctg gtggagctgg   3300
ttaagcagcg cattgaggtc acggatggaa ggctacaagc ggcctttgtc gtgtcgcggg   3360
cgatcaaagg cacgcgcatc ggcggtgagg ttgccgaggc gctggccggg tacgagctgc   3420
ccattcttga gtcccgtatc acgcagcgcg tgagctaccc aggcactgcc gccgccggca   3480
caaccgttct tgaatcagaa cccgagggcg acgctgcccg cgaggtccag gcgctggccg   3540
ctgaaattaa atcaaaactc atttgagtta atgaggtaaa gagaaaatga gcaaaagcac   3600
aaacacgcta agtgccggcc gtccgagcgc acgcagcagc aaggctgcaa cgttggccag   3660
cctggcagac acgccagcca tgaagcgggt caactttcag ttgccggcgg aggatcacac   3720
caagctgaag atgtacgcgg tacgccaagg caagaccatt accgagctgc tatctgaata   3780
catcgcgcag ctaccagagt aaatgagcaa atgaataaat gagtagatga attttagcgg   3840
ctaaaggagg cggcatggaa aatcaagaac aaccaggcac cgacgccgtg gaatgcccca   3900
tgtgtggagg aacgggcggt tggccaggcg taagcggctg ggttgtctgc cggccctgca   3960
atggcactgg aacccccaag cccgaggaat cggcgtgacg gtcgcaaacc atccggcccg   4020
gtacaaatcg gcgcggcgct gggtgatgac ctggtggaga agttgaaggc cgcgcaggcc   4080
gcccagcggc aacgcatcga ggcagaagca cgccccggtg aatcgtggca agcggccgct   4140
gatcgaatcc gcaaagaatc ccggcaaccg ccggcagccg gtgcgccgtc gattaggaag   4200
ccgcccaagg gcgacgagca accagatttt ttcgttccga tgctctatga cgtgggcacc   4260
cgcgatagtc gcagcatcat ggacgtggcc gttttccgtc tgtcgaagcg tgaccgacga   4320
gctggcgagg tgatccgcta cgagcttcca gacgggcacg tagaggtttc cgcagggccg   4380
gccggcatgg ccagtgtgtg ggattacgac ctggtactga tggcggtttc ccatctaacc   4440
gaatccatga accgataccg ggaagggaag ggagacaagc ccggccgcgt gttccgtcca   4500
```

-continued

```
cacgttgcgg acgtactcaa gttctgccgg cgagccgatg gcggaaagca gaaagacgac   4560
ctggtagaaa cctgcattcg gttaaacacc acgcacgttg ccatgcagcg tacgaagaag   4620
gccaagaacg gccgcctggt gacggtatcc gagggtgaag ccttgattag ccgctacaag   4680
atcgtaaaga gcgaaaccgg gcggccggag tacatcgaga tcgagctagc tgattggatg   4740
taccgcgaga tcacagaagg caagaacccg gacgtgctga cggttcaccc cgattacttt   4800
ttgatcgatc ccggcatcgg ccgttttctc taccgcctgg cacgccgcgc cgcaggcaag   4860
gcagaagcca gatggttgtt caagacgatc tacgaacgca gtggcagcgc cggagagttc   4920
aagaagttct gtttcaccgt gcgcaagctg atcgggtcaa atgacctgcc ggagtacgat   4980
ttgaaggagg aggcggggca ggctggcccg atcctagtca tgcgctaccg caacctgatc   5040
gagggcgaag catccgccgg ttcctaatgt acggagcaga tgctagggca aattgcccta   5100
gcaggggaaa aaggtcgaaa aggtctcttt cctgtggata gcacgtacat tgggaaccca   5160
aagccgtaca ttgggaaccg gaacccgtac attgggaacc caaagccgta cattgggaac   5220
cggtcacaca tgtaagtgac tgatataaaa gagaaaaaag gcgatttttc cgcctaaaac   5280
tctttaaaac ttattaaaac tcttaaaacc cgcctggcct gtgcataact gtctggccag   5340
cgcacagccg aagagctgca aaaagcgcct acccttcggt cgctgcgctc cctacgcccc   5400
gccgcttcgc gtcggcctat cgcggccgct ggccgctcaa aaatggctgg cctacggcca   5460
ggcaatctac cagggcgcgg acaagccgcg ccgtcgccac tcgaccgccg gcgcccacat   5520
caaggcaccc tgcctcgcgc gtttcggtga tgacggtgaa aacctctgac acatgcagct   5580
cccggagacg gtcacagctt gtctgtaagc ggatgccggg agcagacaag cccgtcaggg   5640
cgcgtcagcg ggtgttggcg ggtgtcgggg cgcagccatg acccagtcac gtagcgatag   5700
cggagtgtat actggcttaa ctatgcggca tcagagcaga ttgtactgag agtgcaccat   5760
atgcggtgtg aaataccgca cagatgcgta aggagaaaat accgcatcag gcgctcttcc   5820
gcttcctcgc tcactgactc gctgcgctcg gtcgttcggc tgcggcgagc ggtatcagct   5880
cactcaaagg cggtaatacg gttatccaca gaatcagggg ataacgcagg aaagaacatg   5940
tgagcaaaag gccagcaaaa ggccaggaac cgtaaaaagg ccgcgttgct ggcgtttttc   6000
cataggctcc gcccccctga cgagcatcac aaaaatcgac gctcaagtca gaggtggcga   6060
aacccgacag gactataaag ataccaggcg tttccccctg gaagctccct cgtgcgctct   6120
cctgttccga ccctgccgct taccggatac ctgtccgcct ttctcccttc gggaagcgtg   6180
gcgctttctc atagctcacg ctgtaggtat ctcagttcgg tgtaggtcgt tcgctccaag   6240
ctgggctgtg tgcacgaacc ccccgttcag cccgaccgct gcgccttatc cggtaactat   6300
cgtcttgagt ccaacccggt aagacacgac ttatcgccac tggcagcagc cactggtaac   6360
aggattagca gagcgaggta tgtaggcggt gctacagagt tcttgaagtg gtggcctaac   6420
tacggctaca ctagaaggac agtatttggt atctgcgctc tgctgaagcc agttaccttc   6480
ggaaaaagag ttggtagctc ttgatccggc aaacaaacca ccgctggtag cggtggtttt   6540
tttgtttgca agcagcagat tacgcgcaga aaaaaaggat ctcaagaaga tcctttgatc   6600
ttttctacgg ggtctgacgc tcagtggaac gaaaactcac gttaagggat tttggtcatg   6660
cattctaggt actaaaacaa ttcatccagt aaaatataat attttatttt ctcccaatca   6720
ggcttgatcc ccagtaagtc aaaaaatagc tcgacatact gttcttcccc gatatcctcc   6780
ctgatcgacc ggacgcagaa ggcaatgtca taccacttgt ccgccctgcc gcttctccca   6840
agatcaataa agccacttac tttgccatct ttcacaaaga tgttgctgtc tcccaggtcg   6900
```

-continued

```
ccgtgggaaa agacaagttc ctcttcgggc ttttccgtct ttaaaaaatc atacagctcg   6960
cgcggatctt taaatggagt gtcttcttcc cagttttcgc aatccacatc ggccagatcg   7020
ttattcagta agtaatccaa ttcggctaag cggctgtcta agctattcgt atagggacaa   7080
tccgatatgt cgatggagtg aaagagcctg atgcactccg catacagctc gataatcttt   7140
tcagggcttt gttcatcttc atactcttcc gagcaaagga cgccatcggc ctcactcatg   7200
agcagattgc tccagccatc atgccgttca aagtgcagga cctttggaac aggcagcttt   7260
ccttccagcc atagcatcat gtccttttcc cgttccacat cataggtggt ccctttatac   7320
cggctgtccg tcatttttaa atataggttt tcattttctc ccaccagctt atatacctta   7380
gcaggagaca ttccttccgt atcttttacg cagcggtatt tttcgatcag tttttcaat    7440
tccggtgata ttctcatttt agccatttat tatttccttc ctcttttcta cagtatttaa   7500
agataccca agaagctaat tataacaaga cgaactccaa ttcactgttc cttgcattct    7560
aaaaccttaa ataccagaaa acagcttttt caaagttgtt ttcaaagttg gcgtataaca   7620
tagtatcgac ggagccgatt ttgaaaccgc ggtgatcaca ggcagcaacg ctctgtcatc   7680
gttacaatca acatgctacc ctccgcgaga tcatccgtgt ttcaaacccg gcagcttagt   7740
tgccgttctt ccgaatagca tcggtaacat gagcaaagtc tgccgcctta caacggctct   7800
cccgctgacg ccgtcccgga ctgatgggct gcctgtatcg agtggtgatt ttgtgccgag   7860
ctgccggtcg ggagctgtt ggctggctgg tggcaggata tattgtggtg taaacaaatt    7920
gacgcttaga caacttaata acacattgcg gacgttttta atgtactgaa ttaacgccga   7980
attaattcgg gggatctgga ttttagtact ggattttggt tttaggaatt agaaatttta   8040
ttgatagaag tattttacaa atacaaatac atactaaggg tttcttatat gctcaacaca   8100
tgagcgaaac cctataggaa ccctaattcc cttatctggg aactactcac acattattat   8160
ggagaaactc gagcttgtcg atcgacagat ccggtcggca tctactctat ttctttgccc   8220
tcggacgagt gctggggcgt cggtttccac tatcggcgag tacttctaca cagccatcgg   8280
tccagacggc cgcgcttctg cgggcgattt gtgtacgccc gacagtcccg gctccggatc   8340
ggacgattgc gtcgcatcga ccctgcgccc aagctgcatc atcgaaattg ccgtcaacca   8400
agctctgata gagttggtca agaccaatgc ggagcatata cgcccggagt cgtggcgatc   8460
ctgcaagctc cggatgcctc cgctcgaagt agcgcgtctg ctgctccata caagccaacc   8520
acggcctcca gaagaagatg ttggcgacct cgtattggga atccccgaac atcgcctcgc   8580
tccagtcaat gaccgctgtt atgcggccat tgtccgtcag gacattgttg gagccgaaat   8640
ccgcgtgcac gaggtgccgg acttcggggc agtcctcggc ccaaagcatc agctcatcga   8700
gagcctgcgc gacggacgca ctgacggtgt cgtccatcac agtttgccag tgatacacat   8760
ggggatcagc aatcgcgcat atgaaatcac gccatgtagt gtattgaccg attccttgcg   8820
gtccgaatgg gccgaacccg ctcgtctggc taagatcggc cgcagcgatc gcatccatag   8880
cctccgcgac cggttgtaga acagcgggca gttcggtttc aggcaggtct tgcaacgtga   8940
caccctgtgc acggcgggag atgcaatagg tcaggctctc gctaaactcc ccaatgtcaa   9000
gcacttccgg aatcgggagc gcggccgatg caaagtgccg ataaacataa cgatctttgt   9060
agaaaccatc ggcgcagcta tttacccgca ggacatatcc acgccctcct acatcgaagc   9120
tgaaagcacg agattcttcg ccctccgaga gctgcatcag gtcggagacg ctgtcgaact   9180
tttcgatcag aaacttctcg acagacgtcg cggtgagttc aggctttttc atatctcatt   9240
gcccccccgg atctgcgaaa gctcgagaga gatagatttg tagagagaga ctggtgattt   9300
```

-continued

```
cagcgtgtcc tctccaaatg aaatgaactt ccttatatag aggaaggtct tgcgaaggat   9360

agtgggattg tgcgtcatcc cttacgtcag tggagatatc acatcaatcc acttgctttg   9420

aagacgtggt tggaacgtct tctttttcca cgatgctcct cgtgggtggg ggtccatctt   9480

tgggaccact gtcggcagag gcatcttgaa cgatagcctt tcctttatcg caatgatggc   9540

atttgtaggt gccaccttcc ttttctactg tccttttgat gaagtgacag atagctgggc   9600

aatggaatcc gaggaggttt cccgatatta ccctttgttg aaaagtctca atagcccttt   9660

ggtcttctga gactgtatct ttgatattct tggagtagac gagagtgtcg tgctccacca   9720

tgttatcaca tcaatccact tgctttgaag acgtggttgg aacgtcttct ttttccacga   9780

tgctcctcgt gggtgggggt ccatctttgg gaccactgtc ggcagaggca tcttgaacga   9840

tagcctttcc tttatcgcaa tgatggcatt tgtaggtgcc accttccttt tctactgtcc   9900

ttttgatgaa gtgacagata gctgggcaat ggaatccgag gaggtttccc gatattaccc   9960

tttgttgaaa agtctcaata gccctttggt cttctgagac tgtatctttg atattcttgg  10020

agtagacgag agtgtcgtgc tccaccatgt tggcaagctg ctctagccaa tacgcaaacc  10080

gcctctcccc gcgcgttggc cgattcatta atgcagctgg cacgacaggt ttcccgactg  10140

gaaagcgggc agtgagcgca acgcaattaa tgtgagttag ctcactcatt aggcacccca  10200

ggctttacac tttatgcttc cggctcgtat gttgtgtgga attgtgagcg gataacaatt  10260

tcacacagga aacagctatg accatgatta c                                 10291
```

<210> SEQ ID NO 248
<211> LENGTH: 63
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (5)..(5)
<223> OTHER INFORMATION: Xaa = Asn, Ser or Thr
<220> FEATURE:
<221> NAME/KEY: MISC_FEATURE
<222> LOCATION: (6)..(6)
<223> OTHER INFORMATION: Xaa = Gln or Arg
<220> FEATURE:
<221> NAME/KEY: MISC_FEATURE
<222> LOCATION: (7)..(7)
<223> OTHER INFORMATION: Xaa = Tyr or Phe
<220> FEATURE:
<221> NAME/KEY: MISC_FEATURE
<222> LOCATION: (10)..(10)
<223> OTHER INFORMATION: Xaa = Ile or Val
<220> FEATURE:
<221> NAME/KEY: MISC_FEATURE
<222> LOCATION: (12)..(12)
<223> OTHER INFORMATION: Xaa = Gln or Arg
<220> FEATURE:
<221> NAME/KEY: MISC_FEATURE
<222> LOCATION: (27)..(27)
<223> OTHER INFORMATION: Xaa = Lys, Glu or Gln
<220> FEATURE:
<221> NAME/KEY: MISC_FEATURE
<222> LOCATION: (29)..(29)
<223> OTHER INFORMATION: Xaa = Val, Ser, Ile or Ala
<220> FEATURE:
<221> NAME/KEY: MISC_FEATURE
<222> LOCATION: (31)..(31)
<223> OTHER INFORMATION: Xaa = Val, Glu or Ile
<220> FEATURE:
<221> NAME/KEY: MISC_FEATURE
<222> LOCATION: (36)..(36)
<223> OTHER INFORMATION: Xaa = Phe or Tyr -continued

```
<220> FEATURE:
<221> NAME/KEY: MISC_FEATURE
<222> LOCATION: (37)..(37)
<223> OTHER INFORMATION: Xaa = Asn, Ser, Asp, Lys or Gly
<220> FEATURE:
<221> NAME/KEY: MISC_FEATURE
<222> LOCATION: (38)..(38)
<223> OTHER INFORMATION: Xaa = Thr or Ser
<220> FEATURE:
<221> NAME/KEY: MISC_FEATURE
<222> LOCATION: (39)..(39)
<223> OTHER INFORMATION: Xaa = Ala or Pro
<220> FEATURE:
<221> NAME/KEY: MISC_FEATURE
<222> LOCATION: (41)..(41)
<223> OTHER INFORMATION: Xaa = Glu or Lys
<220> FEATURE:
<221> NAME/KEY: MISC_FEATURE
<222> LOCATION: (44)..(44)
<223> OTHER INFORMATION: Xaa = Arg, Met or Lys
<220> FEATURE:
<221> NAME/KEY: MISC_FEATURE
<222> LOCATION: (47)..(47)
<223> OTHER INFORMATION: Xaa = Asp, Gly or any amino acid
<220> FEATURE:
<221> NAME/KEY: MISC_FEATURE
<222> LOCATION: (48)..(48)
<223> OTHER INFORMATION: Xaa = Ala, Val, Ser, Ile or Thr
<220> FEATURE:
<221> NAME/KEY: MISC_FEATURE
<222> LOCATION: (49)..(49)
<223> OTHER INFORMATION: Xaa = Glu or Ala
<220> FEATURE:
<221> NAME/KEY: MISC_FEATURE
<222> LOCATION: (50)..(50)
<223> OTHER INFORMATION: Xaa = Ala or Thr
<220> FEATURE:
<221> NAME/KEY: MISC_FEATURE
<222> LOCATION: (55)..(55)
<223> OTHER INFORMATION: Xaa = Gly or any amino acid
<220> FEATURE:
<221> NAME/KEY: MISC_FEATURE
<222> LOCATION: (56)..(56)
<223> OTHER INFORMATION: Xaa = Lys, Ser, Thr or Asn
<220> FEATURE:
<221> NAME/KEY: MISC_FEATURE
<222> LOCATION: (59)..(59)
<223> OTHER INFORMATION: Xaa = Lys or Glu

<400> SEQUENCE: 248

Arg Lys Arg Lys Xaa Xaa Xaa Arg Gly Xaa Arg Xaa Arg Pro Trp Gly
1               5                   10                  15

Lys Trp Ala Ala Glu Ile Arg Asp Pro Arg Xaa Gly Xaa Arg Xaa Trp
            20                  25                  30

Leu Gly Thr Xaa Xaa Xaa Xaa Glu Xaa Ala Ala Xaa Ala Tyr Xaa Xaa
        35                  40                  45

Xaa Xaa Arg Arg Ile Arg Xaa Xaa Lys Ala Xaa Val Asn Phe Pro
    50                  55                  60


<210> SEQ ID NO 249
<211> LENGTH: 27
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (3)..(3)
<223> OTHER INFORMATION: Xaa = Gly or Asn
<220> FEATURE:
<221> NAME/KEY: MISC_FEATURE
<222> LOCATION: (5)..(5)
<223> OTHER INFORMATION: Xaa = Ala or Ser
```

-continued

```
<220> FEATURE:
<221> NAME/KEY: MISC_FEATURE
<222> LOCATION: (7)..(7)
<223> OTHER INFORMATION: Xaa = His, Lys, Asn, Ser or Thr
<220> FEATURE:
<221> NAME/KEY: MISC_FEATURE
<222> LOCATION: (8)..(8)
<223> OTHER INFORMATION: Xaa = Phe or Tyr
<220> FEATURE:
<221> NAME/KEY: MISC_FEATURE
<222> LOCATION: (10)..(10)
<223> OTHER INFORMATION: Xaa = Ala, Phe, Ile, Lys, Met, Asn, Pro, Thr or
      Val
<220> FEATURE:
<221> NAME/KEY: MISC_FEATURE
<222> LOCATION: (11)..(11)
<223> OTHER INFORMATION: Xaa = Ser or Thr
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (24)..(24)
<223> OTHER INFORMATION: Xaa = Phe or Lys
<220> FEATURE:
<221> NAME/KEY: MISC_FEATURE
<222> LOCATION: (25)..(25)
<223> OTHER INFORMATION: Xaa = Phe or Lys
<220> FEATURE:
<221> NAME/KEY: MISC_FEATURE
<222> LOCATION: (26)..(26)
<223> OTHER INFORMATION: Xaa = Ile, Leu, Met or Ser

<400> SEQUENCE: 249

Trp Arg Xaa Ile Xaa Arg Xaa Xaa Val Xaa Xaa Xaa Thr Pro Thr Gln
1               5                   10                  15

Val Ala Ser His Ala Gln Lys Xaa Xaa Xaa Arg
            20                  25


<210> SEQ ID NO 250
<211> LENGTH: 60
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (3)..(3)
<223> OTHER INFORMATION: Xaa = Ala, Gly, Pro, Gln or Ser
<220> FEATURE:
<221> NAME/KEY: MISC_FEATURE
<222> LOCATION: (4)..(4)
<223> OTHER INFORMATION: Xaa = Asp or Gly
<220> FEATURE:
<221> NAME/KEY: MISC_FEATURE
<222> LOCATION: (5)..(5)
<223> OTHER INFORMATION: Xaa = Asp or Glu
<220> FEATURE:
<221> NAME/KEY: MISC_FEATURE
<222> LOCATION: (6)..(6)
<223> OTHER INFORMATION: Xaa = Phe or Tyr
<220> FEATURE:
<221> NAME/KEY: MISC_FEATURE
<222> LOCATION: (20)..(20)
<223> OTHER INFORMATION: Xaa = Lys or Pro
<220> FEATURE:
<221> NAME/KEY: MISC_FEATURE
<222> LOCATION: (21)..(21)
<223> OTHER INFORMATION: Xaa = Phe, His or Tyr
```

-continued

<220> FEATURE:
<221> NAME/KEY: MISC_FEATURE
<222> LOCATION: (30)..(30)
<223> OTHER INFORMATION: Xaa = Ser or Thr
<220> FEATURE:
<221> NAME/KEY: MISC_FEATURE
<222> LOCATION: (31)..(31)
<223> OTHER INFORMATION: Xaa = Ile, Leu, Met or Val
<220> FEATURE:
<221> NAME/KEY: MISC_FEATURE
<222> LOCATION: (32)..(32)
<223> OTHER INFORMATION: Xaa = Arg or Thr
<220> FEATURE:
<221> NAME/KEY: MISC_FEATURE
<222> LOCATION: (33)..(33)
<223> OTHER INFORMATION: Xaa = Gly or Ser
<220> FEATURE:
<221> NAME/KEY: MISC_FEATURE
<222> LOCATION: (34)..(34)
<223> OTHER INFORMATION: Xaa = Cys or Thr
<220> FEATURE:
<221> NAME/KEY: MISC_FEATURE
<222> LOCATION: (35)..(35)
<223> OTHER INFORMATION: Xaa = Leu or Pro
<220> FEATURE:
<221> NAME/KEY: MISC_FEATURE
<222> LOCATION: (36)..(36)
<223> OTHER INFORMATION: Xaa = Ala or Leu
<220> FEATURE:
<221> NAME/KEY: MISC_FEATURE
<222> LOCATION: (37)..(37)
<223> OTHER INFORMATION: Xaa = Phe, Lys or Arg
<220> FEATURE:
<221> NAME/KEY: MISC_FEATURE
<222> LOCATION: (38)..(38)
<223> OTHER INFORMATION: Xaa = Lys or Asn
<220> FEATURE:
<221> NAME/KEY: MISC_FEATURE
<222> LOCATION: (43)..(43)
<223> OTHER INFORMATION: Xaa = Ala, Cys, Asp or Ser
<220> FEATURE:
<221> NAME/KEY: MISC_FEATURE
<222> LOCATION: (44)..(44)
<223> OTHER INFORMATION: Xaa = Ile, Leu, Met, Pro or Val
<220> FEATURE:
<221> NAME/KEY: MISC_FEATURE
<222> LOCATION: (45)..(45)
<223> OTHER INFORMATION: Xaa = Ala, Asp, Glu or Ser
<220> FEATURE:
<221> NAME/KEY: MISC_FEATURE
<222> LOCATION: (46)..(46)
<223> OTHER INFORMATION: Xaa = Asp or Glu
<220> FEATURE:
<221> NAME/KEY: MISC_FEATURE
<222> LOCATION: (47)..(47)
<223> OTHER INFORMATION: Xaa = Ala, Pro, Ser or Thr
<220> FEATURE:
<221> NAME/KEY: MISC_FEATURE
<222> LOCATION: (48)..(48)
<223> OTHER INFORMATION: Xaa = Ala, Ser or Thr
<220> FEATURE:
<221> NAME/KEY: MISC_FEATURE
<222> LOCATION: (51)..(51)
<223> OTHER INFORMATION: Xaa = Ile, Met or Val
<220> FEATURE:
<221> NAME/KEY: MISC_FEATURE
<222> LOCATION: (56)..(56)
<223> OTHER INFORMATION: Xaa = Asp or Gly
<220> FEATURE:
<221> NAME/KEY: MISC_FEATURE
<222> LOCATION: (57)..(57)
<223> OTHER INFORMATION: Xaa = Asp or Glu
<220> FEATURE:
<221> NAME/KEY: MISC_FEATURE
<222> LOCATION: (59)..(59)
<223> OTHER INFORMATION: Xaa = Cys, His, Asn or Arg

<400> SEQUENCE: 250

```
Ile Pro Xaa Xaa Xaa Xaa Ser Trp Arg Lys Tyr Gly Gln Lys Pro Ile
1               5                   10                  15

Lys Gly Ser Xaa Xaa Pro Arg Gly Tyr Tyr Lys Cys Ser Xaa Xaa Xaa
            20                  25                  30

Xaa Xaa Xaa Xaa Xaa Xaa His Val Glu Arg Xaa Xaa Xaa Xaa Xaa Xaa
        35                  40                  45

Met Leu Xaa Val Thr Tyr Glu Xaa Xaa His Xaa His
    50                  55                  60
```

<210> SEQ ID NO 251
<211> LENGTH: 41
<212> TYPE: PRT
<213> ORGANISM: Artificial Sequence
<220> FEATURE:
<223> OTHER INFORMATION: Vector
<220> FEATURE:
<221> NAME/KEY: MISC_FEATURE
<222> LOCATION: (1)..(1)
<223> OTHER INFORMATION: Xaa = Asp or Glu
<220> FEATURE:
<221> NAME/KEY: MISC_FEATURE
<222> LOCATION: (2)..(2)
<223> OTHER INFORMATION: Xaa = Ile, Leu or Val
<220> FEATURE:
<221> NAME/KEY: MISC_FEATURE
<222> LOCATION: (3)..(3)
<223> OTHER INFORMATION: Xaa = Phe, Ile, Leu, Met or Val
<220> FEATURE:
<221> NAME/KEY: MISC_FEATURE
<222> LOCATION: (4)..(4)
<223> OTHER INFORMATION: Xaa = Cys, Phe, Ile or Leu
<220> FEATURE:
<221> NAME/KEY: MISC_FEATURE
<222> LOCATION: (7)..(7)
<223> OTHER INFORMATION: Xaa = Phe, Ile or Leu
<220> FEATURE:
<221> NAME/KEY: MISC_FEATURE
<222> LOCATION: (8)..(8)
<223> OTHER INFORMATION: Xaa = Ile or Leu
<220> FEATURE:
<221> NAME/KEY: MISC_FEATURE
<222> LOCATION: (9)..(9)
<223> OTHER INFORMATION: Xaa = His or Phe
<220> FEATURE:
<221> NAME/KEY: MISC_FEATURE
<222> LOCATION: (10)..(10)
<223> OTHER INFORMATION: Xaa = Phe or Gln
<220> FEATURE:
<221> NAME/KEY: MISC_FEATURE
<222> LOCATION: (11)..(11)
<223> OTHER INFORMATION: Xaa = Leu or Val
<220> FEATURE:
<221> NAME/KEY: MISC_FEATURE
<222> LOCATION: (14)..(14)
<223> OTHER INFORMATION: Xaa = Phe or Cys
<220> FEATURE:
<221> NAME/KEY: MISC_FEATURE
<222> LOCATION: (15)..(15)
<223> OTHER INFORMATION: Xaa = Phe or Leu
<220> FEATURE:
<221> NAME/KEY: MISC_FEATURE
<222> LOCATION: (16)..(16)
<223> OTHER INFORMATION: Xaa = Lys or Arg
<220> FEATURE:
<221> NAME/KEY: MISC_FEATURE
<222> LOCATION: (17)..(17)
<223> OTHER INFORMATION: Xaa = Phe, Lys, Arg, Val or Tyr
<220> FEATURE:
<221> NAME/KEY: MISC_FEATURE
<222> LOCATION: (18)..(18)
<223> OTHER INFORMATION: Xaa = Ala, Gly or Lys -continued

```
<220> FEATURE:
<221> NAME/KEY: MISC_FEATURE
<222> LOCATION: (19)..(19)
<223> OTHER INFORMATION: Xaa = Cys, Ile or Leu
<220> FEATURE:
<221> NAME/KEY: MISC_FEATURE
<222> LOCATION: (20)..(20)
<223> OTHER INFORMATION: Xaa = Ala, Cys, Gly, Lys or Gln
<220> FEATURE:
<221> NAME/KEY: MISC_FEATURE
<222> LOCATION: (21)..(21)
<223> OTHER INFORMATION: Xaa = a sequence of 1-27 amino acids
<220> FEATURE:
<221> NAME/KEY: MISC_FEATURE
<222> LOCATION: (24)..(24)
<223> OTHER INFORMATION: Xaa = Cys, Phe, Leu, Met or Trp
<220> FEATURE:
<221> NAME/KEY: MISC_FEATURE
<222> LOCATION: (26)..(26)
<223> OTHER INFORMATION: Xaa = Ala, Cys, Asp or Ser
<220> FEATURE:
<221> NAME/KEY: MISC_FEATURE
<222> LOCATION: (27)..(27)
<223> OTHER INFORMATION: Xaa = Leu or Val
<220> FEATURE:
<221> NAME/KEY: MISC_FEATURE
<222> LOCATION: (28)..(28)
<223> OTHER INFORMATION: Xaa = Ile, Leu, Pro or Val
<220> FEATURE:
<221> NAME/KEY: MISC_FEATURE
<222> LOCATION: (31)..(31)
<223> OTHER INFORMATION: Xaa = Cys, Phe, Ile, Leu or Val
<220> FEATURE:
<221> NAME/KEY: MISC_FEATURE
<222> LOCATION: (32)..(32)
<223> OTHER INFORMATION: Xaa = Phe or Leu
<220> FEATURE:
<221> NAME/KEY: MISC_FEATURE
<222> LOCATION: (33)..(33)
<223> OTHER INFORMATION: Xaa = Ala or Gly
<220> FEATURE:
<221> NAME/KEY: MISC_FEATURE
<222> LOCATION: (34)..(34)
<223> OTHER INFORMATION: Xaa = Phe, Trp or Tyr
<220> FEATURE:
<221> NAME/KEY: MISC_FEATURE
<222> LOCATION: (35)..(35)
<223> OTHER INFORMATION: Xaa = Phe, Ile, Leu or Val
<220> FEATURE:
<221> NAME/KEY: MISC_FEATURE
<222> LOCATION: (38)..(38)
<223> OTHER INFORMATION: Xaa = Ile, Leu or Val
<220> FEATURE:
<221> NAME/KEY: MISC_FEATURE
<222> LOCATION: (39)..(39)
<223> OTHER INFORMATION: Xaa = Ile, Leu or Val

<400> SEQUENCE: 251

Xaa Xaa Xaa Xaa Ala Ile Xaa Xaa Xaa Xaa Xaa Gly Val Xaa Xaa Xaa
1               5                   10                  15

Xaa Xaa Xaa Xaa Xaa Glu Phe Xaa Ile Xaa Xaa Xaa Leu Thr Xaa Xaa
            20                  25                  30

Xaa Xaa Xaa Pro Gly Xaa Xaa Tyr Ala
        35                  40


<210> SEQ ID NO 252
<211> LENGTH: 6255
<212> TYPE: DNA
<213> ORGANISM: Artificial Sequence
<220> FEATURE:
<223> OTHER INFORMATION: Vector
```

-continued

<400> SEQUENCE: 252
gcgcacattt ccccgaaaag tgccacctga tgcggtgtga aataccgcac agatgcgtaa 60
ggagaaaata ccgcatcagg aaattgtaag cgttaatatt ttgttaaaat tcgcgttaaa 120
tttttgttaa atcagctcat tttttaacca ataggccgaa atcggcaaaa tcccttataa 180
atcaaaagaa tagaccgaga tagggttgag tgttgttcca gtttggaaca agagtccact 240
attaaagaac gtggactcca acgtcaaagg gcgaaaaacc gtctatcagg gcgatggccc 300
actacgtgaa ccatcaccct aatcaagttt tttggggtcg aggtgccgta aagcactaaa 360
tcggaaccct aaagggagcc cccgatttag agcttgacgg ggaaagccgg cgaacgtggc 420
gagaaaggaa gggaagaaag cgaaaggagc gggcgctagg gcgctggcaa gtgtagcggt 480
cacgctgcgc gtaaccacca cacccgccgc gcttaatgcg ccgctacagg gcgcgtccat 540
tcgccattca ggctgcgcaa ctgttgggaa gggcgatcgg tgcgggcctc ttcgctatta 600
cgccagctgg cgaaaggggg atgtgctgca aggcgattaa gttgggtaac gccagggttt 660
tcccagtcac gacgttgtaa aacgacggcc agtgaattgt aatacgactc actatagggc 720
gaattgggcc cgacgtcgca tgctcccggc cgccatggcg gccgcgggaa ttcgattgat 780
tggcgcgcct taattaacgg gctggtaaaa caaatataag tattaatata aatataatac 840
aatagaagga aaataaataa aatttccctc tgtgccgtgc aaaaatgcac ggcaatgggt 900
tggcccgcac ggcaaaggca tcgttgccgt gtccacggca atgggttggc ccgcacggca 960
aaggcatcgt tgccgtgtcc acgtctttgc cgtgcgcctt ggctctatct ttgccgtgaa 1020
gcgttctttg ccgtgtgcct tttatttctt tgccgtggga tgctgccttt gccgagcgct 1080
gagctggcgc tttgccgtgc gcgtattgtt tgccgtgcgt cctcccagag ctgtacggca 1140
aagaattcat tgccgtgcac gaggcacacg ggaaagaagt ttcgcatggc aaagggcgct 1200
gacagcacac ggcaaagagc ccggcacggc attgagcttt ttttcccgta atgatagacg 1260
gcataatata atggacgcac atgctgatgt caggatgtca cccactcatc ctagtatttg 1320
tgggacgtga attctttgtg agatgggcaa tgggatgtga acaaaataag ttttgtacta 1380
gtagataaac atttttaccc ataaacaatt gttctgtatt gaatgaaaaa ttattttgta 1440
ctggatgaaa atcttctgag taactgtgta agattaacat gaatcaagag acaaatccaa 1500
tggctacaaa gtcaactaat acttgttaaa agttccgata cttaaaatta tcaaaactga 1560
tatatagaat attgcccatc tcgccaccgt gctagtttaa cagacgatgg acgaatatca 1620
gtcttgtatt ggataatcga tgcatgcgag ctatcggtca cctgtccatg cttccagaag 1680
gagccgagac gtggcgactt cgtccgacgc gccgactatc tgcacacgcc cggcttctcg 1740
tcgtgggcga gtcagcagtc acaggctttc cgcctaccaa ctcacacgta gcgccctatc 1800
gtggcgcttg atcgatgcaa cagcgatgcc tatcccagct cctcaagctg cttataagta 1860
tgtcctcggc catcactgct tacacaacaa acacagctac ttatcgcagt gtactaaaca 1920
agacgtacta gctagatttc gtgaggtaaa atcagtgcaa tatcacttgt gcaagccatt 1980
agtctcttca ccttgtccca cctgctcccg ccgcatctca ccagacacca gccatgtgcg 2040
gcagcgcgat cctctccgac atcatcccgc cgccgcgccg ggtcacggac ggcccccctct 2100
ggcggaacca gaagaagaag gggccgacgg gagatgctcc ggtggcgagg cgccgccgcg 2160
cgcccgagga ggaggagagc tacgaggact tcgaggccga cttcgagggc ttcgaggagg 2220
ggctcgggga ggccgagatc tggtccgagg acgaggccaa gcccttctcc gccgccagga 2280
aacgcgtcgc cgcaggtata gccgcccttt ttgggtcacc ggctttggat ctgtggaacc 2340

-continued gcgtgctaat tctgtttacg atttgggaga tagatttgag tttctcaggt gatctgctgc 2400
tcggattaga tagttgcatc ttcgatttgt ttgctatgaa gttaaatctg tgcaattgtt 2460
catctcaagt ccgttaattc agcgggtcca tgttgtcgat tagtctggtc tctagtgctg 2520
tgtctttttt ttaaaaaaac acaatctctg gtgctgtgtc gatccttagt ttttaggata 2580
actctcctaa atcatgaata tggtatcaac tcttattggt gcatacatag atcgagcttc 2640
ctcgcaagca tatgagttgg gctgttcctc aggattagac ttttaatgtc aagtttcgac 2700
ttaccctgac tttctgtatg taaactaaaa tctttatctc actgcttcat cctgattgaa 2760
taaatgcatg tacagctgct gctgttgatg gctgggcatc agagtccgcc aaaaggaaga 2820
gaaagaccca gttcaggggc atccgccgcc gcccttgggg taaatgggct gctgaaatca 2880
gagaccctcg caagggtgtc cgtgtctggc ttggcactta caactctgcc gaggaagctg 2940
ccagagccta tgatgctgaa gcaagaagga tccgtggcaa gaaggcaaag gtcaatttcc 3000
cagatgaggc tcctgtggct tctcaaaagc actgtgctaa gcctaccttt gtgacgttgc 3060
ctgagttcaa caccgaagag aagccgatag tcaacgccgt ggccaacaca aacgcgtatt 3120
cctatcctct tgttgactac accgtctgtg agccatttgt gcagcctcag aacatgtcat 3180
ttgtgccagc ggttaatgca gttgaggttc ctttcatgaa tctttcctct gaccagggta 3240
gcaactcctt tggttgctca gactttagct gggagaatgg taccaagact cctgacatca 3300
catctgtgct tgcatccatt cccacctcga ccgaggttga tgaatctgca ttccttcaga 3360
acaatgccag tgatgcatca ctacctcctg tgatggatac tgccaatgtt gatctcgccg 3420
atttggaacc atacatgaag ttcctcgtgg atggtgcttc agatgagtca cttgacaact 3480
ttctaagctg tgacgggtct gaggacatgg tcagcaacct ggacctttgg actttcgatg 3540
acatgcccat ttctgccgat ttctactgag gctctgaggt caattggtgc ctgtacgtat 3600
agataatggg taagcatctg caactgcgga aataactcac tgttatactt cagtttccat 3660
ttccataact accccacttc acttttcagg aataagtatt ctggacatca agaagtgctt 3720
gtgtcaggcg cctctgttga gcagtagtta tgtttgtata cttttatatc tagcttaaat 3780
ctcagtttga tcgcaagtct gaagtgaagg cctggtttct ccataataat gtgtgagtag 3840
ttcccagata agggaattag ggttcctata gggtttcgct catgtgttga gcatataaga 3900
aacccttagt atgtatttgt atttgtaaaa tacttctatc aataaaattt ctaattccta 3960
aaaccaaaat ccagtactaa aatccagatc cccgaatta attcggcgtt aattcagtat 4020
cggcgcgcct taattaaaat cgaatttcga ccatatggga gagctcccaa cgcgttggat 4080
gcatagcttg agtattctat agtgtcacct aaatagcttg gcgtaatcat ggtcatagct 4140
gtttcctgtg tgaaattgtt atccgctcac aattccacac aacatacgag ccggaagcat 4200
aaagtgtaaa gcctggggtg cctaatgagt gagctaactc acattaattg cgttgcgctc 4260
actgcccgct ttccagtcgg gaaacctgtc gtgccagctg cattaatgaa tcggccaacg 4320
cgcggggaga ggcggtttgc gtattgggcg ctcttccgct tcctcgctca ctgactcgct 4380
gcgctcggtc gttcggctgc ggcgagcggt atcagctcac tcaaaggcgg taatacggtt 4440
atccacagaa tcaggggata acgcaggaaa gaacatgtga gcaaaaggcc agcaaaaggc 4500
caggaaccgt aaaaaggccg cgttgctggc gtttttccat aggctccgcc cccctgacga 4560
gcatcacaaa aatcgacgct caagtcagag gtggcgaaac ccgacaggac tataaagata 4620
ccaggcgttt ccccctggaa gctccctcgt gcgctctcct gttccgaccc tgccgcttac 4680
cggatacctg tccgcctttc tcccttcggg aagcgtggcg ctttctcata gctcacgctg 4740

-continued taggtatctc agttcggtgt aggtcgttcg ctccaagctg ggctgtgtgc acgaaccccc 4800
cgttcagccc gaccgctgcg ccttatccgg taactatcgt cttgagtcca acccggtaag 4860
acacgactta tcgccactgg cagcagccac tggtaacagg attagcagag cgaggtatgt 4920
aggcggtgct acagagttct tgaagtggtg gcctaactac ggctacacta gaagaacagt 4980
atttggtatc tgcgctctgc tgaagccagt taccttcgga aaaagagttg gtagctcttg 5040
atccggcaaa caaaccaccg ctggtagcgg tggttttttt gtttgcaagc agcagattac 5100
gcgcagaaaa aaaggatctc aagaagatcc tttgatcttt tctacggggt ctgacgctca 5160
gtggaacgaa aactcacgtt aagggatttt ggtcatgaga ttatcaaaaa ggatcttcac 5220
ctagatcctt ttaaattaaa aatgaagttt taaatcaatc taaagtatat atgagtaaac 5280
ttggtctgac agttaccaat gcttaatcag tgaggcacct atctcagcga tctgtctatt 5340
tcgttcatcc atagttgcct gactccccgt cgtgtagata actacgatac gggagggctt 5400
accatctggc cccagtgctg caatgatacc gcgagaccca cgctcaccgg ctccagattt 5460
atcagcaata aaccagccag ccggaagggc cgagcgcaga agtggtcctg caactttatc 5520
cgcctccatc cagtctatta attgttgccg ggaagctaga gtaagtagtt cgccagttaa 5580
tagtttgcgc aacgttgttg ccattgctac aggcatcgtg gtgtcacgct cgtcgtttgg 5640
tatggcttca ttcagctccg gttcccaacg atcaaggcga gttacatgat cccccatgtt 5700
gtgcaaaaaa gcggttagct ccttcggtcc tccgatcgtt gtcagaagta agttggccgc 5760
agtgttatca ctcatggtta tggcagcact gcataattct cttactgtca tgccatccgt 5820
aagatgcttt tctgtgactg gtgagtactc aaccaagtca ttctgagaat agtgtatgcg 5880
gcgaccgagt tgctcttgcc cggcgtcaat acgggataat accgcgccac atagcagaac 5940
tttaaaagtg ctcatcattg gaaaacgttc ttcggggcga aaactctcaa ggatcttacc 6000
gctgttgaga tccagttcga tgtaacccac tcgtgcaccc aactgatctt cagcatcttt 6060
tactttcacc agcgtttctg ggtgagcaaa aacaggaagg caaaatgccg caaaaaaggg 6120
aataagggcg acacggaaat gttgaatact catactcttc ctttttcaat attattgaag 6180
catttatcag ggttattgtc tcatgagcgg atacatattt gaatgtattt agaaaaataa 6240
acaaataggg gttcc 6255

<210> SEQ ID NO 253
<211> LENGTH: 5690
<212> TYPE: DNA
<213> ORGANISM: Artificial Sequence
<220> FEATURE:
<223> OTHER INFORMATION: Vector

<400> SEQUENCE: 253
gcgcacattt ccccgaaaag tgccacctga tgcggtgtga aataccgcac agatgcgtaa 60
ggagaaaata ccgcatcagg aaattgtaag cgttaatatt ttgttaaaat tcgcgttaaa 120
tttttgttaa atcagctcat tttttaacca ataggccgaa atcggcaaaa tcccttataa 180
atcaaaagaa tagaccgaga tagggttgag tgttgttcca gtttggaaca agagtccact 240
attaaagaac gtggactcca acgtcaaagg gcgaaaaacc gtctatcagg gcgatggccc 300
actacgtgaa ccatcaccct aatcaagttt tttggggtcg aggtgccgta aagcactaaa 360
tcggaaccct aaagggagcc cccgatttag agcttgacgg ggaaagccgg cgaacgtggc 420
gagaaaggaa gggaagaaag cgaaaggagc gggcgctagg gcgctggcaa gtgtagcggt 480
cacgctgcgc gtaaccacca cacccgccgc gcttaatgcg ccgctacagg gcgcgtccat 540

-continued

```
tcgccattca ggctgcgcaa ctgttgggaa gggcgatcgg tgcgggcctc ttcgctatta    600
cgccagctgg cgaaaggggg atgtgctgca aggcgattaa gttgggtaac gccagggttt    660
tcccagtcac gacgttgtaa aacgacggcc agtgaattgt aatacgactc actatagggc    720
gaattgggcc cgacgtcgca tgctcccggc cgccatggcg gccgcgggaa ttcgattgat    780
tggcgcgcct taattaacgg gctggtaaaa caaatataag tattaatata aatataatac    840
aatagaagga aaataaataa aatttccctc tgtgccgtgc aaaaatgcac ggcaatgggt    900
tggcccgcac ggcaaaggca tcgttgccgt gtccacggca atgggttggc ccgcacggca    960
aaggcatcgt tgccgtgtcc acgtctttgc cgtgcgcctt ggctctatct ttgccgtgaa   1020
gcgttctttg ccgtgtgcct tttatttctt tgccgtggga tgctgccttt gccgagcgct   1080
gagctggcgc tttgccgtgc gcgtattgtt tgccgtgcgt cctcccagag ctgtacggca   1140
aagaattcat tgccgtgcac gaggcacacg ggaaagaagt ttcgcatggc aaagggcgct   1200
gacagcacac ggcaaagagc ccggcacggc attgagcttt ttttcccgta atgatagacg   1260
gcataatata atggacgcac atgctgatgt caggatgtca cccactcatc ctagtatttg   1320
tgggacgtga attctttgtg agatgggcaa tgggatgtga acaaaataag ttttgtacta   1380
gtagataaac atttttaccc ataaacaatt gttctgtatt gaatgaaaaa ttattttgta   1440
ctggatgaaa atcttctgag taactgtgta agattaacat gaatcaagag acaaatccaa   1500
tggctacaaa gtcaactaat acttgttaaa agttccgata cttaaaatta tcaaaactga   1560
tatatagaat attgcccatc tcgccaccgt gctagtttaa cagacgatgg acgaatatca   1620
gtcttgtatt ggataatcga tgcatgcgag ctatcggtca cctgtccatg cttccagaag   1680
gagccgagac gtggcgactt cgtccgacgc gccgactatc tgcacacgcc cggcttctcg   1740
tcgtgggcga gtcagcagtc acaggctttc cgcctaccaa ctcacacgta gcgccctatc   1800
gtggcgcttg atcgatgcaa cagcgatgcc tatcccagct cctcaagctg cttataagta   1860
tgtcctcggc catcactgct tacacaacaa acacagctac ttatcgcagt gtactaaaca   1920
agacgtacta gctagatttc gtgaggtaaa atcagtgcaa tatcacttgt gcaagccatt   1980
agtttgttgc tttcctgtgc catcgactgg catggctcgg aaatgctcca gctgcgggca   2040
taatggccat aactccagga cctgcagtgg caacaacggc ggcggtggtg ccggtggtgg   2100
gctgaggctg ttcggtgtgc agctgcaagt tggtgctgca cctctgaaga agagcttcag   2160
catggagtgc ctctcgtcgt cggcctacta cgcggccgca gcggtggccg cgtccaactc   2220
gtcgtcgtcc gtgtcatcgt catcgtcgct ggtctcggtg gaggagaacg ccgagaagat   2280
gggccacggc tacctctccg atggtctcat gggcagggct caggagagga agaagggtga   2340
gttcgtgtac tggtttcttg agcagttcgt tggtccggta tacctcgctg acacgcttga   2400
tttgctatgc tatggatttt ggatattaat catattatag tatgtgatag cgatctaacc   2460
atcatgcatg atgtctaagg ccagattaag aaaactattc tgaaattttt tttcccccta   2520
gctagagact aaagatctga agattcttgt tgatgcatga gtggttgtat gacttgtttg   2580
tatccaattg tgccatcagt tgctatctgc tatgccagac ttgcaactag ataacaggaa   2640
atacttagtc tttcaggtcc ttaactttca gtaatcatgt ctaatagctt gcacgaatca   2700
gtttgttctt tttttttca cctgaagatg tccagttacg ttgggtgaac taattcgtgt   2760
gacgcatggc atcaggggtt ccatggacgg aggatgagca ccggaggttc ctggccggct   2820
tagagaagct cgggaaaggc gactggcgag gcatctcccg gcacttcgtc gcgacacgca   2880
ccccgacgca ggtggccagc cacgcccaga agtacttcct ccggcaggcc ggcctcgcgc   2940
```

-continued

```
agaagaagcg gaggtccagc ctcttcgacg tggtacgtgc acgcctcaaa acgcaagctg   3000
gagttgtgga cgtagtaaca aaccagctga catgcacgaa ccttcctctc ttttcttcag   3060
gccgagaaga atggcgacaa ggcggcgaag gagagtcgtc cgagactgaa acacgagact   3120
agcagctccg tggacgggat ggcaattcgg tcattccctg ctctgtctct aggacccagc   3180
aggccgaggc ccgacgccgc cgtgcttcca ccatgcctga ccttgatgcc gagctattcg   3240
tcaggcctgg tttctccata ataatgtgtg agtagttccc agataaggga attagggttc   3300
ctatagggtt tcgctcatgt gttgagcata taagaaaccc ttagtatgta tttgtatttg   3360
taaaatactt ctatcaataa aatttctaat tcctaaaacc aaaatccagt actaaaatcc   3420
agatcccccg aattaattcg gcgttaattc agtatcggcg cgccttaatt aaaatcgaat   3480
ttcgaccata tgggagagct cccaacgcgt tggatgcata gcttgagtat tctatagtgt   3540
cacctaaata gcttggcgta atcatggtca tagctgtttc ctgtgtgaaa ttgttatccg   3600
ctcacaattc cacacaacat acgagccgga agcataaagt gtaaagcctg gggtgcctaa   3660
tgagtgagct aactcacatt aattgcgttg cgctcactgc ccgctttcca gtcgggaaac   3720
ctgtcgtgcc agctgcatta atgaatcggc caacgcgcgg ggagaggcgg tttgcgtatt   3780
gggcgctctt ccgcttcctc gctcactgac tcgctgcgct cggtcgttcg gctgcggcga   3840
gcggtatcag ctcactcaaa ggcggtaata cggttatcca cagaatcagg ggataacgca   3900
ggaaagaaca tgtgagcaaa aggccagcaa aaggccagga accgtaaaaa ggccgcgttg   3960
ctggcgtttt tccataggct ccgcccccct gacgagcatc acaaaaatcg acgctcaagt   4020
cagaggtggc gaaacccgac aggactataa agataccagg cgtttccccc tggaagctcc   4080
ctcgtgcgct ctcctgttcc gaccctgccg cttaccggat acctgtccgc ctttctccct   4140
tcgggaagcg tggcgctttc tcatagctca cgctgtaggt atctcagttc ggtgtaggtc   4200
gttcgctcca agctgggctg tgtgcacgaa ccccccgttc agcccgaccg ctgcgcctta   4260
tccggtaact atcgtcttga gtccaacccg gtaagacacg acttatcgcc actggcagca   4320
gccactggta acaggattag cagagcgagg tatgtaggcg gtgctacaga gttcttgaag   4380
tggtggccta actacggcta cactagaaga acagtatttg gtatctgcgc tctgctgaag   4440
ccagttacct tcggaaaaag agttggtagc tcttgatccg gcaaacaaac caccgctggt   4500
agcggtggtt tttttgtttg caagcagcag attacgcgca gaaaaaaagg atctcaagaa   4560
gatcctttga tcttttctac ggggtctgac gctcagtgga acgaaaactc acgttaaggg   4620
attttggtca tgagattatc aaaaaggatc ttcacctaga tccttttaaa ttaaaaatga   4680
agttttaaat caatctaaag tatatatgag taaacttggt ctgacagtta ccaatgctta   4740
atcagtgagg cacctatctc agcgatctgt ctatttcgtt catccatagt tgcctgactc   4800
cccgtcgtgt agataactac gatacgggag ggcttaccat ctggccccag tgctgcaatg   4860
ataccgcgag acccacgctc accggctcca gatttatcag caataaacca gccagccgga   4920
agggccgagc gcagaagtgg tcctgcaact ttatccgcct ccatccagtc tattaattgt   4980
tgccgggaag ctagagtaag tagttcgcca gttaatagtt tgcgcaacgt tgttgccatt   5040
gctacaggca tcgtggtgtc acgctcgtcg tttggtatgg cttcattcag ctccggttcc   5100
caacgatcaa ggcgagttac atgatccccc atgttgtgca aaaaagcggt tagctccttc   5160
ggtcctccga tcgttgtcag aagtaagttg gccgcagtgt tatcactcat ggttatggca   5220
gcactgcata attctcttac tgtcatgcca tccgtaagat gcttttctgt gactggtgag   5280
tactcaacca agtcattctg agaatagtgt atgcggcgac cgagttgctc ttgcccggcg   5340
```

-continued

```
tcaatacggg ataataccgc gccacatagc agaactttaa aagtgctcat cattggaaaa   5400

cgttcttcgg ggcgaaaact ctcaaggatc ttaccgctgt tgagatccag ttcgatgtaa   5460

cccactcgtg cacccaactg atcttcagca tcttttactt tcaccagcgt ttctgggtga   5520

gcaaaaacag gaaggcaaaa tgccgcaaaa aagggaataa gggcgacacg gaaatgttga   5580

atactcatac tcttcctttt tcaatattat tgaagcattt atcagggtta ttgtctcatg   5640

agcggataca tatttgaatg tatttagaaa aataaacaaa taggggttcc              5690
```

<210> SEQ ID NO 254
<211> LENGTH: 6558
<212> TYPE: DNA
<213> ORGANISM: Artificial Sequence
<220> FEATURE:
<223> OTHER INFORMATION: Vector

<400> SEQUENCE: 254

```
gcgcacattt ccccgaaaag tgccacctga tgcggtgtga aataccgcac agatgcgtaa     60

ggagaaaata ccgcatcagg aaattgtaag cgttaatatt ttgttaaaat tcgcgttaaa    120

tttttgttaa atcagctcat tttttaacca ataggccgaa atcggcaaaa tcccttataa    180

atcaaaagaa tagaccgaga tagggttgag tgttgttcca gtttggaaca agagtccact    240

attaaagaac gtggactcca acgtcaaagg gcgaaaaacc gtctatcagg gcgatggccc    300

actacgtgaa ccatcaccct aatcaagttt tttggggtcg aggtgccgta aagcactaaa    360

tcggaaccct aaagggagcc cccgatttag agcttgacgg ggaaagccgg cgaacgtggc    420

gagaaaggaa gggaagaaag cgaaaggagc gggcgctagg gcgctggcaa gtgtagcggt    480

cacgctgcgc gtaaccacca cacccgccgc gcttaatgcg ccgctacagg gcgcgtccat    540

tcgccattca ggctgcgcaa ctgttgggaa gggcgatcgg tgcgggcctc ttcgctatta    600

cgccagctgg cgaaaggggg atgtgctgca aggcgattaa gttgggtaac gccagggttt    660

tcccagtcac gacgttgtaa aacgacggcc agtgaattgt aatacgactc actatagggc    720

gaattgggcc cgacgtcgca tgctcccggc cgccatggcg gccgcgggaa ttcgattgat    780

tggcgcgcct taattaacgg gctggtaaaa caaatataag tattaatata aatataatac    840

aatagaagga aaataaataa aatttccctc tgtgccgtgc aaaaatgcac ggcaatgggt    900

tggcccgcac ggcaaaggca tcgttgccgt gtccacggca atgggttggc ccgcacggca    960

aaggcatcgt tgccgtgtcc acgtctttgc cgtgcgcctt ggctctatct ttgccgtgaa   1020

gcgttctttg ccgtgtgcct tttatttctt tgccgtggga tgctgccttt gccgagcgct   1080

gagctggcgc tttgccgtgc gcgtattgtt tgccgtgcgt cctcccagag ctgtacggca   1140

aagaattcat tgccgtgcac gaggcacacg ggaaagaagt ttcgcatggc aaagggcgct   1200

gacagcacac ggcaaagagc ccggcacggc attgagcttt ttttcccgta atgatagacg   1260

gcataaatata atggacgcac atgctgatgt caggatgtca cccactcatc ctagtatttg   1320

tgggacgtga attctttgtg agatgggcaa tgggatgtga acaaaataag ttttgtacta   1380

gtagataaac atttttaccc ataaacaatt gttctgtatt gaatgaaaaa ttattttgta   1440

ctggatgaaa atcttctgag taactgtgta agattaacat gaatcaagag acaaatccaa   1500

tggctacaaa gtcaactaat acttgttaaa agttccgata cttaaaatta tcaaaactga   1560

tatatagaat attgcccatc tcgccaccgt gctagtttaa cagacgatgg acgaatatca   1620

gtcttgtatt ggataatcga tgcatgcgag ctatcggtca cctgtccatg cttccagaag   1680

gagccgagac gtggcgactt cgtccgacgc gccgactatc tgcacacgcc cggcttctcg   1740
```

-continued

```
tcgtgggcga gtcagcagtc acaggctttc cgcctaccaa ctcacacgta gcgccctatc   1800

gtggcgcttg atcgatgcaa cagcgatgcc tatcccagct cctcaagctg cttataagta   1860

tgtcctcggc catcactgct tacacaacaa acacagctac ttatcgcagt gtactaaaca   1920

agacgtacta gctagatttc gtgaggtaaa atcagtgcaa tatcacttgt gcaagccatt   1980

agtgatctgc tgtgctgtgg tgagagctgc caagaagctg agcagtgcta ctctggagga   2040

gctcaccaaa ggattgtttc tgtttcggtt ttggcaatca ctaaataatg gaggaagtgg   2100

aggaggccaa caggatagcc gttgagagct gccacagagt gctgggcctg ctttcccagt   2160

cgcaggaccc ggcgcagctc aggagcatag ctctgggcac ggacgacgcc tgcgccaagt   2220

tccgcaaggt ggtctccctc ctcggcaacg aaggaggagg gggagcagta agccatccca   2280

gagccaaggt tgcgagcagg aaacagaccc cggccttctt gagccagaag ggcttcctgg   2340

acaacaacac cccggtggtg gtgctgaaca gcagcgccca cccttccact agctccgcgc   2400

aggcgtatcc taggaacacc attctggatt cgcacaccgc gcacccgatc ggagggcctc   2460

ccaagctggt ccagccattg tccgcgcact tccagttcgg caacgtatcg cggtatcagt   2520

tccagcatca gcaccagcag cagaagatgc aggctgagat gttcaagaga agcaacagta   2580

tcagtgggat taacctgaag ttcgacagcc ccagcgcggc cacgggggcg atgtcgtccg   2640

cgagatcctt catgtcatct ttgagcatgg atggtagcgt ggctagcctg gatgccaagt   2700

cttcctcgtt ccatttgatc ggtgggcctg ctatgagtga cccggtgaat gcgcagcagg   2760

cgccgaggag gcggtgcacg gggcgtgggg aggatgggaa tggcaagtgc gctgcaaatg   2820

gcaggtgcca ttgctcaaag aggaggtaaa tactcttatc ttagtgtgta tgattcttgc   2880

ttgctcttct attcaaggta gaataccatg agaattgttc tgttccctat ttcagcagga   2940

agttgcgggt gaagaagacg attaaagttc ctgccattag taataaaatt gctgatatac   3000

ctccagatga atactcatgg aggaagtatg ggcagaagcc aattaagggt tcccctcatc   3060

ccaggtatga actgagcact atctgttagt gtcattttct tgcacacata ttcttgatta   3120

tacggtgatg gagtagtggc aatgatgcta taatcaccat gactcatcaa ttttctaatt   3180

atttatcata tgtataactg cacatatccc ccatgaacta ctcaagtgcc tcatgataaa   3240

tgatggctct gtgataatca gaacacactt tatccatggt ttgcagggtg ttttacatgc   3300

tcctgataat cagaacactc tttatacagt atagtaatca aaactctcct tatgcagggt   3360

gttttgtatg ttcctgaata gttactttgt gaataatgtc tttcattctt cttgtgcaca   3420

ctttcttaaa atagatcaat cccgagtctt aaagtggcca gtggccactt cgtaattcag   3480

tctaccatga ttcagtcttt aagtggacat ctttaatgct atcgtgattc agtctactac   3540

gtactatact ttacctattc atatcacttt cccaccttgt ctatcttaaa tttcctgatg   3600

ataaaataca caaatatagc tatacggtaa tagcaaacgc atgggtatct tttcgagaaa   3660

aaaacaaaca catgggtatg gctgtctgaa ttgagaaaaa acttttcctc tttctagcaa   3720

gcactagata tagaaacacg attcatggcg catctatttt tatctccaat ccacaatgct   3780

aattctgatg tgtctcttaa gaccaatcca ctgattcctt aaacataatg caggggggtac   3840

tacaaatgta gcagtgtcag gggctgccca gccaggaagc atgttgaacg ttgtgtggat   3900

gatgcgtcaa tgctcattgt gacatacgag ggtgaacaca accacacgcg aatgccggct   3960

cagtctgcac aggcttaggg aatcactttg atcatcacac cctctccagg gaatactaac   4020

tcgcctgccc ttgtcgatgg ccgactgcac tgttcttcta aattagaatt acaaagtgac   4080

aaaaactggg ttccatttga gcagttgatg aggcctggtt tctccataat aatgtgtgag   4140
```

-continued tagttcccag ataagggaat tagggttcct atagggtttc gctcatgtgt tgagcatata 4200
agaaaccctt agtatgtatt tgtatttgta aaatacttct atcaataaaa tttctaattc 4260
ctaaaaccaa aatccagtac taaaatccag atcccccgaa ttaattcggc gttaattcag 4320
tatcggcgcg ccttaattaa aatcgaattt cgaccatatg ggagagctcc caacgcgttg 4380
gatgcatagc ttgagtattc tatagtgtca cctaaatagc ttggcgtaat catggtcata 4440
gctgtttcct gtgtgaaatt gttatccgct cacaattcca cacaacatac gagccggaag 4500
cataaagtgt aaagcctggg gtgcctaatg agtgagctaa ctcacattaa ttgcgttgcg 4560
ctcactgccc gctttccagt cgggaaacct gtcgtgccag ctgcattaat gaatcggcca 4620
acgcgcgggg agaggcggtt tgcgtattgg gcgctcttcc gcttcctcgc tcactgactc 4680
gctgcgctcg gtcgttcggc tgcggcgagc ggtatcagct cactcaaagg cggtaatacg 4740
gttatccaca gaatcagggg ataacgcagg aaagaacatg tgagcaaaag gccagcaaaa 4800
ggccaggaac cgtaaaaagg ccgcgttgct ggcgtttttc cataggctcc gcccccctga 4860
cgagcatcac aaaaatcgac gctcaagtca gaggtggcga aacccgacag gactataaag 4920
ataccaggcg tttccccctg gaagctccct cgtgcgctct cctgttccga ccctgccgct 4980
taccggatac ctgtccgcct ttctcccttc gggaagcgtg gcgctttctc atagctcacg 5040
ctgtaggtat ctcagttcgg tgtaggtcgt tcgctccaag ctgggctgtg tgcacgaacc 5100
ccccgttcag cccgaccgct gcgccttatc cggtaactat cgtcttgagt ccaacccggt 5160
aagacacgac ttatcgccac tggcagcagc cactggtaac aggattagca gagcgaggta 5220
tgtaggcggt gctacagagt tcttgaagtg gtggcctaac tacggctaca ctagaagaac 5280
agtatttggt atctgcgctc tgctgaagcc agttaccttc ggaaaaagag ttggtagctc 5340
ttgatccggc aaacaaacca ccgctggtag cggtggtttt tttgtttgca agcagcagat 5400
tacgcgcaga aaaaaaggat ctcaagaaga tcctttgatc ttttctacgg ggtctgacgc 5460
tcagtggaac gaaaactcac gttaagggat tttggtcatg agattatcaa aaaggatctt 5520
cacctagatc cttttaaatt aaaaatgaag ttttaaatca atctaaagta tatatgagta 5580
aacttggtct gacagttacc aatgcttaat cagtgaggca cctatctcag cgatctgtct 5640
atttcgttca tccatagttg cctgactccc cgtcgtgtag ataactacga tacgggaggg 5700
cttaccatct ggccccagtg ctgcaatgat accgcgagac ccacgctcac cggctccaga 5760
tttatcagca ataaaccagc cagccggaag ggccgagcgc agaagtggtc ctgcaacttt 5820
atccgcctcc atccagtcta ttaattgttg ccgggaagct agagtaagta gttcgccagt 5880
taatagtttg cgcaacgttg ttgccattgc tacaggcatc gtggtgtcac gctcgtcgtt 5940
tggtatggct tcattcagct ccggttccca acgatcaagg cgagttacat gatcccccat 6000
gttgtgcaaa aaagcggtta gctccttcgg tcctccgatc gttgtcagaa gtaagttggc 6060
cgcagtgtta tcactcatgg ttatggcagc actgcataat tctcttactg tcatgccatc 6120
cgtaagatgc ttttctgtga ctggtgagta ctcaaccaag tcattctgag aatagtgtat 6180
gcggcgaccg agttgctctt gcccggcgtc aatacgggat aataccgcgc cacatagcag 6240
aactttaaaa gtgctcatca ttggaaaacg ttcttcgggg cgaaaactct caaggatctt 6300
accgctgttg agatccagtt cgatgtaacc cactcgtgca cccaactgat cttcagcatc 6360
ttttactttc accagcgttt ctgggtgagc aaaaacagga aggcaaaatg ccgcaaaaaa 6420
gggaataagg gcgacacgga aatgttgaat actcatactc ttcctttttc aatattattg 6480

-continued aagcatttat cagggttatt gtctcatgag cggatacata tttgaatgta tttagaaaaa 6540
taaacaaata ggggttcc 6558

<210> SEQ ID NO 255
<211> LENGTH: 4683
<212> TYPE: DNA
<213> ORGANISM: Artificial Sequence
<220> FEATURE:
<223> OTHER INFORMATION: Vector

<400> SEQUENCE: 255
gcgcacattt ccccgaaaag tgccacctga tgcggtgtga aataccgcac agatgcgtaa 60
ggagaaaata ccgcatcagg aaattgtaag cgttaatatt ttgttaaaat tcgcgttaaa 120
tttttgttaa atcagctcat tttttaacca ataggccgaa atcggcaaaa tcccttataa 180
atcaaaagaa tagaccgaga tagggttgag tgttgttcca gtttggaaca agagtccact 240
attaaagaac gtggactcca acgtcaaagg gcgaaaaacc gtctatcagg gcgatggccc 300
actacgtgaa ccatcaccct aatcaagttt tttggggtcg aggtgccgta aagcactaaa 360
tcggaaccct aaagggagcc cccgatttag agcttgacgg ggaaagccgg cgaacgtggc 420
gagaaaggaa gggaagaaag cgaaaggagc gggcgctagg gcgctggcaa gtgtagcggt 480
cacgctgcgc gtaaccacca cacccgccgc gcttaatgcg ccgctacagg gcgcgtccat 540
tcgccattca ggctgcgcaa ctgttgggaa gggcgatcgg tgcgggcctc ttcgctatta 600
cgccagctgg cgaaaggggg atgtgctgca aggcgattaa gttgggtaac gccagggttt 660
tcccagtcac gacgttgtaa aacgacggcc agtgaattgt aatacgactc actatagggc 720
gaattgggcc cgacgtcgca tgctcccggc cgccatggcg gccgcgggaa ttcgattgat 780
tggcgcgcct taattaacgg gctggtaaaa caaatataag tattaatata aatataatac 840
aatagaagga aaataaataa aatttccctc tgtgccgtgc aaaaatgcac ggcaatgggt 900
tggcccgcac ggcaaaggca tcgttgccgt gtccacggca atgggttggc ccgcacggca 960
aaggcatcgt tgccgtgtcc acgtctttgc cgtgcgcctt ggctctatct ttgccgtgaa 1020
gcgttctttg ccgtgtgcct tttatttctt tgccgtggga tgctgccttt gccgagcgct 1080
gagctggcgc tttgccgtgc gcgtattgtt tgccgtgcgt cctcccagag ctgtacggca 1140
aagaattcat tgccgtgcac gaggcacacg ggaaagaagt ttcgcatggc aaagggcgct 1200
gacagcacac ggcaaagagc ccggcacggc attgagcttt ttttcccgta atgatagacg 1260
gcataatata atggacgcac atgctgatgt caggatgtca cccactcatc ctagtatttg 1320
tgggacgtga attctttgtg agatgggcaa tgggatgtga acaaaataag ttttgtacta 1380
gtagataaac atttttaccc ataaacaatt gttctgtatt gaatgaaaaa ttattttgta 1440
ctggatgaaa atcttctgag taactgtgta agattaacat gaatcaagag acaaatccaa 1500
tggctacaaa gtcaactaat acttgttaaa agttccgata cttaaaatta tcaaaactga 1560
tatatagaat attgcccatc tcgccaccgt gctagtttaa cagacgatgg acgaatatca 1620
gtcttgtatt ggataatcga tgcatgcgag ctatcggtca cctgtccatg cttccagaag 1680
gagccgagac gtggcgactt cgtccgacgc gccgactatc tgcacacgcc cggcttctcg 1740
tcgtgggcga gtcagcagtc acaggctttc cgcctaccaa ctcacacgta gcgccctatc 1800
gtggcgcttg atcgatgcaa cagcgatgcc tatcccagct cctcaagctg cttataagta 1860
tgtcctcggc catcactgct tacacaacaa acacagctac ttatcgcagt gtactaaaca 1920
agacgtacta gctagatttc gtgaggtaaa atcagtgcaa tatcacttgt gcaagccatt 1980

-continued agtatgggtt cggagacctt tctggagatc ctgctggcca tcctgctgcc gccgctcggc 2040
gttttcctcc gcttcggcat cggcgtaagc taccaaacca ttcagcgatt tcagggtgtg 2100
tatgtaatga tagatatatt gatttgatgg tcggttcatg catgtctgca ggtggagttc 2160
tggatctgcc tgctactcac cctgctgggc tacatccccg gcatcatcta cgccgtcttc 2220
gtccttgttg catagaggcc tggtttctcc ataataatgt gtgagtagtt cccagataag 2280
ggaattaggg ttcctatagg gtttcgctca tgtgttgagc atataagaaa cccttagtat 2340
gtatttgtat ttgtaaaata cttctatcaa taaaatttct aattcctaaa accaaaatcc 2400
agtactaaaa tccagatccc ccgaattaat tcggcgttaa ttcagtatcg gcgcgcctta 2460
attaaaatcg aatttcgacc atatgggaga gctcccaacg cgttggatgc atagcttgag 2520
tattctatag tgtcacctaa atagcttggc gtaatcatgg tcatagctgt ttcctgtgtg 2580
aaattgttat ccgctcacaa ttccacacaa catacgagcc ggaagcataa agtgtaaagc 2640
ctggggtgcc taatgagtga gctaactcac attaattgcg ttgcgctcac tgcccgcttt 2700
ccagtcggga aacctgtcgt gccagctgca ttaatgaatc ggccaacgcg cggggagagg 2760
cggtttgcgt attgggcgct cttccgcttc ctcgctcact gactcgctgc gctcggtcgt 2820
tcggctgcgg cgagcggtat cagctcactc aaaggcggta atacggttat ccacagaatc 2880
aggggataac gcaggaaaga acatgtgagc aaaaggccag caaaaggcca ggaaccgtaa 2940
aaaggccgcg ttgctggcgt ttttccatag gctccgcccc cctgacgagc atcacaaaaa 3000
tcgacgctca agtcagaggt ggcgaaaccc gacaggacta taaagatacc aggcgtttcc 3060
ccctggaagc tccctcgtgc gctctcctgt tccgaccctg ccgcttaccg gatacctgtc 3120
cgcctttctc ccttcgggaa gcgtggcgct ttctcatagc tcacgctgta ggtatctcag 3180
ttcggtgtag gtcgttcgct ccaagctggg ctgtgtgcac gaaccccccg ttcagcccga 3240
ccgctgcgcc ttatccggta actatcgtct tgagtccaac ccggtaagac acgacttatc 3300
gccactggca gcagccactg gtaacaggat tagcagagcg aggtatgtag gcggtgctac 3360
agagttcttg aagtggtggc ctaactacgg ctacactaga agaacagtat ttggtatctg 3420
cgctctgctg aagccagtta ccttcggaaa aagagttggt agctcttgat ccggcaaaca 3480
aaccaccgct ggtagcggtg gtttttttgt ttgcaagcag cagattacgc gcagaaaaaa 3540
aggatctcaa gaagatcctt tgatcttttc tacggggtct gacgctcagt ggaacgaaaa 3600
ctcacgttaa gggattttgg tcatgagatt atcaaaaagg atcttcacct agatcctttt 3660
aaattaaaaa tgaagtttta aatcaatcta aagtatatat gagtaaactt ggtctgacag 3720
ttaccaatgc ttaatcagtg aggcacctat ctcagcgatc tgtctatttc gttcatccat 3780
agttgcctga ctccccgtcg tgtagataac tacgatacgg gagggcttac catctggccc 3840
cagtgctgca atgataccgc gagacccacg ctcaccggct ccagatttat cagcaataaa 3900
ccagccagcc ggaagggccg agcgcagaag tggtcctgca actttatccg cctccatcca 3960
gtctattaat tgttgccggg aagctagagt aagtagttcg ccagttaata gtttgcgcaa 4020
cgttgttgcc attgctacag gcatcgtggt gtcacgctcg tcgtttggta tggcttcatt 4080
cagctccggt tcccaacgat caaggcgagt tacatgatcc cccatgttgt gcaaaaaagc 4140
ggttagctcc ttcggtcctc cgatcgttgt cagaagtaag ttggccgcag tgttatcact 4200
catggttatg gcagcactgc ataattctct tactgtcatg ccatccgtaa gatgcttttc 4260
tgtgactggt gagtactcaa ccaagtcatt ctgagaatag tgtatgcggc gaccgagttg 4320
ctcttgcccg gcgtcaatac gggataatac cgcgccacat agcagaactt taaaagtgct 4380

-continued

| | |
|---|---|
| catcattgga aaacgttctt cggggcgaaa actctcaagg atcttaccgc tgttgagatc | 4440 |
| cagttcgatg taacccactc gtgcacccaa ctgatcttca gcatctttta ctttcaccag | 4500 |
| cgtttctggg tgagcaaaaa caggaaggca aaatgccgca aaaaagggaa taagggcgac | 4560 |
| acggaaatgt tgaatactca tactcttcct ttttcaatat tattgaagca tttatcaggg | 4620 |
| ttattgtctc atgagcggat acatatttga atgtatttag aaaaataaac aaataggggt | 4680 |
| tcc | 4683 |

COMPOSITIONS AND METHODS FOR THE IMPROVEMENT OF PLANTS

CROSS-REFERENCE TO RELATED APPLICATIONS

This application claims priority to U.S. Provisional Application No. 60/853,194, filed Oct. 20, 2006. The priority application is incorporated herein by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled Sequence-Listing-DAIRY94005AUS.txt, created Oct. 20, 2007, which is 443 Kb in size. The information in the electronic format of the Sequence Listing is incorporated herein by reference in its entirety.

BACKGROUND OF THE INVENTION

1. Field of the Invention

The present invention relates to compositions and methods for producing plants with improved stress tolerance.

2. Description of the Related Art

Environmental abiotic stresses, including drought stress, cold stress, freezing stress, heat stress and salinity stress are major factors limiting plant growth and productivity. Crop losses and reduction in yield of major crops including maize, wheat and rice caused by such stresses represent significant economic issues and also lead to food shortages in several underdeveloped countries.

The development of stress tolerant plants has the potential to reduce or solve at least some of these problems. The use of traditional plant breeding strategies to produce new lines of plants that exhibit tolerance to these types of stresses has been slow. Lack of sufficient germplasm resources and incompatibility between distantly related plant species, present significant problems in conventional breeding. Further, the cellular processes leading to tolerance to such stresses are complex and involve multiple mechanisms of cellular adaptation and numerous metabolic pathways. This limits the success of both traditional breeding and that of genetic engineering approaches to development of stress tolerant plants. It would be beneficial to identify genes and proteins involved in controlling the complex processes leading to stress tolerance.

Regulators of gene expression, such as transcription factors, involved in controlling stress tolerance may be particularly useful in genetic engineering of plants, as a single gene may control a whole cascade of genes leading to the tolerance phenotype. Furthermore, there is sometimes commonality in many aspects of the different types of stress tolerant responses referred above. For example, genes that increase tolerance to cold or salt may also improve drought stress tolerance. This has been demonstrated in the case of the transcription factor AtCBF/DREB 1 (Kasuga et al., 1999 Nature Biotech 17: 287-91) and the vacuolar pyrophosphatase, AVP1 (Gaxiola et al., 2001 PNAS 98:11444-19).

Whilst some potentially useful genes have been identified, the identification and cloning of plant genes that confer tolerance to stress remains fragmented and incomplete. Although it is assumed that stress induced proteins may have a role in stress tolerance, evidence is still lacking and the function of many such stress responsive genes is unknown.

The hot and dry weather conditions in New Zealand and other countries in the summer period can have significant effect upon the yield of ryegrass. This is invariably during the dairy milking season and therefore has real effects on cost of dairy production through either reduced milk yield or the use of supplementary feeds and/or irrigation systems.

It would be beneficial to identify genes, which have the capacity to confer stress tolerance in stress susceptible plant species. The development of stress tolerant crops will provide many advantages such as increasing yield and producing plants that may be cultivated in previously unsuitable environmental conditions. Thus, there exists a need for compositions and methods for producing plants with improved stress tolerance relative to their wild-type counterparts.

It is an object of the invention to provide improved compositions and methods for developing plant varieties with improved tolerance of at least one of the following stresses; drought, cold, freezing, heat and salinity, or at least to provide the public with a useful choice.

SUMMARY OF THE INVENTION

In a first aspect the invention provides an isolated polynucleotide comprising the sequence of SEQ ID NO:1 or a variant thereof, wherein the variant encodes a polypeptide which modulates in a plant, tolerance to at least one environmental stress selected from drought, cold, freezing, heat and salinity.

In a further aspect the invention provides an isolated polynucleotide comprising the sequence of SEQ ID NO:2 or a variant thereof, wherein the variant encodes a polypeptide which modulates in a plant, tolerance to at least one environmental stress selected from drought, cold, freezing, heat and salinity.

Preferably the environmental stress is drought stress.

Preferably the variants of SEQ ID NO:1 and 2 encode polypeptides comprising the amino acid sequence:

(SEQ ID NO: 248)

$RKRKX_1X_2X_3RGX_4RX_5RPWGKWAAEIRDPRX_6GX_7RX_8WLGTX_9X_{10}$ $X_{11}X_{12}EX_{13}AAX_{14}AYX_{15}X_{16}X_{17}X_{18}RRIRX_{19}X_{20}KAX_{21}VNFP$ wherein $X_1$=N, S or T, $X_2$=Q or R, $X_3$=Y or F, $X_4$=I or V, $X_5$=Q or R, $X_6$=K, E or Q, $X_7$=V, S, I or A, $X_8$=V, E or I, $X_9$=F or Y, $X_{10}$=N, S, D, K or G, $X_{11}$=T or S, $X_{12}$=A or P, $X_{13}$=E or K, $X_{14}$=R, M or K, $X_{15}$=D, X or G, $X_{16}$=A, V, S, I or T, $X_{17}$=E or A, $X_{18}$=A or T, $X_{19}$=G or X, $X_{20}$=K, S, T or N and $X_{21}$=K or E.

Exemplary polynucleotide variants of SEQ ID NO:1 and SEQ ID NO:2 are disclosed herein and identified as SEQ ID NOs:13-25 of the sequence listing.

In a further aspect the invention provides an isolated polynucleotide comprising the sequence of SEQ ID NO:1.

In a further aspect the invention provides an isolated polynucleotide consisting of the sequence of SEQ ID NO:1.

In a further aspect the invention provides an isolated polynucleotide comprising the sequence of SEQ ID NO:2.

In a further aspect the invention provides an isolated polynucleotide consisting of the sequence of SEQ ID NO:2.

In a further aspect the invention provides polynucleotides comprising fragments of SEQ ID NO:1. Polynucleotides comprising fragments of the polynucleotide variants also form part of the invention.

In a further aspect the invention provides polynucleotides comprising fragments of SEQ ID NO:2. Polynucleotides comprising fragments of the polynucleotide variants also form part of the invention.

In a further aspect the invention provides an isolated polynucleotide comprising the sequence of SEQ ID NO:4 or a variant thereof, wherein the variant encodes a polypeptide which modulates in a plant, tolerance to at least one environmental stress selected from drought, cold, freezing, heat and salinity.

In a further aspect the invention provides an isolated polynucleotide comprising the sequence of SEQ ID NO:5 or a variant thereof, wherein the variant encodes a polypeptide which modulates in a plant, tolerance to at least one environmental stress selected from drought, cold, freezing, heat and salinity.

Preferably the environmental stress is drought stress.

Preferably the variants of SEQ ID NO:4 and SEQ ID NO:5 encode polypeptides comprising the amino acid sequence:

(SEQ ID NO: 249)

$WRX_1IX_2RX_3X_4VX_5X_6X_7TPTQVASHIAQKX_8X_9X_{10}R$ wherein $X_1$=G or N, $X_2$=A or S, $X_3$=H, K, N, S or T, $X_4$=F or Y, $X_5$=A, F, I, K, M, N, P, T or V, $X_6$=S or T, $X_7$=K or R, $X_8$=F or Y, $X_9$=F or Y and $X_{10}$=I, L, M or S.

Exemplary polynucleotide variants of SEQ ID NO:4 and SEQ ID NO:5 are disclosed herein and identified as SEQ ID NOs:39-66 of the sequence listing.

In a further aspect the invention provides an isolated polynucleotide comprising the sequence of SEQ ID NO:4.

In a further aspect the invention provides an isolated polynucleotide consisting of the sequence of SEQ ID NO:4.

In a further aspect the invention provides an isolated polynucleotide comprising the sequence of SEQ ID NO:5.

In a further aspect the invention provides an isolated polynucleotide consisting of the sequence of SEQ ID NO:5.

In a further aspect the invention provides polynucleotides comprising fragments of SEQ ID NO:4. Polynucleotides comprising fragments of the polynucleotide variants also form part of the invention.

In a further aspect the invention provides polynucleotides comprising fragments of SEQ ID NO:5. Polynucleotides comprising fragments of the polynucleotide variants also form part of the invention.

In a further aspect the invention provides an isolated polynucleotide comprising the sequence of SEQ ID NO:7 or a variant thereof, wherein the variant encodes a polypeptide which modulates in a plant, tolerance to at least one environmental stress selected from drought, cold, freezing, heat and salinity.

In a further aspect the invention provides an isolated polynucleotide comprising the sequence of SEQ ID NO:8 or a variant thereof, wherein the variant encodes a polypeptide which modulates in a plant, tolerance to at least one environmental stress selected from drought, cold, freezing, heat and salinity.

Preferably the environmental stress is drought stress.

Preferably the variants of SEQ ID NO:7 and SEQ ID NO:8 encode polypeptides comprising the amino acid sequence:

(SEQ ID NO: 250)

$IPX_1X_2X_3X_4SWRKYGQKPIKGSX_5X_6PRGYYKCSX_7X_8X_9X_{10}X_{11}X_{12}$ $X_{13}X_{14}X_{15}HVERX_{16}X_{17}X_{18}X_{19}X_{20}X_{21}MLX_{22}VTYEX_{23}X_{24}HX_{25}$

H wherein $X_1$=A, G, P, Q or S, $X_2$=D or G, $X_3$=D or E, $X_4$=F or Y, $X_5$=K or P, $X_6$=F, H or Y, $X_7$=S or T, $X_8$=I, L, M or V, $X_9$=R or T, $X_{10}$=G or S, $X_{11}$=C or Y, $X_{12}$=L or P, $X_{13}$=A or L, $X_{14}$=F, K or R, $X_{15}$=K or N, $X_{16}$=A, C, D or S, $X_{17}$=I, L, M, P or V, $X_{18}$=A, D, E or S, $X_{19}$=D or E, $X_{20}$=A, P, S or T, $X_{21}$=A, S or T, $X_{22}$=I, M or V, $X_{23}$=D or G, $X_{24}$=D or E, and $X_{25}$=C, H, N or R.

Exemplary polynucleotide variants of SEQ ID NO:7 and SEQ ID NO:8 are disclosed herein and identified as SEQ ID NOs: 95-126 of the sequence listing.

In a further aspect the invention provides an isolated polynucleotide comprising the sequence of SEQ ID NO:7.

In a further aspect the invention provides an isolated polynucleotide consisting of the sequence of SEQ ID NO:7.

In a further aspect the invention provides an isolated polynucleotide comprising the sequence of SEQ ID NO:8.

In a further aspect the invention provides an isolated polynucleotide consisting of the sequence of SEQ ID NO:8.

In a further aspect the invention provides polynucleotides comprising fragments of SEQ ID NO:7. Polynucleotides comprising fragments of the polynucleotide variants also form part of the invention.

In a further aspect the invention provides polynucleotides comprising fragments of SEQ ID NO:8. Polynucleotides comprising fragments of the polynucleotide variants also form part of the invention.

In a further aspect the invention provides an isolated polynucleotide comprising the sequence of SEQ ID NO:10 or a variant thereof, wherein the variant encodes a polypeptide which modulates in a plant, tolerance to at least one environmental stress selected from drought, cold, freezing, heat and salinity.

In a further aspect the invention provides an isolated polynucleotide comprising the sequence of SEQ ID NO:11 or a variant thereof, wherein the variant encodes a polypeptide which modulates in a plant, tolerance to at least one environmental stress selected from drought, cold, freezing, heat and salinity.

Preferably the environmental stress is drought stress.

Preferably the variants of SEQ ID NO:10 and SEQ ID NO:11 encode polypeptides comprising the amino acid sequence:

(SEQ ID NO: 251)

$X_1X_2X_3X_4AIX_5X_6X_7X_8X_9GVX_{10}X_{11}X_{12}X_{13}X_{14}X_{15}X_{16}ZEFX_{17}$ $IX_{18}X_{19}X_{20}LTX_{21}X_{22}X_{23}X_{24}X_{25}PGX_{26}X_{27}YA$ wherein $X_1$=D or E, $X_2$=I, L or V, $X_3$=F, I, L, M or V, $X_4$=C, F, I or L, $X_5$=F, I or L, $X_6$=I or L, $X_7$=H or P, $X_8$=P or Q, $X_9$=L or V, $X_{10}$=F or C, $X_{11}$=F or L, $X_{12}$=K or R, $X_{13}$=F, K, R, V or Y, $X_{14}$=A, G or K, $X_{15}$=C, I or L, $X_{16}$=A, C, G, K or Q, $X_{17}$=C, F, L, M or W, $X_{18}$=A, C, D or S, $X_{19}$=L or V, $X_{20}$=I, L, P or V, $X_{21}$=C, F, I, L or V, $X_{22}$=F or L, $X_{23}$=A or G, $X_{24}$=F, W or Y, $X_{25}$=F, I, L or V, $X_{26}$=I, L or V, $X_{27}$=I, L or V and wherein Z is a sequence of 1-27 amino acids.

Exemplary polynucleotide variants of SEQ ID NO:10 and SEQ ID NO:11 are disclosed herein and identified as SEQ ID NOs:159-200 of the sequence listing.

In a further aspect the invention provides an isolated polynucleotide comprising the sequence of SEQ ID NO:10.

In a further aspect the invention provides an isolated polynucleotide consisting of the sequence of SEQ ID NO:10.

In a further aspect the invention provides an isolated polynucleotide comprising the sequence of SEQ ID NO:11.

In a further aspect the invention provides an isolated polynucleotide consisting of the sequence of SEQ ID NO:11.

In a further aspect the invention provides polynucleotides comprising fragments of SEQ ID NO:10. Polynucleotides comprising fragments of the polynucleotide variants also form part of the invention.

In a further aspect the invention provides polynucleotides comprising fragments of SEQ ID NO:11. Polynucleotides comprising fragments of the polynucleotide variants also form part of the invention.

The polynucleotides of the invention may be derived from any plant species.

In one embodiment the polynucleotide is derived from a gymnosperm species.

In a further embodiment the polynucleotide is derived from an angiosperm species.

In a preferred embodiment the polynucleotide of the invention is derived from a forage plant species. Preferably the species is selected from those of the following genera: *Lolium, Festuca, Dactylis, Bromus, Trifolium, Medicago, Phleum, Phalaris, Holcus, Lotus, Plantago* and *Cichorium.*

In a more preferred embodiment the polynucleotide of the invention is derived from the genera *Lolium* or *Trifolium*. Particularly preferred are the species *Lolium perenne* and *Trifolium repens*. Most preferably the polynucleotide is derived from *Lolium perenne.*

The isolated polynucleotides of the invention are useful in methods for modulating in a plant, tolerance to at least one environmental stress selected from drought, cold, freezing, heat and salinity.

The isolated polynucleotides of the invention are also useful in methods for selecting plants tolerant to at least one environmental stress selected from drought, cold, freezing, heat and salinity.

In a further aspect the invention provides an isolated polypeptide comprising the sequence of SEQ ID NO:3 or a variant thereof, wherein the variant modulates in a plant, tolerance to at least one environmental stress selected from drought, cold, freezing, heat and salinity.

Preferably the environmental stress is drought stress.

Preferably the variants of SEQ ID NO:3 comprise the amino acid sequence:

(SEQ ID NO: 248)

$RKRKX_1X_2X_3RGX_4RX_5RPWGKWAAEIRDPRX_6GX_7RX_8WLGTX_9X_{10}$ $X_{11}X_{12}EX_{13}AAX_{14}AYX_{15}X_{16}X_{17}X_{18}RRIRX_{19}X_{20}KAX_{21}VNFP$ wherein $X_1$=N, S or T, $X_2$=Q or R, $X_3$=Y or F, $X_4$=I or V, $X_5$=Q or R, $X_6$=K, E or Q, $X_7$=V, S, I or A, $X_8$=V, E or I, $X_9$=F or Y, $X_{10}$=N, S, D, K or G, $X_{11}$=T or S, $X_{12}$=A or P, $X_{13}$=E or K, $X_{14}$=R, M or K, $X_{15}$=D, X or G, $X_{16}$=A, V, S, I or T, $X_{17}$=E or A, $X_{18}$=A or T, $X_{19}$=G or X, $X_{20}$=K, S, T or N and $X_{21}$=K or E.

Exemplary polypeptide variants of SEQ ID NO:3 are disclosed herein and identified as SEQ ID NOs:26-38 of the sequence listing.

In a further aspect the invention provides an isolated polypeptide comprising the sequence of SEQ ID NO:3.

In a further aspect the invention provides an isolated polypeptide consisting of the sequence of SEQ ID NO:3.

In a further aspect the invention provides polypeptides comprising fragments of SEQ ID NO:3. Polypeptides comprising fragments of variants, also form part of the invention.

In a further aspect the invention provides an isolated polypeptide comprising the sequence of SEQ ID NO:6 or a variant thereof, wherein the variant modulates in a plant, tolerance to at least one environmental stress selected from drought, cold, freezing, heat and salinity.

Preferably the environmental stress is drought stress.

Preferably the variants of SEQ ID NO:6 comprise the amino acid sequence:

(SEQ ID NO: 249)

$WRX_1IX_2RX_3X_4VX_5X_6X_7TPTQVASHIAQKX_8X_9X_{10}R$ wherein $X_1$=G or N, $X_2$=A or S, $X_3$=H, K, N, S or T, $X_4$=F or Y, $X_5$=A, F, I, K, M, N, P, T or V, $X_6$=S or T, $X_7$=K or R, $X_8$=F or Y, $X_9$=F or Y and $X_{10}$=1, L, M or S.

Exemplary polypeptide variants of SEQ ID NO:6 are disclosed herein and identified as SEQ ID NOs:67-94 of the sequence listing.

In a further aspect the invention provides an isolated polypeptide comprising the sequence of SEQ ID NO:6.

In a further aspect the invention provides an isolated polypeptide consisting of the sequence of SEQ ID NO:6.

In a further aspect the invention provides polypeptides comprising fragments of SEQ ID NO:6. Polypeptides comprising fragments of variants, also form part of the invention.

In a further aspect the invention provides an isolated polypeptide comprising the sequence of SEQ ID NO:9 or a variant thereof, wherein the variant modulates in a plant, tolerance to at least one environmental stress selected from drought, cold, freezing, heat and salinity.

Preferably the environmental stress is drought stress.

Preferably the variants of SEQ ID NO:9 comprise the amino acid sequence:

(SEQ ID NO: 250)

$IPX_1X_2X_3X_4SWRKYGQKPIKGSX_5X_6PRGYYKCSX_7X_8X_9X_{10}X_{11}X_{12}$ $X_{13}X_{14}X_{15}HVERX_{16}X_{17}X_{18}X_{19}X_{20}X_{21}MLX_{22}VTYEX_{23}X_{24}HX_{25}$

H wherein $X_1$=A, G, P, Q or S, $X_2$=D or G, $X_3$=D or E, $X_4$=F or Y, $X_5$=K or P, $X_6$=F, H or Y, $X_7$=S or T, $X_8$=I, L, M or V, $X_9$=R or T, $X_{10}$=G or S, $X_{11}$=C or Y, $X_{12}$=L or P, $X_{13}$=A or L, $X_{14}$=F, K or R, $X_{15}$=K or N, $X_{16}$=A, C, D or S, $X_{17}$=I, L, M, P or V, $X_{18}$=A, D, E or S, $X_{19}$=D or E, $X_{20}$=A, P, S or T, $X_{21}$=A, S or T, $X_{22}$=I, M or V, $X_{23}$=D or G, $X_{24}$=D or E, and $X_{25}$=C, H, N or R.

Exemplary polypeptide variants of SEQ ID NO:9 are disclosed herein and identified as SEQ ID NOs:127-158 of the sequence listing.

In a further aspect the invention provides an isolated polypeptide comprising the sequence of SEQ ID NO:9.

In a further aspect the invention provides an isolated polypeptide consisting of the sequence of SEQ ID NO:9.

In a further aspect the invention provides polypeptides comprising fragments of SEQ ID NO:9. Polypeptides comprising fragments of variants, also form part of the invention.

In a further aspect the invention provides an isolated polypeptide comprising the sequence of SEQ ID NO:12 or a variant thereof, wherein the variant modulates in a plant, tolerance to at least one environmental stress selected from drought, cold, freezing, heat and salinity.

Preferably the environmental stress is drought stress.

Preferably the variants of SEQ ID NO:12 comprise the amino acid sequence:

(SEQ ID NO: 251)

$X_1X_2X_3X_4AIX_5X_6X_7X_8X_9GVX_{10}X_{11}X_{12}X_{13}X_{14}X_{15}X_{16}ZEFX_{17}$ $IX_{18}X_{19}X_{20}LTX_{21}X_{22}X_{23}X_{24}X_{25}PGX_{26}X_{27}YA$ wherein $X_1$=D or E, $X_2$=I, L or V, $X_3$=F, I, L, M or V, $X_4$=C, F, I or L, $X_5$=F, I or L, $X_6$=I or L, $X_7$=H or P, $X_8$=P or Q, $X_9$=L or V, $X_{10}$=F or C, $X_{11}$=F or L, $X_{12}$=K or R, $X_{13}$=F, K, R, V or Y, $X_{14}$=A, G or K, $X_{15}$=C, I or L, $X_{16}$=A, C, G, K or Q, $X_{17}$=C, F, L, M or W, $X_{18}$=A, C, D or S, $X_{19}$=L or V, $X_{20}$=I, L, P or V, $X_{21}$=C, F, I, L or V, $X_{22}$=F or L, $X_{23}$=A or G, $X_{24}$=F, W or Y, $X_{25}$=F, I, L or V, $X_{26}$=I, L or V, $X_{27}$=I, L or V and wherein Z is a sequence of 1-27 amino acids.

Exemplary polypeptide variants of SEQ ID NO:12 are disclosed herein and identified as SEQ ID NOs:201-242 of the sequence listing.

In a further aspect the invention provides an isolated polypeptide comprising the sequence of SEQ ID NO:12.

In a further aspect the invention provides an isolated polypeptide consisting of the sequence of SEQ ID NO:12.

In a further aspect the invention provides polypeptides comprising fragments of SEQ ID NO:12. Polypeptides comprising fragments of variants, also form part of the invention.

In one embodiment the polypeptide is derived from a gymnosperm species.

In a further embodiment the polypeptide is derived from an angiosperm species.

In a preferred embodiment the polypeptide of the invention is derived from a forage plant species. Preferably the species is selected from those of the following genera: *Lolium, Festuca, Dactylis, Bromus, Trifolium, Medicago, Phleum, Phalaris, Holcus, Lotus, Plantago* and *Cichorium.*

In a more preferred embodiment the polypeptide of the invention is derived from the genera *Lolium* or *Trifolium*. Particularly preferred are the species *Lolium perenne* and *Trifolium repens*. Most preferably the polypeptide of the invention is derived from *Lolium perenne.*

In a further aspect the invention provides a polynucleotide encoding a polypeptide of the invention.

In a further aspect the invention provides a genetic construct which comprises a polynucleotide of the invention.

In a further aspect the invention provides a genetic construct which comprises a polynucleotide encoding a polypeptide of the invention.

In a further aspect the invention provides a genetic construct which comprises a polynucleotide of any one of SEQ ID NO:1, SEQ ID NO:2 or a variant or fragment thereof.

In a further aspect the invention provides a genetic construct which comprises the polynucleotide of SEQ ID NO:1.

In a further aspect the invention provides a genetic construct which comprises the polynucleotide of SEQ ID NO:2.

In a further aspect the invention provides a genetic construct which comprises a polynucleotide of any one of SEQ ID NO:4, SEQ ID NO:5 or a variant or fragment thereof.

In a further aspect the invention provides a genetic construct which comprises the polynucleotide of SEQ ID NO:4.

In a further aspect the invention provides a genetic construct which comprises the polynucleotide of SEQ ID NO:5.

In a further aspect the invention provides a genetic construct which comprises a polynucleotide of any one of SEQ ID NO:7, SEQ ID NO:8 or a variant or fragment thereof.

In a further aspect the invention provides a genetic construct which comprises the polynucleotide of SEQ ID NO:7.

In a further aspect the invention provides a genetic construct which comprises the polynucleotide of SEQ ID NO:8.

In a further aspect the invention provides a genetic construct which comprises a polynucleotide of any one of SEQ ID NO:10, SEQ ID NO:11 or a variant or fragment thereof.

In a further aspect the invention provides a genetic construct which comprises the polynucleotide of SEQ ID NO:10.

In a further aspect the invention provides a genetic construct which comprises the polynucleotide of SEQ ID NO:11.

Preferably the constructs of the invention are expression constructs as herein defined. Preferably expression constructs of the invention include an environmental stress responsive promoter operably linked polynucleotide sequence. Preferably the environmental stress responsive promoter is responsive to at least one environmental stress selected from drought, cold, freezing, heat and salinity.

Preferably the expression construct includes a promoter comprising the sequence of SEQ ID NO:243 or a fragment, region, cis-element or variant of the sequence capable of regulating transcription of an operably linked polynucleotide sequence.

In a further aspect the invention provides a vector which comprises a genetic construct of the invention.

In a further aspect the invention provides a host cell which comprises a genetic construct of the invention.

In a further aspect the invention provides methods for the recombinant production of polypeptide of the invention comprising the steps of:

a) culturing a host cell comprising a genetic construct of the invention, such as an expression construct as defined herein, capable of expressing a polypeptide of the invention, and b) separating the expressed polypeptide.

In a further aspect the invention provides a plant cell which comprises one or more of the genetic constructs of the invention. In a preferred embodiment the genetic construct comprises the polynucleotide sequence of SEQ ID NO:1 or a variant or fragment thereof.

In a further aspect the invention provides a plant cell which comprises one or more of the genetic constructs of the invention. In a preferred embodiment the genetic construct comprises the polynucleotide sequence of SEQ ID NO:2 or a variant or fragment thereof.

In a further aspect the invention provides a plant cell which comprises one or more of the genetic constructs of the invention. In a preferred embodiment the genetic construct comprises the polynucleotide sequence of SEQ ID NO:4 or a variant or fragment thereof.

In a further aspect the invention provides a plant cell which comprises one or more of the genetic constructs of the invention. In a preferred embodiment the genetic construct comprises the polynucleotide sequence of SEQ ID NO:5 or a variant or fragment thereof.

In a further aspect the invention provides a plant cell which comprises one or more of the genetic constructs of the invention. In a preferred embodiment the genetic construct comprises the polynucleotide sequence of SEQ ID NO:7 or a variant or fragment thereof.

In a further aspect the invention provides a plant cell which comprises one or more of the genetic constructs of the invention. In a preferred embodiment the genetic construct comprises the polynucleotide sequence of SEQ ID NO:8 or a variant or fragment thereof.

In a further aspect the invention provides a plant cell which comprises one or more of the genetic constructs of the invention. In a preferred embodiment the genetic construct comprises the polynucleotide sequence of SEQ ID NO:10 or a variant or fragment thereof.

In a further aspect the invention provides a plant cell which comprises one or more of the genetic constructs of the invention. In a preferred embodiment the genetic construct comprises the polynucleotide sequence of SEQ ID NO:11 or a variant or fragment thereof.

In a further aspect the invention provides a plant cell with altered expression of a polynucleotide or polypeptide of the invention.

In a further aspect the invention provides a plant cell genetically modified to alter expression of a polynucleotide or polypeptide of the invention.

In a further aspect the invention provides a plant which comprises a plant cell of the invention.

In a further aspect the invention provides methods for altering in a plant, tolerance to at least one environmental stress selected from drought, cold, freezing, heat and salinity, the method comprising transformation of a plant cell, or plant with a genetic construct of the invention capable of altering expression of a polynucleotide/polypeptide of the invention.

In a further aspect the invention provides methods for altering tolerance to drought stress in a plant, the method comprising transformation of a plant with a genetic construct of the invention capable of altering expression of a polynucleotide/polypeptide of the invention.

In a further aspect the invention provides methods for altering tolerance to cold stress in a plant, the method comprising transformation of a plant with a genetic construct of the invention capable of altering expression of a polynucleotide/polypeptide of the invention.

In a further aspect the invention provides methods for altering tolerance to freezing stress in a plant, the method comprising transformation of a plant with a genetic construct of the invention capable of altering expression of a polynucleotide/polypeptide of the invention.

In a further aspect the invention provides methods for altering tolerance to heat stress in a plant, the method comprising transformation of a plant with a genetic construct of the invention capable of altering expression of a polynucleotide/polypeptide of the invention.

In a further aspect the invention provides methods for altering tolerance to salinity stress in a plant, the method comprising transformation of a plant with a genetic construct of the invention capable of altering expression of a polynucleotide/polypeptide of the invention.

In a further aspect the invention provides methods for altering tolerance to at least one environmental stress selected from drought, cold, freezing, heat and salinity in a plant, the method comprising transformation of a plant with a genetic construct of the invention capable of altering expression of a polynucleotide involved in modulation in a plant of tolerance to at least one environmental stress selected from drought, cold, freezing, heat and salinity.

In a further aspect the invention provides methods for altering tolerance to drought stress in a plant, the method comprising transformation of a plant with a genetic construct of the invention capable of altering expression of a polynucleotide involved in modulation tolerance to drought stress in a plant.

In a further aspect the invention provides methods for altering tolerance to cold stress in a plant the method comprising transformation of a plant with a genetic construct of the invention capable of altering expression of a polynucleotide involved in modulation of tolerance to cold stress in a plant.

In a further aspect the invention provides methods for altering tolerance to freezing stress in a plant, the method comprising transformation of a plant with a genetic construct of the invention capable of altering expression of a polynucleotide involved in modulation of tolerance to freezing stress in a plant.

In a further aspect the invention provides methods for altering tolerance to heat stress in a plant, the method comprising transformation of a plant with a genetic construct of the invention capable of altering expression of a polynucleotide involved in modulation of tolerance to heat stress in a plant.

In a further aspect the invention provides methods for altering tolerance to salinity stress in a plant, the method comprising transformation of a plant with a genetic construct of the invention capable of altering expression of a polynucleotide involved in modulation of tolerance to salinity stress in a plant.

It will be understood by those skilled in the art that transformation of a plant may involve transforming a plant cell(s) and regenerating a transformed plant from the transformed plant cell(s).

In a further aspect the invention provides a method for selecting a plant with increased tolerance to at least one environmental stress selected from drought, cold, freezing, heat and salinity, the method comprising testing of a plant for altered expression of a polynucleotide of the invention.

In a further aspect the invention provides a method for selecting a plant with increased tolerance to drought stress, the method comprising testing of a plant for altered expression of a polynucleotide of the invention.

In a further aspect the invention provides a method for selecting a plant with increased tolerance to cold stress, the method comprising testing of a plant for altered expression of a polynucleotide of the invention.

In a further aspect the invention provides a method for selecting a plant with increased tolerance to freezing stress, the method comprising testing of a plant for altered expression of a polynucleotide of the invention.

In a further aspect the invention provides a method for selecting a plant with increased tolerance to heat stress, the method comprising testing of a plant for altered expression of a polynucleotide of the invention.

In a further aspect the invention provides a method for selecting a plant with increased tolerance to salinity stress, the method comprising testing of a plant for altered expression of a polynucleotide of the invention.

In a further aspect the invention provides a method for selecting a plant with increased tolerance to at least one environmental stress selected from drought, cold, freezing, heat and salinity, the method comprising testing of a plant for altered expression of a polypeptide of the invention.

In a further aspect the invention provides a method for selecting a plant with increased tolerance to drought stress, the method comprising testing of a plant for altered expression of a polypeptide of the invention.

In a further aspect the invention provides a method for selecting a plant with increased tolerance to cold stress, the method comprising testing of a plant for altered expression of a polypeptide of the invention.

In a further aspect the invention provides a method for selecting a plant with increased tolerance to freezing stress, the method comprising testing of a plant for altered expression of a polypeptide of the invention.

In a further aspect the invention provides a method for selecting a plant with increased tolerance to heat stress, the method comprising testing of a plant for altered expression of a polypeptide of the invention.

In a further aspect the invention provides a method for selecting a plant with increased tolerance to salinity stress, the method comprising testing of a plant for altered expression of a polypeptide of the invention.

In a further aspect the invention provides a plant cell or plant produced by a method of the invention.

In a further aspect the invention provides a plant cell selected by a method of the invention.

In a further aspect the invention provides a population or group of plants selected by a method of the invention.

The plant cells and plants of the invention may be from any species.

In one embodiment the plant cells and plants of the invention are from gymnosperm species.

In a further embodiment the plant cells and plants of the invention are from angiosperm species.

In a preferred embodiment the plant cells and plants of the invention are derived from forage plant species. Preferably the forage species is selected from those of the following genera: *Lolium, Festuca, Dactylis, Bromus, Trifolium, Medicago, Phleum, Phalaris, Holcus, Lotus, Plantago* and *Cichorium.*

In a more preferred embodiment of the invention the plant cells and plants are from the genera *Lolium* or *Trifolium*. Particularly preferred are the species *Lolium perenne* and *Trifolium repens*. Most preferably the plant cells and plants of the invention are derived from *Lolium perenne.*

BRIEF DESCRIPTION OF THE DRAWINGS

The present invention will be better understood with reference to the accompanying drawings in which:

FIG. 9 shows the sequence (SEQ ID NO:253) of a vector, for plant transformation, comprising ORF68 and corresponding to the map in FIG. 8. Sequence in bold corresponds to the *Lolium perenne* promoter (SEQ ID NO:243). Sequence in italics corresponds to ORF68. Sequence underlined corresponds to 3'terminator sequence from CaMV35S gene. Sequence in regular font corresponds to vector sequence.

FIG. 12 shows the sequence (SEQ ID NO:246) of a vector, for plant transformation, comprising ORF69 and corresponding to the map in FIG. 11. Sequence in bold corresponds to the CaMV35S promoter. Sequence in italics corresponds to ORF69. Sequence underlined corresponds to 3'terminator sequence from CaMV35S gene. Sequence in regular font corresponds to vector sequence.

FIG. 14 shows the sequence (SEQ ID NO:254) of another vector, for plant transformation, comprising ORF69 and corresponding to the map in FIG. 13. Sequence in bold corresponds to the *Lolium perenne* promoter (SEQ ID NO:243). Sequence in italics corresponds to ORF69. Sequence underlined corresponds to 3'terminator sequence from CaMV35S gene. Sequence in regular font corresponds to vector sequence.

CB879962.1=SEQ ID NO:141; BE361091.1=SEQ ID NO:144; AY077758.1=SEQ ID NO:145; CO210220.1=SEQ ID NO:147., CF205668.1=SEQ ID NO:146; CV291964.1=SEQ ID NO:152; AAD32676.1=SEQ ID NO:155; DAA05115.1=SEQ ID NO: 157; AB020023.1 SEQ ID NO:148; CK295284.1SEQ ID NO:150; BT014501.1=SEQ ID NO:158; CV707436.1=SEQ ID NO:153; AAS66778.1=SEQ ID NO:156; U56834.1=SEQ ID NO:151; BP083458.1=SEQ ID NO:154; BM336249.1=SEQ ID NO:143; BF291316.1=SEQ ID NO:128; CA141214.1=SEQ ID NO: 130; ORF69=SEQ ID NO:9; CV000669.1=SEQ ID NO:149; BM956319.1=SEQ ID NO:142; AK070648.1=SEQ ID NO:127; and CV782162.1=SEQ ID NO:129) and illustrates a consensus region (shown within bold box) identified by the applicants which is present in all of the such sequences.

Figure 16:
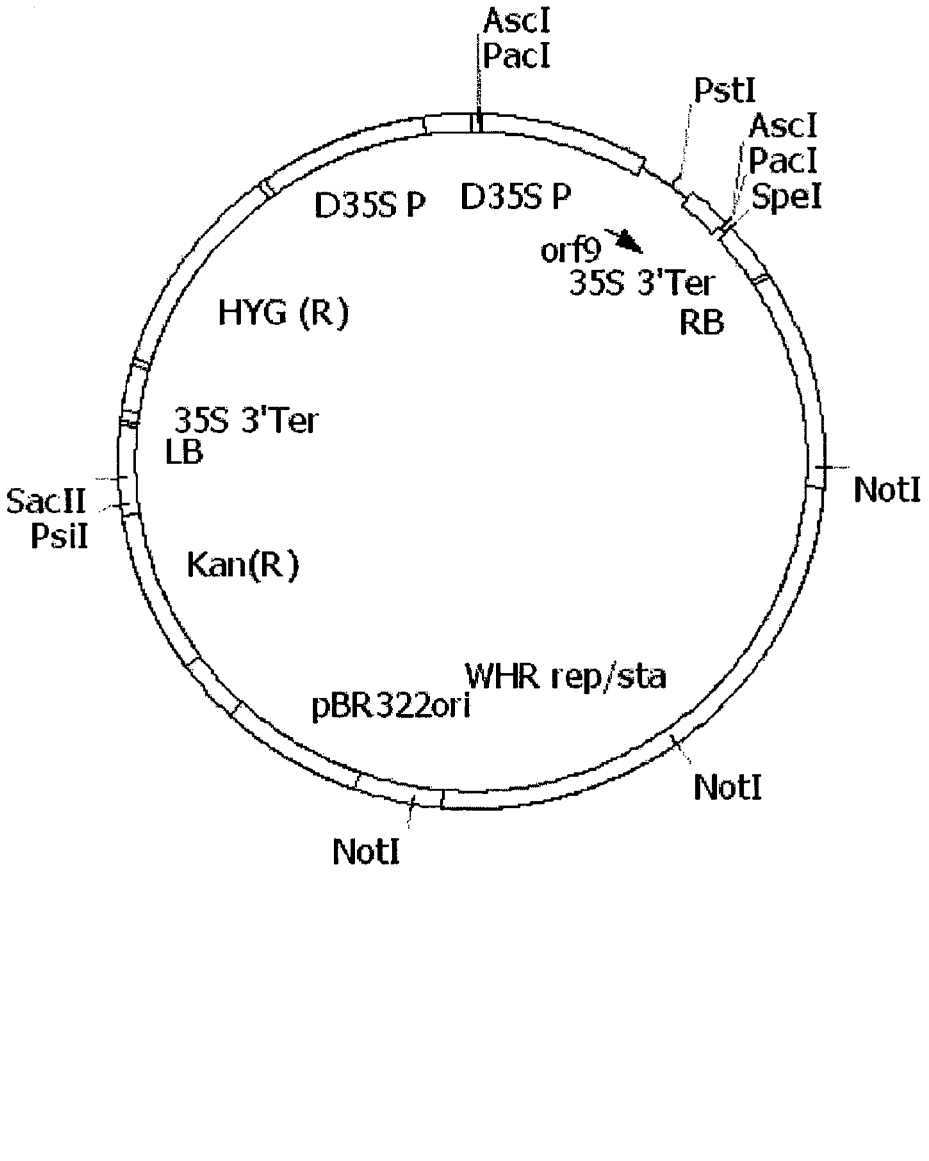

FIG. 16 shows a map of a vector, for plant transformation, comprising ORF9 (SEQ ID NO:11).

FIG. 17 shows the sequence of a vector (SEQ ID NO:247), for plant transformation, comprising ORF9 and corresponding to the map in FIG. 16. Sequence in bold corresponds to the CaMV35S promoter. Sequence in italics corresponds to ORF9. Sequence underlined corresponds to 3'terminator sequence from CaMV35S gene. Sequence in regular font corresponds to vector sequence.

Figure 18:
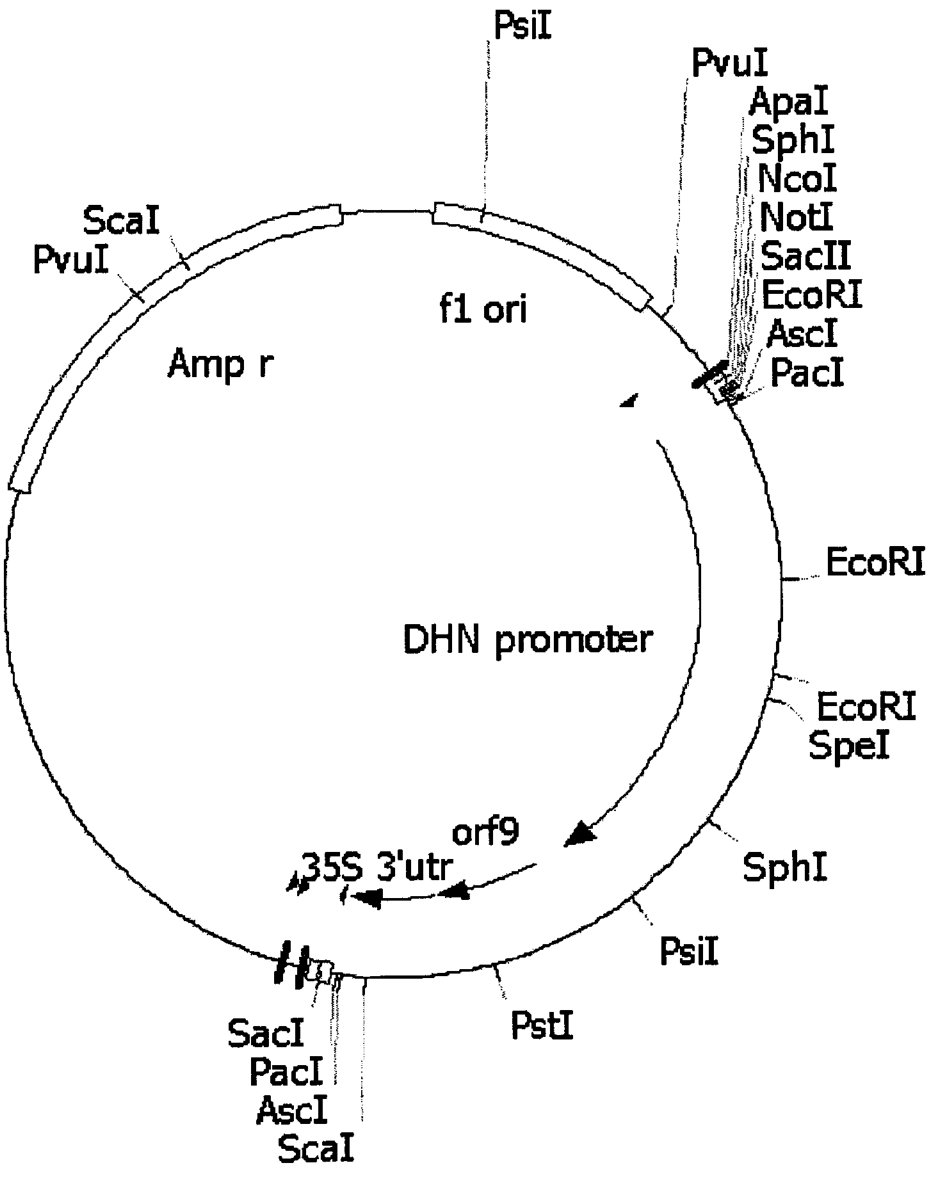

FIG. 18 shows a map of another vector, for plant transformation, comprising ORF9 (SEQ ID NO:11).

Figures 1, 20:
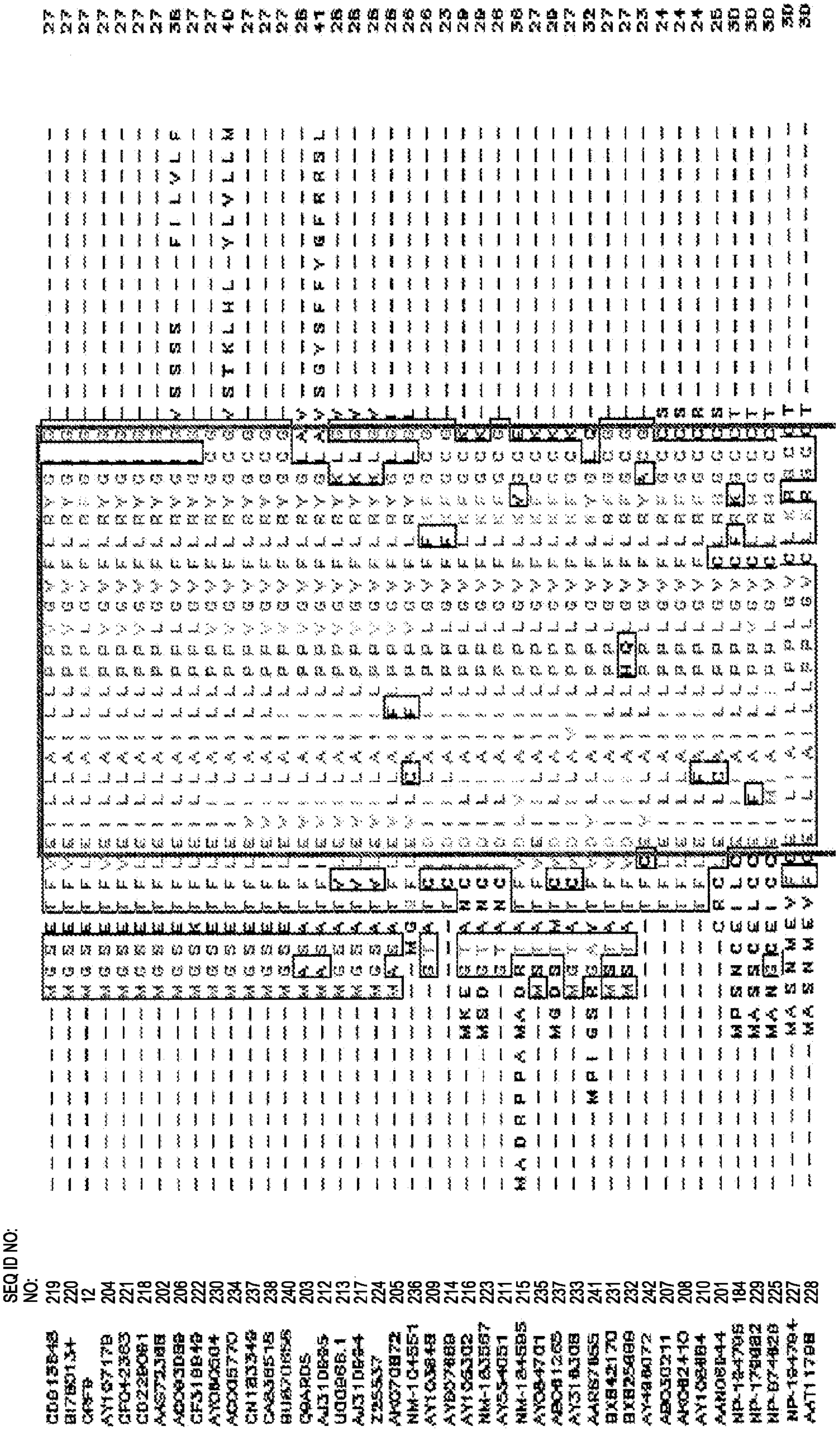
Figures 2, 20:
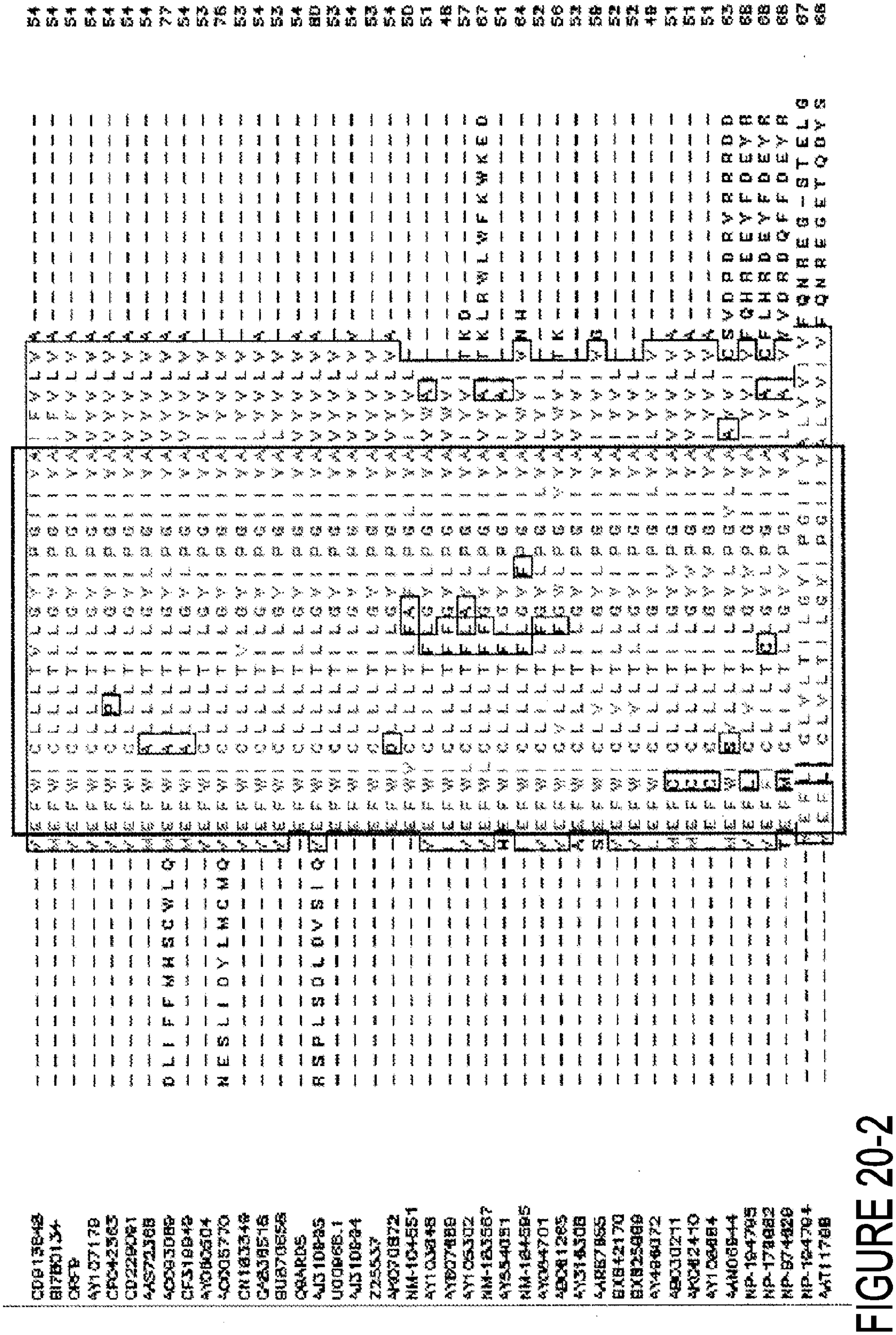

FIG. 19 shows the sequence of another vector (SEQ ID NO:255), for plant transformation, comprising ORF9 and corresponding to the map in FIG. 18. Sequence in bold corresponds to the *Lolium perenne* promoter (SEQ ID NO:243). Sequence in italics corresponds to ORF9. Sequence underlined corresponds to 3'terminator sequence from CaMV35S gene. Sequence in regular font corresponds to vector sequence FIG. 20 shows an alignment of polypeptides of the invention, including ORF9 (SEQ ID NO: 12) and sequences which are variants of SEQ ID NO: 12 from several species (CD913648=SEQ ID NO:219; BI780134=SEQ ID NO:220; ORF9=SEQ ID NO:12; AY107179.1=SEQ ID NO:204; CF042363=SEQ ID NO:221; CD229091=SEQ ID NO:218; AAS72368=SEQ ID NO:202; AC093089=SEQ ID NO:206; CF319949=SEQ ID NO:222; AY060504=SEQ ID NO:230; AC005770=SEQ ID NO:234; CN 183349=SEQ ID NO:239; CA836518=SEQ ID NO:238; BU870658=SEQ ID NO:240; Q9ARD5=SEQ ID NO:203; AJ310995=SEQ ID NO:212; U00966.1=SEQ ID NO:213; AJ310994=SEQ ID NO:217; Z25537=SEQ ID NO:224; AK070872=SEQ ID NO:205; NM 104551=SEQ ID NO:236; AY103848=SEQ ID NO:209; AY607689=SEQ ID NO:214; AY105302=SEQ ID NO:216; NM 183567=SEQ ID NO:223; AY554051=SEQ ID NO:211; NM 184595=SEQ ID NO:215; AY084701=SEQ ID NO:235; AB061265=SEQ ID NO:237; AY316308=SEQ ID NO:233; AAR87655=SEQ ID NO:241; BX842170=SEQ ID NO:231; BX825999=SEQ ID NO:232; AY496072=SEQ ID NO:242; AB030211=SEQ ID NO:207; AK062410=SEQ ID NO:208; AY108684=SEQ ID NO:210; AAN06944=SEQ ID NO:201; NP 194795=SEQ ID NO:184; NP 179982=SEQ ID NO:229; NP 974629=SEQ ID NO:225; NP 194794=SEQ ID NO:227; and AAT11798=SEQ ID NO:228) and illustrates a consensus region (shown within bold box) identified by the applicants which is present in all of the such sequences.

Figure 21:
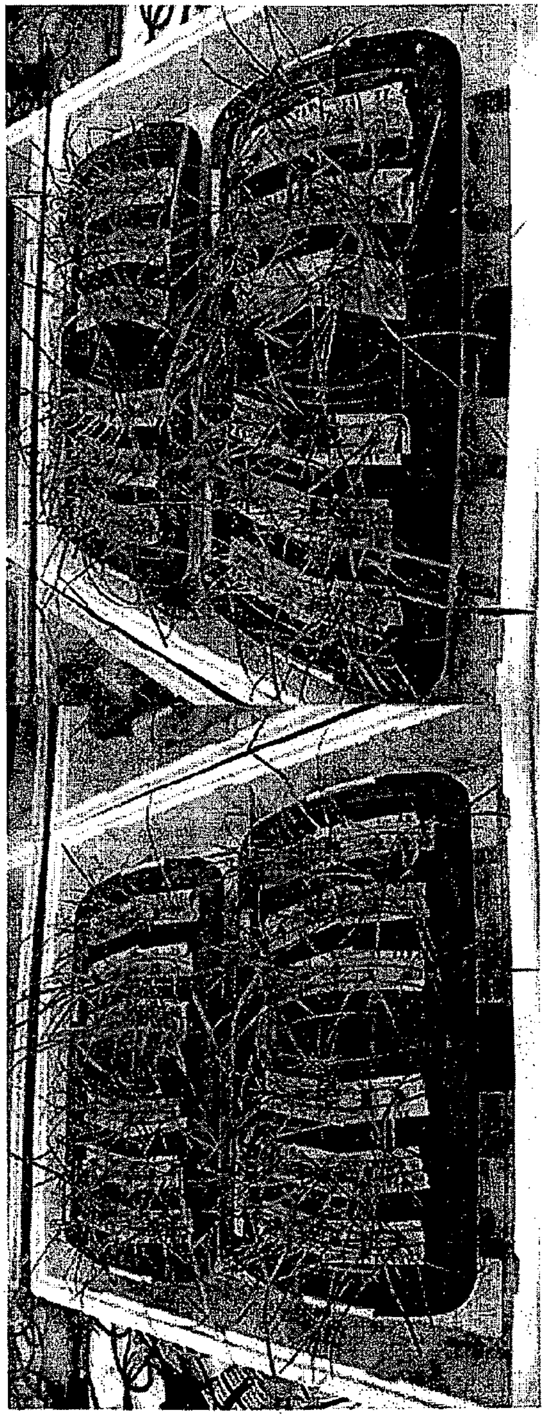

FIG. 21 shows four hydroponic tanks, representing eight randomized blocks with 15 plants in each block (10 transgenic lines and 5 wild type clones), totaling 120 plants (80 transgenic lines and 40 wild type clones).

Figure 22:
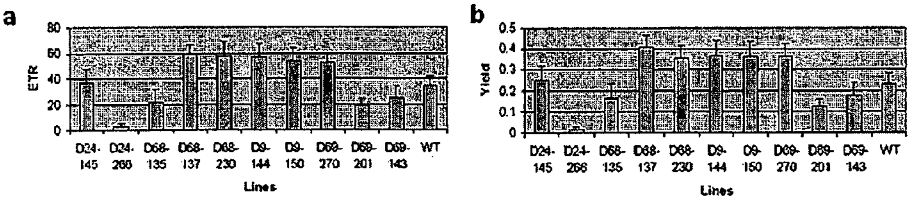

FIG. 22 shows the Electron Transfer Rate (ETR) (a) and yield (b) of photosystem II after 24 hours recovery from 24 hours stress as measured with PAM2000.

Figure 23:
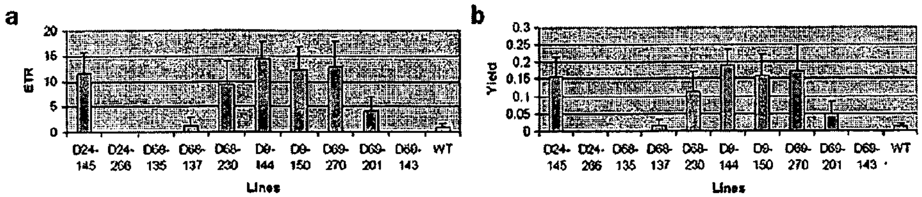

FIG. 23 shows the Electron Transfer Rate (ETR) (a) and yield (b) of photosystem II after 24 hours recovery from 42 hours stress as measured with PAM2000.

Figure 24:
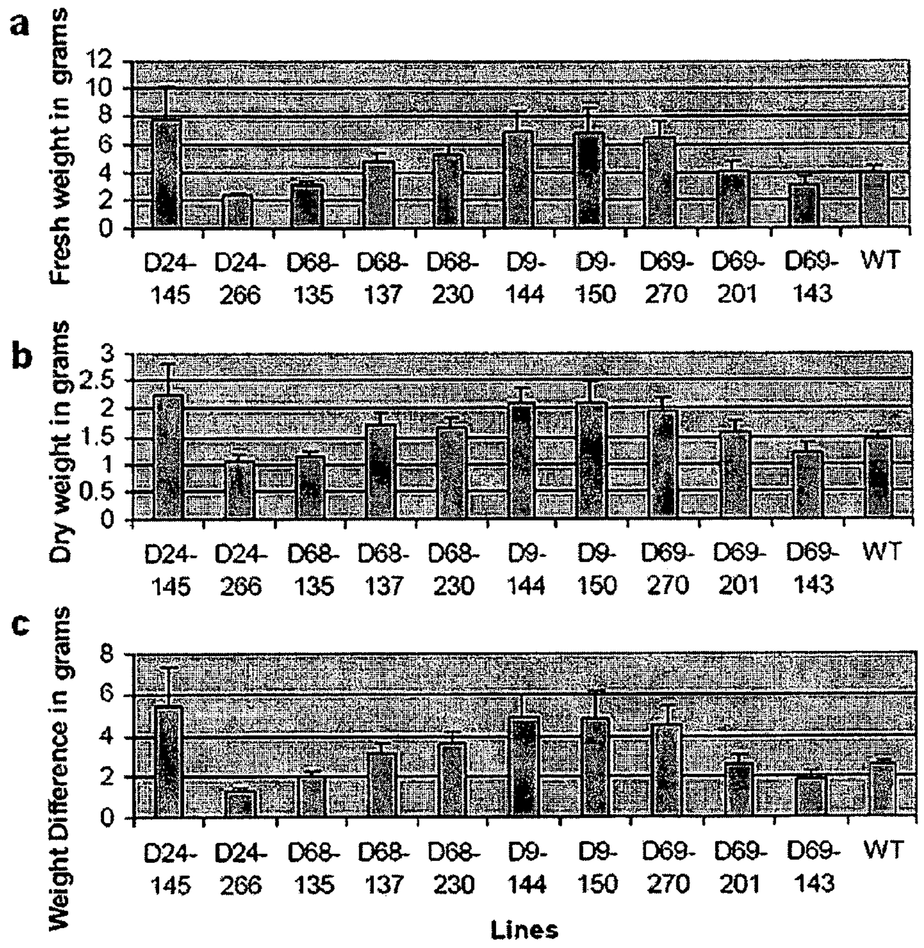

FIG. 24 shows fresh (a) and dry weight (b) of leaves from transgenic and wildtype ryegrass plants and the difference between fresh and dry weights (c) in grams after nine days of recovery from three cycles of drought-stress.

Figure 25:
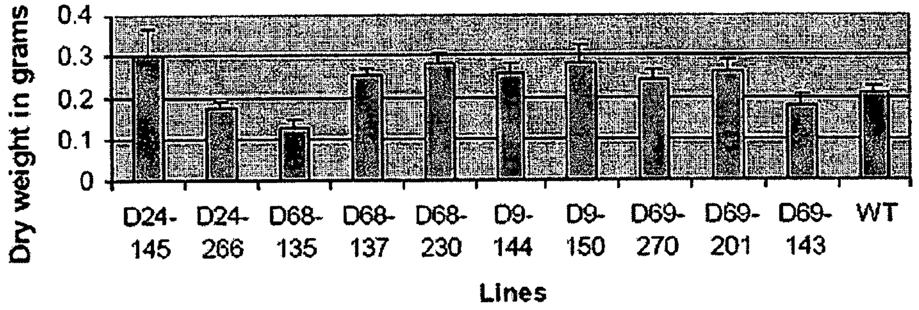

FIG. 25 shows dry weight of roots after nine days of recovery from three cycles of drought-stress.

Figure 26:

FIG. 26 shows the visual appearance of plants after the third drought-stress lasting for 42 hours; a) Wild type (left) transgenic line D24-145 (right); b) Wild type (left) transgenic line D9-144 (right); c) Wild type (left) transgenic line D9-150 (right).

Figure 27:
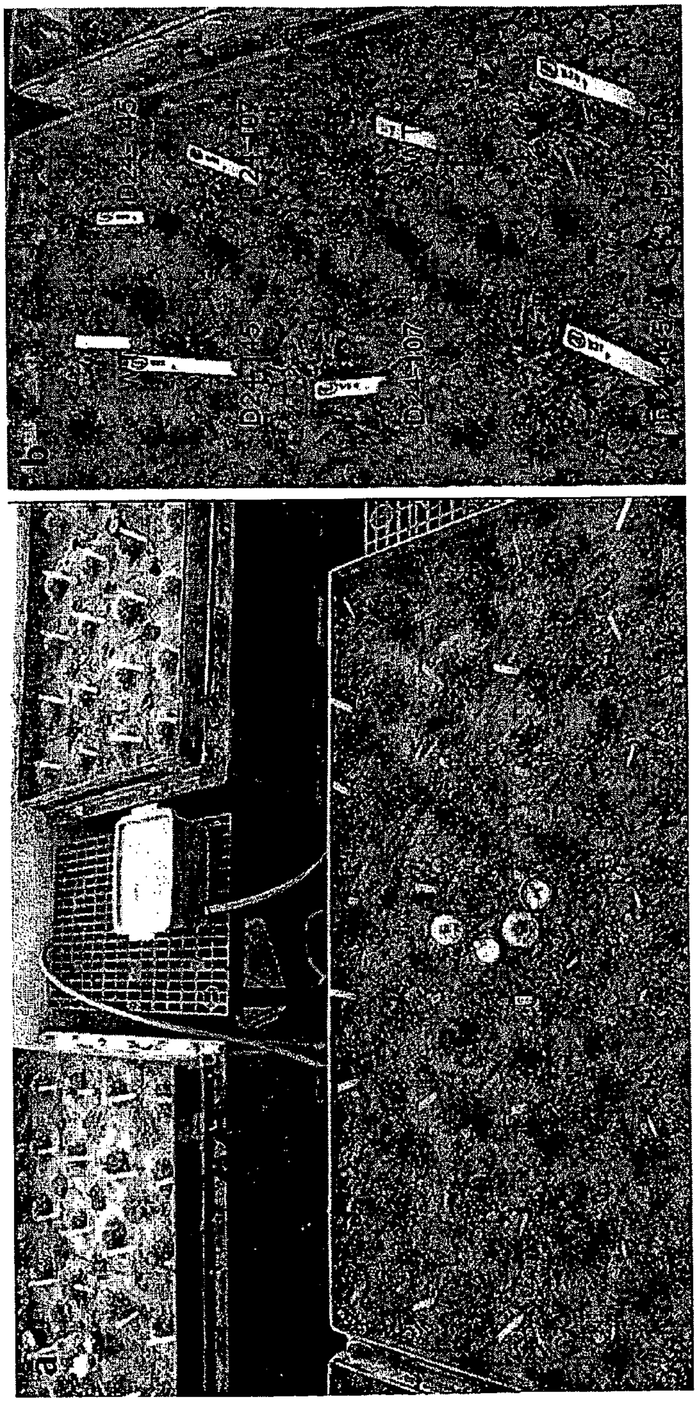

FIG. 27 shows (a) Transgenic ryegrass growing in bins filled with soil during progressive drought stress; (b) Transgenic ryegrass over-expressing ORF 24 in comparison to wildtype at 2.3% soil VWC.

Figure 28:
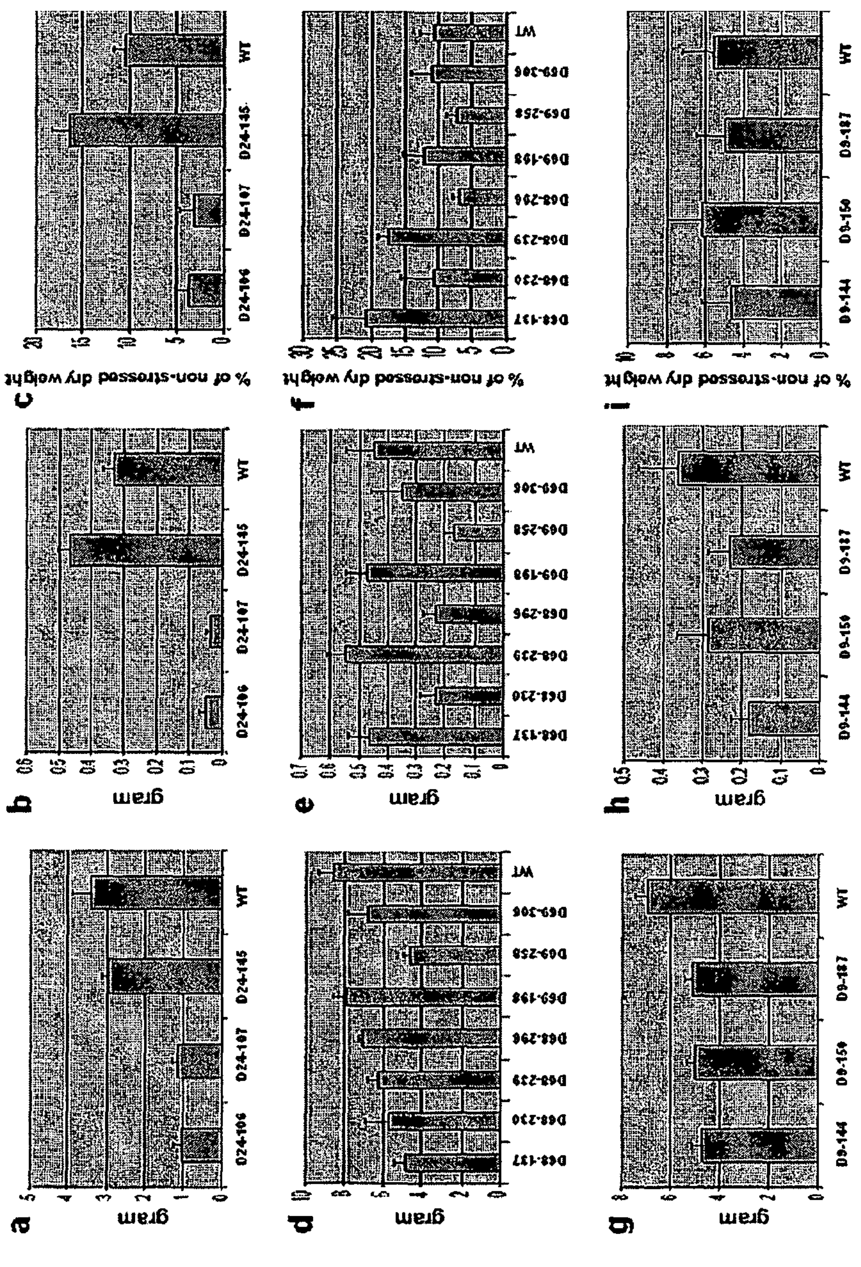

FIG. 28 shows the aboveground biomass (dry weight) produced before (a; d; g) and after drought-stress (b; e; h) and the ability to grow during drought-stress is shown (c, f and i).

DETAILED DESCRIPTION OF THE PREFERRED EMBODIMENT

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "plant" is intended to include a whole plant, any part of a plant, propagules and progeny of a plant.

The term 'propagule' means any part of a plant that may be used in reproduction or propagation, either sexual or asexual, including seeds and cuttings.

The term "tolerance or tolerant to drought stress" is intended to describe a plant or plants which perform more favourably in any aspect of their growth and development under sub-optimal hydration conditions than do suitable control plants in the same conditions.

The term "tolerance or tolerant to drought stress" is also intended to describe a plant or plants which perform more favourably in any aspect of their growth and development after having been subjected to sub-optimal hydration conditions. That is, plants that show improved recovery after a period of sub-optimal hydration.

The term "tolerance or tolerant to cold stress" is intended to describe a plant or plants which perform more favourably in any aspect of their growth and development under sub-optimal-reduced reduced temperature conditions than do suitable control plants in the same conditions.

The term "tolerance or tolerant to freezing stress" is intended to describe a plant or plants which perform more favourably in any aspect of their growth and development under temperature conditions of less than or equal to 0° C., than do suitable control panels in the same conditions.

The term "tolerance or tolerant to heat stress" is intended to describe a plant or plants which perform more favourably in any aspect of their growth and development under sub-optimal elevated temperature conditions than do suitable control plants in the same conditions.

The term "tolerance or tolerant to salinity" is intended to describe a plant or plants which perform more favourably in any aspect of their growth and development under sub-optimal elevated salinity conditions than do suitable control plants in the same conditions.

With reference to the selection methods of the invention, a plant with increased tolerance to environmental stress refers to a plant, selected from a population of plants, which performs more favourably in any aspect of growth and development under stress conditions than does an average member of the population under the same conditions.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

The term "polypeptide", as used herein, encompasses amino acid chains of any length, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity of the polypeptide. Polypeptide fragments are at least 5 amino acids, preferably at least 10 amino acids, more preferably at least 20 amino acids, more preferably at least 30 amino acids in length, more preferably 40 amino acids in length, more preferably 50 amino acids in length.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polynucleotides possess biological activities that are the same or similar to those of the inventive polypeptides or polynucleotides. The term "variant" with reference to polynucleotides and polypeptides encompasses all forms of polynucleotides and polypeptides as defined herein.

Variant polynucleotide sequences preferably exhibit at least 50%, more preferably at least 70%, more preferably at least 80%, more preferably at least 90%, more preferably at least 95%, more preferably at least 98%, and most preferably at least 99% identity to any one of SEQ ID NO:1, 2, 4, 5, 7, 8, 10 and 11. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN from the BLAST suite of programs, version 2.2.5 [Nov. 2002]) in b12seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI. The default parameters of b12seq are utilized except that filtering of low complexity parts should be turned off.

The identity of polynucleotide sequences may be examined using the following UNIX command line parameters:

bl2seq-i nucleotideseq1-j nucleotideseq2-F F-p blastn

The parameter-F F turns off filtering of low complexity sections. The parameter-p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No. 6. pp. 276-277. The European Bioinformatics Institute server also provides the facility to perform EMBOSS-needle global alignments between two sequences.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Use of BLASTN as described above is preferred for use in the determination of sequence identity for polynucleotide variants according to the present invention.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available b12seq program from the BLAST suite of programs (version 2.2.5 [Nov. 2002]) from NCBI.

The similarity of polynucleotide sequences may be examined using the following UNIX command line parameters:

bl2seq-i nucleotideseq1-j nucleotideseq2-F F-p tblastx

The parameter-F F turns off filtering of low complexity sections. The parameter-p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-5}$ more preferably less than $1\times10^{-6}$ more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

Alternatively, variant polynucleotides of the present invention hybridize to the polynucleotide sequences recited in any one of SEQ ID NO:1, 2, 4, 5, 7, 8, 10 and 11, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C−log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available b12seq program from the BLAST suite of programs (version 2.2.5 [Nov. 2002]) from NCBI via the tblastx algorithm as previously described.

The term "variant" with reference to polypeptides encompasses naturally occurring, recombinantly and synthetically produced polypeptides. Variant polypeptide sequences preferably exhibit at least 50%, more preferably at least 70%, more preferably at least 80%, more preferably at least 90%, more preferably at least 95%, more preferably at least 98%, and most preferably at least 99% identity to a sequences any one of SEQ ID NO:3, 6, 9 and 12. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [Nov. 2002]) in b12seq, which is publicly available from NCBI. The default parameters of b12seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available b12seq program from the BLAST suite of programs (version 2.2.5 [Nov. 2002]) from NCBI. The similarity of polypeptide sequences may be examined using the following UNIX command line parameters:

bl2seq-i peptideseq1-j peptideseq2-F F-p blastp

Variant polypeptide sequences preferably exhibit an E value of less than $1\times10^{-5}$, more preferably less than $1\times10^{-6}$, more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

The parameter-F F turns off filtering of low complexity sections. The parameter-p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli.*

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

A "transgenic plant" refers to a plant which contains new genetic material as a result of genetic manipulation or transformation. The new genetic material may be derived from a plant of the same species as the resulting transgenic plant or from a different species.

An "inverted repeat" is a sequence that is repeated, where the second half of the repeat is in the complementary strand, e.g.,

```
(5')GATCTA.......TAGATC(3')

(3')CTAGAT.......ATCTAG(5')
```

Read-through transcription will produce a transcript that undergoes complementary base-pairing to form a hairpin structure provided that there is a 3-5 bp spacer between the repeated regions.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The applicants have identified polynucleotides from ryegrass (SEQ ID NO:1 and SEQ ID NO:2) which encode a polypeptide (SEQ ID NO:3) which modulates in plants, tolerance to at least one environmental stress selected from drought, cold, freezing, heat and salinity. The applicants have also identified polynucleotide variants of SEQ ID NO:1 and SEQ ID NO:2 (SEQ ID NOs:13-25) encoding polypeptide variants of SEQ ID NOs:3 (SEQ ID NOs:26-38) which modulate in plants, tolerance to at least one environmental stress selected from drought, cold, freezing, heat and salinity.

The applicants have identified polynucleotides from ryegrass (SEQ ID NO:4 and SEQ ID NO:5) which encode a polypeptide (SEQ ID NO:6) which modulates in plants, tolerance to at least one environmental stress selected from drought, cold, freezing, heat and salinity. The applicants have also identified polynucleotide variants of SEQ ID NO:4 and SEQ ID NO:5 (SEQ ID NOs:39-66) encoding polypeptide variants of SEQ ID NO:6 (SEQ ID NOs:67-94) which modulate in plants, tolerance to at least one environmental stress selected from drought, cold, freezing, heat and salinity.

The applicants have identified polynucleotides from ryegrass (SEQ ID NO:7 and SEQ ID NO:8) which encode a polypeptide (SEQ ID NO:9) which modulates in plants, tolerance to at least one environmental stress selected from drought, cold, freezing, heat and salinity. The applicants have also identified polynucleotide variants of SEQ ID NO:7 and SEQ ID NO:8 (SEQ ID NOs:95-126) encoding polypeptide variants of SEQ ID NOs:9 (SEQ ID NOs:127-158) which modulate in plants, tolerance to at least one environmental stress selected from drought, cold, freezing, heat and salinity.

The applicants have identified polynucleotides from ryegrass (SEQ ID NO:10 and SEQ ID NO:11) which encode a polypeptide (SEQ ID NO:12) which modulates in plants, tolerance to at least one environmental stress selected from drought, cold, freezing, heat and salinity. The applicants have also identified polynucleotide variants of SEQ ID NO:10 and SEQ ID NO:1 (SEQ BD NOs:159-200) encoding polypeptide variants of SEQ ID NOs:12 (SEQ ID NOs:201-242) which modulate in plants, tolerance to at least one environmental stress selected from drought, cold, freezing, heat and salinity The invention provides plants altered relative to suitable control plants in tolerance to at least one environmental stress selected from drought, cold, freezing, heat and salinity. The invention provides both plants with both increased tolerance to the above and plants with decreased tolerance to above characteristic stresses. The invention also provides methods for the production or selection of such plants.

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention include use of all, or portions of, the any on of the polynucleotides having the sequence set forth in SEQ ID NOs:1, 2, 4, 5, 7, 8, 10, 11 13-25, 39-66, 95-126 and 159-242 as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0 X SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full length polynucleotide sequence. Such methods would include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Variant polynucleotides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Further methods for identifying variant polynucleotides of the invention include use of all, or portions of, the polynucleotides having the sequence set forth in SEQ ID NOs:1, 2, 4, 5, 7, 8, 10 and 11 as hybridization probes to screen a plant genomic or cDNA libraries as described above. Typically probes based on a sequence encoding a conserved region of the corresponding amino acid sequence may be used. Hybridisation conditions may also be less stringent than those used when screening for sequences identical to the probe.

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [Nov. 2002]) including BLASTN, BLASTP, BLASTX, tBLASTN and tBLASTX, which are publicly available from the National Center for Biotechnology Information (NCBI), National Library of Medicine. Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The “hits” to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce “Expect” values for alignments. The Expect value (E) indicates the number of hits one can “expect” to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Proteins can be classified according to their sequence relatedness to other proteins in the same genome (paralogues) or a different genome (orthologues). Orthologous genes are genes that evolved by specification from a common ancestral gene and normally retain the same function as they evolve. Paralogous genes are genes that are duplicated within a genome and genes may acquire new specificities or modified functions which may be related to the original one. Phylogenetic analysis methods are reviewed in Tatusov et al., 1997, Science 278, 631-637,).

In addition to the computer/database methods described above, polypeptide variants of the invention may be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

The function of a variant polynucleotide of the invention in modulating tolerance to environmental stress plant may be assessed by altering expression of the polynucleotide in a plant by methods known in the art and/or described herein, and, analyzing performance of the transformed plant in comparison to a control plant, under conditions of environmental stress. Further plant transformation protocols for several species are known to those skilled in the art. A list of such protocols is provided herein.

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182*, Guide to Protein Purification*,).

Alternatively the polypeptides and variant polypeptides of the invention may be expressed recombinantly in suitable host cells and separated from the cells as discussed below.

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Host cells of the invention may also be useful in methods for production of an enzymatic product generated by an expressed polypeptide of the invention. Such methods may involve culturing the host cells of the invention in a medium suitable for expression of a recombinant polypeptide of the invention, optionally in the presence of additional enzymatic substrate for the expressed polypeptide of the invention. The enzymatic product produced may then be separated from the host cells or medium by a variety of art standard methods.

The invention further provides plant cells which comprise a genetic construct of the invention, and plant cells modified to alter expression of a polynucleotide or polypeptide of the invention. Plants comprising such cells also form an aspect of the invention.

Tolerance to at least one environmental stress selected from drought, cold, freezing, heat and salinity in a plant, may also be altered through methods of the invention. Such methods may involve the transformation of plant cells and plants, with a construct of the invention designed to alter expression of a polynucleotide or polypeptide which modulates for example, tolerance to drought stress, in such plant cells and plants. Such methods also include the transformation of plant cells and plants with a combination of the construct of the invention and one or more other constructs designed to alter expression of one or more polynucleotides or polypeptides which modulate for example, tolerance to drought stress in such plant cells and plants.

Methods for transforming plant cells, plants and portions thereof with polynucleotides are described in Draper et al., 1988, Plant Genetic Transformation and Gene Expression. A Laboratory Manual Blackwell Sci. Pub. Oxford, p. 365; Potrykus and Spangenberg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

A number of plant transformation strategies are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phosphotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3' (coding strand)   3'CTAGAT 5' (antisense strand)

3'CUAGAU 5' mRNA              5'GAUCUA 3' antisense RNA
```

Genetic constructs designed for gene silencing may also include an inverted repeat as herein defined. The preferred approach to achieve this is via RNA-interference strategies using genetic constructs encoding self-complementary "hairpin" RNA (Wesley et al., 2001, Plant Journal, 27: 581-590).

The transcript formed may undergo complementary base pairing to form a hairpin structure. Usually a spacer of at least 3-5 bp between the repeated regions is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve over-expression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9,: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); and cereals (U.S. Pat. No. 6,074,877).

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phage-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods are also provided for selecting plants altered tolerance to at least one environmental stress selected from drought, cold, freezing, heat and salinity. Such methods involve testing of plants for altered for the expression of a polynucleotide or polypeptide of the invention. Such methods may be applied at a young age or early developmental stage to accelerate breeding programs directed toward at least one of the characteristics described which may not be easily assessed until a later age or developmental stage.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered tolerance to at least one environmental stress selected from drought, cold, freezing, heat and salinity. For example an altered level in a plant, of a polypeptide involved in modulating tolerance to drought stress may be used as an indicator of eventual tolerance to drought stress in such a plant. The polynucleotides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered in tolerance to at least one environmental stress selected from drought, cold, freezing, heat and salinity.

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

EXAMPLES

The invention will now be illustrated with reference to the following non-limiting examples.

Example 1

Identification of Polynucleotides which Modulate Tolerance to Environmental Stresses Introduction:

Perennial ryegrass (*Lolium perenne* L.) is a cool temperate pasture plant from the family Gramineae and the tribe Festucaceae. To generate a profile of relative gene expression patterns in ryegrass, RNA was extracted from samples obtained from ambient temperature growth, cold grown, hydrated, dehydrated and rehydrated or dehydration pre- and post-grazed plants during autumn, summer, spring and winter, and used for constructing a SAGE (serial analysis of gene expression) (Velculescu et al. 1995, *Science* 270: 484-487) library.

Materials and Methods:

Perennial ryegrass (*Lolium perenne* L.) cv. Bronsyn was used throughout this study. Field grown samples were collected from active paddocks at Dexcel, Hamilton, New Zealand during the peak of each season. Grass samples were collected from pre-grazed (15 days post grazing) and post-grazed (1 day post grazing) ryegrass swards. Tufts of grass samples were harvested from 3-6 randomly chosen sites and stored in dry-ice after snap-freezing with liquid nitrogen. During spring, immature spike and floral initials were also harvested. For stress-treatment, the following conditions were used on lab-grown ryegrass: Mature lab-grown perennial ryegrass that was grown in growth chamber for 15 months at 85% RH, 20° C./18° C. and 16 h/8 h day/night regime; Hydrated control grown for 55 days at 85% RH, 20° C./18° C. and 16 h/8 h day/night regime; 6 days at 70% RH, 22° C./16° C. and 16 h/8 h day/night regime, seedlings were kept watered throughout their life; Dehydrated sample watered only for 55 days at 85% RH, 20° C./18° C. and 16 h/8 h day/night regime; 3 days at 70% RH, 28° C./20° C. and 16 h/8 h day/night regime; 3 days at 50% RH, 28° C./20° C. and 16 h/8 h day/night regime; Rehydrated samples were from dehydrated plants that was watered for 24 hours and grown at 70% RH, 22° C./16° C. and 16 h/8 h day/night regime; Cold-stressed plants were grown for 55 days at 85% RH, 20° C./18° C. and 16 h/8 h day/night regime; 7 days at 70% RH, 22° C./16° C. and 16 h/8 h day/night regime; 7 days at 70% RH, 6° C./2° C. and 16 h/8 h day/night regime, seedlings were kept watered throughout their life.

Construction of SAGE Libraries

RNA was extracted using TRIZOL® reagent (Invitrogen, Calif., USA) and by the protocol described by the manufacturer from tissue that was ground in liquid nitrogen. For each SAGE library 100 μg of total RNA was used and the libraries were created using I-SAGE™ or I-SAGE™ Long kit (Invitrogen, Calif., USA) according to manufacturer's protocol. From each library 960-1,920 clones were sequenced (Australian Genome Research Facility, Brisbane, Australia) and the tags extracted using the SAGE2000 software.

SAGE Bioinformatics:

The relational database was designed to hold tags, libraries and expression counts of the SAGE experiments. Each tag sequence (including enzyme sequence) was searched against the whole Ryegrass non-overlapping Gene thresher and the EST sets. The search was carried out in both direction and used exact match only. Results were loaded to the relational database using General Feature Format (GFF) approach.

All Ryegrass Gene thresher and the EST sequences were annotated using homology searches against some or all the following public and propriety databases:

AGI TIGR Gene Indices, *Arabidopsis*, release 11, Jan. 2004

OGI TIGR Gene Indices, Rice, release 14-1, Jan. 2004

GENESEQN Derwent patent DNA sequences 2002 Dec. 7

GENESEQP Derwent patent amino acid sequences 2002 Dec. 7

Os_unigene *Oryza sativa* Unigene unique sequences 2004-03-18 est_others Other EST sequences (mammal, fungi, prokaryote) 2003 Mar. 11 est_plant Viridiplantae subset of Non-redundant Database of GenBank+EMBL+DDBJ EST Divisions 2004-03-15 nr All non-redundant GenBank CDS translations+PDB+SwissProt+PIR 2003 Mar. 11 nr_pant Plant subset of HS subset of BT subset of All non-redundant GenBank CDS translations+PDB+SwissProt+PIR 203 Aug. 8 nt All Non-redundant GenBank+EMBL+DDBJ+PDB sequences (but no EST, STS, GSS, or HTGS -sequences) Mar. 11, 2003 nt_monocots Monocot subset of All Non-redundant GenBank+EMBL+DDBJ+PDB sequences (but no EST, STS, GSS, or HTGS sequences) Mar. 11, 2003 swissprot The last major release of the SWISS-PROT protein sequence database (no updates) 2003 Mar. 28

A cutoff of E value less than E-05 was used and maximum of 10 targets per database were stored in the relational database.

Tags Annotation:

Tags with hits to the Ryegrass sets were annotated by creating a summary of all the annotations of the involved sequences. The summary was generated using an algorithm to calculate the frequency of the occurrence of each word in the annotations and rank them in descending order based on the number off occurrences. The summary was limited to 10 words and a void word list was used to filter out insignificant information. The resulting summary line was used as an indication of what the tags were likely to be. Actual numbers are displayed; giving additional information that could be used to evaluate the significance of each of the words in the summary. This method of automatic annotation using keyword counts is similar to the Automatic comment that is used by the ProDom database to annotate the automatically generated protein domain families.

Detailed annotation based on the top hits of the involved sequences was displayed when viewing tags data.

Four polynucleotide sequences of particular interest were identified in the above analysis. These are ORF24 (corresponds to SEQ ID NO:1 and 2) and ORF68 (corresponding to SEQ ID NO:4 and 5), ORF69 (corresponding to SEQ ID NO:7 and 8) and ORF9 (corresponding to SEQ ID NO:10 and 11).

ORF24 appears to encode a heat shock transcription factor. The transcript accumulates in dehydrated and winter tissues. The full transcript profile is shown in table 1.

TABLE 1

| SAGE_TAG | CCCATTTCTG | tpm* | SAGE_TAG | CCCATTTCTGCCGATTT | tpm |
|---|---|---|---|---|---|
| Winter Pre-grazed | 1 | 36 | Winter Pre-grazed | 1 | 36 |
| Winter Post-grazed | 2 | 75 | Winter Post-grazed | 2 | 75 |
| Winter roots | 1 | 61 | Winter roots | 1 | 61 |
| Spring Pre-grazed | 0 | 0 | Spring Pre-grazed | 0 | 0 |
| Spring Post-grazed | 0 | 0 | Spring Post-grazed | 0 | 0 |
| Inflorescence | 1 | 41 | Inflorescence | 1 | 41 |
| Summer Post-grazed | 0 | 0 | Summer Post-grazed | 0 | 0 |
| Autumn Pre-grazed | 0 | 0 | Total | 5 | 30 |
| Autumn Post-grazed | 0 | 0 | | | |
| Mature | 1 | 80 | | | |
| Cold-stressed | 0 | 0 | | | |
| Hydrated | 1 | 64 | | | |
| Dehydrated | 3 | 176 | | | |
| Rehydrated | 1 | 33 | | | |
| Total | 11 | 40 | | | |

*tpm = Tag counts per million tags

ORF68 appears to encode an ethylene responsive element binding protein (EREBP) transcription factor and the transcript accumulates in winter tissues. The full transcript profile is shown in table 2 below.

TABLE 2

| SAGE_TAG | TCGCTGAAGA | tpm* | SAGE_TAG | TCGCTGAAGATCTTGGC | tpm |
|---|---|---|---|---|---|
| Winter Pre-grazed | 1 | 36 | Winter Pre-grazed | 1 | 36 |
| Winter Post-grazed | 1 | 37 | Winter Post-grazed | 1 | 37 |
| Winter roots | 2 | 121 | Winter roots | 2 | 121 |
| Spring Pre-grazed | 0 | 0 | Spring Pre-grazed | 0 | 0 |
| Spring Post-grazed | 0 | 0 | Spring Post-grazed | 0 | 0 |
| Inflorescence | 0 | 0 | Inflorescence | 0 | 0 |
| Summer Post-grazed | 0 | 0 | Summer Post-grazed | 0 | 0 |
| Autumn Pre-grazed | 0 | 0 | Total | 4 | 28 |
| Autumn Post-grazed | 0 | 0 | | | |
| Mature | 0 | 0 | | | |
| Cold-stressed | 0 | 0 | | | |
| Hydrated | 0 | 0 | | | |
| Dehydrated | 0 | 0 | | | |
| Rehydrated | 0 | 0 | | | |
| Total | 4 | 14 | | | |

*tpm = Tag counts per million tags

ORF69 appears to be a MYB-like transcription factor and the transcript accumulates in cold-stressed, dehydrated and rehydrating tissues. The full transcript profile is shown in table 3 below.

TABLE 3

| SAGE_TAG | TATGTAAAGG | tpm* | SAGE_TAG | TATGTAAAGGTTGCGAA | tpm |
|---|---|---|---|---|---|
| Winter Pre-grazed | 0 | 0 | Winter Pre-grazed | 0 | 0 |
| Winter Post-grazed | 0 | 0 | Winter Post-grazed | 0 | 0 |
| Roots (winter) | 0 | 0 | Roots (winter) | 0 | 0 |

TABLE 3-continued

| SAGE_TAG | TATGTAAAGG | tpm* | SAGE_TAG | TATGTAAAGGTTGCGAA | tpm |
|---|---|---|---|---|---|
| Spring Pre-grazed | 0 | 0 | Spring Pre-grazed | 0 | 0 |
| Spring Post-grazed | 0 | 0 | Spring Post-grazed | 0 | 0 |
| Inflorescence | 1 | 41 | Inflorescence | 1 | 41 |
| Summer Post-grazed | 0 | 0 | Summer Post-grazed | 0 | 0 |
| Autumn Pre-grazed | 0 | 0 | Total | 1 | 6 |
| Autumn Post-grazed | 0 | 0 | | | |
| Mature | 1 | 80 | | | |
| Cold-stressed | 1 | 54 | | | |
| Hydrated | 0 | 0 | | | |
| Dehydrated | 1 | 59 | | | |
| Rehydrated | 1 | 33 | | | |
| Total | 5 | 19 | | | |

*tpm = Tag counts per million tags

ORF9 appears to be an extra-cellular stress-tolerance peptide and the transcript accumulates in cold-stressed and rehydrating tissues. The full transcript profile is shown in table 4 below.

TABLE 4

| SAGE_TAG | TTTTTGTGAA | tpm* |
|---|---|---|
| Winter Pre-grazed | 0 | 0 |
| Winter Post-grazed | 1 | 37 |
| Winter roots | 0 | 0 |
| Spring Pre-grazed | 0 | 0 |
| Spring Post-grazed | 1 | 61 |
| Inflorescence | 0 | 0 |
| Summer Post-grazed | 1 | 51 |
| Autumn Pre-grazed | 1 | 35 |
| Autumn Post-grazed | 3 | 108 |
| Mature | 0 | 0 |
| Cold-stressed | 3 | 163 |
| Hydrated | 0 | 0 |
| Dehydrated | 0 | 0 |
| Rehydrated | 3 | 99 |
| Total | 13 | 40 |

*tpm = Tag counts per million tags

Example 2

Identification Variants of ORFs 24, 68, 69 and 9

The polypeptide sequence encoded by the ORFs 24, 68, 69 and 9 were used as seed sequences to perform BLASTP search against NR_PLANT database (release date 30-07-04). Besides BLASTP, a TBLASTN search was also performed against EST_PLANT database (release date Jul. 15, 2004) and NT_PLANT database (release date Jul. 15, 2004). To identify the variants cut-off e value was generally set at greater than 1e-05, which was determined based upon the associated score value.

Selected variant sequences were aligned using the EMBOSS tool EMMA (Thompson, J. D., Higgins, D. G. and Gibson, T. J. 1994, CABIOS, 10, 19-29.), which is an interface to the popular multiple alignment program ClustalW. Aligned sequences were visualised using another EMBOSS tool called prettyplot, which displays aligned sequences with colouring and boxing.

Example 3

Preparation of Vectors Comprising Polynucleotides of the Invention for Plant Transformation Vectors Comprising ORF24

Figure 1:
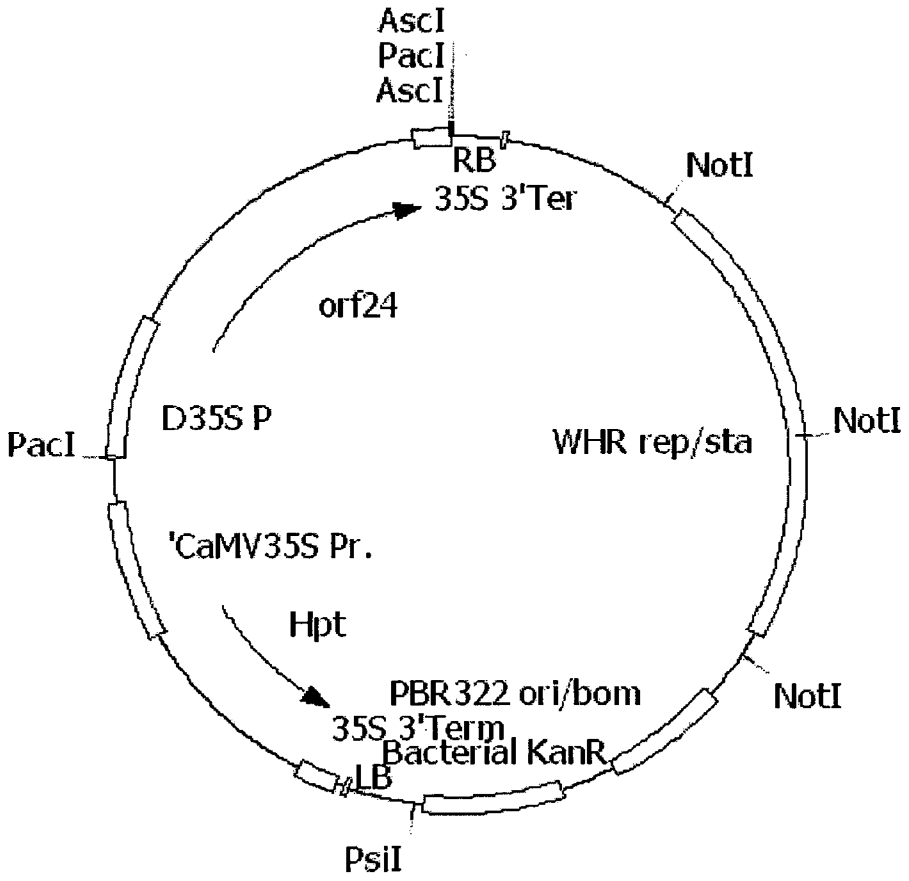
FIG. 1 shows a map of a vector, for plant transformation, comprising ORF24 (SEQ ID NO:2).
Figure 3:
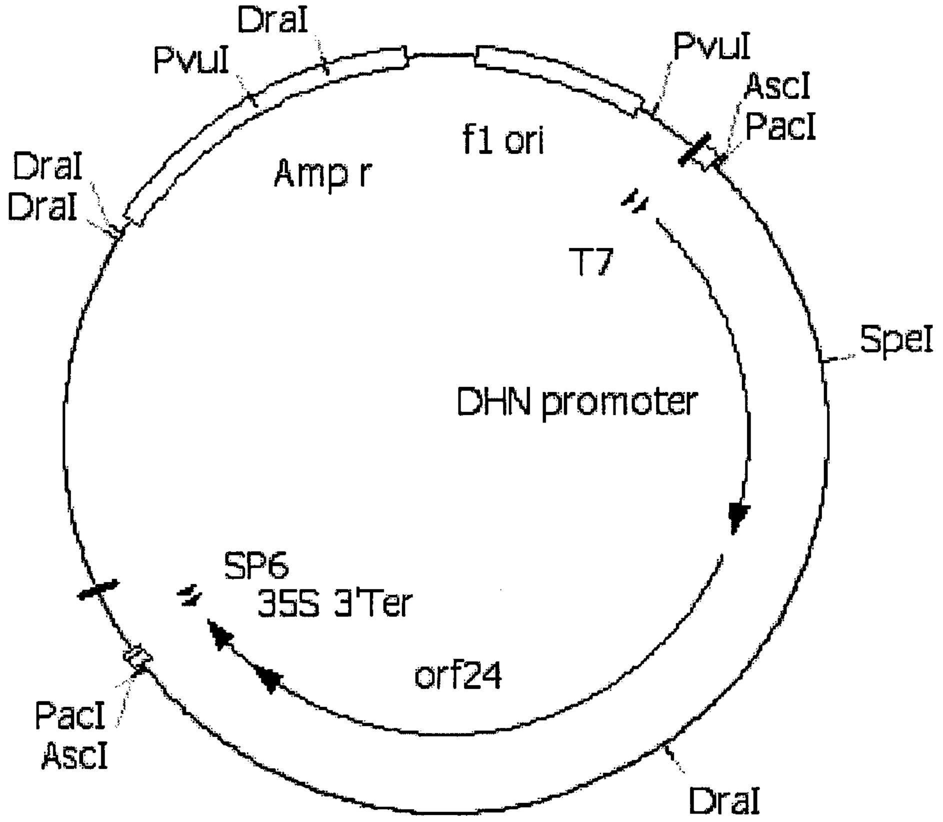
FIG. 3 shows a map of another vector, for plant transformation, comprising ORF24 (SEQ ID NO:2).
Figures 1, 5:
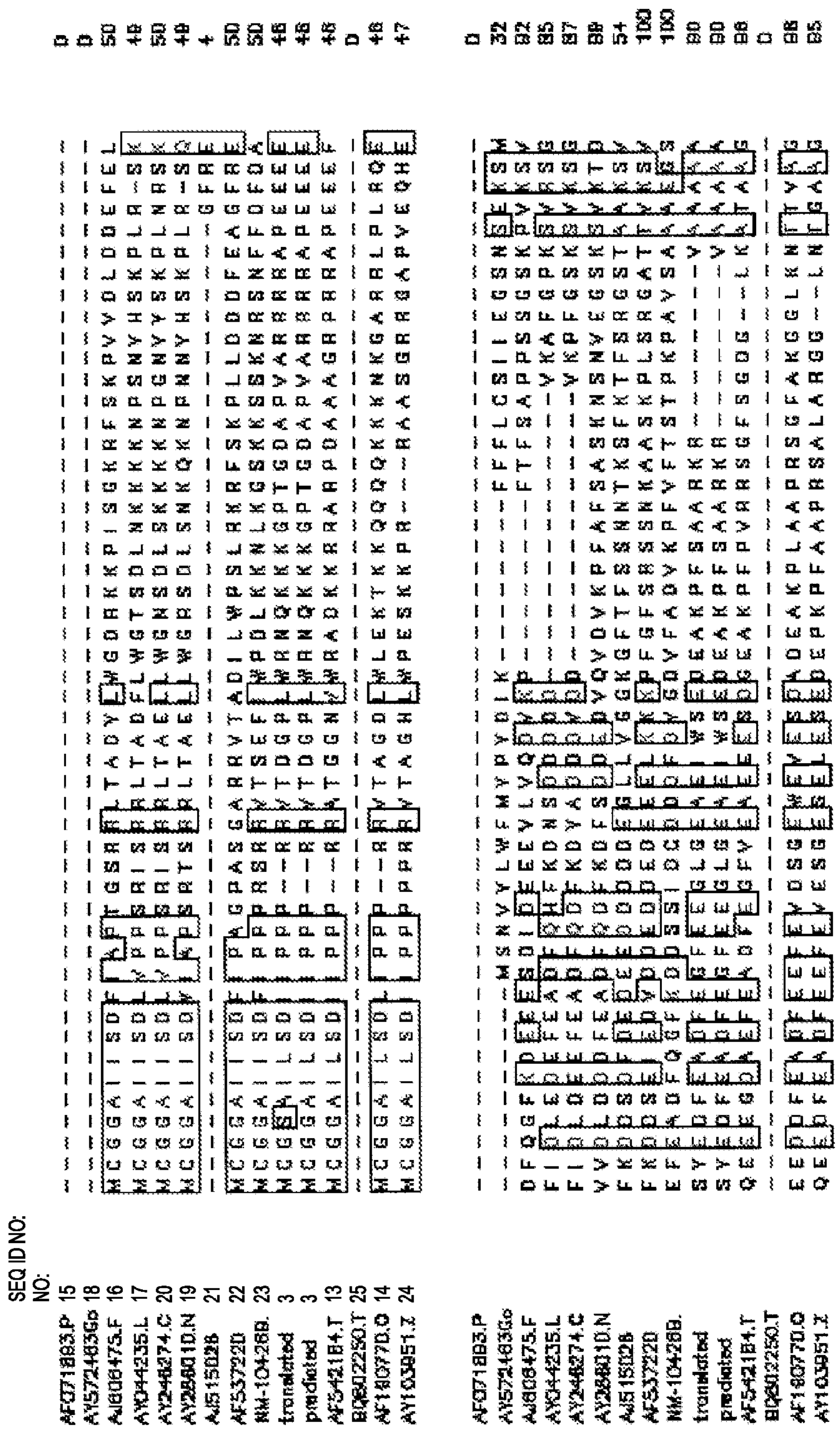
FIG. 5 shows an alignment of polypeptides of the invention, including ORF24 (SEQ ID NO:3 labeled as "translated") and sequences which are variants of SEQ ID NO:3 from several species (AF071893.P=SEQ ID NO:15; AY572463GD=SEQ ID NO:18; AJ606475.F=SEQ ID NO:16; AY044235.L=SEQ ID NO:17; AY246274.0=SEQ ID NO:20; AY286010.N SEQ ID NO:19; AJ515026=SEQ ID NO:21; AF537220=SEQ ID NO:22; NM 104269=SEQ ID NO:23; translated=SEQ ID NO:3; predicted=SEQ ID NO:3; AF542184.T==SEQ ID NO:13; BQ802250.T=SEQ ID NO:25; AF190770.0=SEQ ID NO:14; and AY103951.Z=SEQ ID NO:24) and illustrates a consensus region (shown within bold box) identified by the applicants which is present in all of the such sequences.
Figures 2, 5:
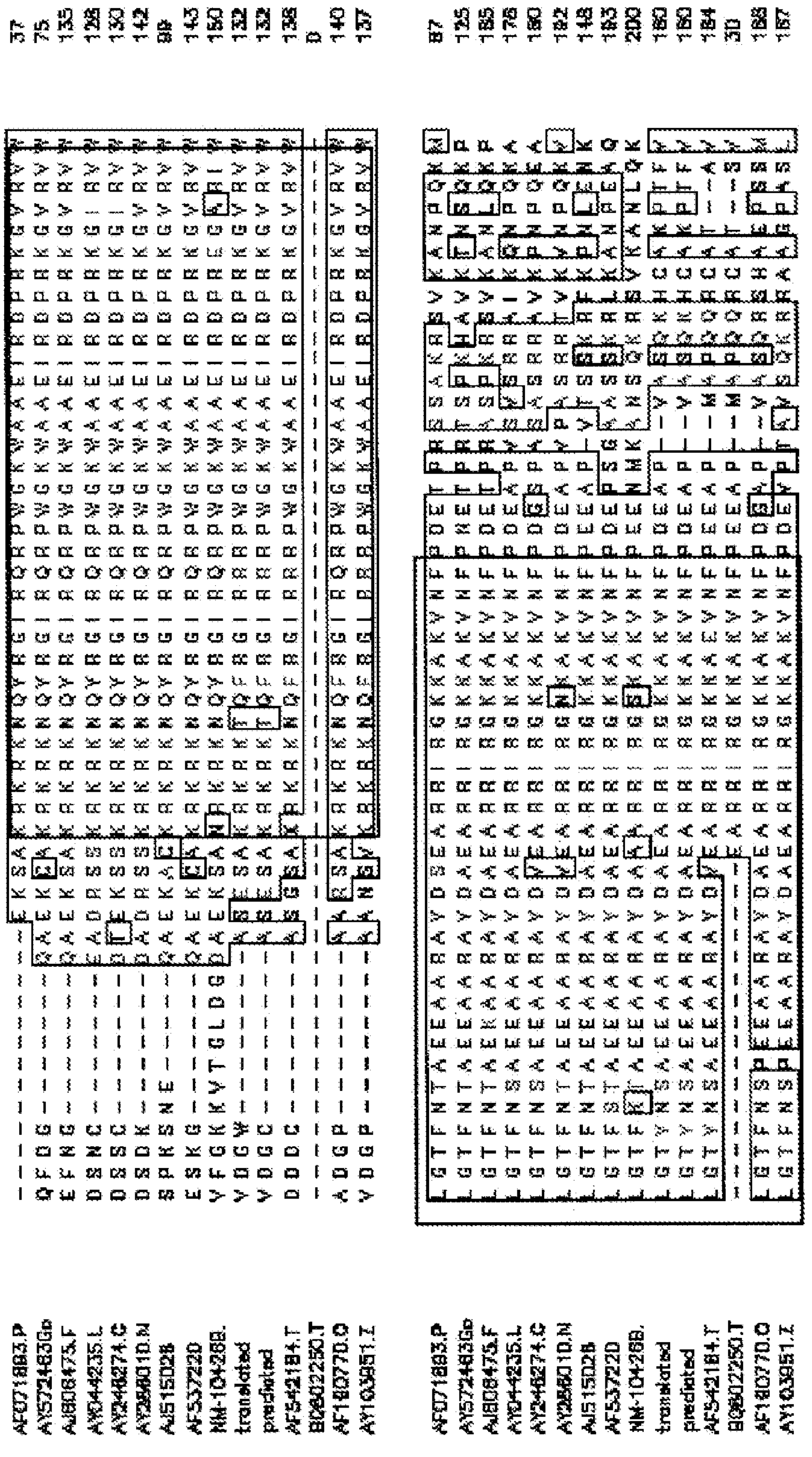
FIG. 2 shows the sequence (SEQ ID NO:244) of a vector, for plant transformation, comprising ORF24 and corresponding to the map in FIG. 1. Sequence in bold corresponds to the CaMV35S promoter. Sequence in italics corresponds to ORF24. Sequence underlined corresponds to 3'terminator sequence from CaMV35S gene. Sequence in regular font corresponds to vector sequence.
Figures 3, 5:
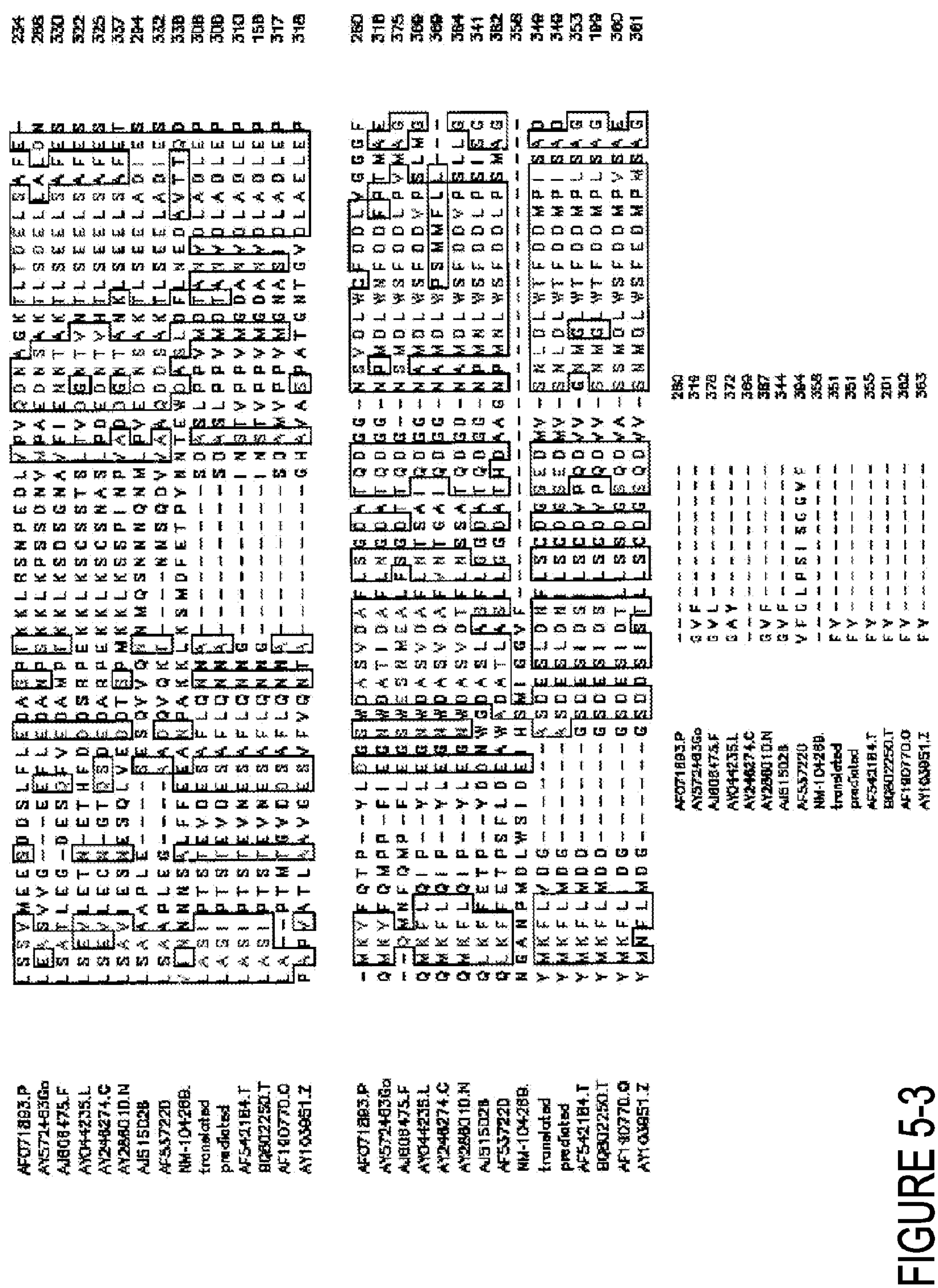
Figures 1, 10:
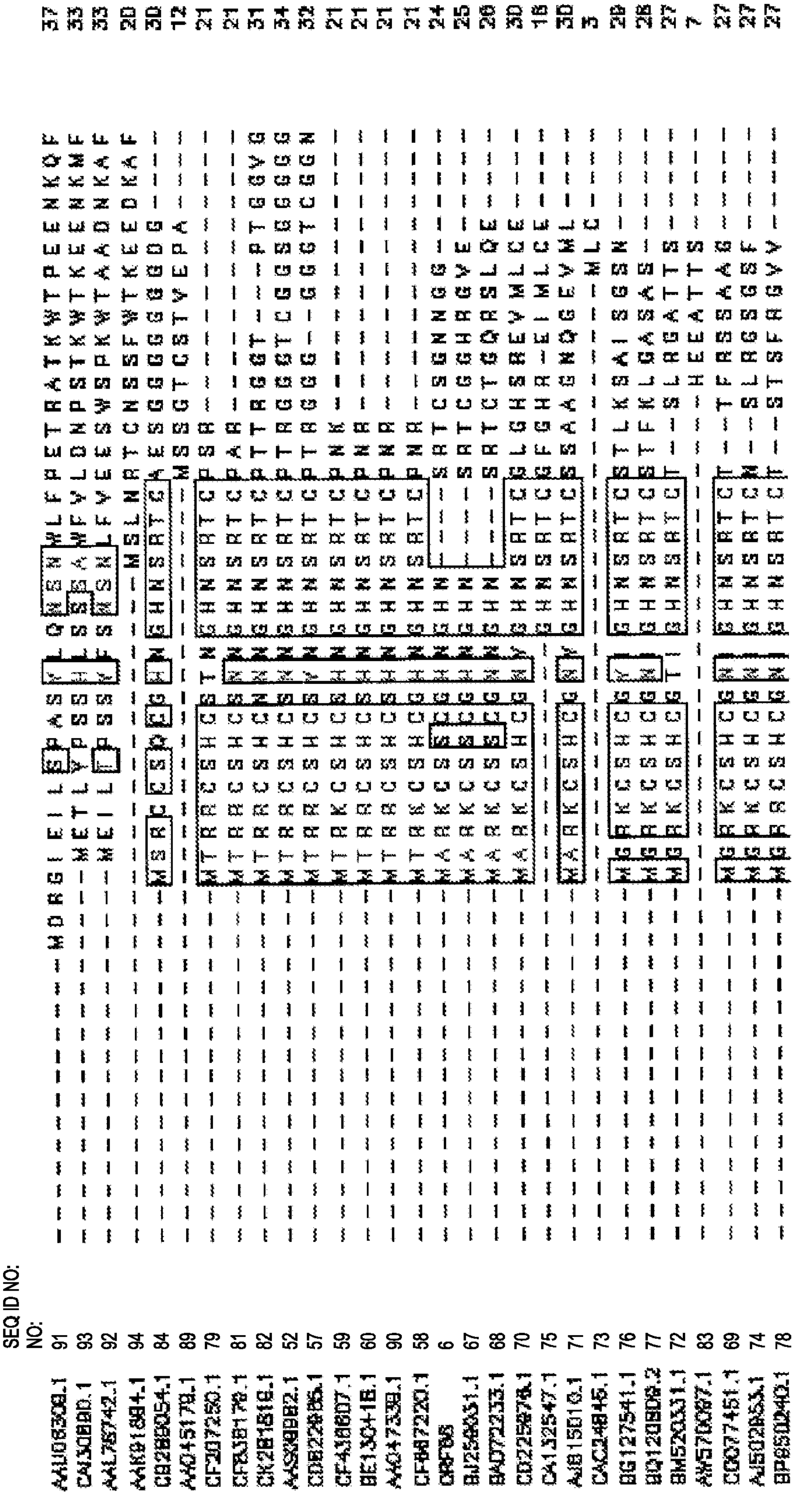
FIG. 10 shows an alignment of polypeptides of the invention, including ORF68 (SEQ ID NO:6) and sequences which are variants of SEQ ID NO:6 from several species (AAU06309.1=SEQ ID NO:91; CAI30890.1=SEQ ID NO:93; AAL78742.1=SEQ ID NO:92; AAK91894.1=SEQ ID NO:94; CB289054.1=SEQ ID NO:84; AA045179.1=SEQ ID NO:89; CF207250.1=SEQ ID NO:79; CF838179.1=SEQ ID NO:81; CK281819.1=SEQ ID NO:82; AAS09982.1=SEQ ID NO:52; CD822965.1=SEQ ID NO:57; CF436607.1 =SEQ ID NO:59; BE130418.1=SEQ ID NO:60; AA047339.1=SEQ ID NO:90; CF667220.1 =SEQ ID NO:58; ORF68 =SEQ ID NO:6; BJ259031.1=SEQ ID NO:67; BAD72233.1=SEQ ID NO:68; CD225976.1=SEQ ID NO:70; CA132547.1=SEQ ID NO:75; AJ615010.1=SEQ ID NO:71; CAC24845.1=SEQ ID NO:73; BG127541.1=SEQ ID NO:76; BQ120809.2=SEQ ID NO:77; BM520331.1=SEQ ID NO: 72; AW570097.1=SEQ ID NO:83; CO077451.1=SEQ ID NO:69; AJ502953.1=SEQ ID NO:74; and BP950240.1=SEQ ID NO:78 and illustrates a consensus region (shown within bold box) identified by the applicants which is present in all of the such sequences.
Figures 2, 10:
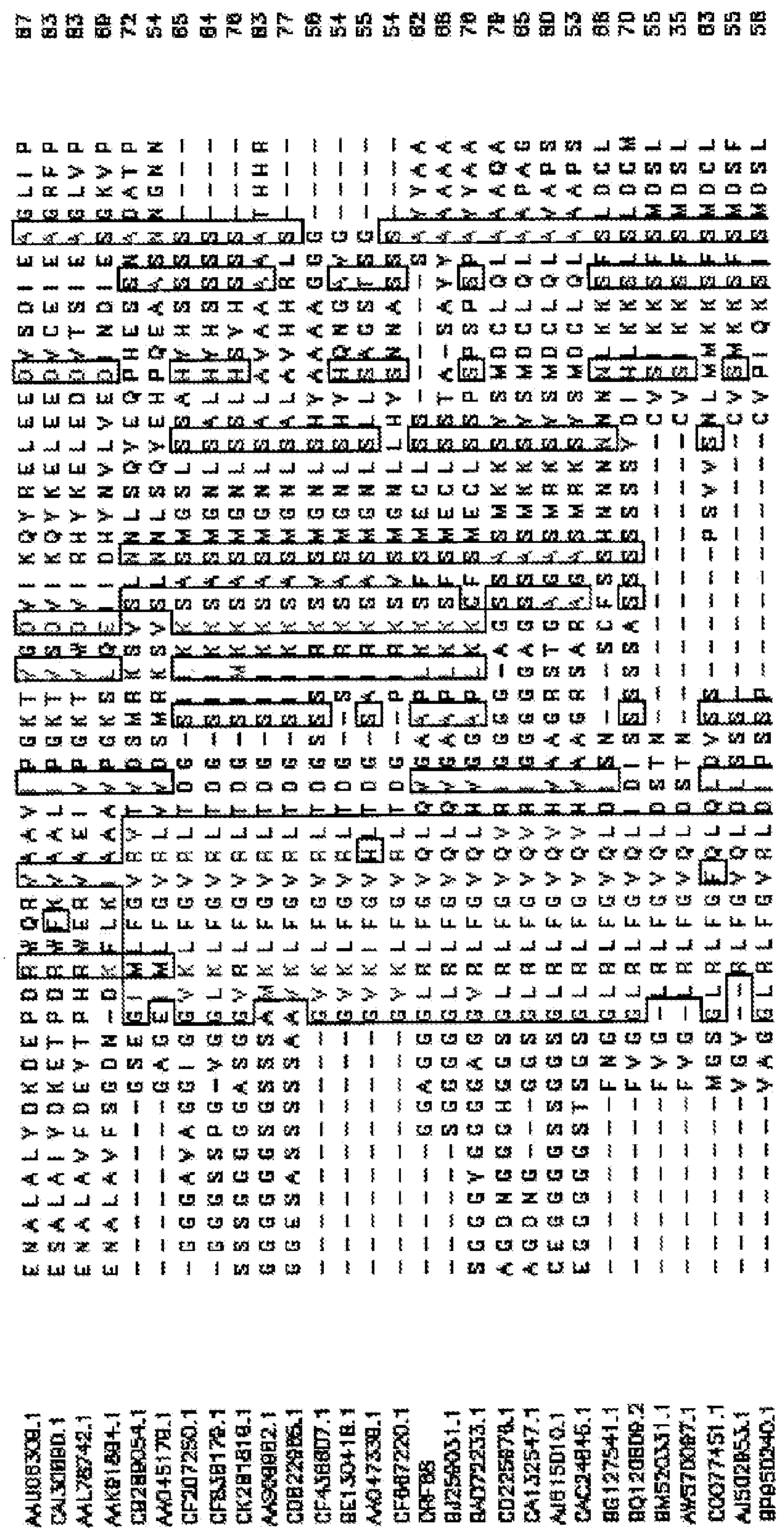
Figures 3, 10:
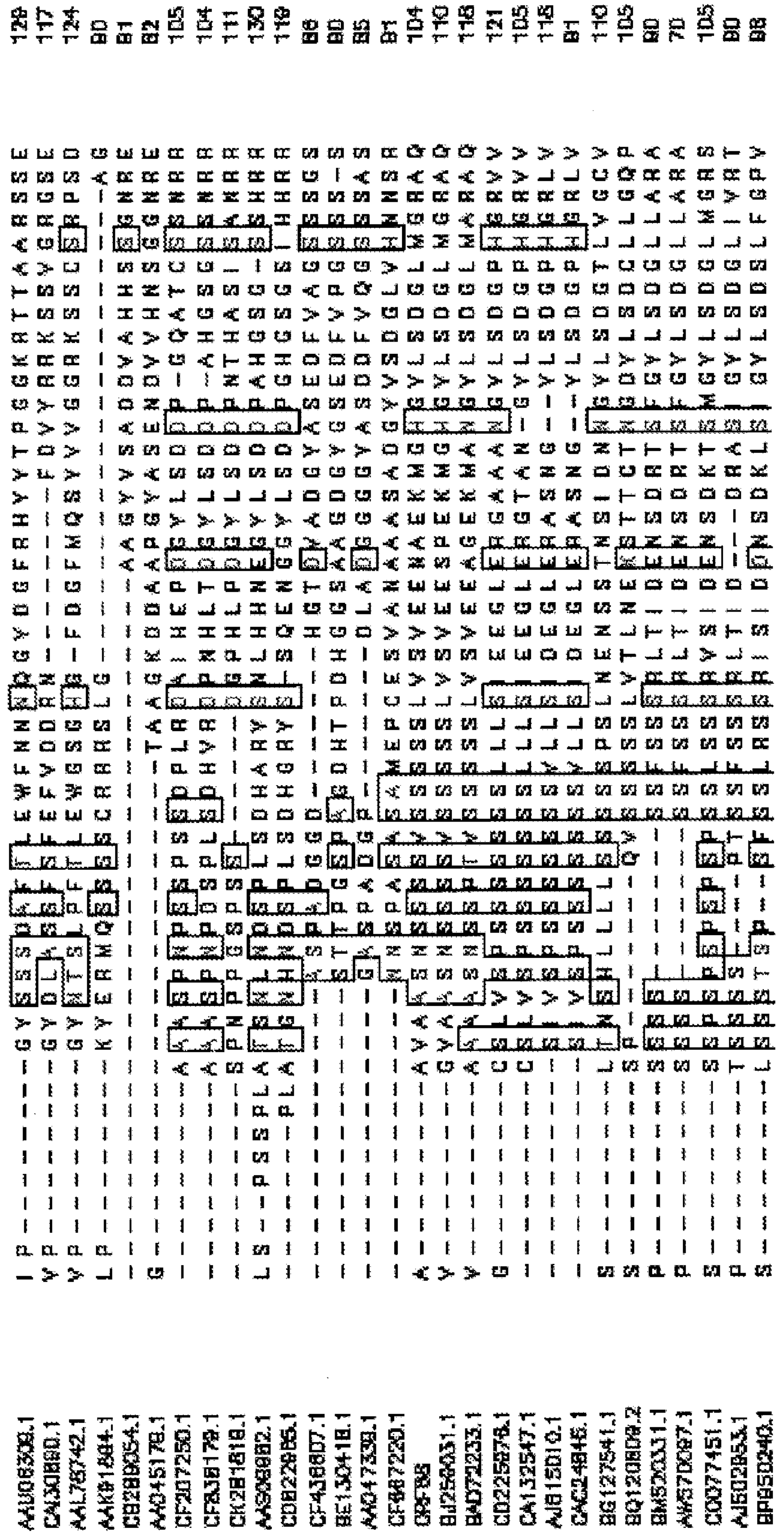
Figures 4, 10:
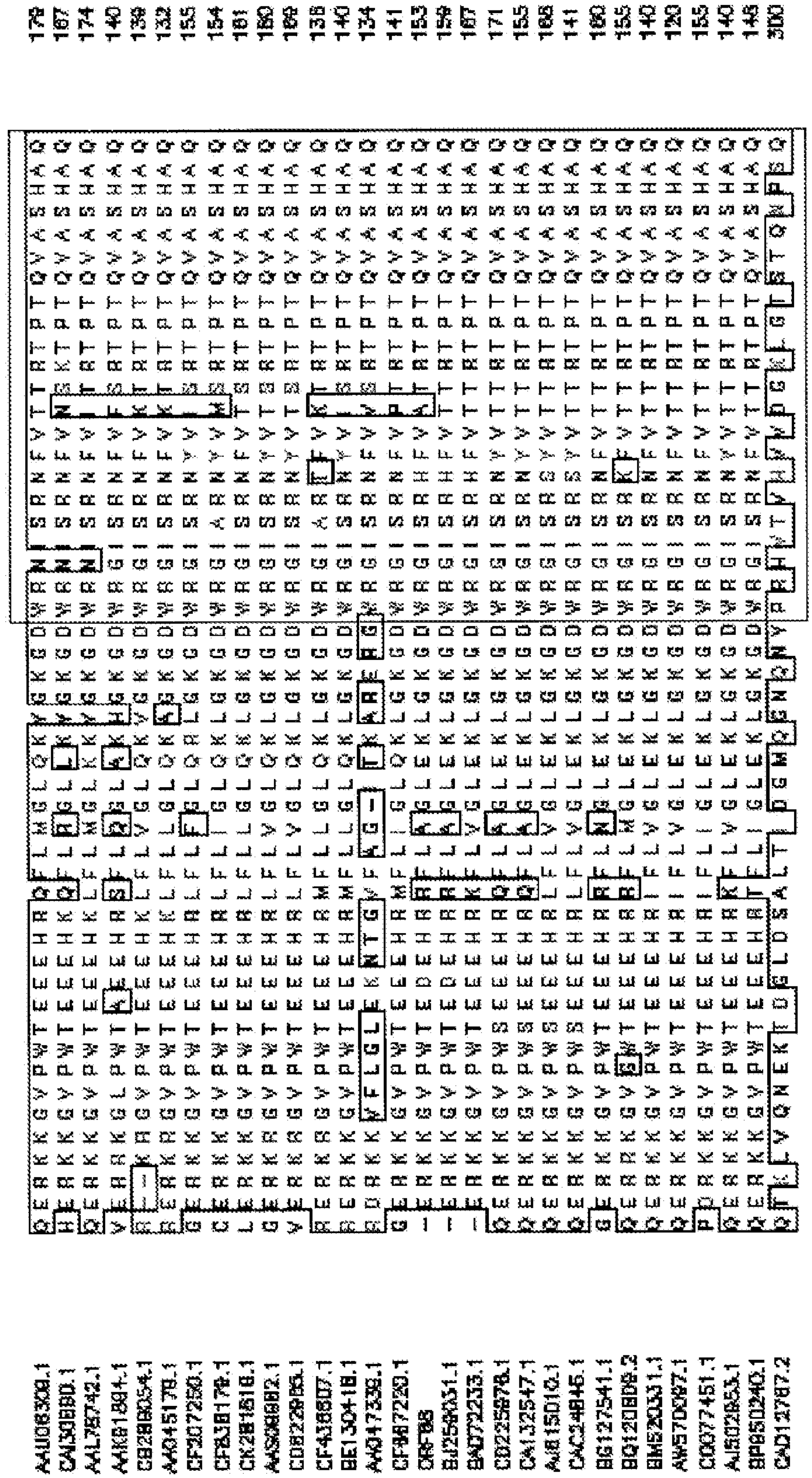
FIG. 4 shows the sequence (SEQ ID NO:252) of another vector, for plant transformation, comprising ORF24 and corresponding to the map in FIG. 3. Sequence in bold corresponds to the *Lolium perenne* promoter (SEQ ID NO:243). Sequence in italics corresponds to ORF24. Sequence underlined corresponds to 3'terminator sequence from CaMV35S gene. Sequence in regular font corresponds to vector sequence.
Figures 5, 10:
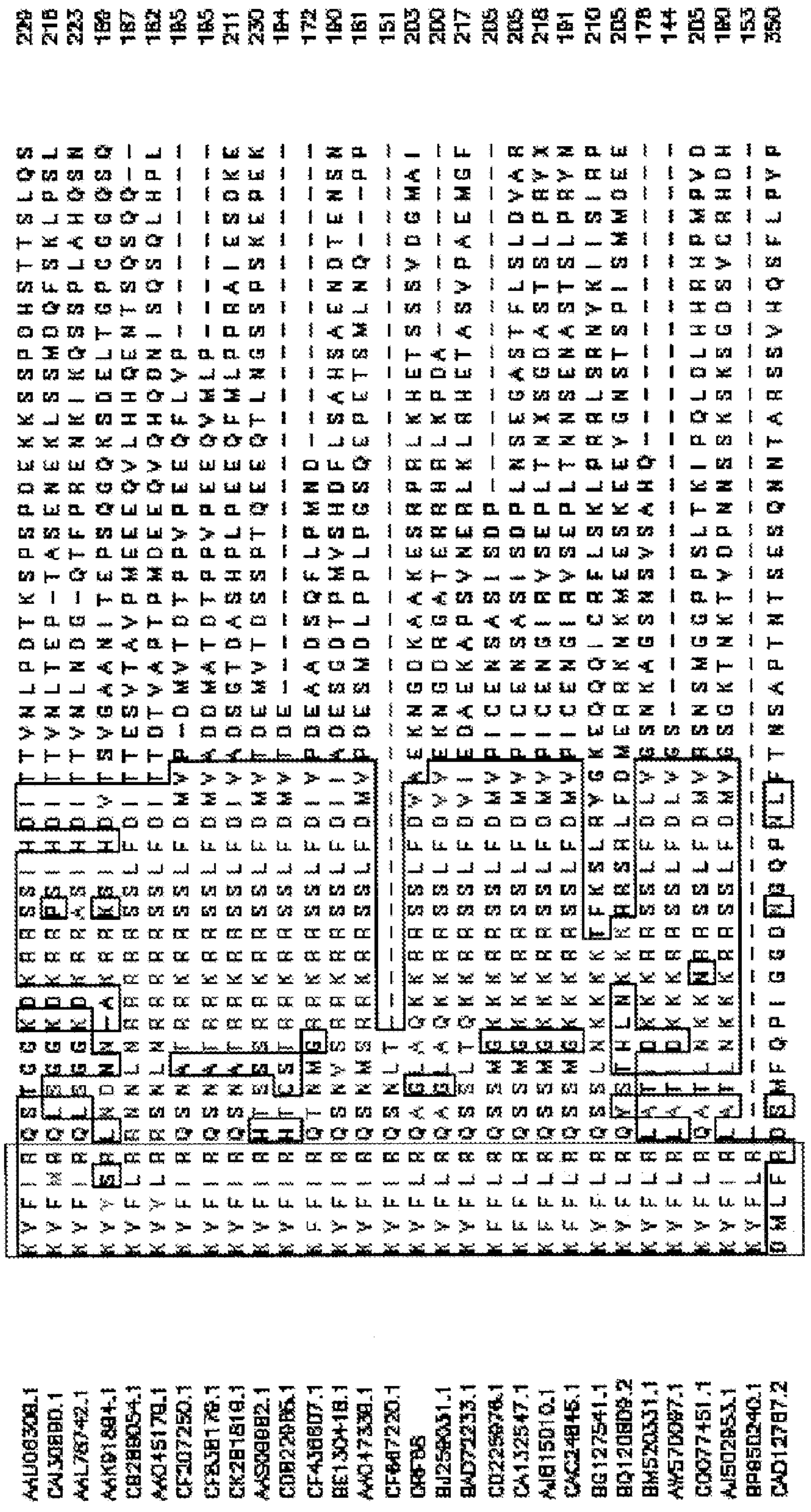

Two vectors for over-expressing ORF24 were produced by standard molecular biology techniques. A map of the first vector (pCORF24) is shown in FIG. 1. The sequence of the first vector is shown in FIG. 2 and SEQ ID NO:244. A map of the second vector (pDORF24) is shown in FIG. 3. The sequence of the second vector is shown in FIG. 4 and SEQ ID NO:252.

Vector Comprising ORF68

Figure 6:
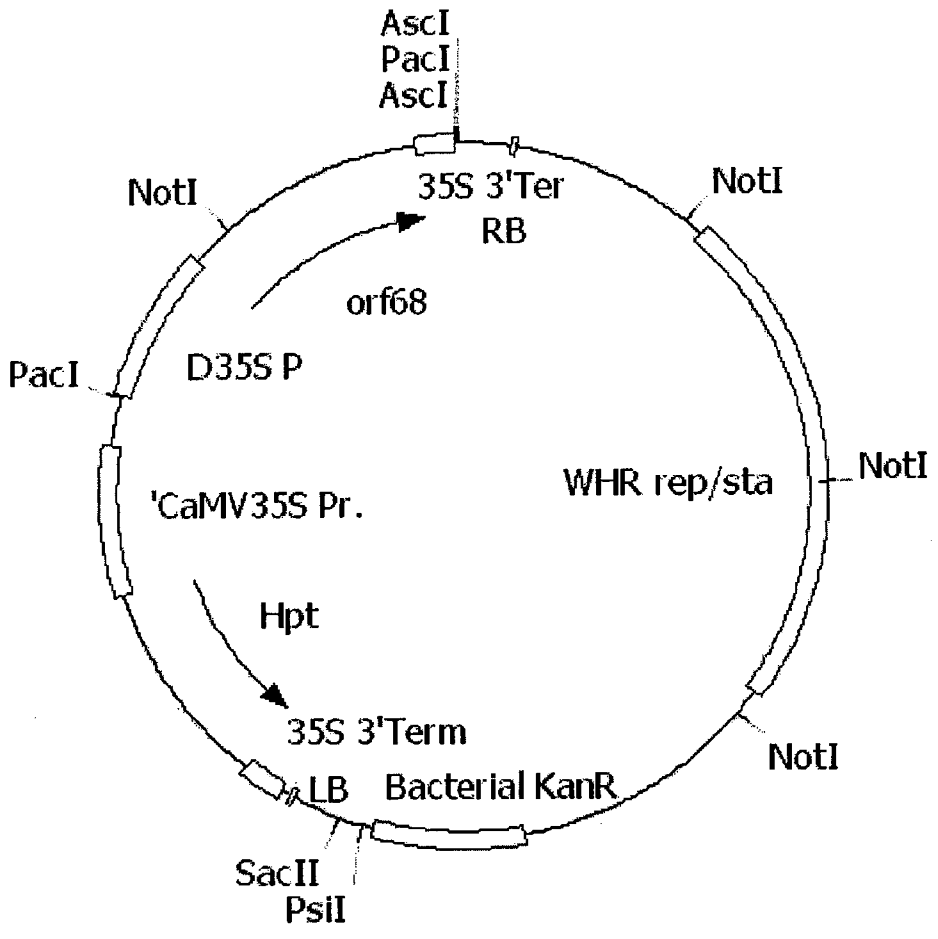
FIG. 6 shows a map of a vector, for plant transformation, comprising ORF68 (SEQ ID NO:5).
Figure 8:
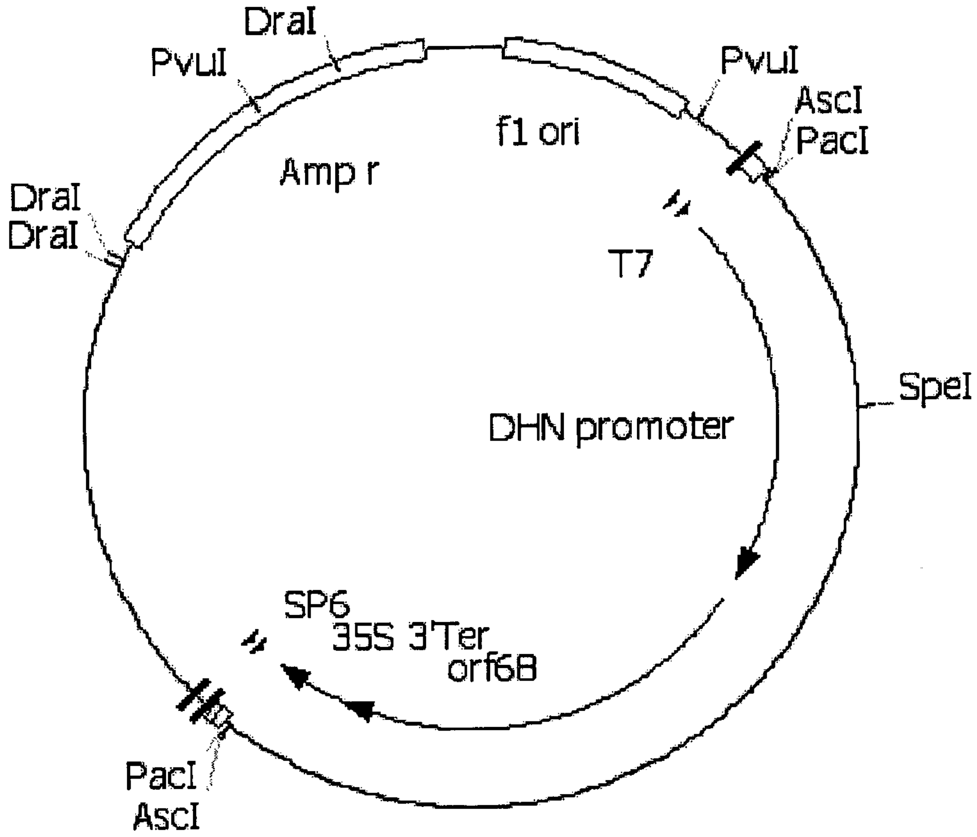
FIG. 8 shows a map of another vector, for plant transformation, comprising ORF68 (SEQ ID NO:5).
Figures 5, 15:
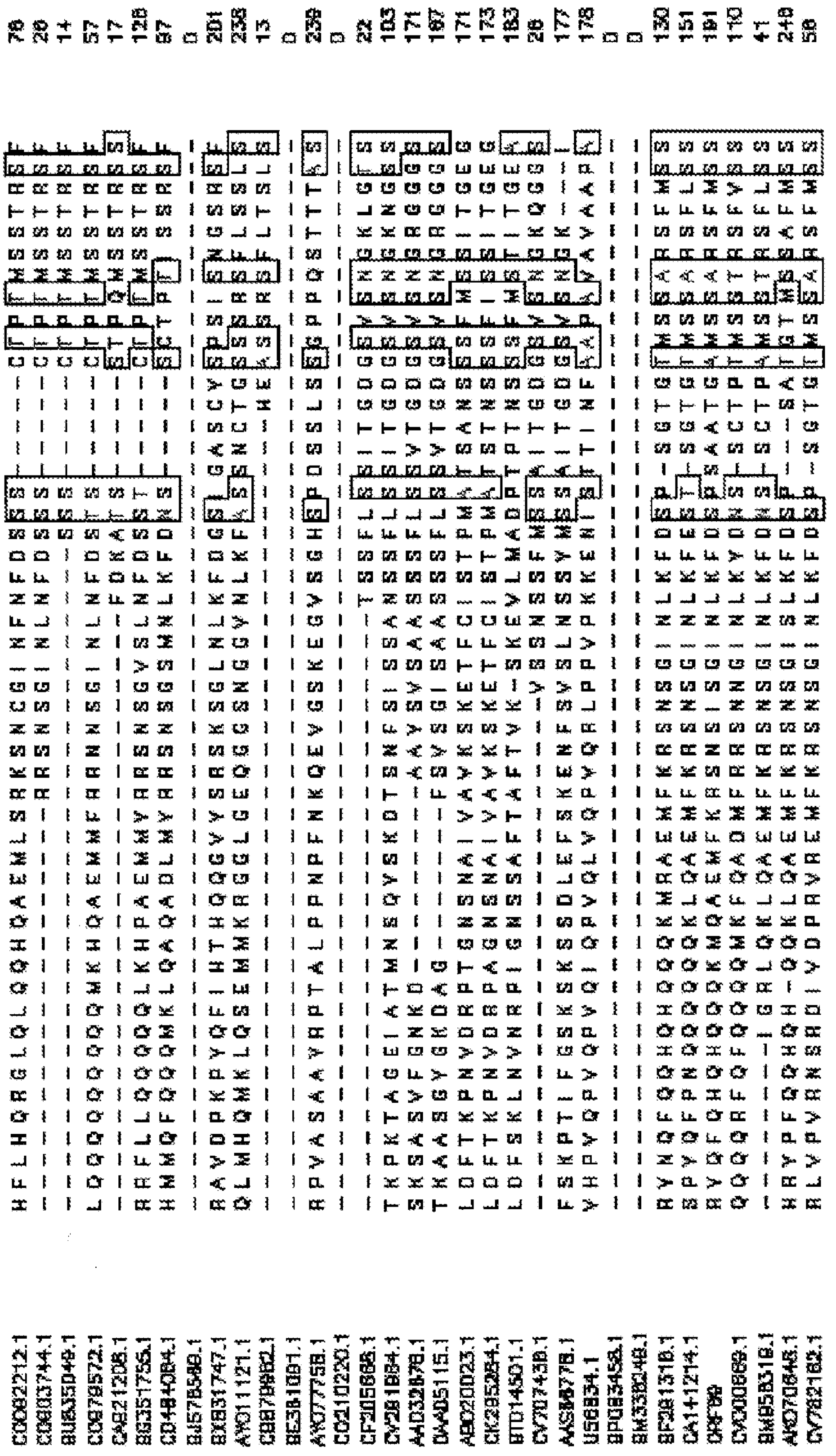
FIG. 15 shows an alignment of polypeptides of the invention, including ORF69 (SEQ ID NO:9) and sequences which are variants of SEQ ID NO:9 from several species (CO092212.1=SEQ ID NO:135; CO903744.1=SEQ ID NO:137; BU835049.1=SEQ ID NO:136; CO979572.1=SEQ ID NO:134; CA921208.1=SEQ ID NO:139; BG351755.1=SEQ ID NO:138; CD484064.1=SEQ ID NO:132; BJ576569.1=SEQ ID NO:140; BX831747.1=SEQ ID NO:133; AY011121.1=SEQ ID NO:131.
Figures 6, 15:
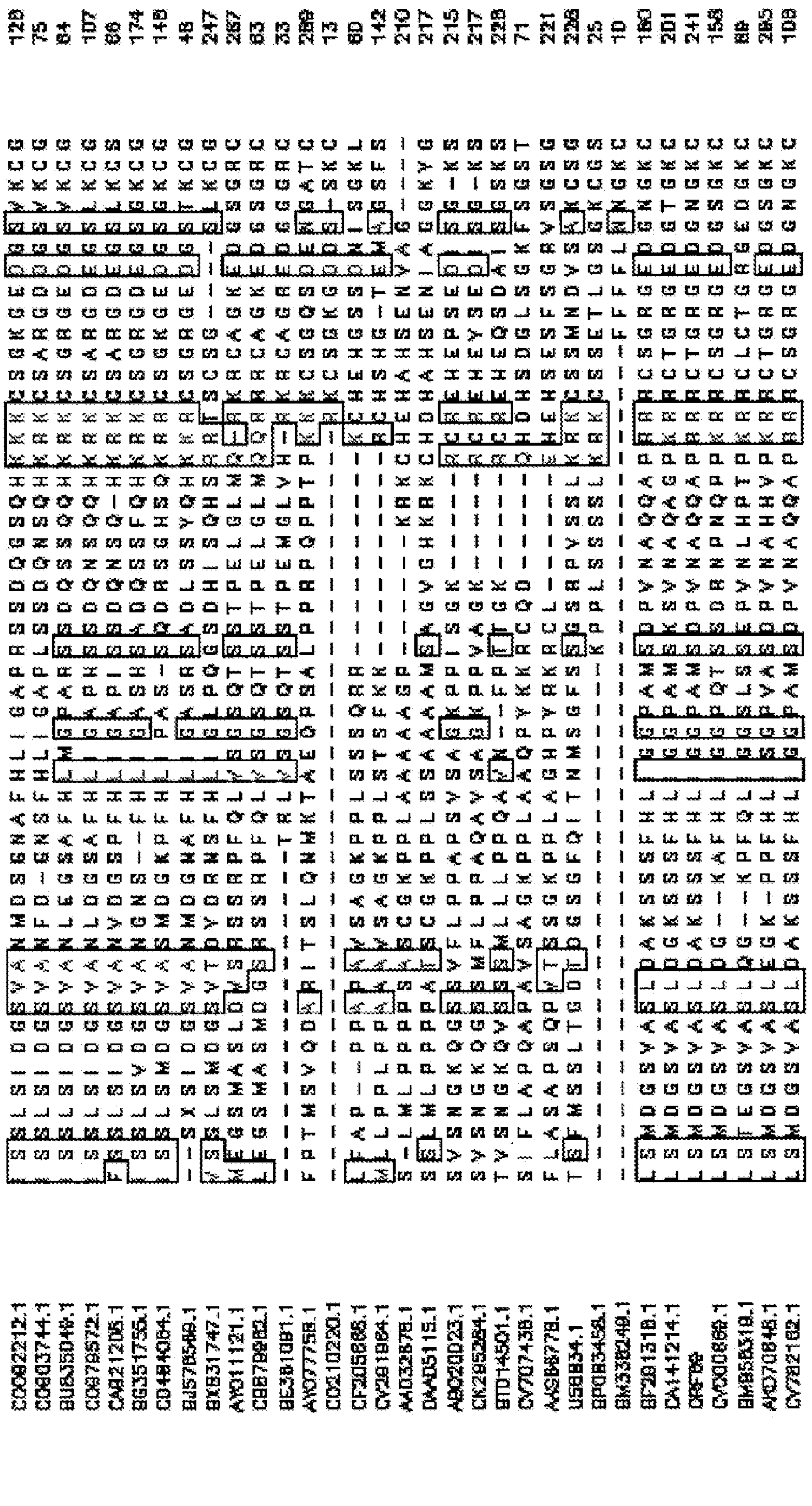
Figures 7, 15:
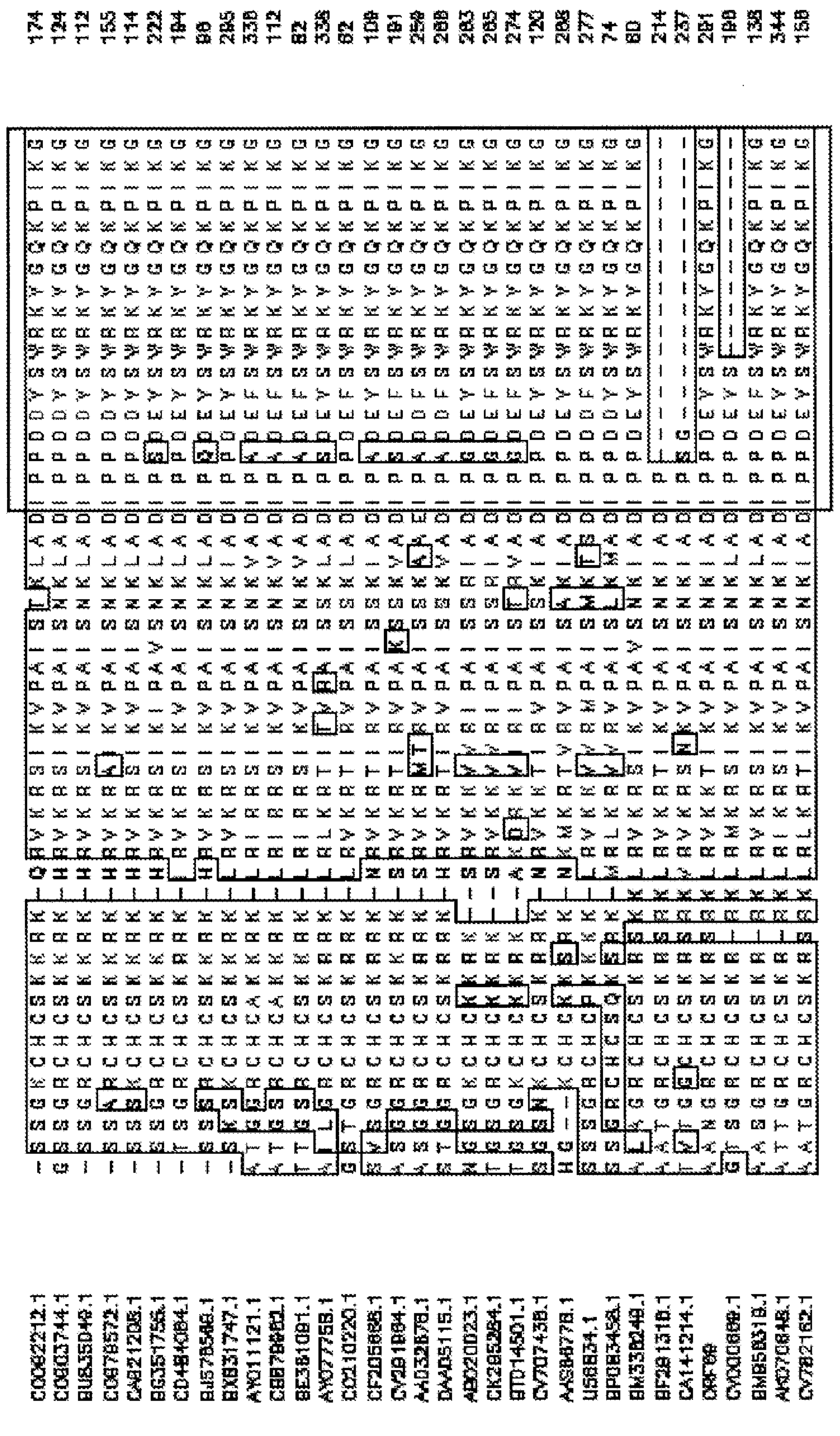
FIG. 7 shows the sequence (SEQ ID NO:245) of a vector, for plant transformation, comprising ORF68 and corresponding to the map in FIG. 6. Sequence in bold corresponds to the CaMV35S promoter. Sequence in italics corresponds to ORF68. Sequence underlined corresponds to 3'terminator sequence from CaMV35S gene. Sequence in regular font corresponds to vector sequence.
Figures 8, 15:
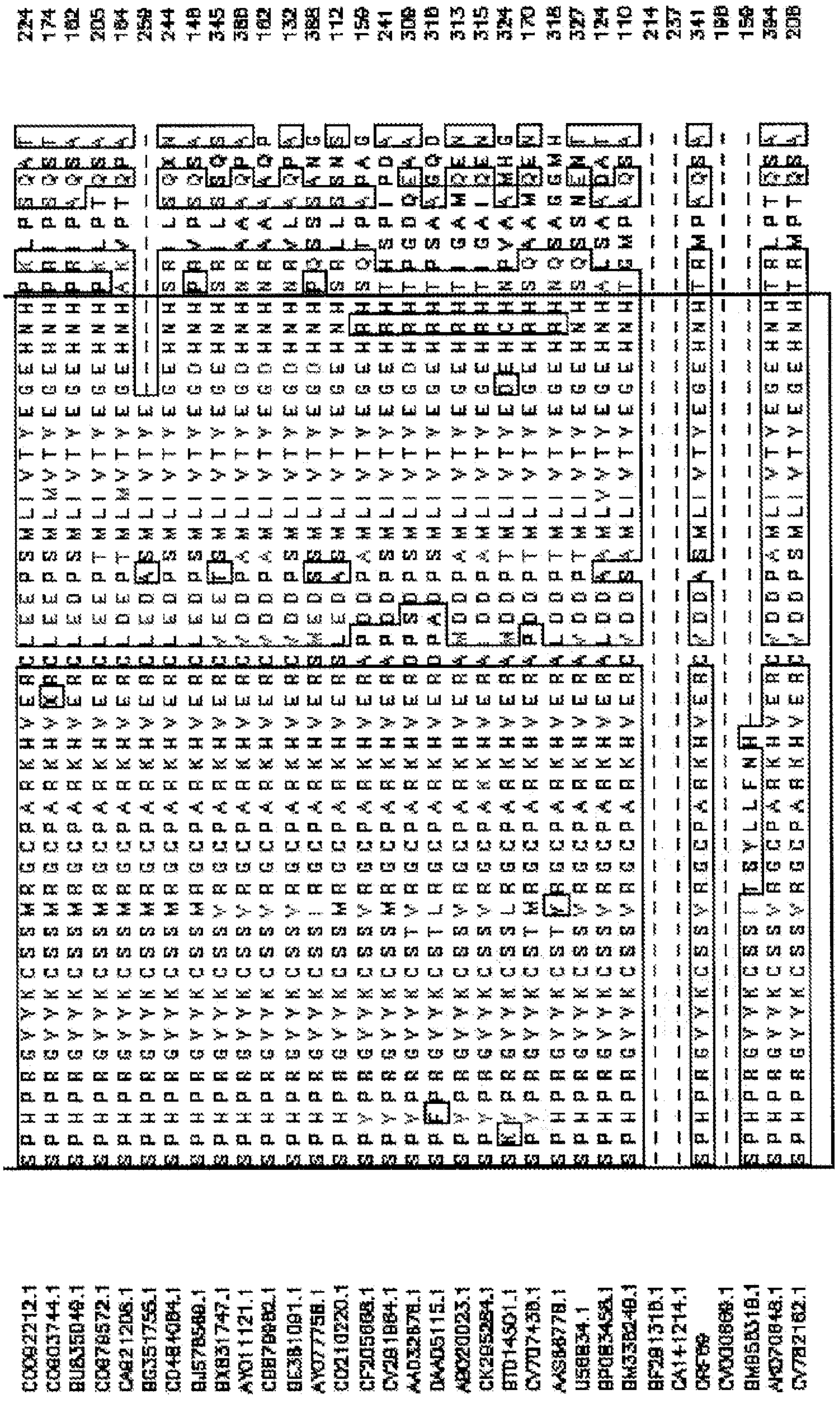

Two vectors for over-expressing ORF68 were produced by standard molecular biology techniques. A map of the first vector (pCORF68) is shown in FIG. 6. The sequence of the first vector is shown in FIG. 7 and SEQ ID NO:245. A map of the second vector (pDORF68) is shown in FIG. 8. The sequence of the second vector is shown in FIG. 9 and SEQ ID NO:253.

Vector Comprising ORF69

Figure 11:
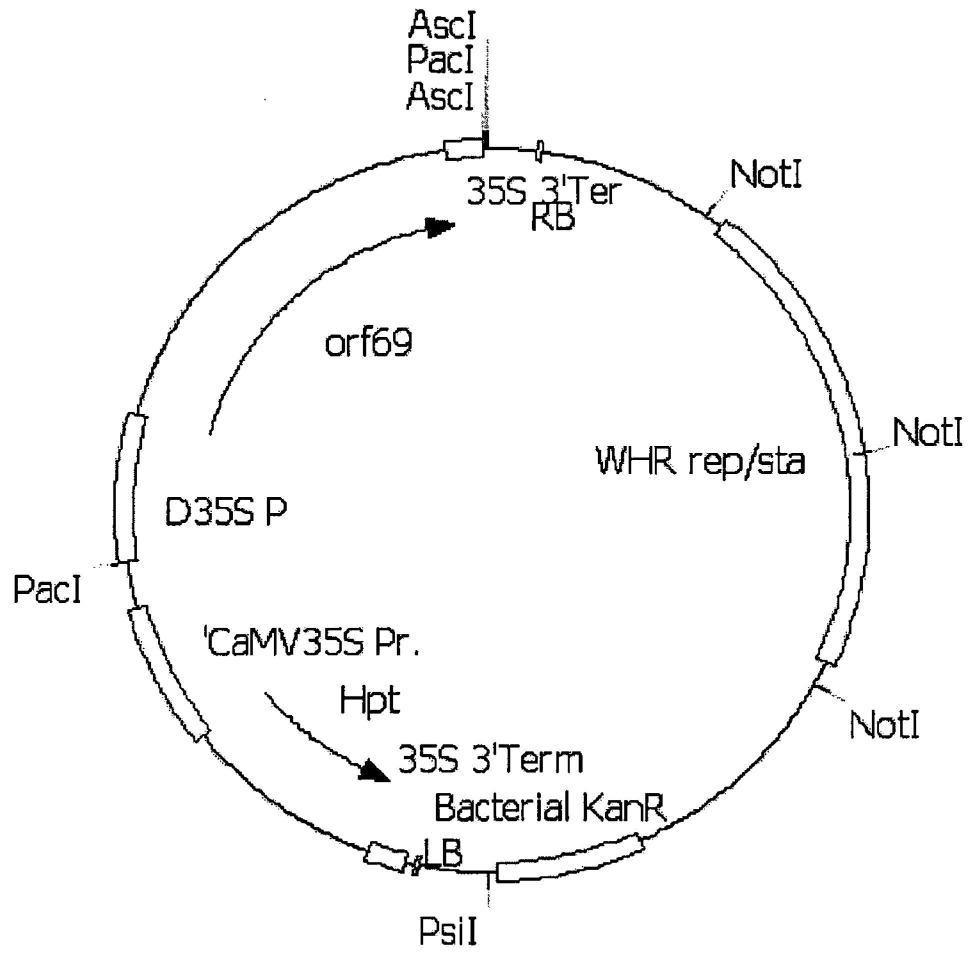
FIG. 11 shows a map of a vector, for plant transformation, comprising ORF69 (SEQ ID NO:8).
Figure 13:
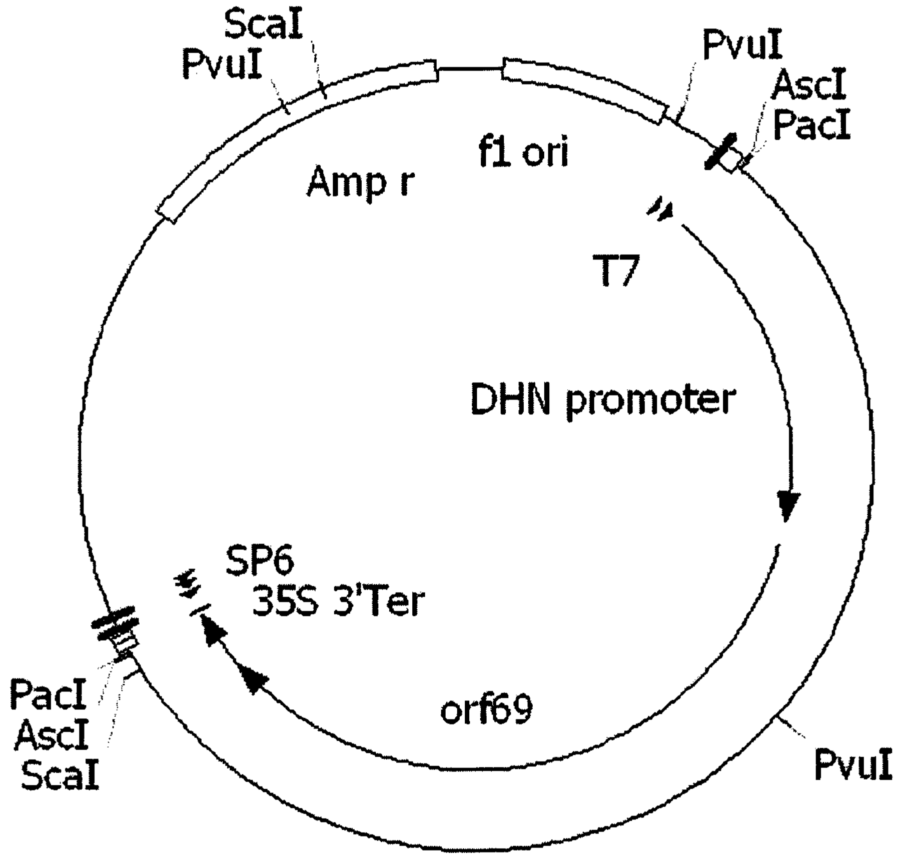
FIG. 13 shows a map of another vector, for plant transformation, comprising ORF69 (SEQ ID NO:8).

Two vectors for over-expressing ORF69 were produced by standard molecular biology techniques. A map of the first vector (pCORF69) is shown in FIG. 11. The sequence of the first vector is shown in FIG. 12 and SEQ ID NO:246. A map of the second vector (pDORF69) is shown in FIG. 13. The sequence of this vector is shown in FIG. 14 and SEQ ID NO:254.

Vector Comprising ORF9

Two vectors for over-expressing ORF9 were produced by standard molecular biology techniques. A map of the first vector (pCORF9) is shown in FIG. 16. The sequence of the first vector is shown in FIG. 17 and SEQ ID NO:247. A map of the second vector (pDORF9) is shown in FIG. 18. The sequence and features of this vector is shown in FIG. 19 (SEQ ID NO:255).

Example 4

Transformation of Plants within the Polynucleotides of the Invention

Donor Plant Production to Obtain Tissue Culture Explants

Seeds to establish contamination free in-vitro cultures were surface sterilized for 3 minutes with 70% (v/v) ethanol;

followed by 60 minutes with sodium hypochlorite solution (2.4% active Chlorine) supplemented with a surfactant (0.1% (w/v) of Tween-20 and five rinses with autoclaved distilled water. Plantlets of perennial ryegrass (*Lolium perenne* L.) cultivar 'Limes' (DSV Lippstadt/Germany) were clonally propagated in a 90 mm petridish, containing Murashige and Skoog basal medium supplemented with 0.1 mg/l Benzylaminopurine; pH 5.8 and was solidified with 3.0 g/l phytagel (Sigma), at 16° C. during night and 20° C. during the day with 14/12 h light/dark cycle. Light intensity of at least 360 $\mu Em^{-2}s^{-1}$ at plant height was maintained with sodium vapor lights (SON-T AGRO 400, Phillips). Axillary buds approximately 4-10 mm in size were excised and placed on callus induction medium. 12 explants were cultured per 90 mm petri-dish at 20 $\mu Em^{-2}s^{-1}$ and 25° C. for 28 to 56 days and calli sub-cultured to fresh medium every 14 days.

Biolistic Gene Transfer, Selection and Regeneration of Transgenic Plants

Calli were bombarded with DNA-coated particles six to ten weeks after culture of explants. Four to six hours prior to biolistic gene transfer calli were sub-cultured on medium with additional 64 $g.l^{-1}$ mannitol and retransferred to mannitol free callus subculture medium after the particle bombardment. Regeneration medium differed from the callus induction medium in the phytohormone composition (no 2,4-D and BAP) and the carbohydrate source and concentration (20 $g\text{-}l^{-1}$ sucrose). Calli were cultured in low light at 20 $\mu E.m^{-2}.s^{-1}$ and 24° C. and regenerated initially at 50 $\mu E.m^{-2}.s^{-1}$ with a 16 h day, 8 h night cycle at 24° C. Two weeks after transfer to regeneration media light intensity was increased to 130 $\mu E.m^{-2}.s^{-1}$ with fluorescent lamps (Philips TL-D 58 W/840R).

The plasmid pJFnpt contains the selectable nptII gene, encoding the enzyme neomycin phosphotransferase II under control of the maize ubiquitin promoter and first intron (Christensen and Quail 1996, Transgenic Res., 5, 213-218). The nptII expression cassette from pJFnpt was inserted into the pPZP 111 vector [Hajdukiewicz et al., 1994, Plant Mol Biol 25 (6) 989-94]. The plasmids pPZP 111, pDORF24, pDORF68, pDORF69, and pDORF9 were isolated as supercoiled DNA using a commercially available DNA Maxiprep Kit (QIAGEN). Vector backbone was removed from both the selectable marker gene expression cassette as well as from the target gene expression cassette by restriction digest, gel electrophoresis and gel purification prior gene transfer. This produced minimal expression cassettes comprising promoter-ORF-terminator for each of the four ORF sequences, and promoter-nptII-terminator from the selectable marker pPZP 111 plasmid. Genetic transformation of perennial ryegrass was essentially carried out as described previously (Altpeter, F., Xu, J. and Ahmed S. 2000, Molecular Breeding, 6, 519-528). In brief, minimal transgene expression cassettes without vector backbone were precipitated on gold particles and delivered to target tissue in a 2:1 molar ratio (target gene expression cassette: selectable marker gene expression cassette) using a DuPont PDS-1000/He (BioRad, USA) device and 1100 psi rupture disks [Sanford et al., 1991 Journal of Methods in Cell and Molecular Biology 3, 3-16]. Particle density was adjusted by the final volume of ethanol in the gold-DNA suspension to 50 μg per bombardment. Five μl of the DNA coated particles were spread on the surface of the microcarrier. Thirty to 35 callus pieces were put in the center of a petridish per bombardment six to ten weeks after callus initiation.

Selection was initiated five to seven days after biolistic gene transfer into calli. Two to three biweekly callus subcultures on CIM medium with 50 $mg.l^{-1}$ paromomycin were followed by two to three biweekly subcultures on 50 mg 1-1 paromomycin containing SRM medium. Four to eight weeks after transfer of selected calli to light, rooted transgenic plants were screened by performing an ELISA for nptII expression using leaf protein extracts. nptII positive plants were further screened by performing a genomic PCR involving ORF24 or ORF68 specific primers as appropriate. Positive primary transformants were transferred to soil under controlled environment conditions and kept at 15° C./12° C. day/night with a 12 hour photoperiod and 400 $\mu E.m^{-2}.s^{-1}$. Illumination was provided by sodium vapor lamps (Philips SON-T AGRO 400) and vegetatively propagated to produce clones of uniform size and growth. RT-PCR was carried out using standard methodology on regenerated plants to determine the transgene expression levels and lines for drought screening were selected based on the transgene expression level.

Transgenic lines transformed with the ryegrass promoter DHN-driven ORF9 cassette excised from pDORF9, used in further experiments included D9-144 and D9-150.

Transgenic lines transformed with the ryegrass promoter DHN-driven ORF24 cassette excised from pDORF24, used in further experiments included D24-106, D24-107, D24-145 and D24-266.

Transgenic lines transformed with the ryegrass promoter DHN-driven ORF68 cassette excised from pDORF68, used in further experiments included D68-135, D68-137, D68-230 and D68-239.

Transgenic lines transformed with the ryegrass promoter DHN-driven ORF69 cassette excised from pDORF69, used in further experiments included D69-270; D69-143 and D69-201.

Example 5

Alteration in Tolerance to Environmental Stress in Plants Transformed with Polynucleotides of the Invention Drought Screening in Growth Chamber Based Hydroponics System.

Clones of selected lines and a non-transgenic control line were established in a hydroponics system that was set up in a growth chamber. The experimental setup involved four hydroponic tanks, representing eight randomized blocks with 15 plants in each block (10 transgenic lines and 5 wild type clones), totaling 120 plants (80 transgenic lines and 40 wild type clones) (FIG. 21). The transgenic lines were D24-145; D24-266, D9-144; D9-150, D68-135; D68-137; D68-230, D69-270; D69-143 and D69-201. After establishment, the plants were exposed to three rounds of drought-stress (plants lifted up from the hydroponic system) comprising of 19 h drought followed by 11 days of recovery in the first cycle and then by 24 hours of drought and 24 h recovery in the second cycle. The third drought stress was performed after 18 days of recovery from the second drought stress and the plants were drought stressed for 42 hours. Biometric parameters such as Quantum yield of Photosystem II (yield) and Electron Transfer Rate (ETR) were measured using a Pulse Modulated Fluorometer (PAM2000) before the drought stress, at the end of the drought cycle, after 24 hours of recovery and at the end of the recovery period. Each data point in the figure represents the average of 12 measurements (three measurements per plant and four plants per line).

After 19-hours first round of drought-stress, ETR and yield was measured before returning the plants to the hydroponics system for recovery. Line D69-270, line D9-144 and line D68-135 had a significant higher yield and ETR than wildtype. All other transgenic lines were not significantly different than wildtype. Following 24-hours recovery from the 19-hour drought-stress, ETR and yield were measured again. Line D68-135 which performed well during stress did not recover well and performed significantly worse than the wildtype. Line D24-145 recovered significantly better than the wildtype. All other lines, including D69-270 and D9-144 did not show differences from wildtype. After 11 days of recovery, Line D68-135 and line D24-266 did not recover well after the first drought stress and performed significantly worse than the wildtype, while line D68-230 and line D9-150 showed significantly better yields and ETR's than the wildtype, and recovered even to pre-stress values. All other lines did not show significant differences to the wildtype (data not shown).

After the 24-hour second cycle of drought-stress, photosystemII measurements identified lines D24-266 and D69-143 to be performing significantly worse while four lines (D24-145, D68-137, D9-150 and D69-270) were found to perform significantly better than the wildtype. Line D24-266 which already performed badly under stress could not recover well even after 24 hours recovery from 24-hour stress, while line D69-201 performed significantly worse than the wildtype. Lines D68-137, D68-230, D9-144, D9-150 and D69-270 recovered significantly better than the wildtype (FIGS. 22*a* and 22*b*).

Yield and ETR were measured after a 24 hours recovery period following the 42-hour third cycle of drought-stress carried out 18 days after the 24-hour drought-stress. Lines D9-144, D9-150, D24-145, D68-230 and D69-270 out performed the wildtype and showed significantly higher yield and ETR than the wildtype while three transgenic lines, D69-143; D68-135 and D24-266, performed poorly (FIGS. 23*a* and 23*b*). Following nine days of recovery from the 42-hour drought stress, fresh and dry weights (after 48 h at 80 degrees C.) were evaluated separately for roots and shoots. The five above-mentioned transgenic lines (D9-144, D9-150, D24-145, D68-230 and D69-270) had a significantly higher fresh weight (FIG. 24*a*) and dry weight (FIG. 24*b*) than the wildtype. The difference between fresh and dry weight (FIG. 24*c*) indicates that transgenic lines D9-144, D9-150, D24-145, D68-230 and D69-270 had significantly more hydrated leaves at the time of harvest then the wildtypes. The root dry weight (FIG. 25), for seven (including the five above-mentioned lines) of the ten transgenic lines were significantly higher than the wildtype.

FIG. 26 indicates how viable the wild type plants and transgenic lines D24-145, D9-144 and D9-150 are after three cycles of drought stress as they appeared just after the end of the third drought stress, which lasted for 42 hours.

Drought Screening in SUN-Lit Chambers

Transgenic lines over-expressing ORF 9, ORF24, ORF68 or ORF69 were selected for a detailed physiological analysis in SUN-LIT chambers following their performance in hydroponic culture. Transgenic ryegrass and a wildtype ryegrass (WT) were vegetatively propagated in the greenhouse before transplanting to the SPAR chamber, i.e., D9-144; D9-150; D9-187; D24-106; D24-107; D24-145; D68-137; D68-230; D68-239; D68-296; D69-198; D69-258; D69-306, non-transgenic WT. These lines were randomized in a block design of 4 to 8 replications and grown in three bins (FIG. 27*a*).

Soil Moisture Monitoring

The soil moisture (VWC, volumetric water content) was recorded with a TDR300 at an interval of two to three days. Measurements were taken in each row between each of the plants at 20 cm depth (there were 28 positions for monitoring soil water status in each chamber). Following the establishment period subsurface irrigation was cut off. Soil moisture content declined and reached volumetric water content (VWC) below 2.3%. A period of no-irrigation was followed by a re-growth period.

Above-Ground Biomass

Leaf clipping dry weight was determined before (>4.3% VWC) and after drought stress (<2.3% VWC). All leaves were cut at 2.5 cm clipping height. The fresh weights (FW) of leaves were measured immediately, then leaves were dried at 80° C. for 48 h and the dry weight (DW) was measured. The difference between fresh weight and dry weight was used as an indicator of early recovery from drought stress. The ability to grow under drought-stress is calculated as percentage of inverse mass loss, which is calculated as the difference of dry weight and dry weight over fresh weight, i.e. (1-[{Fresh weight—Dry weight}/Fresh weight]) %. None of the transgenic lines produced significantly more biomass then the wildtype during the first weeks after establishment (data not shown). However with the onset of drought-stress, line D24-145 (FIG. 27*b* and FIG. 28*c*) and lines D68-137 and D68-239 produced significantly more biomass than wildtype. The aboveground biomass produced before drought-stress is shown in FIGS. 28*a*; 28*d*; 28*g*, after drought-stress is shown in FIGS. 28*b*; 28*e*; 28*h* and the ability to grow during drought-stress is shown in FIGS. 28*c*, 28*f* and 28*i*.

The above examples illustrate practice of the invention. It will be appreciated by those skilled in the art that numerous variations and modifications may be made without departing from the spirit and scope of the invention.

SUMMARY OF SEQUENCES

| SEQ ID NO: | TYPE | SPECIES | REFERENCE |
|---|---|---|---|
| 1 | Polynucleotide | *Lolium perenne* | ORF24 cDNA |
| 2 | Polynucleotide | *Lolium perenne* | ORF24 genomic |
| 3 | Polypeptide | *Lolium perenne* | ORF24 |
| 4 | Polynucleotide | *Lolium perenne* | ORF68 cDNA |
| 5 | Polynucleotide | *Lolium perenne* | ORF68 genomic |
| 6 | Polypeptide | *Lolium perenne* | ORF68 |
| 7 | Polynucleotide | *Lolium perenne* | ORF69 cDNA |
| 8 | Polynucleotide | *Lolium perenne* | ORF69 genomic |
| 9 | Polypeptide | *Lolium perenne* | ORF69 |
| 10 | Polynucleotide | *Lolium perenne* | ORF9 cDNA |
| 11 | Polynucleotide | *Lolium perenne* | ORF9 genomic |
| 12 | Polypeptide | *Lolium perenne* | ORF9 |
| 13 | Polynucleotide | *Triticum aestivum* | AF542184 |
| 14 | Polynucleotide | *Oryza sativa* | AF190770 |
| 15 | Polynucleotide | *Prunus armeniaca* | AF071893 |

-continued

| SEQ ID NO: | TYPE | SPECIES | REFERENCE |
|---|---|---|---|
| 16 | Polynucleotide | *Fagus sylvatica* | AJ606475 |
| 17 | Polynucleotide | *Lycopersicon esculentum* | AY044235 |
| 18 | Polynucleotide | *Gossypium barbade* | AY572463 |
| 19 | Polynucleotide | *Nicotiana tabacum* | AY286010 |
| 20 | Polynucleotide | *Capsicum annuum* | AY246274 |
| 21 | Polynucleotide | *Cicer arietinum* | AJ515026 |
| 22 | Polynucleotide | *Glycine max* | AF537220 |
| 23 | Polynucleotide | *Arabidopsis thaliana* | NM 104269 |
| 24 | Polynucleotide | *Zea mays* | AY103951 |
| 25 | Polynucleotide | *Triticum monococcum* | BQ802250 |
| 26 | Polypeptide | *Triticum aestivum* | AF542184 |
| 27 | Polypeptide | *Oryza sativa* | AF190770 |
| 28 | Polypeptide | *Prunus armeniaca* | AF071893 |
| 29 | Polypeptide | *Fagus sylvatica* | AJ606475 |
| 30 | Polypeptide | *Lycopersicon esculentum* | AY044235 |
| 31 | Polypeptide | *Gossypium barbade* | AY572463 |
| 32 | Polypeptide | *Nicotiana tabacum* | AY286010 |
| 33 | Polypeptide | *Capsicum annuum* | AY246274 |
| 34 | Polypeptide | *Cicer arietinum* | AJ515026 |
| 35 | Polypeptide | *Glycine max* | AF537220 |
| 36 | Polypeptide | *Arabidopsis thaliana* | NM 104269 |
| 37 | Polypeptide | *Zea mays* | AY103951 |
| 38 | Polypeptide | *Triticum monococcum* | BQ802250 |
| 39 | Polynucleotide | *Triticum aestivum* | dbj BJ259031.1 |
| 40 | Polynucleotide | *Oryza sativa* | AP002746 |
| 41 | Polynucleotide | *Gossypium raimondii* | gb CO077451.1 |
| 42 | Polynucleotide | *Sorghum bicolor* | gb CD225976.1 |
| 43 | Polynucleotide | *Triticum turgidum* | emb AJ615010.1 |
| 44 | Polynucleotide | *Glycine soja* | gb BM520331.1 |
| 45 | Polynucleotide | *Hordeum vulgare* | gb AJ303355 |
| 46 | Polynucleotide | *Medicago truncatula* | emb AJ502953.1 |
| 47 | Polynucleotide | *Saccharum officinarum* | gb CA132547.1 |
| 48 | Polynucleotide | *Lycopersicon esculentum* | gb BG127541.1 |
| 49 | Polynucleotide | *Solanum tuberosum* | gb BQ120809.2 |
| 50 | Polynucleotide | *Bruguiera gymnorrhiza* | dbj BP950240.1 |
| 51 | Polynucleotide | *Vitis vinifera* | gb CF207250.1 |
| 52 | Polynucleotide | *Arabidopsis thaliana* | gb AAS09982.1 |
| 53 | Polynucleotide | *Citrus sinensis* | gb CF838179.1 |
| 54 | Polynucleotide | *Nicotiana benthamiana* | gb CK281819.1 |
| 55 | Polynucleotide | *Glycine max* | gb AW570097.1 |
| 56 | Polynucleotide | *Vitis aestivalis* | gb CB289054.1 |
| 57 | Polynucleotide | *Brassica napus* | gb CD822965.1 |
| 58 | Polynucleotide | *Pinus taeda* | gb CF667220.1 |
| 59 | Polynucleotide | *Allium cepa* | gb CF436607.1 |
| 60 | Polynucleotide | *Mesembryanthemum crystallinum* | gb BE130418.1 |
| 61 | Polynucleotide | *Malus xiaojinensis* | gb AY196776 |
| 62 | Polynucleotide | *Zea mays* | AY207047 |
| 63 | Polynucleotide | *Hevea brasiliensis* | AY712938 |
| 64 | Polynucleotide | *Antirrhinum majus* | AY077454 |
| 65 | Polynucleotide | *Cucumis sativus* | AJ870304 |
| 66 | Polynucleotide | *Solanum demissum* | AC091627 |
| 67 | Polypeptide | *Triticum aestivum* | dbj BJ259031.1 |
| 68 | Polypeptide | *Oryza sativa* | dbj BAD72233.1 |
| 69 | Polypeptide | *Gossypium raimondii* | gb CO077451.1 |
| 70 | Polypeptide | *Sorghum bicolor* | gb CD225976.1 |
| 71 | Polypeptide | *Triticum turgidum* | emb AJ615010.1 |
| 72 | Polypeptide | *Glycine soja* | gb BM520331.1 |
| 73 | Polypeptide | *Hordeum vulgare* | emb CAC24845.1 |
| 74 | Polypeptide | *Medicago truncatula* | emb AJ502953.1 |
| 75 | Polypeptide | *Saccharum officinarum* | gb CA132547.1 |
| 76 | Polypeptide | *Lycopersicon esculentum* | gb BG127541.1 |
| 77 | Polypeptide | *Solanum tuberosum* | gb BQ120809.2 |
| 78 | Polypeptide | *Bruguiera gymnorrhiza* | dbj BP950240.1 |
| 79 | Polypeptide | *Vitis vinifera* | gb CF207250.1 |
| 80 | Polypeptide | *Arabidopsis thaliana* | gb AAS09982.1 |
| 81 | Polypeptide | *Citrus sinensis* | gb CF838179.1 |
| 82 | Polypeptide | *Nicotiana benthamiana* | gb CK281819.1 |
| 83 | Polypeptide | *Glycine max* | gb AW570097.1 |
| 84 | Polypeptide | *Vitis aestivalis* | gb CB289054.1 |
| 85 | Polypeptide | *Brassica napus* | gb CD822965.1 |
| 86 | Polypeptide | *Pinus taeda* | gb CF667220.1 |
| 87 | Polypeptide | *Allium cepa* | gb CF436607.1 |
| 88 | Polypeptide | *Mesembryanthemum crystallinum* | gb BE130418.1 |
| 89 | Polypeptide | *Malus xiaojinensis* | gb AAO45179.1 |
| 90 | Polypeptide | *Zea mays* | gb AAO47339.1 |
| 91 | Polypeptide | *Hevea brasiliensis* | gb AAU06309.1 |
| 92 | Polypeptide | *Antirrhinum majus* | gb AAL78742.1 |

-continued

| SEQ ID NO: | TYPE | SPECIES | REFERENCE |
|---|---|---|---|
| 93 | Polypeptide | *Cucumis sativus* | emb CAI30890.1 |
| 94 | Polypeptide | *Solanum demissum* | gb AAK91894.1 |
| 95 | Polynucleotide | *Oryza sativa* | dbj AK070648.1 |
| 96 | Polynucleotide | *Aegilops speltoides* | gb BF291316.1 |
| 97 | Polynucleotide | *Triticum aestivum* | gb CV782162.1 |
| 98 | Polynucleotide | *Saccharum officinarum* | gb CA141214.1 |
| 99 | Polynucleotide | *Dactylis glomerata* | gb AY011121.1 |
| 100 | Polynucleotide | *Amborella trichopoda* | gb CD484064.1 |
| 101 | Polynucleotide | *Arabidopsis thaliana* | emb BX831747.1 CNS0A16X |
| 102 | Polynucleotide | *Glycine max* | gb CO979572.1 |
| 103 | Polynucleotide | *Gossypium raimondii* | gb CO092212.1 |
| 104 | Polynucleotide | *Populus tremula* x *Populus tremuloides* | gb BU835049.1 |
| 105 | Polynucleotide | *Malux* x *domestica* | gb CO903744.1 |
| 106 | Polynucleotide | *Solanum tuberosum* | gb BG351755.1 |
| 107 | Polynucleotide | *Medicago truncatula* | gb CA921208.1 |
| 108 | Polynucleotide | *Ipomoea nil* | dbj BJ576569.1 |
| 109 | Polynucleotide | *Hordeum vulgare* | gb CB879962.1 |
| 110 | Polynucleotide | *Crocus sativus* | gb BM956319.1 |
| 111 | Polynucleotide | *Zea mays* | gb BM336249.1 |
| 112 | Polynucleotide | *Sorghum bicolor* | gb BE361091.1 |
| 113 | Polynucleotide | *Physcomitrella patens* | gb AY077758.1 |
| 114 | Polynucleotide | *Vitis* sp | gb CF205668.1 |
| 115 | Polynucleotide | *Picea engelmannii* x *Picea sitchensis* | gb CO210220.1 |
| 116 | Polynucleotide | *Nicotiana tabacum* | dbj AB020023.1 |
| 117 | Polynucleotide | *Liriodendron tulipifera* | gb CV000669.1 |
| 118 | Polynucleotide | *Nicotiana benthamiana* | gb CK295284.1 |
| 119 | Polynucleotide | *Petroselinum crispum* | gb U56834.1 PCU56834 |
| 120 | Polynucleotide | *Asparagus officinalis* | gb CV291964.1 |
| 121 | Polynucleotide | *Poncirus trifoliata* | gb CV707436.1 |
| 122 | Polynucleotide | *Lotus corniculatus* var. *japonicus* | dbj BP083458.1 |
| 123 | Polynucleotide | *Avena sativa* | gb AAD32676.1 |
| 124 | Polynucleotide | *Capsella rubella* | gb AAS66778.1 |
| 125 | Polynucleotide | *Oryza sativa* subsp. *indica* | tpg DAA05115.1 |
| 126 | Polynucleotide | *Lycopersicon esculentum* | gb BT014501.1 |
| 127 | Polypeptide | Genus species | dbj AK070648.1 |
| 128 | Polypeptide | *Aegilops speltoides* | gb BF291316.1 |
| 129 | Polypeptide | *Triticum aestivum* | gb CV782162.1 |
| 130 | Polypeptide | *Saccharum officinarum* | gb CA141214.1 |
| 131 | Polypeptide | *Dactylis glomerata* | gb AY011121.1 |
| 132 | Polypeptide | *Amborella trichopoda* | gb CD484064.1 |
| 133 | Polypeptide | *Arabidopsis thaliana* | emb BX831747.1 CNS0A16X |
| 134 | Polypeptide | *Glycine* max | gb CO979572.1 |
| 135 | Polypeptide | *Gossypium raimondii* | gb CO092212.1 |
| 136 | Polypeptide | *Populus tremula* x *Populus tremuloides* | gb BU835049.1 |
| 137 | Polypeptide | *Malux* x *domestica* | gb CO903744.1 |
| 138 | Polypeptide | *Solanum tuberosum* | gb BG351755.1 |
| 139 | Polypeptide | *Medicago truncatula* | gb CA921208.1 |
| 140 | Polypeptide | *Ipomoea nil* | dbj BJ576569.1 |
| 141 | Polypeptide | *Hordeum vulgare* | gb CB879962.1 |
| 142 | Polypeptide | *Crocus sativus* | gb BM956319.1 |
| 143 | Polypeptide | *Zea mays* | gb BM336249.1 |
| 144 | Polypeptide | *Sorghum bicolor* | gb BE361091.1 |
| 145 | Polypeptide | *Physcomitrella patens* | gb AY077758.1 |
| 146 | Polypeptide | *Vitis* sp | gb CF205668.1 |
| 147 | Polypeptide | *Picea engelmannii* x *Picea sitchensis* | gb CO210220.1 |
| 148 | Polypeptide | *Nicotiana tabacum* | dbj AB020023.1 |
| 149 | Polypeptide | *Liriodendron tulipifera* | gb CV000669.1 |
| 150 | Polypeptide | *Nicotiana benthamiana* | gb CK295284.1 |
| 151 | Polypeptide | *Petroselinum crispum* | gb U56834.1 PCU56834 |
| 152 | Polypeptide | *Asparagus officinalis* | gb CV291964.1 |
| 153 | Polypeptide | *Poncirus trifoliate* | gb CV707436.1 |
| 154 | Polypeptide | *Lotus corniculatus* var. *japonicus* | dbj BP083458.1 |
| 155 | Polypeptide | *Avena sativa* | gb AAD32676.1 |
| 156 | Polypeptide | *Capsella rubella* | gb AAS66778.1 |
| 157 | polypeptide | *Oryza sativa* subsp. *indica* | tpg DAA05115.1 |
| 158 | Polypeptide | *Lycopersicon esculentum* | gb BT014501.1 |
| 159 | Polynucleotide | *Triticum aestivum* | gb AAN06944.1 |
| 160 | Polynucleotide | *Oryza sativa* | gb AAS72368.1 |
| 161 | Polynucleotide | *Hordeum vulgare* | sp Q9ARD5 LT02 HORVU |

-continued

| SEQ ID NO: | TYPE | SPECIES | REFERENCE |
|---|---|---|---|
| 162 | Polynucleotide | *Zea mays* | gb AY107179.1 |
| 163 | Polynucleotide | *Oryza sativa* | dbj AK070872.1 |
| 164 | Polynucleotide | *Oryza sativa* | gb AC093089.1 |
| 165 | Polynucleotide | *Oryza sativa* | dbj AB030211.1 |
| 166 | Polynucleotide | *Oryza sativa* | dbj AK062410.1 |
| 167 | Polynucleotide | *Zea mays* | gb AY103848.1 |
| 168 | Polynucleotide | *Zea mays* | gb AY108684.1 |
| 169 | Polynucleotide | *Oryza sativa* | gb AY554051.1 |
| 170 | Polynuclotide | *Hordeum vulgare* | emb AJ310995.1 HVU310995 |
| 171 | Polynucleotide | *Lophopyrum elongatum* | gb U00966.1 U00966 |
| 172 | Polynucleotide | *Oryza sativa* | gb AY607689.1 |
| 173 | Polynucleotide | *Oryza sativa* | ref NM 184595.1 |
| 174 | Polynucleotide | *Zea mays* | gb AY105302.1 |
| 175 | Polynucleotide | *Hordeum vulgare* | emb AJ310994.1 HVU310994 |
| 176 | Polynucleotide | *Sorghum bicolor* | gb CD229091.1 CD229091 |
| 177 | Polynucleotide | *Triticum aestivum* | gb CD913648.1 CD913648 |
| 178 | Polynucleotide | *Hordeum vulgare* | gb BI780134.2 BI780134 |
| 179 | Polynucleotide | *Zea mays* | gb CF042363.1 CF042363 |
| 180 | Polynucleotide | *Oryza sativa* | gb CF319949.1 CF319949 |
| 181 | Polynucleotide | *Oryza sativa* | ref NM 183567.1 |
| 182 | Polynucleotide | *Hordeum vulgare* | emb Z25537.1 HVBLT101 |
| 183 | Polynucleotide | *Arabidopsis thaliana* | ref NP 974629.1 |
| 184 | Polynucleotide | *Arabidopsis thaliana* | ref NP 194795.1 |
| 185 | Polynucleotide | *Arabidopsis thaliana* | ref NP 194794.1 |
| 186 | Polynucleotide | *Brassica rapa* | gb AAT11798.1 |
| 187 | Polynucleotide | *Arabidopsis thaliana* | ref NP 179982.1 |
| 188 | Polynucleotide | *Arabidopsis thaliana* | gb AY060504.1 |
| 189 | Polynucleotide | *Arabidopsis thaliana* | emb BX842170.1 CNS09YE9 |
| 190 | Polynucleotide | *Arabidopsis thaliana* | emb BX825999.1 CNS0A6CK |
| 191 | Polynucleotide | *Poncirus trifoliate* | gb AY316308.1 |
| 192 | Polynucleotide | *Arabidopsis thaliana* | gb AC005770.3 |
| 193 | Polynucleotide | *Arabidopsis thaliana* | gb AY084701.1 |
| 194 | Polynucleotide | *Arabidopsis thaliana* | ref NM 104551.1 |
| 195 | Polynucleotide | *Solanum tuberosum* | dbj AB061265.1 |
| 196 | Polynucleotide | *Mesembryanthemum crystallinum* | gb CA836518.1 CA836518 |
| 197 | Polynucleotide | *Citrus sinensis* | gb CN183349.1 CN183349 |
| 198 | Polynucleotide | *Populus balsamifera* | gb BU870658.1 BU870658 |
| 199 | Polynucleotide | *Physcomitrella patens* | gb AAR87655.1 |
| 200 | Polynucleotide | *Physcomitrella patens* | gb AY496072.1 |
| 201 | Polypeptide | *Triticum aestivum* | gb AAN06944.1 |
| 202 | Polypeptide | *Oryza sativa* | gb AAS72368.1 |
| 203 | Polypeptide | *Hordeum vulgare* | sp Q9ARD5 LT02 HORVU |
| 204 | Polypeptide | *Zea mays* | gb AY107179.1 |
| 205 | Polypeptide | *Oryza sativa* | dbj AK070872.1 |
| 206 | Polypeptide | *Oryza sativa* | gb AC093089.1 |
| 207 | Polypeptide | *Oryza sativa* | dbj AB030211.1 |
| 208 | Polypeptide | *Oryza sativa* | dbj AK062410.1 |
| 209 | Polypeptide | *Zea mays* | gb AY103848.1 |
| 210 | Polypeptide | *Zea mays* | gb AY108684.1 |
| 211 | Polypeptide | *Oryza sativa* | gb AY554051.1 |
| 212 | Polypeptide | *Hordeum vulgare* | emb AJ310995.1 HVU310995 |
| 213 | Polypeptide | *Lophopyrum elongatum* | gb U00966.1 U00966 |
| 214 | Polypeptide | *Oryza sativa* | gb AY607689.1 |
| 215 | Polypeptide | *Oryza sativa* | ref NM 184595.1 |
| 216 | Polypeptide | *Zea mays* | gb AY105302.1 |
| 217 | Polypeptide | *Hordeum vulgare* | emb AJ310994.1 HVU310994 |
| 218 | Polypeptide | *Sorghum bicolor* | gb CD229091.1 CD229091 |

-continued

| SEQ ID NO: | TYPE | SPECIES | REFERENCE |
|---|---|---|---|
| 219 | Polypeptide | *Triticum aestivum* | gb CD913648.1 CD913648 |
| 220 | Polypeptide | *Hordeum vulgare* | gb BI780134.2 BI780134 |
| 221 | Polypeptide | *Zea mays* | gb CF042363.1 CF042363 |
| 222 | Polypeptide | *Oryza sativa* | gb CF319949.1 CF319949 |
| 223 | Polypeptide | *Oryza sativa* | ref NM 183567.1 |
| 224 | Polypeptide | *Hordeum vulgare* | emb Z25537.1 HVBLT101 |
| 225 | Polypeptide | *Arabidopsis thaliana* | ref NP 974629.1 |
| 226 | Polypeptide | *Arabidopsis thaliana* | ref NP 194795.1 |
| 227 | Polypeptide | *Arabidopsis thaliana* | ref NP 194794.1 |
| 228 | Polypeptide | *Brassica rapa* | gb AAT11798.1 |
| 229 | Polypeptide | *Arabidopsis thaliana* | ref NP 179982.1 |
| 230 | Polypeptide | *Arabidopsis thaliana* | gb AY060504.1 |
| 231 | Polypeptide | *Arabidopsis thaliana* | emb BX842170.1 CNS09YE9 |
| 232 | Polypeptide | *Arabidopsis thaliana* | emb BX825999.1 CNS0A6CK |
| 233 | Polypeptide | *Poncirus trifoliata* | gb AY316308.1 |
| 234 | Polypeptide | *Arabidopsis thaliana* | gb AC005770.3 |
| 235 | Polypeptide | *Arabidopsis thaliana* | gb AY084701.1 |
| 236 | Polypeptide | *Arabidopsis thaliana* | ref NM 104551.1 |
| 237 | Polypeptide | *Solanum tuberosum* | dbj AB061265.1 |
| 238 | Polypeptide | *Mesembryanthemum crystallinum* | gb CA836518.1 CA836518 |
| 239 | Polypeptide | *Citrus sinensis* | gb CN183349.1 CN183349 |
| 240 | Polypeptide | *Populus balsamifera* | gb BU870658.1 BU870658 |
| 241 | Polypeptide | *Physcomitrella patens* | gb AAR87655.1 |
| 242 | Polypeptide | *Physcomitrella patens* | gb AY496072.1 |
| 243 | Polynucleotide | *Lolium perenne* | promoter |
| 244 | Polynucleotide | vector | ORF24 |
| 245 | Polynucleotide | vector | ORF68 |
| 246 | Polynucleotide | vector | ORF69 |
| 247 | Polynucleotide | vector | ORF9 |
| 248 | Polypeptide | consensus | ORF24 |
| 249 | Polypeptide | consensus | ORF68 |
| 250 | Polypeptide | consensus | ORF69 |
| 251 | Polypeptide | consensus | ORF9 |
| 252 | Polynucleotide | vector | ORF24 |
| 253 | Polynucleotide | vector | ORF68 |
| 254 | Polynucleotide | vector | ORF69 |
| 255 | Polynucleotide | vector | ORF9 |

What is claimed is:

1. An isolated polynucleotide comprising:

a) a sequence encoding a polypeptide with at least 95% identity to the amino acid sequence of SEQ ID NO: 6; or b) the complement of the sequence of a).

2. The isolated polynucleotide of claim 1, wherein the polypeptide comprises the amino acid sequence of SEQ ID NO: 249.

3. The isolated polynucleotide of claim 1, wherein the polypeptide has the amino acid sequence of SEQ ID NO:6.

4. The isolated polynucleotide of claim 1, wherein the polypeptide-encoding sequence in a) has at least 95% identity to the sequence of SEQ ID NO: 4 or 5.

5. The isolated polynucleotide of claim 1, wherein the polypeptide-encoding sequence in a) has at least 95% identity to the coding sequence of SEQ ID NO: 4 or 5.

6. The isolated polynucleotide of claim 1, wherein the polypeptide-encoding sequence in a) has the sequence of SEQ ID NO: 4 or 5.

7. The isolated polynucleotide of claim 1, wherein the polypeptide-encoding sequence in a) has the coding sequence of SEQ ID NO: 4 or 5.

8. An isolated polynucleotide comprising:

a) a sequence with at least 95% identity to the nucleotide sequence of SEQ ID NO: 4 or 5; or b) the complement of the sequence of a).

9. A genetic construct comprising the polynucleotide of claim 1.

10. A host cell comprising the genetic construct of claim 9.

11. A host cell genetically modified to comprise the polynucleotide of claim 1.

12. A plant cell or plant comprising the genetic construct of claim 9.

13. A plant cell or plant genetically modified to comprise the polynucleotide of claim 1.

14. A plant part, propagule, progeny or seed of the plant of claim 13, wherein the plant part, propagule, progeny or seed is genetically modified to comprise a polynucleotide comprising:

a) a sequence encoding a polypeptide with at least 95% identity to the amino acid sequence of SEQ ID NO: 6,; or b) the complement of the sequence of a).

15. A method of producing a plant cell or plant the method comprising the step of transforming a plant cell or plant with at least one polynucleotide of claim 1.

16. A plant produced by the method of claim 15.

17. A plant part, propagule, progeny or seed of the plant of claim 16, wherein the plant part, propagule, progeny or seed comprises the at least one polynucleotide of claim 1 used to transform the plant cell or plant.

* * * * *

UNITED STATES PATENT AND TRADEMARK OFFICE

CERTIFICATE OF CORRECTION

PATENT NO. : 7,847,154 B2
APPLICATION NO. : 11/875656
DATED : December 7, 2010
INVENTOR(S) : Sathish Puthigae et al.

It is certified that error appears in the above-identified patent and that said Letters Patent is hereby corrected as shown below:

In Column 3, Line 22, please change “SHIA” to --SHA--

In Column 6, Line 13, please change “SHIA” to --SHA--

In Column 6, Line 17, please change “1,” to --I,--

In Column 11, Line 59, please change “AY246274.0” to --AY246274.C--

In Column 11, Line 60, please change “AY286010.N SEQ” to --AY286010.N=SEQ--

In Column 11, Line 64, please change “AF190770.0” to --AF190770.O--

In Column 12, Line 24, please change “AA045179.1” to --AAO45179.1--

In Column 12, Line 29, please change “AA047339.1” to --AAO47339.1--

In Column 12, Line 29, please change “CF667220.1 =SEQ” to --CF667220.1=SEQ--

In Column 12, Line 37, please change “NO:78” to --NO:78)--

In Column 13, Line 3, please change “NO:147.,” to --NO:147;--

In Column 13, Line 5, please change “AB020023.1 SEQ” to --AB020023.1=SEQ--

In Column 13, Line 6, please change “CK295284.1SEQ” to --CK295284.1=SEQ--

In Column 13, Line 36, after “sequence” insert --.--

In Column 16, Line 35, please change “BLASTN from” to --BLASTN (from--

In Column 16, Line 36, please change “b12seq” to --bl2seq--

In Column 16, Line 40, please change “b12seq” to --bl2seq--

In Column 16, Line 60, please change “276-277.” to --276-277).--

In Column 17, Line 10, please change “b12seq”to --bl2seq--

In Column 17, Line 27, please change “$1X10^{-5}$” to --$1X10^{-5}$,--

In Column 17, Line 27, please change “$1X10^{-6}$” to --$1X10^{-6}$,--

In Column 18, Line 33, please change “b12seq” to --bl2seq--

In Column 18, Line 53, please change “b12seq” to --bl2seq--

Signed and Sealed this
Twentieth Day of December, 2011

David J. Kappos
*Director of the United States Patent and Trademark Office*

In Column 18, Line 54, please change “b12seq” to --bl2seq--

In Column 19, Line 7, please change “b12seq” to --bl2seq--

In Column 21, Line 33, please change “NO:1” to --NO:11--

In Column 21, Line 33, please change “BD” to --ID--

In Column 21, Line 34, please change “NOs:12” to --NO:12--

In Column 21, Line 36, after “salinity” insert --.--

In Column 21, Line 55, please change “on” to --one--

In Column 23, Line 4, please change “Medicine.” to --Medicine,--

In Column 24, Line 19, please change “specification” to --speciation--

In Column 25, Line 56, please change “Manual” to --Manual.--

In Column 26, Line 62, please change “Berline,” to --Berlin,--

In Column 27, Line 55, after “257)” insert --.--

In Column 30, Line 42, please change “nr_pant” to --nr_plant--

In Column 30, Line 44, please change “203 Aug. 8” to --2003 Aug. 8--

In Column 30, Line 46-47, please change “HTGS -sequences)” to --HTGS sequences)--

In Column 35, Line 62, please change “microcarrier.” to --macrocarrier.--

In Column 36, Line 1, please change “50 mg 1-1” to --50 mg$l^{-1}$--

In Column 38, Line 37, please change “line” to --lines--

In Column 43, Line 10, please change “Polynuclotide” to --Polynucleotide--

In Column 374, Line 29, (Claim 14), please change “6,;” to --6;--